US012747428B2

(12) United States Patent
Johnston et al.

(10) Patent No.: US 12,747,428 B2
(45) Date of Patent: Sep. 29, 2026

(54) EXPRESSION OF NITROGENASE POLYPEPTIDES IN PLANT CELLS

(71) Applicant: Commonwealth Scientific and Industrial Research Organisation, Acton (AU)

(72) Inventors: Ema Jayne Johnston, Canberra (AU); Robert Silas Allen, Downer (AU); Christina Maria Gregg, Canberra (AU); Shoko Okada, Coombs (AU); Amratha Menon, Canberra (AU); Andrew Charles Warden, Ngunnawal (AU); Matthew Craig Taylor, Chifley (AU); Craig Christopher Wood, Dickson (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 950 days.

(21) Appl. No.: 17/767,838

(22) PCT Filed: Oct. 9, 2020

(86) PCT No.: PCT/AU2020/051089

§ 371 (c)(1),
(2) Date: Apr. 8, 2022

(87) PCT Pub. No.: WO2021/068039

PCT Pub. Date: Apr. 15, 2021

(65) Prior Publication Data

US 2024/0117326 A1 Apr. 11, 2024

(30) Foreign Application Priority Data

Oct. 10, 2019 (AU) ................................ 2019903818
Mar. 5, 2020 (AU) ................................ 2020900689

(51) Int. Cl.

| | |
|---|---|
| ***C12N 9/00*** | (2006.01) |
| ***C07K 14/415*** | (2006.01) |
| ***C12N 9/02*** | (2006.01) |
| ***C12N 9/10*** | (2006.01) |
| ***C12N 9/24*** | (2006.01) |
| ***C12N 15/62*** | (2006.01) |
| ***C12N 15/82*** | (2006.01) |

(52) U.S. Cl.

CPC .......... *C12N 9/0095* (2013.01); *C07K 14/415* (2013.01); *C12N 9/1025* (2013.01); *C12N 9/13* (2013.01); *C12N 9/2402* (2013.01); *C12N 15/62* (2013.01); *C12N 15/8243* (2013.01); *C12Y 118/06001* (2013.01); *C12Y 203/03014* (2013.01); *C12Y 208/01007* (2013.01); *C07K 2319/07* (2013.01); *C07K 2319/50* (2013.01)

(58) Field of Classification Search

None

See application file for complete search history.

(56) References Cited

U.S. PATENT DOCUMENTS

| | | | | |
|---|---|---|---|---|
| 11,479,516 | B2 | 10/2022 | Voigt | |
| 11,802,290 | B2 * | 10/2023 | Wood | C12N 15/8261 |
| 2016/0304842 | A1 * | 10/2016 | Donovan | C12Y 118/06001 |
| 2018/0297905 | A1 | 10/2018 | Temme | |
| 2022/0170038 | A1 | 6/2022 | Allen | |

FOREIGN PATENT DOCUMENTS

| | | | | |
|---|---|---|---|---|
| WO | WO 2015/171494 A1 | | 11/2015 | |
| WO | WO-2018141030 A1 | * | 8/2018 | C12N 15/8261 |

OTHER PUBLICATIONS

Extended European Search Report issued May 14, 2024 in connection with European Application No. EP 20 87 3534.
Allen, Robert S., et al., "Plant expression of NifD protein variants resistant to mitochondrial degradation", Proceedings of the National Academy of Sciences, 2020, vol. 117, No. 37, pp. 23165-23173.
Curatti, L. and Rubio, L.M. "Challenges to develop nitrogen-fixing cereals by direct nif-gene transfer", Plant Science, 2014, vol. 225, pp. 130-137.
Mohanty, J. , "A study on nitrogen fixation related proteins", Dissertation, Orissa University of Agriculture and Technology, 2017.
Okada, S. et al., "A Synthetic Biology Workflow Reveals Variation in Processing and Solubility of Nitrogenase Proteins Targeted to Plant Mitochondria, and Differing Tolerance of Targeting Sequences in a Bacterial Nitrogenase Assay", Frontiers in Plant Science, 2020, vol. 11, article 552160.
International Search Report issued May 2, 2018 in connection with PCT International Application No. PCT/AU2018/050084.
Lahiri, S. et al. "Functional NifD-K fusion protein in Azotobacter vinelandii is a homodimeric complex equivalent to the native heterotetrameric MoFe protein," Biochemical and Biophysical Research Communications. 2005, vol. 337, No. 2, pp. 677-684.
Notification of Transmittal of the International Search Report and the Written Opinion of the International Searching Authority, or the Declaration mailed May 2, 2018 in connection with PCT International Application No. PCT/AU2018/050084.
Suh, M. et al. "Functional Expression of a Fusion-dimeric MoFe Protein of Nitrogenase in Azotobacter vinelandii," The Journal of Biological Chemistry. 2003, vol. 278, pp. 5353-5360.

(Continued)

*Primary Examiner* — David R Byrnes
(74) *Attorney, Agent, or Firm* — Gary J. Gershik

(57) ABSTRACT

The present invention relates to methods and means for producing nitrogenase polypeptides in the mitochondria of plant cells.

8 Claims, 62 Drawing Sheets

Figure 1:
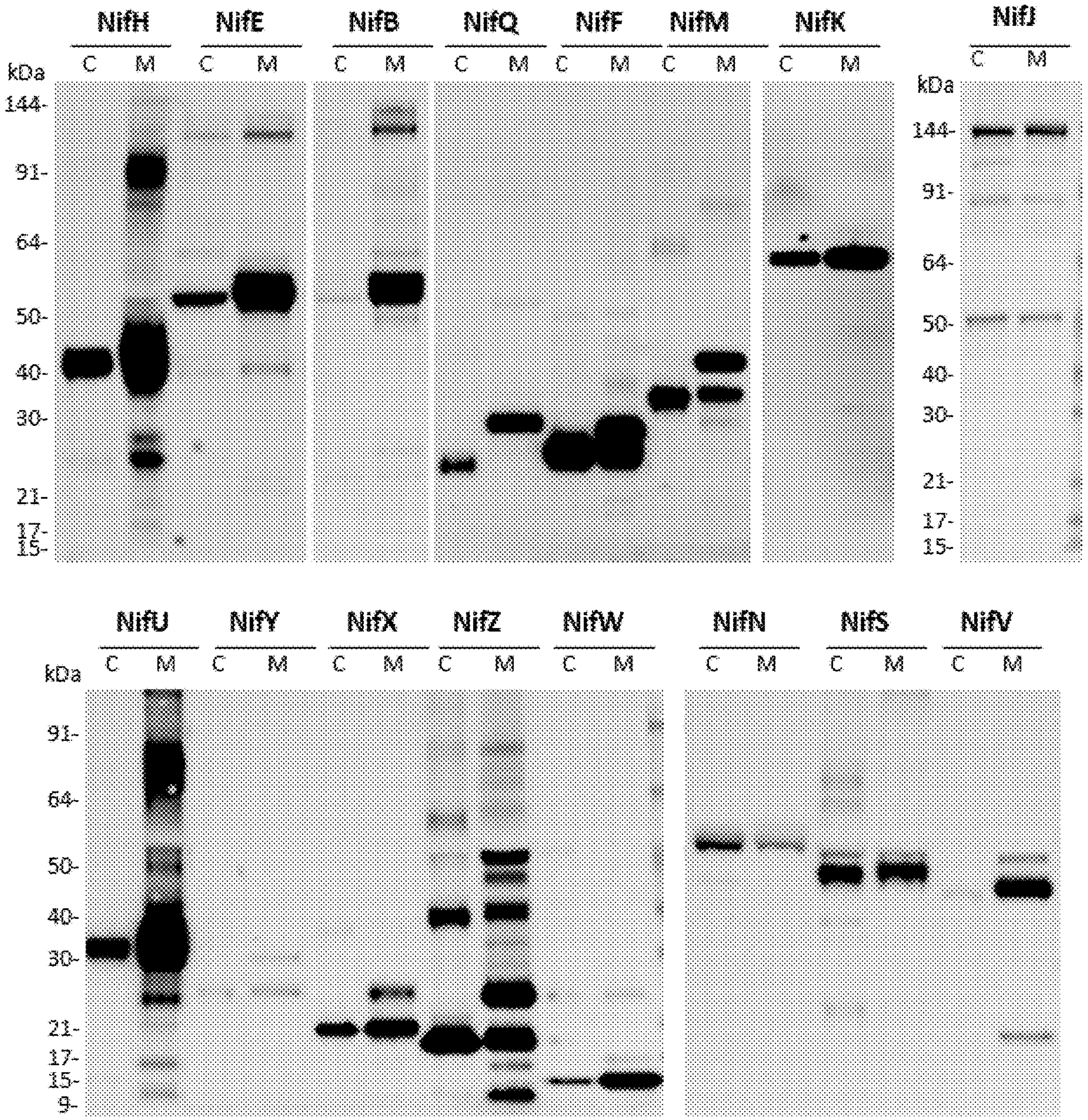

Specification includes a Sequence Listing.

(56) References Cited

OTHER PUBLICATIONS

Suh, M. et al. "Functional expression of the FeMo-cofactor-specific biosynthetic genes nifEN as a NifE-N fusion protein synthesizing unit in Azotobacter vinelandii," Biochemical and Biophysical Research Communications. 2002, vol. 299, pp. 233-240.
Written Opinion (form PCT/ISA/237) issued May 2, 2018 in connection with PCT International Application No. PCT/AU2018/050084.
Allen, R.M. et al. "Biosynthesis of the Iron-Molybdenum Cofactor of Nitrogenase", Critical Reviews of Biotechnology, 14(3): 225-249 (1994).
Allen, R.M. et al. "Incorporation of Iron and Sulfur from NifB Cofactor into the Iron-Molybdenum Cofactor of Dinitrogenase", The Journal of Biological Chemistry, 270(45): 26890-26896 (Nov. 10, 1995).
Balk, J. and Pilon, M. "Ancient and essential: the assembly of iron-sulfur clusters in plants", Trends in Plant Science, 16(4): 218-226 (Apr. 2011).
Becker, T. et al. "Mitochondrial protein import: from transport pathways to an integrated network", Trends in Biochemical Sciences, 37(3): 85-91 (Mar. 2012).
Boison, G. et al. "The rice field cyanobacteria Anabaena azotica and *Anabaena* sp. CH1 express vanadium-dependent nitrogenase", Arch. Microbial 186: 367-376 (2006).
Brigle, K.E. et al. "Products of the Iron-Molybdenum Cofactor-Specific Biosynthetic Genes, nifE and nifN, Are Structurally Homologous to the Products of the Nitrogenase Molybdenum-Iron Protein Genes, nifD and nifK", Journal of Bacteriology, 169(4): 1547-1553 (Apr. 1987).
Burén, S. and Rubio, L.M. "State of the art in eukaryotic nitrogenase engineering", FEMS Microbiology Letters, 365(2): 1-9 (2018).
Burén, S. et al. "Purification and In Vitro Activity of Mitochondria Targeted Nitrogenase Cofactor Maturase NifB", Frontiers in Plant Science, 8(1567): 1-16 (Sep. 2017).
Chen, X. et al. "Fusion protein linkers: Property, design and functionality", Advanced Drug Delivery Reviews 85: 1357-1369 (2013).
Cheng, Q. et al. "The Klebsiella pneumoniae nitrogenase Fe protein gene (nifH) functionally substitutes for the chlL gene in Chlamydomonas reinhardtii", Biochemical and Biophysical Research Communications, 329: 966-975 (2005).
Chiu, H.-S. et al. "MgATP-Bound and Nucleotide-Free Structures of a Nitrogenase Protein Complex between the Leu 127Δ-Fe-Protein and the MoFe-Protein", Biochemistry, 40: 641-650 (2001).
Christiansen, J. et al. "Catalytic and Biochemical Properties of a Nitrogenase Apo-MoFe Protein Produced by a nifB-Deletion Mutant of Azotobacter vinelandii", Biochemistry, 37: 12611-12623 (1998).
Clausen, T. et al. "Crystal structure of the cystine C—S lyase from Synechocystis: Stabilization of cysteine persulfide for FeS cluster biosynthesis", Proc. Nat'l. Acad. Sci. USA, 97: 3856-3861 (Apr. 11, 2000).
Cotton, M.S. et al. "VTVH-MCD Study of the ΔnifBΔnifZ MoFe Protein from Azotobacter vinelandii", J. Am. Chem. Soc., 131 (13): 4558-4559 (2009).
Coutourier, J. et al. "The iron-sulfur cluster assembly machineries in plants: current knowledge and open questions", Frontiers in Plant Science, 4(259): 1-23 (Jul. 24, 2013).
Curatti, L. et al. "NifB-dependent in vitro synthesis of the iron-molybdenum cofactor of nitrogenase", Proc. Nat'l. Acad. Sci. USA, 103(14): 5297-5301 (Apr. 4, 2006).
De Bruijn, F.J. "The Quest for Biological Nitrogen Fixation in Cereals: A Perspective and Prospective", Biological Nitrogen Fixation, vol. 2, First Edition, 1089-1101 (Frans J. de Bruijn ed., 2015).
Dilworth, M.J. et al. "The vanadium nitrogenase of Azotobacter chroococcum", Biochem. J. 249: 745-751 (1988).
Dilworth, M.J. et al. "The molybdenum and vanadium nitrogenases of Azotobacter chroococcum: effect of elevated temperature on N2 reduction", Biochem. J. 289: 395-400 (1993).
Drummond, M.H. "The base sequence of the nifF gene of the Klebsiella pneumoniae and homology of the predicted amino acid sequence of its protein product to other flavodoxins", Biochem. J. 232: 891-896 (1985).
Eady, R.R. "Structure-Function Relationships of Alternative Nitrogenases", Chem. Rev. 96: 3013-3030 (1996).
Fani, R et al. "Molecular Evolution of Nitrogen Fixation: The Evolutionary History of the nifD, nifK, nifE, and nifN Genes", J. Mol. Evol. 51: 1-11 (2000).
Fay, A.W. et al. "Identification and characterization of functional homologs of nitrogenase cofactor biosynthesis protein NifB from methanogens", Proc. Nat'l. Acad. Sci. USA, 112(48): 14829-14833 (Dec. 1, 2015).
Fay, A.W. et al. "Assembly scaffold NifEN: A structural and functional homolog of the nitrogenase catalytic component", Proc. Nat'l. Acad. Sci. USA, 113(34): 9504-9508 (Aug. 23, 2016).
Frazzon, A.P.G. et al. "Functional analysis of *Arabidopsis* genes involved in mitochondrial iron-sulfur cluster assembly", Plant Mol. Biol. 64: 225-240 (2007).
Lee, S.-H. et al. "Genetic Analysis on the NifW by Utilizing the Yeast Two-Hybrid System Revealed that the NifW of Azotobacter vinelandii Interact with the NifZ to Form Higher-Order Complexes", Biochemical and Biophysical Research Communications, 244: 498-504 (1998).
Gavini, N. et al. "Peptidyl-Prolyl cis/trans Isomerase-Independent Functional NifH Mutant of Azotobacter vinelandii", Journal of Bacteriology, 188(16): 6020-6025 (Aug. 2006).
Geddes, B.A. et al. "Use of plant colonizing bacteria as chassis for transfer of N2-fixation to cereals", Current Opinion in Biotechnology, 32: 216-222.
Goodwin, P.J. et al. "The Azotobacter vinelandii NifEN Complex Contains Two Identical [4Fe—4S] Clusters", Biochemistry, 37(29): 10420-10428 (Jun. 29, 1998).
Hu, Y. and Ribbe, M.W. "Biosynthesis of nitrogenase FeMoco", Coordination Chemistry Reviews, 225: 1218-1224 (2011).
Hu, Y. and Ribbe, M.W. "Nitrogenase assembly", Biochimica et Biophysica Acta, 1827: 1112-1122 (2013).
Hu, Y. et al. "Identification of a nitrogenase FeMo cofactor precursor on NifEN complex", Proc. Nat'l. Acad. Sci. USA, 102(9): 3236-3241 (Mar. 1, 2005).
Hu, Y. et al. "FeMO cofactor maturation on NifEN", Proc. Nat'l. Acad. Sci. USA, 103(46): 17119-17124 (Nov. 14, 2006).
Hu, Y. et al. "Assembly of Nitrogenase MoFe Protein", Biochemistry, 47: 3973-3981 (2008).
Huang, S. et al. "Refining the Definition of Plant Mitochondrial Presequences through Analysis of Sorting Signals, N-Terminal Modifications, and Cleavage Motifs", Plant Physiology, 150: 1272-1285 (Jul. 2009).
Igarashi, R.Y. and Seefeldt, L.C. "Nitrogen Fixation: The Mechanism of the Mo-Dependent Nitrogenase", Critical Reviews in Biochemistry and Molecular Biology, 38: 351-384 (2003).
Ivleva, N.B. et al. "Expression of Active Subunit of Nitrogenase via Integration into Plant Organelle Genome", PLOS One, DOI:10.1371/journal.pone.0160951 (Aug. 16, 2016).
Johnson, D.C. et al. "NifU and NifS are required for the maturation of nitrogenase and cannot replace the function of isc-gene products in Azotobacter vinelandii", Biochemical Society Transactions, 33(1): 90-93 (2005).
Kaiser, J.T. et al. "Structure of Precursor-Bound NifEN: A Nitrogenase FeMo Cofactor Maturase/Insertase", Science, 331: 91-94 (Jan. 7, 2011).
Kim, J. and Rees, D.C. "Nitrogenase and Biological Nitrogen Fixation", Biochemistry, 33(2): 389-397 (Jan. 18, 1994).
Lawson, D.M. and Smith, B.E. "Molybdenum Nitrogenases: A Crystallographic and Mechanistic View", Metal Ions in Biological Systems, 39: 75-119 (Jan. 1, 2002).
Lee, S. et al. Characterization of a Major Cluster of nif, fix, and Associated Genes in a Sugarcane Endophyte, Acetobacter diazotrophicus, Journal of Bacteriology, 182(24): 7088-7091 (Dec. 2000).

(56) References Cited

OTHER PUBLICATIONS

López-Torrejón, G et al. "Expression of a functional oxygen-labile nitrogenase component in the mitochondrial matrix of aerobically grown yeast", Nature Communications, DOI:10.1038/ncomms11426 (Apr. 29, 2016).
Masukawa, H. et al. "Effects of Disruption of Homocitrate Synthase Genes on *Nostoc* sp. Strain PCC 7120 Photobiological Hydrogen Production and Nitrogenase", Applied and Environmental Microbiology, 73(23): 7562-7570 (Dec. 2007).
Mayer, S.M. et al. "New Insights into Structure-function Relationships in Nitrogenase: A 1.6 Å Resolution X-ray Crystallographic Study of Klebsiella pneumoniae MoFe-protein", J. Mol. Biol. 292: 871-891 (1999).
Merrick, M. and Dixon, R. "Why don't plants fix nitrogen?" Trends in Biotechnology, 2(6): 162-166 (1984).
Miller, R.W. and Eady, R.R. "Molybdenum and vanadium nitrogenases of Azotobacter chroococcum", Biochem. J. 256: 429-432 (1988).
Mühlenhoff, U. et al. "Components involved in assembly and dislocation of iron-sulfur clusters on the scaffold protein Isu1p", The EMBO Journal, 22(18): 4815-4825 (2003).
Oldroyd, G.E.D. and Dixon, R. "Biotechnological solutions to the nitrogen problem", Current Opinion in Biotechnology, 26: 19-24 (2014).
Petrova, N. et al. "NifH and NifM Proteins Interact as Demonstrated by the Yeast Two-Hybrid System", Biochemical and Biophysical Research Communications, 270: 863-867 (2000).
Pfanner, N. and Geissler, A. "Versatility of the Mitochondrial Protein Machinery", Molecular Cell Biology, 2: 339-394 (May 2001).
Poza-Carrión, C et al. "Kinetics of nif Gene Expression in a Nitrogen-Fixing Bacterium", Journal of Bacteriology, 196(3): 595-603 (Feb. 2014).
Pratte, B.S. et al. "Cross-Functionality of Nitrogenase Components NifH1 and VnfH in Anabaena variabilis", Journal of Bacteriology, 188(16): 5806-5811 (Aug. 2006).
Robson, R.L. et al. "Structural genes for the vanadium nitrogenase from Azotobacter Chroococcum", The EMBO Journal, 8(4): 1217-1224 (1989).
Rubio, L.M. and Ludden, P.M. "Biosynthesis of the Iron-Molybdenum Cofactor of Nitrogenase", Annu. Rev. Microbiol., 62: 93-111 (2008).
Rubio, L.M. et al. "Purification and Characterization of NafY (Apodinitrogenase γ Subunit) from Azotobacter vinelandii", J. Biol. Chem., 279(19): 19739-19746 (May 7, 2004).
Schmid, B. et al. "Structure of a Cofactor-Deficient Nitrogenase MoFe Protein", Science, 296: 352-356 (Apr. 12, 2002).
Seefeldt, L.C. et al. "Mechanismi of Mo-Dependent Nitrogenase", Annu. Rev. Biochem. 78: 701-722 (2009).
Shah, V.K. et al. "Requirement of NifX and Other nif Protein for In Vitro Biosynthesis of the Iron-Molybdenum Cofactor of Nitrogenase", Journal of Bacteriology, 181(9): 2797-2801 (May 1999).
Siddavattam, D. et al. "Structure of the nifQ gene from Enterobacter agglomerans 333 and its overexpression in *Escherichia coli*", Mol. Gen. Genet. 239: 435-440 (1993).
Smanski, M.J. et al. "Functional optimization of gene clusters by combinatorial design and assembly", Nature Biotechnology, doi:10.1038/nbt.3063 (Nov. 24, 2014).
Staples, C.R. et al. "Expression and Association of Group IV Nitrogenase NifD and NifH Homologs in the Non-Nitrogen-Fixing Archaeon Methanocaldococcus jannaschii", Journal of Bacteriology, 189(20): 7392-7398 (Oct. 2007).
Temme, K. et al. "Refactoring the nitrogen fixation gene cluster from Klebsiella oxytoca", Proc. Nat'l. Acad. Sci. USA, 109(18): 7085-7090 (May 1, 2012).
Tezcan, F.A. et al. "Nitrogenase Complexes: Multiple Docking Sites for a Nucleotide Switch Protein", Science, 309: 1377-1380 (Aug. 26, 2005).
Thiel, T. et al. "A second nitrogenase in vegetative cells of a heterocyst-forming bacterium", Proc. Nat'l. Acad. Sci. USA, 92: 9358-9362 (Sep. 1995).
Thiel, T. et al. "Characterization of Genes for a Second Mo-Dependent Nitrogenase in the Cyanobacterium Anabaena variabilis", Journal of Bacteriology, 179(16): 5222-5225 (Aug. 1997).
Wiig, J.A. et al. "NifEN-B complex of Azotobacter vinelandii is fully functional in nitrogenase FeMo cofactor assembly", Proc. Nat'l. Acad. Sci. USA, 108(21): 8623-8627 (May 24, 2011).
Yuvaniyama, P. et al. "NifS-directed assembly of a transient [2Fe—2S] cluster within the NifU protein", Proc. Nat'l. Acad. Sci. USA, 97(2): 599-604 (Jan. 18, 2000).
NCBI Reference Sequence WP_044347161.1, Nitrogenase molybdenum-iron protein alpha chain [Raoultella ornitholytica]. Published Jun. 19, 2019.
NCBI Reference Sequence WP_047370273.1, Multispecies: nitrogenase molybdenum-iron protein alpha chain [Enterobacteriaceae]. Published Sep. 30, 2020.
NCBI Reference Sequence WP_049080161.1, Nitrogenase molybdenum-iron protein subunit beta [Klebsiella michiganensis]. Published Jun. 19, 2019.
NCBI Reference Sequence WP_049123239.1, Multispecies: nitrogenase iron protein [Klebsiella]. Published Jul. 17, 2019.
Office Action and English language translation thereof received Jun. 14, 2021 in connection with Russian Patent Application No. 2019127979/10(054914).
Oct. 6, 2021 Office Action issued in connection with Thai Patent Application No. 1901004785 and English translation thereof.
Oct. 28, 2021 Office Action issued in connection with Russian Patent Application No. 2019127979/10(054914) and English translation thereof.
Nov. 30, 2021 Office Action issued in connection with Japanese Patent Application No. 2019-542372 and English translation thereof.
Apr. 30, 2021 Response to Oct. 20, 2021 Communication under Rule 70(2) and Rule 70a(2) EPC filed in connection with European Patent Application No. 18748533.9.
Mar. 15, 2022 First Substantive Examination Report issued in connection with Malaysian Patent Application No. PI 2019004448.
Mar. 31, 2022 Office Action issued in connection with Vietnamese Patent Application No. 1-2019-04894 including English language translation thereof.
Mar. 25, 2022 Office Action issued in connection with Russian Federation Patent Application No. 2019127979 including English language translation thereof.
Jul. 21, 2022 Office Action issued in connection with Mexican Patent Application No. MX/a/2019/009318 including English language translation thereof.
Sep. 6, 2022 Decision of Final Rejection issued in connection with Japanese Patent Application No. 2019-542372 including English language translation thereof.
Nov. 14, 2022 Response to Mar. 15, 2022 Substantive Examination Report filed in connection with Malaysian Patent Application No. PI 2019004448.
Nov. 16, 2022 Second Substantive Examination Report issued in connection with Malaysian Patent Application No. PI 2019004448.
Nov. 15, 2022 Response to Jul. 17, 2022 Office Action filed in connection with Israeli Patent Application No. 268466.
May 8, 2020 Written Opinion of the International Searching Authority issued in connection with PCT International Patent Application No. PCT/AU2020/050216.
May 8, 2020 International Search Report issued in connection with PCT International Patent Application No. PCT/AU2020/050216.
Aug. 24, 2023 Office Action and Search Report issued in connection with Russian Federation Patent Application No. 2021129210, including English language translations thereof.
Aug. 21, 2023 Office Action issued in connection with Thai Patent Application No. 2101005355, including English language translation thereof.
Nov. 3, 2023 Office Action issued in connection with Chinese Patent Application No. 202080034451.0, including English language translation thereof.
Aug. 14, 2023 Office Action issued in connection with Philippines Patent Application No. 1/2021/500036.

(56) References Cited

OTHER PUBLICATIONS

Jun. 26, 2024 Examination Report issued in connection with Malaysian Patent Application No. PI2021005132.
Jun. 26, 2024 Office Action issued in connection with Philippine patent application No. 1/2021/500036.
Mar. 12, 2024 Office Action issued in connection with Japanese patent application 2021-553130 including English translation thereof.
PCT International Patent Application Publication No. WO 2015/036419 A1, published Mar. 19, 2015 (Universidad Politécnica de Madrid [ES/ES] ).
PCT International Patent Application Publication No. WO 2015/192383 A1, published Dec. 23, 2015 (Peking University [CN/CN] ).
PCT International Patent Application Publication No. WO 2018/141030 A1, published Aug. 9, 2018 (Commonwealth Scientific And Industrial Research Organisation [AU/AU] ).
PCT International Patent Application Publication No. WO 2019/140509 A1, published Jul. 25, 2019 (Her Majesty The Queen In Right Of Canada, As Represented By The Minister Of Agriculture And Agri-Food [CA/CA] ).
PCT International Patent Application Publication No. WO 2020/181324 A1, published Sep. 17, 2020 (Commonwealth Scientific And Industrial Research Organisation [AU/AU] ).
Allen, R.S. et al., "Expression of 16 Nitrogenase Proteins within the Plant Mitochondrial Matrix", Frontiers in Plant Science, 2017, vol. 8, article 287, pp. 1-14.
Allen, R. et al., "Engineering a functional NifDK polyprotein resistant to mitochondrial degradation", bioRxiv 2019, 755116.
Burén, S. et al., "Formation of Nitrogenase NifDK Tetramers in the Mitochondria of *Saccharomyces cerevisiae*", ACS Synthetic Biology, 2017, vol. 6, pp. 1043-1055.
Buren, S. et al., "Biosynthesis of the nitrogenase active-site cofactor precursor NifB-co in *Saccharomyces cerevisiae*", PNAS, 2019, vol. 116, No. 50, pp. 25078-25086.
López-Torrejón, G. et al., "Expression of a functional oxygen-labile nitrogenase component in the mitochondrial matrix of aerobically grown yeast", Nature Communications, 2016, vol. 7, pp. 1-6.
Okada, S. et al., "An experimental workflow identifies nitrogenase proteins ready for expression in plant mitochondria", bioRxiv, 2019, pp. 1-38.
Pérez-González, A. et al., "Adaptation of the GoldenBraid modular cloning system and creation of a toolkit for the expression of heterologous proteins in yeast mitochondria", BMC Biotechnology, 2017, vol. 17, pp. 2-11.
Xiang, N. et al., "Using synthetic biology to overcome barriers to stable expression of nitrogenase in eukaryotic organelles", PNAS, 2020, vol. 117, No. 39, pp. 16537-16545.
International Search Report issued Dec. 24, 2020 in connection with PCT International Application No. PCT/AU2020/051089.
Written Opinion of the International Searching Authority issued Nov. 26, 2020 in connection with PCT International Application No. PCT/IB2020/058268.
Examination Report issued Nov. 4, 2023 in connection with Indonesian Application No. ID P00202205268.
First Examination Report issued Dec. 4, 2023 in connection with Canadian Application No. 3,154,124.
Examination Report issued May 7, 2024 in connection with Vietnamese Patent Application No. 2022-02931.
Extended European Search Report and European Search Opinion issued Sep. 30, 2020 in connection with European Patent Application No. 18748533.9.
Jul. 22, 2024 Examination Report issued in connection with Russian Patent Application No. 2021129210 including English language translation thereof.
Aug. 24, 2024 Examination report issued in connectionw with Chinese patent application 202080084802.9 including English language translation thereof.
Oct. 8, 2024 Examination report issued in connection with Japanese patent application 2022-521436 including English language translation thereof.
Feb. 25, 2025 Examination report issued in connection with Canadian patent application 3,154,124.
Mar. 13, 2025 Examination report issued in connection with Malaysian patent application PI 2022001864.
Dos Santos et al (2012) "Distribution of nitrogen fixation and nitrogenase-like sequences amongst microbial genomes" BMC Genomics, vol. 12, Article 162.
Zheng et al (1997) "Purification of the Azotobacter vinelandii nifV-encoded homocitrate synthesase", Journal of Bacteriology, vol. 179(189): 5963-5966.
Aug. 24, 2024 Examination report issued in connection with Chinese patent application 202080084802.9 including English language translation thereof.
Yan Yongliang et al. (2021) "Establishment of artificial efficiency biological nitrogen fixation system and its agricultural application", Chinese Bulletin of Life Sciences, vol. 33, No. 12, pp. 1532-1543 and machine translation.

* cited by examiner

EXHIBIT B

```
SN66     MMAMAVFRREGRRLLPSIAARPIAAAAAAASSDQEEGLLAAAAAAAAVVRNRGGMMTNAT  60
SN10     MMAMAVFRREGRRLLPSIAARPIAAIRSPLSSDQEEGLLGVRSISTQVVRNRGGMMTNAT  60
         *************************  :  *********.. : :: *************
```

Figure 7

Marked positions: Pro 55, Gly 56, Arg 61, Gly 62, Cys 63, Ala 66, Gly 67, Gly 70, Val 71, Gly 74, Pro 75, Asp 78

| group (number of members): | organism | |
|---|---|---|
| 1 (41): | *Desulfotomaculum ferrireducens* | A N T R T I P G I I T N R G C A Y A G C K G V V L G P L K D V V H I T |
| 20 (11): | *Halanaerobium saccharolyticum* | A N T R T I P G I I T N R G C A Y A G C R G V V L G P L K D V V Q L V |
| 21 (10): | *Clostridium ljungdahlii* | A N I R T V P G V I T S R G C C Y A G C K G V V M G P I K D M V H I T |
| 17 (31): | *Methanosarcina barkeri* | A D D K V I P G I L T N K G C A F A G T K G V V F G P I K D M V H L V |
| 16 (47): | *Desulfovibrio vulgaris* | A N V K T T P G I I T M R G C T Y A G C K G V I L G P T R D I V N I T |
| 19 (21): | *Chlorobium tepidum* | A N V K T V P G I I T Q R G C A Y A G C K G V V L G P T R D I V N I V |
| 2 (17): | *Desulfuromonas acetoxidans* | S N R K I V P G V M S Q R G C A Y A G A K G V V W G P I R D M V H V S |
| 3 (30): | *Geobacter* sp. M21 | S N R K T V P G I M S A R G C A Y A G A K G V V W G P I R D M V H V S |
| 4 (11): | *Heliobacterium modesticaldum* | S N A K T V P G L M T A R G C A F A G A K G V V F G P V K D M V H I S |
| 18 (24): | *Desulfitobacterium hafniense* | S N G K T V P G I M T A R G C A Y A G A K G V V W G P V K D I V H I S |
| 5 (23): | *Franka alni* | S N I K S R P G V M T I R G C A Y A G S K G V V W G P V K D M V T I S |
| 6 (60): | *Paenibacillus durus* | S N I K S R P G V M T P R G C S Y A G S K G V V W G P I K D M V H I S |
| 7 (14): | *Leptolyngbya valderiana* | S N K K S V P G V M T T R G C A Y A G A K G V V W G P V K D M V H L S |
| 8 (155): | *Nostoc* sp. PCC 7120 | S N I K S V P G V M T A R G C A Y A G S K G V V W G P I K D M I H I S |
| 9 (247): | *Azospirillum brasilense* | S N I K S I P G V M T I R G C A Y A G S K G V V W G P I K D M I H I S |
| 10 (287): | *Sinorhizobium fredii* | S N I K S I P G V M T I R G C A Y A G S K G V V W G P V K D M V H I S |
| 11 (158): | *Azotobacter vinelandii* | S N K K S Q P G L M T I R G C A Y A G S K G V V W G P I K D M I H I S |
| 13 (15): | *Vibrio diazotrophicus* | S N R K T L P G V M T V R G C A Y A G S K G V V W G P V K D M I H I S |
| 12 (59): | *Klebsiella oxytoca* | S N R K S Q P G V M T V R G C A Y A G S K G V V F G P I K D M A H I S |
| 14 (17): | *Sulfurospirillum halorespirans* | S N K Q T V P G V M S Q R G C A Y A G S K G V V W G P V K D M I H I S |
| 15 (10): | *Sulfuricurvum kujiense* | S N K K T V P G V M S Q R G C A Y A G S K G V V W G P V K D M I H I S |

Figure 10

| group (number of members): | organism | His 84 Gly 85 Pro 86 · Gly 88 Cys 89 · Arg 97 Arg 98 |
|---|---|---|
| 1 (41): | *Desulfotomaculum ferrireducens* | HGPIGCGYYSWLTRRNKAASS-DPTK |
| 20 (11): | *Halanaerobium saccharolyticum* | HGPIGCSYYAWGMRRHQGVAA-EGGK |
| 21 (10): | *Clostridium ljungdahlii* | HGPVGCSFYSWGGRRNKAKNE-EGSQ |
| 17 (31): | *Methanosarcina barkeri* | HGPIGCAFYTWGTRRNFAKAE-EGGD |
| 16 (47): | *Desulfovibrio vulgaris* | HGPIGCGFYSWLTRRNQTKAPLESSE |
| 19 (21): | *Chlorobium tepidum* | HGPIGCSFYAWLTRRNQTRPETPEHE |
| 2 (17): | *Desulfuromonas acetoxidans* | HGPIGCGVYSWGTRRNLVQGI-PGIT |
| 3 (30): | *Geobacter* sp. M21 | HGPVGCGWYSWGTRRNLVTGV-NGVS |
| 4 (11): | *Heliobacterium modesticaldum* | HGPVGCGYYSWGNRRNLAEGT-LGVD |
| 18 (24): | *Desulfitobacterium hafniense* | HGPVGCGFYSWANRRNLAEGE-VGID |
| 5 (23): | *Franka alni* | HGPVGCGQYSWATRRNYAHGH-LGVD |
| 6 (60): | *Paenibacillus durus* | HGPVGCGQYSWGTRRNYANGT-LGID |
| 7 (14): | *Leptolyngbya valderiana* | HGPVGCGYYSWSGRRNYYVGT-TGVD |
| 8 (155): | *Nostoc* sp. PCC 7120 | HGPVGCGYWSWSGRRNYYVGV-TGIN |
| 9 (247): | *Azospirillum brasilense* | HGPVGCGYYSWSGRRNYYVGD-TGVD |
| 10 (287): | *Sinorhizobium fredii* | HGPVGCGQYSWSQRRNYYVGT-TGVD |
| 11 (158): | *Azotobacter vinelandii* | HGPVGCGQYSRAGRRNYYIGT-TGVN |
| 13 (15): | *Vibrio diazotrophicus* | HGPIGCGQYSRAGRRNYYSGT-TGVD |
| 12 (59): | *Klebsiella oxytoca* | HGPVGCGQYSRAGRRNYYTGV-SGVD |
| 14 (17): | *Sulfurospirillum halorespirans* | HGPVGCGQYSRAGRRNYYIGT-TGVD |
| 15 (10): | *Sulfuricurvum kujiense* | HGPIGCGQYSRAGRRNYYIGV-TGVD |

Figure 10 (continued)

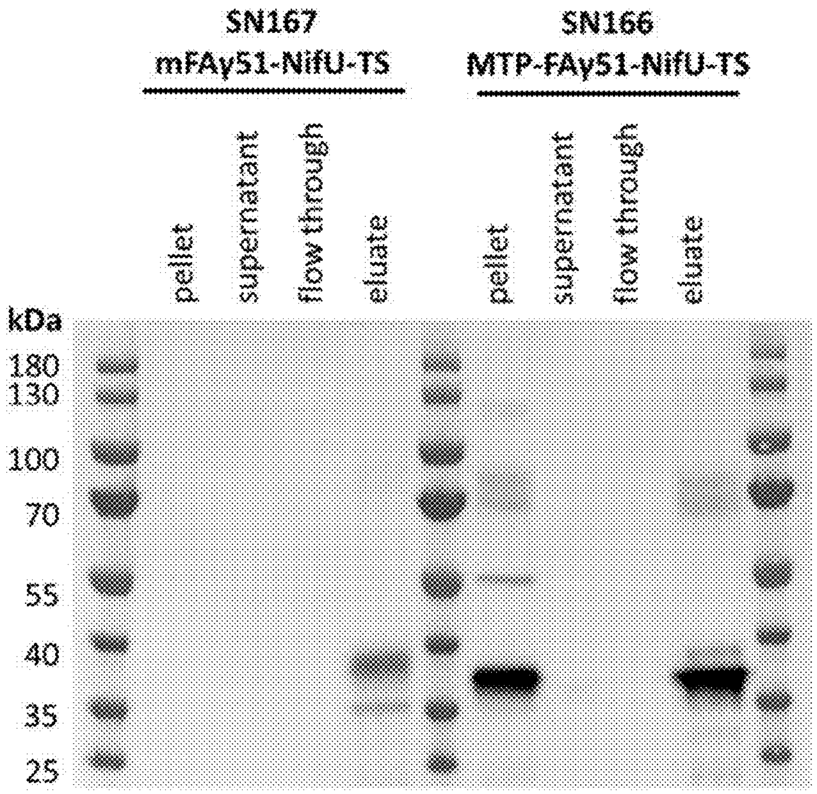
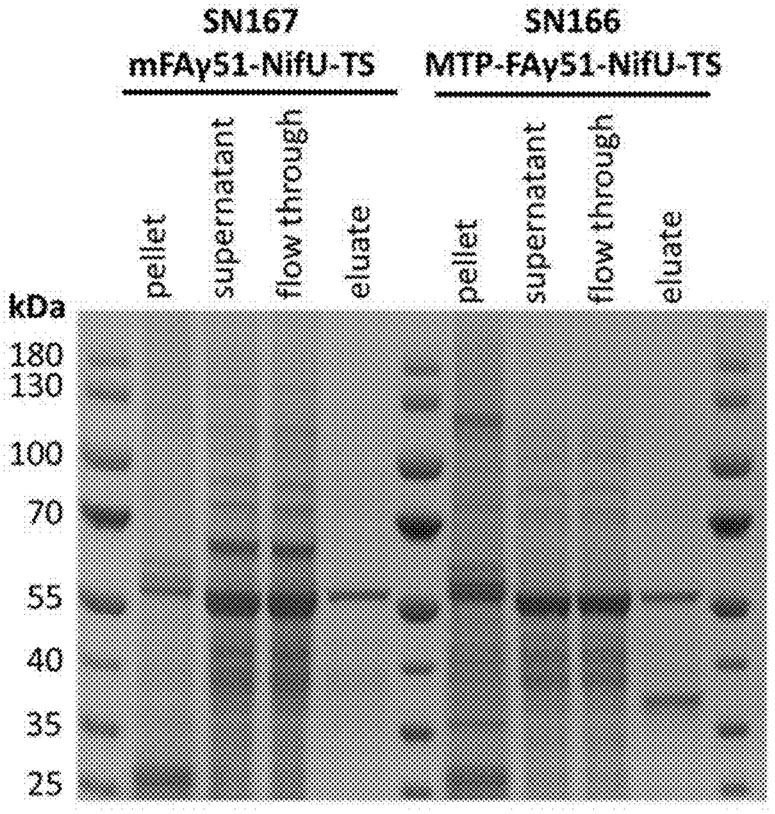
Figure 16

```
                                             10        20        30        40        50
                                    ....|....|....|....|....|....|....|....|....|....|
lclNbv6_ltrP72026 (SEQ ID NO:221) MASITTNHTFSRNLNFSFHPQNPLIQTQALFKFKPSIPN------CSPII
lclNbv6_ltrP20586 (SEQ ID NO:222) MASIYANPTTSLNTSLSSYSKN--IFLRSVFKFMPSITKRCHCPYTSTAV
BAI49592_LjFEN1 (SEQ ID NO:215)   MASKNS--------------------------------------------
PDB3FIG_MtLeuA (SEQ ID NO:223)    -MATSESPDAYTESFGAHTIVKPAGPPRVGQPSWNPQRASSMFVNRYRPF
AFI71011_KoNifV (SEQ ID NO:13)    --------------------------------------------------
CP002466_TbHCS (SEQ ID NO:206)    --------------------------------------------------
CP002028_TpHCS (SEQ ID NO:207)    --------------------------------------------------
CP036483_ScHCS (SEQ ID NO:208)    ------------------------------------MSENNEFQSVTEST
CP007203_NsHCS (SEQ ID NO:209)    --------------------------------------------------
AE006470_CtHCS (SEQ ID NO:211)    --------------------------------------------------
CP001157_AvHCS (SEQ ID NO:163)    --------------------------------------------------
ADG13125_MiHCS1 (SEQ ID NO:212)   MILYKE--------------------------------------------
ADG13175_MiHCS2 (SEQ ID NO:213)   --------------------------------------------------
ADG14004_MiHCS3 (SEQ ID NO:214)   MDLLYE--------------------------------------------
AE010299_MaHCS (SEQ ID NO:215)    --------------------------------------------------
```

Figure 20

```
                              60        70        80        90        100
                          ....|....|....|....|....|....|**..*....|....|....|
lclNbv6_1trF72026         RCA-IRR-RPEYTPSHIPDPKYIRIFDTTLRDGEQSPGATMTTKEKLDVA
lclNbv6_1trF20586         RCTNVRRPRPNYRPGRFSHPNYVGIFDTTLRDGEQAPGAAMTITEKLDIA
BAI49592_LjFEN1           ----IIRNRPEYIPNHIPNPTYVRILDTTLRDGEQSPGAAMTCVQKLETA
PDB3FIG_MtLeuA            AEEVEPIRLRNRTWPDRVIDRAPLWCAVDLRDGNQALIDPMSPARKRRMF
AFI71011_KoNifV           -------------------MERVLINDTTLRDGEQSPGVAFRTSEKVAIA
CP002466_TbHCS            --------------MTLKKGKKVYIVDTTLRDGEQTAGVVFANNEKIRIA
CP002028_TpHCS            -----------------MMEKKITIVDTTLRDGEQTAGVVFANKEKVRIA
CP036483_ScHCS            TAPTTSNPYGPNPADYLSNVKNFQLIDSTLREGEQFANAFFDTEKKIEIA
CP007203_NsHCS            -------------------MNEILINDTTLRDGEQAAGVAFTFEEKVAIA
AE006470_CtHCS            ------------------MIRKPWIIDTTLRDGEQAPGVVFSPHEKKRIA
CP001157_AvHCS            -------------------MASVIIDDTTLRDGEQSAGVAFNADEKIAIA
ADG13125_MiHCS1           -----ENEIIKEALKGLKLPDRVYIFDTTLRDGEQTPGVSLTVDEKVEIA
ADG13175_MiHCS2           --------------------MKVRVFDTTLRDGEQTPGVSLTPSDKLEIA
ADG14004_MiHCS3           -----NTWKAPSPYNPKLKLKDIYIYDTTLRDGEQTPGVCFTKEQKLEIA
AE010299_MaHCS            ----------------MKADIKVSIVDQTINEVVR-----LGVNNPADVR
```

Figure 20 (continued)

```
                              110        120        130        140        150
                     ....|....|.*..|....|....|....|....|....|....|....|
lclNbv6_ltrP72026    RQLAKLGVDIIEAGFPASSEADLEAVKLIAKEVGNGVYEEGHVPVICGLA
lclNbv6_ltrP20586    RQLAKLGVDVIEAGFPAASDADFELVKLVAKEVGNNVDEEGYVPVICAIG
BAI49592_LjFEN1      RQLAKLGVDIIEAGFPCASKQDFMAVKMIAEEVGNCVDGNGYVPVITGVS
PDB3FIG_MtLeuA       DLLVRMGYKEIEVGFPSASQTDFDFVREIIEQGAIP-----DDVTIQVLT
AFI71011_KoNifV      EALYAAGITAMEVGTPAMGDEEIARIQLVRRQLPD--------ATLMTWC
CP002466_TbHCS       QMLDEIGIDQLEVGIPTMGGDEKETVTKIAKLGLN--------ASIMAWN
CP002028_TpHCS       QMLDELGVHQIEAGIPVMGGDEEKAVKDIVKLGLK--------ASIMGWN
CP036483_ScHCS       RALDDFGVDYIELTSPVASEQSRKDCEAICKLGLK--------AKILTHI
CP007203_NsHCS       QFLDAIGVPELEVGIPAMGEAETHAILAISDLGLQ--------ASLLGWN
AE006470_CtHCS       AMLAETGVDEIEVGYPAISAAERKVIREIVAMKLP--------VRLTSWS
CP001157_AvHCS       RALAELGVPELEIGIPSMGEEEREVMHAIAGLGLS--------SRLLAWC
ADG13125_MiHCS1      INLDKLGVDIIEAGFPISSSGEYEAVKKIASLNLD--------AEICALA
ADG13175_MiHCS2      KALDELGVDVIEAGSAITSKGEREGIKLITRENLN--------AEICSFV
ADG14004_MiHCS3      RALDELGVSQIEAGFPIVSKREAEIVKAIASENLN--------ADILALS
AE010299_MaHCS       FMLSVLKKYSFDAADVSLNNLEKNMVEFEADEFSES---------MRCRV
```

Figure 20 (continued)

```
                                    160       170       180       190       200
                           *...|....|....|....|..*.|....|....|....|....|....|
lolNbv6_ltrP72026          RCNKRDIDKAWEAVKYAKKPRIHTFIATSEIHMKFKLK----MSRDEVVE
lolNbv6_ltrP20586          RTTKKDIDRTWEALKYAKKPMISLFIATSDIHMKYKLK----MSKEVVVE
BAI49592_LjFEN1            RCNEKDIATAWEALKHAKRPRLRTFIATSPIHMEYKLR----KSKDQVLE
PDB3FIG_MtLeuA             QCRPELIERTFQACSGAPRAIVHFYNSTSILQRRVVFRANRAEVQAIATD
AFI71011_KoNifV            RMNALEIRQSADLGIDW----VDISIPASDKLRQYKLR----EPLAVLLE
CP002466_TbHCS             RAVVKDVQESLECGVDA----VAISVSTSDIHIEHKLK----KTRQWVLD
CP002028_TpHCS             RAVISDIEETLRCGVDA----VAISISTSDIHIQHKLQ----TSREWVLE
CP036483_ScHCS             RCHMDDARVAVETGVDG----VDVVIGTSKFLRQYSHG----KDMNYIAK
CP007203_NsHCS             RAVLSDIKASITCGLKR----VHIAIPVSGIQIAAKFH----GQWRVSLQ
AE006470_CtHCS             RANMADIELAAECGTDA----VHISFPASRLYLELIHK----KD-DWIQE
CP001157_AvHCS             RLCDVDLAAARSTGVTM----VDLSLPVSDLMLHHKLN----RDRDWALR
ADG13125_MiHCS1            RAVKEDIDRAIDCGVDR----IHTFIATSPLHRKYKLK----MSKEEIVE
ADG13175_MiHCS2            RPLTVDIDAAIECEVDS----IHLVVPSSPIHIKYKLK----KSEDEVLD
ADG14004_MiHCS3            RIRKEDINKAIDCDVDG----IITFIATSPLHIKCKFKG---KRLEDFFD
AE010299_MaHCS             KCSGQEIFRAKKLGFSK------------IVINTSLN-----PLTPIQD
```

Figure 20 (continued)

```
                                   210       220       230       240       250
                              ....|....|....|....|.*.*|....|....|....|....|....|
lclNbv6_ltrP72026 KARSMVAYARSIG--CEDVEFSPEDAGRSDPEFLYHILGEVIKAGATT--
lclNbv6_ltrP20586 KARSMVAYAKTL---CEDVRFCVEDGARSDRKFLYYILGEGIKVGATA--
BAI49592_LjFEN1   TARNMVKFARSLG--CTDIQFGAEDAARSDKEFLYQIFGEVIKAGATT--
PDB3FIG_MtLeuA    GARKCVEQAAKYPGTQWRFEYSPESYTGTELEYAKQVCDAVGEVIAPTPE
AFI71011_KoNifV   RLAMFIHLAHTL---GLKVCIGCEDASRASGQTLRAIAEVAQQCAAAR--
CP002466_TbHCS    NMTEAVKFAKKE---GVYVSVNAEDASRTDMNFLIEFAKCAKQAGADR--
CP002028_TpHCS    NMVKAVEFAKKE---GVYISVNAEDASRSDMEFLIQFARAAKEAGADR--
CP036483_ScHCS    SAVEVIEFVKSK---GIEIRFSSEDSFRSDLVDLLNIYKTVDKIGVNR--
CP007203_NsHCS    RLKDCISFAVDQ---GLWVAVGGEDSSRADPNFLLDVALNAQEWGASR--
AE006470_CtHCS    QLHALVSKARER---FDFVSVGGQDATRSSTDFLQRFMLDAEAAGAKR--
CP001157_AvHCS    EVARLVGEARMA---GLEVCLGCEDASRADLEFVVQVGEVAQAAGARR--
ADG13125_MiHCS1   KAVNAIEYIKEH---GIKVEFSAEDATRTEIDYLKEVYKKAVEAGADI--
ADG13175_MiHCS2   LAVNAIEYAKDH---GLIVELSAEDATRAELNFLIKLFK-AGENLADR--
ADG14004_MiHCS3   TIVECIEYAKSH---GLFVAFSAEDGTRTPLEDLIRVHKLAEEAGADR--
AE010299_MaHCS    MLEPVLQMACSN---DQEIYLSIDNALEFSIRDVETIYPLIPKYGIKR--
```

Figure 20 (continued)

```
                              260       270       280       290       300
                          ....|..*.*....|....|....|....|....|....|*.*.|....|
lclNbv6_ltrP72026         ----LNIPDTVGYTVPSEFGKLIADIKANTPGIGDVIISTHCQNDLGLST
lclNbv6_ltrP20586         ----ICVADTVGSSLPTEFGRLIADIKANTPGIEDVIISVHCHNDLGLAT
BAI49592_LjFEN1           ----LTIPDTVGIAMPFEYGKLIADIKANTPGIENAIMATHCHNDLGLAT
PDB3FIG_MtLeuA            RPIIFNLPATVEMTTPNVYADSIEWMSRNLANRESVILSLHPHNDRGTAV
AFI71011_KoNifV           ----LRYADTVGLLDPFTTAAQISALRD----VWSGEIEMHAHNDLGMAT
CP002466_TbHCS            ----LRFCDTVGFLDPFKTYDMVKAIKE----AVDIDIEMHTHNDFGMAT
CP002028_TpHCS            ----IRYCDTIGILDPFTTYENIQTLKK----HVDIDIEMHTHNDFGMAT
CP036483_ScHCS            ----VGIADTVGCANPRQVYELIRTLKS----VVSCDIECHFHNDTGCAI
CP007203_NsHCS            ----FRFCDTVGVLDPFSTYAKVKQLVS----ALSIPLEIHTHNDFGLAT
AE006470_CtHCS            ----FRIADTVGIATPVSVMALGAALRQ----SSSLPLEFHAHNDLGMAT
CP001157_AvHCS            ----LRFADTVGVMEPFGMLDRFRFLSR----RLDMELEVHAHDDFGLAT
ADG13125_MiHCS1           ----INVPDTVGVMIPRATYYLISELRK---EIDN--ISVHCHNDFGLAV
ADG13175_MiHCS2           ----VCVCDTVGVLTPQKSEELFKKITS---EIKLP-VSVHCHNDFGMAT
ADG14004_MiHCS3           ----VHVADTAGTATPQAMEFICKALTC---SLNKAHVGVHCHNDFGLAV
AE010299_MaHCS            ----LILGDRSGKADPFTTYDKLGFLGN----TIQCPVEYVGYNDYGTAT
```

Figure 20 (continued)

```
                            310       320       330       340       350
                   ....|....|....|....|....|....|....|....|....|....|.
lclNbv6_ltrP72026  ANTLAGACAGARQVEVTINGIGERAGNASLEEVVMALKCRGEQVLGGLYTG
lclNbv6_ltrP20586  ANTLAGACAGARLVDVTVNGIGERAGNGSLEEIVMALKYRGEEVLGGLYSG
BAI49592_LjFEN1    ANTIEGARYGARQLEVTINGIGERAGNASFEEVVMALTCRGIDILGGLHTG
PDB3FIG_MtLeuA     AAAELGFAAGADRIEGCLFGNGERTGNVCLVTLGLNLFS------RGVDPQ
AFI71011_KoNifV    ANTLAAVSAGATSVNTTVLGLGERAGNAALETVALGLER-----CLGVETG
CP002466_TbHCS     ANALAGMRAGANFIGVTVNGLGERAGNAALEEVVMALKH-----VYKIDLG
CP002028_TpHCS     ANALAGIKAGASHVGVTVMGLGERAGNAALEEVVMALKH-----IWQIDLG
CP036483_ScHCS     ANAYTALEGGARLIDVSVLGIGERNGITPLGGLMARMIVAAP---DYVRSK
CP007203_NsHCS     ANALAGIKAGATSVNTTVNGVGERAGNAALEEVVMSIKR-----IYGINLG
AE006470_CtHCS     ANAFTALNEGFEAVSVSVTGLGERAGNAALEELAMALAL-----NGDFDTH
CP001157_AvHCS     ANTLAAVMGGATHINTTVNGLGERAGNAALEECVLALKN-----LHGIDTG
ADG13125_MiHCS1    ANSLAAVEAGAIQCHVTVNGLGERGGNAALEEVVTSLHF-----IYGIKTK
ADG13175_MiHCS2    ANTCSAILGGAVQCHVTVNGIGERAGNAALEEVVTALKF-----LYNIETN
ADG14004_MiHCS3    INSIYGLIGGAKAVSTTVNGIGERAGNTSLEELIMSLIV-----LYDVDLK
AE010299_MaHCS     ANTLSALRAGIEYVATAVSGIG-IPGVAAMEEVLMAARH-----LWKNELV
```

Figure 20 (continued)

```
                           360       370       380       390       400
                      ....|....|....|....|....|....|....|....|....|....|
lclNbv6_ltrP72026     INTQHILMSSKMVEEYTGLHVQPHKAIVGANAFAHESGIHQDGMLK---
lclNbv6_ltrP20586     INTKHIIATSKMVEEYCGLKLQPHKPIVGANAFSHESGIHQDGVLK---
BAI49592_LjFEN1       INTRHILKTSKMVEKYSGLHLQPHKALVGANAFLHESGIHQDGMLK---
PDB3FIG_MtLeuA        IDFSNIDEIRRTVEYCNQLPVHERHPYGGDLVYTAFSGSHQDAINKGLD
AFI71011_KoNifV       VHFSALPALCQRVAEAAQRAIDPQQPLVGELVFTHESGVHVAALLR---
CP002466_TbHCS        IDTTRFREISEYVALASGRQLPAWKAIVGTNVFAHESGIHVDGALK---
CP002028_TpHCS        FKTNMFRDLAEYVSLASGRELPAWKAIVGSNMFAHESGIHADGAIK---
CP036483_ScHCS        YKLHKIRDIENLVADAVEVNIPFNNPITGFCAFTHKAGIHAKAILA---
CP007203_NsHCS        IDTRRLLELSQLVASASNCHVPPWKAIVGENTFAHESGIHAHGVLQ---
AE006470_CtHCS        LDTSMLSRLCDAVATASGRAIQEQKPVVGRSAFQHESGIHCAALLQ---
CP001157_AvHCS        IDTRGIPAISALVERASGRQVAWQKSVVGAGVFTHEAGIHVDGLLK---
ADG13125_MiHCS1       VKTEELYNISKLVEKLTEVKVQPNKAVVGDNAFAHESGIHAHGVLA---
ADG13175_MiHCS2       IKLEKLYEVSRLVARLMKLPVPPNKAIVGDNAFAHEAGIHVDGLIK---
ADG14004_MiHCS3       LNLEVLPKLCRMVEEYSGIKNPKNKPIVGELVFSHESGIHVDAVIE---
AE010299_MaHCS        PDGYSIAADCENILYRAGIMLPGEKAIIGKNVFAHESGIHVDGVLK---
```

Figure 20 (continued)

```
                                  410       420       430       440       450
                             ....|....|....|....|....|....|....|....|....|....|.
lclNbv6_ltrP72026            -----------------HKDTYEIISPEDIGLNRANEAGIVLGKLSGRHAL
lclNbv6_ltrP20586            -----------------KRETYEFVSPEDVGFQRVTGHGIILGKLSGRHAL
BAI49592_LjFEN1              -----------------HRGTYEIISPEDIGLVRSVGDTIVLGKLSGRQAL
PDB3FIG_MtLeuA               AMKLDADAADCDVDDMLWQVPYLPIDPRDVGRTY--EAVIRVNSQSGKGGV
AFI71011_KoNifV              -----------------DSESYQSIAPSLMGRS----YRLVLGKHSGRQAV
CP002466_TbHCS               -----------------NPHTYEIFNPDEVGLE----RQIVIGKHSGTAAL
CP002028_TpHCS               -----------------NPITYEVFAPEEVGLE----RQIVIGKHSGSKAL
CP036483_ScHCS               -----------------NPSTYEILDPHDFGMKR---YIHFANRLTGWNAI
CP007203_NsHCS               -----------------NPLTYEPFAPEEVGWE----RRLVVGKHSGRHLV
AE006470_CtHCS               -----------------DPLSYQPFLPSRVGRSD---FEIVIGKHSGTAAI
CP001157_AvHCS               -----------------HRRNYEGLNPDELGRS----HSLVLGKHSGAHMV
ADG13125_MiHCS1              -----------------HALTYEPIPPELVGQRRR----IILGKHTGTHAI
ADG13175_MiHCS2              -----------------NTKTYEPISPEVVGNKRR----IILGKHSGRKAL
ADG14004_MiHCS3              -----------------NPLTYEPFLPEKIGLKRN----IILGKHSGKRAV
AE010299_MaHCS               -----------------NPNLYEAIKPEEVGLRR----LLVIGKHSGTASL
```

Figure 20 (continued)

```
                    460       470       480       490       500
               ....|....|....|....|....|....|....|....|....|....|
lclNbv6_ltrP72026 KSKMLELG-YDIEGKELEDLFWRFKSVAE----KKKKVTDDDIIALMSD
lclNbv6_ltrP20586 KSKMFELG-YEFEGKELDDIFRRFKSVAE----KKKKITEEDLRALVSD
BAI49592_LjFEN1   RNRLEELG-YKLKDTEVEGVFWQFKAVAE----KKKRITDTDLRALVSN
PDB3FIG_MtLeuA    AYIMKTDHGLSLPRRLQIEFSQVIQKIAEGTAGEGGEVSPKEMWDAFAE
AFI71011_KoNifV   NGVFDQMG-YHLNAAQINQLLPAIRRFAE----NWKRSPKDYELVAIYD
CP002466_TbHCS    INKFKEYG-RVLTEEEANLLLPHVRKLAI----QLKRPLFDKELMYLYE
CP002028_TpHCS    MMKFAEYG-IHLSEADAAQLLPKIRSHAV----ALKRSLFDKELVYIYE
CP036483_ScHCS    KSRVDQLN-LNLTDDQIKEVTAKIKKLGD----VRPLNIDDVDSIIKDF
CP007203_NsHCS    TSLLQQND-IFLNPEETQSVLDAVRQQSV----KQKRNLTVEELLNLVR
AE006470_CtHCS    IAHFNRRG-ITISKKEARELLDLIRSQSD----RLKRALRTDEIDALRE
CP001157_AvHCS    RNTYRDLG-IELADWQSQALLGRIRAFST----RTKRSPQPAELQDFYR
ADG13125_MiHCS1   EAKLKELGYTNINKEQFKEIVKRIKSLGD----KGKRVTDKDVEAIVED
ADG13175_MiHCS2   IYKLKLMG-IEASEEQINKIYEKIKELGD----LGKYVSDADLMAIVKD
ADG14004_MiHCS3   KYKLKLLG-VEVEDKLLDKIVERVKELRE----KGEKIDDEKLLEIVEE
AE010299_MaHCS    VQKLRHLG-LSLSPEKAAALLEKVRNTAI----LQKKPLTDLQLKTLYD
```

Figure 20 (continued)

```
                              510       520       530       540       550
                     ....|....|....|....|....|....|....|....|....|....|.
lclNbv6_ltrP72026    EVFQP---QVVWQLADVQITCGSLGLSTATVKLIDS-DGQDHVACSVGTGP
lclNbv6_ltrP20586    KVCS--------------------------LKLLDA---------------
BAI49592_LjFEN1      EAFNE---QPIWKLGDLQVTCGTVGFSTATVKLFSI-DGSMHVACSIGTGP
PDB3FIG_MtLeuA       EYLAPVRPLERIRQHVDAADDDGGTTSITATVKINGVETEISGSGNGPLAA
AFI71011_KoNifV      ELC--GESALRARG-------------------------------------
CP002466_TbHCS       DVIKNREKAI-----------------------------------------
CP002028_TpHCS       EVFGKKPL-------------------------------------------
CP036483_ScHCS       HAELSTPLLKPVNKGTDDDNIDISNGHVSKKAKVTK---------------
CP007203_NsHCS       EQRYSHAT-------------------------------------------
AE006470_CtHCS       QNSVKHA--------------------------------------------
CP001157_AvHCS       QLCEQGNPELAAGGMA-----------------------------------
ADG13125_MiHCS1      VIGRVSKRERVVDLEQIAVMTGNKVIPTASVALKIN--DNLIKTSAIGVGP
ADG13175_MiHCS2      VLG--KDLEEKIELDELTVVSGNKITPIASVKLHYKGEDRLLIETAYGVGP
ADG14004_MiHCS3      IKR----------IKD-----------------------------------
AE010299_MaHCS       LQMESVKDPNIHLSGKGEMPCD-----------------------------
```

Figure 20 (continued)

```
                          560       570       580       590       600
                    ....|....|....|....|....|....|....|....|....|....|
lclNbv6_ltrP72026  VDAAYKAVDLIVK--VPITLLEYSMNAVTEGIDSIASTRVVIREEDDHA
lclNbv6_ltrP20586  -------------------------------------------------
BAI49592_LjFEN1    VDSAYKAINHIVK--EPAKLVKYTLGAITEGIDATATTSVEISRGDTN-
PDB3FIG_MtLeuA     FVHALADVGFDVAVLDYYEHAMSAGDDAQAAAYVEASVTIASPAQPGEA
AFI71011_KoNifV    -------------------------------------------------
CP002466_TbHCS     -------------------------------------------------
CP002028_TpHCS     -------------------------------------------------
CP036483_ScHCS     -------------------------------------------------
CP007203_NsHCS     -------------------------------------------------
AE006470_CtHCS     -------------------------------------------------
CP001157_AvHCS     -------------------------------------------------
ADG13125_MiHCS1    VDAAVKAIQKAIG--EKIKIKEYHIDAITGGTDALAEVVVTLEG-----
ADG13175_MiHCS2    VDAAINAVRKAISGVADIKLEEYKVEAIGGGTDAIIEVTVKLRK-----
ADG14004_MiHCS3    -------------------------------------------------
AE010299_MaHCS     -------------------------------------------------
```

Figure 20 (continued)

```
                                 610       620       630       640       650
                            ....|....|....|....|....|....|....|....|....|....|....|...
lclNbv6_ltrP72026 ITNGSIGLTLHRTFSGTGADMDVVISSVRAYIGALNKMLSFGKLVSRCNNPEGSVVV-
lclNbv6_ltrP20586 ----------------------------------------------------------
BAI49592_LjFEN1   ----------HPVFSGTGGGTDVVVSSVDAYLSALNNMLRFY----------------
PDB3FIG_MtLeuA    GRHASDPVTIASPAQPGEAGRHASDPVTSKTVWGVGIAPSITTASLRAVVSAVNRAAR
AFI71011_KoNifV   ----------------------------------------------------------
CP002466_TbHCS    ----------------------------------------------------------
CP002028_TpHCS    ----------------------------------------------------------
CP036483_ScHCS    ----------------------------------------------------------
CP007203_NsHCS    ----------------------------------------------------------
AE006470_CtHCS    ----------------------------------------------------------
CP001157_AvHCS    ----------------------------------------------------------
ADG13125_MiHCS1   ---------YGKEITTKAAREDIVRASVEAVIDGINKILKK-----------------
ADG13175_MiHCS2   ---------GVNTVEVKKADSDIIRASVNAVMEGINLLLQ------------------
ADG14004_MiHCS3   ----------------------------------------------------------
AE010299_MaHCS    ----------------------------------------------------------
```

Figure 20 (continued)

Figure 24:
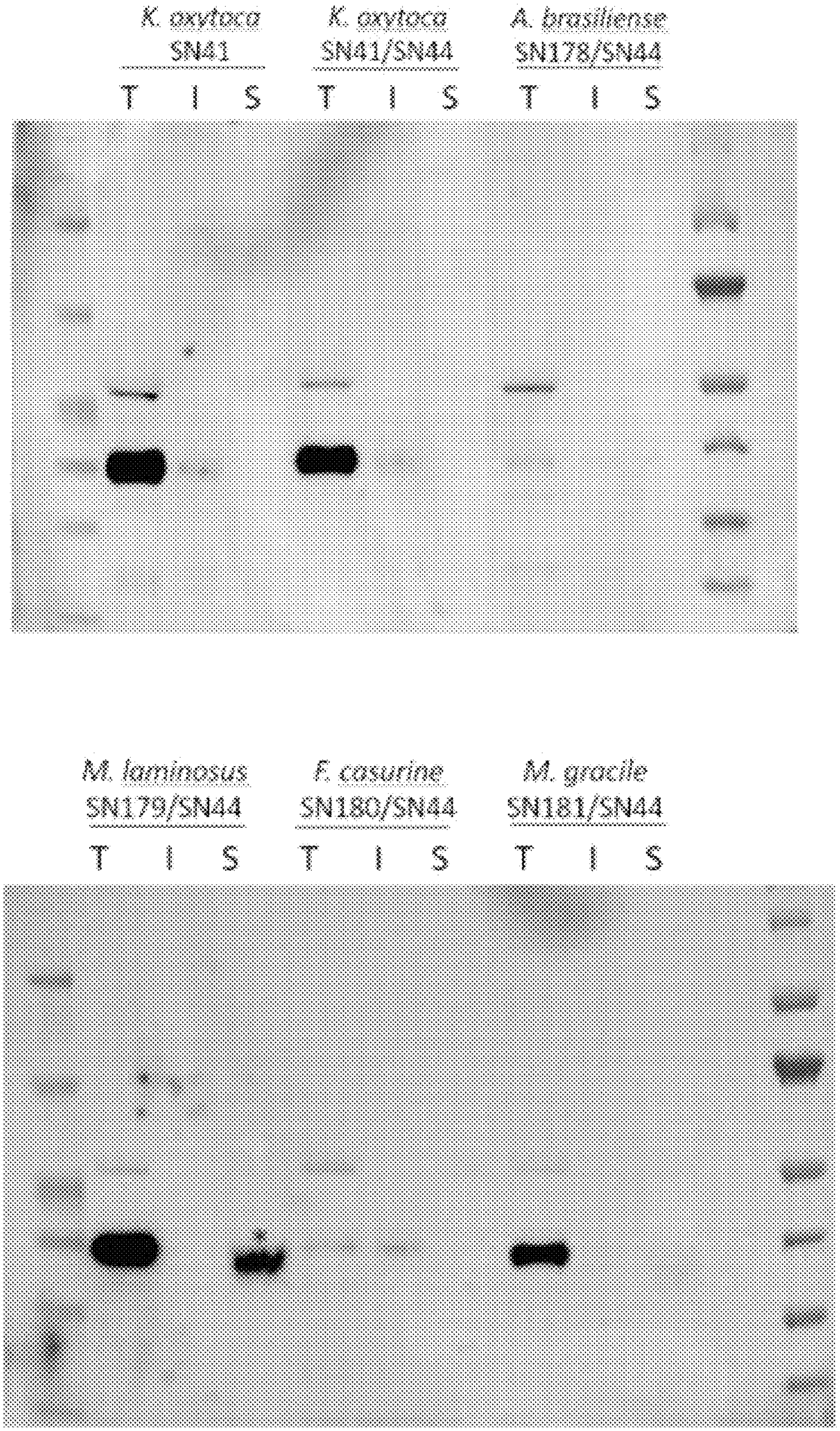
Figure 24:
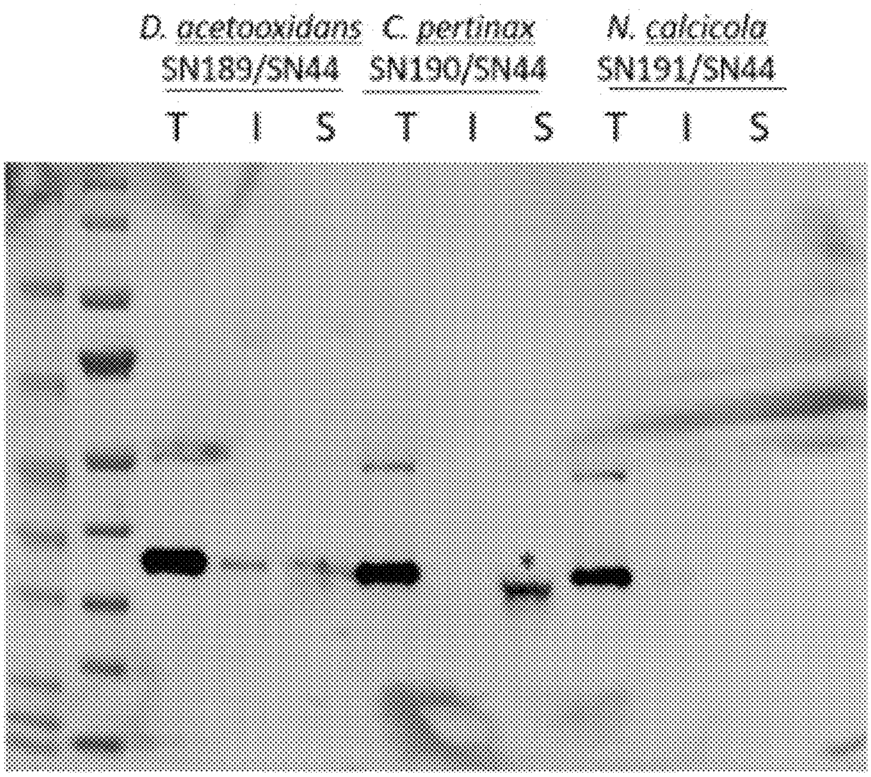

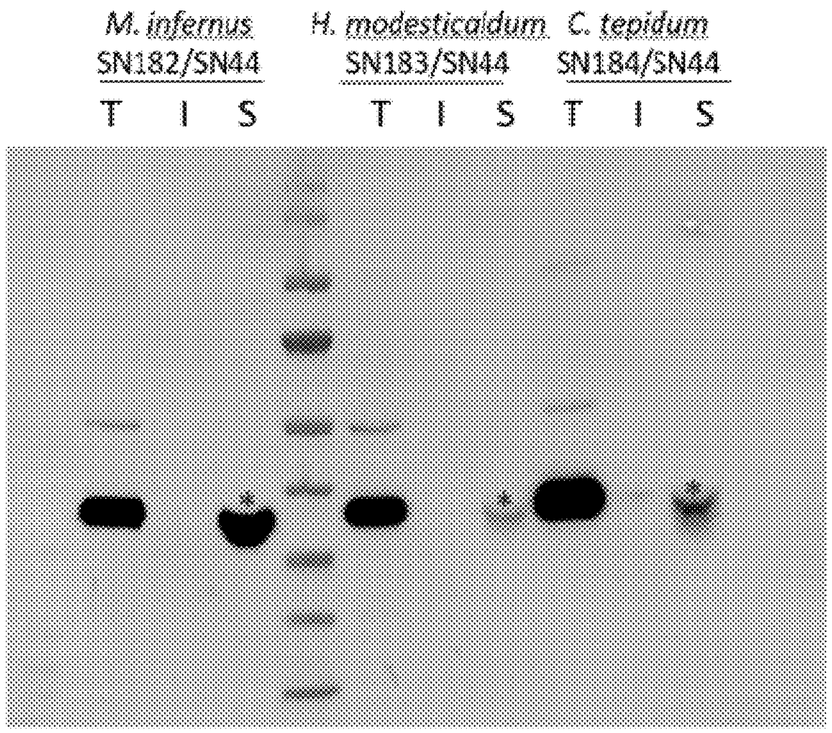
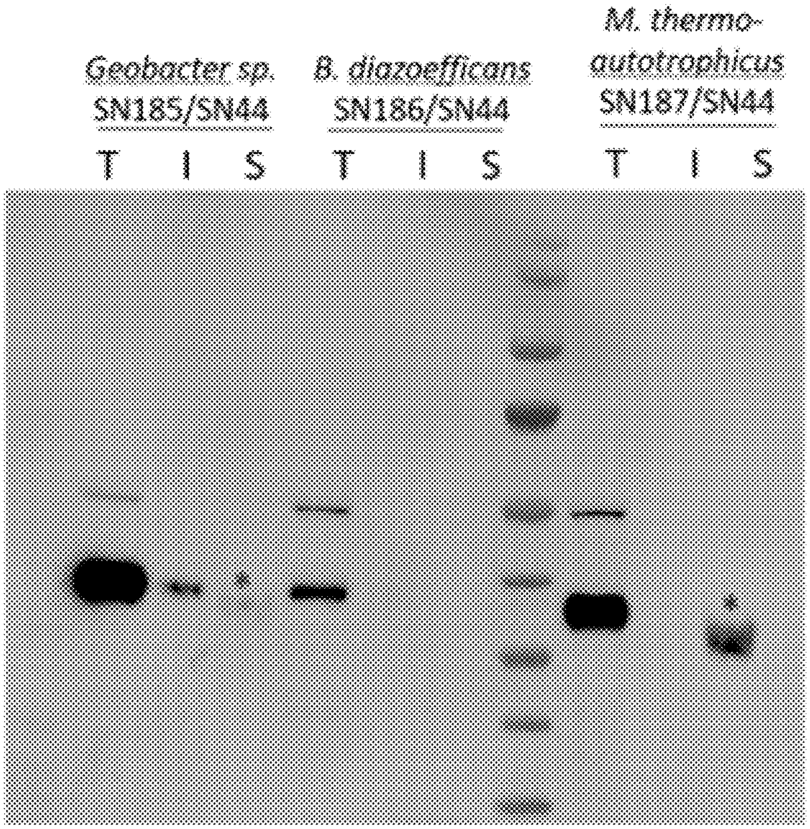
Figure 24 (continued)

EXPRESSION OF NITROGENASE POLYPEPTIDES IN PLANT CELLS

FIELD OF THE INVENTION

The present invention relates to methods and means for producing nitrogenase polypeptides in the mitochondria of plant cells.

BACKGROUND OF THE INVENTION

Diazotrophic bacteria produce ammonia from $N_2$ gas via biological nitrogen fixation (BNF), catalysed by the enzyme complex, nitrogenase. Yet the demands of modern agriculture γr outstrip this source of fixed nitrogen, and consequently industrially-produced nitrogenous fertiliser is used extensively in agriculture (Smil, 2002). However, both fertiliser production and application are causes of pollution (Good and Beatty, 2011) and considered unsustainable (Rockstrom et al., 2009). The majority of fertilizer applied worldwide is not taken up by crops (Cui et al., 2013; de Bruijn, 2015), leading to fertilizer runoff, promotion of weeds and eutrophication of waterways (Good and Beatty, 2011). Resultant algal blooms reduce oxygen levels, causing environmental damage locally and offshore throughout coral reefs (De'ath et al., 2012; Glibert et al., 2014; Sutton et al., 2008). Furthermore although over fertilization is a problem in many developed countries, in certain regions it's availability limits crop yields (Mueller et al., 2012). The production of fertilizer itself requires substantial energy inputs, and costs an estimated $100 USD billon/yr.

Clearly strategies to reduce industrially-produced nitrogenous dependence are required. To this end, the notion of engineering plants capable of biological nitrogen fixation has long attracted considerable interest (Merrick and Dixon, 1984), and has been the focus of recent reviews (de Bruijn, 2015; Oldroyd and Dixon, 2014). Potential approaches include i) extending the symbiotic relationship of diazotrophs from legumes to cereals (Santi et al., 2013), ii) re-engineering endosymbiotic microorganisms to be capable of nitrogen fixation (Geddes et al., 2015), and iii) genetic engineering of nitrogenase into plant cells (Curatti and Rubio, 2014). All of these approaches are ambitious and speculative due to the technical difficulty.

Nitrogenase, the enzyme complex capable of biological nitrogen fixation in diazotrophic bacteria, requires a multi-gene assembly pathway for its biosynthesis and function, reviewed extensively (Hu and Ribbe, 2013; Rubio and Ludden, 2008; Seefeldt et al., 2009). The components of the canonical iron-molybdenum nitrogenase include the catalytic proteins designated NifD and NifK and the electron donor NifH. About 12 other proteins are involved in nitrogenase assembly in diazotrophic bacteria including in the maturation, scaffolding and co-factor insertion of the complex, specifically NifM, NifS, NifU, NifE, NifN, NifX, NifV, NifJ, NifY, NifF, NifZ and NifQ. Genetic lesions, complementation assays between diazotrophs to non-diazotrophic prokaryotes and phylogenetic analyses (Dos Santos et al., 2012; Temme et al., 2012; Wang et al., 2013) have led to a subset of Nif proteins (NifD, NifK, NifB, NifE and NifN) being considered as the core components, whilst others are thought to be required for optimised activity and are considered auxiliary. Specific biochemical conditions are also required for nitrogenase assembly and function. Foremost among these, nitrogenase is extremely oxygen sensitive (Robson and Postgate, 1980). Furthermore large amounts of ATP, reductant, readily available Fe, Mo, S-adenosylmethionine and homocitrate are required for biosynthesis and function of the metalloprotein catalytic centre (Hu and Ribbe, 2013; Rubio and Ludden, 2008). All of these factors contribute to the technical difficulty of producing a functional nitrogenase complex in plant cells.

SUMMARY OF THE INVENTION

The present inventors have determined the importance of expressing a NifD that is resistant to secondary cleavage/degradation in plant cells, in view of the observed difficulty in producing functional NifD in plant cells.

Thus, in an aspect, the present invention provides a plant cell comprising an exogenous polynucleotide which encodes a NifD polypeptide (ND) which is resistant to protease cleavage at a site within an amino acid sequence corresponding to amino acids 97-100 of SEQ ID NO:18.

In a related aspect, the present invention provides a plant cell comprising an exogenous polynucleotide which encodes a NifD polypeptide (ND) which comprises an amino acid sequence other than RRNY (SEQ ID NO:101) at positions corresponding to amino acids 97-100 of SEQ ID NO:18. In a preferred embodiment, the ND is more resistant to protease cleavage at a site within an amino acid sequence corresponding to amino acids 97-100 of SEQ ID NO:18 than a corresponding ND which has the amino acid sequence RRNY (SEQ ID NO:101) at positions corresponding to amino acids 97-100 of SEQ ID NO:18.

In an embodiment of the above aspects, the ND comprises a mitochondrial targeting peptide (MTP), preferably wherein the MTP is at the N-terminal end of the ND.

In a further embodiment, the ND is capable of being cleaved within the MTP, or immediately after the MTP, to yield a processed NifD polypeptide (CND) when the exogenous polynucleotide is expressed in the plant cell, whereby the CND either comprises, at its N-terminal end, an amino acid sequence (scar sequence) from the C-terminal amino acids of the MTP, or does not comprise a scar sequence.

In a preferred embodiment, the MTP is cleaved in the plant cell with an efficiency of at least 50%, and/or wherein the CND is present in the plant cell at a greater level than the ND, preferably at a ratio of greater than 2:1, more preferably greater than 3:1 or 4:1.

In a preferred embodiment, the CND has NifD function.

In a further or another embodiment of the above aspects the exogenous polynucleotide encodes a ND which is a fusion polypeptide (NifD-linker-NifK fusion polypeptide) comprising, in order, a NifD amino acid sequence, a linker amino acid sequence (linker) and a NifK polypeptide (NK) amino acid sequence, wherein the linker amino acid sequence has a length of 8-50 residues, preferably about 30 residues, which is translationally fused to the ND and NK. In a preferred embodiment, the ND further comprises a mitochondrial targeting peptide (MTP), wherein the MTP is translationally fused at the N-terminal end of the NifD amino acid sequence. In a most preferred embodiment, the ND is capable of being cleaved within the MTP, or immediately after the MTP, to yield a processed NifD polypeptide (CND) when the exogenous polynucleotide is expressed in the plant cell, whereby the CND either comprises, at its N-terminal end, a scar sequence, or does not comprise a scar sequence.

In an embodiment of the above aspects, the ND or the CND has NifD function, or the ND (NifD-linker-NifK polypeptide) has both NifD and NifK functions. In an embodiment, the NifD polypeptide is an AnfD polypeptide and the NifK polypeptide is an AnfK polypeptide.

In an embodiment of the above aspects, the MTP comprises any of the MTPs disclosed herein, for example, the MTP comprises about 51 amino acids in length from a F1-ATPase γ-subunit MTP.

In an embodiment, the CND comprises a scar sequence of 1 to 45 amino acids in length, preferably 1 to 20 amino acids, more preferably 1-10 or 11-20 amino acids, translationally fused at the N-terminal end of the NifD amino acid sequence.

In a further or another embodiment, the ND or the CND, or both, for example the NifD-linker-NifK polypeptide, are in mitochondria of the plant cell, preferably in mitochondrial matrix (MM) of the plant cell.

In a further embodiment, the ND or the CND, or both, for example the NifD-linker-NifK polypeptide, are predominantly soluble in the plant mitochondria. Preferably, at least 60% or at least 75% of the CND that is in the plant mitochondria is soluble. The extent of solubility is preferably determined as described in the Examples.

In a further or another embodiment, the ND, for example the NifD-linker-NifK polypeptide, comprises an amino acid other than tyrosine (Y) at a position corresponding to amino acid 100 of SEQ ID NO:18.

In an embodiment, the ND, for example the NifD-linker-NifK polypeptide, comprises a glutamine (Q) or lysine (K) at the position corresponding to amino acid 100 of SEQ ID NO:18, or a leucine (L) or methionine (M) or phenylalanine (F) at the position corresponding to amino acid 100 of SEQ ID NO:18.

In another embodiment, the ND comprises Q, K, L, or M at the position corresponding to amino acid 100 of SEQ ID NO:18.

In another embodiment, the ND comprises L or M at the position corresponding to amino acid 100 of SEQ ID NO:18.

In another embodiment, the ND comprises Q, K, or L at the position corresponding to amino acid 100 of SEQ ID NO:18.

In another embodiment, the ND comprises Q, K, or M at the position corresponding to amino acid 100 of SEQ ID NO:18.

In another embodiment, the ND comprises Q, K, or F at the position corresponding to amino acid 100 of SEQ ID NO18.

In a further or another embodiment, the ND, for example the NifD-linker-NifK polypeptide, comprises the sequence RRNX (SEQ ID NO:154) at positions corresponding to amino acids 97-100 of SEQ ID NO:18, wherein X is any amino acid other than Y.

In an embodiment, X is Q or K, or L, M or F, or L or M, or Q, K or L, or Q, K or M, or Q, K, or F.

In a further embodiment, the plant cell comprises one or more exogenous polynucleotide(s), preferably 2-8 exogenous polynucleotides, which encode one or more Nif fusion polypeptides (NF) other than ND, each NF comprising a MTP at the N-terminal end of the NF, and (ii) a Nif polypeptide sequence (NP), wherein each MTP is independently the same or different and each NP is independently the same or different.

In an embodiment, each NF is capable of being cleaved within its MTP, or immediately after the MTP, to yield a processed Nif polypeptide (CNF) when the one or more exogenous polynucleotide(s) are expressed in the plant cell, whereby each CNF either comprises, at its N-terminal end, a scar sequence, or does not comprise a scar sequence.

In an embodiment, at least one of the NF polypeptides is a NifK polypeptide or a NifH polypeptide, or both NifK and NifH polypeptides.

In a further or another embodiment, the plant cell comprises a NK amino acid sequence, wherein the C-terminus of the polypeptide is a wild-type NifK C-terminus, i.e., the NK lacks any artificially added C-terminal extension.

In a further or another embodiment of the above aspects the exogenous polynucleotide encodes a NifE-linker-NifN fusion polypeptide (NifE-linker-NifN) comprising, in order, a NifE amino acid sequence (NE), a linker amino acid sequence (linker) and a NifN polypeptide (NN) amino acid sequence, wherein the linker amino acid sequence has a length of 20-70 residues, preferably about 46 residues, which is translationally fused to the NE and NN. In a preferred embodiment, the NifE-linker-NifN polypeptide comprises a mitochondrial targeting peptide (MTP), wherein the MTP is translationally fused at the N-terminal end of the NE amino acid sequence. In a most preferred embodiment, the NifE-linker-NifN polypeptide is capable of being cleaved within the MTP, or immediately after the MTP, to yield a processed NifD polypeptide (CNE) when the exogenous polynucleotide is expressed in the plant cell, whereby the CNE either comprises, at its N-terminal end, a scar sequence, or does not comprise a scar sequence.

In a further or another embodiment, the linker of the NifE-linker-NifN polypeptide is at least about 30 amino acids, or at least about 40 amino acids, or about 20 amino acids to about 60 amino acids, or about 30 amino acids to about 70 amino acids, or about 30 amino acids to about 60 amino acids, or about 30 amino acids to about 50 amino acids, or about 25 amino acids, or about 30 amino acids, or about 35 amino acids, or about 40 amino acids, or about 45 amino acids, or about 46 amino acids, or about 50 amino acids, or about 55 amino acids, in length. Most preferred, the linker is about 30 amino acids in length for a NifD-linker-NifK fusion polypeptide, and about 46 amino acids in length for a NifE-linker-NifN fusion polypeptide. In this context, "about 30" means 27, 28, 29, 30, 31, 32 or 33 amino acids, and "about 46" means 41, 42, 43, 44, 45, 46, 47, 48, 49, 50 or 51 amino acids.

In a further or another embodiment, the linker is of sufficient length to allow the ND and the NK or the NE and NN to associate in a functional configuration in a plant cell or a bacterial cell. In an embodiment, the linker is between 8 and 50 amino acids in length. Preferably, the linker is at least about 20 amino acids, at least about 25 amino acids, or at least about 30 amino acids in length. More preferably, the linker is between 25 and 35 amino acids in length for a NifD-linker-NifK fusion polypeptide.

In a further or another embodiment, the fusion polypeptide is capable of being cleaved within its MTP, or immediately after the MTP, to yield a processed polypeptide (CDK) when the exogenous polynucleotide is expressed in the plant cell, whereby the CDK comprises in order, an optional scar sequence, the NifD amino acid sequence, the linker amino acid sequence and the NK amino acid sequence. If cleavage occurs immediately after the MTP, no scar peptide is present.

In an embodiment, the plant cell comprises the fusion polypeptide, the CDK, or both.

In a further or another embodiment, the CDK comprises a scar sequence of 1 to 45 amino acids in length, preferably 1 to 20 amino acids, more preferably 1-10 or 11-20 amino acids, translationally fused at the N-terminal end of the NifD amino acid sequence.

In a further or another embodiment, the CDK has both NifD and NifK function.

In a further or another embodiment, the plant cell further comprises one or more exogenous polynucleotide(s) which encode one or more Nif polypeptides (NF) other than ND and NK, each NF comprising (i) a MTP at the N-terminal end of the NF, and (ii) a Nif polypeptide sequence (NP), wherein each MTP is independently the same or different and each NP is independently the same or different.

In a further of another embodiment, each NF is capable of being cleaved within its MTP, or immediately after the MTP, to yield a processed Nif polypeptide (CNF) when the one or more exogenous polynucleotide(s) are expressed in the plant cell, whereby each CNF either comprises, at its N-terminal end, a scar sequence, or does not comprise a scar sequence.

In an embodiment, at least one of the NF polypeptides is a NifH polypeptide.

In an embodiment, of any of the above aspects, the plant cell comprises exogenous polynucleotides encoding Nif polypeptides comprising (i) NifD, NifH, NifK, NifB, NifE and NifN polypeptides, preferably in the mitochondrial matrix of the plant cell.

In a further or another embodiment of any of the above aspects, each MTP comprises at least 10 amino acids, preferably has a length between 10 and 80 amino acids.

In a further or another embodiment of any of the above aspects, the MTP, or at least one MTP, or all of the MTPs independently comprise an MTP of a mitochondrial protein precursor, or a variant thereof, preferably a plant MTP.

In a further or another embodiment of any of the above aspects, one or more or all of the exogenous polynucleotide(s) are integrated into the nuclear genome of the cell, preferably as a contiguous nucleic acid sequence and/or are expressed in the nucleus of the cell.

In an embodiment of any of the above aspects, the cell is a cell other than an *Arabidopsis thaliana* protoplast or other than a *Nicotiana benthamiana* cell.

The present inventors have also produced plant cells which produce combinations of Nif polypeptides which are at least partially soluble in the plant mitochondria.

Thus, in an aspect, the present invention provides a plant cell comprising mitochondria and at least 3, at least 4, at least 5, at least 6, at least 7, at least 8, at least 9, at least 10 or at least 11 Nif polypeptides, wherein the Nif polypeptides are selected from the group consisting of NifF, NifM, NifN, NifS, NifU, NifW, NifY, NifZ, NifV, NifH and NifD-NifK, and wherein each of the at least 3, at least 4, at least 5, at least 6, at least 7, at least 8, at least 9, at least 10 or at least 11 Nif polypeptides are at least partially soluble in the mitochondria.

In an embodiment, the plant cell comprises a NifV polypeptide. Preferably, the NifV produces homocitrate. More preferably, the NifV polypeptide is at least partially soluble in the mitochondria of the plant cell. In an embodiment, the NifV polypeptide is a NifV of the invention.

In another embodiment, the plant cell comprises at least NifS, NifU, or both NifS and NifU polypeptides, and optionally NifV polypeptides.

In another embodiment, the plant cell comprises at least NifH, NifM, or both NifH and NifM polypeptides, and optionally one or more or all of NifV, NifS and NifU.

In another embodiment, the plant cell comprises NifF, NifH or NifD-NifK polypeptides, or NifH and NifD-NifK, or NifF, NifH and NifD-NifK, and optionally one or more or all of NifV, NifS, NifU, NifH and NifM polypeptides.

In an embodiment, the NifD polypeptide is an AnfD polypeptide, the NifH polypeptide is an AnfH polypeptide, and the NifD-NifK polypeptide is an AnfD-AnfK polypeptide. In a preferred embodiment, the plant cell further comprises an AnfG polypeptide which is at least partially soluble in the mitochondria.

In an embodiment, each of the at least 3, at least 4, at least 5, at least 6, at least 7, at least 8, at least 9, at least 10 or at least 11 Nif polypeptides after cleavage by MPP is independently at least 10%, at least 20%, at least 30%, at least 40%, or at least 50% soluble in the mitochondria. The Nif polypeptides may be up to 80% or up to 90% or even fully soluble in mitochondria of the plant cell.

In an embodiment, the at least 3, at least 4, at least 5, at least 6, at least 7, at least 8, at least 9, at least 10 or at least 11 of the Nif polypeptides each independently comprises a mitochondrial targeting peptide (MTP), or a C-terminal peptide resulting from cleavage of a MTP, or a combination of both MPP-processed and unprocessed forms is present, preferably wherein the MTP is at the N-terminus of each of the at least 3, at least 4, at least 5, at least 6, at least 7, at least 8, at least 9, at least 10 or at least 11 Nif polypeptides, or the MPP-processed form does not have a C-terminal peptide at the N-terminus of the Nif polypeptide.

In an embodiment, each MTP is independently cleaved in the plant cell with an efficiency of at least 50%, and/or wherein each of the at least 3, at least 4, at least 5, at least 6, at least 7, at least 8, at least 9, at least 10 or at least 11 processed Nif polypeptides is independently present in the plant cell at a greater level than the corresponding Nif polypeptide, preferably at a ratio of greater than 1:1, greater than 2:1, greater than 3:1 or greater than 4:1.

In an embodiment, the plant cell comprises a NifD-linker-NifK fusion polypeptide comprising, in order, a NifD amino acid sequence (ND), a linker amino acid sequence and a NifK polypeptide (NK) amino acid sequence, wherein the linker amino acid sequence has a length of 8-50 residues, preferably 16-50 residues, more preferably about 26 or about 30 residues, or most preferably is 26 or 30 residues, which is translationally fused to the ND and NK.

In a further embodiment, the NifD-linker-NifK fusion polypeptide comprises a mitochondrial targeting peptide (MTP), or a C-terminal peptide resulting from cleavage of a MTP, or a combination of both MPP-processed and unprocessed forms is present, wherein the MTP is translationally fused at the N-terminal end of the NifD-NifK fusion polypeptide.

In an embodiment, the at least 3, at least 4, at least 5, at least 6, at least 7, at least 8, at least 9, at least 10 or at least 11 processed Nif polypeptides each independently comprises a C-terminal peptide resulting from cleavage of an MTP of 1 to 45 amino acids in length, preferably 1 to 20 amino acids, more preferably 1-10 or 11-20 amino acids, translationally fused at the N-terminal end of the Nif polypeptide.

In an embodiment, the at least 3, at least 4, at least 5, at least 6, at least 7, at least 8, at least 9, at least 10 or at least 11 Nif polypeptides or the at least 3, at least 4, at least 5, at least 6, at least 7, at least 8, at least 9, at least 10 or at least 11 processed Nif polypeptides are functional Nif polypeptides.

In an embodiment, the at least 3, at least 4, at least 5, at least 6, at least 7, at least 8, at least 9, at least 10 or at least 11 Nif polypeptides or preferably the at least 3, at least 4, at least 5, at least 6, at least 7, at least 8, at least 9, at least 10 or at least 11 processed Nif polypeptides, are in mitochondria of the plant cell, preferably in the mitochondrial matrix (MM) of the plant cell.

In an embodiment, the at least 3, at least 4, at least 5, at least 6, at least 7, at least 8, at least 9, at least 10 or at least 11 Nif polypeptides or preferably the at least 3, at least 4, at least 5, at least 6, at least 7, at least 8, at least 9, at least 10 or at least 11 processed Nif polypeptides, or both, are independently predominantly soluble in the plant mitochondria (i.e., greater than 50% soluble in the mitochondria). The processed Nif polypeptides are preferably up to 80% or up to 90% or even fully soluble in mitochondria of the plant cell. Polypeptide solubility may be determined as described herein.

In an embodiment, the NifD fusion polypeptide or the NifD-linker-NifK fusion polypeptide, or MPP-cleaved products thereof, is present in the plant cell and is (a) resistant to protease cleavage at a site within an amino acid sequence corresponding to amino acids 97-100 of SEQ ID NO:18 and/or (b) comprises an amino acid sequence other than RRNY (SEQ ID NO:101) at positions corresponding to amino acids 97-100 of SEQ ID NO:18. In an embodiment, the ND comprises an amino acid other than tyrosine (Y) at a position corresponding to amino acid 100 of SEQ ID NO:18. In an embodiment, the ND comprises a glutamine (Q) or lysine (K) at the position corresponding to amino acid 100 of SEQ ID NO:18, or a leucine (L) or methionine (M) or a phenylalanine (F) at the position corresponding to amino acid 100 of SEQ ID NO:18.

In an embodiment, the MTP is about 51 amino acids in length from a F1-ATPase γ-subunit MTP.

In an embodiment, the plant cell comprises a NK amino acid sequence, wherein the C-terminus of the polypeptide is a wild-type NifK C-terminus.

In an embodiment, the linker is at least about 20 amino acids, or at least about 30 amino acids, or at least about 40 amino acids, or about 20 amino acids to about 70 amino acids, or about 30 amino acids to about 70 amino acids, or about 30 amino acids to about 60 amino acids, or about 30 amino acids to about 50 amino acids, or about 25 amino acids, or about 30 amino acids, or about 35 amino acids, or about 40 amino acids, or about 45 amino acids, or about 46 amino acids, or about 50 amino acids, or about 55 amino acids, in length.

In an embodiment, the NifD-linker-NifK fusion polypeptide is capable of being cleaved within its MTP, or immediately after the MTP, to yield a processed polypeptide (CDK), whereby the CDK comprises in order, an optional C-terminal peptide resulting from cleavage of an MTP, the NifD amino acid sequence (ND), the linker amino acid sequence and the NK amino acid sequence.

In an embodiment, the plant cell further comprises the fusion polypeptide or the CDK, or both.

In an embodiment, the CDK comprises a scar sequence of 1 to 45 amino acids in length, preferably 1 to 20 amino acids, more preferably 1-10 or 11-20 amino acids, translationally fused at the N-terminal end of the NifD amino acid sequence.

In an embodiment, the CDK has both NifD and NifK function.

In an embodiment, the ND is an AnfD and the NK is an AnfK.

In an embodiment, the MTP is about 51 amino acids in length from a F1-ATPase γ-subunit MTP.

In an embodiment, each MTP comprises at least 10 amino acids, preferably has a length between 10 and 80 amino acids.

In an embodiment, the MTP, or at least one MTP, or all of the MTPs independently comprise an MTP of a mitochondrial protein precursor, or a variant thereof, preferably a plant MTP.

In an embodiment, the at least 3, at least 4, at least 5, at least 6, at least 7, at least 8, at least 9, at least 10 or at least 11 Nif polypeptides are encoded by at least 3, at least 4, at least 5, at least 6, at least 7, at least 8, at least 9, at least 10 or at least 11 exogenous polynucleotide(s), at least 3, at least 4, at least 5, at least 6, at least 7, at least 8, at least 9, at least 10 or at least 11 of which are integrated into the nuclear genome of the cell, preferably as a contiguous nucleic acid sequence, and/or are expressed in the nucleus of the plant cell.

In another embodiment of any of the above aspects, the cell is a cell other than an *Arabidopsis thaliana* protoplast or other than a *Nicotiana benthamiana* cell.

The present inventors have also successfully expressed, in plant mitochondria, the combination of Nif polypeptides required for a minimal nitrogenase complex.

Thus, in another aspect, the present invention provides a plant cell comprising mitochondria and exogenous polynucleotides which encode at least 8 or at least 9 Nif fusion polypeptides, wherein the exogenous polynucleotides each comprise a promoter which is operably linked to a nucleotide sequence which encodes one of the Nif fusion polypeptides and which expresses the nucleotide sequence in the plant cell, wherein each Nif fusion polypeptide independently comprises a mitochondrial targeting peptide (MTP), wherein the Nif fusion polypeptides comprise (i) NifH, NifB, NifF, NifJ, NifS, NifU and NifV fusion polypeptides and either (ii) a NifD fusion polypeptide and a NifK fusion polypeptide or (iii) a NifD-linker-NifK fusion polypeptide which comprises a NifD sequence having a C-terminus, an oligopeptide linker and a NifK sequence having a N-terminus, wherein the oligopeptide linker is translationally fused to the C-terminus of the NifD sequence and the N-terminus of the NifK sequence, wherein mitochondrial processing protease (MPP)-cleaved products of at least the NifH, NifF, NifS and NifU fusion polypeptides are each at least partially soluble in mitochondria of a plant cell, wherein MPP-cleaved products of the NifD and NifK fusion polypeptides of (ii) if present in the plant cell are at least partially soluble in mitochondria of a plant cell, or a MPP-cleaved product of the NifD-linker-NifK fusion polypeptide of (iii) if present in the plant cell is at least partially soluble in mitochondria of a plant cell, and wherein the NifV fusion polypeptide and/or a MPP-cleaved product thereof produces homocitrate in the plant cell and is at least partially soluble in mitochondria of a plant cell.

In another aspect, the present invention provides a plant cell comprising mitochondria and exogenous polynucleotides which encode at least 2, at least 3, at least 4, at least 5 or at least 6 Nif fusion polypeptides, wherein the exogenous polynucleotides each comprise a promoter which is operably linked to a nucleotide sequence which encodes one of the Nif fusion polypeptides and which expresses the nucleotide sequence in the plant cell, wherein each Nif fusion polypeptide independently comprises a mitochondrial targeting peptide (MTP), wherein the Nif fusion polypeptides comprise (i) one or more than one or all of NifW, NifX, NifY, and NifZ fusion polypeptides, and either (ii) a NifD fusion polypeptide and a NifK fusion polypeptide or (iii) a NifD-linker-NifK fusion polypeptide which comprises a NifD sequence having a C-terminus, an oligopeptide linker and a NifK sequence having a N-terminus, wherein the oligopeptide linker is translationally fused to the C-terminus of the NifD sequence and the N-terminus of the NifK sequence, wherein mitochondrial processing protease (MPP)-cleaved products of at least the NifW, NifX, NifY and NifZ fusion polypeptides if present in the plant cell are each at least partially soluble in mitochondria of a plant cell, wherein either MPP-cleaved products of the NifD and NifK fusion polypeptides of (ii) if present in the plant cell are at least partially soluble in mitochondria of a plant cell, or a MPP-cleaved product of the NifD-linker-NifK fusion polypeptide of (iii) if present in the plant cell is at least partially soluble in mitochondria of a plant cell, and wherein the MPP-cleaved products of the NifD fusion polypeptide and NifK fusion polypeptide of ii) or the MPP-cleaved product of the NifD-linker-NifK fusion polypeptide of iii) is present in the plant cell in greater amount than the amount of the MPP-cleaved products of the NifD fusion polypeptide and NifK fusion polypeptide or the MPP-cleaved product of the NifD-linker-NifK fusion polypeptide present in a corresponding plant cell lacking the exogenous polynucleotides encoding the one or more than one or all of NifW, NifX, NifY and NifZ fusion polypeptides of (i).

In another aspect, the present invention provides a plant cell comprising mitochondria and exogenous polynucleotides which encode at least 5, at least 6, at least 7, at least 8 or at least 9 Nif fusion polypeptides, wherein the exogenous polynucleotides each comprise a promoter which is operably linked to a nucleotide sequence which encodes one of the Nif fusion polypeptides and which expresses the nucleotide sequence in the plant cell, wherein each Nif fusion polypeptide independently comprises a mitochondrial targeting peptide (MTP), wherein the Nif fusion polypeptides comprise (i) NifH, NifS and NifU fusion polypeptides and optionally a NifM polypeptide, (ii) one or more than one or all of NifW, NifX, NifY, and NifZ fusion polypeptides and either (iii) a NifD fusion polypeptide and a NifK fusion polypeptide or (iv) a NifD-linker-NifK fusion polypeptide which comprises a NifD sequence having a C-terminus, an oligopeptide linker and a NifK sequence having a N-terminus, wherein the oligopeptide linker is translationally fused to the C-terminus of the NifD sequence and the N-terminus of the NifK sequence, wherein mitochondrial processing protease (MPP)-cleaved products of the NifS and NifU fusion polypeptides are at least partially soluble in mitochondria of a plant cell, wherein MPP-cleaved products of the NifW, NifX, NifY and NifZ fusion polypeptides, if present in the plant cell, are at least partially soluble in mitochondria of a plant cell, wherein MPP-cleaved products of the NifD and NifK fusion polypeptides of (iii), if present in the plant cell, are at least partially soluble in mitochondria of a plant cell, wherein a MPP-cleaved product of the NifD-linker-NifK fusion polypeptide of (iv), if present in the plant cell, is at least partially soluble in mitochondria of a plant cell, and wherein either the MPP-cleaved products of the NifD fusion polypeptide and NifK fusion polypeptide of iii) or the MPP-cleaved product of the NifD-linker-NifK fusion polypeptide of iv) are present in the plant cell as a complex with P-cluster.

In an embodiment, the plant cell comprises a NifH fusion polypeptide which is an AnfH fusion polypeptide, wherein the NifD fusion polypeptide if present is an AnfD fusion polypeptide, the NifK fusion polypeptide if present is an AnfK fusion polypeptide, the NifD-linker-NifK fusion polypeptide if present is an AnfD-linker-AnfK fusion polypeptide, and the plant cell further comprises an exogenous polynucleotide which encodes an AnfG fusion polypeptide which comprises a MTP, wherein the exogenous polynucleotide which encodes the AnfG fusion polypeptide comprises a promoter which is operably linked to a nucleotide sequence which encodes the AnfG fusion polypeptide and which expresses said nucleotide sequence in the plant cell, and wherein a MPP-cleaved product of the AnfG fusion polypeptide is at least partially soluble in mitochondria of a plant cell.

In an embodiment of the above three aspects, the NifD fusion polypeptide or the NifD-linker-NifK fusion polypeptide is present in the plant cell and is (a) resistant to protease cleavage at a site within an amino acid sequence corresponding to amino acids 97-100 of SEQ ID NO:18 and/or (b) comprises an amino acid sequence other than RRNY (SEQ ID NO:101) at positions corresponding to amino acids 97-100 of SEQ ID NO:18.

In another aspect, the present invention provides a plant cell comprising mitochondria and exogenous polynucleotides which encode at least 2, at least 3 or 4 Anf fusion polypeptides, wherein the exogenous polynucleotides each comprise a promoter which is operably linked to a nucleotide sequence which encodes one of the Anf fusion polypeptides and which expresses the nucleotide sequence in the plant cell, wherein each Anf fusion polypeptide independently comprises a mitochondrial targeting peptide (MTP), wherein the Anf fusion polypeptides comprise (i) an AnfG fusion polypeptide or AnfG and AnfH fusion polypeptides, and either (ii) an AnfD fusion polypeptide and an AnfK fusion polypeptide or (iii) an AnfD-linker-AnfK fusion polypeptide which comprises an AnfD sequence having a C-terminus, an oligopeptide linker and an AnfK sequence having a N-terminus, wherein the oligopeptide linker is translationally fused to the C-terminus of the AnfD sequence and the N-terminus of the AnfK sequence, wherein mitochondrial processing protease (MPP)-cleaved products of at least the AnfG and AnfH fusion polypeptides if present in the plant cell are each at least partially soluble in mitochondria of a plant cell, wherein either MPP-cleaved products of the AnfD and AnfK fusion polypeptides of (ii) if present in the plant cell are at least partially soluble in mitochondria of a plant cell, or a MPP-cleaved product of the AnfD-linker-AnfK fusion polypeptide of (iii) if present in the plant cell is at least partially soluble in mitochondria of a plant cell, and wherein the MPP-cleaved products of the AnfD fusion polypeptide and the AnfK fusion polypeptide of ii) or the MPP-cleaved product of the AnfD-linker-AnfK fusion polypeptide of iii) if present in the plant cell form a protein complex in the plant cell with the MPP-cleaved product of the AnfG fusion polypeptide.

In some embodiments, the plant cell further comprises one or more exogenous polynucleotides encoding one or more Nif fusion polypeptides as defined herein.

As a person skilled in the art would appreciate, embodiments of Nif polypeptides provided herein will equally apply specifically to the corresponding Nif polypeptide which is an Anf polypeptide. For example, embodiments of NifD, NifK, and NifH polypeptides described herein for one aspect of the invention equally apply specifically to AnfD, AnfK, and AnfH polypeptides respectively.

The present inventors are the first, to their knowledge, to produce a plant cell comprising a NifV polypeptide which is at least partially soluble in mitochondria. Thus, in another aspect the present invention provides a plant cell comprising a NifV polypeptide (NV), wherein the NV is at least partially soluble, preferably at least 50%, at least 60%, at least 70%, at least 80%, at least 90% or even fully soluble in mitochondria of a plant cell, preferably in the MM of the plant cell.

In an embodiment, the NV is capable of, or is, producing homocitrate in the cell.

In an embodiment, the NV polypeptide comprises amino acids having a sequence as provided as any one of SEQ ID NOs: 163, 206 to 209, 211, or 212, a biologically active fragment thereof, or has an amino acid sequence which is at least 30% identical, at least 40% identical, at least 50% identical, at least 60% identical, at least 70% identical, at least 80% identical, at least 90% identical, at least 95% identical, at least 97% identical, or at least 99% identical, to that provided in any one or more of SEQ ID NOs: 163, 206 to 209, 211, or 212, and is capable of producing homocitrate in a cell.

In an embodiment of this aspect, the present invention provides a plant cell comprising mitochondria and an exogenous polynucleotide which encodes a NifV polypeptide (NV), wherein the exogenous polynucleotide comprises a promoter which is operably linked to a nucleotide sequence which encodes the NV and which expresses said nucleotide sequence in the plant cell, wherein the NV produces homocitrate in the plant cell and is at least partially soluble in mitochondria of a plant cell, wherein the exogenous polynucleotide is preferably integrated into the nuclear genome of the plant cell and/or is expressed in the nucleus of the plant cell, and optionally wherein the NV comprises a mitochondrial targeting peptide (MTP).

In another aspect, the present invention provides a plant cell comprising an exogenous polynucleotide which encodes a NifD polypeptide (ND) which is (a) resistant to protease cleavage at a site within an amino acid sequence corresponding to amino acids 97-100 of SEQ ID NO:18, and/or (b) comprises an amino acid sequence other than RRNY (SEQ ID NO:101) at positions corresponding to amino acids 97-100 of SEQ ID NO:18, wherein the exogenous polynucleotide comprises a promoter which is operably linked to a nucleotide sequence which encodes the ND and which expresses said nucleotide sequence in the plant cell, and wherein the NifD polypeptide preferably comprises a MTP.

In some embodiments, the plant cell further comprises one or more exogenous polynucleotides encoding one or more or all of the Nif fusion polypeptides as defined herein that are present in the cell, and/or wherein a cleaved product of the Nif fusion polypeptide is present in the cell. Preferably, the plant cell comprises an exogenous polynucleotide for each Nif fusion polypeptide and/or cleaved product present in the cell.

In an embodiment, the plant cell comprises an exogenous polynucleotide which encodes a NifK polypeptide (NK), wherein the exogenous polynucleotide which encodes the NK comprises a promoter which is operably linked to a nucleotide sequence which encodes the NK and which expresses said nucleotide sequence in the plant cell, wherein the ND has a C-terminus and the NK has an N-terminus, and wherein either (i) the NK comprises a mitochondrial targeting peptide (MTP), or (ii) the ND and NK are translationally fused as a NifD-linker-NifK fusion polypeptide which comprises an oligopeptide linker, wherein the oligopeptide linker is translationally fused to the C-terminus of the ND and the N-terminus of the NK.

In an embodiment, the plant cell comprises an exogenous polynucleotide which encodes a NifH fusion polypeptide (NH), wherein the exogenous polynucleotide which encodes the NH comprises a promoter which is operably linked to a nucleotide sequence which encodes the NH and which expresses said nucleotide sequence in the plant cell, wherein the NH comprises a mitochondrial targeting peptide (MTP), and preferably wherein the NH and/or a MPP-cleaved product thereof is at least partially soluble in mitochondria of a plant cell.

In an embodiment, a MPP-cleaved product of at least one or more or preferably all of the Nif fusion polypeptides is at least partially soluble in mitochondria of a plant cell, preferably wherein a MPP-cleaved product of each of the NifD, NifK and NifD-linker-NifK fusion polypeptides, if present in the plant cell, and the NifH polypeptide is at least partially soluble in mitochondria of a plant cell.

The present inventors are also the first, to their knowledge, to produce a plant cell comprising a NifH polypeptide which is at least partially soluble in mitochondria. Thus, in another aspect the present invention provides a plant cell comprising a NifH polypeptide (NH), wherein the NH is at least partially soluble in mitochondria.

In an embodiment, the NH is encoded by an exogenous polynucleotide, one which is integrated into the nuclear genome of the cell, preferably as a contiguous nucleic acid sequence with exogenous polynucleotides encoding the NifD, NifK and NifD-linker-NifK fusion polypeptides, if present in the plant cell.

In another aspect, the present invention provides a plant cell comprising an exogenous polynucleotide which encodes a NifH fusion polypeptide (NH), wherein the exogenous polynucleotide comprises a promoter which is operably linked to a nucleotide sequence which encodes the NH and which expresses said nucleotide sequence in the plant cell, wherein the NH comprises a mitochondrial targeting peptide (MTP), wherein a MPP-cleaved product of the NH is at least partially soluble in mitochondria of a plant cell, and optionally wherein the exogenous polynucleotide is integrated into the nuclear genome of the plant cell and/or is expressed in the nucleus of the plant cell.

In some embodiments, the plant cell further comprises one or more exogenous polynucleotides encoding one or more Nif fusion polypeptides as defined herein that are present in the cell, and/or wherein a cleaved product of the Nif fusion polypeptide is present in the cell. Preferably, the plant cell comprises an exogenous polynucleotide for each Nif fusion polypeptide and/or cleaved product present in the cell.

In embodiments of each of the above aspects, the plant cell further comprises an exogenous polynucleotide which encodes a NifM polypeptide (NM), wherein the exogenous polynucleotide which encodes the NM comprises a promoter which is operably linked to a nucleotide sequence which encodes the NM and which expresses said nucleotide sequence in the plant cell, and wherein the NM optionally comprises a mitochondrial targeting peptide (MTP).

In embodiments of each of the above aspects, the plant cell comprises exogenous polynucleotides which encode NifS and NifU fusion polypeptides, wherein the exogenous polynucleotides each comprise a promoter which is operably linked to a nucleotide sequence which encodes one of the Nif fusion polypeptides and which expresses the nucleotide sequence in the plant cell, and wherein the NifS and NifU fusion polypeptides each comprise a mitochondrial targeting peptide (MTP).

In embodiments of each of the above aspects, each Nif polypeptide is produced in the plant cell as a Nif fusion polypeptide comprising a mitochondrial targeting peptide (MTP), wherein each MTP is independently the same or different, preferably wherein the MTP is at the N-terminus of at least one or more than one or all of the Nif fusion polypeptides.

In embodiments of each of the above aspects, each Nif fusion polypeptide produced in the plant cell is independently cleaved by MPP either (i) within the MTP sequence to yield a MPP-cleaved Nif polypeptide, whereby the MPP-cleaved Nif polypeptide comprises, at its N-terminal end, a C-terminal peptide from the MTP (scar peptide), or (ii) immediately after the MTP whereby the MPP-cleaved Nif polypeptide does not comprise a C-terminal peptide from the MTP.

In embodiments of each of the above aspects, each MTP is independently cleaved in the plant cell with an efficiency of at least 50%, and/or wherein each cleaved Nif polypeptide is independently present in the plant cell at a greater level than a corresponding uncleaved Nif fusion polypeptide, preferably at a ratio of greater than 1:1, 2:1 or 3:1.

In embodiments of each of the above aspects, each Nif fusion polypeptide is at least partially cleaved in its MTP sequence in the plant cell to produce a MPP-cleaved Nif polypeptide, wherein each MPP-cleaved Nif polypeptide independently comprises a peptide (scar peptide) of 1 to 45 amino acids in length, preferably 1 to 20 amino acids, more preferably 1 to 11 amino acids or 11 to 20 amino acids derived from the MTP sequence, translationally fused at the N-terminal end of the MPP-cleaved Nif polypeptide. In embodiments, one or more of the scar peptides are independently 2, 3, 4, 5, 6, 7, 8, 9 or 10 amino acids in length. In embodiments, one or more of the scar peptides are independently 11, 12, 13, 14, 15, 16, 17, 18, 19 or 20 amino acids in length, or 20-30, 20-40 or 20-50 amino acids in length even though shorter scar sequences are preferred. In these embodiments, as used herein, the scar peptide includes any linker sequence such as, for example the Gly-Gly linker used in the Examples herein, fused to the N-terminus of the Nif sequence. In embodiments, the Nif sequence retains a Met (translation start Met) from its wild-type sequence at its N-terminus, which Met is not included in the scar sequence. Alternatively, the translation start Met is omitted from the Nif sequence. In embodiments, additional amino acids may be trimmed from the N-terminus of the Nif sequence relative to a corresponding wild-type Nif sequence, provided that the Nif sequence after trimming retains its Nif function.

In embodiments of each of the above aspects, the plant cell further comprises an exogenous polynucleotide which encodes a ferredoxin fusion polypeptide, preferably a FdxN fusion polypeptide, wherein the exogenous polynucleotide which encodes the ferredoxin fusion polypeptide comprises a promoter which is operably linked to a nucleotide sequence which encodes the ferredoxin fusion polypeptide and which expresses said nucleotide sequence in the plant cell, and wherein the ferredoxin fusion polypeptide comprises a mitochondrial targeting peptide (MTP).

In an embodiment, a MPP-cleaved product of the ferredoxin fusion polypeptide is at least partially soluble in mitochondria of a plant cell, and preferably wherein the exogenous polynucleotide is integrated into the nuclear genome of the plant cell and/or is expressed in the nucleus of the plant cell.

In an embodiment, the plant cell comprises a NifD-linker-NifK fusion polypeptide comprising, in order, a NifD amino acid sequence (ND), an oligopeptide linker and a NifK polypeptide (NK) amino acid sequence, wherein the oligopeptide linker has a length of 8-50 residues, preferably 16-50 residues in length, more preferably about 26 or about 30 residues in length, or most preferably is 30 residues in length, which is translationally fused to the ND and NK.

In an embodiment, each Nif fusion polypeptide is cleaved in the plant cell to produce a Nif polypeptide which is a functional Nif polypeptide.

In an embodiment, the plant cell comprises an exogenous polynucleotide which encodes a NifD fusion polypeptide (ND) or a NifD-linker-NifK fusion polypeptide, wherein the ND or the NifD-linker-NifK fusion polypeptide comprises an amino acid sequence other than RRNY (SEQ ID NO:101) at positions corresponding to amino acids 97-100 of SEQ ID NO:18, and wherein the ND or the NifD-linker-NifK fusion polypeptide preferably comprises an amino acid other than tyrosine (Y) at a position corresponding to amino acid 100 of SEQ ID NO:18.

In an embodiment, the ND or the NifD-linker-NifK fusion polypeptide comprises a glutamine (Q) or lysine (K) at the position corresponding to amino acid 100 of SEQ ID NO:18, or a leucine (L) or methionine (M) or a phenylalanine (F) at the position corresponding to amino acid 100 of SEQ ID NO:18.

In an embodiment, the plant cell comprises an exogenous polynucleotide which encodes a NifK fusion polypeptide or a NifD-linker-NifK fusion polypeptide, wherein the NifK fusion polypeptide or the NifD-linker-NifK fusion polypeptide has a C-terminal amino acid sequence which is the same as a C-terminal amino acid sequence of a wild-type NifK polypeptide. In some embodiments, at least the last two, at least the last three, at least the last four amino acids of the sequence are the same as that of a wild-type NifK polypeptide. Suitable wild-type NifK polypeptide sequences include SEQ ID NO:3, as well as Accession numbers WP_049080161.1, WP_044347163.1, SBM87811.1, WP_047370272.1, WP_014333919.1, WP_012728880.1, WP_011912506.1, WP_065303473.1, WP_018989051.1, prf||2106319A, WP_011021239.1, and others.

In an embodiment, the NifK fusion polypeptide or the NifD-linker-NifK fusion polypeptide, and the MPP-cleaved product therefrom, has an amino acid sequence whereby the last four amino acids of the sequence are the same as the last four amino acids of a wild-type NifK polypeptide.

In an embodiment, the amino acid sequence of the NifK polypeptide of the invention has at its C-terminus the amino acids DLVR (SEQ ID NO:58). In another embodiment, the NifK polypeptide has at its C-terminus the amino acids DLIR (SEQ ID NO:239), DVVR (SEQ ID NO:240), DIIR (SEQ ID NO:241), DLTR (SEQ ID NO:242) or INVW (SEQ ID NO:243). In an embodiment, the AnfK polypeptide has at its C-terminus the amino acids LNVW (SEQ ID NO:244), LNTW (SEQ ID NO:245), LNMW (SEQ ID NO:246), LAMW (SEQ ID NO:247) or LSVW (SEQ ID NO:248).

In embodiments of the above aspects, the plant cell comprises an exogenous polynucleotide which encodes a AnfD-linker-AnfK fusion polypeptide, wherein the AnfD-linker-AnfK fusion polypeptide comprises an AnfD sequence which has a C-terminus, an oligopeptide linker and an AnfK sequence which comprises an N-terminus, wherein the oligopeptide linker is translationally fused to the C-terminus of the AnfD sequence and the N-terminus of the AnfK sequence, wherein the oligopeptide linker has a length of at least about 20 amino acids, at least about 30 amino acids, at least about 40 amino acids, about 20 amino acids to about 70 amino acids, about 30 amino acids to about 70 amino acids, about 30 amino acids to about 60 amino acids, about 30 amino acids to about 50 amino acids, about 25 amino acids, about 30 amino acids, about 35 amino acids, about 40 amino acids, about 45 amino acids, about 46 amino acids, about 50 amino acids or about 55 amino acids. That is, in these embodiments the NifD sequence of the above embodiments is an AnfD sequence and the NifK sequence is an AnfK sequence.

In an embodiment, at least one or more than one or preferably all of the exogenous polynucleotides are integrated into the nuclear genome of the plant cell and/or are expressed in the nucleus of the plant cell.

In an embodiment, each MTP comprises at least 10 amino acids, preferably has a length between 10 and 80 amino acids.

In an embodiment, at least one of the Nif fusion polypeptides comprises an MTP which is about 51 amino acids in length from a F1-ATPase γ-subunit polypeptide.

In an embodiment, the MTP, or at least one MTP, or all of the MTPs independently comprise an MTP of a mitochondrial protein precursor, or a variant thereof, preferably a plant MTP.

In an embodiment, the at least 3, at least 4, at least 5, at least 6, at least 7, at least 8, at least 9, at least 10 or at least 11 Nif polypeptides are encoded by at least 3, at least 4, at least 5, at least 6, at least 7, at least 8, at least 9, at least 10 or at least 11 exogenous polynucleotide(s), at least 3, at least 4, at least 5, at least 6, at least 7, at least 8, at least 9, at least 10 or at least 11 of which are integrated into the nuclear genome of the cell, preferably as a contiguous nucleic acid sequence.

In embodiments of the above aspects, the cell is not capable of giving rise to progeny cells, for example is not capable of regenerating a cell culture or living plant.

In an embodiment, the plant cell of the invention is further defined by one or more of the features mentioned herein. Each possible combination of features is clearly contemplated.

In a further aspect, the present invention provides a plant or plant part, organ or tissue comprising a plant cell of the invention, preferably a transgenic plant or part thereof, wherein the transgenic plant or part thereof is transgenic for at least the one or more exogenous polynucleotide(s) encoding the Nif polypeptide(s).

In an embodiment, the plant part is a seed. In an embodiment, the seed is capable of germinating, or alternatively has been processed or treated so that it is no longer capable of germinating. The cells of the seed may not be capable of regeneration into a cell culture or living plant.

In embodiments of the above aspects, one or more of the one or more exogenous polynucleotide(s) are expressed in roots of a plant, preferably expressed at a greater level in the roots of the plant than in leaves of the plant. In such cases, a promoter sequence is used which provides the desired tissue specificity of expression.

In an embodiment, the transgenic plant has an altered phenotype relative to a corresponding wild-type plant which is increased yield, biomass, growth rate, vigor, nitrogen gain derived from biological nitrogen fixation, nitrogen use efficiency, abiotic stress tolerance, and/or tolerance to nutrient deficiency relative to the corresponding wild-type plant.

In an alternative embodiment, the transgenic plant has the same growth rate and/or phenotype relative to a corresponding wild-type plant.

In embodiments of the above aspects, the plant cell, plant or part thereof is a cereal plant cell, plant or part thereof, such as for example wheat, rice, maize, *Triticale*, oat or barley, preferably wheat.

In embodiments of the above aspects, the plant cell, plant or part thereof is homozygous or heterozygous for the one or more exogenous polynucleotide(s), preferably homozygous for all of the exogenous polynucleotides.

In embodiments of the above aspects, the plant cell, plant or part thereof is a monocotyledonous plant cell, plant or part thereof such as, for example, a cereal plant cell, plant or part thereof such as for example wheat, rice, maize, *Triticale*, oat, or barley, preferably wheat, or a dicotyledonous plant cell, plant or part thereof.

In a further or another embodiment, the transgenic plant is growing in a field or the plant plant part was harvested from a plant that was grown in a field. Alternatively, the plant was grown in a glasshouse.

In a further aspect, the present invention provides a population of at least 100 plants according to the invention growing in a field or in a glasshouse, or plant parts harvested therefrom.

In a another aspect, the present invention provides an isolated or recombinant NifD polypeptide (ND) which is resistant to protease cleavage at a site within an amino acid sequence corresponding to amino acids 97-100 of SEQ ID NO:18.

In a further aspect, the present invention provides an isolated or recombinant NifD polypeptide (ND) which comprises an amino acid sequence other than RRNY (SEQ ID NO:101) at positions corresponding to amino acids 97-100 of SEQ ID NO:18.

The isolated or recombinant ND may be further defined by any of the above recited features which are applicable to Nif polypeptides. All possible combinations of the features recited above are contemplated as part of the invention.

In a related aspect, the present invention provides a NifD fusion polypeptide comprising a mitochondrial targeting peptide (MTP) translationally fused to a NifD polypeptide (ND), or a cleaved product thereof which comprises the ND and optionally a scar peptide, wherein the NifD fusion polypeptide or the cleaved product thereof is (a) resistant to protease cleavage at a site within an amino acid sequence corresponding to amino acids 97-100 of SEQ ID NO:18 and/or (b) comprises an amino acid sequence other than RRNY (SEQ ID NO:101) at positions corresponding to amino acids 97-100 of SEQ ID NO:18.

In an embodiment, the NifD fusion polypeptide comprises an oligopeptide linker and a NifK polypeptide (NK) which are translationally fused as a NifD-linker-NifK fusion polypeptide, wherein the ND comprises a C-terminus and the NK comprises an N-terminus, wherein the oligopeptide linker is translationally fused to the C-terminus of the ND and the N-terminus of the NK.

In another aspect, the present invention provides a cleaved product of the NifD fusion polypeptide of the Mention, wherein the cleaved product comprises the ND, an oligopeptide linker and the NK, wherein the oligopeptide linker is translationally fused to the C-terminus of In an embodiment, the NifD fusion polypeptide or the cleaved product thereof is at least partially soluble in mitochondria of a plant cell when the NifD fusion polypeptide is produced in the plant cell.

In an embodiment, the NifD fusion polypeptide is an AnfD fusion polypeptide, the NK is an AnfK polypeptide, and the NifD-linker-NifK fusion polypeptide is an AnfD-linker-AnfK fusion polypeptide.

In another aspect, the present invention provides a NifK fusion polypeptide comprising a mitochondrial targeting peptide (MTP) translationally fused to a NifK polypeptide (NK), wherein the NifK fusion polypeptide or a cleaved product thereof is at least partially soluble in mitochondria of a plant cell when the NifK fusion polypeptide or the cleaved product thereof is produced in the plant cell.

In another aspect, the present invention provides a cleaved product of the NifK fusion polypeptide of the invention, which comprises the NK and optionally a scar peptide, wherein the cleaved product is at least partially soluble in mitochondria of a plant cell when the cleaved product is produced in the plant cell.

In an embodiment, the NK is an AnfK polypeptide (AK).

In an embodiment, the NifK polypeptide has a C-terminal amino acid sequence which is the same as the C-terminal amino acid sequence of a wild-type NifK polypeptide. Suitable wild-type NifK polypeptide sequences are described herein.

In another aspect, the present invention provides an AnfD fusion polypeptide comprising a mitochondrial targeting peptide (MTP) and an AnfD polypeptide (AD), or a cleaved product thereof comprising the AD and optionally a scar peptide, preferably which is at least partially soluble in mitochondria of a plant cell when the AnfD fusion polypeptide or the cleaved product thereof is produced in the plant cell.

In another aspect, the present invention provides an AnfH fusion polypeptide comprising a mitochondrial targeting peptide (MTP) and an AnfH polypeptide (AH), or a cleaved product thereof comprising the AH and optionally a scar peptide, preferably which is at least partially soluble in mitochondria of a plant cell when the AnfH fusion polypeptide or the cleaved product thereof is produced in the plant cell.

In another aspect, the present invention provides an AnfG fusion polypeptide comprising a mitochondrial targeting peptide (MTP) and an AnfG polypeptide (AG), or a cleaved product thereof comprising the AG and optionally a scar peptide, preferably which is at least partially soluble in mitochondria of a plant cell when the AnfG fusion polypeptide or the cleaved product thereof is produced in the plant cell.

In another aspect, the present invention provides an AnfD-linker-AnfK fusion polypeptide or a cleaved product thereof, comprising an AnfD polypeptide (AD), an oligopeptide linker and an AnfK polypeptide (AK) which are translationally fused, wherein the AD comprises an N-terminus and a C-terminus, and the AK comprises an N-terminus, wherein the oligopeptide linker is translationally fused to the C-terminus of the AD and the N-terminus of the AK, preferably wherein the fusion polypeptide comprises a mitochondrial targeting peptide (MTP) or the cleaved product comprises a scar peptide translationally fused to the N-terminus of the AD.

In another aspect, the present invention provides a combination of Anf polypeptides, being Anf polypeptides according to the aspects described herein, preferably a combination of the cleaved products of the Anf fusion polypeptides. Preferably, at least one or more or all of the cleaved products comprises a scar peptide e.g. fused at the N-terminus of the Anf polypeptide. Preferred combinations are the AnfD and AnfK, the AnfD, AnfK and AnfG, the AnfD-linker-AnfK and AnfG, more preferably the AnfD, AnfK, AnfG and AnfH, or the AnfD-linker-AnfK, AnfG and AnfH polypeptides. In embodiments, the features of the Nif polypeptides described herein apply to the corresponding Anf polypeptides. In a preferred embodiment, the combination of Anf polypeptides, preferably of the cleaved products, is present in a plant cell, a transgenic plant or part thereof, or a product therefrom as described herein.

In another aspect, the present invention provides a protein complex comprising (i) the cleaved product of the NifD fusion polypeptide, preferably the AnfD fusion polypeptide, (ii) the cleaved product of the NifK fusion polypeptide, preferably the AnfK fusion polypeptide, and optionally (iii) an Fe—S cluster, preferably a P-cluster. Preferably, at least one or more or all of the cleaved products comprises a scar peptide e.g. fused at the N-terminus of the Anf polypeptide.

In another aspect, the present invention provides a protein complex comprising (i) the cleaved products of the AnfD fusion polypeptide and the AnfK fusion polypeptide, and optionally the cleaved product of the AnfG fusion polypeptide, or (ii) the cleaved products of the AnfD-linker-AnfK fusion polypeptide and the AnfG fusion polypeptide, and optionally (iii) an Fe—S cluster, preferably a P-cluster. Preferably, at least one or more or all of the cleaved products comprises a scar peptide e.g. fused at the N-terminus of the Anf polypeptide.

In an embodiment, the protein complex of the invention is in a plant cell, preferably in a mitochondrion of the plant cell, or a transgenic plant or part thereof. In an embodiment, the plant cell, transgenic plant or part thereof comprising the Anf polypeptide, combination of Anf polypeptides or protein complex of the invention is used in a method of the invention as des In another aspect, the present invention provides a substantially purified or recombinant NifV polypeptide (NV) which when expressed in a plant cell is at least partially soluble in the plant mitochondria.

In a related aspect, the present invention provides an isolated or recombinant NifV polypeptide, or a NifV fusion polypeptide comprising a mitochondrial targeting peptide (MTP) translationally fused to a NifV polypeptide (NV), or a cleaved product thereof which comprises the NV and optionally a scar peptide, wherein the NifV polypeptide and/or the NifV fusion polypeptide and/or the cleaved product thereof is at least partially soluble in a plant cell when produced in the plant cell, preferably is at least partially soluble in mitochondria of the plant cell.

In an embodiment, the isolated or recombinant NifV polypeptide or the NifV fusion polypeptide or a cleaved product thereof is capable of producing homocitrate in a plant cell, preferably in mitochondria of a plant cell.

In another aspect, the present invention provides a substantially purified or recombinant NifH polypeptide (NH) which when expressed in a plant cell, preferably in a transgenic plant, is at least partially soluble in the plant mitochondria.

In another aspect, the present invention provides a NifH fusion polypeptide comprising a mitochondrial targeting peptide (MTP) translationally fused to a NifH polypeptide (NH), or a cleaved product thereof which comprises the NH and optionally a scar peptide, wherein the NifH fusion polypeptide and/or the cleaved product thereof is at least partially soluble in mitochondria of a plant cell. In embodiments of these aspects, the NH polypeptide is at least partially cleaved in its MTP sequence in the plant cell to produce a MPP-cleaved Nif polypeptide, wherein the MPP-cleaved NH comprises a peptide (scar peptide) of 1 to 45 amino acids in length, preferably 1 to 20 amino acids, more preferably 1 to 11 amino acids or 11 to 20 amino acids derived from the MTP sequence, translationally fused at the N-terminal end of the NH. In embodiments, one or more of the scar peptides are independently 2, 3, 4, 5, 6, 7, 8, 9 or 10 amino acids in length. In embodiments, one or more of the scar peptides are independently 11, 12, 13, 14, 15, 16, 17, 18, 19 or 20 amino acids in length, or 20-30, 20-40 or 20-50 amino acids in length even though shorter scar sequences are preferred.

In an embodiment of these aspects, the NH is an AnfH polypeptide.

In an embodiment, the NifH fusion polypeptide or preferably its MPP-cleavage product is bound to one or two Fe—S clusters, preferably one or two $Fe_4$—$S_4$ clusters.

In another aspect, provided is an isolated or exogenous polynucleotide encoding a NifV polypeptide (NV), wherein the NV when expressed in a plant cell is at least partially soluble in the plant mitochondria.

In an embodiment, the NV polypeptide comprises amino acids having a sequence as provided as any one of SEQ ID NO's: 163, 206 to 209, 211, or 212, a biologically active fragment thereof, or has an amino acid sequence which is at least 30% identical, at least 40% identical, at least 50% identical, at least 60% identical, at least 70% identical, at least 80% identical, at least 90% identical, at least 95% identical, at least 97% identical, or at least 99% identical, to that provided in any one or more of SEQ ID NO's: 163, 206 to 209, 211, or 212.

In an embodiment, a polypeptide of the invention is an isolated or recombinant polypeptide. In another embodiment, a polypeptide of the invention such as, for example, a recombinant polypeptide is present in a cell, preferably in a plant cell.

Suitable amino acid sequences for the Nif polypeptides of any of the above aspects are known in the art and include those provided herein.

In an embodiment, the NifH polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:1;
ii. SEQ ID NO:218;
iii. SEQ ID NO:224;
iv. Accession No. WP_049123239.1;
v. Accession No. WP_048638817.1;
vi. Accession No. WP_013029017.1;
vii. Accession No. WP_013010353.1;
viii. Accession No. WP_014258951.1;
ix. Accession No. WP_011744626.1;
x. Accession No. WP_013718497.1;
xi. Accession No. WP_009565928.1;
xii. Accession No. WP_013099472.1;
xiii. Accession No. WP_007781874.1;
xiv. Accession No. WP_012703362;
xv. Accession No. WP_153472986;
xvi. Accession No. WP_015854293;
xvii. Accession No. WP_123927773;
xviii. Accession No. WP_073538802; and
xix. Accession No. RCV6483.

In an embodiment, the NifH polypeptide comprises one or more of the amino acid sequence motifs provided in SEQ ID NOs:225-231.

In an embodiment, the NifH polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:1.

In an embodiment, the NifH polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:218.

In an embodiment, the NifD polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:2;
ii. SEQ ID NO:18;
iii. SEQ ID NO:148;
iv. SEQ ID NO:149;
v. SEQ ID NO:150;
vi. SEQ ID NO:151;
vii. SEQ ID NO:152;
viii. SEQ ID NO:153;
ix. SEQ ID NO:216;
x. Accession No. WP_044347161.1;
xi. Accession No. WP_047370273.1;
xii. Accession No. WP_038902190.1;
xiii. Accession No. WP_024872642.1;
xiv. Accession No. WP_024078601.1;
xv. Accession No. WP_013298320.1;
xvi. Accession No. WP_010877172.1;
xvii. Accession No. WP_014258953.1;
xviii. Accession No. WP_066665786.1;
xix. Accession No. WP_015773055.1;
xx. Accession No. WP_016867598.1;
xxi. Accession No. WP_009512873.1;
xxii. Accession No. WP_012703361;
xxiii. Accession No. WP_075356167;
xxiv. Accession No. WP_038590013;
xxv. Accession No. WP_023922817;
xxvi. Accession No. WP_011021232; and
xxvii. Accession No. OAV73823.

In an embodiment, the NifD polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:2.

In an embodiment, the NifD polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:216.

In an embodiment, the NifK polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:3;
ii. SEQ ID NO:217;
iii. Accession No. WP_049080161.1;
iv. Accession No. WP_044347163.1;
v. Accession No. SBM87811.1;
vi. Accession No. WP_047370272.1;
vii. Accession No. WP_014333919.1;
viii. Accession No. WP_012728880.1;
ix. Accession No. WP_011912506.1;
x. Accession No. WP_065303473.1;
xi. Accession No. WP_018989051.1;
xii. Accession No. prf||2106319A;
xiii. Accession No. WP_011021239.1;
xiv. Accession No. WP_012703359;
xv. Accession No. WP_144571040;
xvi. Accession No. WP_077859050;

xvii. Accession No. WP_122630336; and
xviii. Accession No. WP_088520366.

In an embodiment, the NifK polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:3.

In an embodiment, the NifK polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:217.

In an embodiment, the NifB polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:4;
ii. Accession No. WP_041145602.1;
iii. Accession No. WP_043953592.1;
iv. Accession No. WP_040003311.1;
v. Accession No. WP_011094468.1;
vi. Accession No. WP_048638849.1;
vii. Accession No. WP_011813098.1;
viii. Accession No. WP_048108879.1;
ix. Accession No. WP_050355163.1;
x. Accession No. WP_015850328.1; and
xi. Accession No. P10930.

In an embodiment, the NifB polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:4.

In an embodiment, the NifE polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:5;
ii. Accession No. WP_049114606.1;
iii. Accession No. SBM87755.1;
iv. Accession No. WP_012764127.1;
v. Accession No. WP_012728883.1;
vi. Accession No. WP_003297989.1;
vii. Accession No. WP_012698965.1;
viii. Accession No. WP_013190624.1;
ix. Accession No. WP_025698318.1;
x. Accession No. WP_013460149.1;
xi. Accession No. AIS31022.1;
xii. Accession No. WP_018701501.1; and
xiii. Accession No. WP_048514099.1.

In an embodiment, the NifE polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:5.

In an embodiment, the NifF polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:6;
ii. Accession No. WP_004122417.1;
iii. Accession No. WP_040968713.1;
iv. Accession No. WP_035885760.1;
v. Accession No. WP_039999438.1;
vi. Accession No. WP_048638838.1;
vii. Accession No. WP_064006977.1;
viii. Accession No. WP_012698862.1;
ix. Accession No. WP_010933399.1;
x. Accession No. WP_002949173.1; and
xi. Accession No. WP_039801725.1.

In an embodiment, the NifF polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:6.

In an embodiment, the AnfG polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:219;
ii. Accession No. WP_012703360;
iii. Accession No. WP_144571041;
iv. Accession No. HBE76208;
v. Accession No. WP_144349445;
vi. Accession No. WP_112317428; and
vii. Accession No. WP_048515315.

In an embodiment, the AnfG polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:219.

In an embodiment, the NifJ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:7;
ii. Accession No. WP_024360006.1;
iii. Accession No. WP_044347157.1;
iv. Accession No. WP_050533844.1;
v. Accession No. WP_064566543.1;
vi. Accession No. WP_057084649.1;
vii. Accession No. WP_014683040.1;
viii. Accession No. WP_013149847.1;
ix. Accession No. WP_053341220.1;
x. Accession No. WP_014454638.1; and
xi. Accession No. CSA83023.1.

In an embodiment, the NifJ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:7.

In an embodiment, the NifM polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:8;
ii. Accession No. WP_064342940.1;
iii. Accession No. WP_004122413.1;
iv. Accession No. WP_044347181.1;
v. Accession No. WP_064566543.1;
vi. Accession No. WP_063105800.1;
vii. Accession No. WP_035885759.1;
viii. Accession No. WP_011094472.1;
ix. Accession No. WP_048638837.1;
x. Accession No. CAA75544.1;
xi. Accession No. WP_051692859.1; and
xii. Accession No. WP_018415157.1.

In an embodiment, the NifM polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:8.

In an embodiment, the NifN polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:9;
ii. Accession No. WP_064391778.1;
iii. Accession No. WP_047370268.1;
iv. Accession No. WP_014683026.1;
v. Accession No. WP_048638830.1;
vi. Accession No. WP_027147663.1;
vii. Accession No. WP_015195966.1;
viii. Accession No. WP_023593609.1;
ix. Accession No. WP_025677480.1; and
x. Accession No. WP_018306265.1.

In an embodiment, the NifN polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:9.

In an embodiment, the NifQ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:10;
ii. Accession No. WP_064391765.1;
iii. Accession No. CTQ06350.1;
iv. Accession No. WP_047370257.1;
v. Accession No. WP_043878077.1;
vi. Accession No. WP_008878174.1;
vii. Accession No. WP_011501504.1;
viii. Accession No. WP_027196569.1;
ix. Accession No. GAU06296.1; and
x. Accession No. WP_063239464.1.

In an embodiment, the NifQ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:10.

In an embodiment, the NifS polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:11;
ii. SEQ ID NO:19;
iii. Accession No. WP_004138780.1;
iv. Accession No. WP_045858151.1;
v. Accession No. WP_047370265.1;
vi. Accession No. WP_014333911.1;
vii. Accession No. WP_055731597.1;
viii. Accession No. WP_014239770.1;
ix. Accession No. WP_054691765.1;
x. Accession No. WP_021802294.1;
xi. Accession No. WP_026894054.1; and
xii. Accession No. WP_061575621.1.

In an embodiment, the NifS polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:11.

In an embodiment, the NifS polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:19.

In an embodiment, the NifU polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:12;
ii. Accession No. WP_049136164.1;
iii. WP_050887862.1;
iv. WP_057084657.1;
v. WP_048638833.1;
vi. WP_012728889.1;
vii. WP_055731596.1;
viii. WP_028587630.1;
ix. WP_044417303.1;
x. WP_001051984.1; and
xi. KIM05011.1.

In an embodiment, the NifU polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:12.

In an embodiment, the NifV polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:13;
ii. SEQ ID NO:163;
iii. SEQ ID NO:164;
iv. SEQ ID NO:206;
v. SEQ ID NO:207;
vi. SEQ ID NO:208;
vii. SEQ ID NO:209;
viii. SEQ ID NO:210;
ix. SEQ ID NO:211;
x. SEQ ID NO:212;
xi. SEQ ID NO:213;
xii. SEQ ID NO:214;
xiii. SEQ ID NO:215;
xiv. Accession No. WP_049083341.1;
xv. Accession No. WP_045858154.1;
xvi. Accession No. WP_047370264.1;
xvii. Accession No. WP_038912041.1;
xviii. Accession No. WP_048638835.1;
xix. Accession No. WP_011712856.1;
xx. Accession No. WP_037528703.1;
xxi. Accession No. OAA29062.1; and
xxii. Accession No. EKQ56006.1.

In an embodiment, the NifV polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:13.

In an embodiment, the NifX polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:14;
ii. Accession No. WP_049070199.1;
iii. Accession No. WP_064342937.1;
iv. Accession No. WP_044347173.1;
v. Accession No. WP_044612922.1;
vi. Accession No. WP_043953583.1;
vii. Accession No. WP_039999416.1;
viii. Accession No. WP_047608097.1;
ix. Accession No. WP_039800848.1;
x. Accession No. WP_062149047.1; and
xi. Accession No. WP_020165972.1.

In an embodiment, the NifX polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:14.

In an embodiment, the NifY polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:15;
ii. Accession No. WP_049089500.1;
iii. Accession No. WP_064342935.1;
iv. Accession No. WP_044524054.1;
v. Accession No. WP_049010739.1;
vi. Accession No. WP_047370270.1;
vii. Accession No. WP_039999411.1;
viii. Accession No. WP_037382461.1;
ix. Accession No. WP_014683024.1;
x. Accession No. AEX25784.1; and
xi. Accession No. WP_012698835.1.

In an embodiment, the NifY polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:15.

In an embodiment, the NifZ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:16;
ii. Accession No. WP_057173223.1;
iii. Accession No. WP_064342939.1;
iv. Accession No. WP_043875005.1;
v. Accession No. WP_043953588.1;
vi. Accession No. WP_065368553.1;
vii. Accession No. WP_062627625.1;
viii. Accession No. WP_011491838.1;
ix. Accession No. WP_014029050.1; and
x. Accession No. WP_015665422.1.

In an embodiment, the NifZ polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:16.

In an embodiment, the NifW polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:17;
ii. Accession No. WP_064342938.1;
iii. Accession No. WP_049080155.1;
iv. Accession No. WP_095103586.1;
v. Accession No. WP_065877373.1;
vi. Accession No. WP_095699971.1;
vii. Accession No. WP_012764136.1;
viii. Accession No. WP_053085547.1;
ix. Accession No. WP_077299824.1;

x. Accession No. OGI40729;
xi. Accession No. ACO76430.1; and
xii. Accession No. BBA37427.1.

In an embodiment, the NifW polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:17.

In an embodiment, the ferredoxin polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:232;
ii. Accession No. WP_012703542;
iii. Accession No. WP_065835964.1;
iv. Accession No. WP_069124666.1;
v. Accession No. WP_101942980;
vi. Accession No. WP_049076934.1;
vii. Accession No. WP_072048756.1;
viii. Accession No. WP_130674512.1; and
ix. Accession No. WP_103805005.1.

In an embodiment, the ferredoxin polypeptide comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:232.

Suitable amino acid sequences for MTPs in relation to any of the above aspects are known in the art and include those provided herein. In an embodiment, the MTP comprises amino acids having a sequence which is at least 30% identical, at least 40% identical, at least 50% identical, at least 60% identical, at least 70% identical, at least 80% identical, at least 90% identical, at least 95% identical, at least 97% identical, or at least 99% identical, to any one or more of the following sequences:

i. SEQ ID NO:36;
ii. SEQ ID NO:21;
iii. amino acids 1-77 of SEQ ID NO:20;
iv. SEQ ID NO:28;
v. SEQ ID NO:29;
vi. SEQ ID NO:30;
vii. SEQ ID NO:31;
viii. SEQ ID NO:32;
ix. SEQ ID NO:33;
x. SEQ ID NO:34;
xi. SEQ ID NO:35;
xii. SEQ ID NO:37; and
xiii. SEQ ID NO:38.

In an embodiment, the MTP comprises amino acids having a sequence which is at least 30% identical, at least 40% identical, at least 50% identical, at least 60% identical, at least 70% identical, at least 80% identical, at least 90% identical, at least 95% identical, at least 97% identical, at least 99% identical, or is identical to the sequence provided in SEQ ID NO:36.

In another aspect, the present invention provides a polynucleotide encoding any one or more of the polypeptides of the invention.

In an embodiment, a protein coding region of the polynucleotide has been codon-modified for expression in a plant cell, relative to a corresponding protein coding region of a naturally-occurring polynucleotide in a bacterium. In an embodiment, most, or even all, of the protein coding regions have been codon-optimised for expression in a plant cell, preferably the plant cell of the invention.

In a further embodiment, each exogenous polynucleotide comprises a promoter operably linked to the polynucleotide and/or translational regulatory elements operably linked to the polynucleotide.

In another embodiment, the promoter confers expression of the one or more polynucleotide(s) in roots, leaves and/or stem of a plant, preferably the promoter confers expression of the one or more polynucleotide(s) in one, or more, or all of the roots, leaves or a stem of the plant relative to seed of the plant.

In another embodiment, the one or more or all of the polynucleotides are present in a plant cell or a bacterial cell, preferably integrated into the nuclear genome of the plant cell, for example as a contiguous DNA sequence integrated into the chloroplast genome or preferably the nuclear genome of the plant cell. The plant cell may contain multiple copies of the contiguous DNA sequence integrated into the nuclear genome, for example as multiple T-DNAs.

In an embodiment, each polynucleotide, or each sequence within it encoding a polypeptide, is operably linked to a promoter and optionally, a transcription termination sequence.

In a further or another embodiment, the promoter confers expression of one, or more of the polynucleotide(s) in roots, leaves and/or stem of a plant, preferably the one or more polynucleotide(s) is preferentially expressed in one, or more, or all of the roots, leaves or a stem of the plant relative to seed of the plant.

In a further aspect provided is a chimeric vector comprising or encoding a polynucleotide of the invention.

In another aspect, the present invention provides a vector comprising the polynucleotide of the invention.

In an embodiment, the vector comprises polynucleotides which encode at least 3, at least 4, or at least 5 Nif fusion polypeptides.

In another aspect, the present invention provides a vector comprising polynucleotides which encode at least 3, at least 4, or at least 5 of the Nif fusion polypeptides defined in any one of the above aspects of the invention.

In an embodiment, the vector comprises polynucleotides encoding a) the NifD fusion polypeptide and the NifK fusion polypeptide, or the NifD-linker-NifK fusion polypeptide; and
b) the NifH fusion polypeptide and the NifV fusion polypeptide; and
c) optionally, the AnfG fusion polypeptide and/or the ferredoxin fusion polypeptide.

In an embodiment, the vector comprises polynucleotides encoding a) the NifF, NifJ, NifU and NifB fusion polypeptides and optionally the NifS fusion polypeptide; and/or
b) the NifW, NifX, NifY and NifZ fusion polypeptides.

In a further aspect, the present invention provides a cell comprising one, or more, of the polypeptides according to the invention, one, or more of the exogenous polynucleotides according to the invention, and/or a vector according to the invention.

In a related aspect, the present invention provides a cell, preferably a plant cell, comprising a fusion polypeptide or cleaved product according to the invention, or a combination of two or more of said fusion polypeptides or cleaved products, a protein complex according to the invention, and/or a polynucleotide according to the invention or a vector according to the invention. In a preferred embodiment, the cell comprises an exogenous polynucleotide for each fusion polypeptide or cleaved product present in the cell.

In an embodiment, the fusion polypeptide or cleaved product, or combination of fusion polypeptides or cleavage products, or protein complex, is in mitochondria of the cell. As would be understood readily, not all of the fusion polypeptide or cleaved product needs to be in the mitochondria of the cell, so long as at least some is in the mitochondria.

In an embodiment, the cell is a plant cell or a bacterial cell, preferably a cell of a transgenic plant, more preferably wherein at least one of exogenous polynucleotides is integrated in the nuclear genome of the cell.

In a further embodiment, the plant cell is a monocotyledonous plant cell such as, for example, a cereal plant cell such as a wheat cell, a rice cell, a maize cell, a *Triticale* cell, an oat cell, or a barley cell, preferably a wheat cell, or a dicotyledonous plant cell. The plant cell may be further characterized by the polypeptides or polynucleotides defined by any of the above recited features. All possible combinations of the features recited above are contemplated as part of the invention in the context of the plant cell, and other aspects of the invention.

In a further aspect, the present invention provides a transgenic plant or a transgenic part thereof, preferably seed, comprising one, or more, of the polypeptides according to the invention, one, or more of the exogenous polynucleotides according to the invention, and/or a vector according to the invention.

In an embodiment, the transgenic plant is a monocotyledonous plant such as, for example, a cereal plant such as wheat, rice, maize, *Triticale*, oat, or barley, preferably wheat, or a dicotyledonous plant. The plant or part thereof may be further characterized by the polypeptides or polynucleotides defined by any of the above recited features. All possible combinations of the features recited above are contemplated as part of the invention in the context of the plant or part thereof, and other aspects of the invention.

In a further aspect, the present invention provides a method of producing a polypeptide according to the invention, the method comprising expressing in a cell a polynucleotide according to the invention.

In a further aspect, the present invention provides a method of producing a cell according to the invention, the method comprising the step of introducing one or more polynucleotides according to the invention, and/or a vector according to the invention, into a cell.

In another aspect, the present invention provides a method of producing homocitrate in a plant cell, the method comprising expressing the recombinant NifV polypeptide or the NifV fusion polypeptide of the invention in the plant cell, wherein the recombinant NifV polypeptide or the NifV fusion polypeptide, and/or a cleaved product thereof, produces homocitrate in the plant cell.

In an embodiment, the method further comprises introducing a polynucleotide encoding the recombinant NifV polypeptide or the NifV fusion polypeptide into the plant cell.

In another aspect, the present invention provides use of the NifV polypeptide of the invention for producing homocitrate in a plant cell.

In another aspect, the present invention provides a method of increasing the amount of a NifD, NifK or NifD-linker-NifK fusion polypeptide in a plant cell, the method comprising expressing one or more or all of NifW, NifX, NifY and NifZ fusion polypeptides in the plant cell, wherein each Nif fusion polypeptide independently comprises a mitochondrial targeting peptide (MTP), wherein the amount of the NifD, NifK or NifD-linker-NifK fusion polypeptide in the plant cell is increased relative to a corresponding plant cell not expressing one or more or all of the NifW, NifX, NifY and NifZ fusion polypeptides.

In an embodiment, the method further comprises
- i) introducing one or more polynucleotides encoding the NifD, NifK or NifD-linker-NifK fusion polypeptide into the plant cell; and
- ii) introducing one or more polynucleotides encoding one or more or all of the NifW, NifX, NifY and NifZ fusion polypeptides into the plant cell.

In another aspect, the present invention provides a method of increasing the amount of a NifY polypeptide in a plant cell, the method comprising expressing one or more or all of NifW, NifX and NifZ fusion polypeptides in the plant cell, wherein each Nif fusion polypeptide independently comprises a mitochondrial targeting peptide (MTP), wherein the amount of the NifY polypeptide in the plant cell is increased relative to a corresponding plant cell not expressing one or more or all of the NifW, NifX and NifZ fusion polypeptides.

In an embodiment, the method further comprises
- i) introducing a polynucleotide encoding a NifY fusion polypeptide into the plant cell; and
- ii) introducing one or more polynucleotides encoding the one or more or all of the NifW, NifX and NifZ fusion polypeptides into the plant cell.

In another aspect, the present invention provides use of one or more polynucleotides encoding one or more or all of NifW, NifX and NifZ fusion polypeptides to increase the amount of a NifY polypeptide in a plant cell.

In another aspect, the present invention provides use of a polynucleotide of the invention, and/or a vector of the invention, for producing a transgenic plant cell.

In another aspect, the present invention provides a method of producing a transgenic plant, the method comprising the steps of
- i) introducing one or more polynucleotides of the invention, and/or one or more vectors of the invention, into a cell of a plant,
- ii) from the cell of step i), regenerating a transgenic plant of the invention, and
- iii) optionally, producing transgenic seed and/or progeny plants from the transgenic plant regenerated in step ii).

In a further aspect, the present invention provides a method of producing transgenic seed, comprising
- i) harvesting seed from the transgenic plant of the invention, and/or
- ii) harvesting seed from one or more transgenic progeny plants produced by the method of the invention.

In a further aspect, the present invention provides a method of producing a plant which has integrated into its genome a polynucleotide according to the invention, the method comprising the steps of
- i) crossing two parental plants, wherein at least one plant comprises the polynucleotide,
- ii) screening one or more progeny plants from the cross for the presence or absence of the polynucleotide, and
- iii) selecting a progeny plant which comprises the polynucleotide, thereby producing the plant.

In a further or another embodiment, at least one of the parental plants is a tetraploid or hexaploid wheat plant.

In a further or another embodiment, step ii) comprises analysing a sample comprising DNA from the one or more progeny plants for the polynucleotide.

In a further or another embodiment, step iii) comprises i) selecting a progeny plant which is homozygous for the polynucleotide, and/or ii) analysing the plant or the one or more progeny plants thereof for presence and/or expression of the polynucleotide or for an altered phenotype as defined above.

In one or a further embodiment, the method further comprises:

iv) backcrossing the progeny of the cross of step i) with a plant of the same genotype as a first parent plant lacking the polynucleotide for a sufficient number of times to produce a plant with a majority of the genotype of the first parent but comprising the polynucleotide, and v) selecting a progeny plant which comprises the polynucleotide and/or has an altered phenotype as defined above.

In a further or another embodiment, the method further comprises the step of analysing the plant or progeny plant for at least one other genetic marker.

In a further aspect, the present invention provides a plant produced using a method according to the invention.

In a further aspect, the present invention provides use of a polynucleotide according to the invention, and/or a vector according to the invention, to produce a recombinant cell and/or a transgenic plant.

In an embodiment, the transgenic plant has an altered phenotype as defined above when compared to a corresponding plant lacking the exogenous polynucleotide, and/or the vector.

In a further aspect, the present invention provides a method for identifying a plant comprising a polynucleotide according to the invention, the method comprising the steps of i) obtaining a nucleic acid sample from a plant, and ii) screening the sample for the presence or absence of the polynucleotide.

In an embodiment, the presence of the polynucleotide indicates that the plant has an altered phenotype as defined above, when compared to a corresponding plant lacking the exogenous polynucleotide.

In a further or another embodiment, the method identifies a plant according to the invention.

In a further or another embodiment, the method further comprises producing a plant from a seed before step i).

In another aspect, the present invention provides a transgenic plant part comprising a plant cell of the invention or obtained from the transgenic plant of the invention.

In an embodiment, the plant part is a seed that comprises the polynucleotide of the invention.

In another aspect, the present invention provides a method of producing flour, wholemeal, starch, oil, seed meal or other product obtained from seed, the method comprising;

a) obtaining the seed of the invention, and/or b) extracting the flour, wholemeal, starch, oil or other product, or producing the seed meal.

In a further aspect, the present invention provides a product produced from the transgenic plant of the invention and/or the plant part of the invention comprising the polypeptide of the invention and/or the polynucleotide of the invention.

In an embodiment, the plant part is a seed.

In a further or another embodiment, the product is a food ingredient or beverage ingredient or a food product or beverage product. Preferably, i) the food ingredient or product is selected from the group consisting of: flour, starch, oil, leavened or unleavened breads, pasta, noodles, animal fodder, breakfast cereals, snack foods, cakes, malt, pastries and foods containing flour-based sauces, or ii) the beverage product is juice, beer or malt. Methods of producing such products are well known to those skilled in the art.

In an alternative embodiment, the product is a non-food product. Examples of non-food products include, but are not limited to, films, coatings, adhesives, building materials and packaging materials. Methods of producing such products are well known to those skilled in the art.

In a further aspect, the present invention provides a method of preparing a food product, the method comprising mixing seed of the invention, or flour, wholemeal, starch, oil or other product from the seed, with another food ingredient, or processing the seed or flour or wholemeal, preferably by milling, cracking, polishing, flaking, parboiling, cooking or baking the seed or a composition comprising the seed and/or flour or wholemeal obtained from the seed.

In a further aspect, the present invention provides method of preparing malt, comprising the step of germinating seed according to the invention.

In a further aspect, the present invention provides use of a plant or part thereof according to the invention as animal feed, or to produce feed for animal consumption or food for human consumption.

In a further aspect, the present invention provides a composition comprising a polypeptide according to the invention, a polynucleotide according to the invention, a vector according to the invention, or a cell according to the invention, and one or more acceptable carriers.

In a further aspect, the present invention provides a method for reconstitution of a nitrogenase protein complex in a plant cell, the method comprising introducing two or more polynucleotides according to the invention, two or more nucleic acid constructs according to the invention, and/or a vector according to the invention into the cell, and culturing the plant cell for a sufficient time for the polynucleotides or vector to be expressed.

In another aspect, the present invention provides a plant cell comprising mitochondria and 3, 4, 5, 6, 7, 8, 9, 10 or 11 Nif polypeptides, wherein the Nif polypeptides are selected from the group consisting of NifF, NifM, NifN, NifS, NifU, NifW, NifY, NifZ, NifV, NifH and NifD-NifK, and wherein each of the 3, 4, 5, 6, 7, 8, 9, 10 or 11 Nif polypeptides are at least partially soluble in the mitochondria.

In an embodiment, the plant cell comprises NifV. Preferably, the NifV produces homocitrate. In an embodiment, the NifV is a NifV of the invention.

In another embodiment, the plant cell comprises NifS, NifU, or both NifS and NifU, and optionally NifV In another embodiment, the plant cell comprises NifH, NifM, or both NifH and NifM, and optionally one or more of all of NifV, NifS and NifU.

In another embodiment, the plant cell comprises NifF, NifH or NifD-NifK, or NifH and NifD-NifK, or NifF, NifH and NifD-NifK, and optionally one or more of all of NifV, NifS, NifU, NifH and NifM In an embodiment, the NifH polypeptide is an AnfH polypeptide, and the NifD-NifK polypeptide is an AnfD-AnfK polypeptide.

In a further embodiment, the plant comprises an AnfG polypeptide which is at least partially soluble in the mitochondria.

In an embodiment, each of the 3, 4, 5, 6, 7, 8, 9, 10 or 11 Nif polypeptides is at least 10%, at least 20%, at least 30%, or at least 40%, up to 50% soluble in the mitochondria.

In an embodiment, the 3, 4, 5, 6, 7, 8, 9, 10 or 11 of the Nif polypeptides each independently comprises a mitochondrial targeting peptide (MTP), or a C-terminal peptide resulting from cleavage of a MTP, or both, preferably wherein the MTP or C-terminal peptide or both is at the N-terminus of each of the 3, 4, 5, 6, 7, 8, 9, 10 or 11 Nif polypeptides, or does not have an MTP and does not have a C-terminal peptide at the N-terminus of the Nif polypeptide.

In a further embodiment, the 3, 4, 5, 6, 7, 8, 9, 10 or 11 Nif polypeptides are each independently cleaved within the MTP, or immediately after the MTP, to yield 3, 4, 5, 6, 7, 8, 9, 10 or 11 processed Nif polypeptides, whereby each of the 3, 4, 5, 6, 7, 8, 9, 10 or 11 processed Nif polypeptides comprises, at its N-terminal end, the C-terminal peptide from the MTP, or does not comprise a C-terminal peptide from the MTP.

In another or further embodiment, the 3, 4, 5, 6, 7, 8, 9, 10 or 11 Nif polypeptides are each independently cleaved within the MTP, or immediately after the MTP, to yield 3, 4, 5, 6, 7, 8, 9, 10 or 11 processed Nif polypeptides, whereby each of the 3, 4, 5, 6, 7, 8, 9, 10 or 11 processed Nif polypeptides comprises, at its N-terminal end, the C-terminal peptide from the MTP, or does not comprise a C-terminal peptide from the MTP.

In an embodiment, each MTP is independently cleaved in the plant cell with an efficiency of at least 50%, and/or wherein each of the 3, 4, 5, 6, 7, 8, 9, 10 or 11 processed Nif polypeptides is independently present in the plant cell at a greater level than the corresponding Nif polypeptide, preferably at a ratio of greater than 1:1, 2:1 or 3:1.

In an embodiment, the plant cell comprises NifD-NifK fusion polypeptide comprising, in order, a NifD amino acid sequence (ND), a linker amino acid sequence and a NifK polypeptide (NK) amino acid sequence, wherein the linker amino acid sequence has a length of 8-50 residues, preferably 16-50 residues, more preferably about 26 or about 30 residues, or most preferably is 26 or 30 residues, which is translationally fused to the ND and NK.

In a further embodiment, the NifD-NifK fusion polypeptide comprises a mitochondrial targeting peptide (MTP), or a C-terminal peptide resulting from cleavage of a MTP, or both, wherein the MTP or C-terminal peptide resulting from cleavage of a MTP, or both, is translationally fused at the N-terminal end of the NifD-NifK fusion polypeptide.

In an embodiment, the 3, 4, 5, 6, 7, 8, 9, 10 or 11 processed Nif polypeptides each independently comprises a C-terminal peptide resulting from cleavage of an MTP of 1 to 45 amino acids in length, preferably 1 to 20 amino acids, translationally fused at the N-terminal end of the Nif polypeptide.

In an embodiment, the 3, 4, 5, 6, 7, 8, 9, 10 or 11 Nif polypeptides or the 3, 4, 5, 6, 7, 8, 9, 10 or 11 processed Nif polypeptides, or both, are functional Nif polypeptides.

In an embodiment, the 3, 4, 5, 6, 7, 8, 9, 10 or 11 Nif polypeptides or preferably the 3, 4, 5, 6, 7, 8, 9, 10 or 11 processed Nif polypeptides, or both, are in mitochondria of the plant cell, preferably in the mitochondrial matrix (MM) of the plant cell.

In an embodiment, the 3, 4, 5, 6, 7, 8, 9, 10 or 11 Nif polypeptides or preferably the 3, 4, 5, 6, 7, 8, 9, 10 or 11 processed Nif polypeptides, or both, are independently predominantly soluble in the plant mitochondria (i.e., greater than 50% soluble in the mitochondria).

In an embodiment, the ND comprises an amino acid other than tyrosine (Y) at a position corresponding to amino acid 100 of SEQ ID NO:18.

In an embodiment, the ND comprises a glutamine (Q) or lysine (K) at the position corresponding to amino acid 100 of SEQ ID NO:18, or a leucine (L) or methionine (M) or a phenylalanine (F) at the position corresponding to amino acid 100 of SEQ ID NO:18.

In an embodiment, the MTP is about 51 amino acids in length from a F1-ATPase γ-subunit MTP.

In an embodiment, the plant cell comprises a NK amino acid sequence, wherein the C-terminus of the polypeptide is a wild-type NifK C-terminus.

In an embodiment, the linker is at least about 20 amino acids, or at least about 30 amino acids, or at least about 40 amino acids, or about 20 amino acids to about 70 amino acids, or about 30 amino acids to about 70 amino acids, or about 30 amino acids to about 60 amino acids, or about 30 amino acids to about 50 amino acids, or about 25 amino acids, or about 30 amino acids, or about 35 amino acids, or about 40 amino acids, or about 45 amino acids, or about 46 amino acids, or about 50 amino acids, or about 55 amino acids, in length.

In an embodiment, the fusion polypeptide is capable of being cleaved within its MTP, or immediately after the MTP, to yield a processed polypeptide (CDK), whereby the CDK comprises in order, an optional C-terminal peptide resulting from cleavage of an MTP, the NifD amino acid sequence (ND), the linker amino acid sequence and the NK amino acid sequence.

In an embodiment, the plant cell further comprises the fusion polypeptide or the CDK, or both.

In an embodiment, the CDK comprises a scar sequence of 1 to 45 amino acids in length, preferably 1 to 20 amino acids, translationally fused at the N-terminal end of the NifD amino acid sequence.

In an embodiment, the CDK has both NifD and NifK function.

In an embodiment, the ND is an AnfD and the NK is an AnfK.

In an embodiment, the MTP is about 51 amino acids in length from a F1-ATPase γ-subunit MTP.

In an embodiment, each MTP comprises at least 10 amino acids, preferably has a length between 10 and 80 amino acids.

In an embodiment, the MTP, or at least one MTP, or all of the MTPs independently comprise an MTP of a mitochondrial protein precursor, or a variant thereof, preferably a plant MTP.

In an embodiment, the 3, 4, 5, 6, 7, 8, 9, 10 or 11 Nif polypeptides are encoded by 3, 4, 5, 6, 7, 8, 9, 10 or 11 exogenous polynucleotide(s), 3, 4, 5, 6, 7, 8, 9, 10 or 11 of which are integrated into the nuclear genome of the cell, preferably as a contiguous nucleic acid sequence.

In another embodiment of any of the above aspects, the cell is a cell other than an *Arabidopsis thaliana* protoplast.

The present inventors are the first to produce a plant cell comprising a NifV polypeptide which at least partially soluble in the mitochondria. Thus, in another aspect the present invention provides plant cell comprising a NifV polypeptide (NV), wherein the NV is at least partially soluble in the mitochondria.

In an embodiment, the NV is capable of, or is, producing homocitrate in the cell.

In an embodiment, the NV polypeptide comprises amino acids having a sequence as provided as any one of SEQ ID NO's: 205 to 209, or 211, a biologically active fragment thereof, or has an amino acid sequence which is at least 30% identical, at least 40% identical, at least 50% identical, at least 60% identical, at least 70% identical, at least 80% identical, at least 90% identical, at least 95% identical, at least 97% identical, or at least 99% identical, to that provided in any one or more of SEQ ID NO's: 205 to 209, or 211.

The present inventors are also the first to produce a plant cell comprising a NifH polypeptide which at least partially soluble in the mitochondria. Thus, in another aspect the present invention provides a plant cell comprising a NifH polypeptide (NH), wherein the NH is at least partially soluble in the mitochondria.

In an embodiment, the NH is encoded by an exogenous polynucleotide, one which is integrated into the nuclear genome of the cell, preferably as a contiguous nucleic acid sequence.

In an embodiment, the plant cell of one or both of the above two aspects is further defined by one or more of the features mentioned herein.

In a further aspect, the present invention provides a transgenic plant comprising a plant cell of the invention, wherein the transgenic plant is transgenic for the one or more exogenous polynucleotide(s) encoding the Nif polypeptide(s).

In an embodiment, one, or more of the one or more exogenous polynucleotide(s) are expressed in roots of the plant, preferably expressed at a greater level in the roots of the plant than in leaves of the plant.

In a further or another embodiment, the transgenic plant has an altered phenotype relative to a corresponding wild-type plant which is increased yield, biomass, growth rate, vigor, nitrogen gain derived from biological nitrogen fixation, nitrogen use efficiency, abiotic stress tolerance, and/or tolerance to nutrient deficiency relative to the corresponding wild-type plant.

In an alternative embodiment, the transgenic plant has the same growth rate and/or phenotype relative to a corresponding wild-type plant.

In an embodiment, the plant is a cereal plant such as wheat, rice, maize, *Triticale*, oat or barley, preferably wheat.

In an embodiment, the plant is homozygous or heterozygous for the one or more exogenous polynucleotide(s), preferably homozygous for all of the exogenous polynucleotides.

In another embodiment, the transgenic plant is a monocotyledonous plant such as, for example, a cereal plant such as wheat, rice, maize, *Triticale*, oat, or barley, preferably wheat, or a dicotyledonous plant.

In a further or another embodiment, the transgenic plant is growing in a field.

In a further aspect, the present invention provides a population of at least 100 plants according to the invention growing in a field.

Also provided is a substantially purified or recombinant NifV polypeptide (NV) which when expressed in a plant cell is at least partially soluble in the plant mitochondria.

Further provided is a substantially purified or recombinant NifH polypeptide (NH) which when expressed in a plant cell is at least partially soluble in the plant mitochondria.

In another aspect, provided is an isolated or exogenous polynucleotide encoding a NifV polypeptide (NV), wherein the NV when expressed in a plant cell is at least partially soluble in the plant mitochondria.

In an embodiment, the NV polypeptide comprises amino acids having a sequence as provided as any one of SEQ ID NO's: 205 to 209, or 211, a biologically active fragment thereof, or has an amino acid sequence which is at least 30% identical, at least 40% identical, at least 50% identical, at least 60% identical, at least 70% identical, at least 80% identical, at least 90% identical, at least 95% identical, at least 97% identical, or at least 99% identical, to that provided in any one or more of SEQ ID NO's: 205 to 209, or 211.

In further aspect, provided is an isolated or exogenous polynucleotide encoding a NifH polypeptide (NH) of the invention, wherein the NH when expressed in a plant cell is at least partially soluble in the plant mitochondria.

In an embodiment, a protein coding region of the polynucleotide has been codon-modified for expression in a plant cell, relative to a corresponding protein coding region of a naturally-occurring polynucleotide in a bacterium.

In a further embodiment, the polynucleotide further comprises a promoter operably linked to the polynucleotide and/or translational regulatory elements operably linked to the polynucleotide.

In another embodiment, the promoter confers expression of the one or more polynucleotide(s) in roots, leaves and/or stem of a plant, preferably the promoter confers expression of the one or more polynucleotide(s) in one, or more, or all of the roots, leaves or a stem of the plant relative to seed of the plant.

In another embodiment, the polynucleotide is present in a plant cell or a bacterial cell, preferably integrated into the nuclear genome of the plant cell, for example as a contiguous DNA sequence integrated into the nuclear genome or the chloroplast genome of the plant cell. The plant cell may contain multiple copies of the contiguous DNA sequence integrated into the nuclear genome.

In a further aspect provided is a chimeric vector comprising or encoding a polynucleotide of the invention.

In an embodiment, the polynucleotide, or each sequence within it encoding a polypeptide, is operably linked to a promoter and optionally, a transcription termination sequence.

In a further or another embodiment, the promoter confers expression of one, or more of the polynucleotide(s) in roots, leaves and/or stem of a plant, preferably the one or more polynucleotide(s) is preferentially expressed in one, or more, or all of the roots, leaves or a stem of the plant relative to seed of the plant.

In a further aspect, the present invention provides a cell comprising one, or more, of the polypeptides according to the invention, one, or more of the exogenous polynucleotides according to the invention, and/or a vector according to the invention.

In an embodiment, the cell is a plant cell or a bacterial cell.

In a further embodiment, the plant cell is a monocotyledonous plant cell such as, for example, a cereal plant cell such as a wheat cell, a rice cell, a maize cell, a *Triticale* cell, an oat cell, or a barley cell, preferably a wheat cell, or a dicotyledonous plant cell.

In a further aspect, the present invention provides a transgenic plant or a transgenic part thereof, preferably seed, comprising one, or more, of the polypeptides according to the invention, one, or more of the exogenous polynucleotides according to the invention, and/or a vector according to the invention.

In an embodiment, the transgenic plant is a monocotyledonous plant such as, for example, a cereal plant such as wheat, rice, maize, *Triticale*, oat, or barley, preferably wheat, or a dicotyledonous plant.

In a further aspect, the present invention provides a method of producing a polypeptide according to the invention, the method comprising expressing in a cell a polynucleotide according to the invention.

In a further aspect, the present invention provides a method of producing a cell according to the invention, the method comprising the step of introducing one or more polynucleotides according to the invention, and/or a vector according to the invention, into a cell.

In another aspect, the present invention provides a method of producing a transgenic plant, the method comprising the steps of i) introducing a polynucleotide of the invention, and/or the vector of the invention, into a cell of a plant,
ii) from the cell of step i), regenerating a transgenic plant of the invention, and
iii) optionally, producing one or more transgenic progeny plants from the transgenic plant regenerated in step ii).

In a further aspect, the present invention provides a method of producing transgenic seed, comprising i) harvesting seed from the transgenic plant of the invention, and/or
ii) harvesting seed from one or more transgenic progeny plants produced by the method of the invention.

In a further aspect, the present invention provides a method of producing a plant which has integrated into its genome a polynucleotide according to the invention, the method comprising the steps of i) crossing two parental plants, wherein at least one plant comprises the polynucleotide,
ii) screening one or more progeny plants from the cross for the presence or absence of the polynucleotide, and
iii) selecting a progeny plant which comprises the polynucleotide, thereby producing the plant.

In a further or another embodiment, at least one of the parental plants is a tetraploid or hexaploid wheat plant.

In a further or another embodiment, step ii) comprises analysing a sample comprising DNA from the one or more progeny plants for the polynucleotide.

In a further or another embodiment, step iii) comprises i) selecting a progeny plant which is homozygous for the polynucleotide, and/or
ii) analysing the plant or the one or more progeny plants thereof for presence and/or expression of the polynucleotide or for an altered phenotype as defined above.

In one or a further embodiment, the method further comprises:

iv) backcrossing the progeny of the cross of step i) with a plant of the same genotype as a first parent plant lacking the polynucleotide for a sufficient number of times to produce a plant with a majority of the genotype of the first parent but comprising the polynucleotide, and
iv) selecting a progeny plant which comprises the polynucleotide and/or has an altered phenotype as defined above.

In a further or another embodiment, the method further comprises the step of analysing the plant or progeny plant for at least one other genetic marker.

In a further aspect, the present invention provides a plant produced using a method according to the invention.

In a further aspect, the present invention provides use of a polynucleotide according to the invention, and/or a vector according to the invention, to produce a recombinant cell and/or a transgenic plant.

In an embodiment, the transgenic plant has an altered phenotype as defined above when compared to a corresponding plant lacking the exogenous polynucleotide, and/or the vector.

In a further aspect, the present invention provides a method for identifying a plant comprising a polynucleotide according to the invention, the method comprising the steps of i) obtaining a nucleic acid sample from a plant, and
ii) screening the sample for the presence or absence of the polynucleotide.

In an embodiment, the presence of the polynucleotide indicates that the plant has an altered phenotype as defined above, when compared to a corresponding plant lacking the exogenous polynucleotide.

In a further or another embodiment, the method identifies a plant according to the invention.

In a further or another embodiment, the method further comprises producing a plant from a seed before step i).

In another aspect, the present invention provides a transgenic plant part comprising a plant cell of the invention or obtained from the transgenic plant of the invention.

In an embodiment, the plant part is a seed that comprises the polynucleotide of the invention.

In another aspect, the present invention provides a method of producing flour, wholemeal, starch, oil, seed meal or other product obtained from seed, the method comprising;

a) obtaining seed of the invention, and
b) extracting the flour, wholemeal, starch, oil or other product, or producing the seed meal.

In a further aspect, the present invention provides a product produced from the transgenic plant of the invention and/or the plant part of the invention comprising the polypeptide of the invention and/or the polynucleotide of the invention.

In an embodiment, the plant part is a seed.

In a further or another embodiment, the product is a food ingredient or beverage ingredient or a food product or beverage product. Preferably, i) the food ingredient or product is selected from the group consisting of: flour, starch, oil, leavened or unleavened breads, pasta, noodles, animal fodder, breakfast cereals, snack foods, cakes, malt, pastries and foods containing flour-based sauces, or ii) the beverage product is juice, beer or malt. Methods of producing such products are well known to those skilled in the art.

In an alternative embodiment, the product is a non-food product. Examples of non-food products include, but are not limited to, films, coatings, adhesives, building materials and packaging materials. Methods of producing such products are well known to those skilled in the art.

In a further aspect, the present invention provides a method of preparing a food product, the method comprising mixing seed of the invention, or flour, wholemeal, starch, oil or other product from the seed, with another food ingredient.

In a further aspect, the present invention provides method of preparing malt, comprising the step of germinating seed according to the invention.

In a further aspect, the present invention provides use of a plant or part thereof according to the invention as animal feed, or to produce feed for animal consumption or food for human consumption.

In a further aspect, the present invention provides a composition comprising a polypeptide according to the invention, a polynucleotide according to the invention, a vector according to the invention, or a cell according to the invention, and one or more acceptable carriers.

Any embodiment herein shall be taken to apply mutatis mutandis to any other embodiment unless specifically stated otherwise. For instance, as the skilled person would understand, examples of Nif polypeptides outlined above for one aspect of the invention equally apply to other aspects the invention.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Western blot analysis using anti-HA antibody to detect individual unprocessed and MPP-processed pFAγ51::Nif::HA or 6×HIS::Nif::HA polypeptides after transient expression in *Nicotiana benthamiana* leaves. C, cytoplasmic expression (6×His); M, mitochondrially targeted.

Figure 2:
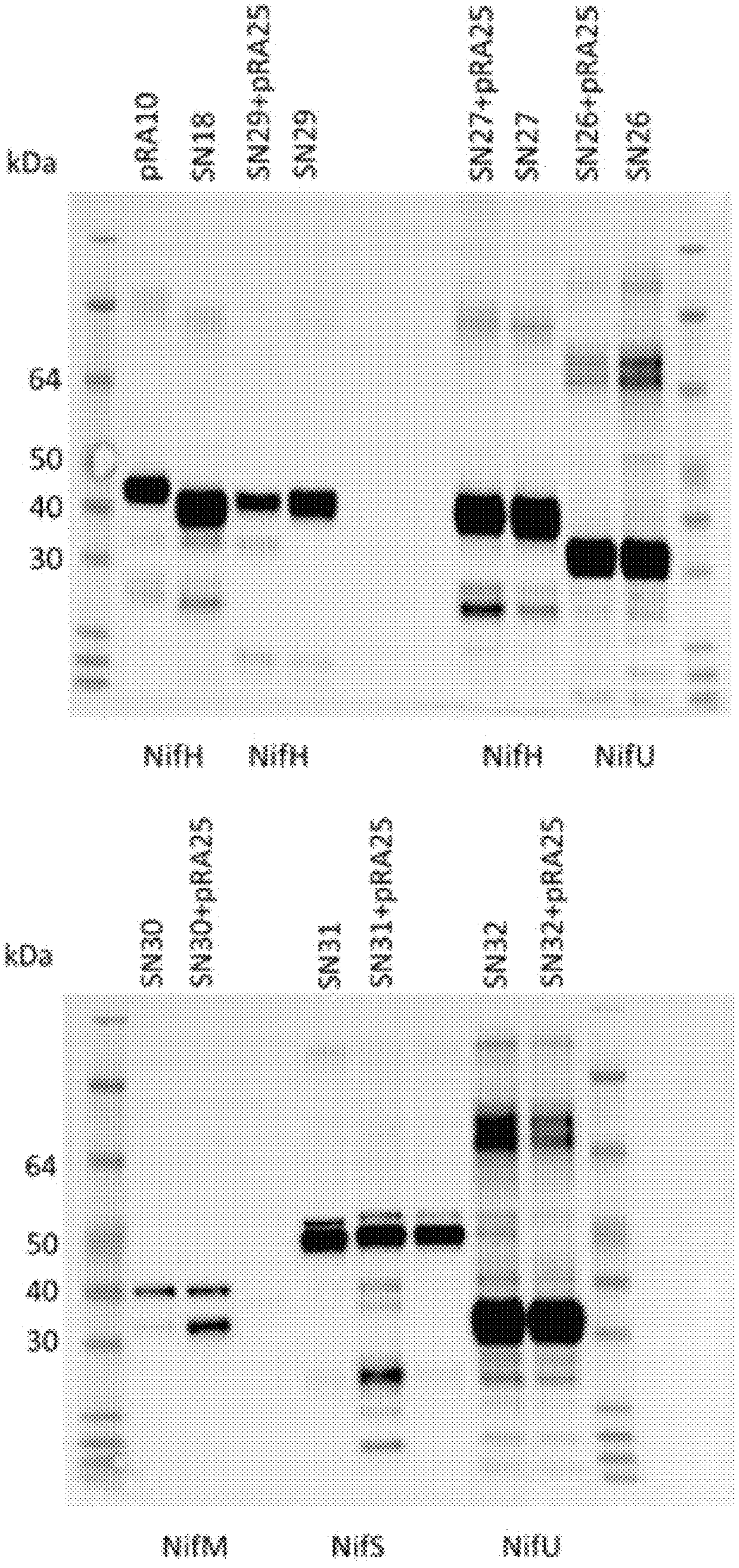

FIG. 2. Western blots of protein extracts after introduction of MTP:Nif genetic constructs into *N. benthamiana* leaf cells. The first and last lanes on each blot show indicative molecular weight markers in kDa from the Invitrogen Prestained BenchMark ladder. The genetic construct(s) used for each sample is indicated above each lane and the Nif polypeptide included in each fusion polypeptide is indicated below the lanes. For constructs SN26-SN32, paired infiltrations were carried out either with or without co-infiltration of pRA25 which encodes a MTP-FAγ77::NifK fusion polypeptide (WO2018/141030). The Western blots were probed with HA-antibody.

Figure 3:
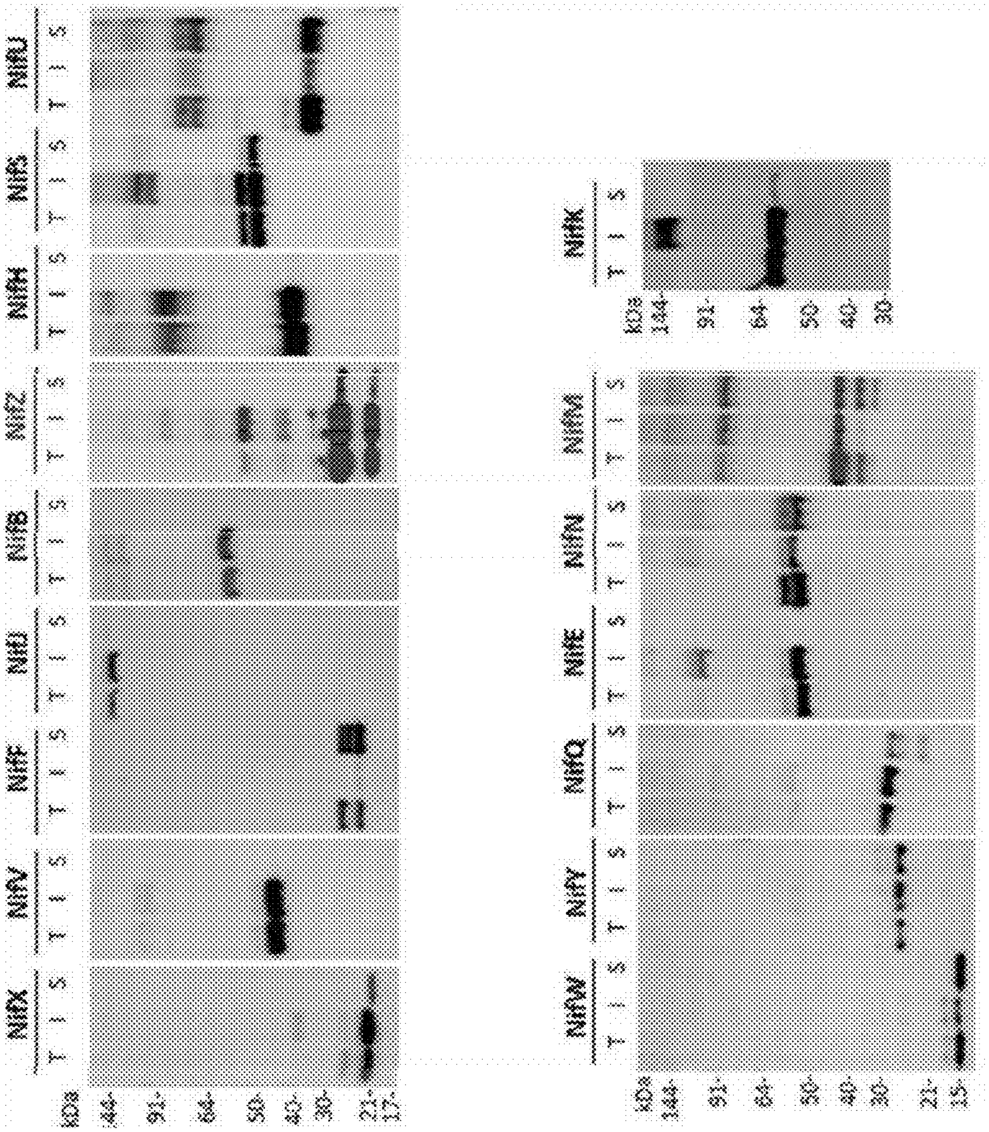

FIG. 3. Western blot analysis using anti-HA antibody of individual MTP-FAγ51::Nif::HA polypeptides (with the exception of MTP-FAγ51::HA::NifK) and MPP-processed products thereof after expression in *Nicotiana benthamiana* leaf cells. T, total protein; I, insoluble fraction; S, soluble fraction.

Figure 4:
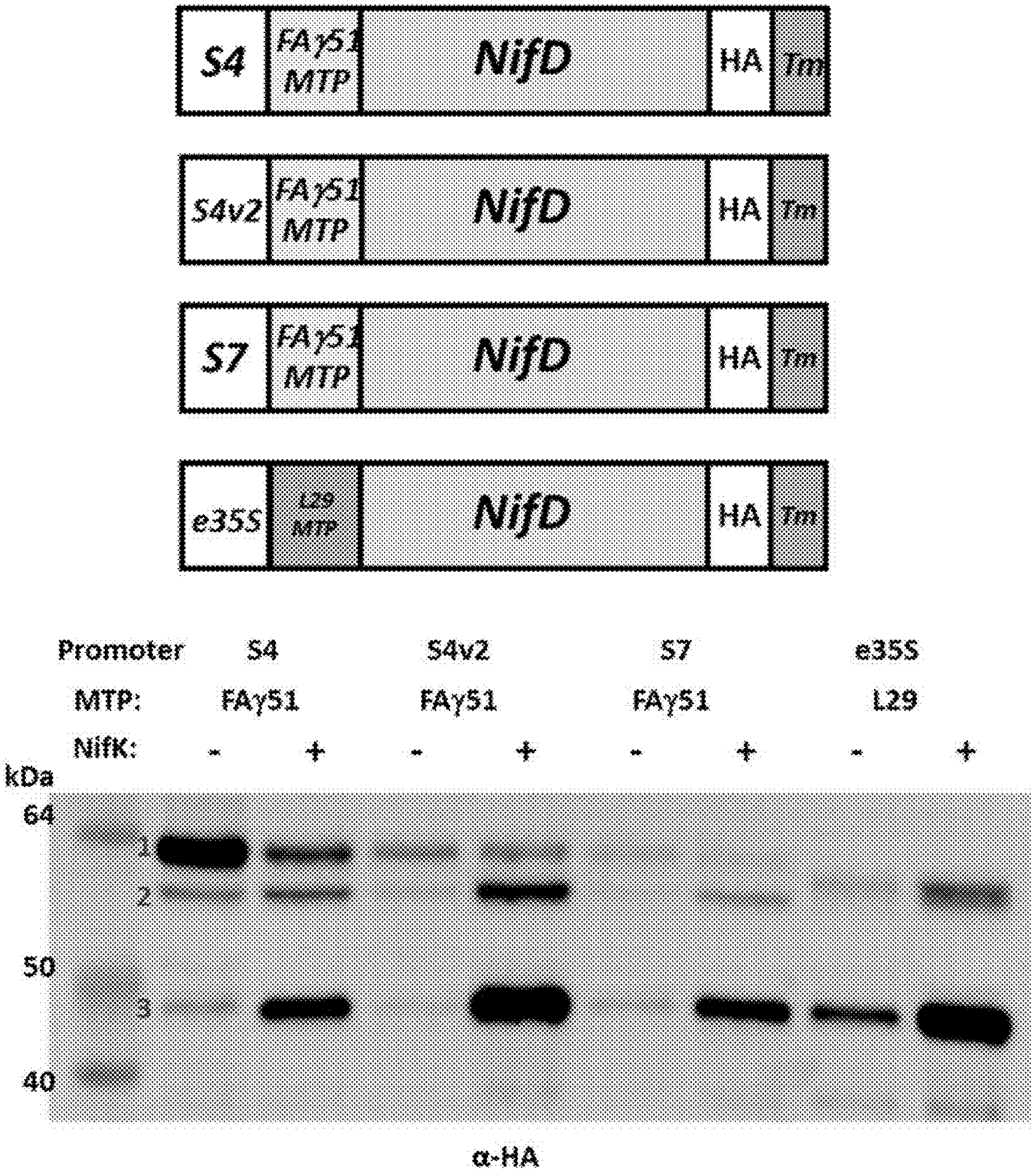

FIG. 4. Upper panel shows a schematic of the genetic constructs tested for production of a secondary cleavage product from wild-type NifD fusion polypeptides. MTP was either the FAγ51 or the L29 sequence, NifD was the wild-type *K. oxytoca* sequence, and HA=HA epitope. Lower panel shows a Western blot of protein extracts after introduction of the genetic constructs into *N. benthamiana* leaf cells. The Western blot was probed with HA-antibody. Lane 1 shows molecular weight markers using Prestained Benchmark ladder. Paired lanes show either the absence (−) or presence (+) of the NifK construct pRA25. Band 1=unprocessed MTP::NifD fusion polypeptide, band 2=MPP-processed fusion polypeptide and band 3 is the ~48 kDa degradation product.

Figure 5:
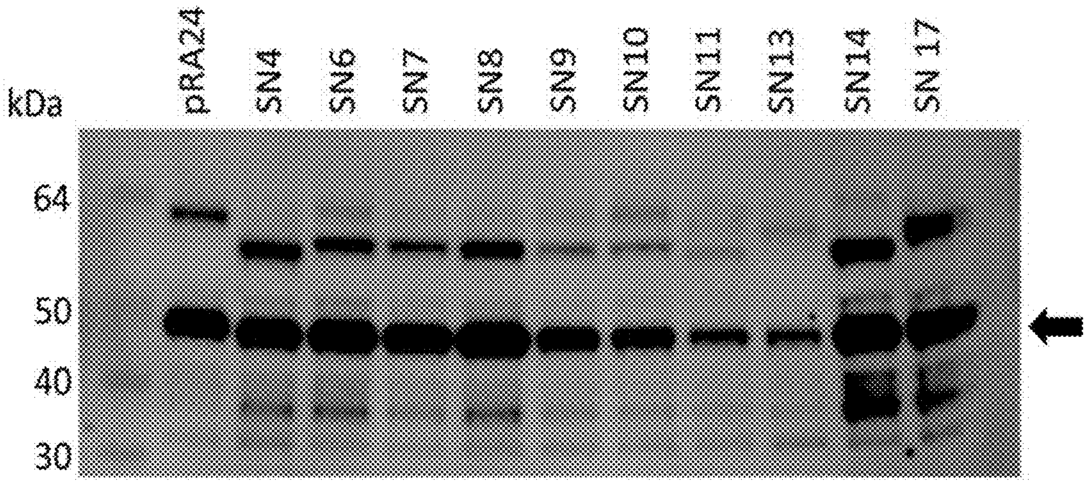

FIG. 5. Western blot of protein extracts after introduction of MTP:NifD genetic constructs into *N. benthamiana* leaf cells. Lane 1 shows molecular weight markers in kDa, using ThermoFisher Prestained Benchmark ladder. The genetic construct used in each sample is indicated above each lane. pRA24 encoded a MTP-FAγ::NifD::HA polypeptide where the NifD coding region was codon optimised for *Arabidopsis* (WO2018/141030). Each construct was introduced into the plant cells together with pRA25 (MTP-FAγ77::NifK) to enhance the NifD fusion polypeptide accumulation. The Western blot was probed with HA-antibody. The arrow shows the position of the ~48 kDa secondary cleavage polypeptide from NifD.

Figure 6:
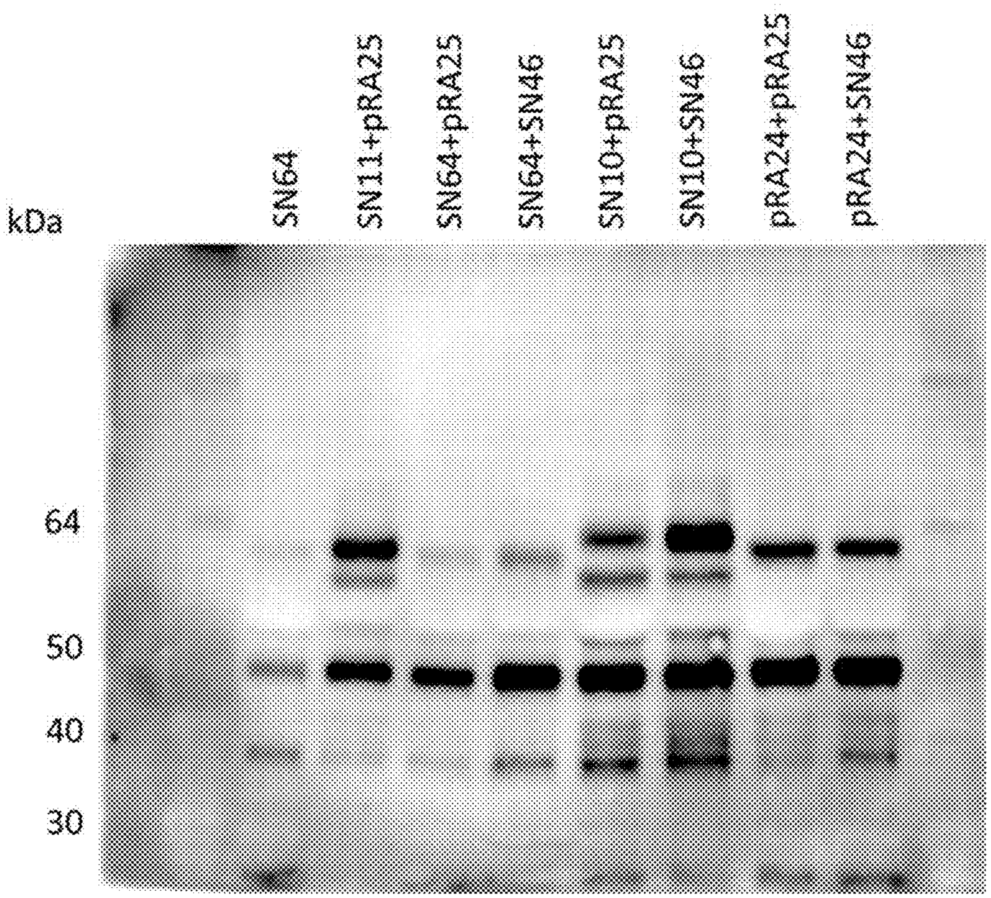

FIG. 6. Western blot of protein extracts after introduction of MTP:NifD genetic constructs into *N. benthamiana* leaf cells. Lane 1 shows molecular weight markers in kDa using ThermoFisher Prestained Benchmark ladder. The genetic construct used in each sample is indicated above each lane. SN64 encoded a mMTP-CPN60::NifD polypeptide where the mMTP-CPN60 amino acid sequence had been altered with substitution of amino acids with alanines, thereby rendering it resistant to cleavage by MPP. pRA24 encoded a MTP-FAγ::NifD::HA polypeptide where the NifD coding region was codon optimised for *Arabidopsis* (WO2018/141030). The Western blot was probed with HA-antibody.

FIG. 7. Alignment of the mutant mMTP-FAγ51 amino acid sequence (SEQ ID NO:59) in SN66 with the unmodified MTP-FAγ51 sequence (SEQ ID NO:21) in SN10 (SEQ ID NO:122). Regions of 5 and 8 consecutive amino acid residues were substituted with alanines, to inactivate MPP processing.

Figure 8:
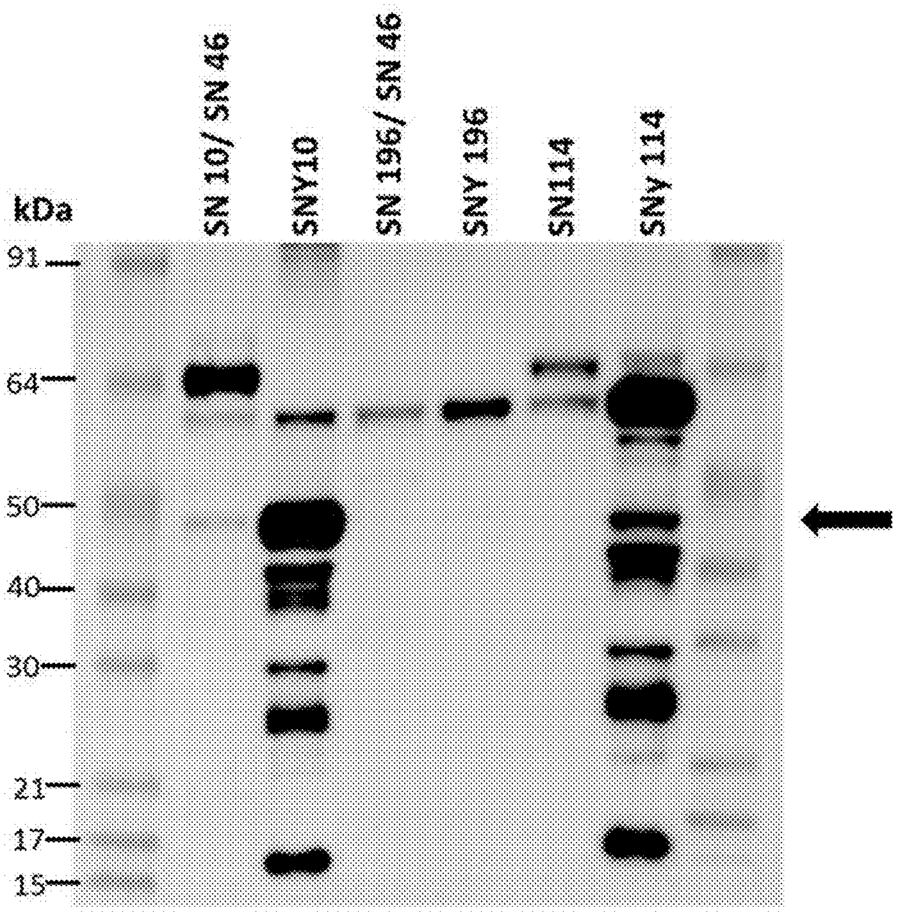

FIG. 8. Western blot of protein extracts after introduction of MTP:Nif genetic constructs into plant cells or yeast cells, probed with HA-antibody, demonstrating NifD secondary cleavage/degradation in yeast cells and reduction of cleavage with a Y100Q amino acid substitution (SN114, SNY114). Protein extracts from *N. benthamiana* leaf cells (SN10, SN196, SN114) or from yeast (SNY10, SNY196, SNY114) were electrophoresed in the lanes as indicated. Lanes 1 and 8 show molecular weight markers in kDa, using ThermoFisher Prestained Benchmark ladder. The band at ~64 kDa represents unprocessed MTP::NifD::HA fusion polypeptide, the band at ~58 kDa represents MPP-processed fusion polypeptide. The arrow points to the ~48 kDa C-terminal polypeptide produced by the secondary cleavage.

Figure 9:
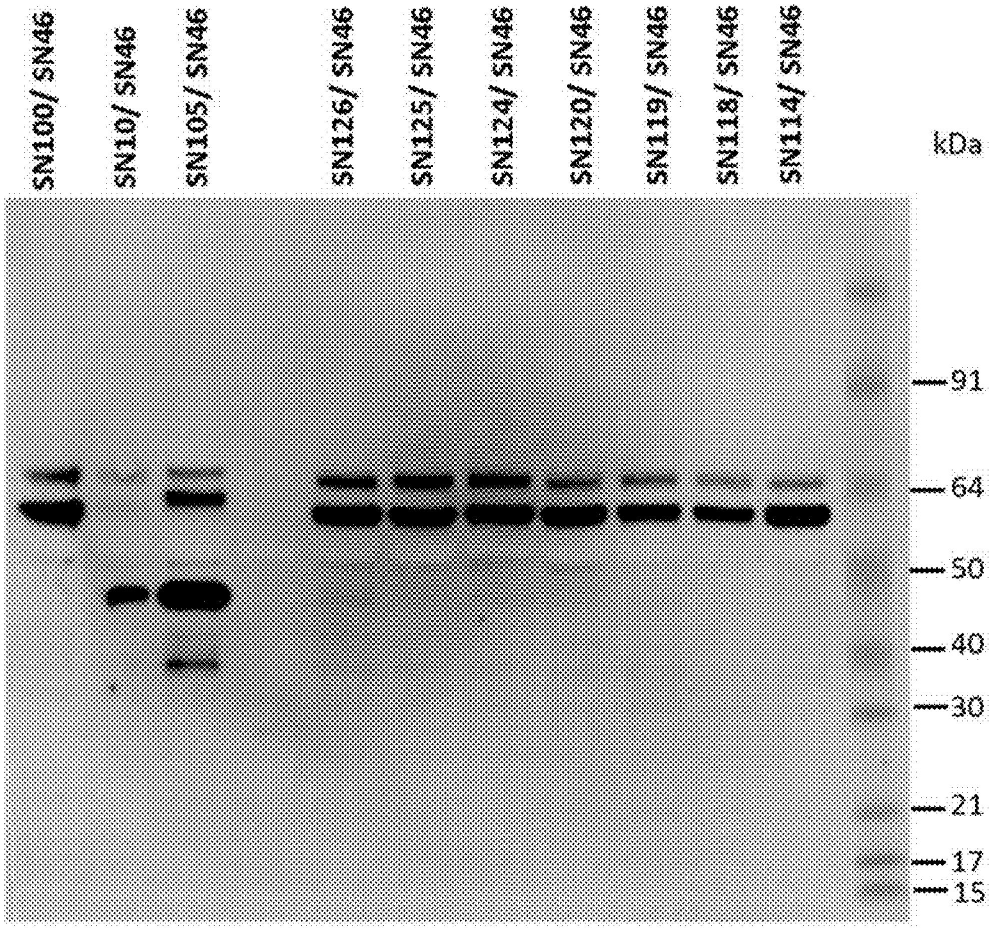

FIG. 9. Western blot of protein extracts from *N. benthamiana* leaf cells after introduction of genetic constructs encoding MTP::NifD::HA amino acid substitution variants, each together with SN46 (MTP-Su9::NifK). Lane 12 shows molecular weight markers in kDa using ThermoFisher Prestained Benchmark ladder. The most intense band at ~58 kDa in lanes 5-11 was MPP-processed MTP-FAγ51::NifD. Lanes 2 and 3 show the 48 kDa polypeptide produced by secondary cleavage. Note the absence of the 48 kDa polypeptide in lanes 5-11.

FIG. 10. Amino acid sequence alignment of a region of wild-type NifD polypeptides corresponding to amino acids 49-108 of *K. oxytoca* NifD (SEQ ID NO:18). A representative sequence was chosen from each cluster that contained at least 10 members in the sequence similarity network. The number of members in each cluster of NifD sequences is shown in parentheses. Completely conserved amino acids are shown above the alignment.

Figure 11:
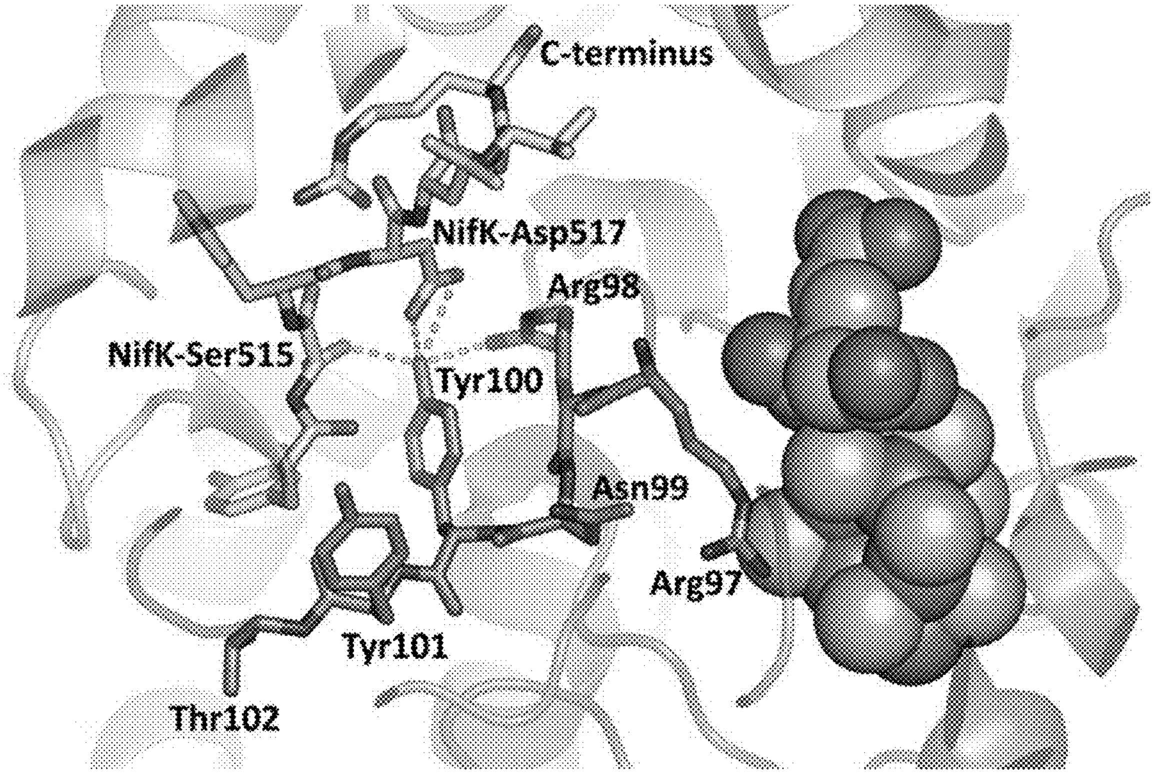

FIG. 11. Location of the proposed secondary cleavage site shown in the crystal structure of the NifD polypeptide from *K. oxytoca* (PDB:1QGU). Cofactor FeMoco is shown as spheres to the right. NifK-Ser515, NifK-Asp517, C-terminus and the structures to the top left are from NifK polypeptide. Arg97, Arg98, Asn99, Tyr100, Tyr101, Thr102 and structures to the lower right aside from FeMoco are from NifD. Dashed lines indicate possible hydrogen bonds between the hydroxyl of Tyr100 and Ser515, Asp517 and Arg98.

Figure 12:
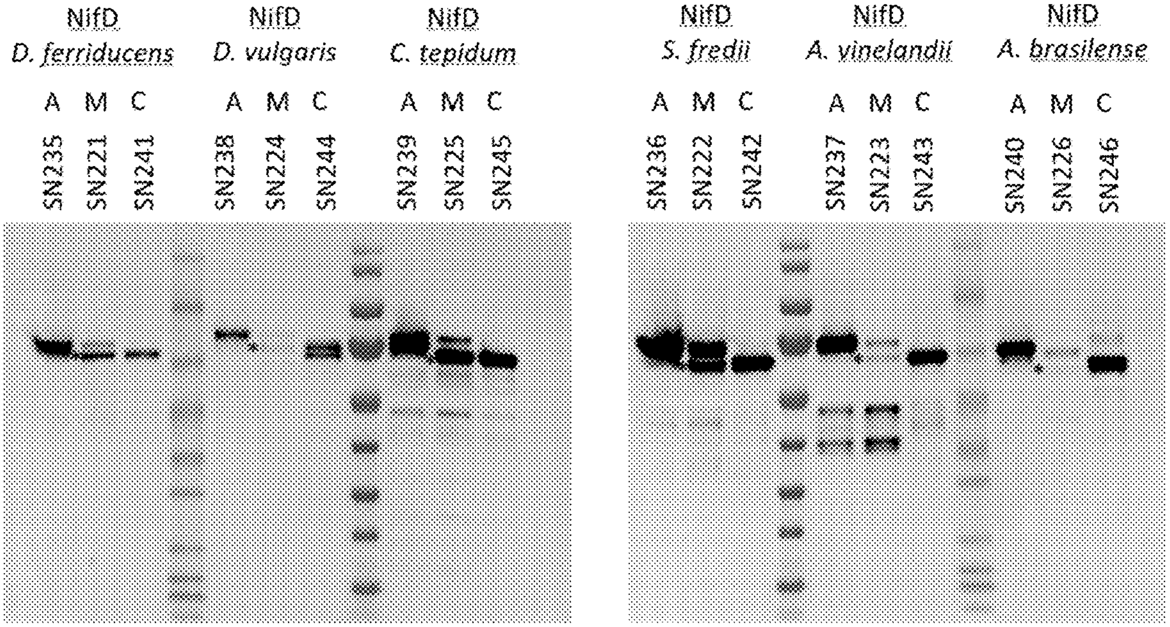

FIG. 12. Western blot analysis showing mitochondrial processing of NifD fusion polypeptides from six different bacteria. Three constructs, in adjacent lanes, were analysed for each NifD sequence: encoding an mMTP-FAγ51::NifD::HA fusion polypeptide which was not cleaved by the MPP at the canonical MPP cleavage site (lanes marked A), MTP-FAγ51::NifD::HA, which was targeted to mitochondria (lanes marked M), and 6×His::NifD::HA, which was expected to be cytoplasmically located (lanes marked C) and corresponding in size to the MPP-processed size.

Figure 13:
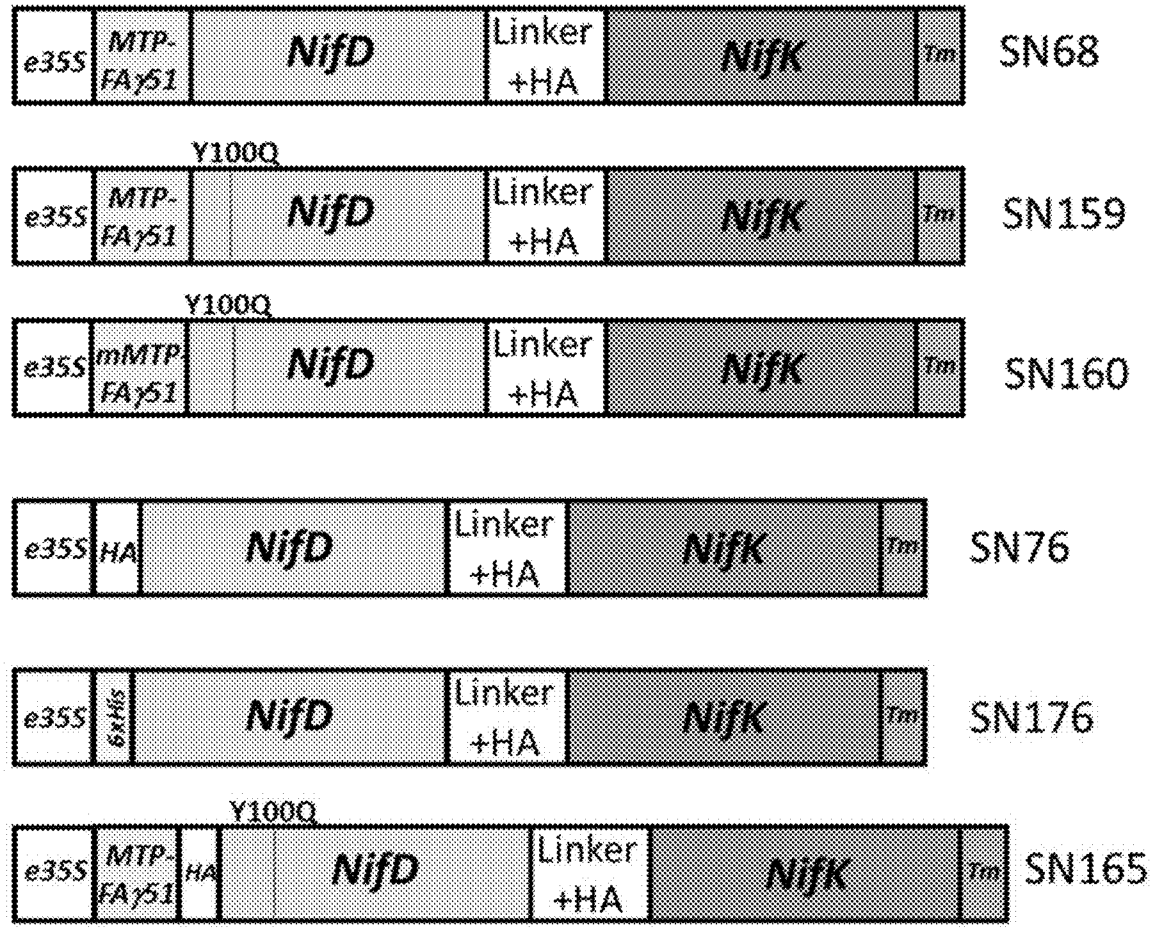

FIG. 13. Schematic maps of genetic constructs encoding NifD::linker(HA)::NifK fusion polypeptides, not drawn to scale. mMTP-FAγ refers to the mutant MTP having alanine substitutions to prevent cleavage by MPP. Y100Q refers to the presence of the amino acid substitution in the NifD sequence.

Figure 14:
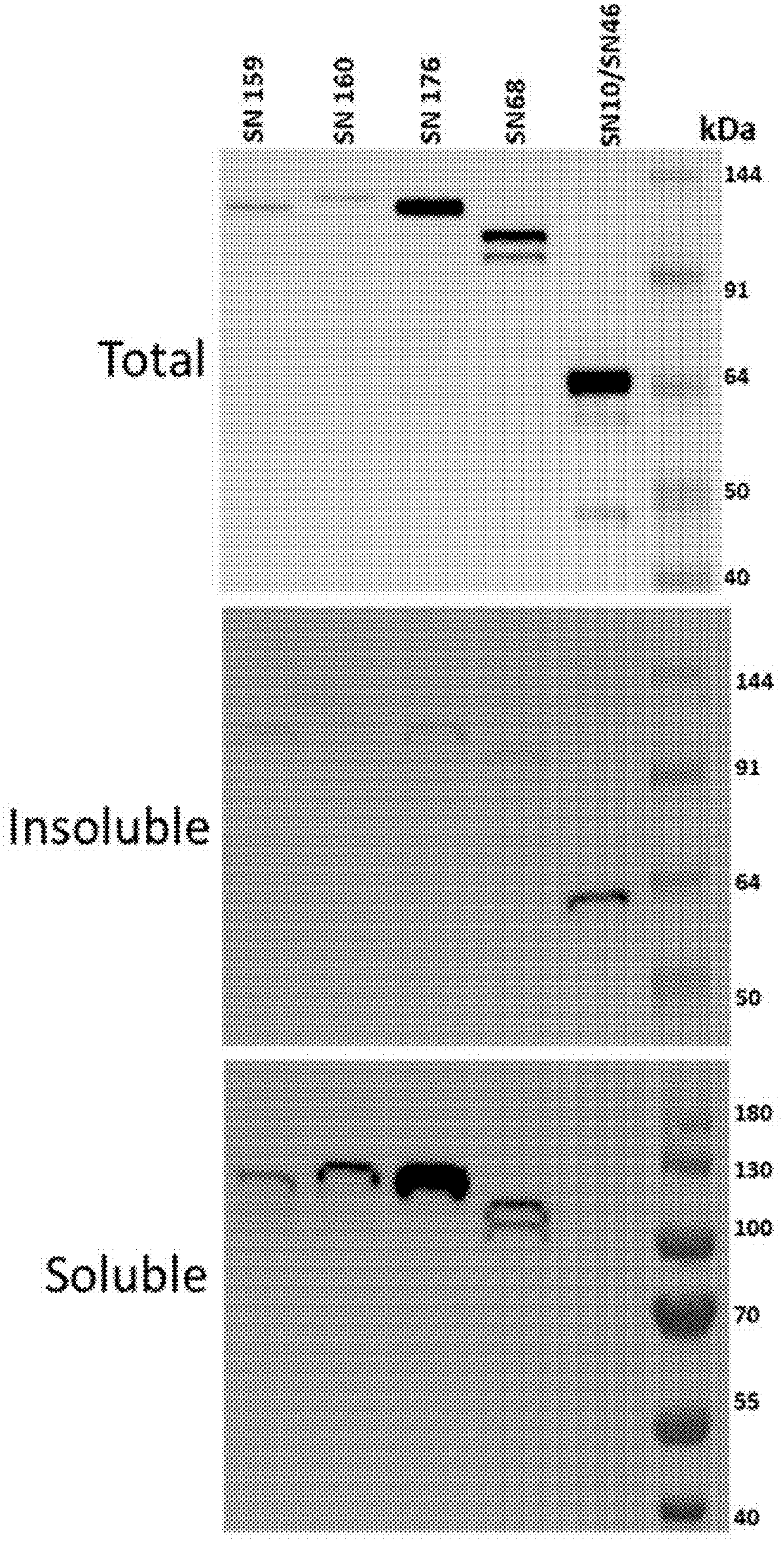

FIG. 14. Solubility of NifD-linker(HA)-NifK polypeptides after expression in *N. benthamiana*. Proteins from infiltrated leaf samples were isolated as "Total" protein or fractionated into Insoluble and Soluble fractions as described in Example 1. The protein ladder marker shown the ThermoFisher Prestained Benchmark ladder was used in blots for 'Total' and 'Insoluble' samples and the Invitrogen PageRuler ladder was used in the blot for the 'Soluble' samples.

Figure 15:
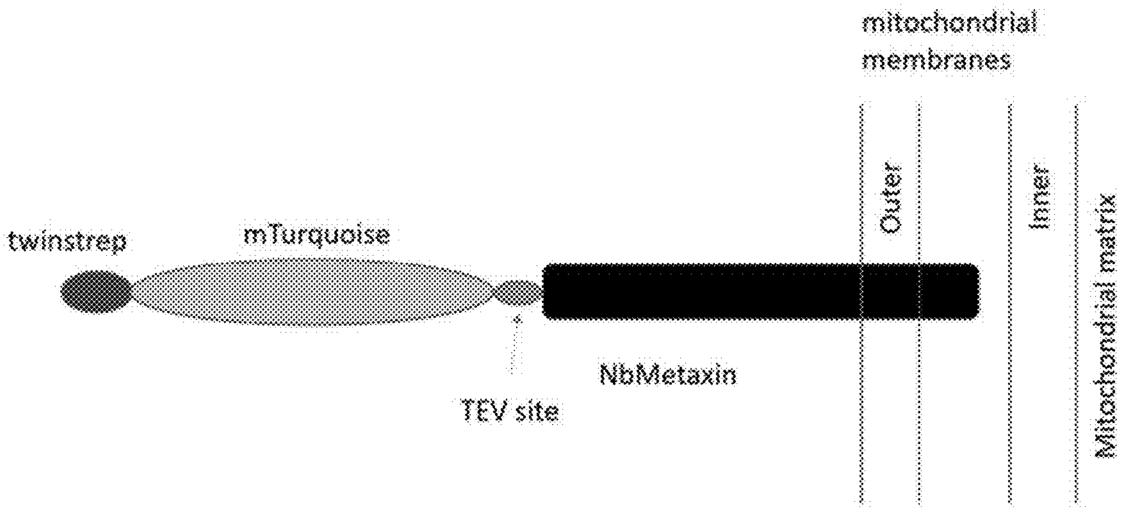

FIG. 15. Schematic of a metaxin fusion polypeptide encoded by a gene on SN197 and its localisation in the outer membrane of mitochondria with most of the polypeptide from the N-terminus into the cytoplasm. This construct used the *N. benthamiana* metaxin sequence.

FIG. 16: Western blot showing that purification of mitochondrially targeted MTP-FAγ51::NifU::TS from SN166 resulted in purification of a processed form of the NifU polypeptide. Upper panel: probed with anti-Strep antibody. Lower panel: Coomassie blue stained gel.

Figure 17:
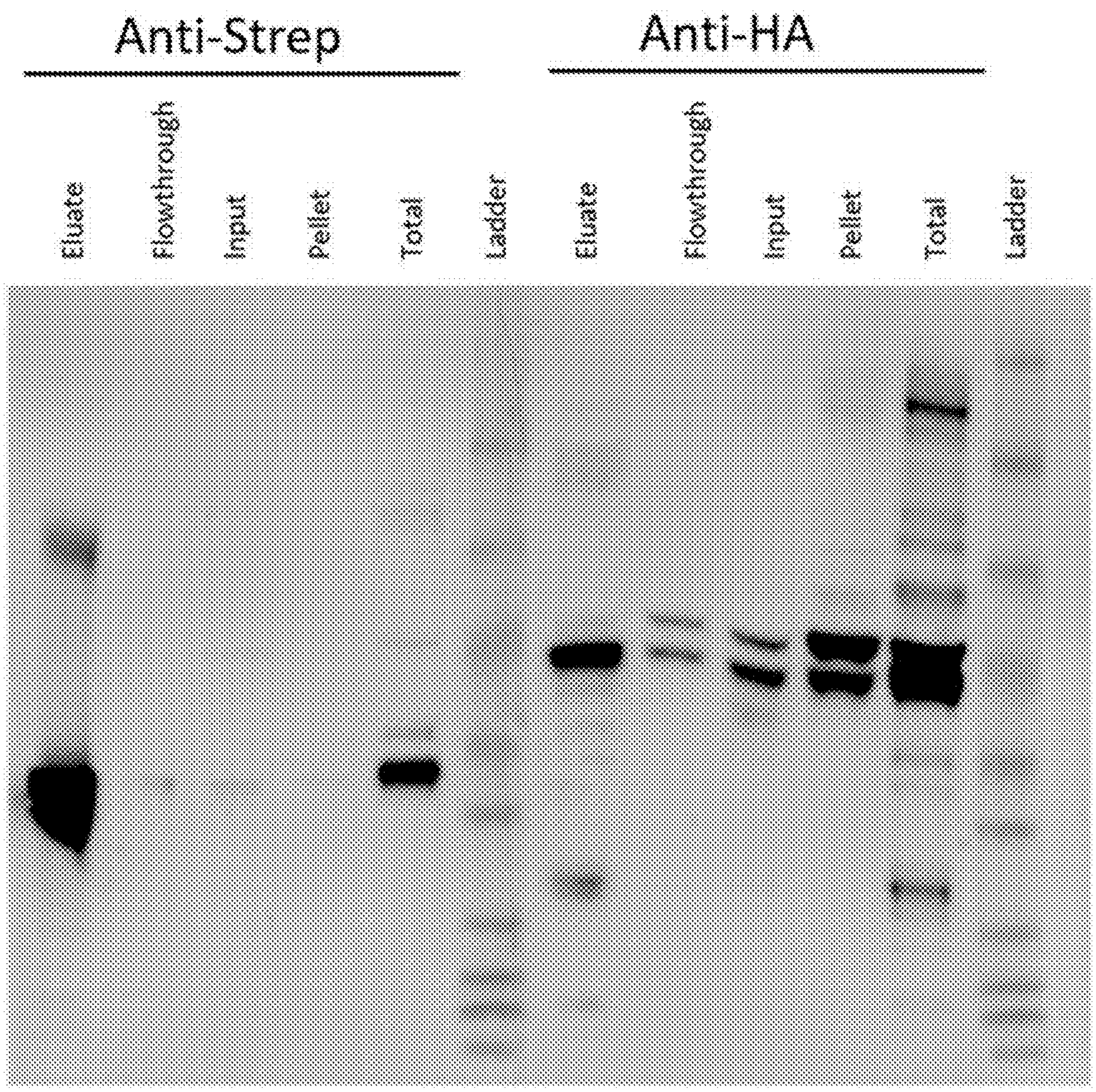

FIG. 17. Western blot showing that purification of mitochondrially targeted scar9::GG::NifU::TS resulted in co-purification of scar9::GG::NifS::HA. Samples from steps (i) to (v) in the purification process of the first purification experiment were subjected to SDS-PAGE and Western blotting using either anti-Strep antibody to detect the NifU polypeptide or anti-HA antibody to detect the NifS polypeptide. The two bands for NifS correspond to the unprocessed and processed forms. The presence of the processed NifS form in the eluate showed that co-purification had occurred.

Figure 18:
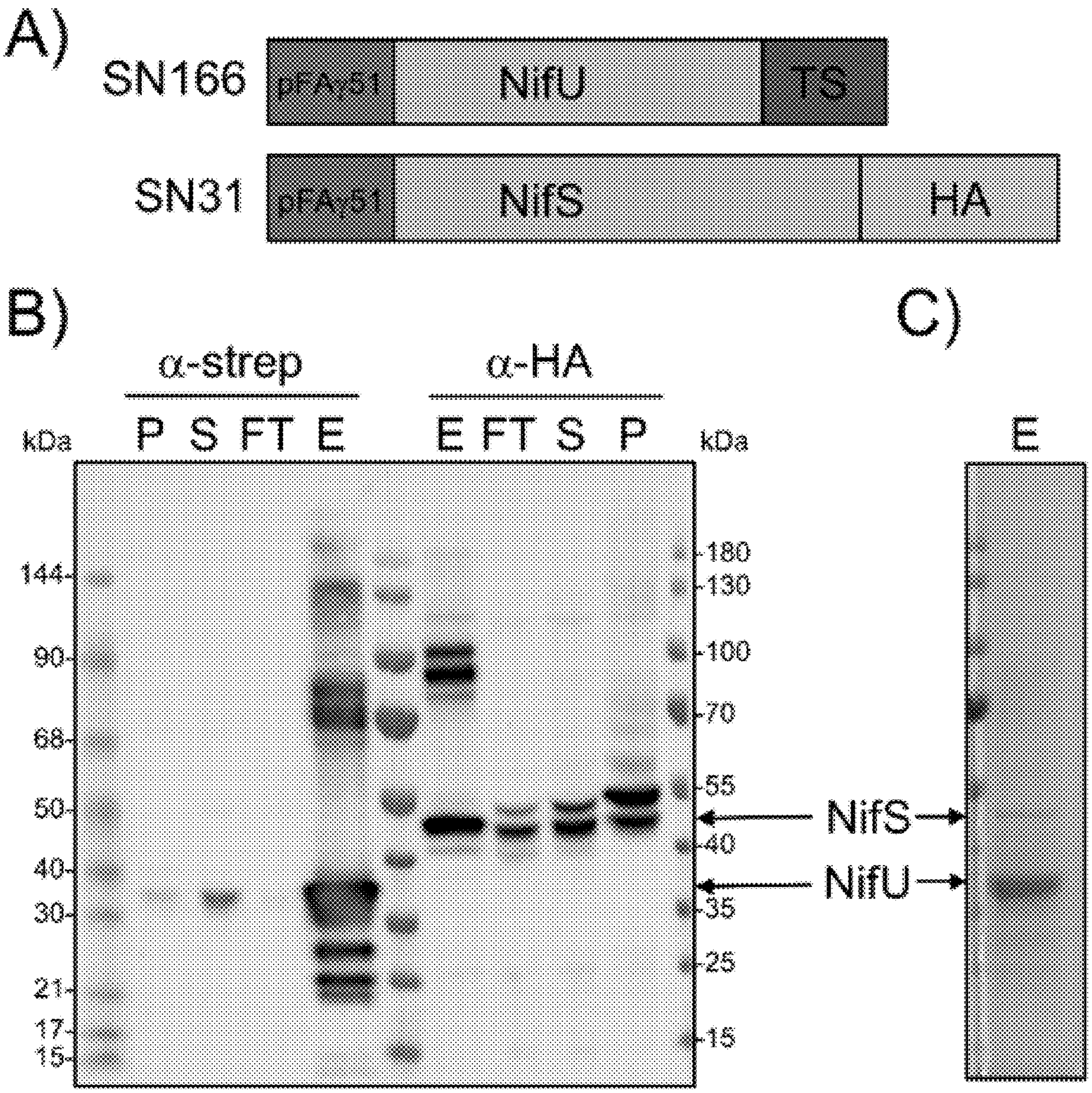

FIG. 18. Western blot of the purification of NifU from *N. benthamiana* in a third purification experiment, showing that NifS co-purifies with NifU. Panel A) Schematic of constructs that were infiltrated into *N. benthamiana* (not drawn to scale). B) Western blot analysis of the purification. P=pellet, S=supernatant, FT=flow through and E=eluate. All samples were loaded in duplicate and subjected to immunodetection using either a strep-antibody (α-strep) or a HA-antibody (α-HA). C) Coomassie stain of the eluate, which shows a major band for NifU and a faint band for NifS.

Figure 19:
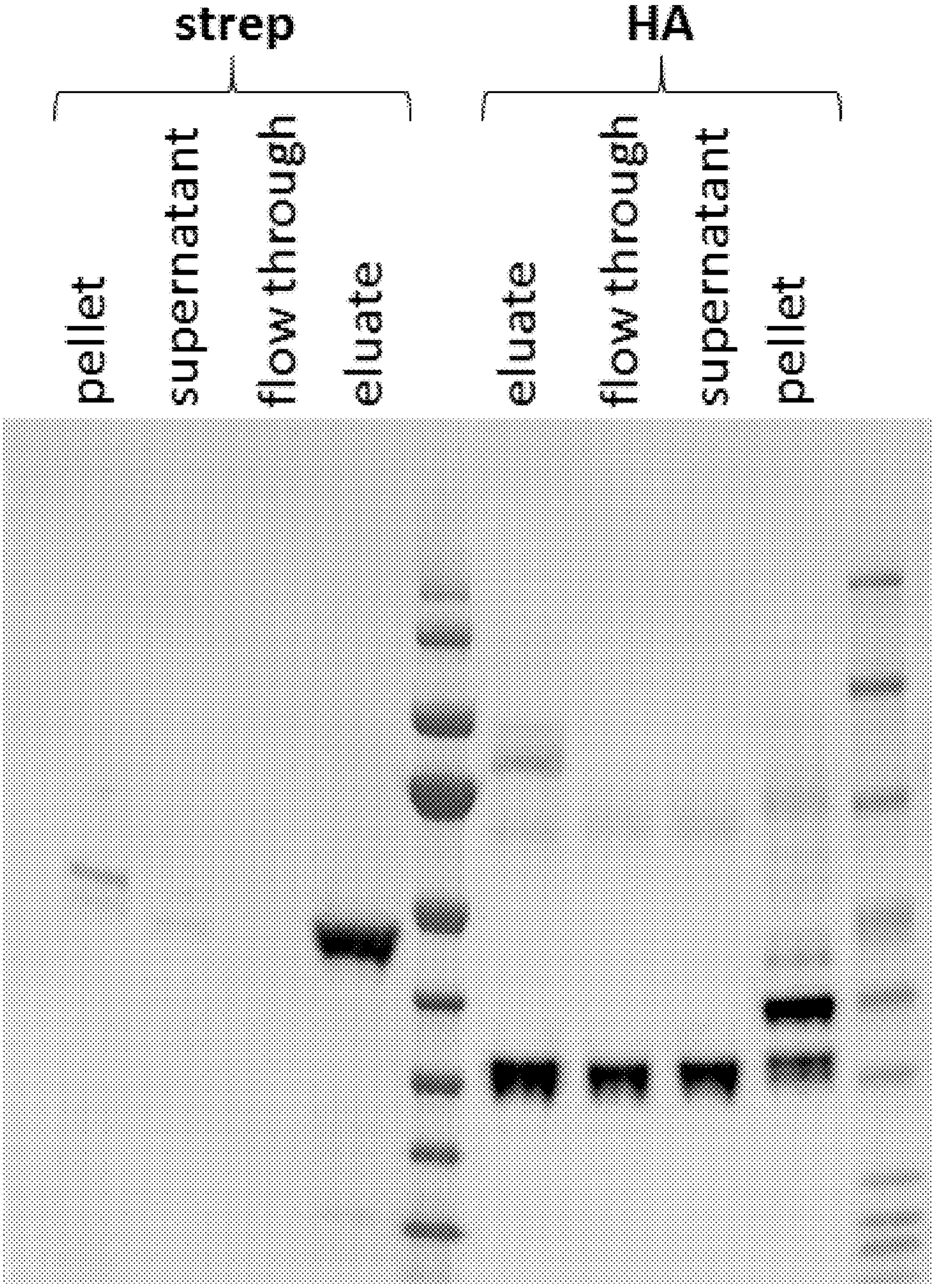

FIG. 19. Western blot showing that purification of mitochondrially targeted MTP-FAγ51::NifS::TS resulted in co-purification of scar9::GG::NifU::HA. Samples from steps (ii) to (v) were subjected to SDS-PAGE and Western blotting using either anti-Strep antibody to detect the NifS polypeptide or anti-HA antibody to detect the NifU polypeptide. The two bands for NifS correspond to the unprocessed and processed forms. The presence of the processed NifU form in the eluate showed that co-purification had occurred.

FIG. 20. ClustalW alignment of the first 300 amino acid residues of selected NifV/HCS-like amino acid sequences in this study along with *N. benthamiana* P72026 (SEQ ID NO:221) and P20586 (SEQ ID NO:222) translation, *K. oxytoca* NifV (SEQ ID NO:13), *Lotus japonicus* FEN1 (SEQ ID NO:215), and *Mycobacterium tuberculosis* α-isopropylmalate synthase (MtLeuA, SEQ ID NO:223). Other HCS sequences are from *Thermoanaerobacter brockii* (TbHCS; SEQ ID NO:206), *Thermincola potens* (TpHCS; SEQ ID NO:207), *Saccharomyces cerevisiae* (ScHCS; SEQ ID NO:208), *Nodularia spumigena* (NsHCS; SEQ ID NO:209), *Methanosarcina acetivorans* (MaHCS; SEQ ID NO:210), *Chlorobaculum tepidum* (CtHCS; SEQ ID NO:211) and *Methanocaldococcus infernus* (MiHCS1, SEQ ID NO:212; MiHCS2, SEQ ID NO:213; MiHCS, SEQ ID NO:214). Conserved residues in the active site of LeuA are identified by *. The four amino acid residues at positions R81, D82, H291, H293 hold $Zn^{2+}$, and the two amino acid residues E224, T260, along with $Zn^{2+}$ in its position forms the substrate binding pocket of MtLeuA (Koon et al., 2004).

Figure 21:
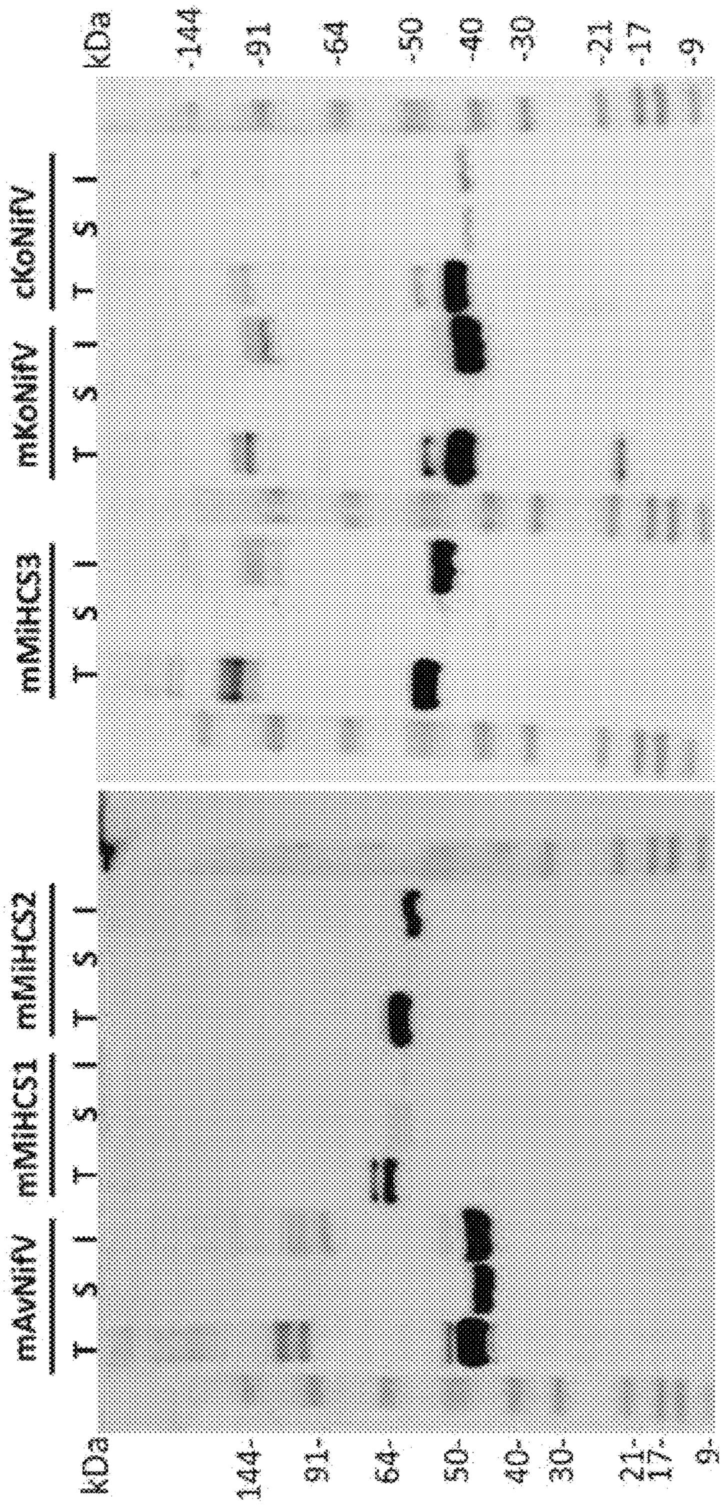
Figure 21:
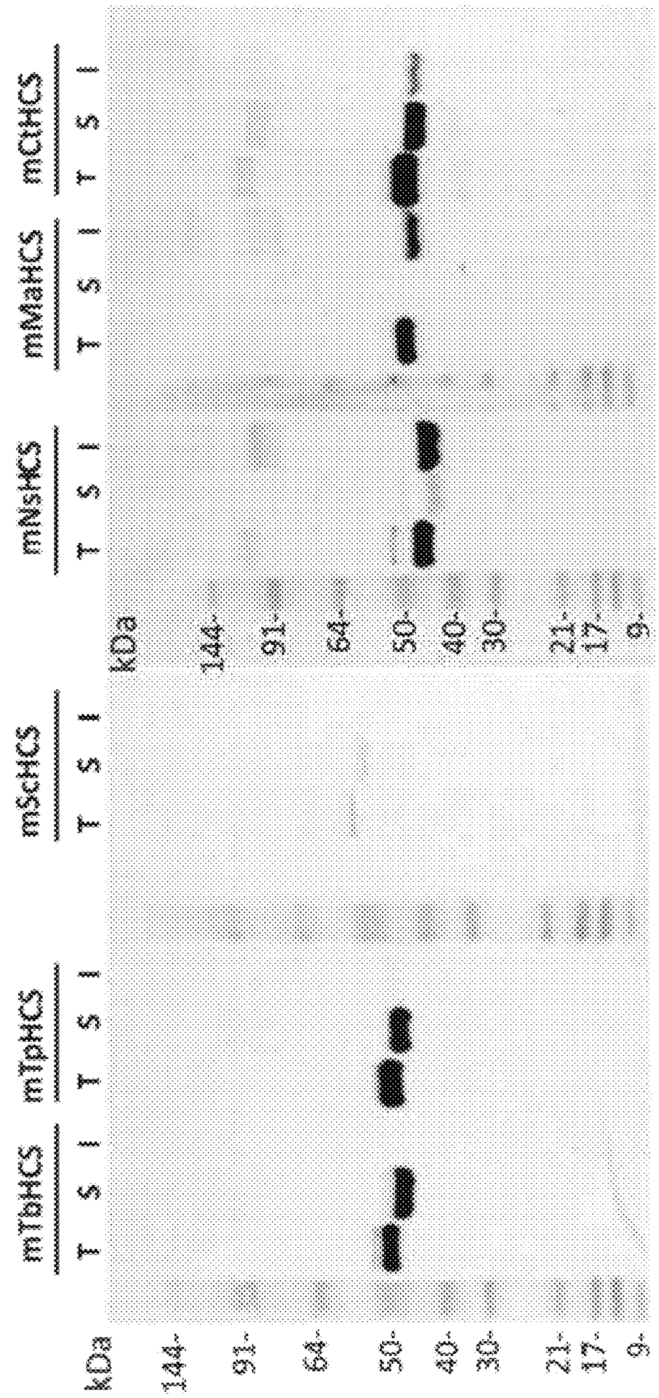

FIG. 21. Western blot analysis using anti-HA antibody of total, insoluble and soluble fractions of NifV/HCS-like fusion polypeptides (MTP-FAγ51::HA::NifV/HCS) after expression in *N. benthamiana* leaves. T, total protein; I, insoluble (pellet) fraction of total protein; S, soluble (supernatant) fraction of total protein. m, mitochondrial-targeted polypeptide; c, cytoplasmically-targeted polypeptide.

Figure 22:
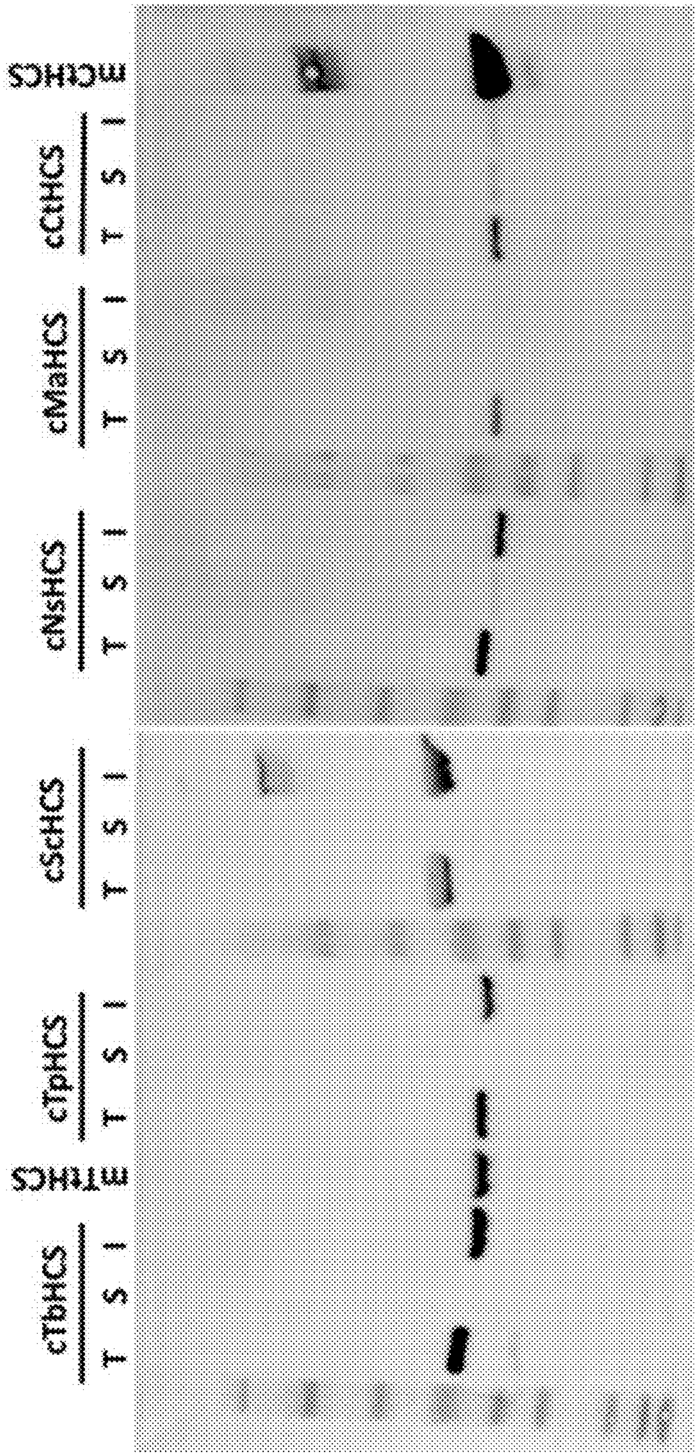
Figure 22:
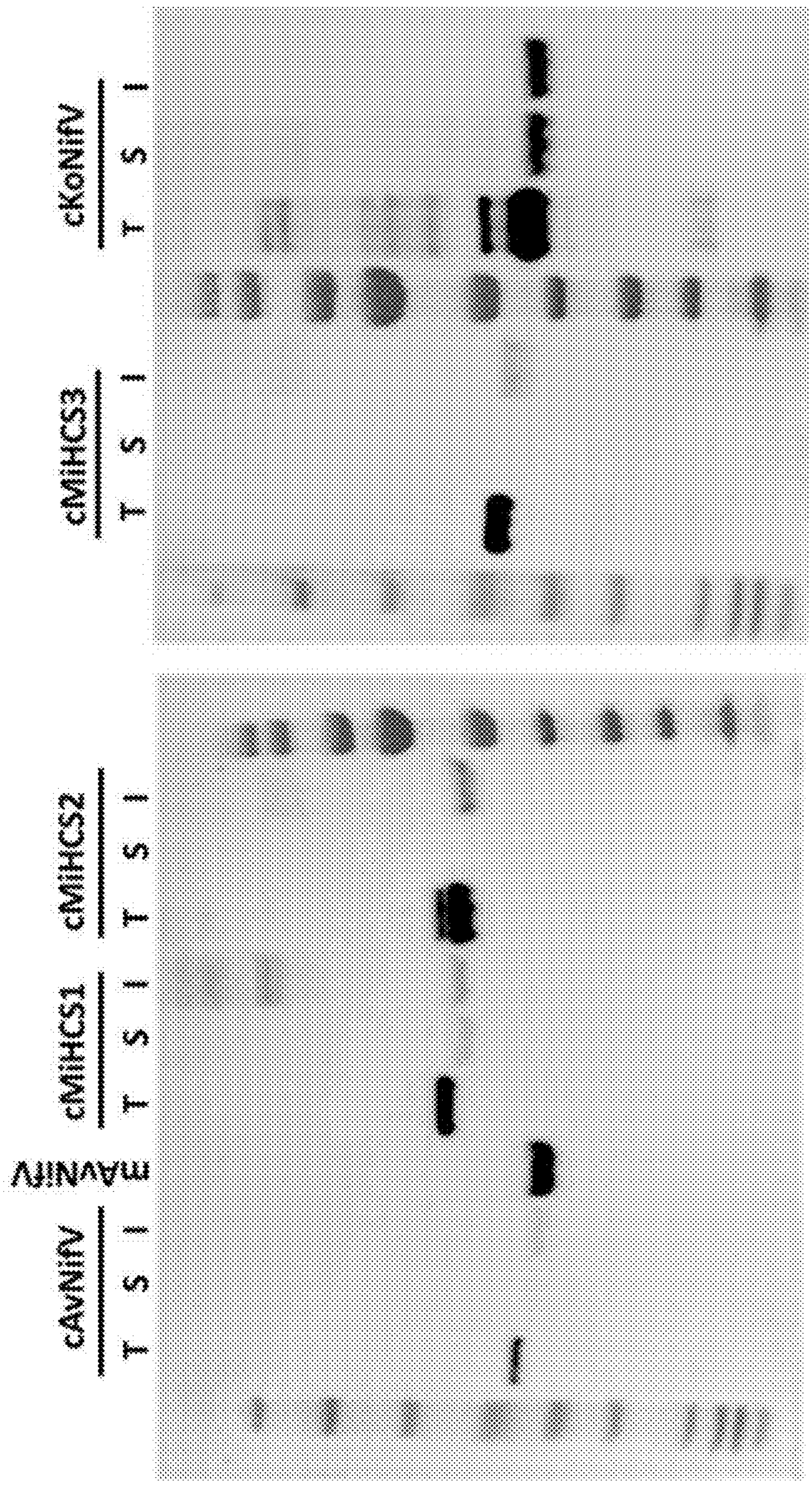

FIG. 22. Western blot analysis using anti-HA antibody of total, insoluble and soluble fractions of cytoplasmically-localised NifV/HCS-like fusion polypeptides (HA::NifV/HCS) after expression in *N. benthamiana* leaves, used as comparators for the corresponding mitochondrially-localised fusion polypeptides. T, total protein; I, insoluble (pellet) fraction of total protein; S, soluble (supernatant) fraction of total protein. c, cytoplasmically-targeted polypeptide; m, mitochondrial-targeted polypeptide.

Figure 23:
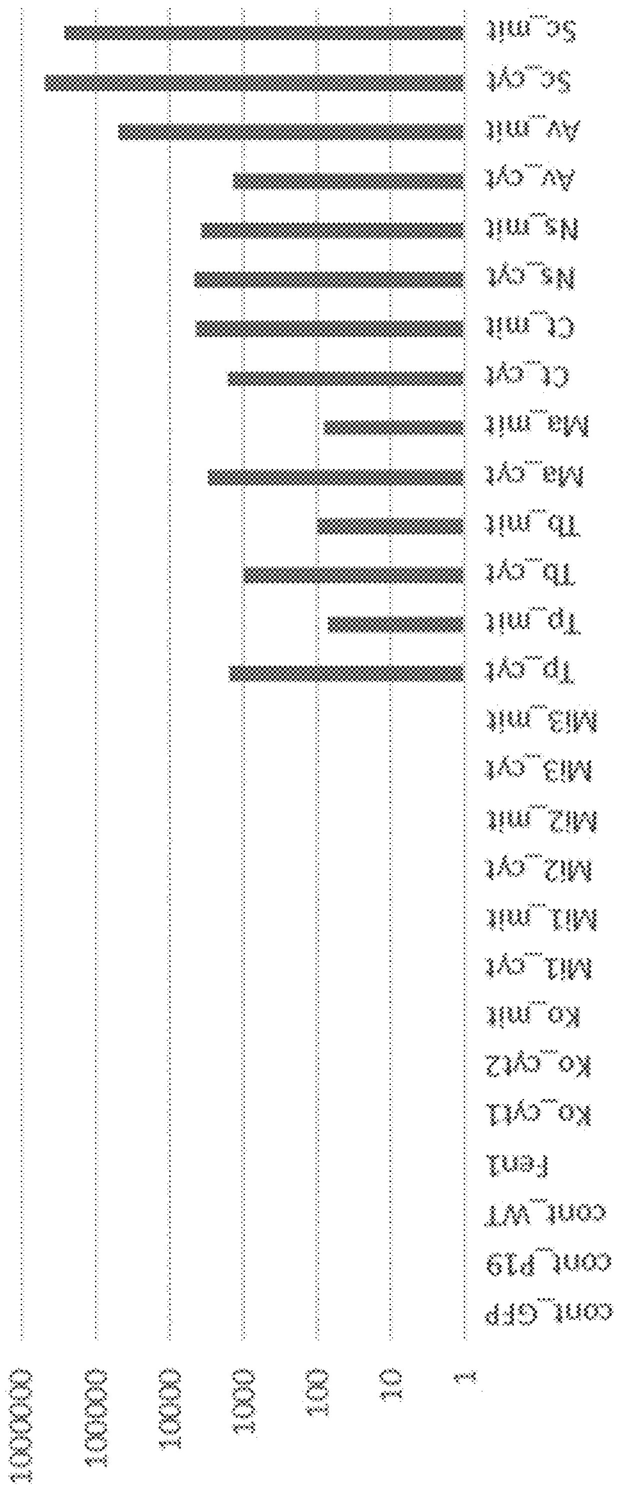

FIG. 23. Homocitrate target ion peak area after baseline subtraction (Login scale)

FIG. 24: Western blot analysis of the solubility of NifH fusion polypeptides in a transient leaf expression system in *N. benthamiana* leaves, using anti-Strep antibody to detect polypeptides having the TwinStrep epitope. All of the NifH genetic constructs were co-infiltrated with SN44 encoding a NifM fusion polypeptide from *K. oxytoca*. Protein samples were prepared under aerobic conditions.

Figure 25:
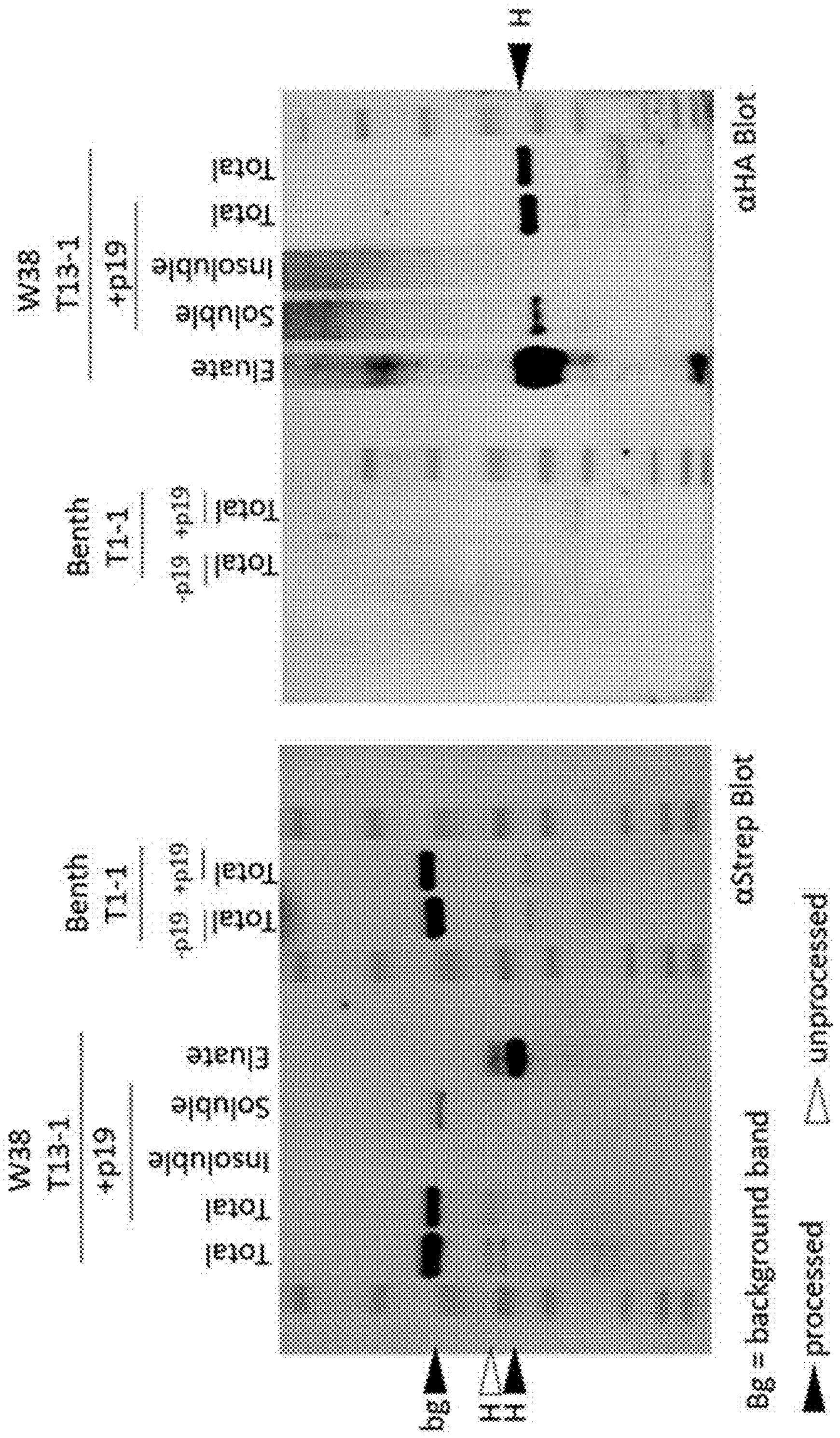

FIG. 25. Western blot showing the results of purification of a NifH fusion polypeptide encoded by SL6 in stably transformed tobacco. The NifH gene encoded a MTP-CoxIV::TwinStrep::KoNifH::HA fusion polypeptide. Samples of 5 μL from stages in the purification process were analysed by Western blot and probed with antibodies recognising either the Strep or HA epitopes. Samples from the total, insoluble and soluble fractions are indicated above the lanes. Closed arrowheads indicate unprocessed NifH polypeptide, black arrowheads indicate the processed form.

Figure 26:
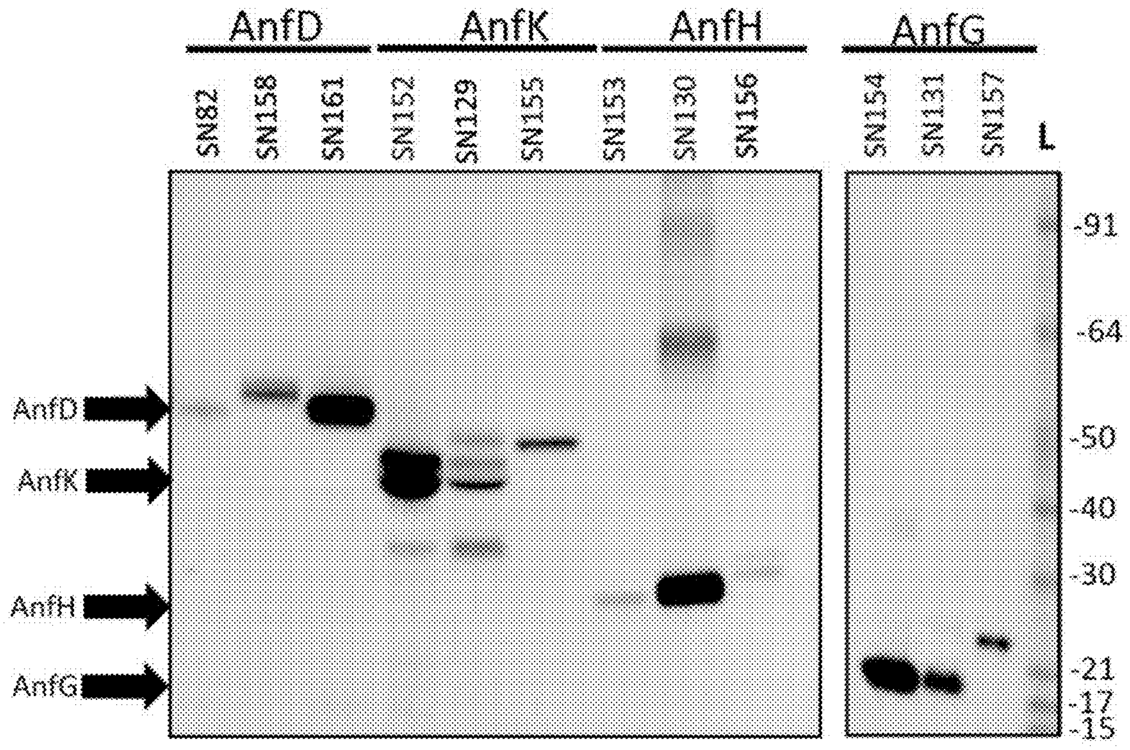

FIG. 26. Western blot analysis of the expression and processing of Anf fusion polypeptides after transient introduction of genetic constructs in *N. benthamiana* leaves. The blot had sets of three adjacent lanes for (left to right) AnfD, AnfK, AnfH and AnfG fusion polypeptides. Each set included the test fusion polypeptide MTP-FAγ51::HA::Anf and the two control polypeptides HA::Anf and mFAγ51::HA::Anf as molecular weight markers. L, Ladder of molecular weight markers (kDa).

Figure 27:
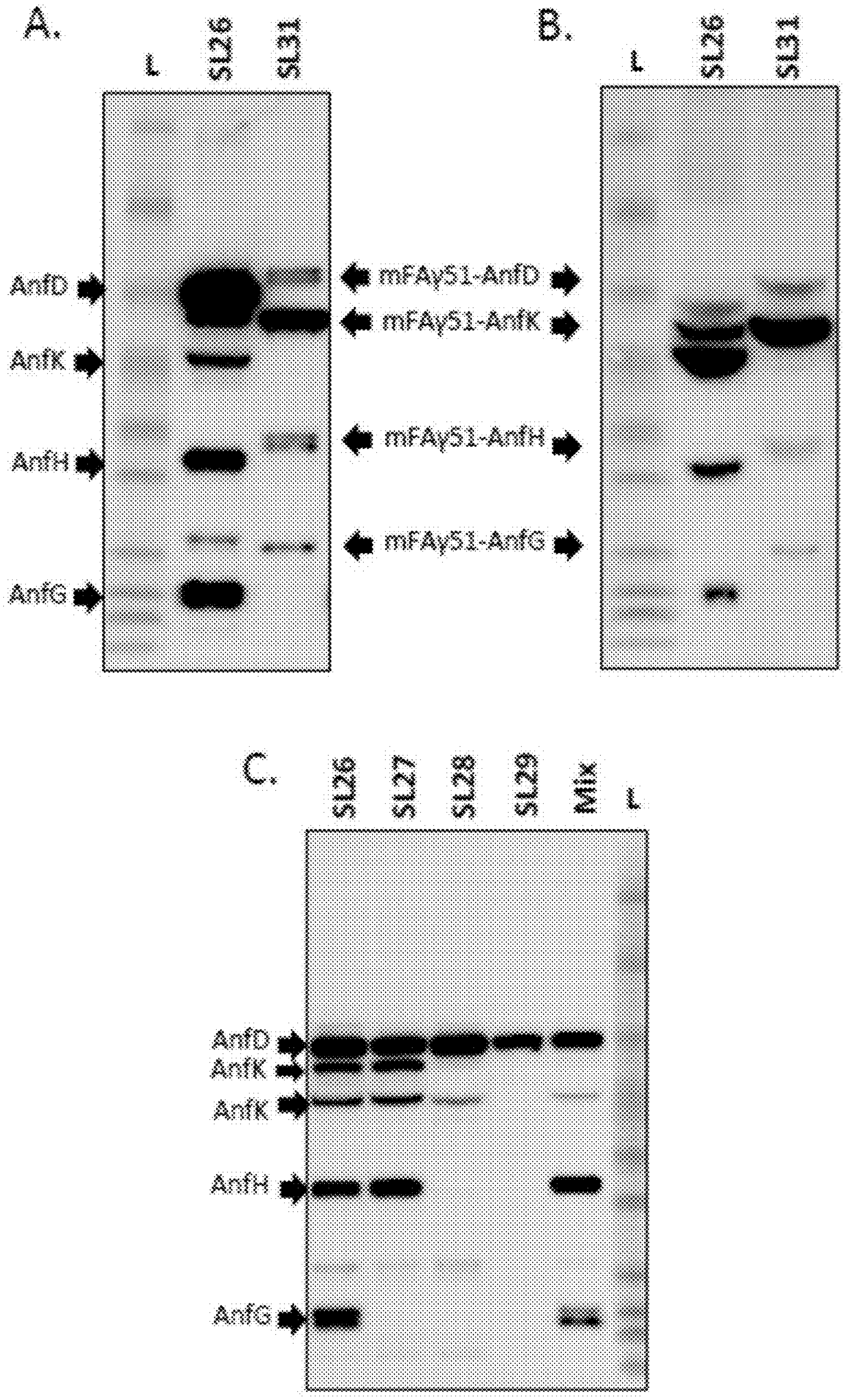

FIG. 27. Western blot showing expression and processing of all four of the AnfD, AnfK, AnfH and AnfG fusion polypeptides when expressed from multi-gene constructs in *N. benthamiana* leaves. A. Western blot analysis of mitochondrially-targeted AnfD, AnfK, AnfG and AnfH fusion polypeptides expressed from SL26 and unprocessed polypeptides from SL31, detected in total protein extracts from the transient leaf assay. B. Western blot analysis of proteins resulting from expression of mitochondrially-targeted AnfD, AnfK, AnfG and AnfH fusion polypeptides from SL26, and unprocessed fusion polypeptides from SL31. C. Western blot showing expression and processing of fusion polypeptides from the multigene constructs SL26, SL27 and SL28, the single gene construct SL29, and a mixture (Mix) of the four single gene constructs SN161, SN129, SN130 and SN131. When present, AnfK showed an upper, unprocessed band and a lower, processed band.

Figure 28:
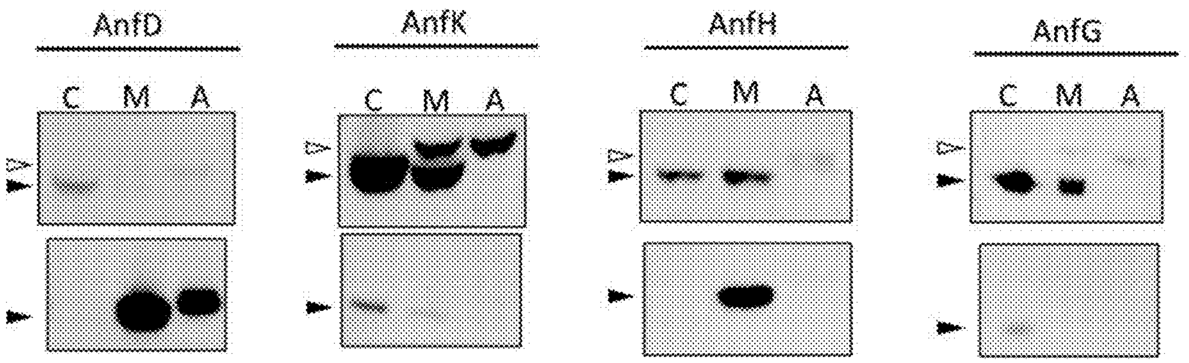

FIG. 28. Western blot showing solubility of individual Anf polypeptides expressed from single gene vectors in *N. benthamiana* leaf cells when localised to the cytoplasm or mitochondria. Upper panels, soluble fractions for the AnfD, AnfK, AnfH and AnfG fusion polypeptides; lower panel, insoluble fractions for the AnfD, AnfK, AnfH and AnfG fusion polypeptides. C, cytoplasmic localisation; M, mitochondrial localisation; A, alanine substituted mMTP-FAγ51. Black arrowheads indicate the positions of the MPP-cleaved proteins, open arrowheads the unprocessed polypeptides. See Table 20 for the predicted molecular weights of each Anf in the unprocessed and MPP-processed polypeptides.

Figure 29:
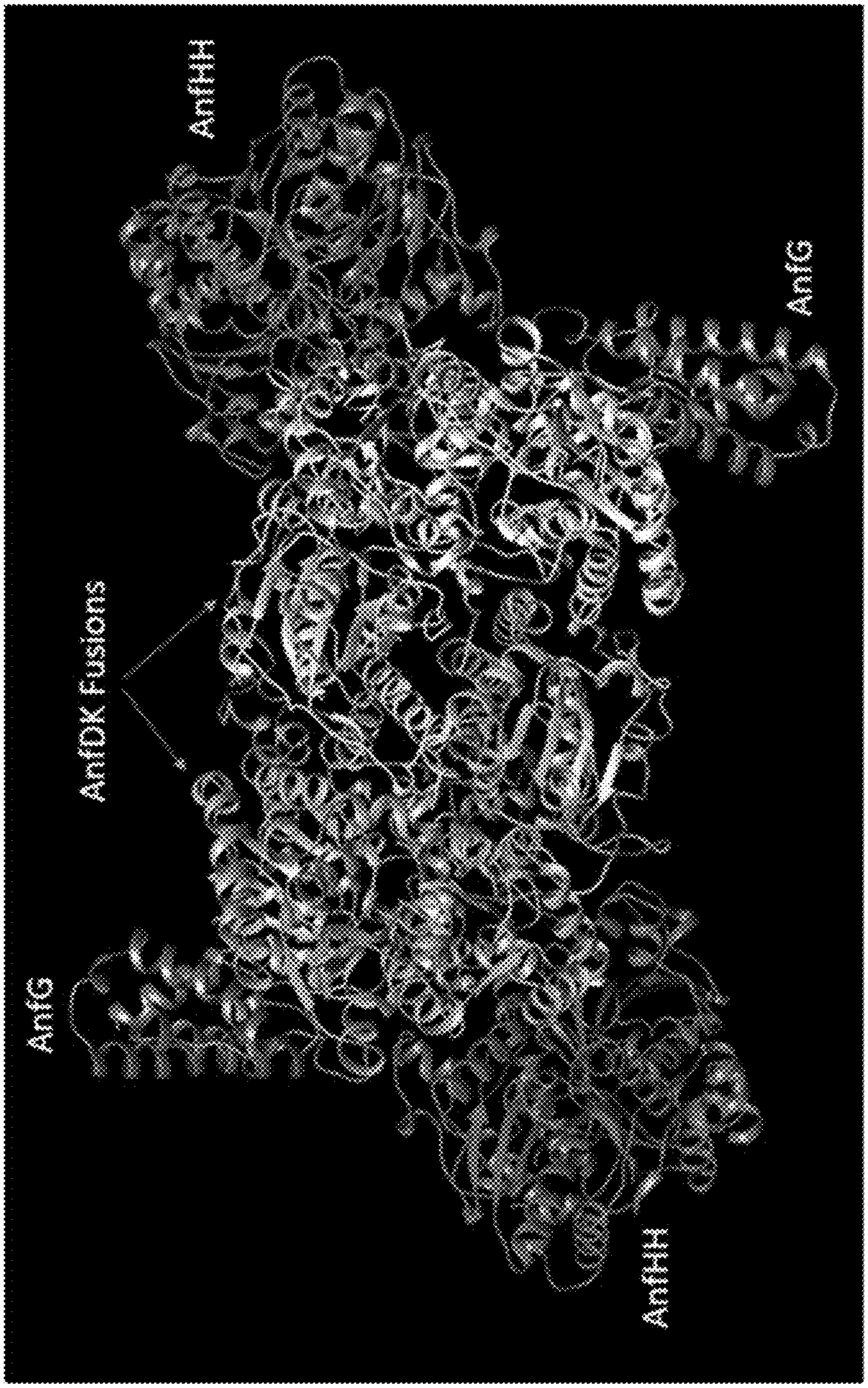

FIG. 29. Homology model of the AnfDKHG complex for the Fe-nitrogenase, based on the *A. vinelandii* Anf amino acid sequences with a linker joining the AnfD and AnfK polypeptides. Initial coordinates prior to the 20 ns simulation. The predicted structure of the AnfD::Linker::AnfK polypeptide, using a 16-amino acid linker, was complexed with AnfH dimers and AnfG. The dimer of AnfH is annotated as AnfHH.

Figure 30:
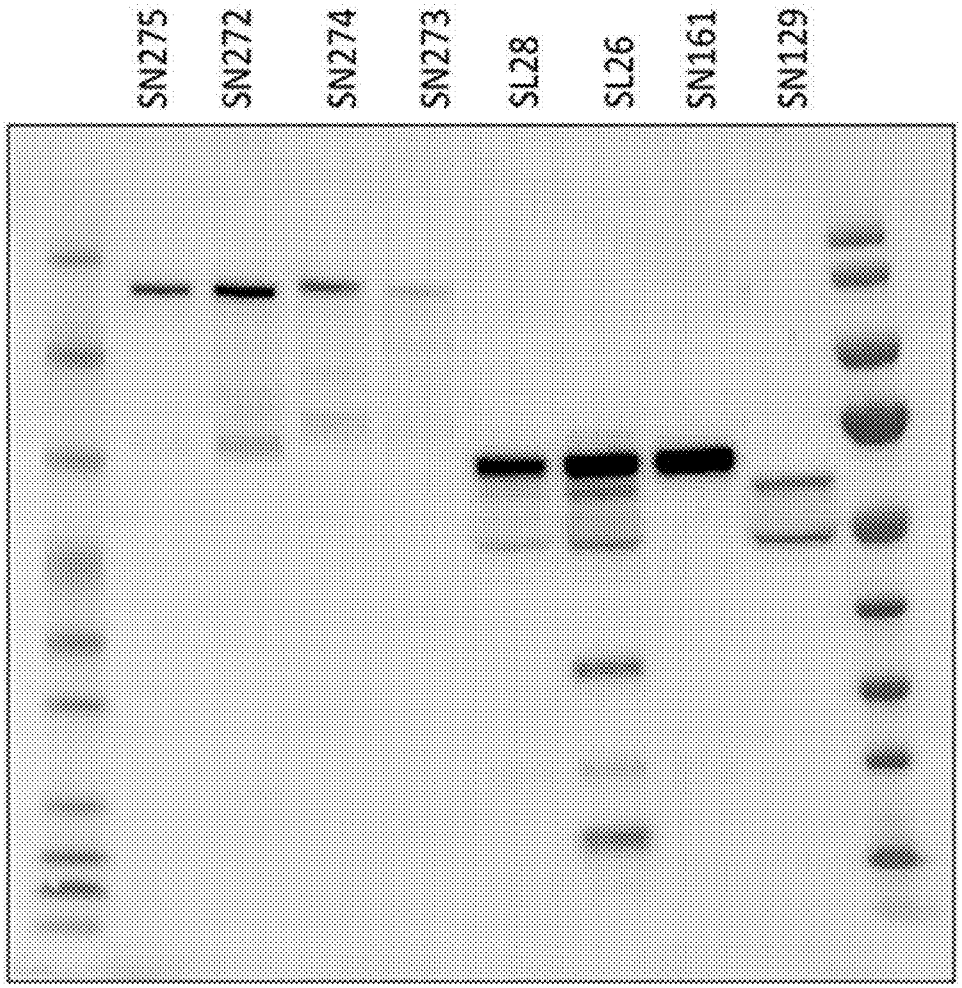

FIG. 30. Western blot analysis of total protein extracts from *N. benthamiana* leaves infiltrated with genetic constructs for expression of AnfD and AnfK polypeptides, either fused or separate. The blot was probed with anti-HA antibody. The expression of AnfD-linker-AnfK fusion polypeptides from SN272-SN275 was compared to the expression from separate genes on the vectors SL26 and SL28. SN161 and SN129 provided the controls for the expression individually of AnfD and AnfK, respectively.

Figure 31:
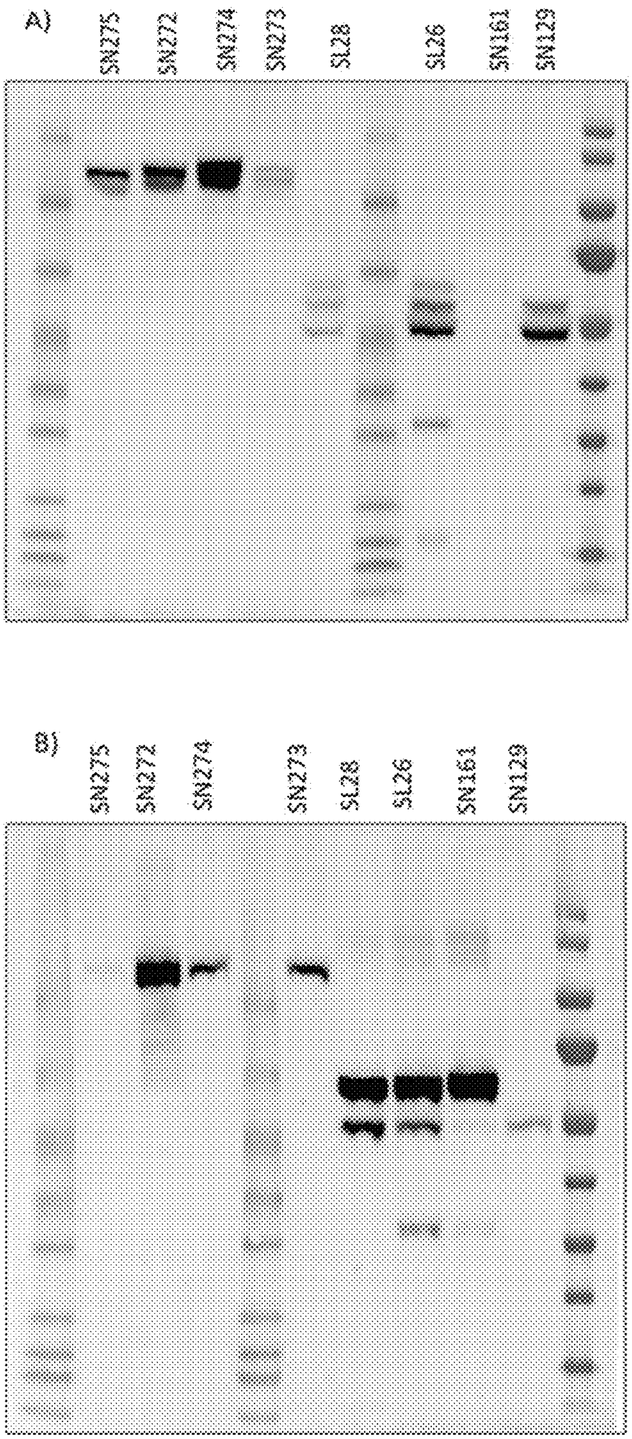

FIG. 31. Western blot analysis of (A) soluble and (B) insoluble fractions of proteins from *N. benthamiana* leaves infiltrated with genetic constructs for expression of AnfD and AnfK genes. SN272-SN275 each encoded AnfD-linker-AnfK fusion polypeptides whereas SL26 and SL28 expressed separate polypeptides.

Figure 32:
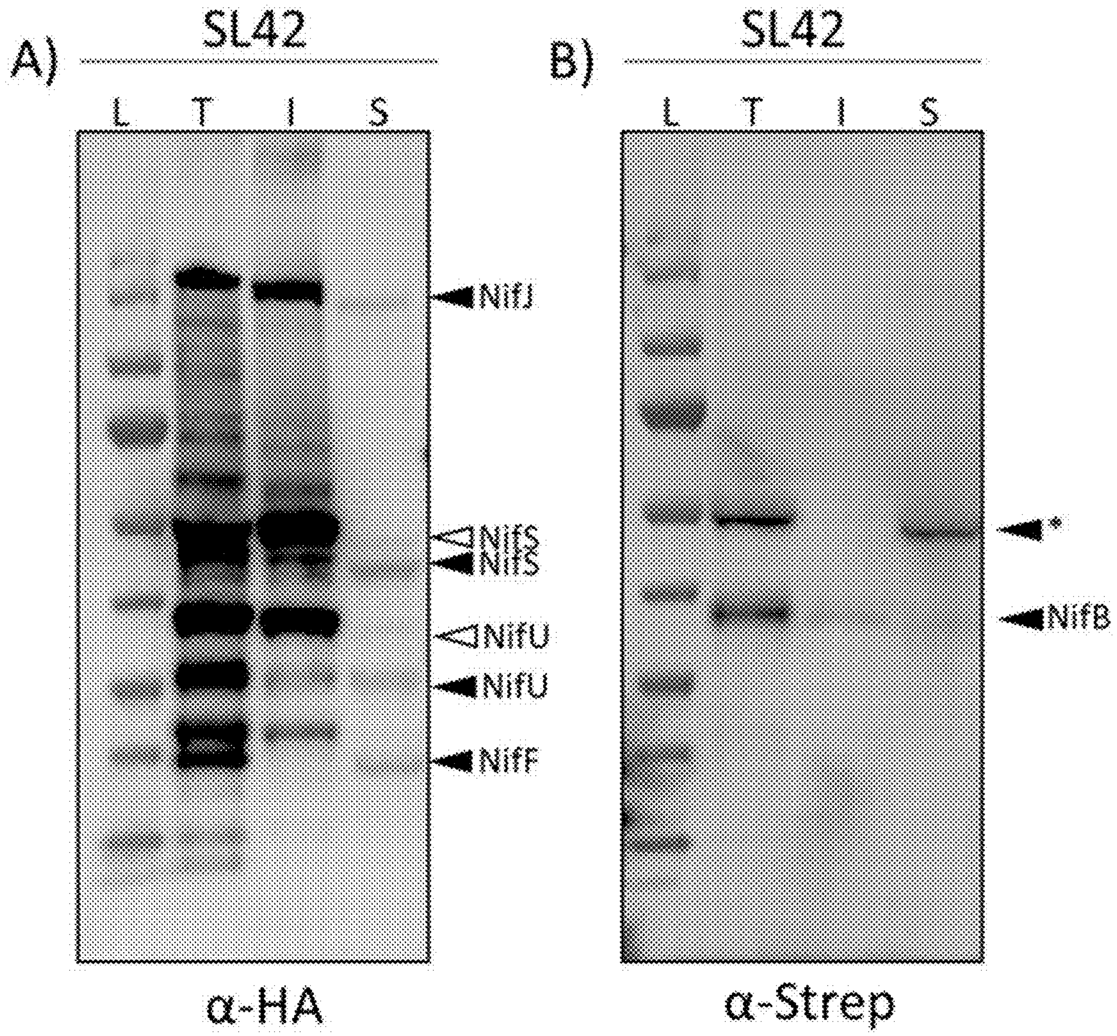

FIG. 32. Western blot analysis of polypeptides produced from SL42 in *N. benthamiana* leaves, including total (T), insoluble (I) and soluble (S) fractions using the anti-HA (panel A) or anti-Strep antibody (panel B) for detection. Black arrowheads indicate the positions of the processed polypeptide bands after mitochondrial cleavage by MPP, white arrowheads indicate the bands for the unprocessed polypeptides. Panel B probed with the anti-Strep antibody shows the processed NifB polypeptide.

Figure 33:
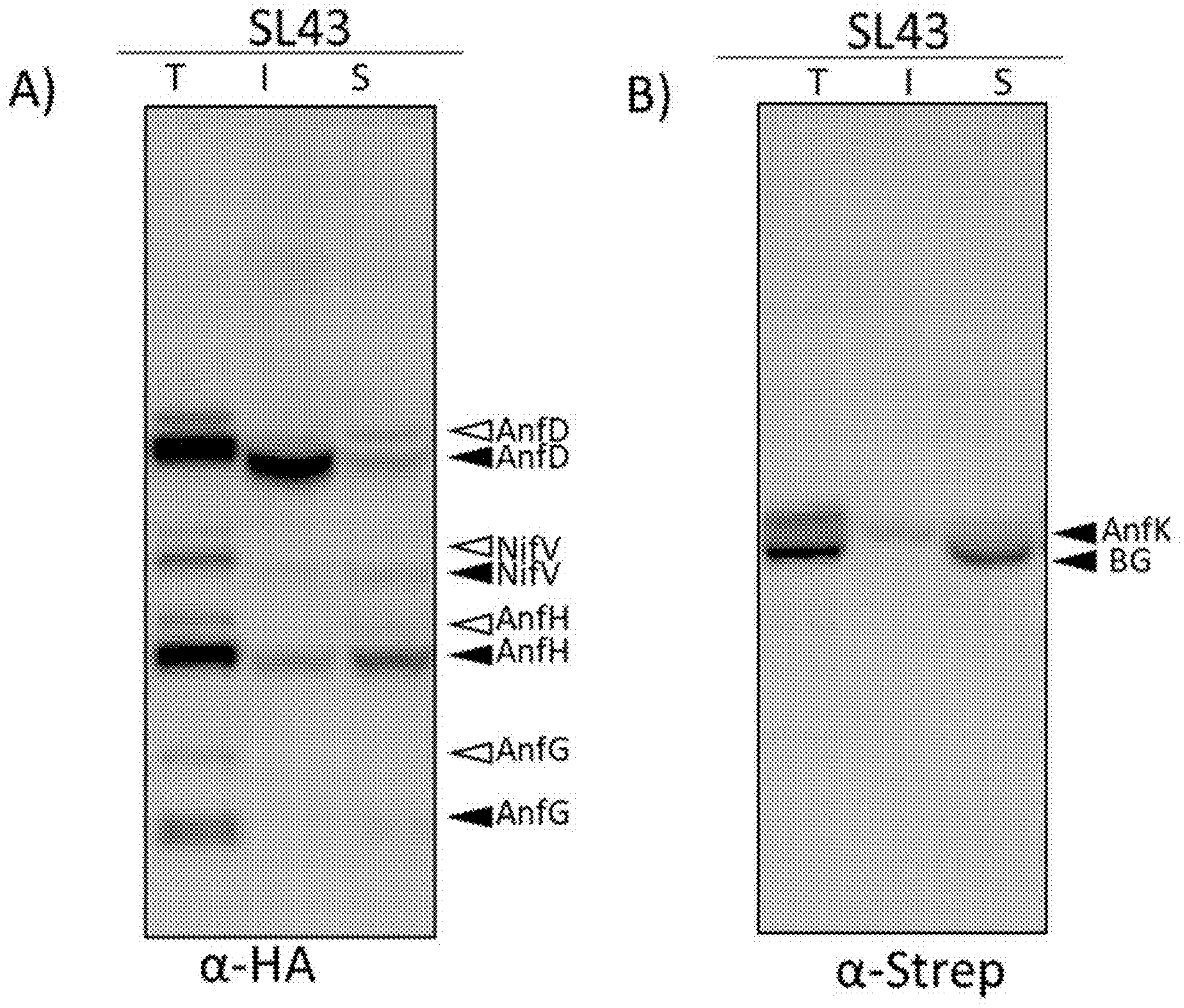

FIG. 33. Western blot analysis of polypeptides produced from SL43 in *N. benthamiana* leaves, including total (T), insoluble (I) and soluble (S) fractions using the anti-HA (panel A) or anti-Strep antibody (panel B) for detection. Black arrowheads indicate the positions of the processed polypeptide bands after mitochondrial cleavage by MPP, white arrowheads indicate the bands for the unprocessed polypeptides. Panel B probed with the anti-Strep antibody shows the processed AnfK polypeptide.

Figure 34:
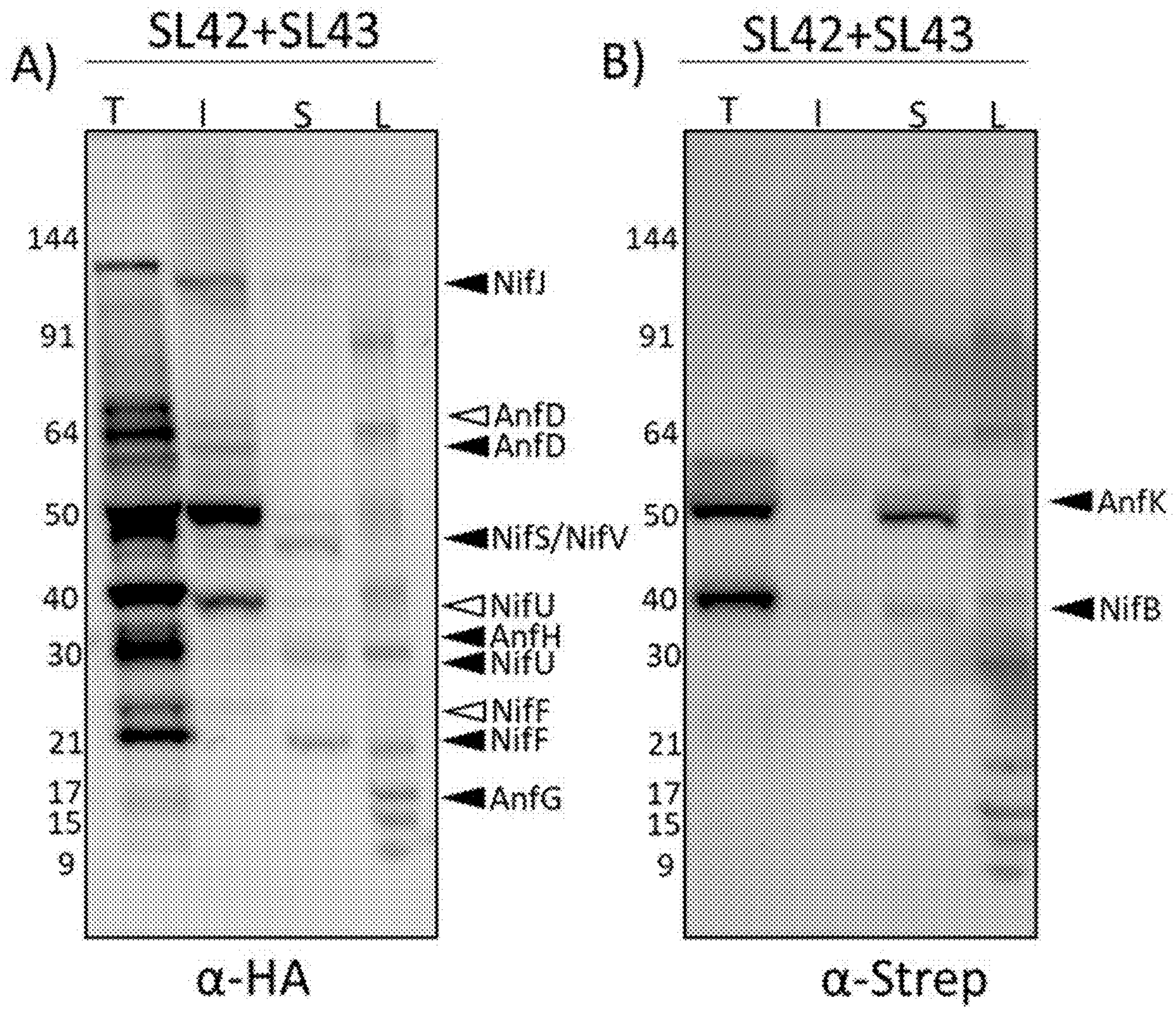

FIG. 34. Western blot analysis of polypeptides produced from SL42 and SL43 introduced together into *N. benthamiana* leaves, including total (T), insoluble (I) and soluble (S) fractions using the anti-HA (panel A) or anti-Strep antibody (panel B) for detection. The numbers to the side of panel A) and B) indicate the molecular weights (kDa) of the markers in the first lane. Black arrowheads indicate the positions of the processed polypeptide bands after mitochondrial cleavage by MPP, white arrowheads indicate the bands for the unprocessed polypeptides.

Figure 35:
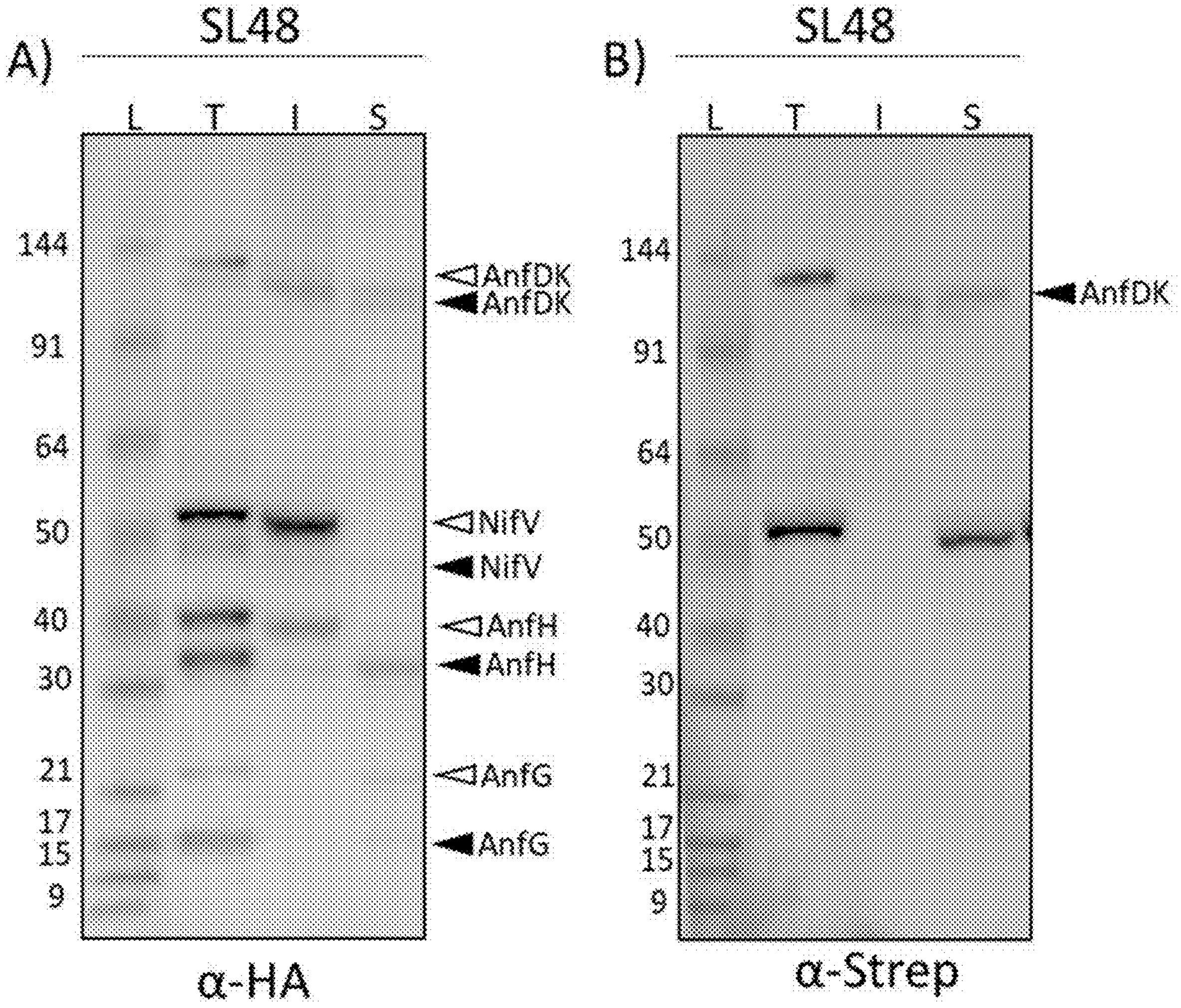

FIG. 35. Western blot analysis of polypeptides produced from SL48 in *N. benthamiana* leaves, including total (T), insoluble (I) and soluble (S) fractions using the anti-HA (panel A) or anti-Strep antibody (panel B) for detection. The numbers to the side of panel A) and B) indicate the molecular weights (kDa) of the markers in the first lane. Black arrowheads indicate the positions of the processed polypeptide bands after mitochondrial cleavage by MPP, white arrowheads indicate the bands for the unprocessed polypeptides. Panel B probed with the anti-Strep antibody shows the processed NifB polypeptide.

Figure 36:
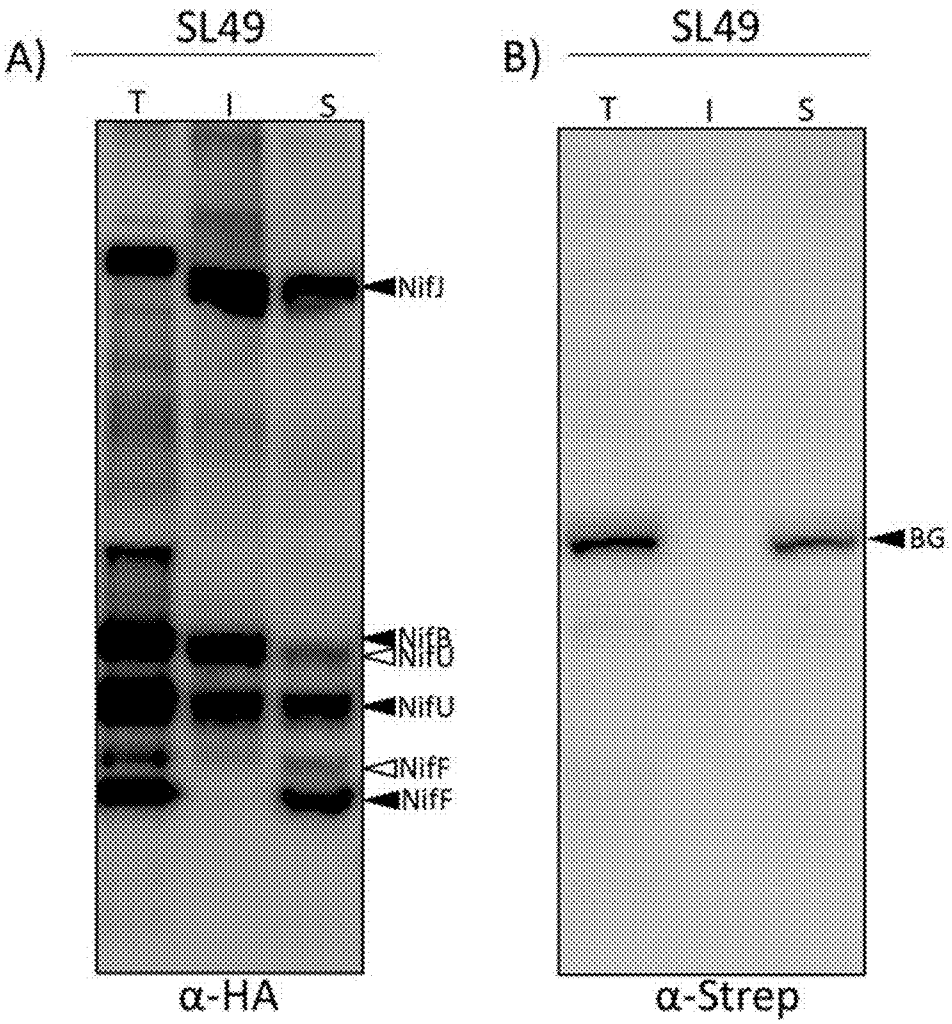

FIG. 36. Western blot analysis of polypeptides produced from SL49 in *N. benthamiana* leaves, including total (T), insoluble (I) and soluble (S) fractions using the anti-HA (panel A) or anti-Strep antibody (panel B) for detection. Black arrowheads indicate the positions of the processed polypeptide bands after mitochondrial cleavage by MPP, white arrowheads indicate the bands for the unprocessed polypeptides. Panel B probed with the anti-Strep antibody shows the processed AnfK polypeptide.

Figure 37:
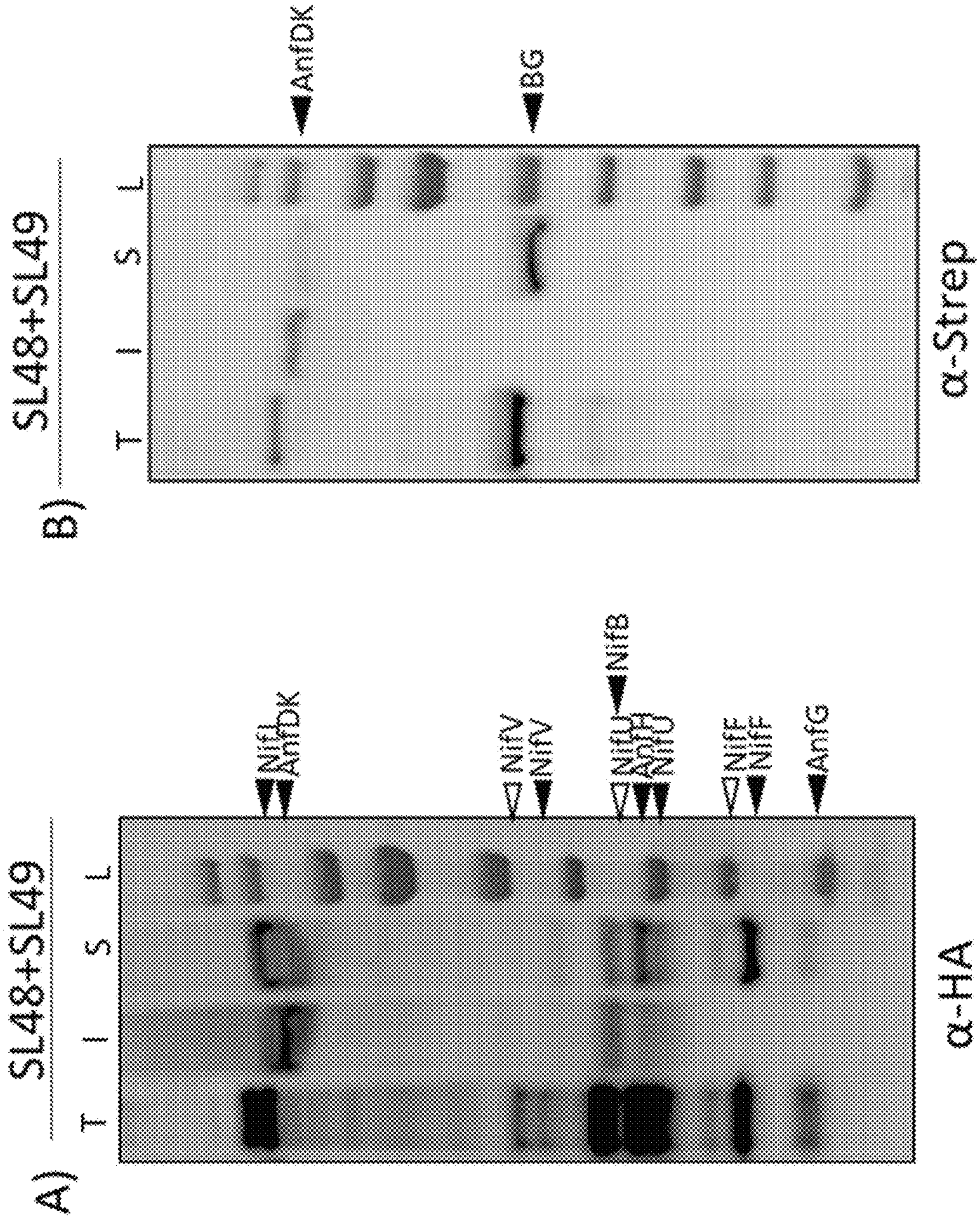

FIG. 37. Western blot analysis of polypeptides produced from SL48 and SL49 introduced together into *N. benthamiana* leaves, including total (T), insoluble (I) and soluble (S) fractions using the anti-HA (panel A) or anti-Strep antibody (panel B) for detection. Black arrowheads indicate the positions of the processed polypeptide bands after mitochondrial cleavage by MPP, white arrowheads indicate the bands for the unprocessed polypeptides.

Figure 38:
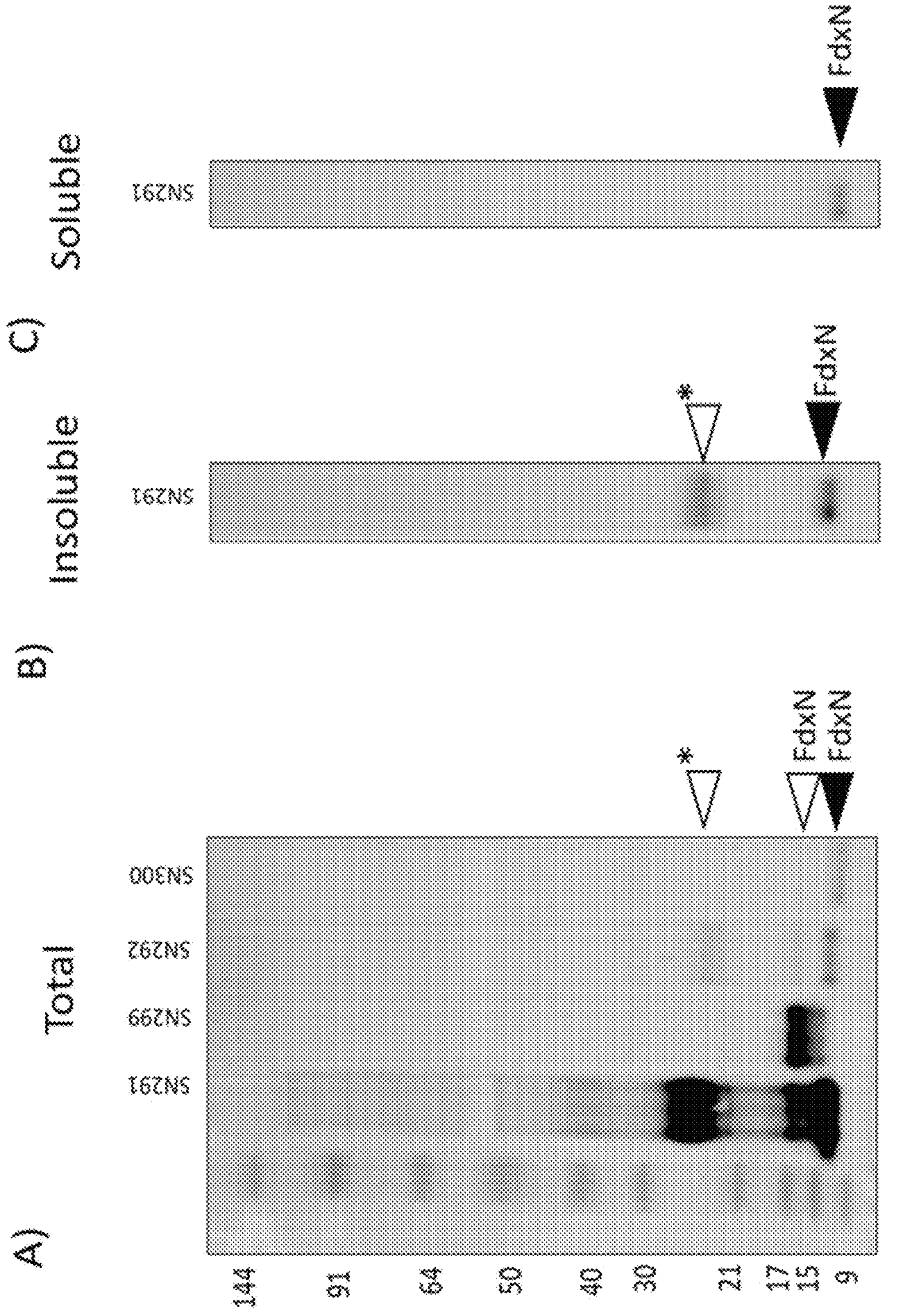

FIG. 38. Western blot analysis of polypeptides produced from SN292, SN291, SN299 and SN300 in *N. benthamiana* leaves, including total, panel A), insoluble, panel B), and soluble, panel C), fractions using the anti-HA for detection. The numbers to the side indicate the molecular weights (kDa) of the markers in the first lane. Black arrowheads indicate the positions of the processed polypeptide bands after mitochondrial cleavage, white arrowheads indicate the bands for the unprocessed polypeptides, the * indicates a potential dimer of the FdxN protein.

Figure 39:
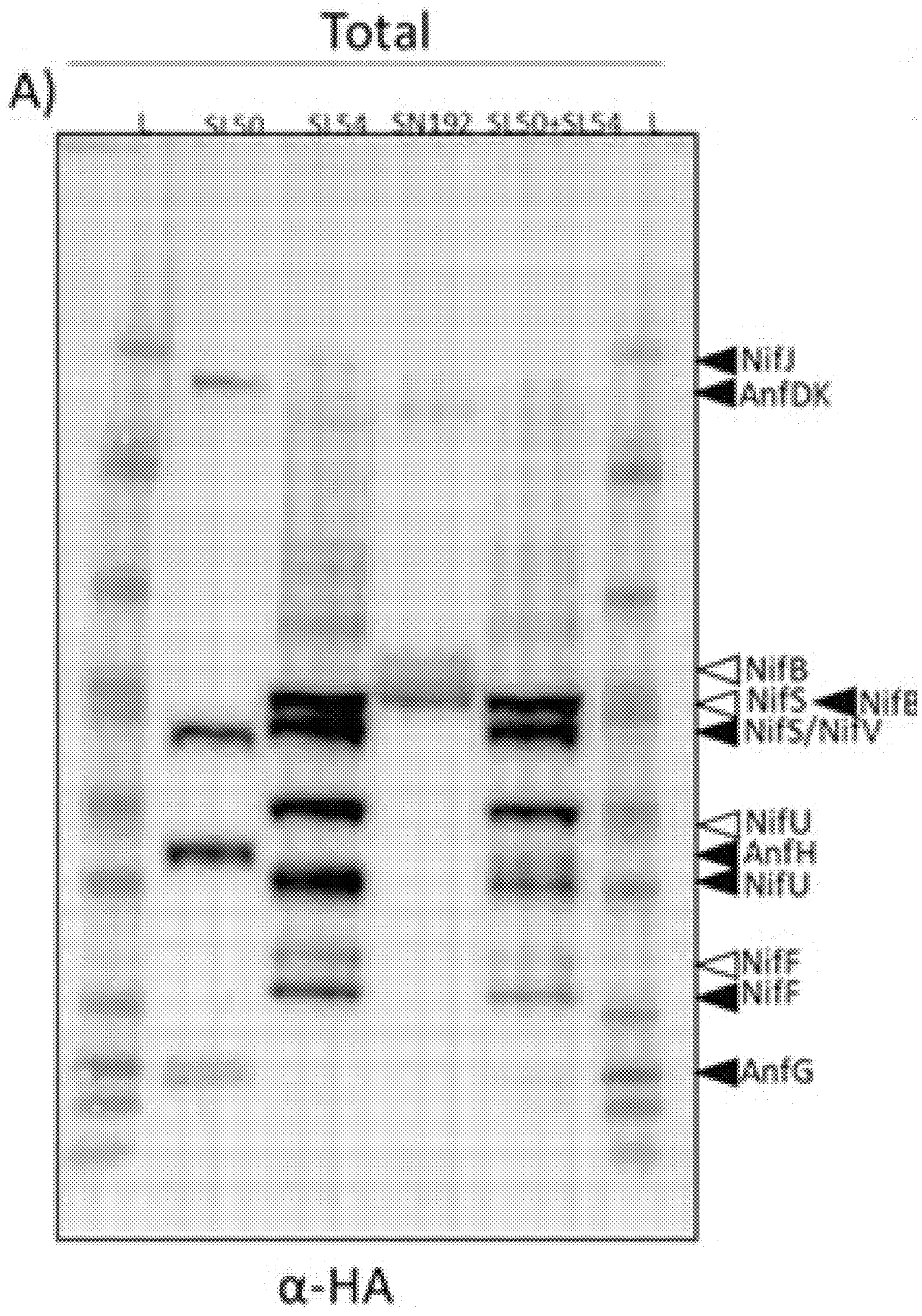
Figure 39:
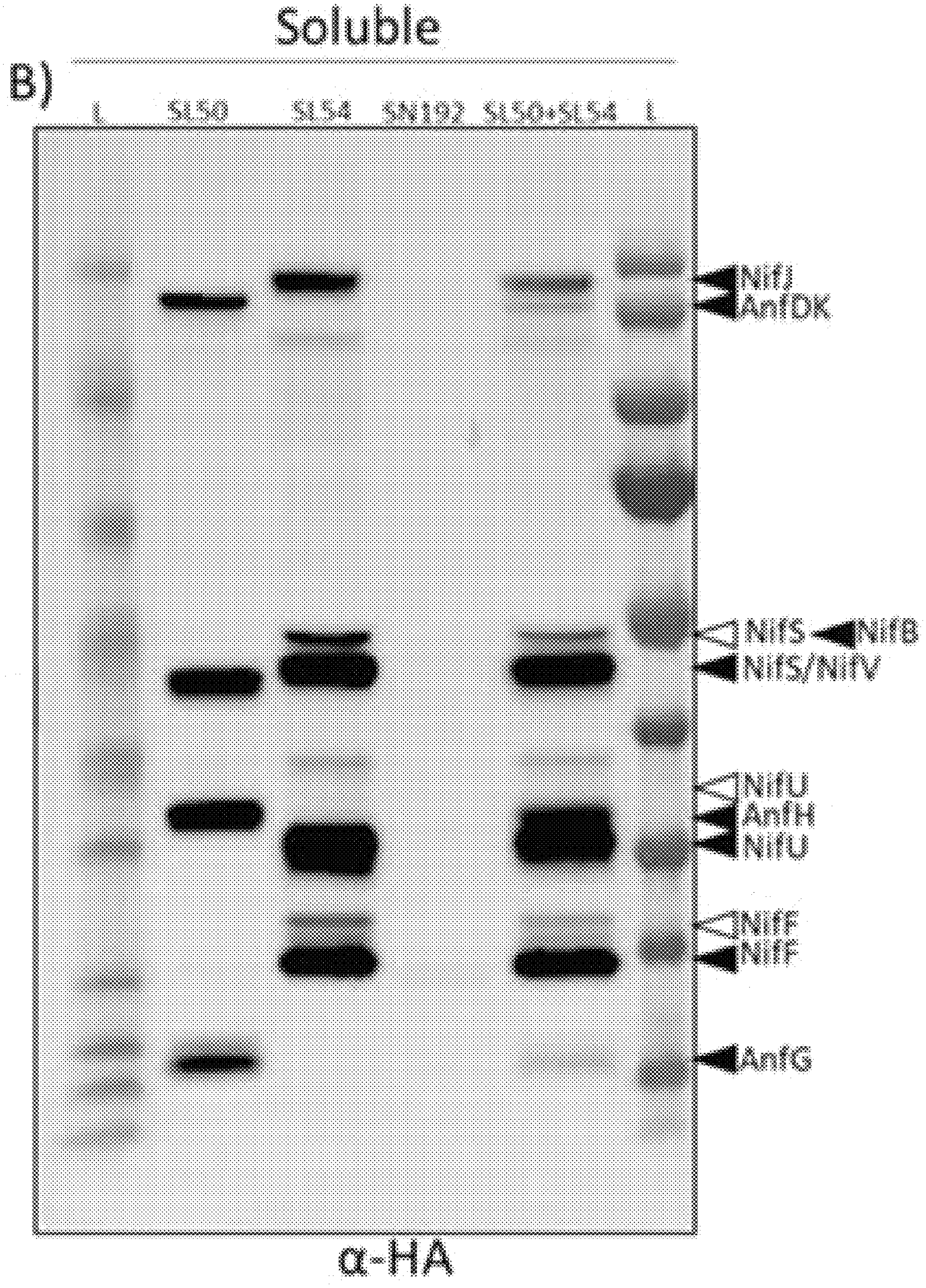
Figure 39:
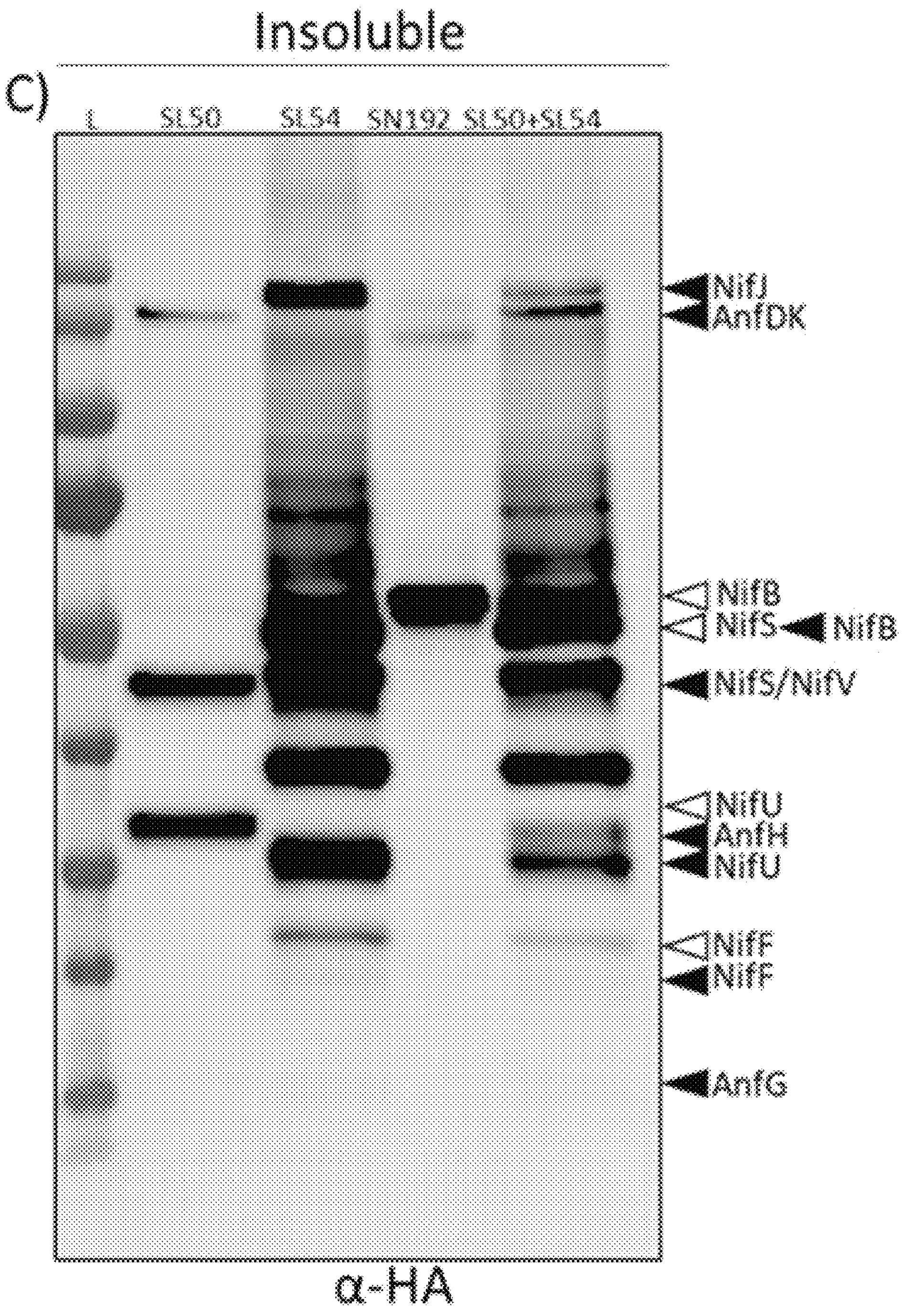

FIG. 39. Western blot analysis of polypeptides produced from SN192, SL50 and SL54 introduced individually, as well as SL50 and SL54 together into *N. benthamiana* leaves, including Total (panel A), Soluble (panel B) and Insoluble (panel C) fractions using the anti-HA for detection. Black arrowheads indicate the positions of the processed polypeptide bands after mitochondrial cleavage, white arrowheads indicate the bands for the unprocessed polypeptides.

Figure 40:
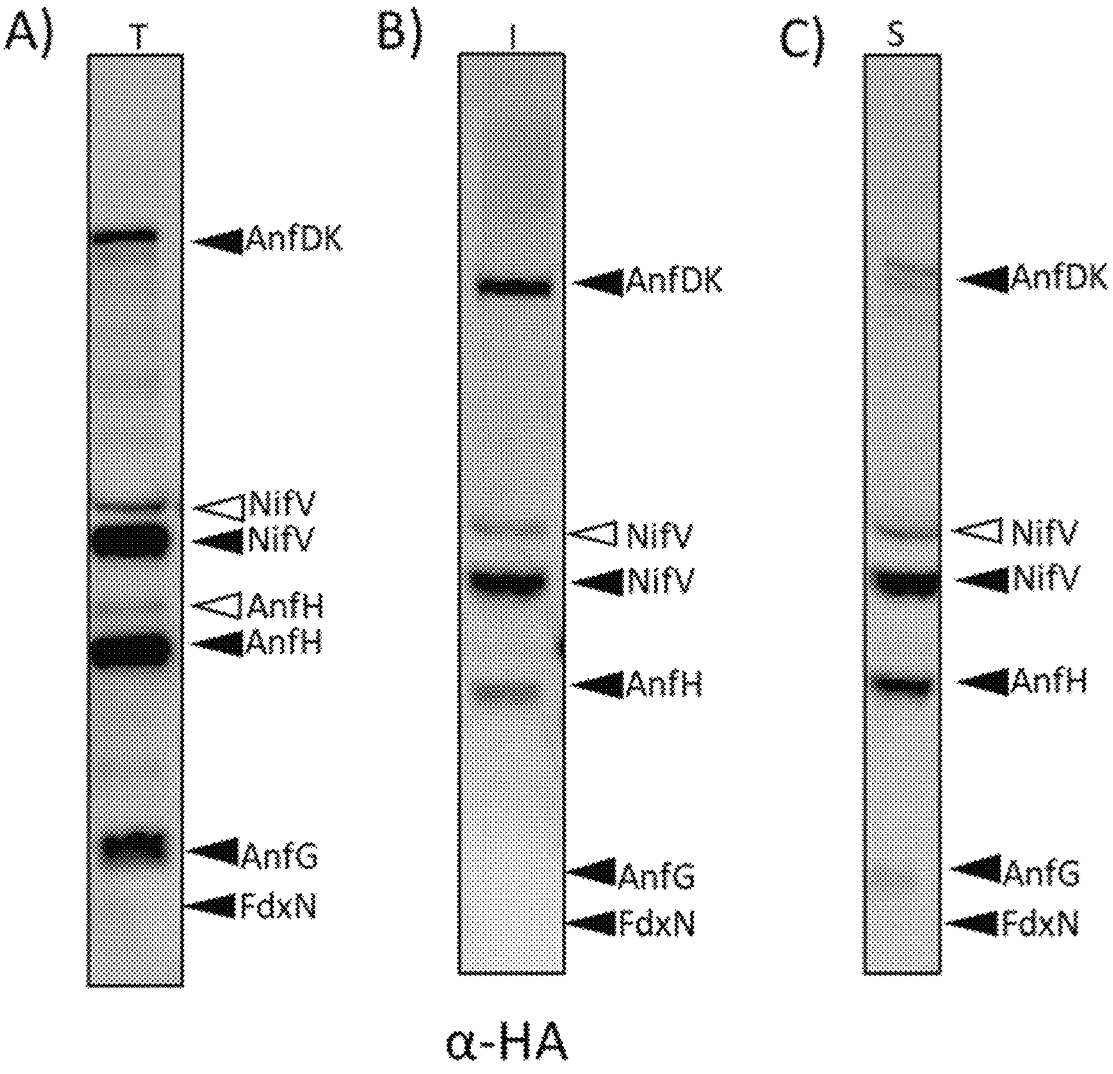

FIG. 40. Western blot analysis of polypeptides produced from SL50 in *N. benthamiana* leaves, including total, panel A), insoluble, panel B), and soluble, panel C), fractions using the anti-HA for detection. Black arrowheads indicate the positions of the processed polypeptide bands after mitochondrial cleavage, white arrowheads indicate the bands for the unprocessed polypeptides.

Figure 41:
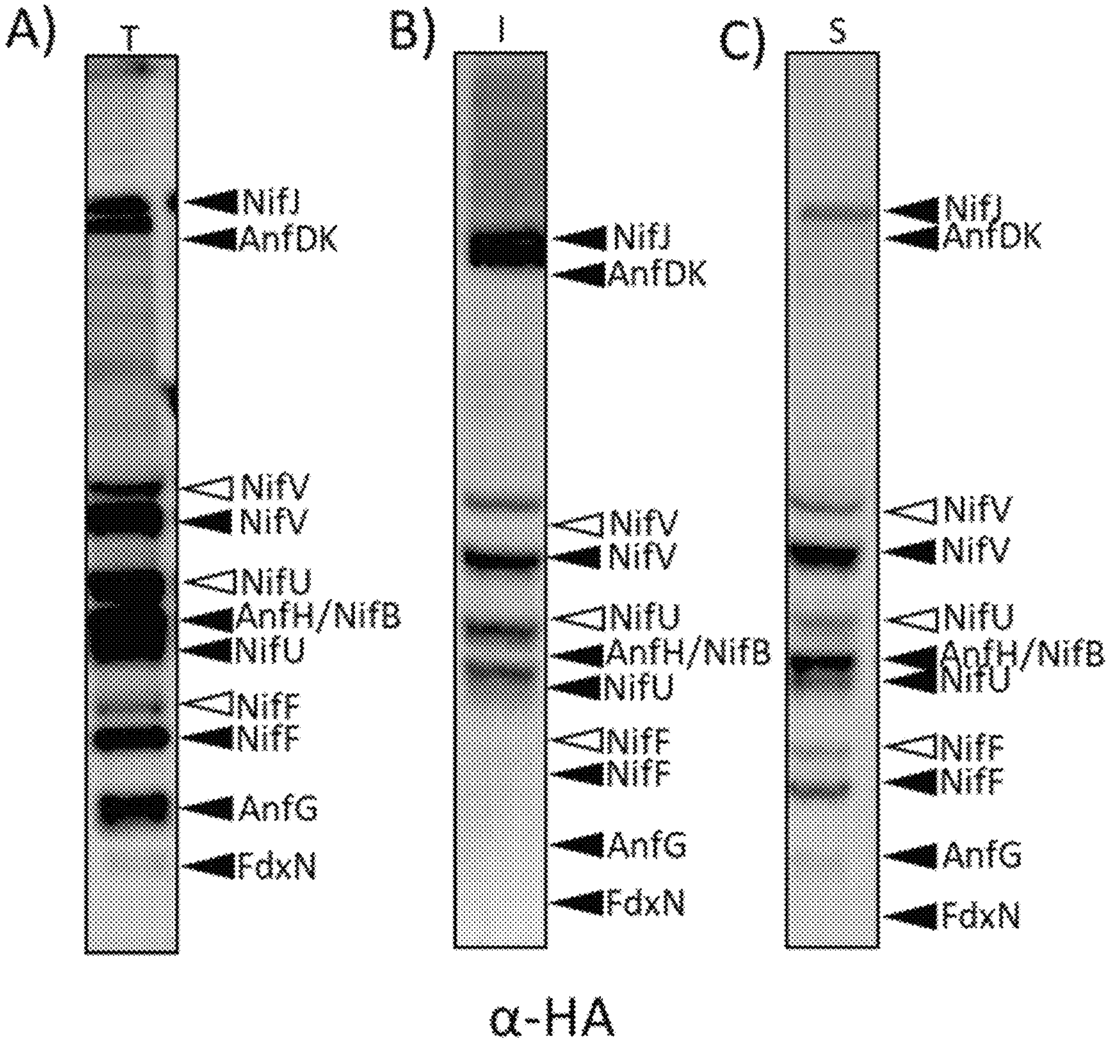

FIG. 41. Western blot analysis of polypeptides produced from SL50 and SL49 in *N. benthamiana* leaves, including total, panel A), insoluble, panel B), and soluble, panel C), fractions using the anti-HA for detection. Black arrowheads indicate the positions of the processed polypeptide bands after mitochondrial cleavage, white arrowheads indicate the bands for the unprocessed polypeptides.

Figure 42:
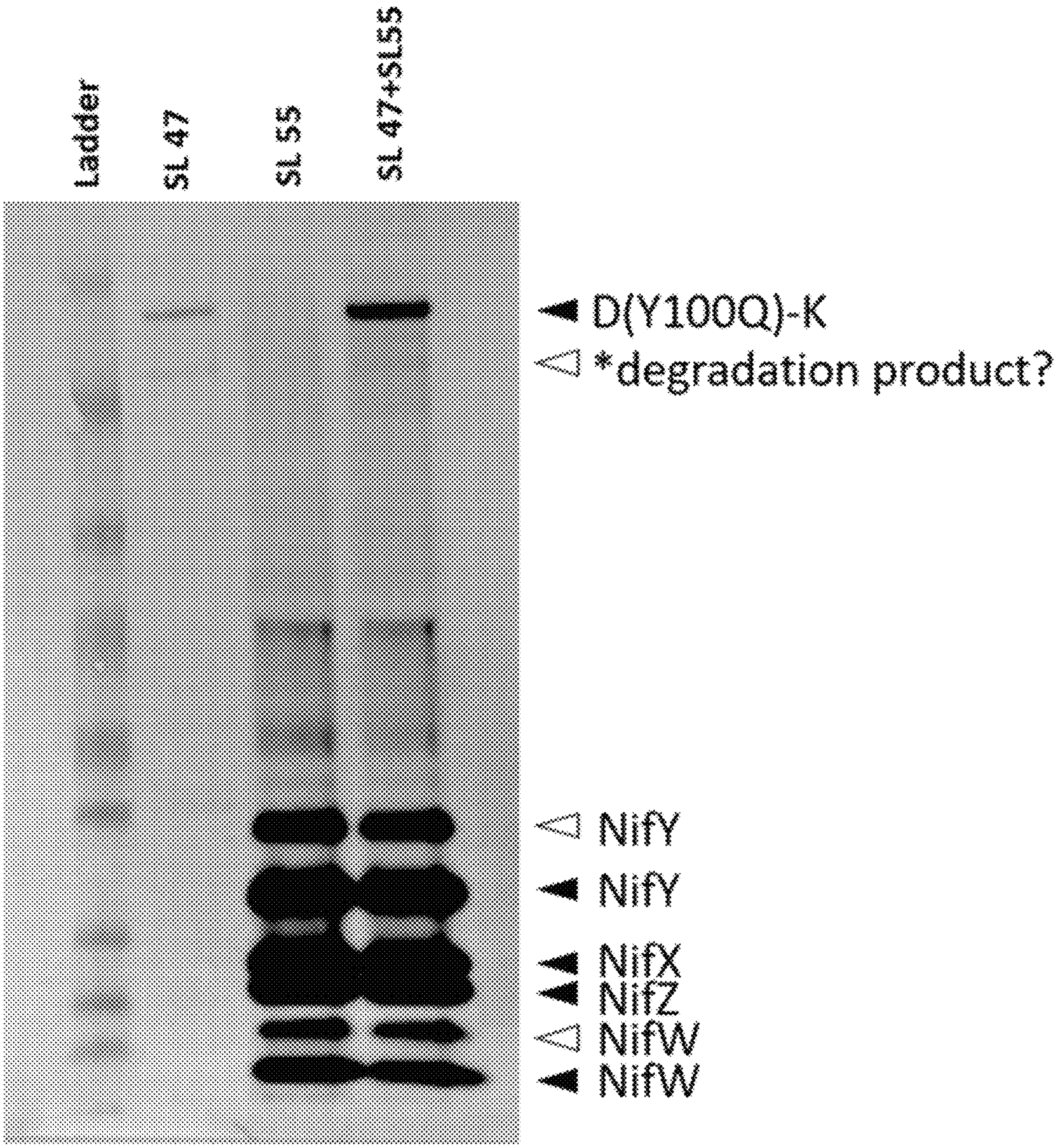

FIG. 42. Western blot analysis of polypeptides produced from SL47 and SL55, separately or in combination, in *N. benthamiana* leaves using anti-HA for detection. The first lane shows molecular weights (kDa) markers. Black arrowheads indicate the positions of the processed polypeptide bands after mitochondrial cleavage by MPP, white arrowheads indicate the bands for the unprocessed polypeptides.

Figure 43:
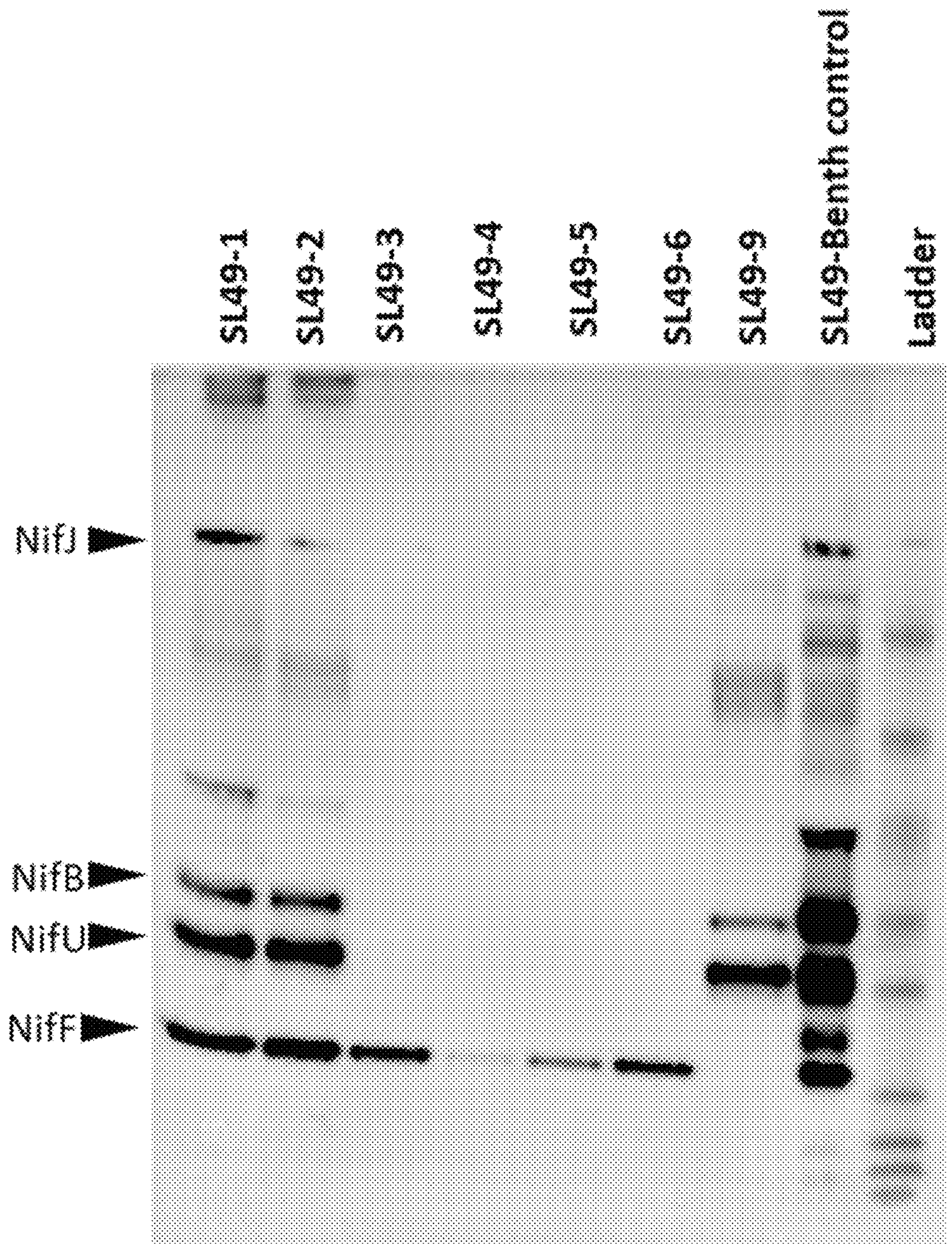

FIG. 43. Western blot of proteins extracted from leaf samples of transgenic *Arabidopsis* plants transformed with SL49, probed with anti-HA antibody. Positions of the NifJ, NifB, NifU and NifF fusion polypeptides are indicated by arrows, based on the positions of the same polypeptides after transient expression of SL49 in *N. benthamiana* leaves (Benth control).

KEY TO THE SEQUENCE LISTING

SEQ ID NO:1 Amino acid sequence of NifH polypeptide from *K. oxytoca,* 293aa.

SEQ ID NO:2 Amino acid sequence of wild-type NifD polypeptide from *K. oxytoca*, according to Accession No. X13303.1; 483aa (The Temme sequence is SEQ ID NO:18).

SEQ ID NO:3 Amino acid sequence of NifK polypeptide from *K. oxytoca*, according to Temme et al. (2012); 520aa.

SEQ ID NO:4 Amino acid sequence of NifB polypeptide from *K. oxytoca,* 468aa.

SEQ ID NO:5 Amino acid sequence of NifE polypeptide from *K. oxytoca,* 457aa.

SEQ ID NO:6 Amino acid sequence of NifF polypeptide from *K. oxytoca,* 176 aa; NCBI Accession No. X03214.

SEQ ID NO:7 Amino acid sequence of NifJ polypeptide from *K. oxytoca,* 1171 aa; NCBI Accession No. 43862.; Cannon et al., 1988 Nucleic Acids Res. 16:11379).

SEQ ID NO:8 Amino acid sequence of NifM polypeptide from *K. oxytoca,* 266 aa; NCBI Accession No. X05887; Paul and Merrick (1987).

SEQ ID NO:9 Amino acid sequence of NifN polypeptide from *K. oxytoca*, NCBI Accession No. P08738; 461aa; (Arnold et al., 1988). This sequence is identical to a *K. michiganensis* sequence Accession No. WP_064371582 and is 85% identical to a sequence annotated as *K. oxytoca* NifN, Accession No. WP_061153953.

SEQ ID NO:10 Amino acid sequence of NifQ polypeptide from *Klebsiella*. NCBI Accession No. WP_004138772. This sequence is 95% identical to another *K. oxytoca* sequence annotated as NifQ, Accession No. AAA25108.1.

SEQ ID NO:11 Amino acid sequence of NifS polypeptide from *K. oxytoca,* 400aa.

SEQ ID NO:12 Amino acid sequence of NifU polypeptide from *K. oxytoca;* 274aa. NCBI Accession No. P05343.2 (Arnold et al., 1988). This sequence is identical to Accession No. WP_004138782 and also is 272/273 identical to another *K. oxytoca* sequence, Accession No. AAA25155.

SEQ ID NO:13 Amino acid sequence of NifV polypeptide from *K. oxytoca;* 381aa. NCBI Accession No. CAA31119.1 (Arnold et al., 1988).

SEQ ID NO:14 Amino acid sequence of NifX polypeptide from *K. oxytoca,* 156aa (Accession No. P09136).

SEQ ID NO:15 Amino acid sequence of NifY polypeptide from *K. oxytoca,* 220aa; NCBI Accession No. CAA31670 (Arnold et al., 1988).

SEQ ID NO:16 Amino acid sequence of NifZ polypeptide from *K. oxytoca,* 148aa; NCBI Accession No. P0A3U2 (Arnold et al., 1988).

SEQ ID NO:17. Amino acid sequence of NifW polypeptide from *K. oxytoca.*

SEQ ID NO:18. Amino acid sequence of wild-type *K. oxytoca* NifD according to Temme et al. (2012).

SEQ ID NO:19. Amino acid sequence of wild-type *K. oxytoca* NifS according to Temme et al. (2012).

SEQ ID NO:20. Amino acid sequence of the N-terminal extension comprising the MTP-FAγ77 (amino acids 1-77) and the amino acid triplet GAP (78-80). Cleavage by MPP occurs between amino acid residues 42 and 43.

SEQ ID NO:21. Amino acid sequence of the MTP-FAγ51 polypeptide with additional N-terminal Met and C-terminal GG. Cleavage by MPP occurs between amino acid residues 43 and 44.

SEQ ID NO:22. Amino acid sequence of the FAγ-scar9 polypeptide.

SEQ ID NO:23. Amino acid sequence of the MTP-FAγ77::NifH::HA fusion polypeptide encoded by pRA10. Amino acids 1-77 correspond to MTP-FAγ77, amino acids 78-80 are the GAP, amino acids 81-372 correspond to *K. oxytoca* NifH amino acids (SEQ ID NO:1 without the initiator Met) and amino acids 373-389 include the HA epitope.

SEQ ID NO:24. Amino acid sequence of the MTP-FAγ51::NifH::HA fusion polypeptide encoded by pRA34. Amino acids 1-51 correspond to MTP-FAγ51, amino acids 52-54 are the GAP, amino acids 55-346 correspond to *K. oxytoca* NifH (SEQ ID NO:1 without the initiator Met) and amino acids 347-363 include the HA epitope.

SEQ ID NO:25. Amino acid sequence of the MTP-FAγ51::NifH::HA fusion polypeptide encoded by SN18. Amino acids 1-54 correspond to the MTP-FAγ51 with GG, amino acids 55-347 correspond to *K. oxytoca* NifH (SEQ ID NO:1) and amino acids 348-358 include the HA epitope.

SEQ ID NO:26. Amino acid sequence of the MTP-FAγ51::HA::NifH fusion polypeptide encoded by SN29. Amino acids 1-53 correspond to the MTP-FAγ51 with GG, amino acids 54-64 include the HA epitope, amino acids 65-357 correspond to *K. oxytoca* NifH (SEQ ID NO:1), and amino acids 358-371 were a C-terminal extension.

SEQ ID NO:27. 6×His sequence used instead of a MTP sequence, with N-terminal Met and C-terminal GG.

SEQ ID NO:28. Amino acid sequence of the CPN60 MTP.

SEQ ID NO:29. Amino acid sequence of the CPN60/No GGlinker MTP.

SEQ ID NO:30. Amino acid sequence of the Superoxide dismutase (SOD) MTP.

SEQ ID NO:31. Amino acid sequence of the Superoxide dismutase doubled (2SOD) MTP.

SEQ ID NO:32. Amino acid sequence of the Superoxide dismutase, modified (SODmod) MTP.

SEQ ID NO:33. Amino acid sequence of the Superoxide dismutase, modified (2SODmod) doubled MTP.

SEQ ID NO:34. Amino acid sequence of the L29 MTP (At1G07830).

SEQ ID NO:35. Amino acid sequence of the *Neurospora crassa* F0 ATPase subunit 9 (SU9) MTP.

SEQ ID NO:36. Amino acid sequence of the gATPase gamma subunit (FAγ51) MTP, without the additional N-terminal Met (SEQ ID NO:21 has an additional N-terminal Met). Cleavage by MPP occurs between amino acid residues 42 and 43.

SEQ ID NO:37. Amino acid sequence of the CoxIV twin strep (ABM97483) MTP.

SEQ ID NO:38. Amino acid sequence of the CoxIV 10×His (ABM97483) MTP.

SEQ ID NO:39. Amino acid sequence of the predicted scar for the Superoxide dismutase (SOD) MTP with GG and for the Superoxide dismutase, doubled (2SOD) MTP with GG.

SEQ ID NO:40. Amino acid sequence of the predicted scar for the L29 MTP with GG.

SEQ ID NO:41. Amino acid sequence of the predicted scar for the *Neurospora crassa* F0 ATPase subunit 9 (SU9) MTP with GG.

SEQ ID NO:42. Amino acid sequence of the predicted scar for the gATPase gamma subunit (FAγ51) MTP with GG.

SEQ ID NO:43. Amino acid sequence of the predicted scar for the CoxIV twin strep MTP with GG.

SEQ ID NO:44. Amino acid sequence of the predicted scar for the CoxIV 10×His MTP with GG.

SEQ ID NO:45. Oligonucleotide primer MIT_V2.1_SbfInifH_FW2.

SEQ ID NO:46. Oligonucleotide primer MIT_V2.1_SbfInifJ_RV2.

SEQ ID NO:47. Oligonucleotide primer MIT_V2.1_SbfInifB_FW.

SEQ ID NO:48. Oligonucleotide primer MIT_V2.1_SbfIori_RV.

SEQ ID NO:49. Amino acid sequence of mscar9 from MTP-FAγ51 having substitution of the N-terminal Ile residue with a Met for translation initiation.

SEQ ID NO:50. Tryptic peptide.

SEQ ID NO:51. Amino acid sequence of MTP-FAγ9 scar without N-terminal Met and with C-terminal Met.

SEQ ID NOs:52-54. Oligonucleotide primers.

SEQ ID NO:55. Tryptic peptide.

SEQ ID NO:56. Tryptic peptide.

SEQ ID NO:57. Amino acid sequence of the MTP-FAγ77::NifK fusion polypeptide (pRA25), lacking any C-terminal extension Amino acids 1-77 correspond to the MTP-FAγ77, amino acids 78-80 are GAP, and amino acids 81-599 correspond to *K. oxytoca* NifK without the initiator Met.

SEQ ID NO:58. Amino acid sequence of the last four amino acid residues at the C-terminus of the NifK polypeptide from *K. oxytoca.*

SEQ ID NO:59. Amino acid sequence of the mutant MTP-FAγ51 polypeptide which is not cleaved by MPP.

SEQ ID NOs:60-107. Peptide sequences.

SEQ ID NOs:108-113. Oligonucleotide primers.

SEQ ID NO:114. Amino acid sequence of an 11-residue section from a linker region from *Hypocrea jecorina* cellobiohydrolase II (Accession no. AAG39980.1).

SEQ ID NO:115. Amino acid sequence of 9-residue HA epitope.

SEQ ID NO:116. Amino acid sequence of a linker for the NifD::linker::NifK fusion polypeptide. The linker is 30 residues in length and has SEQ ID NO:114 with the final arginine replaced by an alanine, then an 9-residue HA epitope (SEQ ID NO:115) followed by another copy of SEQ ID NO:114 with the arginine replaced by an alanine.

SEQ ID NO:117. Oligonucleotide primer.

SEQ ID NO:118. Oligonucleotide primer.

SEQ ID NO:119. Scar peptide sequence.

SEQ ID NO:120. Scar peptide sequence.

SEQ ID NO:121. Amino acid sequence of the metaxin fusion polypeptide encoded by construct SN197. The TwinStrep epitope corresponds to amino acids 1-31, mTurquoise to amino acids 32-273, a TEV cleavage site to amino acids 274-282 and the metaxin sequence to amino acids 283-603.

SEQ ID NO:122 Amino acid sequence of the MTP-FAγ51::NifD::HA fusion polypeptide encoded by SN10. Amino acids 1-54 correspond to the MTP-FAγ51 with GG at its C-terminus, amino acids 55-536 correspond to *K. oxytoca* NifD (SEQ ID NO:18) with its initiator Met, and amino acids 537-547 include the HA epitope.

SEQ ID NO:123. Amino acid sequence of the MTP-FAγ51::NifM::HA fusion polypeptide encoded by SN30. Amino acids 1-54 correspond to the MTP-FAγ51 with GG at its C-terminus, amino acids 55-320 correspond to *K. oxytoca* NifM (SEQ ID NO:8) with its initiator Met, and amino acids 321-331 include the HA epitope.

SEQ ID NO:124. Amino acid sequence of the MTP-FAγ51::NifS::HA fusion polypeptide encoded by SN31. Amino acids 1-54 correspond to the MTP-FAγ51 with GG at its C-terminus, amino acids 55-454 correspond to *K. oxytoca* NifS (SEQ ID NO:19) with its initiator Met, according to Temme et al. (2012), and amino acids 455-465 include the HA epitope.

SEQ ID NO:125. Amino acid sequence of the MTP-FAγ51::NifU::HA fusion polypeptide encoded by SN32. Amino acids 1-54 correspond to the MTP-FAγ51 with GG at its C-terminus, amino acids 55-328 correspond to *K. oxytoca* NifU (SEQ ID NO:12) with its initiator Met, and amino acids 329-339 include the HA epitope.

SEQ ID NO: 126. Amino acid sequence of the MTP-FAγ51::NifE::HA fusion polypeptide encoded by SN38. Amino acids 1-54 correspond to the MTP-FAγ51 with GG at its C-terminus, amino acids 55-511 correspond to *K. oxytoca* NifE with its initiator Met according to Temme et al. (2012), and amino acids 512-522 include the HA epitope.

SEQ ID NO:127. Amino acid sequence of the MTP-FAγ51::NifN::HA fusion polypeptide encoded by SN39. Amino acids 1-54 correspond to the MTP-FAγ51 with GG at its C-terminus, amino acids 55-515 correspond to *K. oxytoca* NifN (SEQ ID NO:9) with its initiator Met, and amino acids 516-526 include the HA epitope.

SEQ ID NO:128. Amino acid sequence of the MTP-CoxIV-Twin-Strep::NifH::HA fusion polypeptide encoded by SN42. Amino acids 1-61 correspond to the MTP-CoxIV-Twin-Strep with GG at its C-terminus, amino acids 62-354 correspond to *K. oxytoca* NifH amino acids (SEQ ID NO:1) with its initiator Met, and amino acids 355-365 include the HA epitope.

SEQ ID NO: 129. Amino acid sequence of the MTP-Su9::NifK fusion polypeptide encoded by SN46. Amino acids 1-70 correspond to the MTP-Su9 with GG at its C-terminus, amino acids 71-590 correspond to *K. oxytoca* NifK (SEQ ID NO:3) with its initiator Met.

SEQ ID NO:130. Amino acid sequence of the MTP-L29::NifV::HA fusion polypeptide encoded by SN51. Amino acids 1-34 correspond to the MTP-L29 with GG at its C-terminus, amino acids 35-415 correspond to *K. oxytoca* NifV (SEQ ID NO:13) with its initiator Met, and amino acids 416-426 include the HA epitope.

SEQ ID NO:131. Amino acid sequence of the MTP-FAγ51::NifD::linker(HA)::NifK fusion polypeptide encoded by SN68. Amino acids 1-54 correspond to the MTP-FAγ51 with GG at its C-terminus, amino acids 55-536 correspond to wild-type *K. oxytoca* NifD amino acids (SEQ ID NO:18 without N-terminal Met), amino acids 537-566 correspond to the linker including the HA epitope, and amino acids 567-1085 correspond to NifK (SEQ ID NO:3) without its N-terminal Met and with its wild-type C-terminus.

SEQ ID NO:132. Amino acid sequence of the MTP-FAγ51::HA::NifD::HA fusion polypeptide encoded by SN75. Amino acids 1-53 correspond to the MTP-FAγ51 with GG at its C-terminus, amino acids 54-64 correspond to the first HA epitope, amino acids 65-546 correspond to wild-type *K. oxytoca* NifD amino acids (SEQ ID NO:18), and amino acids 547-557 include the HA epitope.

SEQ ID NO:133. Amino acid sequence of the MTP-FAγ51::NifD::HA fusion polypeptide encoded by SN99. Amino acids 1-54 correspond to the MTP-FAγ51 with GG at its C-terminus, amino acids 55-536 correspond to *K. oxytoca* NifD comprising the alanine substitution mutations at amino acids 148-152, and amino acids 537-547 include the HA epitope.

SEQ ID NO:134. Amino acid sequence of the MTP-FAγ51::NifD::HA fusion polypeptide encoded by SN100. Amino acids 1-54 correspond to the MTP-FAγ51 with GG at its C-terminus, amino acids 55-536 correspond to *K. oxytoca* NifD amino acids comprising the alanine substitution mutations at amino acids 153-157, and amino acids 537-547 include the HA epitope.

SEQ ID NO:135. Amino acid sequence of the MTP-Su9::NifW fusion polypeptide encoded by SN104. Amino acids 1-70 correspond to the MTP-Su9 with GG at its C-terminus, amino acids 71-158 correspond to *K. oxytoca* NifW (SEQ ID NO:17) with its initiator Met, and amino acids 159-167 include the HA epitope.

SEQ ID NO:136. Amino acid sequence of the MTP-FAγ51::NifD::HA fusion polypeptide encoded by SN114. Amino acids 1-54 correspond to the MTP-FAγ51 with GG at its C-terminus, amino acids 55-536 correspond to *K. oxytoca* NifD comprising the Y100Q substitution mutation at amino acid 154, and amino acids 537-547 include the HA epitope.

SEQ ID NO:137. Amino acid sequence of the MTP-FAγ51::NifF::HA fusion polypeptide encoded by SN138. Amino acids 1-54 correspond to the MTP-FAγ51 with GG, amino acids 55-230 correspond to *K. oxytoca* NifF (SEQ ID NO:6) and amino acids 231-241 include the HA epitope.

SEQ ID NO:138. Amino acid sequence of the MTP-FAγ51::NifJ::HA fusion polypeptide encoded by SN139. Amino acids 1-54 correspond to the MTP-FAγ51 with GG, amino acids 55-1225 correspond to *K. oxytoca* NifJ (SEQ ID NO:7), and amino acids 1226-1236 include the HA epitope.

SEQ ID NO:139. Amino acid sequence of the MTP-FAγ51::HA::NifK fusion polypeptide encoded by SN140. Amino acids 1-53 correspond to the MTP-FAγ51 with GG, amino acids 54-64 include the HA epitope, and amino acids 65-584 correspond to *K. oxytoca* NifK (SEQ ID NO:3) with wild-type C-terminus.

SEQ ID NO:140. Amino acid sequence of the MTP-FAγ51::NifQ::HA fusion polypeptide encoded by SN141. Amino acids 1-54 correspond to the MTP-FAγ51 with GG, amino acids 55-221 correspond to *K. oxytoca* NifQ (SEQ ID NO:10) and amino acids 222-232 include the HA epitope.

SEQ ID NO:141. Amino acid sequence of the MTP-FAγ51::NifV::HA fusion polypeptide encoded by SN142. Amino acids 1-54 correspond to the MTP-FAγ51 with GG, amino acids 55-435 correspond to *K. oxytoca* NifV (SEQ ID NO:13) and amino acids 436-446 include the HA epitope.

SEQ ID NO:142. Amino acid sequence of the MTP-FAγ51::NifW::HA fusion polypeptide encoded by SN143. Amino acids 1-54 correspond to the MTP-FAγ51 with GG, amino acids 55-140 correspond to *K. oxytoca* NifW (SEQ ID NO:17), and amino acids 141-151 include the HA epitope.

SEQ ID NO:143. Amino acid sequence of the MTP-FAγ51::NifX::HA fusion polypeptide encoded by SN144. Amino acids 1-54 correspond to the MTP-FAγ51 with GG, amino acids 55-210 correspond to *K. oxytoca* NifX (SEQ ID NO:14), and amino acids 211-221 include the HA epitope.

SEQ ID NO:144. Amino acid sequence of the MTP-FAγ51::NifY::HA fusion polypeptide encoded by SN145. Amino acids 1-54 correspond to the MTP-FAγ51 with GG, amino acids 55-274 correspond to *K. oxytoca* NifY according to Temme et al. (2012), and amino acids 275-285 include the HA epitope.

SEQ ID NO:145. Amino acid sequence of the MTP-FAγ51::NifZ::HA fusion polypeptide encoded by SN146. Amino acids 1-54 correspond to the MTP-FAγ51 with GG, amino acids 55-202 correspond to *K. oxytoca* NifZ (SEQ ID NO:16), and amino acids 203-213 include the HA epitope.

SEQ ID NO:146. Amino acid sequence of MTP-FAγ51::NifD(Y100Q)::linker(HA)::NifK fusion polypeptide encoded by SN159. Amino acids 1-54 correspond to the MTP-FAγ51 with GG at its C-terminus, amino acids 55-536 correspond to *K. oxytoca* NifD with the Y100Q substitution, amino acids 537-566 correspond to the linker including the HA epitope, and amino acids 567-1085 correspond to NifK (SEQ ID NO:3) without its N-terminal Met and with its wild-type C-terminus.

SEQ ID NO:147. Amino acid sequence of the MTP-FAγ51::NifB::HA fusion polypeptide encoded by SN192. Amino acids 1-54 correspond to the MTP-FAγ51 with GG, amino acids 55-522 correspond to *K. oxytoca* NifB according to Temme et al. (2012), and amino acids 523-533 include the HA epitope.

SEQ ID NO:148. Amino acid sequence of wild-type *Azospirillum brasilense* NifD polypeptide, UniProt A0A060DN91; 479aa.

SEQ ID NO:149. Amino acid sequence of wild-type *Azotobacter vinelandii* NifD polypeptide, UniProt C1DGZ7; 492aa.

SEQ ID NO:150. Amino acid sequence of wild-type *Sinorhizobium fredii* NifD polypeptide, 504aa.

SEQ ID NO:151. Amino acid sequence of wild-type *Chlorobium tepidum* NifD polypeptide, Uniprot Q8KC89; 543aa.

SEQ ID NO:152. Amino acid sequence of wild-type *Desulfovibrio vulgaris* NifD polypeptide, Uniprot B8DR77; 544aa.

SEQ ID NO:153. Amino acid sequence of wild-type *Desulfotomaculum ferrireducens* NifD polypeptide, 539aa.

SEQ ID NO:154. Peptide sequence, where X is any amino acid other than Tyr.

SEQ ID NO:155. Tryptic peptide sequence from NifM.

SEQ ID NO:156. Tryptic peptide sequence from NifM.

SEQ ID NO:157. Tryptic peptide sequence from CAT.

SEQ ID NO:158. Tryptic peptide sequence from CAT.

SEQ ID NO:159. Tryptic peptide sequence from CAT.

SEQ ID NO:160. Amino acid sequence of the MTP-FAγ51::NifU::TwinStrep fusion polypeptide encoded by SN166. Amino acids 1-54 are the MTP-FAγ51 sequence with an additional methionine translational start and C-terminal GG, amino acids 55-328 are the NifU sequence, and amino acids 329-358 are the sequence including a Twinstrep motif.

SEQ ID NO:161. Amino acid sequence of the MTP-FAγ51::NifS::TwinStrep fusion polypeptide encoded by SN231. Amino acids 1-54 are the MTP-FAγ51 sequence with an additional methionine translational start and C-terminal GG, amino acids 55-454 are the NifS sequence, and amino acids 455-484 are the sequence including a Twinstrep motif.

SEQ ID NO:162. Tryptic peptide sequence from scar9.

SEQ ID NO:163. Amino acid sequence of the NifV polypeptide from *A. vinelandii* (AvNifV; Accession No. WP_012698855).

SEQ ID NO:164. Amino acid sequence of the KoNifV variant sequence (Accession No. WP_004138778).

SEQ ID NO:165. N-terminal ScHCS extension (scar sequence).

SEQ ID NO:166. N-terminal AvNifV extension (scar sequence).

SEQ ID NO:167. Amino acid sequence of the MTP-FAγ51::HA::KoNifM polypeptide encoded by SN43. Amino acids 1-53 correspond to the MTP-FAγ51 sequence including a GG at its C-terminus, amino acids 54-64 correspond to the HA epitope including a GG at its C-terminus, and amino acids 65-330 correspond to the NifM sequence from *K. oxytoca.*

SEQ ID NO:168. Amino acid sequence of the MTP-CoxIV::TwinStrep::NifH polypeptide encoded by SN178. Amino acids 1-31 correspond to the MTP-CoxIV sequence, amino acids 32-61 correspond to the TwinStrep sequence including a GG at its C-terminus, and amino acids 62-354 correspond to the NifH sequence from *Azospirillum brasilense* (Accession No. WP_014239786).

SEQ ID NO:169. Amino acid sequence of the MTP-CoxIV::TwinStrep::NifH polypeptide encoded by SN179. Amino acids 1-31 correspond to the MTP-CoxIV sequence, amino acids 32-61 correspond to the TwinStrep sequence including a GG at its C-terminus, and amino acids 62-356 correspond to the NifH sequence from *Mastigocladus laminosus* (Accession No. WP_016865872).

SEQ ID NO:170. Amino acid sequence of the MTP-CoxIV::TwinStrep::NifH polypeptide encoded by SN180. Amino acids 1-31 correspond to the MTP-CoxIV sequence, amino acids 32-61 correspond to the TwinStrep sequence including a GG at its C-terminus, and amino acids 62-348 correspond to the NifH sequence from *Frankia casurinae* (Accession No. WP_0011438842).

SEQ ID NO:171. Amino acid sequence of the MTP-CoxIV::TwinStrep::NifH polypeptide encoded by SN181. Amino acids 1-31 correspond to the MTP-CoxIV sequence, amino acids 32-61 correspond to the TwinStrep sequence including a GG at its C-terminus, and amino acids 62-354 correspond to the NifH sequence from *Marichromatium gracile* biotype *thermosufidiphilum* (Accession No. WP_062275270).

SEQ ID NO:172. Amino acid sequence of the MTP-CoxIV::TwinStrep::NifH polypeptide encoded by SN182. Amino acids 1-31 correspond to the MTP-CoxIV sequence, amino acids 32-61 correspond to the TwinStrep sequence including a GG at its C-terminus, and amino acids 62-345 correspond to the NifH sequence from *Methanocaldococcus infernus* (Accession No. WP_013099459).

SEQ ID NO:173. Amino acid sequence of the MTP-CoxIV::TwinStrep::NifH polypeptide encoded by SN183. Amino acids 1-31 correspond to the MTP-CoxIV sequence, amino acids 32-61 correspond to the TwinStrep sequence including a GG at its C-terminus, and amino acids 62-345 correspond to the NifH sequence from *Heliobacterium modesticaldum* (Accession No. WP_012282218).

SEQ ID NO:174. Amino acid sequence of the MTP-CoxIV::TwinStrep::NifH polypeptide encoded by SN184. Amino acids 1-31 correspond to the MTP-CoxIV sequence, amino acids 32-61 correspond to the TwinStrep sequence including a GG at its C-terminus, and amino acids 62-335 correspond to the NifH sequence from *Chlorobium tepidum* (Accession No. WP_010933198).

SEQ ID NO:175. Amino acid sequence of the MTP-CoxIV::TwinStrep::NifH polypeptide encoded by SN185. Amino acids 1-31 correspond to the MTP-CoxIV sequence, amino acids 32-61 correspond to the TwinStrep sequence including a GG at its C-terminus, and amino acids 62-350 correspond to the NifH sequence from *Geobacter* sp. M21 (Accession No. WP_015837436).

SEQ ID NO:176. Amino acid sequence of the MTP-CoxIV::TwinStrep::NifH polypeptide encoded by SN186. Amino acids 1-31 correspond to the MTP-CoxIV sequence, amino acids 32-61 correspond to the TwinStrep sequence including a GG at its C-terminus, and amino acids 62-355 correspond to the NifH sequence from *Bradyrhizobium diazoefficans* (Accession No. AHY57040).

SEQ ID NO:177. Amino acid sequence of the MTP-CoxIV::TwinStrep::NifH polypeptide encoded by SN187. Amino acids 1-31 correspond to the MTP-CoxIV sequence, amino acids 32-61 correspond to the TwinStrep sequence including a GG at its C-terminus, and amino acids 62-336 correspond to the NifH sequence from *Methanobacterium thermoautotrophicum* (Accession No. AAB86034).

SEQ ID NO:178. Amino acid sequence of the MTP-CoxIV::TwinStrep::NifH polypeptide encoded by SN188. Amino acids 1-31 correspond to the MTP-CoxIV sequence, amino acids 32-61 correspond to the TwinStrep sequence including a GG at its C-terminus, and amino acids 62-334 correspond to the NifH sequence from *Methanosarcina* (Accession No. WP_048121466).

SEQ ID NO:179. Amino acid sequence of the MTP-CoxIV::TwinStrep::NifH polypeptide encoded by SN189. Amino acids 1-31 correspond to the MTP-CoxIV sequence, amino acids 32-61 correspond to the TwinStrep sequence including a GG at its C-terminus, and amino acids 62-336 correspond to the NifH sequence from *Desulfotomaculum acetoxidans* (Accession No. WP_015756624).

SEQ ID NO:180. Amino acid sequence of the MTP-CoxIV::TwinStrep::NifH polypeptide encoded by SN190. Amino acids 1-31 correspond to the MTP-CoxIV sequence, amino acids 32-61 correspond to the TwinStrep sequence including a GG at its C-terminus, and amino acids 62-336 correspond to the NifH sequence from *Carboxydothermus pertinax* (Accession No. WP_075859892).

SEQ ID NO:181. Amino acid sequence of the MTP-CoxIV::TwinStrep::NifH polypeptide encoded by SN191. Amino acids 1-31 correspond to the MTP-CoxIV sequence, amino acids 32-61 correspond to the TwinStrep sequence including a GG at its C-terminus, and amino acids 62-335 correspond to the NifH sequence from *Nostoc calcicole* (Accession No. WP_073644321).

SEQ ID NO:182. Amino acid sequence of the MTP-FAγ51::AnfD::HA polypeptide encoded by SN81. Amino acids 1-54 correspond to the MTP-FAγ51 sequence including a GG linker at its C-terminus, amino acids 55-572 correspond to the AnfD sequence from *A. vinelandii*, and amino acids 573-583 correspond to the HA epitope.

SEQ ID NO:183. Amino acid sequence of the HA::AnfD polypeptide encoded by SN82. Amino acids 1-12 correspond to the HA epitope sequence including a GG linker at its C-terminus, and amino acids 13-530 correspond to the AnfD sequence from *A. vinelandii.*

SEQ ID NO:184. Amino acid sequence of the MTP-FAγ51::HA::AnfK polypeptide encoded by SN129. Amino acids 1-53 correspond to the MTP-FAγ51 sequence including a GG linker at its C-terminus, amino acids 54-64 correspond to the HA epitope, and amino acids 65-526 correspond to the AnfK sequence from *A. vinelandii.*

SEQ ID NO:185. Amino acid sequence of the MTP-FAγ51::HA::AnfH polypeptide encoded by SN130. Amino acids 1-53 correspond to the MTP-FAγ51 sequence including a GG linker at its C-terminus, amino acids 54-64 correspond to the HA epitope with a GG linker at its C-terminus, and amino acids 65-339 correspond to the AnfH sequence from *A. vinelandii.*

SEQ ID NO:186. Amino acid sequence of the MTP-FAγ51::HA::AnfG polypeptide encoded by SN131. Amino acids 1-53 correspond to the MTP-FAγ51 sequence including a GG linker at its C-terminus, amino acids 54-64 correspond to the HA epitope with a GG linker at its C-terminus, and amino acids 65-196 correspond to the AnfG sequence from *A. vinelandii.*

SEQ ID NO:187. Amino acid sequence of the HA::AnfK polypeptide encoded by SN152. Amino acids 1-12 correspond to the HA epitope sequence including a GG linker at its C-terminus, and amino acids 13-474 correspond to the AnfK sequence from *A. vinelandii.*

SEQ ID NO:188. Amino acid sequence of the HA::AnfH polypeptide encoded by SN153. Amino acids 1-12 correspond to the HA epitope sequence including a GG linker at its C-terminus, and amino acids 13-287 correspond to the AnfH sequence from *A. vinelandii.*

SEQ ID NO:189. Amino acid sequence of the HA::AnfG polypeptide encoded by SN154. Amino acids 1-12 correspond to the HA epitope sequence including a GG linker at its C-terminus, and amino acids 13-144 correspond to the AnfG sequence from *A. vinelandii.*

SEQ ID NO:190. Amino acid sequence of the mFAγ51::HA::AnfK polypeptide encoded by SN155. Amino acids 1-53 correspond to the mutant mFAγ51 sequence including a GG linker at its C-terminus, amino acids 54-64 correspond to the HA epitope with a GG linker at its C-terminus, and amino acids 65-526 correspond to the AnfK sequence from *A. vinelandii.*

SEQ ID NO:191. Amino acid sequence of the mFAγ51::HA::AnfH polypeptide encoded by SN156. Amino acids 1-53 correspond to the mutant mFAγ51 sequence including a GG linker at its C-terminus, amino acids 54-64 correspond to the HA epitope with a GG linker at its C-terminus, and amino acids 65-339 correspond to the AnfH sequence from *A. vinelandii.*

SEQ ID NO:192. Amino acid sequence of the mFAγ51::HA::AnfG polypeptide encoded by SN157. Amino acids 1-53 correspond to the mutant mFAγ51 sequence including a GG linker at its C-terminus, amino acids 54-64 correspond to the HA epitope with a GG linker at its C-terminus, and amino acids 65-196 correspond to the AnfG sequence from *A. vinelandii.*

SEQ ID NO:193. Amino acid sequence of the mFAγ51::HA::AnfD polypeptide encoded by SN158. Amino acids 1-53 correspond to the mutant mFAγ51 sequence including a GG linker at its C-terminus, amino acids 54-64 correspond to the HA epitope with a GG linker at its C-terminus, and amino acids 65-582 correspond to the AnfD sequence from *A. vinelandii.*

SEQ ID NO:194. Amino acid sequence of the MTP-FAγ51::HA::AnfD polypeptide encoded by SN161. Amino acids 1-53 correspond to the MTP-FAγ51 sequence including a GG linker at its C-terminus, amino acids 54-64 correspond to the HA epitope with a GG linker at its C-terminus, and amino acids 65-582 correspond to the AnfD sequence from *A. vinelandii.*

SEQ ID NO:195. Amino acid sequence of the MTP-FAγ51::AnfD::Twin Strep polypeptide encoded by SN177. Amino acids 1-54 correspond to the MTP-FAγ51 sequence including a GG linker at its C-terminus, amino acids 55-572 correspond to the AnfD sequence from *A. vinelandii*, and amino acids 573-604 correspond to the TwinStrep epitope.

SEQ ID NO:196. Amino acid sequence of the MTP-CoxIV::Twin Strew AnfK polypeptide encoded by SN195. Amino acids 1-41 correspond to the MTP-CoxIV sequence including a GG linker at its C-terminus, amino acids 42-61 correspond to the TwinStrep epitope including a GG at the C-terminus, and amino acids 62-523 correspond to the AnfK sequence from *A. vinelandii.*

SEQ ID NO:197. Peptide sequence.

SEQ ID NO:198. Linker sequence.

SEQ ID NO:199. Amino acid sequence of AnfD::linker16::AnfK polypeptide used for modelling the structure (Example 20) Amino acids 1-509 correspond to the AnfD sequence (*A. vinelandii*) omitting the N-terminal methionine, amino acids 510-525 correspond to the 16-amino acid linker, and amino acids 526-984 to AnfK (*A. vinelandii*).

SEQ ID NO:200. Linker sequence.

SEQ ID NO:201. Amino acid sequence of AnfD::linker26 (HA)::AnfK polypeptide. Amino acids 1-517 correspond to the AnfD sequence, amino acids 518-543 correspond to the 26-amino acid linker, and amino acids 544-1004 to AnfK.

SEQ ID NO:202. Amino acid sequence of the MTP-FAγ51::AnfD::linker26(HA)::AnfK polypeptide encoded by SN272. Amino acids 1-64 correspond to the MTP-FAγ51-HA sequence including the GG at its C-terminus, amino acids 65-581 correspond to the AnfD sequence (*A. vinelandii*), amino acids 582-607 correspond to the 26-amino acid linker (Linker26 (HA)), and amino acids 608-1068 to AnfK (*A. vinelandii*).

SEQ ID NO:203. Amino acid sequence of the MTP-CoxIV::AnfD::linker26(HA)-AnfK polypeptide encoded by SN273. Amino acids 1-61 correspond to the MTP-CoxIV sequence including the GG at its C-terminus, amino acids 62-578 correspond to the AnfD sequence (*A. vinelandii*), amino acids 579-604 correspond to the 26-amino acid linker (Linker26 (HA)), and amino acids 605-1065 to AnfK (*A. vinelandii*).

SEQ ID NO:204. Amino acid sequence of the mFAγ51::AnfD::linker26(HA)::AnfK polypeptide encoded by SN274. Amino acids 1-64 correspond to the mFAγ51 sequence including the alanine substitutions that don't allow for MPP-cleavage and the GG at its C-terminus, amino acids 65-581 correspond to the AnfD sequence (*A. vinelandii*), amino acids 582-607 correspond to the 26-amino acid linker (Linker26(HA)), and amino acids 608-1068 to AnfK (*A. vinelandii*).

SEQ ID NO:205. Amino acid sequence of the HISx6::AnfD::linker26(HA)::AnfK polypeptide encoded by SN275, which does not have an MTP sequence and would be cytoplasmically located. Amino acids 1-9 correspond to the HISx6 sequence including the GG at its C-terminus, amino acids 10-526 correspond to the AnfD sequence (*A. vinelandii*), amino acids 527-552 correspond to the 26-amino acid linker (Linker26 (HA)), and amino acids 553-1013 to AnfK (*A. vinelandii*).

SEQ ID NO:206. Amino acid sequence of the TbHCS polypeptide (Accession No. CP002466).

SEQ ID NO:207. Amino acid sequence of the TpHCS polypeptide (Accession No. CP002028).

SEQ ID NO:208. Amino acid sequence of the ScHCS polypeptide (Accession No. CP036483).

SEQ ID NO:209. Amino acid sequence of the NsHCS polypeptide (Accession No. CP007203).

SEQ ID NO:210. Amino acid sequence of the MaHCS polypeptide (Accession No AE010299)

SEQ ID NO:211. Amino acid sequence of the CtHCS polypeptide (Accession No. AE006470).

SEQ ID NO:212. Amino acid sequence of the MiHCS1 polypeptide (Accession No. ADG13125).

SEQ ID NO:213. Amino acid sequence of the MiHCS2 polypeptide (Accession No. ADG13175).

SEQ ID NO:214. Amino acid sequence of the MiHCS3 polypeptide (Accession No. ADG14004).

SEQ ID NO:215. Amino acid sequence of the LjFEN1 polypeptide (Accession No. BAI49592).

SEQ ID NO:216. Amino acid sequence of AnfD from *A. vinelandii* (Accession No. WP_012703361); 518aa.

SEQ ID NO:217. Amino acid sequence of AnfK from *A. vinelandii* (Accession No. WP_012703359); 462aa.

SEQ ID NO:218. Amino acid sequence of AnfH from *A. vinelandii* (Accession No. WP_012703362); 275aa.

SEQ ID NO:219. Amino acid sequence of AnfG from *A. vinelandii* (Accession No. WP_012703360); 132aa.

SEQ ID NO:220. Peptide sequence.

SEQ ID NO:221. *N. benthamiana* P72026 amino acid sequence; 606aa.

SEQ ID NO:222. *N. benthamiana* P20586 amino acid sequence; 470aa.

SEQ ID NO:223. Amino acid sequence of *Mycobacterium tuberculosis* α-isopropylmalate synthase (MtLeuA); 644aa.

SEQ ID NO:224; Amino acid sequence of the NifH polypeptide from *A. vinelandii* (AvNifH; Accession No. WP_012698831); 290aa.

SEQ ID NO:225. Peptide sequence, AnfH motif I, where X represents any amino acid.

SEQ ID NO:226. Peptide sequence, AnfH motif II.

SEQ ID NO:227. Peptide sequence, AnfH motif III.

SEQ ID NO:228. Peptide sequence, AnfH motif IV.

SEQ ID NO:229. Peptide sequence, AnfH motif V, where X represents any amino acid.

SEQ ID NO:230. Peptide sequence, AnfH motif VI.

SEQ ID NO:231. Peptide sequence, AnfH motif VII, where X represents any amino acid.

SEQ ID NO:232. Amino acid sequence of the FdxN protein of *A. vinelandii*; Accession No. WP_012703542; 92aa.

SEQ ID NO:233. Amino acid sequence of the MTP-FAγ51-FdxN-HA fusion polypeptide of SN291; 157aa. Amino acids 1-54 correspond to the MTP-FAγ51 sequence with a GG linker, amino acids 55-145 correspond to the FdxN sequence without the N-terminal methionine, and amino acids 146-157 correspond to the HA epitope.

SEQ ID NO:234. Amino acid sequence of the MTP-FAγ51-HA-FdxN fusion polypeptide of SN292; 156aa. Amino acids 1-53 correspond to the MTP-FAγ51 sequence with a GG linker, amino acids 54-64 correspond to the HA epitope with a GG linker, and amino acids 65-156 correspond to the FdxN sequence without the N-terminal methionine.

SEQ ID NO:235. Amino acid sequence of the mFAγ51-HA-FdxN fusion polypeptide of SN299; 156aa Amino acids 1-53 correspond to the mFAγ51 sequence with a GG linker, amino acids 54-64 correspond to the HA epitope with a GG linker, and amino acids 65-156 correspond to the FdxN sequence without the N-terminal methionine.

SEQ ID NO:236. Amino acid sequence of the HA-FdxN fusion polypeptide of SN300; 104aa. Amino acids 1-12 correspond to the HA epitope with a GG linker, and amino acids 13-104 correspond to the FdxN sequence without the N-terminal methionine.

SEQ ID NO:237. Amino acid sequence of the MTP-FAγ51-HA-NifV fusion polypeptide of SN254; 448aa. Amino acids 1-53 correspond to the MTP-FAγ51 sequence with a GG linker, amino acids 54-64 correspond to the HA epitope with a GG linker, and amino acids 65-448 correspond to the NifV sequence from *A. vinelandii*.

SEQ ID NO:238. Amino acid sequence of the NafY polypeptide from *A. vinelandii* (AvNafY; Accession No. AGK13761).

SEQ ID NO:239. C-terminal amino acid sequence of a NifK polypeptide.

SEQ ID NO:240. C-terminal amino acid sequence of a NifK polypeptide.

SEQ ID NO:241. C-terminal amino acid sequence of a NifK polypeptide.

SEQ ID NO:242. C-terminal amino acid sequence of a NifK polypeptide.

SEQ ID NO:243. C-terminal amino acid sequence of a NifK polypeptide.

SEQ ID NO:244. C-terminal amino acid sequence of an AnfK polypeptide.

SEQ ID NO:245. C-terminal amino acid sequence of an AnfK polypeptide.

SEQ ID NO:246. C-terminal amino acid sequence of an AnfK polypeptide.

SEQ ID NO:247. C-terminal amino acid sequence of an AnfK polypeptide.

SEQ ID NO:248. C-terminal amino acid sequence of an AnfK polypeptide.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, or more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Nitrogenase

Nitrogenase is the enzyme in eubacteria and archaeobacteria that catalyses the reduction of the strong, triple bond of nitrogen ($N_2$) to produce ammonia ($NH_3$). Nitrogenase is found naturally only in bacteria. It is a complex of two enzymes that can be purified separately, namely dinitrogenase and dinitrogenase reductase. Dinitrogenase, also referred to as component I or the molybdenum-iron (MoFe) protein, is a tetramer of two NifD and two NifK polypeptides ($\alpha_2\beta_2$) that also contains two "P-clusters" and two "FeMo-cofactors" (FeMo-co). Each pair of NifD-NifK subunits contains one P-cluster and one FeMo-co. FeMo-co is a metallocluster composed of a $MoFe_3$—$S_3$ cluster complexed with a homocitrate molecule, which is coordinated to the molybdenum atom, and bridged to a $Fe_4$—$S_3$ cluster by three sulfur ligands. FeMo-co is assembled separately in cells and is then incorporated into apo-MoFe protein. The P-cluster is also a metallocluster and contains 8 Fe atoms and 7 sulfur atoms with a structure similar but different to FeMo-co. The P-clusters are located at the αβ subunit interface of dinitrogenase and are coordinated by cysteinyl residues from both subunits. Dinitrogenase reductase, also referred to as component II or the "Fe protein" is a dimer of NifH polypeptides which also contains a single $Fe_4$—$S_4$ cluster at the subunit interface and two Mg-ATP binding sites, one at each subunit. This enzyme is the obligatory electron donor to the dinitrogenase, where the electrons are transferred from the $Fe_4$—$S_4$ cluster to the P-cluster and in turn to the FeMo-co, the site for $N_2$ reduction.

Although the Mo-containing nitrogenase is the most commonly found nitrogenase in bacteria, there are two homologous nitrogenases that are genetically distinct but have similar cofactor and subunit compositions, namely the vanadium-containing nitrogenase and the Fe-only nitrogenase, encoded by the Vnf (vanadium nitrogen fixation) and Anf (alternative nitrogen fixation) genes, respectively. Some bacteria in nature possess all three types of nitrogenases, other bacteria contain only the Mo- and V-containing enzymes or only the Mo-containing enzyme, for example, *Klebsiella pneumoniae*.

A variety of nitrogen fixation (Nif) genes are required for the biosynthesis of FeMo-co and maturation of the nitrogenase components to their catalytically active forms. Roles for the NifB, NifE, NifH, NifN, NifQ, NifV and NifX polypeptides in FeMo-co synthesis have been described (Rubio and Ludden, 2008).

Biological $N_2$ fixation, catalyzed by the prokaryotic enzyme nitrogenase, is an alternative to the use of synthetic $N_2$ fertilizers. The sensitivity of nitrogenase to oxygen is a major barrier to engineering biological nitrogen fixation into plants, for example, into cereal crops, by direct Nif gene transfer.

The present inventors considered that targeting Nif polypeptides to the mitochondrial matrix (MM) of plant cells might overcome the oxygen sensitivity problem. The MM possesses oxygen consuming enzymes that allow other enzymes that contain an oxygen sensitive Fe—S cluster to function. The mitochondrial Fe—S cluster assembly machinery is similar to diazotrophic equivalents (Balk and Pilon, 2011; Lill and Mühlenhoff, 2008). Therefore some of the requisites for nitrogenase biosynthesis may already be in place in the MM, reducing the number of Nif genes required for reconstitution. There is also a high reducing potential and concentration of ATP (Geigenberger and Fernie, 2014; Mackenzie and McIntosh, 1999), both prerequisites for nitrogenase enzyme catalysis. Additionally the presence of glutamate synthase in mitochondria provides an entry point for any ammonium fixed by nitrogenase to enter plant metabolism. Given these characteristics, and the fact that mitochondria themselves are of α-proteobacterial origin, the present inventors considered that this organelle was well suited as a location for attempting functional reconstitution of nitrogenase.

As a first step towards reconstitution of nitrogenase in plant cell mitochondria, evidence was needed that individual Nif proteins can be correctly targeted to the MM. For this purpose, the inventors chose the model plant *Nicotiana benthamiana* as an expression platform (Wood et al., 2009) to provide for expression of transgenes either singly or, more importantly, in combinations. As most MM-located proteins are nuclear-encoded, the present inventors relied upon recent advances in understanding the subcellular signalling and transport process (Huang et al., 2009; Murcha et al., 2014), using a previously characterised N-terminal peptide targeting signal (Lee et al., 2012).

The model bacterial diazotroph *Klebsiella pneumoniae* uses 16 unique proteins for the biosynthesis and catalytic function of nitrogenase. The present inventors re-engineered all 16 Nif proteins from the *K. pneumoniae* for targeting to the plant MM and assessed their expression and processing in *N. benthamiana* leaves. All 16 Nif polypeptides were transiently expressed and tested for sequence specific MM processing. The present inventors have established that all of the 16 Nif polypeptides can be individually expressed as MTP:Nif fusion polypeptides in plant leaf cells. Furthermore, the present inventors provide evidence that these proteins can be targeted to the mitochondrial matrix (MM), a subcellular location potentially accommodating for nitrogenase function and can be cleaved by mitochondrial processing protease (MPP). This represents important progress towards the aim of engineering endogenous nitrogen fixation in plants.

Mitochondrial Protein Import in Plants

Almost all mitochondrial proteins are nuclear encoded and translated in the cytosol, therefore requiring their translocation into the mitochondria. Signal sequences within the polypeptides direct their import to four different intramitochondrial locations: the outer membrane (OM), the intermembrane space (IS), the inner membrane (IM), or the matrix (MM). These signal sequences are distinguished by their biochemical properties and guide trafficking via at least four distinct import pathways which direct the polypeptides to one or more of the four locations (Chacinska et al., 2009). These four pathways are: (1) the general import pathway, also referred to as the "classical" pre-sequence pathway, which directs polypeptides to the MM, the IS or the IM; (2) the carrier import pathway, used for transport to the IM, (3) the mitochondrial intermembrane space (MIA) assembly pathway, and (4) the sorting and assembly machinery (SAM) pathway used for transport of polypeptides to the OM. The general import pathway imports polypeptides having a cleavable pre-sequence, also known as a signal sequence. These polypeptides may also have a hydrophobic sorting signal (HSS). The carrier import pathway imports polypeptides with internal pre-sequence like signals and a hydrophobic region. The MIA pathway imports polypeptides with twin cysteine residues. The SAM pathway imports polypeptides that contain a 13 signal and a putative TOM20 signal. All of these pathways make use of a translocase of the outer membrane (TOM) and the first and second pathways also use a TIM23 translocase of the intermembrane complex. Only the first pathway uses matrix processing peptidase (matrix processing protease, MPP).

A common characteristic of all mitochondrial targeted polypeptides is the presence of at least one domain within the polypeptide that guides transport to the correct location. The best studied of these is the "classic" N-terminal pre-sequence domain that is cleaved in the matrix by MPP (Murcha et al., 2004). It has been estimated that about 70% of plant and animal mitochondrial proteins have a cleavable pre-sequence but both internal and C-terminal signal sequences have also been found (reviewed in Pfanner and Geissler (2001), Schleiff and Soll (2000)). In *Arabidopsis*, these pre-sequences range in length from 11 to 109 amino acid residues with an average length of 50 amino acid residues. Although there is no consensus sequence that fully defines a pre-sequence for the first pathway, they tend to contain a high proportion of hydrophobic and positively charged amino acids. A further characteristic is their ability to form an amphiphilic α-helix, usually starting within the first 10 amino acid residues (Roise et al., 1986). These domains are rich in hydrophobic (Ala, Leu, Phe, Val), hydroxylated (Ser, Thr) and positively charged (Arg, Lys) amino acid residues, and deficient in acidic amino acids. Over a large number of mitochondrial proteins, serine (16-17%) and alanine (12-13%) are greatly over-represented in mitochondrial signal peptides, and arginine is abundant (12%). The MPP cleavage point is defined for most pre-sequences by the presence of a conserved arginine residue, usually at position P2 (−2 aa from the scissile bond), or P3 in most other cases (Huang et al., 2009).

Mitochondrial pre-sequences interact with the Tom20 receptor through hydrophobic residues. Studies have shown that the hydrophobic surface of the α-helix facilitates recognition of the peptide by the TOM20 component of the TOM import complex, whereas the positive charges are recognised by the TOM22 subunit (Abe et al., 2000). Finally, most pre-sequences guide transport of the polypeptide in association with Hsp70, and accordingly nearly all plant pre-sequences contain at least one binding motif for Hsp70 molecular chaperone (Zhang and Glaser, 2002). The chaperone Hsp70 is involved in protein folding, prevents protein aggregations, and functions as a molecular motor, pulling the precursor across the mitochondrial membranes. The electrical membrane potential ($\Delta\psi$) (~100 mV, negative inside) across the inner membrane also drives translocation of the positively charged pre-sequence via an electrophoretic effect.

The majority of proteins with cleavable pre-sequences are destined for the mitochondrial matrix via the general import pathway, which utilises the transporter of the outer membrane (TOM) complex and the transporter of the inner membrane 23 complex (TIM23). However some proteins with cleavable pre-sequences can assemble in the inner membrane (Murcha et al., 2004) or the inter membrane space, if they also contain a hydrophobic sorting signal (HSS) (Glick et al., 1992). There are very few examples of matrix localised proteins that do not have their pre-sequences cleaved. In *Arabidopsis*, only Glutamate dehydrogenase has been found in the matrix with an unprocessed full length pre-sequence (Huang et al., 2009).

For proteins that are not matrix targeted, a variety of internal non-cleavable localisation signals are employed. These are typically associated with a specific trafficking pathway, and are additionally tailored for the particular class of protein. In plants, no studies thus far have determined what precisely constitutes an internal signal sequence for intermembrane space proteins. However, it appears a motif with twin cysteine residues is associated with transport via the mitochondrial intermembrane space assembly pathway (MIA) (Carrie et al., 2010; Darshi et al., 2012). Finally, non-cleavable internal sequences are also utilised by proteins destined for the inner membrane via the carrier pathway, which utilises the TOM and TIM22 apparatus to insert proteins with multiple transmembrane regions (Kerscher et al., 1997; Sirrenberg et al., 1996). These sequences typically contain a hydrophobic region followed by a pre-sequence like internal sequence, and are thus similar to N-terminal pre-sequences, but distinguished by their internal location within their cognate protein.

In photosynthetic organisms, nuclear encoded mitochondrial proteins have a requirement for differentiation between chloroplast and mitochondrial trafficking, despite many similarities between these two organelles and their proteomes. The α-helix that occurs mostly in mitochondria pre-sequences is usually absent in chloroplast pre-sequences (Zhang and Glaser, 2002), which tend to be more unstructured and show high β sheet domain structure (Bruce, 2001).

In plants, the MPP is anchored to the inner membrane bound Cytbc$_1$ complex, although the active MPP site is located facing the matrix, and the functions of the two proteins are independent (Glaser and Dessi, 1999).

Mitochondrial Targeting Peptide

As used herein, the term "mitochondrial targeting peptide" or "MTP" means an amino acid sequence, comprising at least 10 amino acids and preferably between 10 and about 80 amino acid residues in length that directs a target protein to a mitochondrion and which can be used heterologously in an MTP-target protein translational fusion to direct a selected target protein such as a Nif polypeptide, Gus, GFP etc to a mitochondrion.

The MTP typically comprises at its N-terminus a translation initiator methionine of the polypeptide from which it is derived. The MTP is translationally fused to a Nif polypeptide or "target protein" by a peptide bond to the Met residue that corresponds to the initiator Met of the target protein, or that Met residue may be omitted and the peptide bond is directly fused to the amino acid residue that in the wild-type is the second amino acid of the target protein. The MTP is typically rich in basic and hydroxylated amino acids and usually lacks acidic amino acids or extended hydrophobic stretches. The MTP may form amphiphilic helices.

While not wanting to be limited by theory, the MTP typically comprises an uptake-targeting sequence that binds to receptors on the outer membrane of the mitochondrion. Upon binding to the outer membrane, the fusion polypeptide preferably undergoes membrane translocation to transport channel proteins, and passages through the double membrane of the mitochondrion to the mitochondrial matrix (MM). The uptake-targeting sequence is then typically cleaved and the mature fusion protein folded.

The MTP may comprise additional signals that subsequently target the protein to different regions of the mitochondria, such as the mitochondrial matrix (MM). In an embodiment, the uptake-targeting sequence is a matrix targeting sequence.

The MTP may be cleavable or non-cleavable when translationally fused to the Nif polypeptide. Thus, in an embodiment, the MTP-Nif fusion polypeptide is at least partially cleaved. In this regard, the phrase "at least partially cleaved" refers to a detectable amount of cleavage of a MTP-Nif fusion polypeptide when expressed in a plant cell. In an embodiment, at least 50% of the MTP-Nif fusion polypeptide that is produced in the cell is cleaved within the MTP sequence, preferably at least 75% is cleaved, more preferably at least 90% is cleaved. In an alternative embodiment, less than 50% of the MTP-Nif fusion polypeptide is cleaved in the cell, for example, the MTP is not cleaved. In an embodiment, the MTP does not comprise a cleavage site for MPP. The MTP may comprise a cleavage site. Upon cleavage, the N-terminal part of the resultant processed product (i.e., the mature NP) may comprise one or more C-terminal amino acids of the MTP, also referred to herein as a "scar sequence" or "scar peptide", or it may not comprise any C-terminal amino acids of the MTP. When present, the scar sequence is preferable 1 to 45 amino acids in length, more preferably 1 to 20 amino acids, even more preferably 1 to 12 amino acids. Alternatively, the cleavage site may be located within the fusion polypeptide such that the entire MTP sequence is cleaved off, for example, the linker may comprise the cleavage sequence.

Native mitochondrial targeting peptides are localized at the N-terminus of the precursor proteins and a N-terminal part are typically cleaved off during or after import into mitochondria. Cleavage is typically catalysed by the general matrix processing protease (MPP), which, in plants, is integrated into the bc$_1$ complex of the respiratory chain. This protease recognizes the cleavage sites of nearly 1000 precursor proteins that have a wide range of amino acid sequences which show little conservation. In an embodiment, the MTP comprises a protease cleavage site for MPP. In a further embodiment, the processed product is produced by cleavage of the fusion protein within, or immediately after, the MTP by MPP. In this context, the phrase "immediately after" means that following cleavage by MPP, there are no amino acids remaining from the MTP fused to the Nif polypeptide. Thus, where the fusion polypeptide is cleaved "immediately after" the MTP, the MPP cleavage site is immediately after the C-terminal amino acid of the MTP.

The terms "cleaved product" or "cleavage product", as used herein in the context of a MTP fusion polypeptide, refer to a polypeptide resulting from protease cleavage either within or immediately after the MTP amino acid sequence. In this regard, the cleaved product of the MTP fusion polypeptide is obtainable by cleavage by MPP. The cleaved product may retain one or more amino acids from the MTP after cleaveage (i.e., a scar peptide), or it may not have any amino acids remaining from the MTP after cleavage. In an embodiment, a cleaved product of a Nif fusion polypeptide of the invention comprises at least 95% or all of the amino acids present in the Nif polypeptide sequence.

In an embodiment, the MTP is not cleaved. The present inventors have demonstrated that incorporation of the MTP did not always lead to complete processing of Nif proteins. In some instances (NifX-FLAG, NifD-HA$_{opt1}$ and NifDK-HA), both processed and unprocessed Nif proteins were observed. Considering there is no general consensus sequence for MTPs, and internal protein sequences can influence mitochondrial targeting (Becker et al., 2012), it is perhaps not surprising that the present inventors found differences in processing efficiency amongst the Nif proteins.

Suitable MTPs that can be used in the context of the present invention include, without limitation, peptides having the general structure as defined by von Heijne (1986) or by Roise and Schatz (1988). Non limiting examples of MTPs are the mitochondrial targeting peptides defined in Table I of von Heijne (1986) or disclosed herein.

In an embodiment, the MTP is an F1-ATPase γ-subunit (MTP-FAγ). An example of a suitable FAγ MTP is that from *A. thaliana* (Lee et al., 2012). In an embodiment, the MTP-FAγ is 77 amino acids in length, the cleavage of which by an MMP leaves 35 MTP residues at the N-terminal end of the fusion polypeptide. In a preferred embodiment, the MTP-FAγ is less than 77 amino acids in length. For example, the MTP-FAγ may be about 51 amino acids in length, the cleavage of which by an MMP leaves 9 MTP residues at the N-terminal end of the fusion polypeptide.

The skilled person will appreciate that software exists for predicting mitochondrial proteins and their targeting sequence, for example, MitoProtII, PSORT, TargetP and NNPSL.

MitoProtII is a program that predicts mitochondrial localization of a sequence based on several physiochemical parameters (e.g., amino acid composition in the N-terminal part, or the highest total hydrophobicity for a 17 residues window). P SORT is a program that predicts subcellular locations based on various sequence-derived features such as the presence of sequence motifs and amino acid compositions. TargetP predicts the subcellular location of eukaryotic proteins based on the predicted presence of any of the N-terminal presequences: chloroplast transit peptide, mitochondrial targeting peptide or secretory pathway signal peptide. TargetP requires the N-terminal sequence as an input into two layers of artificial neural networks (ANN), utilizing the earlier binary predictors, SignalP and ChloroP. For the sequences predicted to contain an N-terminal presequence a potential cleavage site can also be predicted. NNPSL is another ANN-based method using the amino acid composition to assign one of four subcellular localization (cytosolic, extracellular, nuclear and mitochondrial) to a query sequence.

The skilled person would be readily able to determine if the chosen MTP targeted the fusion polypeptide to the mitochondrial matrix based on routine methods and methods disclosed herein. The present inventors chose a targeting peptide previously demonstrated as capable of transporting GFP in *Arabidopsis* protoplasts (Lee et al., 2012), and which is relatively long, to assist detection of processed protein. As shown in the Examples herein, the chosen MTP targeted all of the selected nitrogenase proteins to the MM. This conclusion is based on several lines of evidence. Firstly, the sizes observed for *N. benthamiana* expressed Nif polypeptides were consistent with the expected size resulting from MM peptidase processing. This was also reflected by the difference in size observed between bacterial (full length unprocessed), and plant mitochondrial expressed Nifs of small sizes (NifF and NifZ). Additionally, mutation of the MTP, rendering it incapable of being processed by the mitochondrial import machinery, produced a larger band for both NifD and GFP fusions, consistent with the difference in size between processed and unprocessed protein. Finally, mass spectrometry for an exemplary fusion polypeptide determined that MTP-NifH was cleaved between residues 42-43 of the MTP as predicted for specific processing in the matrix.

It may be useful in some embodiments of this invention to use multiple tandem copies of a chosen MTP. The coding sequence for a duplicated or multiplied targeting peptide may be obtained through genetic engineering from an existing MTP. The amount of MTP can be measured by cellular fractionation, followed by, for example, quantitative immunoblot analysis. Thus, in the present invention, the term "mitochondrial targeting peptide" or "MTP" encompasses one or more copies of one amino acid peptide that directs a target Nif protein to the mitochondria. In a preferred embodiment, the MTP comprises two copies of a chosen MTP. In another embodiment, the MTP comprises three copies of a chosen MTP. In another embodiment, the MTP comprises four copies or more of a chosen MTP.

The skilled person will appreciate that the MTP sequence is not limited to native MTP sequences but may comprise amino acid substitutions, deletions and/or insertions, relative to a naturally-occurring MTP, provided that the sequence variant still functions for mitochondrial targeting.

The skilled person will understand that the MTP may be flanked by amino acids at its N- or C-terminal ends as a result of the cloning strategy and may function as a linker. These additional amino acids may be considered to form part of the MTP.

The skilled person will also understand that the MTP may be N- or C-terminally fused to an oligopeptide linker and/or tag such as an epitope tag. In a preferred embodiment, one or more or all of the Nif fusion polypeptides of the invention produced in a plant cell lack added epitope tags relative to a corresponding wild-type Nif polypeptide.

Mitochondrial Targeting Peptide (MTP)-Nif Fusion Polypeptides

The present invention relates to mitochondrial targeting peptide (MTP)-Nif fusion polypeptides and their cleaved polypeptide products. When an MTP-Nif fusion polypeptide of the invention is expressed in a plant cell, either the MTP-Nif fusion polypeptide and/or the cleaved polypeptide product is targeted to the mitochondrial matrix (MM). Preferably, the fusion polypeptides confer nitrogenase reductase and/or nitrogenase activity to the plant cell, or an activity which is the same as that conferred by a corresponding wild-type Nif polypeptide in bacteria.

As used herein, the term "fusion polypeptide" means a polypeptide which comprises two or more polypeptide domains which are covalently joined by a peptide bond. Typically, the fusion polypeptide is encoded as a single polypeptide chain by a chimeric polynucleotide of the invention. In an embodiment, fusion polypeptides of the invention comprise a mitochondrial targeting peptide (MTP) and a Nif polypeptide (NP). In this embodiment, the C-terminal end of the MTP is translationally fused to the N-terminal end of the NP. In an alternative embodiment, fusion polypeptides of the invention comprise a C-terminal part of an MTP and a NP, where the C-terminal part results from cleavage of the MTP by MPP. Such a C-terminal part of an MTP is referred to herein as a "scar" sequence. In this embodiment, the C-terminal amino acid of the C-terminal part of the MTP is translationally fused to the N-terminal amino acid of the NP. In these embodiments, the fusion polypeptide may comprise one or more additional amino acids between the MTP and the NP, such as a GlyGly sequence, and/or an added methionine as a translation start amino acid. In an embodiment, the fusion polypeptide comprises two Nif polypeptides, preferably a NifD polypeptide translationally fused via a linker sequence to a NifK polypeptide or a NifE polypeptide translationally fused via a linker sequence to a NifN polypeptide. Both of these fused polypeptides may be present. In these embodiments, it is preferred that the second Nif polypeptide in the fusion polypeptide has its wild-type C-terminus, i.e., lacking any C-terminal extension.

As used herein, the term "translationally fused at the N-terminal end" means that the C-terminal end of the MTP polypeptide or linker polypeptide is covalently joined by a peptide bond to the N-terminal end of a NP, thereby being a fusion polypeptide. In an embodiment, the NP does not comprise its native translation start methionine (Met) residue or its two N-terminal Met residues relative to a corresponding wild-type NP. In an alternative embodiment, the NP comprises the translation start Met or one or both of the two N-terminal Met residues of the wild-type NP polypeptide such as, for example, for NifD.

Such polypeptides are typically produced by expression of a chimeric protein coding region where the translational reading frame of the nucleotides encoding the MTP are joined in-frame with the reading frame of the nucleotides encoding the NP. The skilled person will appreciate that the C-terminal amino acid of the MTP can be translationally fused to the N-terminal amino acid of the NP without a linker or via a linker of one or more amino acid residues, for example of 1-5 amino acid residues. Such a linker can also be considered to be part of the MTP. Expression of the protein coding region may be followed by cleavage of the MTP in the MM of a plant cell, and such cleavage (if it occurs) is included in the concept of production of the fusion polypeptide of the invention.

The fusion polypeptide or the processed Nif polypeptide preferably has functional Nif activity. In a preferred embodiment, the activity is similar to that of the corresponding wild-type Nif polypeptide. The functional activity of the fusion polypeptide or the processed Nif polypeptide may be determined in bacterial and biochemical complementation assays. In a preferred embodiment, the fusion polypeptide or the processed Nif polypeptide has between about 70-100% of the activity of the wild-type Nif activity. Nif polypeptides which do not have Nif function still have utility, for example, as research tools to test for expression levels from genetic constructs or for association with other Nif polypeptides.

The fusion polypeptide may comprise more than one MTP and/or more than one NP, for example, the fusion polypeptide may comprise a MTP, a NifD polypeptide and a NifK polypeptide. The fusion polypeptide may also comprise an oligopeptide linker, for example, linking two NPs. Preferably, the linker is of sufficient length to allow the two or more functional domains, for example, two NPs such as NifD and NifK or NifE and NifN, to associate in a functional configuration in a plant cell. In a preferred embodiment, the NifD polypeptide is an AnfD polypeptide and the NifK polypeptide is an AnfK polypeptide. Such a linker may be between 8 and 50 amino acid residues in length, preferably about 25-35 amino acids in length, more preferably about 30 amino acid residues in length or about 26 amino acid residues in length for an AnfD-linker-AnfK fusion polypeptide. A fusion polypeptide may be obtained by conventional means, e.g., by means of gene expression of the polynucleotide sequence encoding for said fusion polypeptide in a suitable cell.

As used herein, a "substantially purified polypeptide" means a polypeptide which is substantially free from components (e.g., lipids, nucleic acids, carbohydrates) that normally associate with the polypeptide, for example, in a cell. Preferably, the substantially purified polypeptide is at least 90% free from said components.

Plant cells, transgenic plants and parts thereof of the invention comprise a polynucleotide encoding a polypeptide of the invention. Polypeptides of the invention are not naturally occurring in plant cells, in particular not in the mitochondria of plant cells, and therefore the polynucleotide encoding the polypeptide may be referred to herein as an exogenous polynucleotide since it is not naturally occurring in a plant cell but has been introduced into the plant cell or a progenitor cell. The cells, plants and plant parts of the invention which produce a polypeptide of the invention can therefore be said to produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the plant cell, plant or plant part comprises a non-endogenous gene that causes an amount of the polypeptide to be produced, at least at some time in the life-cycle of the plant cell or plant. Preferably the exogenous polynucleotide is integrated into the nuclear genome of the plant cell and/or is transcribed in the nucleus of the cell.

In an embodiment, a polypeptide of the invention is not a naturally occurring polypeptide. In an alternative embodiment, the polypeptide of the invention is naturally occurring but is present in a plant cell, preferably in a mitochondrion of a plant cell, in which it does not naturally occur.

In an embodiment, a polypeptide of the invention (e.g., a MTP fusion polypeptide or cleaved product thereof) is at least partially soluble in mitochondria of a plant cell. In this context, the phrase "at least partially soluble" means that the polypeptide is detectable in the soluble fraction of a homogenised sample comprising mitochondria of a plant cell. Suitable methods for detecting solubility of polypeptides are known in the art and include those that are described in Example 1. In an embodiment, at least 5%, at least 10%, at least 15%, at least 20%, at least 25%, at least 30%, at least 40%, at least 50%, at least 60%, at least 70%, at least 80%, or at least 90% of the polypeptide present in the cell is soluble.

Nif Polypeptides

As used herein, the terms "Nif polypeptide" and "Nif protein" are used interchangeably and mean a polypeptide which is related in amino acid sequence to naturally occurring polypeptides involved in nitrogenase activity, where the Nif polypeptide of the invention is selected from the group consisting of a NifD polypeptide, a NifH polypeptide, a NifK polypeptide, a NifB polypeptide, a NifE polypeptide, a NifN polypeptide, a NifF polypeptide, a NifJ polypeptide, a NifM polypeptide, a NifQ polypeptide, a NifS polypeptide, a NifU polypeptide, a NifV polypeptide, a NifW polypeptide, a NifX polypeptide, a NifY polypeptide and a NifZ polypeptide, each of which as defined herein. Nif polypeptides of the invention include "Nif fusion polypeptides" which, as used herein, means a polypeptide homolog of a naturally occurring Nif polypeptide that has additional amino acid residues joined to the N-terminus or C-terminus, or both, relative to a corresponding naturally occurring Nif polypeptide. As mentioned above, the Nif fusion polypeptide may be lacking the translation initiation Met or the two N-terminal Met residues relative to a corresponding wild-type Nif polypeptide. The amino acid residues of a Nif fusion polypeptide that correspond to the naturally occurring Nif polypeptide, i.e., without the additional amino acid residues joined to the N-terminus or C-terminus or both, are also referred to herein as a Nif polypeptide, abbreviated in this case to "NP", or as a NifD polypeptide ("ND") etc. In a preferred embodiment, the "additional amino acid residues joined to the N-terminus or C-terminus or both" comprise a mitochondrial targeting peptide (MTP) or a processed MTP joined to the N-terminus of the NP, or an epitope sequence ("tag") which is N-terminal or C-terminal to the NP or both, or both an MTP or processed MTP and an epitope sequence.

Naturally occurring Nif polypeptides occur only in some bacteria including the nitrogen-fixing bacteria, including free living nitrogen fixing bacteria, associative nitrogen fixing bacteria and symbiotic nitrogen fixing bacteria. Free living nitrogen fixing bacteria are capable of fixing significant levels of nitrogen without the direct interaction with other organisms. Without limitation, said free living nitrogen fixing bacteria include the members of the genera *Azotobacter, Beijerinckia, Klebsiella, Cyanobacteria* (classified as aerobic organisms) and the members of the genera *Clostridium, Desulfovibrio* and the named purple sulphur bacteria, purple non-sulphur bacteria and green sulphur bacteria. Associative nitrogen fixing bacteria are those prokaryotic organisms that are able to form close associations with several members of the Poaceae (grasses). These bacteria fix appreciable amounts of nitrogen within the rhizosphere of the host plants. Members of the genera *Azospirillum* are representative of associative nitrogen fixing bacteria. Symbiotic nitrogen fixation bacteria are those bacteria which fix nitrogen symbiotically by partnering with a host plant. The plant provides sugars from photosynthesis that are utilized by the nitrogen fixing bacteria for the energy it needs for nitrogen fixation. Members of the genera *Rhizobia* are representative of associative nitrogen fixing bacteria.

The Nif polypeptide or Nif fusion polypeptide of the invention is selected from the group consisting of NifH, NifD, NifK, NifB, NifE, NifN, NifF, NifJ, NifM, NifQ, NifS, NifU, NifV, NifW, NifX, NifY and NifZ polypeptides. Function of these polypeptides has been reviewed recently by Burén et al. (2020).

Other polypeptides of the invention are considered to be VnfG and AnfG involved in the V-nitrogenase and Fe-nitrogenase, respectively, nitrogenase associated factors (Naf polypeptides) such as, for example, NafY, and ferredoxin polypeptides such as FdxN polypeptides. These polypeptides are preferably encoded and expressed as MTP-fusion polypeptides for mitochondrial targeting.

A polypeptide or class of polypeptides may be defined by the extent of identity (% identity) of its amino acid sequence to a reference amino acid sequence and/or by the presence of certain amino acid motifs or protein family domains, or by having a greater % identity to one reference amino acid sequence than to another. A polypeptide or class of polypeptides may also be defined by having the same biological activity as a naturally occurring Nif polypeptide, in addition to the extent of identity in sequence.

The % identity of a polypeptide is determined by GAP (Needleman and Wunsch, 1970) analysis (GCG program) with a gap creation penalty=5, and a gap extension penalty=0.3, or by Blastp version 2.5 or updated versions thereof (Altschul et al., 1997), where in each case the analysis aligns two sequences including a reference sequence over the entire length of the reference sequence. As used herein, reference sequences include those provided for naturally occurring Nif polypeptides from *K. pneumoniae* (renamed as *K. oxytoca*), SEQ ID NOs:1-17.

In the following definitions, the extent of identity of an amino acid sequence to a reference sequence provided as a SEQ ID NO is determined by Blastp, version 2.5 or updated versions thereof (Altschul et al, 1997), using the default parameters except for the maximum number of target sequences which is set at 10,000, and is determined along the full length of the reference amino acid sequence.

A NifH polypeptide in naturally occurring bacteria is a structural component of nitrogenase complex and is often termed the iron (Fe) protein. It forms a homodimer, with a $Fe_4S_4$ cluster bound between the subunits and two ATP-binding domains. NifH is the obligate electron donor to the nitrogenase protein (NifD/NifK heterotetramer) and therefore functions as the nitrogenase reductase (EC 1.18.6.1). NifH of the molybdenum type is also involved in FeMo-co biosynthesis and apo-MoFe protein maturation (Jasniewski et al., 2018). As reviewed therein, NifH has three primary recognised functions: (i) involvement in the insertion of Mo and homocitrate in the synthesis of FeMo-co, also involving the NifE-NifN complex, (ii) a reductase function in the formation of P-cluster on NifD-NifK from what is termed P* cluster, which may also involve a small chaperone-like polypeptide NifZ, and (iii) as electron donor to the nitrogenase protein.

As used herein, a "NifH polypeptide" means a polypeptide comprising amino acids whose sequence is at least 41% identical to the amino acid sequence provided as SEQ ID NO:1 and which comprises one or more of the domains TIGR01287, PRK13236, PRK13233 and cd02040. The TIGR01287 domain is present in each of molybdenum-iron nitrogenase reductase (NifH), vanadium-iron nitrogenase reductase (VnfH), and iron-iron nitrogenase reductase (AnfH) but excludes the homologous protein from the light-independent protochlorophyllide reductase. As used herein, NifH polypeptides therefore include the subclass of iron-binding polypeptides which comprise amino acids whose sequence is at least 41% identical to SEQ ID NO:1, the VnfH iron-binding polypeptides and the AnfH iron-binding polypeptides. A naturally occurring NifH polypeptide typically has a length of between 260 and 300 amino acids and the natural monomer has a molecular weight of about 30 kDa. A great number of NifH polypeptides have been identified and numerous sequences are available in publically available databases. For example, NifH polypeptides have been reported from *Klebsiella michiganensis* (Accession No. WP_049123239.1, 99% identical to SEQ ID NO:1), *Brenneria goodwinii* (WP_048638817.1, 93% identical), *Sideroxydans lithotrophicus* (WP_013029017.1, 84% identical), *Denitrovibrio acetiphilus* (WP_013010353.1, 80% identical), *Desulfovibrio africanus* (WP_014258951.1, 72% identical), *Chlorobium phaeobacteroides* (WP_011744626.1, 69% identical), *Methanosaeta concilii* (WP_013718497.1, 64% identical), *Rhodobacter* (WP_009565928.1, 61% identical), *Methanocaldococcus infernus* (WP_013099472.1, 42% identical) and *Desulfosporosinus youngiae* (WP_007781874.1, 41% identical). NifH polypeptides have been described and reviewed in Thiel et al. (1997), Pratte et al. (2006), Boison et al. (2006) and Staples et al. (2007).

As used herein, a functional NifH polypeptide is a NifH polypeptide which is capable of forming a functional nitrogenase protein complex together with the other required subunits, for example, NifD and NifK, and the FeMo-, FeV- or FeFe-cofactor.

As used herein, an "AnfH polypeptide" is a NifH polypeptide which is a member of the nitrogenase conserved superfamily cl25403 (TIGR01287) containing the PRK13233 conserved domain and having at least 69% amino acid sequence identity to the *Azotobacter vinelandii* AnfH polypeptide (SEQ ID NO:218; Accession No. WP_012703362) when measured along the full-length of SEQ ID NO:218. This amino acid sequence is used herein as the reference sequence for AnfH. TIGR01287:AnfH represents the all-iron variant of the nitrogenase component II, also known as nitrogenase reductase. As used herein, the AnfH polypeptides are a subset of the NifH polypeptides. AnfH polypeptides do not include the molybdenum type NifH polypeptides and the vanadium type NifH polypeptides (VnfH). The amino acid sequences of AnfH polypeptides in sequence databases were usually annotated as an AnfH polypeptide. As of January 2020, there were 314 specific amino acid sequences in the NCBI protein database in the AnfH set, all of which had amino acid residues specific to AnfH and which were distinct from the molybdenum-type NifH and VntH, which subsets looked more alike but still distinct. Examples of naturally occurring AnfH polypeptides include AnfH polypeptides from *Rhodocyclus tenuis* (Accession No. WP_153472986; 92.36% identical), *Dickeya paradisiaca* (Accession No. WP_015854293; 88.36% identical), *Thermodesulfitimonas autotrophica* (Accession No. WP_123927773; 78.91% identical), *Clostridium kluyveri*

(Accession No. WP_073538802; 76.36% identical) and *Methanophagales archaeon* (Accession No. RCV64832; 69.37% identical), each with reference to SEQ ID NO:218.

As described in Example 23 herein, 16 amino acids were identified at defined positions in AnfH sequences that were conserved and characteristic of AnfH polypeptides relative to the molybdenum-type NifH sequence of AvNifH. These can be used to distinguish AnfH polypeptides from other NifH sequences which do not have all 16 amino acids in common. AvNifH, KoNifH (SEQ ID NO:1) and other molybdenum type NifH sequences had motifs III and IV but did not have motifs I, II, V-VII, and therefore these motifs (SEQ ID NOs:225-231) could also be used to distinguish the AnfH subset from other NifH polypeptides.

Analogous to other functional NifH polypeptides, functional AnfH polypeptides are capable of functioning as a nitrogenase reductase, being the obligate electron donor to FeFe complex. Analogous to the molybdenum-type NifH, AnfH is potentially involved in FeFe-co biosynthesis and maturation of the apo-FeFe complex (AnfD-AnfK-AnfG).

As used herein, a "NifD polypeptide" means a polypeptide comprising amino acids whose sequence is at least 33% identical to the amino acid sequence provided as SEQ ID NO:2 and which comprises (i) one or both of the domains TIGR01282 and COG2710, both of which are found in the iron-molybdenum binding polypeptides including the polypeptide having the amino acid sequence shown in SEQ ID NO:2, or (ii) the iron-vanadium binding domain TIGR01860 in which case the NifD polypeptide is in the subclass of VnfD polypeptides, or (iii) the iron-iron binding domain TIGR1861 in which case the NifD polypeptide is in the subclass of AnfD polypeptides. The NifD polypeptide may be part of a fusion polypeptide, for example, fused to a MTP and/or NifK, or alternatively may not comprise any N- or C-terminal extensions. In a preferred embodiment, the NifD polypeptide when associated with a NifK polypeptide, binds FeMo-cofactor.

As used herein, NifD polypeptides include the subclass of iron-molybdenum (FeMo-co) binding polypeptides comprising amino acids whose sequence is at least 33% identical to SEQ ID NO:2, the VnfD iron-vanadium polypeptides and the AnfD polypeptides. A naturally occurring NifD polypeptide typically has a length of between 470 and 540 amino acids. A great number of NifD polypeptides have been identified and numerous sequences are available in publically available databases. For example, NifD polypeptides have been reported from *Raoultella ornithinolytica* (Accession No. WP_044347161.1, 96% identical to SEQ ID NO:2), *Kluyvera intermedia* (WP_047370273.1, 93% identical), *Dickeya dadantii* (WP_038902190.1, 89% identical), *Tolumonas* sp. BRL6-1 (WP_024872642.1, 81% identical), *Magnetospirillum gryphiswaldense* (WP_024078601.1, 68% identical), *Thermoanaerobacterium thermosaccharolyticum* (WP_013298320.1, 42% identical), *Methanothermobacter thermautotrophicus* (WP_010877172.1, 38% identical), *Desullovibrio africanus* (WP_014258953.1, 37% identical), *Desulfotomaculum* sp. LMa1 (WP_066665786.1, 37% identical), *Desulfomicrobium baculatum* (WP_015773055.1, 36% identical), the VnfD polypeptide of *Fischerella muscicola* (WP_016867598.1, 34% identical) and the AnfD polypeptide from *Opitutaceae bacterium* TAV5 (WP_009512873.1, 33% identical). NifD polypeptides have been described and reviewed in Lawson and Smith (2002), Kim and Rees (1994), Eady (1996), Robson et al. (1989), Dilworth et al. (1988), Dilworth et al. (1993), Miller and Eady (1988), Chiu et al. (2001), Mayer et al. (1999), and Tezcan et al. (2005).

NifD polypeptides of the iron-molybdenum subclass are a key subunit of nitrogenase complexes, being the a subunit of the $\alpha_2\beta_2$ MoFe protein complex at the core of nitrogenase, and the site of substrate reduction with the FeMo cofactor. As used herein, a functional NifD polypeptide is a NifD polypeptide which is capable of forming a functional nitrogenase protein complex together with the other required subunits, for example, NifH and NifK, and the FeMo or other cofactor.

As used herein a "a NifD polypeptide (ND) which is resistant to protease cleavage" is resistant to cleavage at a defined site or within a defined region, for example within an amino acid sequence corresponding to amino acids 97-100 of SEQ ID NO:18, when the ND is introduced into plant mitochondria by use of an MTP. As used herein "resistant to protease cleavage" means yielding <10% cleavage when the NifD polypeptide is introduced into plant mitochondria by use of an MTP. In preferred embodiments, less than 5% of the NifD polypeptide is cleaved at the site or within the region, more preferably essentially not cleaved, or cleavage is not detected. The NifD polypeptide may be "relatively resistant to cleavage" compared to a NifD polypeptide comprising the amino acid sequence provided as SEQ ID NO:18, being cleaved at least 5-fold less often, preferably at least 10-fold less often, as a NifD polypeptide comprising the amino acid sequence provided as SEQ ID NO:18.

As used herein, an "amino acid sequence other than RRNY (SEQ ID NO:101) at positions corresponding to amino acids 97-100 of SEQ ID NO:18" refers to a sequence which comprises four residues at positions corresponding to amino acids 97-100 of SEQ ID NO:18 and which is not RRNY.

As used herein, an "AnfD polypeptide" is a NifD polypeptide which is specifically a member of the oxidoreductase nitrogenase conserved superfamily cl30843, containing the TIGR01861 conserved domain, and having at least 71% amino acid sequence identity to the *Azotobacter vinelandii* AnfD polypeptide (SEQ ID NO:216; Accession No. WP_012703361) when measured along the full-length of SEQ ID NO:216. This amino acid sequence is used herein as the reference sequence for AnfD TIGR01861:AnfD represents the all-iron variant of the nitrogenase component I $\alpha$-chain. As used herein, an AnfD polypeptide is therefore a subset of the NifD polypeptides. AnfD polypeptides do not include the molybdenum type NifD polypeptides and the vanadium type NifD polypeptides (VnfD) and also do not include protochlorophyllide or chlorophyllide reductase polypeptides (Boyd and Peters, 2013). The amino acid sequences of AnfD polypeptides in the protein sequence database are usually annotated as an AnfD polypeptide. As of January 2020, there were 156 specific amino acid sequences in the NCBI protein database in the AnfD set. Examples of naturally occurring AnfD polypeptides include AnfD polypeptides from *Desulfovibrio* sp. DV (Accession No. WP_075356167; 87.47% identical), *Paenibacillus* sp. FSL H7-0357 (Accession No. WP_038590013; 85.52% identical), *Rhodobacter capsulatus* (Accession No. WP 023922817; 80.31% identical), *Methanosarcina acetivorans* C2A (Accession No. WP_011021232; 77.13% identical) and *Bacteroidales bacterium* Barb7 (Accession No. OAV73823; 71.25% identical), each with reference to SEQ ID NO:216. Further examples were reported in McRose et al. (2017).

Analogous to other NifD polypeptides which are functional, functional AnfD polypeptides are capable of functioning as the $\alpha$ protein structural component of the $\alpha_2\beta_2\delta_2$ heterohexameric nitrogenase with the $\beta$ protein (AnfK) and the δ protein (AnfG), providing the catalytic complex binding FeFe-co for dinitrogen reduction.

As used herein, a "NifK polypeptide" means a polypeptide comprising amino acids whose sequence is at least 31% identical to the amino acid sequence provided as SEQ ID NO:3 and which comprises one or more of the conserved domains cd01974, TIGR01286, or cd01973 in which case the NifK polypeptide is in the subclass of VnfK polypeptides, or cl02775 containing the TIGR02931 conserved domain in which case the NifK polypeptide is in the subclass of AnfK polypeptides. As used herein, NifK polypeptides include the VnfK polypeptides from iron-vanadium nitrogenase and the AnfK iron-binding polypeptides. A naturally occurring NifK polypeptide typically has a length of between 430 and 530 amino acids. A great number of NifK polypeptides have been identified and numerous sequences are available in publically available databases. For example, NifK polypeptides have been reported from *Klebsiella michiganensis* (Accession No. WP_049080161.1, 99% identical to SEQ ID NO:3), *Raoultella ornithinolytica* (WP_044347163.1, 96% identical), *Klebsiella variicola* (SBM87811.1, 94% identical), *Kluyvera intermedia* (WP_047370272.1, 89% identical), *Rahnella aquatilis* (WP_014333919.1, 82% identical), *Tolumonas auensis* (WP_012728880.1, 75% identical), *Pseudomonas stutzeri* (WP_011912506.1, 68% identical), *Vibrio natriegens* (WP_065303473.1, 65% identical), *Azoarcus toluclasticus* (WP_018989051.1, 54% identical), *Frankia* sp. (prf||2106319A, 50% identical) and *Methanosarcina acetivorans* (WP_011021239.1, 31% identical). There are some examples of polypeptides in databases annotated as "NifK" which have less than 31% identity to SEQ ID NO:3 but do not contain any of the domains listed above and are therefore not included as NifK polypeptides herein. NifK polypeptides have been described and reviewed in Kim and Rees (1994), Eady (1996), Robson et al. (1989), Dilworth et al. (1988), Dilworth et al. (1993), Miller and Eady (1988), Igarashi and Seefeldt (2003), Fani et al. (2000) and Rubio and Ludden (2008).

NifK polypeptides of the iron-molybdenum subclass are a key subunit of nitrogenase complexes, being the β subunit of the $\alpha_2\beta_2$ MoFe protein complex at the core of nitrogenase. As used herein, a functional NifK polypeptide is a NifK polypeptide which is capable of forming a functional nitrogenase protein complex together with the other required subunits, for example, NifD and NifH, and the FeMo or other cofactor. In a preferred embodiment, when aligned with the amino acid sequence SEQ ID NO:3, the amino acid sequence of the NifK polypeptide of the invention has at its C-terminus the amino acids DLVR (SEQ ID NO:58), the arginine being the C-terminal amino acid. That is, the NifK polypeptide and the NifK fusion polypeptide of the invention preferably has the same C-terminus as the native NifK polypeptides, i.e., it does not have an artificial addition to the C-terminus. Such preferred NifK polypeptides are better able to form a functional nitrogenase complex with NifD and NifH polypeptides.

NifK polypeptides of the iron-molybdenum subclass are a key subunit of nitrogenase complexes, being the β subunit of the $\alpha_2\beta_2$ MoFe protein complex at the core of nitrogenase. As used herein, a functional NifK polypeptide is a NifK polypeptide which is capable of forming a functional nitrogenase protein complex together with the other required subunits, for example, NifD and NifH, and the FeMo or other cofactor. In a preferred embodiment, when aligned with the amino acid sequence SEQ ID NO:3, the amino acid sequence of the NifK fusion polypeptide and the cleaved NifK polypeptide of the invention have at its C-terminus the amino acids DLVR (SEQ ID NO:58), the arginine being the C-terminal amino acid. In other preferred embodiments, the amino acid sequence of the NifK fusion polypeptide and the cleaved NifK polypeptide of the invention have at its C-terminus the amino acid sequence DLIR (SEQ ID NO:239), DVVR (SEQ ID NO:240), DIIR (SEQ ID NO:241), DLTR (SEQ ID NO:242) or INVW (SEQ ID NO:243), which are typically not present in native AnfK sequences. The NifK polypeptide and the NifK fusion polypeptide of the invention, and the cleaved NifK polypeptide therefrom, preferably has the same C-terminus as a native NifK polypeptide, i.e., it does not have an artificial addition to the C-terminus, and it does not have any amino acids deleted from the C-terminus when aligned with a native NifK polypeptide. Such preferred NifK polypeptides are better able to form a functional nitrogenase complex with NifD and NifH polypeptides.

As used herein, an "AnfK polypeptide" is a polypeptide which is a member of the oxidoreductase nitrogenase conserved superfamily cl02775, containing the TIGR02931 conserved domain, and having at least 54% amino acid sequence identity to the *Azotobacter vinelandii* AnfK polypeptide (SEQ ID NO:217; Accession No. WP_012703359) when measured along the full-length of SEQ ID NO:217. This amino acid sequence is used herein as the reference sequence for AnfK. TIGR02931:AnfK represents the all-iron variant of the nitrogenase component I β-chain. As used herein, an AnfK polypeptide may be a NifK polypeptide, having at least 31% amino acid identity to SEQ ID NO:3. Other AnfK polypeptides are less homologous and are only 25-31% identical to SEQ ID NO:3 but are nevertheless included in AnfK polypeptides of the invention AnfK polypeptides do not include the molybdenum type NifK polypeptides and the vanadium type NifK polypeptides (VnfK). The AnfK fusion polypeptide and the cleaved AnfK polypeptide of the invention preferably have the same C-terminus as a native AnfK polypeptide, i.e., it does not have an artificial addition to the C-terminus, and it does not have any amino acids deleted from the C-terminus when aligned with a native AnfK polypeptide such as SEQ ID NO:217. In preferred embodiments, the amino acid sequence of the AnfK fusion polypeptide and the cleaved AnfK polypeptide of the invention has at its C-terminus the amino acid sequence LNVW (SEQ ID NO:244), LNTW (SEQ ID NO:245), LNMW (SEQ ID NO:246), LAMW (SEQ ID NO:247) or LSVW (SEQ ID NO:248). The amino acid sequences of AnfK polypeptides in the protein sequence database are usually annotated as an AnfK polypeptide. As of January 2020, there were 155 specific amino acid sequences in the protein database in the AnfK set, which were distinct from the molybdenum-type NifK and VnfK polypeptide sequences. Examples of naturally occurring AnfK polypeptides include AnfK polypeptides from *Azomonas agilis* (Accession No. WP_144571040; 91.34% identical), *Clostridium* sp. BL-8 (Accession No. WP_077859050; 78.35% identical), *Lucifera butyrica* (Accession No. WP_122630336; 62.34% identical) and *Rhodoblastus acidophilus* (Accession No. WP_088520366; 54% identical), each with reference to SEQ ID NO:217.

Analogous to other NifK polypeptides which are functional, functional AnfK polypeptides are capable of functioning as the β protein structural component of the $\alpha_2\beta_2\delta_2$ heterohexameric nitrogenase with the α protein (AnfD) and the δ protein (AnfG) to form the complex having the active site for dinitrogen reduction on FeFe-co.

A NifB polypeptide in naturally occurring bacteria is a protein which converts [4Fe-4S] clusters into NifB-co, an Fe—S cluster of higher nuclearity with a central C atom that serves as a precursor of FeMo-co, FeV-co and FeFe-co synthesis (Guo et al., 2016). NifB therefore catalyses the first committed step in the FeMo-co, FeV-co and FeFe-co synthesis pathways and is therefore essential for nitrogenase function. The NifB-co product of NifB is able to bind to the NifE-NifN complex and can be shuttled from NifB to NifE-NifN by the metallocluster carrier protein NifX.

As used herein, a "NifB polypeptide" means a polypeptide whose amino acid sequence comprises amino acids whose sequence is at least 27% identical to the amino acid sequence provided as SEQ ID NO:4. Most NifB polypeptides comprise one or more of the conserved domain TIGR01290, the NifB conserved domain cd00852, the NifX-NifB superfamily conserved domain cl00252 and the Radical_SAM conserved domain cd01335. As used herein, NifB polypeptides include naturally occurring polypeptides which have been annotated as having NifB function but which do not have one of these domains. NifB polypeptides from *Klebsiella, Azotobacter, Rhizobium, Bradyrhizobium* and other bacteria have a C-terminal NifX-like extension, whereas most archeal NifB polypeptides lack the NifX-like domain and are referred to as "truncated NifB polypeptides". A naturally occurring NifB polypeptide typically has a length of between 440 and 500 amino acids and the natural monomer has a molecular weight of about 50 kDa. A great number of NifB polypeptides have been identified and numerous sequences are available in publically available databases. For example, NifB polypeptides have been reported from *Raoultella ornithinolytica* (Accession No. WP_041145602.1, 91% identical to SEQ ID NO:4), *Kosakonia radicincitans* (WP_043953592.1, 80% identical), *Dickeya chrysanthemi* (WP_040003311.1, 76% identical), *Pectobacterium atrosepticum* (WP_011094468.1, 70% identical), *Brenneria goodwinii* (WP_048638849.1, 63% identical), *Halorhodospira halophila* (WP_011813098.1, 59% identical, lacking a NifX domain), *Methanosarcina barkeri* (WP_048108879.1, 50% identical, lacking a NifX domain), *Clostridium purinilyticum* (WP_050355163.1, 40% identical, lacking a NifX domain) and *Desulfovibrio salexigens* (WP_015850328.1, 27% identical). As used herein, a "functional NifB polypeptide" is a NifB polypeptide which is capable of forming NifB-co from [4Fe-4S] clusters. Functional NifB requires S-adenosylmethionine (SAM) for its function. NifB polypeptides have been described and reviewed in Curatti et al. (2006) and Allen et al. (1995).

Boyd et al. (2011) investigated the phylogenetic relationship of Anf/Vnf/NifDKEN and NifB from 40 taxa and made the following conclusions: (1) Lateral gene transfer of the Nif cluster encoding a NifB lacking a C-terminal NifX domain occurred from a methanogen ancestor in the order Methanosarcinales to an anaerobic *Firmicutes* ancestor, where the two organisms coexisted in an anaerobic environment and where molybdenum was available, and (2) after this lateral gene transfer event, fusion of NifB and NifX occurred in the *Firmicutes*, from which the diazotrophic bacterial lineage evolved. The following evidence was provided to support this theory: (1) None of the methanogenic archaea (Methanococcales, Methanosarcinales and Methanobacteriales) have a NifB with a C-terminal NifX domain, (2) NifB sequences from Methanobacteriales and Methanococcales indicate early divergence from those of Methanosarcinales and Bacteria, and (3) some of the anaerobic *Firmicutes*, Chloroflexi and Proteobacteria that have a NifB without the C-terminal NifX domain diverged early from the Firmicute lineage, supposedly shortly after the Nif lateral gene transfer event.

To determine the presence or absence of a C-terminal NifX domain in NifB polypeptides, a NifB amino acid sequence can be aligned using Constraint-based Multiple Alignment Tool (COBALT, NCBI, www.ncbi.nlm.nih.gov/tools/cobalt/re_cobalt/cgi) with representative NifB sequences such as from *Klebsiella michiganensis* NifB (Accession No. P10930), *Klebsiella michiganensis* NifX (KZT46636.1), NifY (KZT46633.1), *A. vinelandii* NifX (AGK13791.1), NifY (AGK13792.1), NafY (AGK13761.1), and NifX/NifY/NafY/VnfX family protein (AGK14217.1). The 'dinitrogenase FeMo-cofactor binding site' (Pfam family PF02579) in each sequence can be identified by PfamScan (EMBL-EBI, www.ebi.ac.uk/Tools/pfa/pfamscan/), using the Pfam-A database with the expectation value set to 10.

The NifEN complex is a scaffold complex that is required for the correct assembly of dinitrogenase, functioning as the scaffold for NifB-co maturation into FeMo-co which process also requires NifH function, and is also structurally similar to the dinitrogenase (Fay et al., 2016). The NifEN complex is comprised of 2 subunits of each of NifE and NifN, respectively, forming a heterotetramer, here termed $EN\alpha_2\beta_2$. A NifE polypeptide in naturally occurring bacteria is a polypeptide which is the a subunit of the $EN\alpha_2\beta_2$ tetramer with the NifN polypeptide, and this $EN\alpha_2\beta_2$ tetramer is required for FeMo-co synthesis and is proposed to function as a scaffold on which FeMo-co is synthesized.

As used herein, a "NifE polypeptide" means a polypeptide comprising amino acids whose sequence is at least 32% identical to the amino acid sequence provided as SEQ ID NO:5 and which comprises one or both of the domains TIGR01283 and PRK14478. Members of TIGR01283 domain protein family are also members of the superfamily cl02775. A naturally occurring NifE polypeptide typically has a length of between 440 and 490 amino acids and the natural monomer has a molecular weight of about 50 kDa. A great number of NifE polypeptides have been identified and numerous sequences are available in publically available databases. For example, NifE polypeptides have been reported from *Klebsiella michiganensis* (Accession No. WP_049114606.1, 99% identical to SEQ ID NO:5), *Klebsiella variicola* (SBM87755.1, 92% identical), *Dickeya paradisiaca* (WP_012764127.1, 89% identical), *Tolumonas auensis* (WP_012728883.1, 75% identical), *Pseudomonas stutzeri* (WP_003297989.1, 69% identical), *Azotobacter vinelandii* (WP_012698965.1, 62% identical), *Trichormus azollae* (WP_013190624.1, 55% identical), *Paenibacillus durus* (WP_025698318.1, 50% identical), *Sulfitricurvum kujiense* (WP_013460149.1, 44% identical), *Methanobacterium formicicum* (AIS31022.1, 39% identical), *Anaeromusa acidaminophila* (WP_018701501.1, 35% identical) and *Megasphaera cerevisiae* (WP_048514099.1, 32% identical). As used herein, a "functional NifE polypeptide" is a NifE polypeptide which is capable of forming a functional tetramer together with NifN such that the complex is capable of synthesizing FeMo-co. This synthesis of FeMo-co involves other polypeptides including NifH and NifB and may involve NifX. NifE polypeptides have been described and reviewed in Fay et al. (2016), Hu et al. (2005), Hu et al. (2006) and Hu et al. (2008).

A NifF polypeptide in naturally occurring diazotrophs is a flavodoxin which is an electron donor to NifH. As used herein, a "NifF polypeptide" means a polypeptide comprising amino acids whose sequence is at least 34% identical to the amino acid sequence provided as SEQ ID NO:6 and which comprises one or both of the flavodoxin long domain domain TIGR01752 and the flavodoxin FLDA domain found on Nif proteins from Azobacter and other bacterial genera PRK09267. NifF polypeptides encompass flavodoxins associated with pyruvate formate-lyase activation and cobalamin-dependent methionine synthase activity in non-nitrogen fixing bacteria but exclude other flavodoxins involved in broader functions. A naturally occurring NifF polypeptide typically has a length of between 160 and 200 amino acids and the natural monomer has a molecular weight of about 19 kDa. A great number of NifF polypeptides have been identified and numerous sequences are available in publically available databases. For example, NifF polypeptides have been reported from *Klebsiella michiganensis* (Accession No. WP_004122417.1, 99% identical to SEQ ID NO:6), *Klebsiella variicola* (WP_040968713.1, 85% identical), *Kosakonia radicincitans* (WP_035885760.1, 76% identical), *Dickeya chrysanthemi* (WP_039999438.1, 72% identical), *Brenneria goodwinii* (WP_048638838.1, 62% identical), *Methylomonas methanica* (WP_064006977.1, 56% identical), *Azotobacter vinelandii* (WP_012698862.1, 50% identical), *Chlorobaculum tepidum* (WP_010933399.1, 39% identical), *Campylobacter showae* (WP_002949173.1, 37% identical) and *Azotobacter chromococcum* (WP_039801725.1, 34% identical). As used herein, a "functional NifF polypeptide" is a NifF polypeptide which is capable of being an electron donor to a NifH polypeptide. NifF polypeptides have been described and reviewed in Drummond (1985).

As used herein, an "AnfG polypeptide" is a member of the nitrogenase conserved superfamily cl03910 (pfam03139-AnfG), containing the TIGR02929 conserved domain, and having at least 42% amino acid sequence identity to the *Azotobacter vinelandii* AnfG polypeptide (SEQ ID NO:219; Accession No. WP_012703360) when measured along the full-length of SEQ ID NO:219. This amino acid sequence is used herein as the reference sequence for AnfG. TIGR02929 represents the all-iron variant of the nitrogenase component I δ-chain. AnfG polypeptides do not include the vanadium type NifG polypeptides (VnfG). The amino acid sequences of AnfG polypeptides in the protein sequence database are usually annotated as an AnfG polypeptide. As of January 2020, there were 150 specific amino acid sequences in the protein database in the AnfG set. Examples of naturally occurring AnfG polypeptides include AnfG polypeptides from *Azomonas agilis* (Accession No. WP_144571041; 84.73% identical), *Firmicutes bacterium* (Accession No. HBE76208; 70.37% identical), *Sporomusa termitida* (Accession No. WP_144349445; 68.75% identical), *Rhodovulum viride* (Accession No. WP_112317428; 57.14% identical) and *Megasphaera cerevisiae* (Accession No. WP_048515315; 42.86% identical), each with reference to SEQ ID NO:219.

Functional AnfG polypeptides are capable of functioning as the δ protein structural component of the $\alpha_2\beta_2\delta_2$ hetero-hexameric nitrogenase.

A NifJ polypeptide in naturally occurring bacteria is a pyruvate:flavodoxin (ferredoxin) oxidoreductase which is an electron donor to NifH. As used herein, a "NifJ polypeptide" means a polypeptide comprising amino acids whose sequence is at least 40% identical to the amino acid sequence provided as SEQ ID NO:7 and which comprises the conserved domain TIGR02176. A naturally occurring NifJ polypeptide typically has a length of between 1100 and 1200 amino acids and the natural monomer has a molecular weight of about 128 kDa. A great number of NifJ polypeptides have been identified and numerous sequences are available in publically available databases. For example, NifJ polypeptides have been reported from *Klebsiella michiganensis* (Accession No. WP_024360006.1, 99% identical to SEQ ID NO:7), *Raoultella ornithinolytica* (WP_044347157.1, 95% identical), *Klebsiella quasipneumoniae* (WP_050533844.1, 92% identical), *Kosakonia oryzae* (WP_064566543.1, 82% identical), *Dickeya solani* (WP_057084649.1, 78% identical), *Rahnella aquatilis* (WP_014683040.1, 72% identical), *Thermoanaerobacter mathranii* (WP_013149847.1, 64% identical), *Clostridium botulinum* (WP_053341220.1, 60% identical), *Spirochaeta africana* (WP_014454638.1, 52% identical) and *Vibrio cholerae* (CSA83023.1, 40% identical). As used herein, a "functional NifJ polypeptide" is a NifJ polypeptide which is capable of being an electron donor to a NifH polypeptide. NifJ polypeptides have been described and reviewed in Schmitz et al. (2001).

A NifM polypeptide in naturally occurring bacteria is a polypeptide required for maturation of some but not all NifH polypeptides. In the absence of NifM, *K. oxytoca* NifH was present at only low levels in *E. coli* and yeast when expressed heterologously and was not able to donate electrons to NifD-NifK. As used herein, a "NifM polypeptide" means a polypeptide comprising amino acids whose sequence is at least 26% identical to the amino acid sequence provided as SEQ ID NO:8 and which comprises the domain TIGR02933. NifM polypeptides are homologous to peptidyl-prolyl cis-trans isomerases (PPIase), a group of enzymes that promote protein folding by catalysing the cis-trans isomerisation of proline imidic peptide bonds, having a PpiC-type domain, and appear to be accessory proteins for some NifH polypeptides, including at least some VnfH and AnfH polypeptides. A naturally occurring NifM polypeptide typically has a length of between 240 and 300 amino acids and the natural monomer has a molecular weight of about 30 kDa. A great number of NifM polypeptides have been identified and numerous sequences are available in publically available databases. For example, NifM polypeptides have been reported from *Klebsiella oxytoca* (Accession No. WP_064342940.1, 99% identical to SEQ ID NO:8), *Klebsiella michiganensis* (WP_004122413.1, 97% identical), *Raoultella ornithinolytica* (WP_044347181.1, 85% identical), *Klebsiella variicola* (WP_063105800.1, 75% identical), *Kosakonia radicincitans* (WP_035885759.1, 59% identical), *Pectobacterium atrosepticum* (WP_011094472.1, 42% identical), *Brenneria goodwinii* (WP_048638837.1, 33% identical), *Pseudomonas aeruginosa* PAO1 (CAA75544.1, 28% identical), *Marinobacterium* sp. AK27 (WP_051692859.1, 27% identical) and *Teredinibacter turnerae* (WP_018415157.1, 26% identical). As used herein, a "functional NifM polypeptide" is a NifM polypeptide which is capable of complexing with a NifH polypeptide for maturation of the NifH polypeptide. NifM polypeptides have been described and reviewed in Petrova et al. (2000).

A NifN polypeptide in naturally occurring bacteria is the β subunit of the $EN\alpha_2\beta_2$ tetramer with the NifE polypeptide, and the $EN\alpha_2\beta_2$ tetramer is required for FeMo-co synthesis and is proposed to function as a scaffold on which FeMo-co is synthesized. As used herein, a "NifN polypeptide" means (i) a polypeptide comprising amino acids whose sequence is at least 76% identical to the sequence provided as SEQ ID NO:9 and/or (ii) a polypeptide comprising amino acids whose sequence is at least 34% identical to the sequence provided as SEQ ID NO:9 and which comprises one or more of the conserved domains TIGR01285, cd01966 and PRK14476. NifN is related in structure to the molybdenum-iron protein β chain NifK. Polypeptides comprising the conserved TIGR01285 covers most examples of NifN polypeptides but excludes some NifN polypeptides, such as the putative NifN of *Chlorobium tepidum*, and therefore the definition of NifN is not limited to polypeptides comprising the conserved TIGR01285 domain. Members of PRK14476 domain protein family are also members of the superfamily cl02775. A naturally occurring NifN polypeptide typically has a length of between 410 and 470 amino acids, although when fused naturally to NifE it may have about 900 amino acid residues, and the natural monomer has a molecular weight of about 50 kDa. A great number of NifN polypeptides have been identified and numerous sequences are available in publically available databases. For example, NifN polypeptides have been reported from *Klebsiella oxytoca* (Accession No. WP_064391778.1, 97% identical to SEQ ID NO:9), *Kluyvera intermedia* (WP_047370268.1, 80% identical), *Rahnella aquatilis* (WP_014683026.1, 70% identical), *Brenneria goodwinii* (WP_048638830.1, 65% identical), *Methylobacter tundripaludum* (WP_027147663.1, 46% identical), *Calothrix parietina* (WP_015195966.1, 41% identical), *Zymomonas mobilis* (WP_023593609.1, 37% identical), *Paenibacillus massiliensis* (WP_025677480.1, 35% identical) and *Desulfitobacterium hafniense* (WP_018306265.1, 34% identical). As used herein, a "functional NifN polypeptide" is a NifN polypeptide which is capable of forming a functional tetramer together with NifE such that the complex is capable of synthesizing FeMo-co. NifN polypeptides have been described and reviewed in Fay et al. (2016), Brigle et al. (1987), Fani et al. (2000), and Hu et al. (2005).

A NifQ polypeptide in naturally occurring bacteria is a polypeptide involved in FeMo-co synthesis, probably in early $MoO_4^{2-}$ processing. The conserved C-terminal cysteine residues may be involved in metal binding. As used herein, a "NifQ polypeptide" means a polypeptide comprising amino acids whose sequence is at least 34% identical to the amino acid sequence provided as SEQ ID NO:10 and which is a member of the CL04826 domain protein family and a member of the pfam04891 domain protein family. A naturally occurring NifQ polypeptide typically has a length of between 160 and 250 amino acids, although they may be as long as 350 amino acid residues, and the natural monomer has a molecular weight of about 20 kDa. A great number of NifQ polypeptides have been identified and numerous sequences are available in publically available databases. For example, NifQ polypeptides have been reported from *Klebsiella oxytoca* (Accession No. WP_064391765.1, 95% identical to SEQ ID NO:10), *Klebsiella variicola* (CTQ06350.1, 75% identical), *Kluyvera intermedia* (WP_047370257.1, 63% identical), *Pectobacterium atrosepticum* (WP_043878077.1, 59% identical), *Mesorhizobium metallidurans* (WP_008878174.1, 46% identical), *Rhodopseudomonas palustris* (WP_011501504.1, 42% identical), *Paraburkholderia sprentiae* (WP_027196569.1, 41% identical), *Burkholderia stabilis* (GAU06296.1, 39% identical) and *Cupriavidus oxalaticus* (WP_063239464.1, 34% identical). As used herein, a "functional NifQ polypeptide" is a NifQ polypeptide which is capable of processing $MoO_4^{2-}$. NifQ polypeptides have been described and reviewed in Allen et al. (1995) and Siddavattam et al. (1993).

A NifS polypeptide in naturally occurring bacteria is a cysteine desulfurase involved in iron-sulfur (FeS) cluster biosynthesis e.g. which is involved in mobilisation of sulfur for Fe—S cluster synthesis and repair. As used herein, a "NifS polypeptide" means (i) a polypeptide comprising amino acids whose sequence is at least 90% identical to the amino acid sequence provided as SEQ ID NO:19 and/or (ii) a polypeptide comprising amino acids whose sequence is at least 36% identical to the sequence provided as SEQ ID NO:19 and which comprises one or both of the conserved domains TIGR03402 and COG1104. The TIGR03402 domain protein family includes a Glade nearly always found in extended nitrogen fixation systems plus a second Glade more closely related to the first than to IscS and also part of NifS-like/NifU-like systems. The TIGR03402 domain protein family does not extend to a more distant Glade found in the epsilon proteobacteria such as *Helicobacter pylori*, also named NifS in the literature, built instead in TIGR03403. The COG1104 domain protein family includes cysteine sulfinate desulfinase/cysteine desulfurase or related enzymes. Some NifS polypeptides include the asparate aminotransferase domain cl18945. A naturally occurring NifS polypeptide typically has a length of between 370 and 440 amino acids and the natural monomer has a molecular weight of about 43 kDa. A great number of NifS polypeptides have been identified and numerous sequences are available in publically available databases. For example, NifS polypeptides have been reported from *Klebsiella michiganensis* (Accession No. WP_004138780.1, 99% identical to SEQ ID NO:19), *Raoultella terrigena* (WP_045858151.1, 89% identical), *Kluyvera intermedia* (WP_047370265.1, 80% identical), *Rahnella aquatilis* (WP_014333911.1, 73% identical), *Agarivorans gilvus* (WP_055731597.1, 64% identical), *Azospirillum brasilense* (WP_014239770.1, 60% identical), *Desulfosarcina cetonica* (WP_054691765.1, 55% identical), *Clostridium intestinale* (WP_021802294.1, 47% identical), *Clostridiisalibacter paucivorans* (WP_026894054.1, 36% identical) and *Bacillus coagulans* (WP_061575621.1, 42% identical and which is in COG1104). As used herein, a "functional NifS polypeptide" is a NifS polypeptide which is capable of functioning in iron-sulfur (FeS) cluster biosynthesis and/or repair. NifS polypeptides have been described and reviewed in Clausen et al. (2000), Johnson et al. (2005), Olson et al. (2000) and Yuvaniyama et al. (2000).

A NifU polypeptide in naturally occurring bacteria is a molecular scaffold polypeptide involved in iron-sulfur (FeS) cluster biosynthesis for nitrogenase components. As used herein, a "NifU polypeptide" means a polypeptide comprising amino acids whose sequence is at least 31% identical to the sequence provided as SEQ ID NO:12 and which comprises the domain TIGR02000. Members of the TIGR02000 domain protein family are specifically involved in nitrogenase maturation. NifU comprises an N-terminal domain (pfam01592) and a C-terminal domain (pfam01106). Three different but partially homologous Fe—S cluster assembly systems have been described: Isc, Suf, and Nif. The Nif system, of which NifU is a part, is associated with donation of an Fe—S cluster to nitrogenase in a number of nitrogen-fixing species. Isc and Suf homologs with an equivalent domain architecture from *Helicobacter* and *Campylobacter* are excluded from the definition of NifU herein. NifU, therefore, is specific for NifU polypeptides involved in nitrogenase maturation. Members of the related TIGR01999 domain protein family which are IscU proteins (from for example, *Escherichia. coli* and *Saccharomyces cerevisiae* and *Homo sapiens*) that comprise a homolog of the N-terminal region of NifU are also excluded from the definition of NifU herein. A naturally occurring NifU polypeptide typically has a length of between 260 and 310 amino acids and the natural monomer has a molecular weight of about 29 kDa. A great number of NifU polypeptides have been identified and numerous sequences are available in publically available databases. For example, NifU polypeptides have been reported from *Klebsiella michiganensis* (Accession No. WP_049136164.1, 97% identical to SEQ ID NO:12), *Klebsiella variicola* (WP_050887862.1, 90% identical), *Dickeya solani* (WP_057084657.1, 80% identical), *Brenneria goodwinii* (WP_048638833.1, 73% identical), *Tolumonas auensis* (WP_012728889.1, 66% identical), *Agarivorans gilvus* (WP_055731596.1, 58% identical), *Desulfocurvus vexinensis* (WP_028587630.1, 54% identical), *Rhodopseudomonas palustris* (WP_044417303.1, 49% identical), *Helicobacter pylori* (WP_001051984.1, 31% identical) and *Sulfitrovum* sp. PC08-66 (KIM05011.1, 31% identical). As used herein, a "functional NifU polypeptide" is a NifU polypeptide which is capable of functioning as a molecular scaffold polypeptide involved in iron-sulfur (FeS) cluster biosynthesis. NifU polypeptides have been described and reviewed in Hwang et al. (1996), Mühlenhoff et al. (2003) and Ouzounis et al. (1994).

NifS is a pyridoxal phosphate (PLP, vitamin B6) dependent cysteine desulfurase which generates the inorganic sulphide required for Fe—S cluster synthesis from cysteine. The reaction produces alanine as a byproduct. The reaction proceeds via a protein-bound cysteine persulfide intermediate that is formed by the nucleophilic attack of a highly conserved cysteine residue (Cys325 in *Azotobacter vinelandii*) on the cysteine-PLP adduct (Zheng et al., 1994). The sulphide is the provided to NifU for the sequential formation of [$Fe_2S_2$] and [$Fe_4S_4$] clusters. The NifS enzyme functions in bacteria as a homodimer.

NifU provides a scaffold for [$Fe_4S_4$] cluster formation, functioning as a homodimer. The NifU polypeptide contains three domains, namely a N-terminal scaffolding domain, a central domain and a C-terminal scaffolding domain (Smith et al., 2005). The N-terminal domain has a high sequence homology to IscU proteins from bacteria and Isu proteins from eukaryotes, while the C-terminal domain is homologous to Nfu proteins found in mitochondria and chloroplasts. The central domain contains one permanent redox-active [$Fe_2S_2$]$^{2+}$ cluster per NifU subunit which, due to its stability, is thought not to be transferred to other Nif proteins. That cluster is thought to be coordinated by four conserved cysteine residues (Cys137, 139, 172 and 175 in *A. vinelandii* NifU) (Fu et al., 1994). In bacteria, NifU forms a homodimer and its N-terminal domain can bind one [$Fe_2S_2$] cluster per monomer. The [$Fe_2S_2$] clusters in the monomers can be reductively fused to form one [$Fe_4S_4$] cluster per NifU dimer. A pair of [$Fe_4S_4$] clusters are then delivered from NifU to NifB and processed into an 8Fe core on NifB which is subsequently used for the synthesis of FeMoco. In a divergent pathway for the Fe—S clusters, one [$Fe_4S_4$] cluster bound to either the N-terminal or C-terminal scaffolding domain of NifU is transferred to apo-NifH for maturation of nitrogenase reductase, the NifH protein (Smith et al., 2005). It has been proposed that NifU also donates two [$Fe_4S_4$] clusters to a NifD-NifK protein complex (designated herein as stage 0 D-K), and that NifH condenses that pair of clusters into a mature P-cluster [$Fe_8$—$S_7$] (Dos Santos et al., 2004). These N-terminal clusters are thought to be extremely labile and are not retained during purification (Smith et al., 2005). The C terminal domain can hold one [$Fe_4S_4$] cluster per monomer. In contrast to the N-terminal cluster, the assembly of the C terminal [$Fe_4S_4$] cluster is rapid and no intermediate [$Fe_2S_2$] cluster has been detected (Smith et al., 2005). The C-terminal clusters are more stable than the N-terminal clusters and can be retained during purification. However, upon reduction with dithionite, the C-terminal clusters are rapidly degraded (Smith et al., 2005). Using cysteine to alanine mutations in NifU, Dos Santos and colleagues showed that both the N- and C-terminal clusters can be transferred to apo-NifH.

López-Torrejón et al. (2016) reported that a NifH protein capable of donating electrons to holoNifD-NifK can be generated within yeast mitochondria via the expression of both NifH and NifM. These authors found that, in the yeast cells, NifS and NifU were not required for the generation of NifH protein with this function. They concluded that endogenous iron sulphur cluster assembly pathways in the yeast cells, presumably mitochondrial-located Nfs1 and Nfu1 proteins which are related proteins in yeast, were capable of donating [$Fe_4S_4$] clusters to NifH. It therefore is possible that NifS and NifU will not be required for reconstituting the NifH protein, the Fe-protein or dinitrogenase reductase in yeast, but NifS and NifU may be required for NifB and/or NifD-NifK maturation and function. Whether plant mitochondria have similar endogenous ability for forming sufficient [$Fe_4S_4$] clusters for nitrogenase activity is unknown.

A NifV polypeptide in naturally occurring bacteria is a homocitrate synthase (EC 2.3.3.14), producing homocitrate by the transfer of the acetyl group from acetyl-coenzyme A (acetyl-CoA) to 2-oxoglutarate. Homocitrate is then used in the synthesis of FeMo-co, FeV-co and FeFe-co. As used herein, a "NifV polypeptide" means a polypeptide comprising amino acids whose sequence is at least 39% identical to the amino acid sequence provided as SEQ ID NO:13 and which comprises one or both of the domains TIGR02660 and DRE TIM. Members of the TIGR02660 domain protein family are homologous to enzymes that include 2-isopropylmalate synthase, (R)-citramalate synthase, and homocitrate synthase associated with processes other than nitrogen fixation. The cd07939 domain protein family also includes the NifV proteins of *Heliobacterium chlorum* and *Gluconacetobacter diazotrophicus*, which appear to be orthologous to FrbC. This family belongs to the DRE-TIM metallolyase superfamily. DRE-TIM metallolyases include 2-isopropylmalate synthase (IPMS), alpha-isopropylmalate synthase (LeuA), 3-hydroxy-3-methylglutaryl-CoA lyase, homocitrate synthase, citramalate synthase, 4-hydroxy-2-oxovalerate aldolase, re-citrate synthase, transcarboxylase 5S, pyruvate carboxylase, AksA, and FrbC. These members all share a conserved triose-phosphate isomerase (TIM) barrel domain consisting of a core beta(8)-alpha(8) motif with the eight parallel beta strands forming an enclosed barrel surrounded by eight alpha helices. The domain has a catalytic center containing a divalent cation-binding site formed by a cluster of invariant residues that cap the core of the barrel. In addition, the catalytic site includes three invariant residues—an aspartate (D), an arginine (R), and a glutamate (E)—which is the basis for the domain name "DRE-TIM". A naturally occurring NifV polypeptide typically has a length of between 360 and 390 amino acids, although some members are about 490 amino acid residues in length, and the natural monomer has a molecular weight of about 41 kDa. A great number of NifV polypeptides have been identified and numerous sequences are available in publically available databases. For example, NifV polypeptides have been reported from *Klebsiella michiganensis* (Accession No. WP_049083341.1, 95% identical to SEQ ID NO:13), *Raoultella ornithinolytica* (WP_045858154.1, 86% identical), *Kluyvera intermedia* (WP_047370264.1, 81% identical), *Dickeya dadantii* (WP_038912041.1, 70% identical), *Brenneria goodwinii* (WP_048638835.1, 59% identical), *Magnetococcus marinus* (WP_011712856.1, 46% identical), *Sphingomonas wittichii* (WP_037528703.1, 43% identical), *Frankia* sp. EI5c (OAA29062.1, 41% identical) and *Clostridium* sp. Maddingley MBC34-26 (EKQ56006.1, 39% identical). As used herein, a "functional NifV polypeptide" is a NifV polypeptide which is capable of functioning as a homocitrate synthase. NifV polypeptides have been described and reviewed in Hu et al. (2008), Lee et al. (2000), Masukawa et al. (2007) and Zheng et al. (1997).

NifX polypeptide in *Azotobacter vinelandii* binds NifB-co ($Fe_6$—$S_9$—C), which is passed on to NifE-NifN for FeMo-co assembly (Hernandez et al., 2007). It has also been shown to exchange VK-clusters ($Fe_8$—$S_9$—C or Mo—$Fe_7$—$S_9$—C, Jimenez-Vincente et al., 2015) between NifE-NifN, suggesting its role as a transient reservoir for FeMo-co precursors. Hernandez et al. (2007) reported that NifX may act as a chaperone that stabilises the NifE-NifN or NifD-NifK complexes during transfer of FeMo-co to apo-NifD-NifK, and/or reposition the proteins in a favorable orientation for FeMoco transfer and so act to regulate FeMoco synthesis. Activation of apo-NifD-NifK by exogenous FeMo-co with dinitrogenase complexes extracted from *A. vinelandii* mutants deficient in different accessory protein combinations of NifY/NafY/NifX indicated that NifX can also assist in FeMo-co insertion of apo-NifD-NifK (Rubio et al., 2002). This additional function of NifX may be responsible for the retention of acetylene reduction activity in the *Klebsiella* ΔnifY mutant shown by Homer et al. (1993).

A NifX polypeptide in naturally occurring bacteria is a polypeptide which is involved in FeMo-co synthesis, at least assisting in transferring FeMo-co precursors from NifB to NifE-NifN or FeMo-co to NifD-NifK. As used herein, a "NifX polypeptide" means a polypeptide comprising amino acids whose sequence is at least 29% identical to the amino acid sequence provided as SEQ ID NO:14 and which comprises one or both of the conserved domains TIGR02663 and cd00853. NifX is included in a larger family of iron-molybdenum cluster-binding proteins that includes some NifB sequences and NifY, in that NifX, NafY and the C-terminal region of some NifB polypeptides all comprise the pfam02579 domain, and each are involved in the synthesis of one or more or all of FeMo-co, FeV-co or FeFe-co. Other NifB polypeptides, specifically from methanogenic archaea and some anaerobic *Firmicutes*, lack a NifX-like domain (Boyd et al., 2011), including NifB from *H. halophila, M. barkeri* and *C. purinilyticum* mentioned above. Some NifX polypeptides have been annotated in databases as NifY, and vice versa. A naturally occurring NifX polypeptide, produced on its own rather than as a natural fusion as part of a NifB polypeptide, typically has a length of between 110 and 160 amino acids and the natural monomer has a molecular weight of about 15 kDa. A great number of NifX polypeptides have been identified and numerous sequences are available in publically available databases. For example, NifX polypeptides have been reported from *Klebsiella michiganensis* (Accession No. WP_049070199.1, 97% identical to SEQ ID NO:14), *Klebsiella oxytoca* (WP_064342937.1, 97% identical), *Raoultella ornithinolytica* (WP_044347173.1, 91% identical), *Klebsiella variicola* (WP_044612922.1, 83% identical), *Kosakonia radicincitans* (WP_043953583.1, 75% identical), *Dickeya chrysanthemi* (WP_039999416.1, 68% identical), *Rahnella aquatilis* (WP_047608097.1, 58% identical), *Azotobacter chroococcum* (WP_039800848.1, 34% identical), *Beggiatoa leptomitiformis* (WP_062149047.1, 33% identical) and *Methyloversatilis discipulorum* (WP_020165972.1, 29% identical). As used herein, a "functional NifX polypeptide" is a NifX polypeptide which is capable of transferring FeMo-co precursors from NifB to NifE-NifN. NifX polypeptides have been described and reviewed in Allen et al. (1994) and Shah et al. (1999).

A NifY polypeptide in naturally occurring bacteria is a polypeptide which is involved in FeMo-co synthesis, at least assisting in transferring FeMo-co precursors from NifB to NifE-NifN. As used herein, a "NifY polypeptide" means a polypeptide comprising amino acids whose sequence is at least 34% identical to the amino acid sequence provided as SEQ ID NO:15 and which comprises one or both of the conserved domains TIGR02663 and cd00853. NifY is included in a larger family of iron-molybdenum cluster-binding proteins that includes NifB and NifX, in that NifX, NafY and the C-terminal region of NifB all comprise the pfam02579 domain, and each are involved in the synthesis of FeMo-co. A great number of NifY polypeptides have been identified and numerous sequences are available in publically available databases. For example, NifY polypeptides have been reported from *Klebsiella michiganensis* (Accession No. WP_049089500.1, 99% identical to SEQ ID NO:15), *Klebsiella oxytoca* (WP_064342935.1, 98% identical), *Klebsiella quasipneumoniae* (WP_044524054.1, 90% identical), *Klebsiella variicola* (WP_049010739.1, 81% identical), *Kluyvera intermedia* (WP_047370270.1, 69% identical), *Dickeya chrysanthemi* (WP_039999411.1, 62% identical), *Serratia* sp. ATCC 39006 (WP_037382461.1, 57% identical), *Rahnella aquatilis* (WP_014683024.1, 47% identical), *Pseudomonas putida* (AEX25784.1, 37% identical) and *Azotobacter vinelandii* (WP_012698835.1, 34% identical). As used herein, a "functional NifY polypeptide" is a NifY polypeptide which is capable of transferring FeMo-co precursors from NifB to NifE-NifN.

When isolated from NifB or NifB-NifE mutant strains of either *K. oxytoca* or *A. vinelandii*, apo-NifD-NifK was associated with an additional polypeptide termed the γ protein (Paustian et al, 1990; Homer et al., 1993), forming a heterohexamer with NifD and NifK polypeptides ($\alpha_2\beta_2\gamma_2$). In *K. oxytoca*, the third polypeptide was encoded by the NifY gene (Homer et al., 1993) and the addition of purified FeMo-co to purified heterohexamer $\alpha_2\beta_2\gamma_2$ complex was sufficient to yield catalytically active nitrogenase. Addition of FeMo-co resulted in dissociation of NifY from the complex with formation of the holoenzyme ($\alpha_2\beta_2$). In *A. vinelandii*, the third polypeptide was encoded by the NafY gene (nitrogenase associated factor Y; Accession No. AGK13761, Rubio et al., 2002) which was different but related to the product of the NifY gene in *A. vinelandii* (Accession No. AGK13792). The third polypeptide in each case was thought to be involved in assisting in the insertion of FeMo-co to form the active enzyme. This was supported by the ability of NafY and NifY to bind FeMo-co (Homer et al., 1995).

*A. vinelandii* NifY and NafY bind to apo-NifD-NifK, at different stages of NifD-NifK holoenzyme maturation, to either α-$Cys^{275}$ or α-$His^{442}$ of NifD, both amino acid residues of which covalently anchor FeMo-co (Jimenez-Vincente et al., 2018). That is, NifY and NafY do not bind to apo-NifD-NifK simultaneously. The order of binding of NifY and NafY to apo-NifD-NifK is currently unknown. Dissociation of NifY from NifD-NifK upon FeMo-co insertion has been demonstrated for *K. oxytoca* nitrogenase (Homer et al., 1993) and NafY from NifD-NifK upon FeMo-co insertion for *A. vinelandii* (Homer et al., 1995). NafY is also thought to bind FeMo-co through $His^{121}$ and possibly NifB-co as well, suggesting its role as a FeMo-co or FeMo-co precursor insertase (Rubio et al., 2004). *A.*

*vinelandii* NifY seems to be functionally redundant based on lack of a phenotype in ΔnifY mutants (Rubio et al., 2002) and NafY is proposed to be the primary accessory protein to apo-NifD-NifK that supports FeMo-co insertion. On the other hand, *Klebsiella* species do not have a NafY gene and only have NifY to support FeMo-co insertion into apo-NifD-NifK, although a *Klebsiella* ΔnifY mutant still retained 60% of acetylene reduction activity (Homer et al., 1993). This retention of function indicated presence of another accessory protein in *Klebsiella* that could partially cover NifY function in its absence, such as NifX as described above.

As used herein, a "NafY polypeptide" means a polypeptide comprising amino acids whose sequence is at least 50% identical to the sequence provided as SEQ ID NO:238 (*A. vinelandii* NafY, Accession No. AGK13761, 243aa) along its full-length and which comprises the conserved domain pfam16844. This domain of about 91 amino acid residues in length is found by itself in some members and in the amino terminal half of longer NafY proteins. This region is negatively charged and appears to function for recognising and interacting with apo-NifD-NifK. A naturally occurring NafY polypeptide typically has a length of between 230 and 250 amino acids and the natural monomer has a molecular weight of ~25-28 kDa. A great number of NafY polypeptides have been identified and numerous sequences are available in publically available databases; some have been annotated as NifX polypeptides because of the relatedness of NafY and NifX sequences. For example, NafY polypeptides have been reported from *Azotobacter beijerinckii* (WP_090728988, 93% identical to SEQ ID NO:238), *Pseudomonas stutzeri*, (WP_011912501, 69% identical), *Halomonas endophytica* (WP_102654474, 68% identical), *Pseudomonas linyingensis* (WP_090313081, 67% identical), *Acidihalobacter prosperus* (WP_038093031, 56% identical), *Oscillatoriales cyanobacterium* (WP_009769409, 50% identical) As used herein, a "functional NafY polypeptide" is a NafY polypeptide which is capable of binding to apo-NifD-NifK and to FeMo-co. The three-dimensional structure of NafY polypeptide from *A. vinelandii* and a comparison and distinction of NafY and NifY, NifX, VnfX and NifB polypeptide sequences was reported in Dyer et al. (2003).

A NifZ polypeptide in naturally occurring bacteria is a polypeptide which is involved in Fe—S cluster synthesis, specifically functioning in the coupling of a second $Fe_4S_4$ pair in the formation of the second P-cluster of the MoFe protein. NifZ is thought to act as a chaperone that induces a conformational change in at least the second half of apo-MoFe protein, allowing for the formation of the second P-cluster together with NifH. Deletion of NifZ in *A. vinelandii* decreased MoFe protein activity by 66% but had no effect on NifH activity. As used herein, a "NifZ polypeptide" means a polypeptide comprising amino acids whose sequence is at least 28% identical to the sequence provided as SEQ ID NO:16 and which comprises the conserved domain pfam04319. This domain of about 75 amino acid residues is found in isolation in some members and in the amino terminal half of the longer NifZ proteins. A naturally occurring NifZ polypeptide typically has a length of between 70 and 150 amino acids and the natural monomer has a molecular weight of about 9 to about 16 kDa. A great number of NifZ polypeptides have been identified and numerous sequences are available in publically available databases. For example, NifZ polypeptides have been reported from *Klebsiella michiganensis* (Accession No. WP_057173223.1, 93% identical to SEQ ID NO:16), *Klebsiella oxytoca* (WP_064342939.1, 95% identical), *Klebsiella variicola* (WP_043875005.1, 77% identical), *Kosakonia radicincitans* (WP_043953588.1, 67% identical), *Kosakonia sacchari* (WP_065368553.1, 58% identical), *Ferriphaselus amnicola* (WP_062627625.1, 47% identical), *Paraburkholderia xenovorans* (WP_011491838.1, 41% identical), *Acidithiobacillus ferrivorans* (WP_014029050.1, 35% identical) and *Bradyrhizobium oligotrophicum* (WP_015665422.1, 28% identical). As used herein, a "functional NifZ polypeptide" is a NifZ polypeptide which is capable of coupling a $Fe_4S_4$ cluster in Fe—S cluster synthesis. NifZ polypeptides have been described and reviewed in Cotton (2009) and Hu et al. (2004).

A NifW polypeptide in naturally occurring bacteria is a polypeptide which associates with NifZ polypeptide to form higher order complexes (Lee et al., 1998), and is involved in MoFe protein (NifD-NifK) synthesis or activity. NifW and NifZ appear to be involved in the formation or accumulation of MoFe protein (Paul and Merrick, 1987). As used herein, a "NifW polypeptide" means a polypeptide whose amino acid sequence comprises amino acids whose sequence is at least 28% identical to the amino acid sequence provided as SEQ ID NO:17 and which comprises the conserved NifW superfamily protein domain, architecture ID number 10505077 and is in Pfamily PF03206. A number of NifW polypeptides have been identified and numerous sequences are available in publically available databases. For example, NifW polypeptides have been reported from *Klebsiella oxytoca* (Accession No. WP_064342938.1, 98% identical to SEQ ID NO:17), *Klebsiella michiganensis* (WP_049080155.1, 94% identical), *Enterobacter* sp. 10-1 (WP_095103586.1, 90% identical), *Klebsiella quasipneumoniae* (WP_065877373.1, 81% identical), *Pectobacterium polaris* (WP_095699971.1, 69% identical), *Dickeya paradisiaca* (WP_012764136.1, 58% identical), *Brenneria goodwinii* (WP_053085547.1, 36% identical), *Aquaspirillum* sp. LM1 (WP_077299824.1, 44% identical), *Candidatus muproteobacteria bacterium* RBG_16_64_10 (OGI40729, 34% identical), *Azotobacter vinelandii* (ACO76430.1, 32% identical) and *Methylocaldum marinum* (BBA37427.1, 28% identical). As used herein, a "functional NifW polypeptide" is a NifW polypeptide which promotes or enhances one or more of the formation, accumulation or activity of MoFe protein. A functional NifW may interact with NifZ and/or play a role in the oxygen protection of the MoFe-protein (Gavini et al., 1998).

Most organisms including both bacteria and eukaryotes such as plants have numerous ferredoxins. For example, there are 15 or 16 proteins annotated as ferredoxin or ferredoxin-like in the *A. vinelandii* DJ and CA genomes, respectively. As used herein, a "ferredoxin polypeptide" is an electron carrier protein having one or two iron-sulfur clusters of the [2Fe-2S], [3Fe-4S] and/or [4Fe-4S] type that form their reactive centers, see review by Matsubara and Saeki (1992). They are involved in a variety of metabolic processes, including ferredoxin polypeptides which are involved in nitrogen fixation, generally of lower molecular weight than those not involved in nitrogenase. Based on the wide diversity of ferredoxins in most cells and the variations observed in several studies on the compatibility or specificity of different ferredoxins in complementing the function of FdxN for NifB-co synthesis (Yates, 1972; Jimenez-Vincente et al., 2014), ferredoxins including ones such as FdxN are best defined based on the presence of the iron-sulfur clusters and their function rather than on amino acid identity to a standard sequence such as *A. vinelandii* FdxN (SEQ ID NO:232; Accession No. WP_012703542). As used herein, a "FdxN polypeptide" is a ferredoxin or ferredoxin-like polypeptide which functions for donating electrons to mature dinitrogenase reductase NifH and/or for NifB-co synthesis for nitrogenase and/or serves as an intermediate carrier of [4Fe-4S] clusters. FdxN may function by donating electrons to mature dinitrogenase reductase NifH which then transfers the electrons to NifD-NifK heterohexamer (see Yang et al., 2017; *Rhizobium japonicum* FdxN, Carter et al., 1980; *R. meliloti* FdxN, Riedel et al., 1995; *Rhodobacter capsulatus* FdxN, Jouanneau et al., 1995), or donating electrons to NifB polypeptide for NifB-co synthesis (*A. vinelandii*: Jimenez-Vincente et al., 2014), or serves as an intermediate carrier of [4Fe-4] clusters (*A. vinelandii*: Burén et al., 2019), or a combination of any of these functions.

Representative examples of FdxN polypeptides include the following, identified by searching the non-redundant protein database using SEQ ID NO:232 as query in BLASTP and showing percentage identity to that sequence: *Pseudomonas syringae* (WP_065835964.1, 85.87%), *Candidatus thiodiazotropha endolucinida* (WP_069124666.1, 70.65%), *Uliginosibacterium* sp. TH139 (WP_101942980, 64.47%), *Klebsiella michiganensis* (WP_049076934.1, 44.26%), *Escherichia coli* (WP_072048756.1, 44.26%), *Rhizobium leguminosarum* (WP_130674512.1, 43.86%) and *Flavobacterium alvei* (WP_103805005.1, 28.57%).

Sequence Identity and Substitutions

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides defined herein can be prepared by introducing appropriate nucleotide changes into a nucleic acid defined herein, or by in vitro synthesis of the desired polypeptide. Such mutants include for example, one or more amino acid deletions, insertions, or substitutions. A combination of deletion, insertion and substitution mutations can be made to arrive at the final construct, provided that the final polypeptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if their expression in a plant alters its phenotype relative to a corresponding wild-type plant, for example, if their expression results in increased yield, biomass, growth rate, vigor, nitrogen gain derived from biological nitrogen fixation, nitrogen use efficiency, abiotic stress tolerance, and/or tolerance to nutrient deficiency relative to the corresponding wild-type plant.

In designing amino acid sequence mutants, the location of the mutation site and the nature of the mutation will depend on characteristic(s) to be modified. The sites for mutation can be modified individually or in series for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Where it is desirable to maintain a certain activity it is preferable to make no, or only conservative substitutions, at amino acid positions which are highly conserved in the relevant protein family. Examples of conservative substitutions are shown in Table 1 under the heading of "exemplary substitutions".

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs or domains which are highly conserved between the different polypeptides of the invention. As the skilled person would be aware, such minor changes can reasonably be predicted not to alter the activity of the polypeptide when expressed in a recombinant cell.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

The primary amino acid sequence of a polypeptide of the invention can be used to design variants/mutants thereof based on comparisons with closely related polypeptides. As the skilled person will appreciate, residues highly conserved amongst closely related proteins are less likely to be able to be altered, especially with non-conservative substitutions, and activity maintained than less conserved residues (see above). A more stringent test to identify conserved amino acid residues is to align more distantly related polypeptides of the same function. Highly conserved residues should be maintained in order to retain function, whereas non-conserved residues are more amenable to substitutions or deletion while maintaining function.

Also included within the scope of the invention are polypeptides of the present invention which are differentially modified during or after synthesis in a cell, e.g., by glycosylation, acetylation, phosphorylation or proteolytic cleavage.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). See, for example, Example 10 herein. Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interactive Protein Redesign and Optimization), EGAD (A Genetic Algorithm for Protein Design), Rosetta Design, Sharpen, and Abalone.

Linkers

As used herein in the context of polypeptides, the term "linker" or "oligopeptide linker" means one or more amino acids that covalently join two or more functional domains, for example, the MTP and the NP, two NPs, a NP and a tag. The amino acids are covalently joined through peptide bonds, both within the linker and between linker and functional domains. The linker may provide for freedom of movement of one functional domain with respect to the other, without causing a substantial detrimental effect on the function of the two or more domains. The linker may help promote proper folding and functioning of one or both of the functional domains. The skilled person will understand that the size of a linker can be determined empirically or can be modelled based on protein folding information.

The linker may comprise a cleavage site for a protease such as MPP, Such a linker can also be considered to be part of an MTP.

The skilled person will appreciate that the C-terminal end of the MTP can be translationally fused to the N-terminal amino acid of the NP without a linker or via a linker of one or more amino acid residues, for example of 1-5 amino acid residues, Such a linker can also be considered to be part of the MTP.

In embodiments, the linker comprises at least 1 amino acid, at least 2 amino acids, at least 3 amino acids, at least 4 amino acids, at least 5 amino acids, at least 6 amino acids, at least 7 amino acids, at least 8 amino acids, at least 9 amino acids, at least 10 amino acids, at least 12 amino acids, at least 14 amino acids, at least 16 amino acids, at least 18 amino acids, at least 20 amino acids, at least 25 amino acids, at least 30 amino acids, at least 35 amino acids, at least 40 amino acids, the least 45 amino acids, at least 50 amino acids, at least 60 amino acids, at least 70 amino acids, at least 80 amino acids, at least 90 amino acids, or about 100 amino acids. In embodiments, the maximal size of the linker is 100 amino acids, preferably 60 amino acids, more preferably 40 amino acids.

In some embodiments, the linker will permit the movement of one functional domain with respect to the other in order to increase stability of the fusion polypeptide. If desired, the linker can encompass either: repetitions of poly-glycine or combinations of glycine, proline and alanine residues.

Linkers for joining two Nif polypeptides such as NifD-linker-NifK and NifE-linker-NifN are preferably selected, for the number and sequence of the amino acids in the linker, based on several criteria. These are: a lack of cysteine residues to avoid formation of unwanted disulphide linkages, few or preferably no charged residues (Glu, Asp, Arg, Lys) to reduce the likelihood of unwanted surface salt bridge interactions, few or no hydrophobic residues (Phe, Trp, Tyr, Met, Val, Ile, Leu) as such residues may promote a tendency to penetrate the surface of the polypeptide, and lacking amino acids which may be post-translationally modified. In this context "few charged residues" means less than 10% of the amino acid residues in the linker, and "few hydrophobic residues" means less than 15% of the amino acid residues in the linker.

In an embodiment, the linker does not comprise a cysteine residue.

In an embodiment, the linker comprises four, three, or two, or one, or no charged residues. Preferably, in total the linker comprises four, three, or two, or one, or no glutamic acid, asparartic acid, argninine and lysine residues.

In an embodiment, the linker comprises four, three, or two, or one or no hydrophobic residues. Preferably, in total the linker comprises four, three, or two, or one or no phenylalanine, tryptophan, tyrosine, methionine, valine, isoleunce and leucine residues.

In an embodiment, at least 70%, or at least 80%, or at least 90%, of the linker comprises residues selected from threonine, serine, glycine and alanine.

The use of oligopeptide linkers in modifying polypeptides is reviewed in Chen et al. (2013) and Zhang et al. (2009).

Tags

In a particular embodiment, the fusion polypeptide comprises at least one tag adequate for detection or purification of the fusion polypeptide or a processed product thereof. The tag is typically bound to the C-terminal or N-terminal domain of the fusion polypeptide. In a preferred embodiment, the tag is bound to the C-terminal end of the Nif polypeptide. The tag is generally a peptide or amino acid sequence capable of binding to one or more ligands, for example, one or more ligands of an affinity matrix such as a chromatography support or bead, or an antibody, with high affinity. The skilled person will understand that the tag is preferably located in the fusion protein at a location which does not result in the removal of the tag from the NP once the MTP is cleaved off after import into the mitochondria. Further, the tag should not interfere with the mitochondria import machinery. In a preferred embodiment, the polynucleotide of the invention encodes a fusion polypeptide that comprises, in the N- to C-terminal order, a N-terminal MTP, the Nif polypeptide and the detection/purification tag. In an alternate embodiment, the fusion polypeptide comprises, in the N- to C-terminal order, a N-terminal MTP, the detection/purification tag and the Nif polypeptide.

Additional illustrative, non-limiting examples of tags useful for detecting, isolating or purifying a fusion polypeptide or a processed product thereof include, human influenza hemagglutinin (HA) tag, histidine tags comprising for example, 6 or 8 histidine residues, fluorescent tags such as fluorescein, resorufin and derivatives thereof, Arg-tag, FLAG-tag, Strep-tag, an epitope capable of being recognized by an antibody, such as c-myc-tag (recognized by an anti-c-myc antibody), SBP-tag, S-tag, calmodulin binding peptide, cellulose binding domain, chitin binding domain, glutathione 5-transferase-tag, maltose binding protein, NusA, TrxA, DsbA, Avi-tag, etc.

Translational Fusions Involving Nif Polypeptides

Translational fusions have been made to several Nif polypeptides as reported in the scientific literature. These are summarised in Table 2 and in the review by Burén and Rubio (2018). Most of them involve the artificial addition of epitopes or binding domains such as Histidine tags or Strep tags to the proteins for detection and purification purposes and only a few have been expressed in plant cells. There are a few reports of naturally occurring fusions between Nif polypeptides, in bacteria. For assays in bacterial hosts, His tags of different lengths (7-10 histidines) were added to NifD (Christiansen et al., 1998), NifE (Goodwin et al., 1998), NifM (Gavini et al., 2006) and both full length and truncated versions of NifB (Fay et al., 2015). In each case, Nif function was retained for the modified Nif polypeptide as demonstrated in bacteria or in in vitro nitrogenase reconstitution assays.

TABLE 2

Summary of gene fusions of Nif polypeptides as reported in the literature

| Gene fusion | Naturally or synthetic | Number of amino acid residues changed | Function and which organism (no, partial, yes, not tested) | Reference |
|---|---|---|---|---|
| | | Bacterial expression | | |
| GST-NafY | synthetic | 26 kDa on N terminus | Yes, in bacteria | Rubio et al., 2004 |
| NifD-7xHis at the C terminus | synthetic | 7 extra histidines | Yes, in bacteria | Christiansen et al., 1998 |
| NifE-NifN | Natural: *Anabaena variabilis* | Deletion of about 10 amino acids | Yes, in bacteria | Thiel et al., 1995 |
| 7xHis-NifE | synthetic | 7 His at N terminus | Yes, in bacteria | Goodwin et al., 1998 |
| N-(zero linker)-B | Naturally occurring in *Clostridium pasteruienum* | | Yes, in bacteria | Dean and Jackobson, cited in Wiig et al., 2011 |
| 8xHis-N-zero linker-B | synthetic | Direct NifN-NifB fusion, zero length linker | Yes, in bacteria | Wiig et al., 2011 |
| NifD-NifK | synthetic | Net deletion of 3 amino acids, 7 substitutions | partial (50%), in bacteria | Suh et al., 2003 |
| 7-10xHis-NifM | synthetic | Not specified (7-10?) at the N terminus | Yes, in bacteria | Gavini et al 2006 |
| | | Eukaryotic expression | | |
| His-NifU | synthetic | Epitope at the N terminus | Yes, yeast, Cytoplasmic location, and functional if the yeast are grown anaerobically | Lopez-Torrejon et al., 2016 |
| NifB-truncated-10xHis | Synthetic | 10xHis at C terminus of a NifB truncated for the NifX-like domain | Yes, tested in yeast grown aerobically | Burén et al., 2017a |
| MTP-Strep tag-NifB (truncated) | Synthetic | 28 amino acid N terminal Strep tag, between the MTP and NifB | Expressed in plants, targeted to MM, more soluble than the full length version, not tested for function | Burén et al., 2017a |
| 6xHis-NifB-truncated | synthetic | 6 His at N terminus of a NifB truncated for the NifX-like domain at the C-terminus | Yes, tested in yeast | Fay et al., 2015 PNAS |

TABLE 2-continued

Summary of gene fusions of Nif polypeptides as reported in the literature

| Gene fusion | Naturally or synthetic | Number of amino acid residues changed | Function and which organism (no, partial, yes, not tested) | Reference |
|---|---|---|---|---|
| CPN-60-NifS | synthetic | MTP targeting in *Nicotiana* ssp | Yes, in vitro | US2016/0304842 |
| CPN-60-NifU | synthetic | MTP targeting in *Nicotiana* ssp | Yes, in vitro | US2016/0304842 |
| CPN-60-NifH | synthetic | MTP targeting in *Nicotiana* ssp | Yes, in vitro | US2016/0304842 |
| CPN-60-NifM | synthetic | MTP targeting in *Nicotiana* ssp | Yes, in vitro | US2016/0304842 |

Thiel et al. (1995) identified a naturally occurring deletion of 29 nucleotides and therefore deleting 9 amino acids and the NifE stop codon in the intergenic region between the NifE and NifN genes in the blue-green alga *Anabaena variabilis*. The deletion resulted in a NifE-NifN polypeptide fusion which retained at least some nitrogenase function of the NifE and NifN polypeptides. The NifE-NifN fusion polypeptide also had 19 other amino acid substitutions in the region of the fusion junction, which might have affected Nif function but in unknown ways. The fusion gene was expressed but only under strictly anaerobic conditions. It was not reported if there was a reduction in activity relative to the non-fused genes.

Suh et al. (2003) created an artificial junction between the NifD and NifK genes of the chromosome of *A. vinelandii* by a deletion including the stop codon of NifD and the translation start codon (ATG) of NifK, forming a vector designated pBG1404. The deletion resulted in a net loss of three amino acids and seven amino acid substitutions in amino acids 2-10 of the NifK polypeptide. The *A. vinelandii* host cells containing pBG1404 were compromised in their growth in low nitrogen media relative to the corresponding wild-type bacteria.

Wiig at al. (2011) used a naturally occurring translational fusion between NifN and NifB genes found in *Clostridium pastuerianum* and determined that it is functional for NifN and NifB activity in bacterial and biochemical complementation assays. This fusion was direct without any peptide linker, i.e. the C-terminal end of NifN was directly covalently linked to the N-terminal end of NifB.

In yeast and plant cells, translational fusions have been used to direct proteins encoded in the nucleus to mitochondrial matrix. In yeast expression assays, translational fusions of mitochondrial targeting peptide (MTP) and some Nif polypeptides (NifH, NifM, NifS, and NifU) were shown to be functional when grown under aerobic conditions (Lopez-Torrejon et al., 2016). Epitope fusions (FLAG and HIS) were also shown to be functional when fused to NifH, NifM, NifS and NifU, although these fusions were intended for localisation within the yeast cytoplasm and were only functional when the yeast were grown under anaerobic conditions. Burén et al. (2017b) showed that a mitochondrial-matrix targeted version of a soluble variant of NifB was functional in in vitro complementation assays when re-isolated from the mitochondria of yeast. This version of NifB included a N-terminal MTP, a truncated variant of NifB (without the NifX-like domain) and a C-terminal 10×His epitope tag. A large number of MTP-Nif fusions were also generated in yeast expression assays. However, this large ensemble of co-expressed proteins failed to show activity in yeast (Burén et al., 2017b).

An MTP from a CPN-60 gene was fused to the N-terminal end of NifH, NifM, NifS and NifU and shown to be functional via in vitro complementation assays when the FeProtein was re-isolated from plants grown under reduced oxygen tension at 10% oxygen (US2016/0304842).

Polynucleotides

The terms "polynucleotide" and "nucleic acid" are used interchangeably herein. They mean a polymeric form of nucleotides of any length, either deoxyribonucleotides or ribonucleotides, or analogs thereof. A polynucleotide defined herein may be of genomic, cDNA, semisynthetic, or synthetic origin, single-stranded or preferably double-stranded and by virtue of its origin or manipulation: (1) is not associated with all or a portion of a polynucleotide with which it is associated in nature (e.g., a Nif polynucleotide that does not comprise a native promoter encoding sequence), (2) is linked to a polynucleotide other than that to which it is linked in nature (e.g., a Nif polynucleotide linked to a MTP encoding nucleotide sequence and/or a non-native promoter encoding sequence), or (3) does not occur in nature (e.g., polynucleotides encoding MTP-Nif fusion polypeptides of the invention). The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, chimeric DNA of any sequence, nucleic acid probes, and primers. A polynucleotide may comprise modified nucleotides such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization such as by conjugation with a labeling component.

An "isolated polynucleotide" is substantially free from components that are normally linked (e.g., regulatory sequences) or associate with the polynucleotide. Thus, an isolated polynucleotide is substantially free of other cellular material, or culture medium when produced by recombinant techniques, or substantially free of chemical precursors or other chemicals when chemically synthesized. Preferably, the isolated polynucleotide is at least 60% free, more preferably at least 75% free, and more preferably at least 90% free from said components.

As used herein, the phrase "exogenous polynucleotide" refers to a polynucleotide that has a sequence originating from outside the cell or organism that the exogenous polynucleotide is present in.

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, translation and transcription termination and/or polyadenylation signals that are naturally associated with a given gene, or heterologous control signals, in which case, the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns", "intervening regions", or "intervening sequences." Introns are segments of a gene which are transcribed into nuclear RNA (nRNA). Introns may contain regulatory elements such as enhancers. Introns are removed or "spliced out" from the nuclear or primary transcript; introns therefore are absent in the mRNA transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, "chimeric DNA", also referred to herein as a "DNA construct", means any DNA molecule that is not naturally found in nature but which artificially joins two DNA parts into a single molecule, each part of which might be found in nature but the whole is not found in nature. For example, a DNA construct encoding a MTP-Nif fusion polypeptide of the invention. Typically, chimeric DNA comprises regulatory and transcribed or protein coding sequences that are not naturally found together in nature (e.g., a Nif polynucleotide linked to a non-native promoter encoding sequence). Accordingly, chimeric DNA may comprise regulatory sequences and coding sequences that are derived from different sources, or regulatory sequences and coding sequences derived from the same source, but arranged in a manner different than that found in nature. The open reading frame may or may not be linked to its natural upstream and downstream regulatory elements. The open reading frame may be incorporated into, for example, the plant genome, in a non-natural location, or in a replicon or vector where it is not naturally found such as a bacterial plasmid or a viral vector. The term "chimeric DNA" is not limited to DNA molecules which are replicable in a host, but includes DNA capable of being ligated into a replicon by, for example, specific adaptor sequences.

A "transgene" is a gene that has been introduced into the genome by a transformation procedure. The term includes a gene in a progeny cell, plant, seed, non-human organism or part thereof which was introducing into the genome of a progenitor cell thereof. Such progeny cells etc may be at least a $3^{rd}$ or $4^{th}$ generation progeny from the progenitor cell which was the primary transformed cell. Progeny may be produced by sexual reproduction or vegetatively such as, for example, from tubers in potatoes or ratoons in sugarcane. The term "genetically modified", and variations thereof, is a broader term that includes introducing a gene into a cell by transformation or transduction, mutating a gene in a cell and genetically altering or modulating the regulation of a gene in a cell, or the progeny of any cell modified as described above.

A "genomic region" as used herein refers to a position within the genome where a transgene, or group of transgenes (also referred to herein as a cluster), have been inserted into a cell, or predecessor thereof. Such regions only comprise nucleotides that have been incorporated by the intervention of man such as by methods described herein.

A "recombinant polynucleotide" of the invention refers to a nucleic acid molecule which has been constructed or modified by artificial recombinant methods. The recombinant polynucleotide may be present in a cell in an altered amount or expressed at an altered rate (e.g., in the case of mRNA) compared to its native state. In one embodiment, the polynucleotide is introduced into a cell that does not naturally comprise the polynucleotide. Typically an exogenous DNA is used as a template for transcription of mRNA which is then translated into a continuous sequence of amino acid residues coding for a polypeptide of the invention within the transformed cell. In another embodiment, the polynucleotide is endogenous to a bacterial cell and its expression is altered by recombinant means, for example, an exogenous control sequence is introduced upstream of an endogenous gene of interest to enable the transformed cell to express the polypeptide encoded by the gene.

A recombinant polynucleotide of the invention includes polynucleotides which have not been separated from other components of the cell-based or cell-free expression system, in which it is present, and polynucleotides produced in said cell-based or cell-free systems which are subsequently purified away from at least some other components. The polynucleotide can be a contiguous stretch of nucleotides existing in nature (e.g., Nif polynucleotide), or comprise two or more contiguous stretches of nucleotides from different sources (naturally occurring and/or synthetic) joined to form a single polynucleotide (e.g., a Nif polynucleotide linked to a MTP encoding nucleotide sequence and/or a non-native promoter encoding sequence). Typically, such chimeric polynucleotides comprise at least an open reading frame encoding a polypeptide of the invention operably linked to a promoter suitable of driving transcription of the open reading frame in a cell of interest. Reference to "a promoter" herein encompasses a single promoter or multiple promoters.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of, or useful for, the present invention may selectively hybridise, under stringent conditions, to a polynucleotide defined herein. As used herein, stringent conditions are those that: (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS, and/or (3) employ low ionic strength and high temperature for washing, for example, 0.015 M NaCl/0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above).

Polynucleotides of the invention may be codon-modified for expression in a plant cell. The skilled person will appreciated that the protein coding region may be codon optimised relative to, for example, the coding region of a naturally occurring polynucleotide in a nitrogen fixing bacterium.

Nucleic Acid Constructs

The present invention includes nucleic acid constructs comprising one or more polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the gene from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term "constitutive" as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in roots, leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter, a leaf-specific promoter or a promoter which directs gene expression in an aerial part of the plant (at least stems and leaves) (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136.

In an embodiment, the promoter is a root specific promoter, Examples of root specific promoters include, but are not limited to, the promoter for the acid chitinase gene and specific subdomains of the CaMV 35S promoter.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as, for example, described by Joshi (1987).

Vectors

The present invention includes use of vectors for manipulation or transfer of genetic constructs. A vector is a nucleic acid molecule, preferably a DNA molecule, that can be used to artificially carry foreign genetic material; into another cell, where it can be replicated or expressed. A vector containing foreign DNA is referred to as a "recombinant vector". Examples of vectors include, but are not limited to, plasmids, viral vectors, cosmids, extrachromosomal elements, minichromosomes, artificial chromosomes. The vector may comprise a transposable element.

A vector preferably is double-stranded DNA and contains one or more unique restriction sites and may be capable of autonomous replication in a defined host cell including a target cell or tissue or a progenitor cell or tissue thereof, or capable of integration into the genome, preferably the nuclear genome, of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome, preferably the nuclear genome, of the recipient cell and replicated together with the chromosome(s) into which it has been integrated. A vector system may comprise a single vector or plasmid, two or more vectors or plasmids, which together contain the total DNA to be introduced into the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, for example, pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the host cell, preferably a plant host cell. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327; an acetyltransferase gene from *Streptomyces viridochromogenes* conferring resistance to the selective agent phosphinothricin as, for example, described in EP 275957; a gene encoding a 5-enolshikimate-3-phosphate synthase (EPSPS) conferring tolerance to N-phosphonomethylglycine as, for example, described by Hinchee et al. (1988); a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which comprises at least one polynucleotide defined herein, and is capable of delivering the polynucleotide into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

Recombinant vectors of the invention comprise fusion sequences which lead to the expression of nucleic acid molecules as fusion proteins.

Recombinant vectors may also include intervening and/or untranslated sequences surrounding and/or within the nucleic acid sequence of a polynucleotide defined herein.

Preferably, the recombinant vector is stably incorporated into the genome of a host cell such as a plant cell. Accordingly, the recombinant vector may comprise appropriate elements which allow the vector to be incorporated into the genome, or into a chromosome of the cell.

Recombinant Cells

Another embodiment of the present invention includes a recombinant cell, for example, a recombinant plant cell, which is a host cell transformed with one or more polynucleotides, constructs, or vectors of the present invention, or progeny cells thereof. The term "recombinant cell" is used interchangeably with the term "transgenic cell" herein.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed cell in such a manner that their ability to be expressed is retained.

Preferred host cells are plant cells, more preferably cells of a cereal plant, more preferably barley or wheat cells, and even more preferably a wheat cell.

The recombinant cell may be a cell in culture, a cell in vitro, or in an organism such as, for example, a plant, or in an organ such as, for example, a root, leaf or stem. Preferably, the cell is in a plant, more preferably in roots, leaves, and/or stems of a plant.

In an embodiment, expression of active NifDK in a plant cell requires expression of NifD, NifK, NifH, NifB, NifE, NifN and optionally, NifU, NifS, NifO, NifV, NifY, NifW, and/or NifZ.

In another or further embodiment, expression of active NifH in a plant cell requires expression of NifH and NifM and optionally, NifU and/or NifN.

In an embodiment, reconstitution of nitrogenase activity in a plant cell requires expression of at least NifD, NifK, NifH, NifB, NifE, NifN and NifM.

The skilled person will appreciate that a smaller subset of Nif proteins may result in functional nitrogenase reconstitution in a plant cell. To the best of the inventors' knowledge, the only report of nitrogenase gene transfer to any photosynthetic organism described introduction of NifH in the chloroplast genome of *Chlamydomonas* (Cheng et al., 2005). NifH was able to complement a chlorophyll biosynthesis mutant, despite the fact that the NifH biosynthetic precursor proteins NifM, NifS and NifU were not co-expressed. This demonstrated that endogenous eukaryotic equivalents may functionally substitute for certain Nif proteins. Indeed a recent report, demonstrating that *E. coli* can reconstitute nitrogenase function using only eight Nif proteins (Wang et al., 2013), implies achieving function is plants may be less complex than expressing the full complement of Nif proteins. Whilst the inventors have yet to establish functionality of Nif proteins in planta, it is promising that the repertoire of biosynthetic and functional Nif proteins can be expressed in an environment potentially supportive of nitrogenase function.

Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. In a preferred embodiment, the plant part is a seed. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant, preferably the nuclear genome. The introduced genetic material may comprise sequences that naturally occur in the same species but in a rearranged order or in a different arrangement of elements, for example an antisense sequence. Plants containing such sequences are included herein in "transgenic plants".

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A "non-transgenic plant" is one which has not been genetically modified by the introduction of genetic material by recombinant DNA techniques. As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); grapes; beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, *Triticale*, oats or barley, even more preferably wheat.

As used herein, the term “wheat” refers to any species of the Genus *Triticum*, including progenitors thereof, as well as progeny thereof produced by crosses with other species. Wheat includes “hexaploid wheat” which has genome organization of AABBDD, comprised of 42 chromosomes, and “tetraploid wheat” which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed “breadwheat”). Tetraploid wheat includes *T. durum* (also referred to herein as durum wheat or *Triticum turgidum* ssp. durum), *T. dicoccoides, T. dicoccum, T. polonicum*, and interspecies cross thereof. In addition, the term “wheat” includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to *Triticale*.

As used herein, the term “barley” refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Methods for Producing Transgenic Plants

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agro-*

*bacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a polynucleotide of the invention. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Plant/Grain Processing

Grain/seed of the invention, preferably cereal grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated “212 micrometers (U.S. Wire 70)”. The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention, (ii) steeping said grain, (iii) germinating the steeped grains under predetermined conditions and (iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of speciality malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

Detection of Nitrogenase Complex

Detection of the nitrogenase complex can be carried out by any method which allows for the detection of the interaction between the NifDK protein complex and the NifH protein. Methods suitable for detecting the interaction between the NifDK protein complex and the NifH protein include any method known in the art for detecting protein-protein interaction including co-immunoprecipitation, affinity blotting, pull down, FRET and the like.

Alternatively, the detection of the nitrogenase complex can be carried out by measuring the activity of the resulting nitrogenase complex.

Methods suitable for measuring nitrogenase activity include any method known in the art for detecting the enzymatic reduction of dinitrogen to ammonia wherein electrons are transferred from the NifH protein to the NifDK protein complex. For example, the nitrogen fixation activity can be estimated by the acetylene reduction assay. Briefly, this technique is an indirect method which uses the ability of the nitrogenase complex to reduce triple bounded substrates. The nitrogenase enzyme reduces acetylene ($C_2H_2$) to ethylene ($C_2H_4$). Both gases can be quantified using gas chromatography. Nitrogen fixation may also be measured by the hydrogen evolution assay. $H_2$ is an obligate by-product of $N_2$ fixation. An indirect measure of nitrogenase activity can therefore be obtained by quantifying the $H_2$ concentration in a gas stream using a flowthrough $H_2$ sensor or gas chromatograph.

Detection of $N_2$ Fixation

Nitrogen fixation can be estimated by determining a net increase in total N of a plant-soil system (N balance method); 2) separating plant N into the fraction taken up from the soil and the fraction derived from the $N_2$ fixation (N difference, 15N natural abundance, 15N isotype dilution and ureide methods) and 3) measuring the activity of the nitrogenase (acetylene reduction and hydrogen evolution assays).

EXAMPLES

Example 1. Materials and Methods

Expression of Genes in Plant Cells in a Transient Expression System

Genes were expressed in plant cells using a transient expression system essentially as described by Wood et al. (2009), with various modifications as outlined below. *Nicotiana benthamiana* plants were grown in a growth chamber at 23° C. under a 16:8 h light:dark cycle with 90 μmmol/min light intensity provided by cool white fluorescent lamps. Binary vectors containing the coding region to be expressed in plant cells by a strong, constitutive 35S promoter or the enhanced 35S promoter (e35S; Kay et al., 1987) were introduced into *Agrobacterium tumefaciens* strain GV3101. A chimeric binary vector, 35S::p19, for expression of the p19 viral silencing suppressor was separately introduced into *A. tumefaciens* strain AGL1, as described in WO2010/057246. This viral silencing suppressor was routinely included in the method to maintain gene expression of transgenes introduced together with it. The recombinant *A. tumefaciens* cells were grown to stationary phase at 28° C. in LB broth supplemented with 50 mg/L carbenicillin or 50 mg/L kanamycin, according to the selectable marker gene on the vector, and 50 mg/L rifampicin. Acetosyringone was added to the culture to a final concentration of 100 μM and the culture then incubated at 28° C. with shaking for another 2.5 hr. The bacteria were then pelleted by centrifugation at 5000×g for 10 min at room temperature. The supernatant was discarded and the pellet was resuspended in a solution containing 10 mM MES pH 5.7, 10 mM $MgCl_2$ and 100 μM acetosyringone after which the OD600 was measured. A volume of each culture, including the culture containing the viral suppressor construct 35S::p19, required to reach a final concentration of OD600=0.10 was added to a fresh tube. The final volume was made up with the infiltration buffer. Leaves were then infiltrated with the culture mixture and the plants were typically grown for a further three to five days after infiltration before leaf discs were recovered for analysis. A control infiltration was typically included which had only the viral suppressor construct 35S::p19.

For over-expression of more than one gene of interest in combination, each additional gene was introduced separately into an *A. tumefaciens* strain and grown as described above. Bacterial suspensions were mixed so that each bacterial strain was at a final concentration of OD600=0.10. The bacterial strain containing the gene encoding the viral silencing suppressor 35S::p19 was included in all mixtures at the same concentration. For example, to express four genes in a transient leaf assay and including the viral suppressor construct, the final OD600 of the infiltrated mixture was 5×0.10=0.50 units. The simultaneous over-expression of at least five genes each from separate T-DNA vectors within plant cells in the transient assay format has previously been demonstrated using *Nicotiana benthamiana* (Wood et al., 2009).

Construction of Plasmids for Expression of Nif Genes in *N. benthamiana* Leaves

Unless otherwise stated, plasmids for transient expression of genes in *N. benthamiana* leaves were constructed using a modular cloning system with Golden Gate assembly (Weber et al., 2011). DNA parts as individual plasmids (Thermo Fisher Scientific, ENSA), each containing the 35S CaMV promoter (EC51288), the gene coding for the first 51 amino acids of the *Arabidopsis thaliana* F1-ATPase γ subunit (MTP-FAγ51), plant codon-optimised nifH (EC38011), nifK (EC38015), nifY (EC38019), nifE (EC38016), nifN (EC38024), nifJ (EC38022), nifB (EC38017), nifQ (EC38025), nifF (EC38021), nifU (EC38026), nifS (EC38018), nifV (EC38020), nifW (EC38027), nifZ (EC38029), nifM (EC38023), nifX (EC38028), plant codon optimised HA epitope tag (EC38003), and a CaMV polyadenylation sequence/transcription terminator region (EC41414) were assembled into backbone vectors (EC47772, EC47742, EC47751, EC47761, EC47781) using Type IIS restriction cloning.

RNA Extraction, cDNA Synthesis and Analysis

In order to extract RNA from plant leaf samples such as those which have been infiltrated with *Agrobacterium*, leaf pieces of about 2×2 cm in area are frozen with liquid nitrogen, ground to a powder, and 500 μl of Trizol buffer (Thermo Fisher Scientific) added per sample. Following this, the Trizol supplier's instructions are followed except with these modifications: the chloroform extraction is repeated and the RNA is dissolved at 37° C. The extracted RNA is treated with RQ1 DNAse (Promega) to remove any extracted DNA. The RNA preparations are then further purified using Plant RNeasy columns (Qiagen). When performed, cDNA synthesis is carried out using Superscript III reverse transcriptase (Thermo Fisher Scientific) according to the supplier's protocol with an oligo-dT primer. For RT-PCR analysis of each RNA sample, three separate cDNA synthesis reactions are carried out. The 20 μl cDNA reactions are diluted 20-fold in nuclease free water. qRT-PCR is carried out on a Qiagen rotor gene Q real-time PCR machine. 9.6 μl of each cDNA is added to 10 μl of 2× sensifast no ROX SYBR Taq (Bioline) and 0.4 μl of forward and reverse primers at 10 μmol each, for a final reaction volume of 20 μl. All qPCR reactions (for both reference and specific genes) are carried out in triplicate under the following cycling conditions: 1 cycle of 95° C./5 min, 45 cycles of 95° C./15 sec, 60° C./15 sec and 72° C./20 sec. Fluorescence is measured at the 72° C. step. A 55° C. to 99° C. melting cycle is then carried out. Control amplifications for a constitutively expressed *N. benthamiana* GADPH mRNA are used to normalise gene expression using the comparative quantitation program in the rotor gene software package. The values for each set of three cDNAs, representing the average of triplicate assays, are averaged, allowing for a calculation of the standard error of the mean (SEM).

Protein Extraction from Bacterial Cells

Protein was isolated from *E. coli* cells by extraction with Urea/SDS buffer (8 M Urea, 2% SDS, 100 mM Tris-HCl pH 8.5, 65 mM DTT). 300 μl of extraction buffer was added and the mixture vortexed for 10 sec and centrifuged at 12,000×g for 2 min. Supernatants containing the extracted proteins ("total proteins") were stored at ~80° C. prior to processing. Protein estimations were performed using the microtiter Bradford protein assay (Bio-Rad, California, USA) according to the manufacturer's instructions. For this, extracted proteins from different samples were diluted in water over two dilutions (1:20, 1:40) in duplicate and measurements were made at 595 nm using a SpectraMax Plus. Bovine serum albumin (BSA) standard was used in the linear range 0.05 mg/mL to approximately 0.5 mg/mL. The BSA concentration was determined by high sensitivity amino acid analysis at the Australian Proteomics Analysis Facility (Sydney, Australia). Blank-corrected standard curves were run in duplicate. Linear regression was used to fit the standard curve.

Protein Extraction from Leaf Tissue

To analyse the amount and properties of specific polypeptides produced in plant cells after T-DNA introduction, especially the size of the polypeptides as an indicator of processing in mitochondria, *N. benthamiana* leaf samples were harvested by excising about 180 mm$^2$ leaf pieces from the infiltrated regions 4 or 5 days after infiltration, unless otherwise stated. These were frozen in liquid nitrogen and, when to be processed, were ground to a powder using a mortar and pestle. 300 μL, of buffer was added to each powder sample. The buffer contained 125 mM Tris-HCl pH 6.8, 4% (w/v) sodium dodecyl sulphate (SDS), 20% (w/v) glycerol, 60 mM dithiothreitol (DTT) and 0.002% (w/v) bromophenol blue. Samples were heated at 95° C. for 3 min before centrifugation at 12000×g for 2 min. Supernatant containing the extracted polypeptides, referred to herein as "total protein" samples, was removed and 10 μL to 100 μL, used for Western blotting depending on the expected level of polypeptide to be detected.

Preparation of Total, Insoluble and Soluble Protein Fractions from Leaf Tissue

*N. benthamiana* leaf samples were harvested by excising about 180 mm$^2$ leaf pieces from the infiltrated regions 4 or 5 days after infiltration. These were frozen in liquid nitrogen and, when to be processed, were ground to a powder using a mortar and pestle.

For solubility testing the harvested leaf tissue was ground in liquid nitrogen and transferred to a microfuge tube containing extraction buffer (100 mM Tris pH 8.0, 150 mM NaCl, 0.25 M mannitol, 5% (v/v) glycerol, 1% (v/v) Tween 20, 1% (w/v) PVP, 2 mM TCEP, 0.2 mM PMSF, 10 μM leupeptin). The sample was centrifuged at 20,000×g for 5 min to divide the sample into soluble (supernatant) and insoluble (pellet) fractions. The supernatant was transferred to a fresh microfuge tube and centrifuged again at 20,000×g for 5 min, and the pellet was washed three times with extraction buffer. Laemmli buffer was added to the resulting soluble and insoluble fractions and subjected to SDS-PAGE followed by Western blot analysis as described in Allen et al. (2017).

300 μL of cold solubility buffer was added to each ground sample. The solubility buffer contained 50 mM Tris-HCl pH 8.0, 75 mM NaCl, 100 mM mannitol, 2 mM DTT, 0.5% (w/v) polyvinylpyrrolidone (average mol wt 40,000), 5% (v/v) glycerol, 0.2 mM PMSF, 10 μM leupeptin and 0.5% (v/v) Tween® 20. The samples were centrifuged for 5 min at 16,000×g at 4° C. The supernatant was transferred to a fresh tube and the pellet was resuspended in 300 μL of cold solubility buffer. Both, the supernatant (sample 1) and the resuspended pellet (sample 2) were centrifuged again for 5 min at 16,000×g at 4° C. From sample 1, a sample was taken from the supernatant, which is referred to as the soluble fraction. This sample was mixed with an equivalent amount of 4×SDS buffer. 4×SDS buffer contained 250 mM Tris-HCl pH 6.8, 8% (w/v) SDS, 40% (v/v) glycerol, 120 mM DTT and 0.004% (w/v) bromophenol blue. After the second centrifugation step, the supernatant of sample 2 was discarded. The pellet is referred to as the insoluble fraction. The pellet was resuspended in 300 μL 4×SDS buffer and 300 μL of solubility buffer were added. When soluble and insoluble fractions were compared to the amount of total protein, the leaf piece for the total protein sample was ground as described above. However, the ground sample was resuspended in 300 μL 4×SDS buffer and 300 μL of solubility buffer were added. Samples for the total, insoluble and soluble fractions were heated at 95° C. for 3 min and then centrifuged at 12000×g for 2 min. 20 μL of the supernatant containing the extracted polypeptides was loaded on a NuPAGE Bis Tris 4-12% gels (Thermo Fisher Scientific) for gel electrophoresis and Western blot analysis.

For Western blot analysis of anaerobically extracted proteins, the extractions were carried out in an anaerobic chamber (COY Laboratory Products) filled with a $H_2/N_2$ atmosphere (2-3%/97-98%). Anaerobic extraction solutions were prepared at a Schlenk line in a bottle equipped with a butyl rubber septum by at least four cycles of evacuating and purging with $N_2$.

Purification from Plants of Polypeptides Fused to a Twin-Strep Epitope

*N. benthamiana* leaf samples were harvested five days after infiltration with *Agrobacterium* containing the genetic construct of interest, or from stably transformed plant leaves, and treated as follows. Leaf material of 15-20 g was macerated in 100 ml cold extraction buffer under anaerobic conditions (<5 ppm $O_2$) using a stick blender with 6× five second pulses, keeping the mixture cold on ice throughout. The homogenised mixture was filtered through four layers of mira cloth and the filtrate (70-80 ml) centrifuged for 30 min at 3800 g at 4° C. The supernatant was decanted and filtered through a 0.45 μM filter PVDF membrane to further remove fine particulates. The filtrate (60-70 ml) was loaded onto a StreptactinXT column (2 mL bed volume) at 2 mL/min. The column was washed with 20 mL wash buffer before eluting the polypeptides containing the TS epitope using buffer containing 50 mM biotin, 50 mM Tris pH 8.0 and 75 mM NaCl (Elution buffer). The collected fraction numbers 2-8 of 3 mL each were further concentrated over a 10 kDa molecular weight cut-off membrane (10 Kda MWCO, Amersham) by centrifugation for 30 min at 3800×g. The purified protein concentrate was snap frozen in liquid nitrogen for future analysis. Samples were retained from each step of the purification process for Western blot analysis conducted at normal atmosphere. Samples and molecular weight markers (BenchMark ladder) were electrophoresed on 4-20% NuPage gels for 60 minutes at 200V, using 20 μL of sample per lane. Proteins in the gels were blotted to PVDF membrane using an iBLOT apparatus and proteins containing an epitope detected by using anti-HA (1:10000) and anti-STREP:HRP (1-step) antibodies.

Western Blot Analysis

Polypeptides in extracted samples were separated by SDS-polyacrylamide gel electrophoresis (SDS-PAGE) on NuPAGE Bis Tris 4-12% gels (Thermo Fisher Scientific) at 200 V for about 1 hr. The separated polypeptides were transferred from each gel to a PVDF membrane using a dry apparatus (iBLOT) according to the supplier's instructions (Thermo Fisher Scientific) using a three-step 7 min transfer program (1 min at 20 V, 4 min at 23 V and 2 min at 25 V. After blotting, the gels were retained and stained with Coomassie stain (SimplyBlue SafeStain, Thermo Fisher Scientific) overnight, then rinsed in water for visualisation of remaining proteins to confirm that transfer of the polypeptides had occurred. The staining with Coomassie stain also provided confirmation of the equal loading of protein amounts per gel lane, using the levels of highly abundant proteins such as Rubisco large and small subunits as an indicator of equal protein loading per lane. Membranes with bound polypeptides were blocked overnight in TBST buffer containing 5% skim milk powder at 4° C. TBST buffer contained 50 mM Tris-HCl, pH 7.5, 150 mM NaCl and 0.1% (v/v) Tween® 20. Monoclonal anti-HA antibody produced in mouse and anti-rabbit IgG (whole molecule)-peroxidase antibody produced in goat were purchased from Sigma-Aldrich Immun-Star Goat Anti-Mouse (GAM)-HRP conjugate was purchased from Bio-Rad. Anti-isocitrate dehydrogenase (IDH) antibody produced in rabbit was purchased from Agrisera. StrepMABclassic-HRP conjugate antibody was purchased from IBA. Anti-GFP antibody was a gift from Leila Blackman (Australian National University, Canberra, Australia). Anti-HA, anti-IDH and anti-GFP antibodies were added at a 1:5000 dilution, StrepMABclassic-HRP conjugate antibody was added at a 1:10000 dilution in TBST with 5% skim milk powder and the membranes were incubated in the solution for 1 to 2 h. Membranes were then washed for 3×20 min with TBST. When the StrepMABclassic-HRP conjugate antibody was used, the antibodies were detected at this stage using the Amersham ECL reagent (GE Healthcare) and membranes were developed on an Amersham imager 600 (GE Healthcare). For anti-HA and anti-GFP, the secondary antibody anti-Mouse-HRP conjugate was added at 1:5000 in TBST containing 5% skim milk and the membranes incubated for 1 h. For anti-IDH, the secondary antibody anti-rabbit-peroxidase was added at a dilution of 1:5000 in TBST containing 5% skim milk and the membranes were incubated for 1 hour. The membranes were washed for 3×15 min with TBST. For secondary antibody detection, Amersham ECL reagent was used and membranes were developed on an Amersham imager.

Treatment of Protein Extracts with Trypsin Prior to LC-MS Analyses

When used for LC-MS analysis, protein samples were subjected to filter-aided sample preparation (FASP), a method used for the on-filter digestion of proteins prior to mass-spectrometry-based analyses (Wisniewski et al., 2011). In brief, 100 μl (~200 μg) of protein was diluted in 100 μL of 8 M urea, 100 mM Tris-HCl, pH 8.5 (UA buffer) and loaded onto a 10 kDa molecular weight cut-off (MWCO) centrifugal filter (Merck Millipore, Australia) and centrifuged at 20,800 g for 15 min at room temperature (RT). The filter with retained proteins >10 kDa was washed with 200 μL of UA buffer and centrifuged at 20,800 g for 15 min at RT. To chemically reduce bisulfide bonds in the protein on the filter, 200 μL of 50 mM dithiothreitol solution was added and the mixture incubated at room temperature for 50 min with shaking. The filter was washed with two 200 μL volumes of UA buffer with centrifugation each time at 20,800×g for 15 min. For cysteine alkylation, 100 μL of iodoacetamide (IAM) solution (50 mM IAM in UA buffer) was added and the mixture incubated in the dark for 30 min at RT before centrifugation (20,800 g, 15 min). The retained protein was washed with two 200 μL volumes of UA buffer with centrifugation (20,800×g, 15 min) followed by two subsequent wash/centrifugation steps with 200 μL of 50 mM ammonium bicarbonate. 200 μL of the trypsin (sequencing grade, Promega, Alexandria, Australia) solution (20 μg/mL in 50 mM ammonium bicarbonate and 1 mM $CaCl_2$) was loaded onto the filter and incubated for 1 h or 18 h at 37° C. in a wet chamber. The tryptic peptides were collected by centrifugation (20,800×g, 15 min) followed by an additional wash with 200 μL, of 50 mM ammonium bicarbonate. The combined filtrates were lyophilised and stored at ~20° C.

LC-MS Analysis of Proteins

The trypsin digested peptides were dissolved in 50 μL of 1% formic acid (FA) and a 4 μL aliquot loaded onto an Ekspert nanoLC415 (Eksigent, Dublin, CA, U.S.A.) for chromatographic separation, directly coupled to a 6600 TripleTOF MS (SCIEX, Redwood City, CA, USA). The peptides were desalted for 5 min on a ChromXP C18 (3 μm, 120 Å, 10 mm×0.3 mm) trap column at a flow rate of 10 μL/min using 0.1% FA, and separated on a ChromXP C18 (3 μm, 120 Å, 150 mm×0.3 mm) column at a flow rate of 5 μL/min at 30° C. A linear gradient from 3-25% solvent B over 68 min was employed followed by: 5 min from 25% B to 35% B; 2 min 35% B to 80% B; 3 min at 80% B, 80-3% B, 1 min; and 8 min re-equilibration. The solvents were: (A) 5% DMSO, 0.1% FA, 94.9% water; (B) 5% DMSO, 0.1% FA, 90% acetonitrile, 4.9% water. The instrument parameters were: ion spray voltage 5500 V, curtain gas 25 psi, GS1 15 psi and GS2 15 psi, heated interface 150° C. Data were acquired in information-dependent acquisition (IDA) mode comprising a time-of-flight (TOF)-MS survey scan followed by 30 MS/MS, each with a 40 ms accumulation time. First stage MS analysis was performed in positive ion mode, mass range m/z 400-1250 and 0.25 s accumulation time. Tandem mass spectra were acquired on precursor ions >150 counts/s with charge state 2-5 and dynamic exclusion for 15 s with a 100 ppm mass tolerance. Spectra were acquired over the mass range of m/z 100-1500 using the manufacturer's rolling collision energy (CE) based on the size and charge of the precursor ion. For proteins extracted from *E. coli*, protein identification was undertaken using ProteinPilot™ 5.0 software (SCIEX) with searches conducted against the *E. coli* subset of the Uniprot database appended with a custom nitrogenase (Nif+Mit2Nif) database including the control chloramphenicol resistance protein (CAT/P62577) and a contaminant database (Common Repository of Adventitious Proteins). For proteins extracted from *N. benthamiana*, the searches were conducted using a *N. benthamiana* subset of the Uniprot database appended with the custom nitrogenase (Nif+Mit2Nif) database and the contaminant database (Common Repository of Adventitious Proteins).

From the identified peptides, two NifM peptides, namely DAFAPLAQR (SEQ ID NO:155) and DYLWQQSQQR (SEQ ID NO:156) that were fully tryptic, contained no unusual cleavages and/or modifications and showed high response in the MS as judged by peak intensity, were selected for multiple reaction monitoring (MRM) scanning to confirm the detection of the nitrogenase (NifM) proteins in the *E. coli* JM109 expression system.

The enzyme chloramphenicol acetyltransferase (CAT; P62577), which provides chloramphenicol resistance in bacteria, was expressed from the selectable marker gene in all of the transformed *E. coli* (strain JM109) cells containing the modified or unmodified pMIT2.1 genetic constructs. This polypeptide was therefore selected as a control to standardize protein expression levels. Three tryptic peptides (four transitions/peptide) from CAT polypeptide were selected to measure the level of CAT, namely ITGYTTVDISQWHR (SEQ ID NO:157), LMNAHPEFR (SEQ ID NO:158) and YYTQGDK (SEQ ID NO:159).

Targeted Liquid Chromatography-Multiple Reaction Monitoring-Mass Spectrometry (LC-MRM-MS)

Reduced and alkylated tryptic peptides (5 μL) were chromatographically separated on a Kinetex C18 column (2.1 mm×100 mm, Phenomenex) using a linear gradient of 5-45% acetonitrile in 0.1% formic acid, over 10 min at a flow rate of 400 μL/min. The eluent from the Shimadzu Nexera UHPLC was directed to a QTRAP 6500 mass spectrometer (SCIEX) equipped with a TurboV ionisation source operated in positive ion mode for data acquisition and analysis. The MS parameters were as follows: ion spray voltage, 5500 V; curtain gas, 35; GS1, 35; GS2, 40; source temperature, 500° C.; declustering potential, 70 V; and entrance potential, 10 V. Peptides were fragmented in the collision cell with nitrogen gas using rolling collision energy dependent on the size and charge on the size and charge of the precursor ion. Relative quantitation using scheduled multiple reaction monitoring (MRM) scanning experiments with a 40 second detection window around the expected retention time (RT) and a 0.3 second cycle time. Data were acquired using Analyst v1.7 software. Peak areas of four MRM transitions were integrated using Skyline (MacLean, Bioinformatics 2010) wherein all transitions were required to co-elute with a signal-to-noise (S/N)>3 and intensity >1000 counts per second (cps) for detection.

Acetylene Reduction Assays Using the pMIT2.1 System in *E. coli*

Cells of *E. coli* strain JM109 were transformed with the plasmids pMIT2.1 (or one of its derivatives that was being tested) and the controller plasmid pN249 which conferred resistance to the antibiotics chloramphenicol and spectinomycin, respectively, as described in Temme et al., 2012. The transformed cells were selected by growth on LB medium (10 g/L tryptone, 5 g/L yeast extract, 10 g/L NaCl) containing chloramphenicol (34 mg/L) and spectinomycin (80 mg/L). Transformed cells were grown aerobically overnight at 37° C. in LB medium with antibiotics to an optical density at 600 nm of 1.0. The cultures were centrifuged at 10,000 g for 1 minute and the supernatant discarded. The cells were re-suspended in one volume of an induction medium which was free of N sources, containing 25 g/L $Na_2HPO_4$, 3 g/L $KH_2PO_4$, 0.25 g/L $MgSO_4 \cdot 7H_2O$, 1 g/L NaCl, 0.1 g/L $CaCl_2 \cdot 2H_2O$, 2.9 mg/L $FeCl_3$, 0.25 mg/L $Na_2MoO_4 \cdot 2H_2O$ and 20 g/L sucrose (minimal medium) supplemented with 1.5 ml/L of 10% serine, 600 μl/L 0.5% Casamino acids, 5 mg/L biotin and 10 mg/L para-aminobenzoic acid (Yang et al., 2018). The medium was sparged with argon gas for 20 minutes prior to mixture with the bacteria and antibiotics. Stock solutions were filter sterilized. For induction of Nif gene expression, the medium was supplemented with isopropyl-β-D-1-thiogalactopyranoside (IPTG; Gold Bio #I2481C25 259) at a final concentration of 0.1 mM, 0.5 mM or 1.0 mM unless otherwise stated, generally 1.0 mM. The cell suspensions were transferred to 3.5 cc culture flasks and capped with gas-tight rubber seals using a crimp-lock system and the headspace was sparged with pure argon gas for 20 min. The suspensions were then incubated at 30° C. with shaking at 200 rpm for 5 hours. After this, acetylene reduction assays (ARA) were started by the injection of 0.5 cc of pure $C_2H_2$ (BOC gases, instrument grade; final concentration 10% $C_2H_2$ in argon) and further incubation for 18 hours. Production of ethylene at the final time was measured by gas chromatography with flame ionisation detection (GC-FID) using an Agilent 6890N GC instrument. Headspace samples (0.5 cc) were removed and manually injected into a split/splitless inlet on a 10:1 split mode. The instrument was operated under the following parameters: inlet and FID temperatures of 200° C., average velocity for the carrier He of 35 cm/sec, isothermal oven temperature at 120° C. A RT-Alumina Bond/MAPD column (30 m×0.32 mm×5 μm) was used with a 5 m particle trap column coupled to the detector end. Analytical performance of the instrument was assessed by running suitable blanks and standards. Under these conditions, ethylene emitted from the column at about 2.3 minutes and acetylene at about 3.1 minutes. This GC system was able to detect ethylene at levels as low as 0.00001% atm with clear resolution from acetylene as the only other detectable peak in this format, so was extremely sensitive.

The assay system using wild-type pMIT2.1 and pN249 in *E. coli* strain JM109 as the positive control produced only a trace level of ethylene when no IPTG was added to the growth medium, whereas addition of IPTG to the growth medium at 0.1 mM, 0.5 mM or 1.0 mM greatly increased the amount of ethylene produced. The rate of ethylene production increased greatly from 3 hr sampling to 18 hr, and also as the IPTG concentration was increased, indicating increased nitrogenase activity with increased Nif gene expression. Therefore, the assays generally used 1.0 mM IPTG and sampling after 18 hr.

Yeast Transformation and Culture Conditions for Recombinant Protein Expression

Transformation of yeast strain INVSc1 (Thermo Fisher Scientific) was performed using the Yeast Transformation Kit (Sigma Aldrich) according to the manufacturer's protocol. For vectors having a Ura gene as selectable marker, transformed colonies were selected by plating the transformation mixture onto minimal medium without uracil (SCMM-U) agar plates, which contained 6.7 g/L yeast nitrogen base, 1.92 g/L synthetic dropout medium without uracil (Sigma Aldrich), 20 g/L glucose, and 20 g/L agar. After 2-3 days of incubation at 30° C., single colonies were restreaked onto fresh SCMM-U agar plates. The presence of the genetic construct including a NifD gene or other Nif was confirmed by PCR using gene specific primers. A single colony that contained the genetic construct was inoculated into SCMM-U liquid media (containing the same components as SCMM-U agar but without the agar), grown at 30° C. with shaking for 2 days. Glycerol was added to a final concentration of 20% and aliquots stored in −80° C. until further use.

For expression of the genes contained in the genetic construct, an inoculant from the glycerol stock was grown in SCMMM-U liquid media at 30° C. with shaking for 2 days. The cells were collected from the culture by centrifugation and resuspended in SCMM-U induction medium which was identical to SCMM-U liquid media except that the glucose was replaced with 20 g/L galactose, to a final OD600 of 0.4. The culture for induction was grown at 30° C. with shaking for 2 days and the yeast cells were collected by centrifugation for protein extraction and Western blot analysis.

Example 2. Production of Nif Polypeptides in Mitochondria of Plant Cells by Expressing MTP-Nif Fusion Polypeptides The inventors have previously reported the successful production of 16 different Nif polypeptides in mitochondria of plant cells by introducing chimeric genes encoding translational fusions of mitochondrial targeting peptides (MTP) linked to the N-termini of the Nif polypeptides (Allen et al., 2017; WO2018/141030). The MTP sequences used included one of 77 amino acids in length (amino acids 1-77 of SEQ ID NO:20) derived from an *A. thaliana* F1-ATPase (At2G33040; Lee et al, 2012) and designated herein as MTP-FAγ77, which, with a 3-amino acid linker of Gly-Ala-Pro (GAP) linking the MTP to the N-terminus of the Nif polypeptides, provided an 80 amino acid N-terminal extension to the translated Nif polypeptides. Cleavage by MPP occurred after 42 amino acids, leaving an N-terminal extension of 38 amino acid residues fused to the Nif polypeptide of interest, 35 residues coming from MTP-FAγ77 plus the GAP. This N-terminal extension was termed FAγ-scar38. The natural translation initiation methionine residue of each Nif polypeptide was thereby replaced by the scar-38 sequence. Those experiments did not test for the normal function of the Nif polypeptides that were produced.

The inventors sought to shorten the MTP sequence from the 77 amino acids of MTP-FAγ77 for use with Nif polypeptides in plant cells, while still retaining MTP function. The inventors examined whether 26 amino acids could be trimmed from the C-terminus of MTP-FAγ77 to generate an MTP designated as MTP-FAγ51 (SEQ ID NO:21). This sequence had a C-terminal GG added as a consequence of the cloning procedure. The inventors predicted that MTP-FAγ51 would be cleaved by MPP after amino acid 42, leaving 9 amino acids (ISTQVVRNR; SEQ ID NO:22) from MTP-FAγ51 at the N-terminus of the processed fusion polypeptide and a linking GG as a result of the cloning procedure. This 9-amino acid sequence was designated as FAγ-scar9 or simply as scar9.

To test the function of MTP-FAγ51 relative to the longer version, a genetic construct was first made encoding this MTP fused to NifH. The modified NifH gene was identical to the NifH gene in pRA10 (encoding MTP-FAγ77+GAP::NifH::HA; SEQ ID NO:23) except that the encoded polypeptide had MTP-FAγ51 fused to the N-terminus of NifH rather than MTP-FAγ77. The polypeptide still included the GAP amino acids for cloning purposes. The NifH coding region in both constructs was codon optimised for expression in human cells, based on the nucleotide sequence in pRA10. Both constructs included a sequence encoding a HA epitope tag at the C-terminus of the Nif polypeptide to provide for detection and purification of the polypeptides with HA-antibody. The shortened construct was designated pRA34 (encoding MTP-FAγ51+GAP::NifH::HA, SEQ ID NO:24).

A second construct was made, designated SN18 and encoding a NifH fusion polypeptide having the amino acid sequence provided as SEQ ID NO:25, which included several modifications relative to pRA34 aimed at increasing expression levels. An enhanced 35S promoter (e35S; Kay et al., 1987) was used to express the fusion protein, an additional N-terminal Met was added as a translation start, a TMV 5'-UTR was added upstream of the protein coding region and the codon usage was switched to *A. thaliana* codon usage. All of these modifications were made to increase the expression level at both the transcriptional and translational level. Additionally, the amino acids GG were used instead of GAP immediately after the MTP. A third construct was also made, designated SN29 and encoding a NifH fusion polypeptide having the amino acid sequence provided as SEQ ID NO:26, where the polypeptide had the HA epitope tag immediately after the MTP-FAγ51 sequence (SEQ ID NO:36) and before the GG and NifH sequences (MTP-FAγ51::HA::NifH). Both of these constructs were made by GoldenGate cloning methods (Weber et al., 2011) which provided for assembly of genetic components into the construct in a modular fashion with specific components as described by Engler (2014).

These constructs were tested in the *N. benthamiana* leaf system and compared to the longer construct pRA10. Protein extracts were produced from the infiltrated leaf tissues and subjected to SDS PAGE and Western blot analysis using HA-antibody to assess protein expression levels and MPP processing efficiency. As a control for the size of the unprocessed fusion polypeptides, protein extracts from *E. coli* expressing pRA34 and pRA10 were run in adjacent lanes on the gels. The bacterial extracts yielded polypeptide bands of the expected sizes for unprocessed MTP::NifH. In contrast, protein extracts from the *N. benthamiana* leaf tissues infiltrated with these constructs yielded polypeptide bands of smaller sizes, corresponding to the sizes expected for the MPP-processed polypeptides. Expression of the MTP-FAγ51::NifH::HA from pRA34 and SN18, and MTP-FAγ51::HA::NifH polypeptide from SN29, each yielded a band at a smaller MW than MTP-FAγ77+GAP::NifH::HA in accordance with the difference in expected size between the polypeptides, due to the shortened MTP sequence. Expression from SN18 was at least as strong as from pRA34; both were strong. The inventors concluded that the shortened MTP-FAγ51 was capable of directing a synthetic NifH fusion polypeptide to the mitochondria of plant cells and provided for processing by MPP in the mitochondria.

Based on the success with pRA34, SN18 and SN29 encoding NifH polypeptides, the shorter MTP sequence was tested with the other 15 Nif polypeptides, encoding the corresponding MTP-FAγ51 versions. A series of genetic constructs were made (Tables 3 and 4) for this using the GoldenGate approach (Weber et al., 2011). The GoldenGate cloning system was used for assembling the different gene elements, including the promoters, 5'-UTR, 3'-UTR, N- and C-terminal extensions and terminators. Each element had defined boundaries that allowed for modular assembly and easy exchange of elements. This cloning system with components as described by Engler et al. (2014), was therefore used for testing a large variety of different genetic constructs for production of MTP::Nif fusion polypeptides in the following Examples. Since the GoldenGate cloning system utilised type IIS restriction enzymes that cut outside their recognition sequence, it was possible to avoid the use of restriction enzyme cloning sites within the junction sequences. This allowed construction of genes encoding MTP::Nif fusions without the Gly-Ala-Pro sequence present in the earlier constructs. As above, a Gly-Gly bridge at the junction of the MTP::polypeptide fusions was used instead, to fit the GoldenGate system. Glycine was chosen as the standard amino acid for this linkage due to its common occurrence at the −1 position of MTP sequences. As an exception to this, the construct to express the NifK fusion polypeptide (SN140) had the HA epitope inserted between the MTP-FAγ51 and the NifK sequence, separated by a Gly-Gly bridge, and a wild-type C-terminal end. This variation was made as it had been observed previously that the NifK polypeptide required a wild-type C-terminus, with no C-terminal extension, for activity (WO2018/141030).

A second, parallel set of genetic constructs was made which encoded cytoplasmically localized Nif polypeptides rather than mitochondrially localized polypeptides. This was done by replacing the MTP-FAγ51 encoding sequence in the constructs with a nucleotide sequence encoding a 6×His amino acid motif (SEQ ID NO:27). The 6×His motif was of a similar molecular weight to the FAγ-scar9 motif resulting from MPP-mediated cleavage of the MTP-FAγ51 sequence. The polypeptides fused to 6×His were otherwise identical to the MTP-FAγ51::Nif::HA polypeptides, including the presence of the C-terminal HA epitope. Thereby, the 6×His versions of the polypeptides provided suitable molecular weight controls to the corresponding MPP-processed FAγ-scar9::Nif::HA polypeptides on the Western blots. The exception to this was the control (cytoplasmic localised) construct to express NifK (SN72) which had an N-terminal fused HA epitope, without an MTP sequence, rather than the 6×His motif. The genetic constructs and the predicted molecular weight of the fusion polypeptides for the unprocessed MTP-FAγ51::Nif::HA polypeptides and the 6×His fusion polypeptides are listed in Table 3.

TABLE 3

Plasmids were constructed to test mitochondrial targeting efficiency and protein solubility of Nif polypeptides expressed in *N. benthamiana* leaves. The plasmids encoding cytoplasmically localized polypeptides had a 6xHis motif instead of the MTP sequence. The predicted polypeptide sizes (kDa) were calculated using VNti software.

| | Mitochondrially targeted | | | Cytoplasmically localized | |
|---|---|---|---|---|---|
| Nif | Construct ID | Polypeptide description | Molecular weight (kDa) | Construct ID | Molecular weight (kDa) |
| B | SN192 | pFAγ51::NifB::HA | 59 | SN201 | 54 |
| D | SN10 | pFAγ51::NifD::HA | 61.1 | SN196 | 56.3 |
| E | SN38 | pFAγ51::NifE::HA | 57.2 | SN203 | 52.4 |
| F | SN138 | pFAγ51::NifF::HA | 26.2 | SN204 | 21.4 |
| H | SN18/SN27 | pFAγ51::NifH::HA | 39.0 | SN205 | 34.2 |
| J | SN139 | pFAγ51::NifJ::HA | 135.2 | SN206 | 130.4 |
| K | SN140 | pFAγ51::HA::NifK | 65.3 | SN72 | 59.7 |
| M | SN30 | pFAγ51::NifM::HA | 37.7 | SN207 | 32.9 |
| N | SN39 | pFAγ51::NifN::HA | 57.6 | SN208 | 52.8 |
| Q | SN141 | pFAγ51::NifQ::HA | 26.7 | SN209 | 21.9 |
| S | SN31 | pFAγ51::NifS::HA | 50.3 | SN210 | 45.5 |
| U | SN32 | pFAγ51::NifU::HA | 36.5 | SN211 | 31.7 |
| V | SN142 | pFAγ51::NifV::HA | 48.2 | SN212 | 43.4 |
| W | SN143 | pFAγ51::NifW::HA | 17.2 | SN213 | 12.4 |
| X | SN144 | pFAγ51::NifX::HA | 25.3 | SN214 | 20.5 |
| Y | SN145 | pFAγ51::NifY::HA | 31.5 | SN215 | 26.7 |
| Z | SN146 | pFAγ51::NifZ::HA | 23.7 | SN216 | 20.9 |

The NifD and NifS polypeptide sequences used in these fusions were the sequences according to Temme et al. (2012). These amino acid sequences are provided in SEQ ID NO:18 and SEQ ID NO:19, respectively. The NifD amino acid sequence of SEQ ID NO:18 differed from the sequence of 483 amino acids provided as SEQ ID NO:2 by six amino acid substitutions, at positions 39, 41, 87, 96, 355 and 483. The NifS amino acid sequence of SEQ ID NO:19 differed from the sequence of 400 amino acids provided as SEQ ID NO:11 by four amino acid substitutions, at positions 110, 113, 124 and 290. All of the genetic constructs designated herein with an SN number which contained a NifD sequence or a NifS sequence used the sequences according to Temme et al. (2012).

Each of the constructs was introduced into *N. benthamiana* leaf cells and, after 5 days, proteins extracted from the infiltrated leaf tissue and analysed by the Western blot method. Samples from the constructs expressing the 6×His polypeptides, included as molecular weight markers on the Western blots for the corresponding MPP-processed FAγ-scar9::Nif::HA polypeptides (see Table 3), were electrophoresed in adjacent lanes on the gels. Detection of the polypeptides used the HA epitope fused to the C-terminus of each Nif polypeptide.

The results for processing by MPP are shown in FIG. 1 and summarised in Table 4. When translationally fused as a MTP::Nif fusion, MTP-FAγ51 yielded a cleaved MTP::Nif polypeptide for almost all of the Nif polypeptides, but not all with equal efficiency. NifQ was the least processed, with only a trace of the processed form detected when total protein was analysed by Western blot in one experiment, none in another. The NifF, NifM, NifV, NifX, NifY and NifZ fusion polypeptides were only partially processed when fused to FAγ51, whereas the other Nif fusion polypeptides including NifB, NifE, NifK, NifN, NifS, NifU and NifW were processed efficiently, demonstrating that processing efficiency for different Nifs can vary for the one MTP. The NifD fusion polypeptide was detected at low levels but consistently showed a degradation product (see below). As for relative levels of expression, the genetic construct encoding NifY yielded lower levels of the polypeptide than the others with the exception of NifD. It was thought this was due to lower expression levels of the NifY gene such as lower translation rates compared to the other Nif proteins and/or instability of the polypeptides. Fusing the NifY coding region with a different MTP than FAγ51 is one approach to improving levels of polypeptide accumulation.

A difference was observed for some Nif polypeptides in the amount of the cytoplasmically localized polypeptide (6×His) relative to the mitochondrially-localized polypeptide. In particular, the NifB, NifE, NifH, NifU and NifV polypeptides targeted to the mitochondria accumulated to a greater level than the corresponding polypeptide targeted to the cytoplasm, whereas the level of accumulation of the other Nif polypeptides was approximately equal between the mitochondrial and cytoplasmic forms. The only exception to this trend was NifN, where the cytoplasmically-targeted polypeptide accumulated to a greater level than the mitochondrial counterpart.

Some higher-molecular weight polypeptide bands were also observed in the Western blots from constructs encoding NifE, NifH, NifB, NifU and NifZ (FIG. 1). It was considered that those bands might correspond to dimerization complexes that were resistant to the strong denaturing conditions used in the sample preparation. Previously, similar high-molecular weight bands were observed for various mitochondrially-targeted Nif proteins using a different MTP (Allen et al., 2017).

A Western blot comparing pRA10 and SN18 is shown in FIG. 2, as well as constructs encoding NifH, NifM, NifS and NifU. The samples for FIG. 2 included proteins extracted from paired infiltrations either with or without co-infiltration of pRA25 which encodes a MTP-FAγ77::NifK fusion polypeptide (WO2018/141030), in order to test whether addition of NifK would affect expression and/or MPP-processing. No differences were observed by adding NifK for expression and processing of NifH, NifM, NifS and NifU.

It was concluded from these experiments that the MTP-FAγ51 amino acid sequence was capable of targeting all of the Nif polypeptides to the mitochondrial matrix in plant cells and provided for processing by MPP, with the exception of processing of the NifQ polypeptide. The polypeptide expression levels and processing efficiencies were as good as for the longer FAγ MTP. Additionally, in some cases fewer polypeptide bands of smaller sizes, thought to indicate degradation products, were detected with the HA antibody in the blots, for example for pRA34. The inventors concluded that the shorter MTP sequence could unexpectedly reduce MTP::Nif degradation.

Alternative MTPs

A range of different MTP sequences were tested to assess their performance in translocating Nif polypeptides to the mitochondrial matrix of plant cells. Several MTPs of differing lengths (30-70 amino acid residues) were selected. These were predicted to leave different lengths of remaining amino acid residues ("scar sequence" or simply "scar") fused at the N-termini of the Nif polypeptides after cleavage by MPP (Table 5). The scar sequences ranged from 0-36 amino acid residues in length. Using the GoldenGate cloning system, 17 different genetic constructs were assembled using combinations of these MTPs with several Nifs for expression in plant cells, particularly for expressing NifD fusion polypeptides since NifD was the most difficult of the Nif polypeptides to express (WO2018/141030). The promoters, 5' and 3'UTRs and terminators were identical for these constructs.

*A. tumefaciens* cultures containing these constructs, each mixed with the construct producing P19 silencing suppressor protein, were individually introduced into *N. benthamiana* leaves as described in Example 1 and protein extracts produced 5 days post-infiltration. SDS-PAGE and Western blot analyses were carried out on the protein extracts. For infiltrations with the MTP::NifD construct, SN46 (pSu9::NifK) was co-infiltrated, since co-expression of NifK without a C-terminal extension had been shown to enhance NifD abundance (WO2018/141030).

Two versions were tested of the CPN60 MTP fused to NifD. In one version, the MTP was fused such that a Gly-Gly linker was placed between the CPN60 MTP (SEQ ID NO:28) and NifD (SN11). In each case where present, the Gly-Gly linker was inserted by the GoldenGate cloning procedure but could be considered to be part of the MTP sequence. In the other version (SN4), the CPN60 MTP (SEQ ID NO:29) was fused directly to the first methionine of NifD polypeptide. As CPN60 was predicted to be cleaved immediately after the C-terminal tyrosine in its amino acid sequence, this construct would theoretically produce NifD polypeptide with a wild-type N-terminus, i.e. no "scar", whereas the SN11 construct was predicted to leave a Gly-Gly extension after cleavage of the MTP(GlyGly)::NifD fusion. Surprisingly, these very similar constructs produced differing outcomes as evidenced by Western blot analysis:

SN11 yielded a polypeptide band at the size expected for unprocessed CPN60(GlyGly)::NifD, whereas SN4 yielded bands corresponding to both processed and unprocessed polypeptides, with more unprocessed polypeptide present than processed polypeptide. Furthermore, when protein from the infiltrations with SN4 was compared by Western blot to protein extracted from a parallel pRA24+pSN46 (FAγ77+GAP::NifD::HA+Su9::NifK) infiltration, it was apparent that the SN4 construct produced considerably less correctly processed polypeptide than the pRA24 construct. Therefore, it appeared that, although the CPN60 MTP was able to target the fusion polypeptide and allowed for matrix processing to produce a wild-type NifD polypeptide, the expression level and processing efficiency was low (US2016/0304842). For SN11, the Gly-Gly linkage between CPN60 and NifD may have prevented processing of the MTP.

Several MTPs derived from superoxide dismutase (SOD) polypeptides were also tested, either as single or tandem MTPs, and either with or without the inclusion of Ile and Gln at the C terminus prior to the Gly-Gly linkage. Polypeptides were not detected by Western blot analysis for the versions containing the SOD MTP (SN15, SEQ ID NO:32 and SN16, SEQ ID NO:33) that did not contain the Ile and Gln residues, whereas the versions having SOD MTP that retained the Ile and Gln residues (SN12, SEQ ID NO:30 and SN13, SEQ ID NO:31) did produce detectable polypeptides, although it appeared that they were not processed by the MPP. In contrast, another MTP tested, L29 (SN17, SEQ ID NO:34), yielded strong polypeptide signals when fused to NifD. Due to the small difference in size between processed and unprocessed forms with this MTP, additional experiments will be required to determine processing efficiency. It is expected that the L29 MTP yielded cleaved Nif polypeptide in an efficient manner. The inventors also tested a CoxIV MTP with a twin strep tag (Burén et al., 2017) fused at the C terminus of the MTP, but upstream of the Gly-Gly linkage (SN19, SEQ ID NO:37). This MTP when fused to NifD also gave strong signals by Western blot analysis, of a size consistent with mitochondrial matrix processing.

TABLE 4

Summary of level of MPP processing of MTP::Nif polypeptides, solubility within plant mitochondria and functionality of scar9-Nif in a bacterial assay. Yes (p) indicates partial (less than 50%) MPP-processing. Solubility scores for processed Nifs are: –, Insoluble or slightly soluble; +, partially soluble, ++ mostly or fully soluble. Nt: not tested. Functional testing was in *E. coli* JM109 using MIT2.1 vector system.

| Construct ID | Nif | MTP | SEQ ID NO of fusion polypeptide | MTP Processed | Solubility in MM | % Function in JM109 |
|---|---|---|---|---|---|---|
| SN192 | B | FAγ51 | 147 | Yes | – | 100 |
| SN10 | D | FAγ51 | 122 | Yes (p) | – | 50 |
| SN38 | E | FAγ51 | 126 | Yes | – | 30 |
| SN138 | F | FAγ51 | 137 | Yes (p) | ++ | 100 |
| SN18/SN27 | H | FAγ51 | 25 | Yes | – | 100 |
| SN42 | H | CoxIV-twin strep | 128 | Yes | – | Nt |
| SN139 | J | FAγ51 | 138 | Yes | – | 200 |
| SN140 | K | FAγ51 | 139 | Yes | – | 70 |
| SN30 | M | FAγ51 | 123 | Yes (p) | ++ | 10 |
| SN39 | N | FAγ51 | 127 | Yes | + | 50 |
| SN141 | Q | FAγ51 | 140 | trace | + | 100 |
| SN31 | S | FAγ51 | 124 | Yes | + | 50 |
| SN32 | U | FAγ51 | 125 | Yes | ++ | 80 |
| SN142 | V | FAγ51 | 141 | Yes | – | 90 |
| SN51 | V | L29 | 130 | Yes (p) | – | Nt |
| SN104 | W | Su9 | 135 | Yes | ++ | Nt |
| SN143 | W | FAγ51 | 142 | Yes | + | 85 |
| SN144 | X | FAγ51 | 143 | Yes (p) | + | Nt |
| SN145 | Y | FAγ51 | 144 | Yes (p) | + | 60 |
| SN146 | Z | FAγ51 | 145 | Yes (p) | + | 60 |

TABLE 5

Details of MTPs used for testing in plants using the GoldenGate system. kDa F/P: full length size of unprocessed MTP/processed size of MTP in kDa. Scar = predicted amino acid sequence of the remaining N-terminal extension after MPP processing.

| MTP Name | MTP | kDa F/P | Scar |
|---|---|---|---|
| gATPase gamma subunit (FAγ51); (Huang et al., 2009) | MAMAVFRREGRRLLPSIAARPI AAIRSPLSSDQEEGLLGVRSIST QVVRNR**GG** (SEQ ID NO: 36) | 5.75/ 1.19 | ISTQVVRNRGG (SEQ ID NO: 42) |
| CPN60 (At2G33040) (Prasad and Stewart, 1992) | MYRFASNLASKARIAQNARQV SSRMSWSRNY**GG** (SEQ ID NO: 28) | 3.77/ 0.13 | GG |
| CPN60/No GG linker (At2G33040); (Prasad and Stewart, 1992) | MYRFASNLASKARIAQNARQV SSRMSWSRNY (SEQ ID NO: 29) | 3.65/ 0 | none |
| Superoxide dismutase (SOD) (At3G10920) (Huang et al., 2009) | MAIRCVASRKTLAGLKETSSRL LRIRGIQ**GG** (SEQ ID NO: 30) | 3.34/ 0.37 | IQGG (SEQ ID NO: 39) |

TABLE 5-continued

Details of MTPs used for testing in plants using the GoldenGate system. kDa F/P: full length size of unprocessed MTP/processed size of MTP in kDa. Scar = predicted amino acid sequence of the remaining N-terminal extension after MPP processing.

| MTP Name | MTP | kDa F/P | Scar |
|---|---|---|---|
| Superoxide dismutase doubled (2SOD) (At3G10920); (Huang et al., 2009) | MAIRCVASRKTLAGLKETSSRL LRIRGIQMAIRCVASRKTLAGL KETSSRLLRIRGIQ**GG** (SEQ ID NO: 31) | 6.65/ 0.37 | IQGG (SEQ ID NO: 39) |
| Superoxide dismutase modified (SODmod) (At3g10920); (Marques et al., 2014) | MAIRCVASRKTLAGLKETSSRL LRIRG**GG** (SEQ ID NO: 32) | 3.1/ 0.13 | GG |
| Superoxide dismutase modified (2SODmod) doubled (At3g10920) (Marques et al., 2014) | MAIRCVASRKTLAGLKETSSRL LRIRGMAIRCVASRKTLAGLKE TSSRLLRIRG**GG** (SEQ ID NO: 33) | 6.07/ 0.13 | GG |
| L29 (At1G07830) (Huang et al., 2009) | MFLTRFVGRRFLAAASARSEST TAAAAASTIR**GG** (SEQ ID NO: 34) | 3.5/ 1.36 | ESTTAAAAASTIRGG (SEQ ID NO: 40) |
| *Neurospora crassa* F0 ATPase subunit 9 MTP (SU9); (Buren et al., 2017) | MASTRVLASRLASQMAASAKV ARPAVRVAQVSKRTIQTGSPLQ TLKRTQMTSIVNATTRQAFQK RAYS**GG** (SEQ ID NO: 35) | 7.5/ 0.38 | YSGG (SEQ ID NO: 41) |
| CoxIV twin strep (ABM97483) (Burén et al., 2017) | MLSLRQSIRFFKPATRTLCSSRY LLQQKPSAWSHPQFEKGGGSG GGSGGSAWSHPQFEK**GG** (SEQ ID NO: 37) | 6.61/ 3.64 | QQKPSAWSHPQFEKGG GSGGGSGGSAWSHPQFE KGG (SEQ ID NO: 43) |
| CoxIV 10xHis (ABM97483) (unpublished) | MLSLRQSIRFFKPATRTLCSSRY LLQQKPGGHHHHHHHHHH**GG** (SEQ ID NO: 38) | 5.07/ 1.84 | QQKPGGHHHHHHHHHH GG (SEQ ID NO: 44) |

Example 3. Solubility of Nif Fusion Polypeptides in Plant Mitochondria

Solubility of nitrogenase protein components in the mitochondrial matrix is considered to be a prerequisite for functional reconstitution of nitrogenase in the mitochondria of plant cells. Although Nif polypeptides such as NifD are soluble in nitrogen fixing bacteria, it was not known if expression of synthetic MTP::NifD fusion polypeptides in plant cells would provide soluble polypeptides that could associate with the other Nif components, particularly in the mitochondrial matrix. Insolubility could be a consequence of many factors, including formation of aggregates and association with cell membranes, and would likely prevent function.

The inventors therefore evaluated the MTP-FAγ51::Nif::HA polypeptides and several others for solubility after expression of the genetic constructs (see Table 4) in *N. benthamiana* leaf cells. Protein extracts for the soluble and insoluble fractions were prepared as described in Example 1 as well as the unfractionated "total protein" samples which included both the soluble and insoluble proteins. The buffer for the preparation of the soluble fraction contained the non-ionic detergent Tween® 20 which was added to lyse membranes and release mitochondrial matrix proteins. That mild non-ionic detergent was considered unlikely to denature Nif polypeptides. In contrast, the proteins of the insoluble fraction were solubilised prior to gel electrophoresis with a buffer containing a relatively high concentration of SDS, a strong anionic detergent that is known to denature proteins efficiently, and treatment with high temperature. The samples were then subjected to gel electrophoresis and Western blotting using anti-HA antibody to detect the polypeptides on the blots.

Several observations were made to test whether the method properly distinguished soluble and insoluble proteins. Coomassie staining of the remaining polypeptides on the gels post-transfer showed that Rubisco was present in the soluble fraction, as expected. Only trace amounts of Rubisco were found in the insoluble fraction. Western blots were also analysed with an isocitrate dehydrogenase (IDH) antibody. IDH is an oxidoreductase that participates in the citric acid cycle and is known to be located in the mitochondrial matrix and soluble. The Western blots showed the presence of IDH in the soluble fraction, indicating that mitochondria were successfully lysed and mitochondrial matrix proteins expected to be soluble were indeed present in the soluble fraction. These observations indicated that soluble proteins were successfully extracted and fractionated into the soluble sample by the methods used.

The method was then applied to the Nif fusion polypeptides; a representative Western blot is shown in FIG. 3 and the results are summarised in Table 4. The abundance of MPP-processed Nif polypeptides in the soluble fraction varied for the different pFAγ51::Nif::HA. The following MPP-processed polypeptides from the MTP-FAγ51::Nif::HA fusion polypeptide translation products appeared to be soluble or mostly soluble in the mitochondria: NifF, NifM and NifU. For the other fusion polypeptides, NifN, NifQ, NifS, NifW, NifY and NifZ were partly soluble/partly insoluble. The following appeared to be insoluble or only slightly soluble: NifB, NifD, NifE, NifH, NifJ, NifK (with a HA epitope tag N-terminal of the NifK sequence), NifV and NifX Notably, pFAγ51::NifQ::HA produced a faint band approximately the size of the correctly processed form in the soluble fraction, which was not detectable in the total protein lane. Of particular importance, each of the MTP-FAγ51::NifD::HA (from SN10), MTP-FAγ51::NifE::HA (from SN38) and MTP-FAγ51::HA::NifK (from SN140) polypeptides, when expressed on their own as a single polypeptide, were essentially insoluble—almost no mitochondrial-soluble forms of these polypeptides were detected even though considerable amounts of the polypeptides accumulated in the *N. benthamiana* leaf cells. For the NifH fusion polypeptides, MTP-FAγ77::NifH (from SN150) when expressed on its own as a single polypeptide was essentially insoluble, whereas only a small amount of MTP-CoxIV::twin strep::NifH (from SN42) when expressed on its own as a single polypeptide was soluble. Moreover, the MTP-FAγ51::NifD (from SN10) polypeptide, when co-expressed with the MTP-Su9::NifK polypeptide from SN46, was likewise essentially insoluble. It was concluded that each of these four, essential polypeptides for nitrogenase function were problematic in terms of solubility when expressed for import into the mitochondrial matrix.

To assess if atmospheric oxygen affected Nif protein solubility, the same 16 pFAγ51::Nif::HA proteins were isolated from infiltrated plants under anaerobic conditions as described in Example 1 and subjected to Western blot analysis as before. It was observed that anaerobic conditions during protein extraction did not significantly change the solubility of the Nif fusion polypeptides. It was concluded that the observed insolubility of some of the Nif polypeptides was not due to exposure to oxygen, even though many of the Nif polypeptides are oxygen sensitive.

Further Western blot analyses showed the following: The MTP-FAγ51::NifB::HA polypeptide (produced from SN192) was insoluble, with no band detected in the soluble fraction. NifB is also essential to nitrogenase function. The MTP-FAγ51::NifF::HA polypeptide (SN138) was almost entirely soluble for both the polypeptides before and after MPP-processing—two bands showed on the blots which were presumed to represent MPP-processed and unprocessed forms. The MTP-FAγ51::NifJ:HA polypeptide (SN139) was essentially insoluble, with only a very faint band detected in the soluble fraction. The MTP-FAγ51::NifM::HA polypeptide (SN30) was mostly soluble after MPP-processing. For MTP-FAγ51::NifS::HA (SN31), two bands were observed on the blots which were presumed to represent MPP-processed and unprocessed polypeptides. Both were partially soluble. The MTP-FAγ51::NifV::HA polypeptide (SN142) was essentially insoluble, with only a very faint band detected in the soluble fraction. The MTP-FAγ51::NifX::HA (SN144) polypeptide was partially soluble after MPP-processing. The MTP-FAγ51::NifY::HA polypeptide (SN145) was mostly soluble, although expressed only at a low level in this experiment. The MTP-FAγ51::NifZ::HA polypeptide (SN146) was partly in the soluble fraction, partly insoluble. In this experiment, both Rubisco and IDH were present in the "total protein" and the soluble fractions and essentially absent from the insoluble fractions, showing that the method used for fractionation was effective and that soluble proteins were indeed extracted.

In an attempt to determine the cause of these solubility problems, genetic constructs encoding versions of the NifD, NifH and NifK fusion polypeptides were made which lacked an N-terminal MTP sequence. These polypeptides were predicted to be located in the cytoplasm of the plant cells, not in the mitochondria. Constructs encoding NifD (SN33), NifH (SN71), NifK (SN72) were made using GoldenGate assembly methods, each polypeptide having only a Gly-Gly linked HA epitope tag fused to the N terminus of the Nif sequence. For example, SN33 encoded a HA:NifD fusion polypeptide without the C-terminal HA epitope tag, so essentially the N-terminal MTP-FAγ51 sequence was replaced with an HA epitope sequence. Each of these three constructs was introduced separately into *N. benthamiana* cells via *A. tumefaciens* and Western blot analysis of the polypeptides carried out on soluble and insoluble protein fractions. The Western blots showed that each of the polypeptides was essentially fully soluble in the plant cells. It was concluded that the solubility problems for the NifD, NifH and NifK fusion polypeptides when fused to the MTP sequence were somehow associated with the targeting of the Nif polypeptides to plant mitochondria.

Example 4. Functional Testing of Nif Fusion Polypeptides after MTP Cleavage

Example 2 described the production of Nif fusion polypeptides in the *N. benthamiana* leaf cells and delivery and processing of the fusion polypeptides in mitochondria. The fusion polypeptides were designed to have in-frame fusions of a MTP added to the N-terminus of the Nif polypeptides and an epitope tag added, sometimes as an N-terminal extension but most often as a C-terminal extension. Although modelling of protein folding and association predicted that most of the N-terminal and C-terminal extensions should not prevent complex formation and nitrogenase function, the inventors wanted to test whether these extensions might affect the function of the fusion polypeptides relative to the native Nif polypeptides. A bacterial system for testing nitrogenase function using derivatives of the pMITv2.1 vector (Smanski et al., 2014; referred to herein as pMIT2.1 or MIT2.1) was established for this. All of the wild-type genes required for nitrogenase activity were contained within the single, bacterial expression vector, pMIT2.1, where expression of the genes was controlled with an inducible promoter/T7-RNA polymerase system from a second plasmid, pN249. When expressed in *E. coli*, the full set of wild-type bacterial Nif polypeptides were produced and together provided a nitrogenase enzyme complex whose activity could be assayed by the production of ethylene from acetylene (acetylene reduction assay, ARA), a de facto measurement for nitrogenase activity.

This system allowed each modified polypeptide to be assayed individually, in *E. coli*, by addition to the otherwise wild-type nitrogenase system. This was done by replacing a Nif gene in pMIT2.1 encoding a wild-type Nif polypeptide with the corresponding, modified Nif gene encoding the Nif fusion polypeptide to be tested. Combinations of modifications to two or more Nif polypeptides could also be tested in this system. However, the pMIT2.1 vector was very large at 22,946 bp, making it unwieldy for incorporating genetic modifications. To make the pMIT2.1 vector system more workable, the MIT2.1 plasmid was first split into two halves by PCR. The first half containing the NifHDKYENJ genes was amplified using primers incorporating SbfI restriction enzyme sites at each end, namely MIT_V2.1_SbfInifH_FW2 5'-AACCTGCAGGTGACGTCTAAGAAAAGGAATAT-TCAGCAAT-3' (SEQ ID NO:45) and MIT_V2.1_SbfInifJ_RV2 5'-AACCTGCAGGGCTAACTAACTAAC-CACGGACAAA AAACC-3' (SEQ ID NO:46), and ligated into recipient vector pCR Blunt II TOPO (Thermo Fisher Scientific), forming a vector herein designated as pTopoH-J. The second half of the Nif gene cluster containing the NifBQFUSVWZM genes was amplified using primers which also incorporated SbfI restriction enzyme sites at each end, namely MIT_V2.1_SbfInifB_FW 5'-AACCTGCAGGTACTCTAACCC-CATCGGCCGTCTTA-3' (SEQ ID NO:47), and MIT_V2.1_SbfIori_RV 5'-AACCTGCAGGTACGTAGCAATCAACT-CACTGGCTC-3' (SEQ ID NO:48). This PCR product was digested with SbfI and self-ligated to form a self-replicating vector, herein designated pB-ori. To reform pMIT2.1 and its derivatives, both pTopoH-J and pB-ori, or a derivative with a modification, were digested with SbfI and the two halves of the Nif gene cluster ligated together.

As described in Example 2, the MTP-FAγ51 amino acid sequence was cleaved in plant mitochondria to leave 9 amino acid residues (FAγ-scar9; SEQ ID NO:22), plus an intervening Gly-Gly linker in the case of the SN constructs, fused to the N-terminus of the Nif polypeptide of the processed Nif fusion polypeptides. In order to test each of the fusion polypeptides for their function in the otherwise wild-type nitrogenase complex, a DNA fragment encoding the 9 amino acids except for substitution of the N-terminal Ile residue with a Met for translation initiation (MSTQVVRNR, SEQ ID NO:49, designated mscar9) was inserted immediately upstream of the translation start codon of each Nif gene in pMIT2.1 using the strategy described above. The exception was NifX since pMIT2.1 does not include NifX and therefore a modified NifX could not be tested in this system. For each construct, the DNA fragment was designed so that, when fused in-frame directly upstream of the start codon of a gene encoding any one of the Nif polypeptides, the chimeric gene would encode a translational fusion to the selected Nif polypeptide. It was expected that the translation initiation Met would be removed post-translationally in *E. coli* because the serine in the second position is known to promote starting Met removal by the enzyme MAP (Hirel 1989, Xiao 2010). If that happened, the resultant N-terminal extension would be of 8 amino acid residues. The removal of the starting Met residue was confirmed by enhanced production ion scanning of the target multiple reaction monitoring ion of the semi-tryptic peptide STQVVR (SEQ ID NO:50) with Q-TRAP liquid chromatography tandem mass spectrometry (see below).

For wild-type bacterial Nif polypeptides where the translation initiating Met residue was removed post-translationally in bacteria, the length of the N-terminal extension of each Nif protein was 9 amino acids with a sequence of STQVVRNRM (SEQ ID NO:51) fused to the remainder of Nif, where the terminal Met was the translation initiation amino acid of the Nif polypeptide.

As an example of the modification of pMIT2.1 and its testing, in this case to introduce a translational fusion of the nine amino acid mscar9 peptide MSTQVVRNR (SEQ ID NO:49) to the N-terminus of the Nif polypeptides, a nucleotide sequence coding for those amino acids was added to the 5' end of a forward primer that hybridised to the 5' end of the coding sequence for each Nif gene. For each Nif gene being modified, a reverse primer was designed adjacent to the 5' end of the particular Nif gene. The amplified PCR product was ligated using ligation cycling reaction (LCR; de Kok et al., 2014), after which the other half of pMIT2.1 that was not modified was religated with the modified half after digestion with SbfI. For example, to introduce a translational fusion of MSTQVVRNR (SEQ ID NO:49) to the N-terminus of NifB, primers 5'-ATGTCAACTCAAGTGGTGCGTAACCG-CATGACCTCTTGTTCGTCGTT-3' (SEQ ID NO:52) and 5'-TTTAGCCCTCCTATGATTGATTTGATGTATTA-CAGAGAGG-3' (SEQ ID NO:53) were used in PCR with pB-ori as template to give a 11,565 bp product. The PCR fragment was ligated by LCR with the bridging oligo 5'-GGTTACGCACCACTTGAGTTGACATTT-TAGCCCTCCTATGATTGATTTGATG-3' (SEQ ID NO:54) using the method of de Kok et al. (2014) and used to transform *E. coli* DH5α. The resulting construct pB-ori_scar9B was digested with SbfI and ligated to the SbfI fragment from pTopoH-J containing the unmodified NifHDKYENJ genes, yielding the modified pMIT2.1 vector encoding a fusion polypeptide having a N-terminal extension added to NifB, herein designated as pSO006. The nucleotide sequences of the resultant modified genetic constructs were confirmed to be correct by sequencing of the modified half, whether the pTopoH-J half or the pB-ori half.

Each genetic construct was introduced into *E. coli* strain JM109 containing pN249 and cultures of cells transformed with both vectors were grown as described in Example 1. As a negative control, pB-ori lacking 7 of the 16 Nif genes was used. An altered pMIT2.1 lacking NifM, designated ΔNifM was included in the experiments (cf. Lei et al., 1999; Howard et al., 1986). The transformed cells were tested for ethylene production in acetylene reduction assays after induction of gene expression with IPTG. The results summarised in Tables 4 and 5 show the percentage function in JM109 calculated as the acetylene reduction activity in *E. coli* JM109 containing the modified pMIT2.1 relative to that seen with JM109 containing the unmodified pMIT2.1. The control, unmodified pMIT2.1, yielded positive ethylene production. These assays showed that the addition of the 9 amino acid extension mscar9 to the N-terminus of NifB slightly increased nitrogenase function when compared to the level of ethylene production seen with the unmodified pMIT2.1.

In analogous manner, the remaining 15 Nifs also tolerated the 9 amino acid extension at their respective N-termini, with full activity for NifH, NifJ, NifQ, and NifF but with some reduction of activity for other Nifs. In a first experiment, the 9 amino acid extensions to the N-termini of NifH, NifD, NifK, NifE and NifN yielded levels of acetylene reduction activity which were 100%, 50%, 70%, 30%, and 50% compared to that of the unmodified pMIT2.1, respectively. The other Nif polypeptides, namely NifJ, NifY, NifQ, NifF, NifU, NifS, NifV, NifW, NifZ and NifM, showed 200%, 60%, 100%, 100%, 80%, 50%, 90%, 30%, 60% and 10% activity, respectively, compared to that of the unmodified pMIT2.1 (Table 4).

The experiment was repeated multiple times and the average date (n=2 to 6) is shown in Table 6. This functional testing of the individual scar9::Nif polypeptides in *E. coli* showed that activity was retained for all 16 Nif fusion polypeptides although there was considerable variation in activity levels for the different Nifs. Notably, scar9::NifJ had three times the activity of the positive control, and scar9::

NifQ, scar9::NifH, scar9::NifB and scar9::NifF were significantly increased in ARA activity relative to the corresponding wild-type Nif polypeptides, but showing about 130-150% activity relative to the unmodified pMIT2.1 and so less than the increase observed with scar9::NifJ. In contrast, scar9::NifM only retained about 10% activity relative to the wild-type NifM.

Given the high activity of scar9-NifJ (pSO028) in the pMIT2.1 system, being 2 to 3-fold more active compared to the unmodified control, the impact of modifying NifJ was further investigated. The entire NifJ region of pMIT2.1 was removed, yielding ΔNifJ-MIT2.1 (pSO014). Acetylene reduction assays with pSO014 found that its activity was similar to pMIT2.1, indicating that NifJ was redundant in the ARA assay system in JM109. Therefore, the increased activity with scar9-NifJ (pSO028) in the pMIT2.1 system may have been due to a gene dosage effect.

From the experiments described in Examples 2-4, the inventors concluded that the abundance, MPP processing and solubility of the 16 different MTP::Nif polypeptides varied, despite the use of the same MTP and promoter for each expression construct. However, all of the Nif fusion polypeptides functioned to some extent for nitrogenase activity in *E. coli* when the other Nif proteins were expressed as the wild-type polypeptides, indeed some with increased activity. The observed variation indicated that each Nif polypeptide had intrinsic features that influenced the amount of polypeptide that accumulated, its transport and processing by MPP. The critical components NifH and NifK were readily expressed and detected; these proteins are known to be needed at high levels for nitrogenase activity. However, they were insoluble in the leaf experiments, along with NifB, NifD, NifE, NifJ and NifV. With the exception of NifD, the NifY fusion polypeptide was expressed at the lowest level of the Nif polypeptides in these experiments. Some of the Nif polypeptides were successfully cleaved by MPP within the matrix and accumulated to higher levels relative to their cytoplasmic counterparts, suggesting that mitochondrial localization was a way of stabilizing the fusion polypeptides after cleavage by MPP. The MTP::NifQ fusion polypeptide was poorly cleaved, perhaps because the NifQ preprotein was less able to enter the mitochondrial matrix due to resistance to unfolding or mistargeting.

In these experiments, the fusion polypeptide having NifH from *K. oxytoca* was insoluble in the plant mitochondrial matrix. As NifM may be required for stability and solubility of NifH in bacteria (Lei et al., 1999; Howard et al., 1986) a later experiment tested a combination of mitochondrially targeted NifH and NifM in transient leaf assays.

The fusion polypeptide having *K. oxytoca* NifB was insoluble when mitochondrially localized, consistent with the results described for *A. vinelandii* NifB when targeted to yeast and plant mitochondria (Burén et al 2017a).

Considering these data together, the inventors concluded that 7 of the Nif fusion polypeptides were expressed at good levels, were processed efficiently and were localized to the mitochondrial matrix in predominantly soluble form, namely NifF, NifN, NifS, NifU, NifW, NifY and NifZ, although the abundance of NifY was relatively low. These N-terminal fusion polypeptides, after cleavage by MPP, retained reasonable levels of activity (Table 6).

TABLE 6

Effect of pFAγ51 nine amino acid ‘scar’ (scar9) peptide translationally fused to individual Nif proteins on nitrogenase function in *E. coli*. Values are presented as % acetylene reduction activity compared to pMIT2.1. pB-ori, negative control; ΔNifM, NifM coding sequence removed from pMIT2.1.

| Construct ID | Nitrogenase activity (% of pMIT2.1) | Standard Deviation |
|---|---|---|
| pMIT2.1 (wild-type) | 100 | 18 |
| scar9::NifJ | 309 | 86 |
| scar9::NifQ | 158 | 22 |
| scar9::NifH | 148 | 15 |
| scar9::NifB | 144 | 34 |
| scar9::NifF | 131 | 8 |
| scar9::NifD | 110 | 9 |
| scar9::NifW | 95 | 8 |
| scar9::NifV | 81 | 11 |
| scar9::NifU | 80 | 4 |
| scar9::NifY | 65 | 4 |
| scar9::NifK | 60 | 10 |
| scar9::NifN | 46 | 9 |
| scar9::NifE | 42 | 1 |
| scar9::NifS | 41 | 1 |
| scar9::NifZ | 37 | 18 |
| scar9::NifM | 9 | 1 |
| ΔnifM | 6 | 4 |
| pB-ori (ΔNifHDKENJ) | 0 | 0 |

Example 5. Detection of Scar9-Nif Fusion Polypeptides

To detect specific fusion polypeptides expressed in the bacterial system, liquid chromatography-mass spectrometry (LC-MS) methods were adopted. The method combined the physical separation capabilities of liquid chromatography with the mass analysis capabilities of mass spectrometry (MS) to detect specific peptides produced by digestion of protein extracts with trypsin.

*E. coli* strain JM109 separately containing each of the modified pMIT2.1 vectors together with pN249 were cultured and proteins extracted as described in Example 1. Protein samples were stored at −20° C. prior to reduction, alkylation and tryptic digestion. Protein samples were reduced, alkylated and treated with trypsin using a filter-assisted sample preparation (FASP) protocol as described in Example 1, and analysed by LC-MS as described in Example 1. The samples that were tested are listed in Table 7. Each genetic construct for samples 5-19 encoded one modified Nif polypeptide with the other 15 Nif polypeptides being wild-type as for *K. oxytoca*. Samples 1-4 did not have any polypeptides including the scar9.

TABLE 7

Genetic constructs used for fusion polypeptide detection by LC-MS

| Sample ID | Genetic construct in JM109 | Modified Nif description | Scar9 peptide detected? |
|---|---|---|---|
| 1 | pMIT2.1 | positive control | |
| 2 | pB-ori | negative control | |
| 3 | pSO014 | ΔNifJ | |
| 4 | pSO051 | ΔNifM | |
| 5 | pSO006 | FAγ-Scar9-NifB | Yes |
| 6 | pSO026 | FAγ-Scar9-NifE | Yes |
| 7 | pSO028 | FAγ-Scar9-NifJ | Yes |
| 8 | pSO032 | FAγ-Scar9-NifF | Yes |
| 9 | pSO012 | FAγ-Scar9-NifH | Yes |
| 10 | pSO029 | FAγ-Scar9-NifK | Yes |
| 11 | pSO038 | FAγ-Scar9-NifM | Yes |
| 12 | pSO027 | FAγ-Scar9-NifN | Yes |

TABLE 7-continued

Genetic constructs used for fusion polypeptide detection by LC-MS

| Sample ID | Genetic construct in JM109 | Modified Nif description | Scar9 peptide detected? |
|---|---|---|---|
| 13 | pSO031 | FAγ-Scar9-NifQ | Yes |
| 14 | pSO034 | FAγ-Scar9-NifS | Yes |
| 15 | pSO033 | FAγ-Scar9-NifU | Yes |
| 16 | pSO035 | FAγ-Scar9-NifV | nd |
| 17 | pSO036 | FAγ-Scar9-NifW | Yes |
| 18 | pSO030 | FAγ-Scar9-NifY | Yes |
| 19 | pSO037 | FAγ-Scar9-NifZ | Yes |

nd: not done

Initially, 4 samples were assessed for trypsin digestion efficiency. Samples 5 (NifB) and 6 (NifE) were digested with trypsin for two incubation times, 30 min and overnight (16-18 h). From each sample, 4 μL of the tryptic peptides were injected on the 6600 Triple TOF Mass Spectrometer using an Eksigent microLC (85 min). Data were processed using ProteinPilot against the species-specific UniProt Knowledgebase (UniProtKB) databases appended with the custom and contaminant databases: Uniprot-Swiss Prot *E. coli*+Custom database (Mit2Nif)+ Common Repository of Adventitious Proteins; Mit2Nif+Mit2.1 Nif-Scar. These databases included all of the predicted peptides produced by digestion of the Nif proteins with trypsin. The protein samples 5 and 6 from the constructs encoding FAγ-Scar9-NifB and FAγ-Scar9-NifE were expected to contain 16 Nif proteins, 15 of them being wild-type and the sixteenth having the scar9 on NifB and NifE, respectively.

The shorter duration trypsin digest of 30 min yielded more protein/peptide identifications than the longer digest. The full panel of *E. coli* samples (#1-19) were then digested with trypsin for 1 h rather than the overnight digestion.

The peptide identifications for the N-terminal scar9 sequence were investigated. Limited IDA (6600TF LC-MS/MS) evidence was found for the fully cleaved MSTQVVR (SEQ ID NO:55) and the semi-tryptic MSTQVVRNR (SEQ ID NO:49) peptides, with low peptide identification confidence. Peptides having either an unmodified or oxidised methionine residue were also assessed using MRM. However, these peptides could not be confirmed in the test samples using either discovery 6600TF LC-MS/MS and ProteinPilot database searches or targeted MRM 6500 QTRAP LC-MS/MS.

The possibility was considered that the translation initiating methionine might have been cleaved off post-translationally in the bacteria, as an explanation for the low peptide identification confidence. When recombinant proteins are expressed in bacterial expression systems, it is thought that the initiating methionine is often cleaved off by methionine aminopeptidase (MAP) with an efficiency based on the size of the residue adjacent to the N-methionine (Hirel 1989, Xiao 2010). When the residue at position 2 was a Ser residue, as was the case for the FAγ-scar9-Nif polypeptides, it was estimated that the N-terminal Met was often cleaved off (84% efficiency).

Therefore, additional modified peptides were assessed from the Nif fusion polypeptides: STQVVR (+1, +2) (SEQ ID NO:50) and the semi-tryptic peptide STQVVRNR (+2, +3) (SEQ ID NO:56). The peptide STQVVR (SEQ ID NO:50) was short and had not been identified in the previous analyses, probably for three reasons. Firstly, it had a mass (688 Da) that would yield an m/z value (345.2, +2) lower than set in the standard LC-MS parameters (m/z range 350-2000), secondly it had low hydrophobicity and therefore might not have been retained on the column, and thirdly it was too short for database search algorithms to confidently match the sequence. Initially, samples #1-19 (Table 7) were pooled and run on the 6600TF LC-MS/MS under different conditions e.g. lowering the mass range from m/z 350 to 300 and expanding the monitored charge states to include +1 rather than only +2 to +5, and by defining inclusion lists which encapsulated the predicted target masses. None of these changes yielded a positive identification of STQVVR (SEQ ID NO:50) in either the spectral data or the database searches.

The tryptic peptide STQVVR (SEQ ID NO:50) and semi-tryptic peptide STQVVRNR (SEQ ID NO:56) were then assessed using Multiple Reaction Monitoring (MRM) on the 6500 QTRAP using 4 transitions with 2 charge states. This yielded a peak for STQVVR (SEQ ID NO:50) that was investigated by Enhanced Production Ion (EPI) scanning to acquire full scan MS/MS spectra for the target MRM. This confirmed the presence of the modified truncated N-terminal peptide lacking the N-terminal Met. Encouragingly, it was concluded that the specific FAγ-Scar9-Nif polypeptides could be detected by this method from complex protein mixtures.

The method was then used to compare the expression level of each of the different FAγ-Scar9-Nif polypeptides when expressed from the modified pMIT2.1 vectors in *E. coli*. A comprehensive MRM method with 230 transitions was developed to assess the samples from JM109 (Table 7). This included high responding peptides (4 transitions/peptide) identified for the following Nif proteins: B, D, E, F, H, K, M, N, Q, S, U, W, Y and Z. Control peptides from the FAγ-Scar9 and the chloramphenicol acetyltransferase protein (CAT) were also included. The amount of a peptide specific to CAT in each sample was measured in order to standardize Nif levels between the different constructs, as described in Example 1. Care was taken to use equal total protein amounts in each of the samples. The amount of the CAT-specific peptide detected was similar across all experimental samples, indicating that the amount of Nif polypeptides generated in different samples from the pN249/pMIT2.1 assay system could properly be compared. The amount of peptide STQVVR (SEQ ID NO:50) derived from FAγ-Scar9 was observed to be highest in samples 9 (FAγ-Scar9-NifH) and 11 (FAγ-Scar9-NifM), both of which were strongly expressed relative to the others, followed by samples 10 (FAγ-Scar9-NifK), 14 (FAγ-Scar9-NifS) and 15 (FAγ-Scar9-NifU). Lower amounts were detected in the other samples 5-19 with the possible exception of NifV. There was no STQVVR (SEQ ID NO:50) peptide present in the negative control samples 1-4, as expected for the absence of the MTP-FAγ-scar9 sequence.

The amount of the scar9::NifD, scar9::NifK, scar9::NifH, scar9::NifS and scar9::NifM polypeptides in the *E. coli* cells was measured using targeted multiple reaction monitoring mass spectrometry (MRM-MS) as described in Example 1. The measurements showed that the amount of specific peptides for the NifS fusion polypeptide were about the same across all of the samples. In contrast, the greatest difference was found for scar9::NifM, where the amount of the NifM fusion polypeptide was about 50-fold increased relative to the samples where the wild-type NifM was expressed. In similar manner but to a lesser extent, the scar9 peptide fused to NifH resulted in a 2-3 fold increase in NifH abundance compared to the amount of wild-type NifH in the other strains. In the control samples in which the NifM gene was deleted (ΔNifM), peptides specific to NifM were not detected, as expected. Likewise, peptides specific for NifD, NifK and NifH were not detected in samples from *E. coli* containing pB-ori where these genes were not present. These analyses also showed that the abundance of NifD and NifK was reasonably consistent across all the samples, with the notable exception that in the presence of scar9::NifY, the amounts of NifD and NifK were reduced to about 30% of the levels found in the strains having the wild-type NifY. This reduction in NifD and NifK levels was confirmed by Western blot analysis of extracts from the *E. coli* cells, using antibodies that bound to wild-type NifD or NifK polypeptides. The inventors concluded that the addition of the scar9 motif to the N-terminus of Nif polypeptides, representing the product of the MPP-mediated cleavage of the MTP-FAγ51 fusions, when expressed in *E. coli* could influence the level of accumulation of the polypeptides, while preserving at least some activity for nitrogenase function.

In these analyses, the NifH-specific peptides were increased about 2-3-fold relative to control cells when, and only when, scar9-NifH was produced in the cells. In contrast, NifS and NifE were examples of polypeptides that accumulated consistently across all pMIT2.1-derived vectors, where the level of 2 NifS-specific peptides, or 2 NifE-specific peptides, and the scar9 extension peptide fused to CAT only varied by approximately 20% across all samples. These results indicated that the N-terminal alterations to the NifH and NifM polypeptides significantly increased the abundance of these two proteins relative to all other Nif proteins and CAT.

These results and those summarised in Table 4 provided some insight to the performance of scar9-extensions on NifH, NifM and NifE in nitrogenase function as measured by the ARA. Although the scar9-NifH polypeptide abundance was increased about 2-3-fold in the bacteria containing pSO012, the scar9-NifH provided 110% activity in the ARA assay relative to the wild-type control. On the other hand, the scar9-NifM accumulated much more relative to the wild-type control, but the ARA assay yielded only approximately 10% activity relative to the control. This result suggested that these high levels of scar9-NifM polypeptide might have been acting as a negative regulator to ARA function.

The LC-MS method was also used to detect specific fusion polypeptides in plant cells (Example 12), showing its general applicability.

Example 6. Expression of *K. oxytoca* MTP-NifD in Plant and Yeast Cells Results in Production of a Secondary Cleavage Product A previous report from the inventors had shown that of all the 16 Nif polypeptides, the most difficult to produce in plant cells was NifD (Allen et al., 2017). They also reported that when a MTP-FAγ::NifD::HA fusion polypeptide, having a wild-type *K. oxytoca* NifD amino acid sequence, was produced in *N. benthamiana* cells, additional bands of lower molecular weight showed on the Western blots. The additional bands included an intense band of ~48 kDa. These additional bands were suggested to correspond to degradation products of the NifD fusion polypeptide, the result of a secondary cleavage at a cryptic protease site, or possibly the product of alternative transcription or translation initiation signals.

Effect of Changing Promoters and MTP Sequences

To confirm these observations and to test whether the additional bands were due to the combination of certain promoters or MTP sequences with the NifD sequence, a series of genetic modifications were made to the construct SN10. The starting construct SN10 encoded a MTP-FAγ51::NifD::HA fusion polypeptide (SEQ ID NO:122) where the NifD amino acid sequence was as set forth in SEQ ID NO:18, expressed from the enhanced e35S promoter and using codon optimisation for *N. benthamiana*. In some of the modifications, the e35S promoter of SN10 was substituted with a different promoter, for example with the S4, S4v2 or S7 promoters of Subterranean Clover Stunt Virus (SCSV). In others, the MTP-FAγ51 was substituted with another MTP, for example MTP-L29 (SEQ ID NO:34) or MTP-CPN60 (SEQ ID NO:28). The constructs used in this experiment are listed in Table 8 and included some of those described in Example 2. These constructs were made via the GoldenGate cloning system (Weber et al., 2011) with specific components as described by Engler (2014). Some of the chimeric genes are shown schematically in FIG. 4 (upper panel).

These constructs in *A. tumefaciens* were infiltrated into *N. benthamiana* leaf cells as described in Example 1 and protein extracts were analysed by Western blotting using HA-antibody. For each of the constructs, paired infiltrations were carried out either in the absence of the construct pRA25 or in the presence of pRA25 (encoding the MTP-FAγ::NifK fusion polypeptide; SEQ ID NO:57), since co-expression of NifK without a C-terminal extension had been shown to enhance NifD abundance (WO2018/141030). Representative Western blots are shown in FIGS. 4 and 5. It was observed that both the MPP-processed and unprocessed forms of the fusion polypeptide were produced for each construct, as was the ~48 kDa polypeptide. In every case where pRA25 was present (FIG. 4, lower panel), the intensity of the ~48 kDa band was greater than the intensity of the processed MTP::NifD polypeptide (band 2). This was also observed for all of the variants using a different MTP sequence; the 48 kDa polypeptide was the most intense of the polypeptide bands on the Western blots, irrespective of the MTP sequence used (FIG. 5). It was also observed that, once again, the presence of the MTP-NifK expression construct often increased the amount of all NifD polypeptides, including the dominant band at approximately 48 kDa.

A different construct encoding a NifK fusion polypeptide, SN46, was made. This construct had the enhanced e35S promoter and a 5'-UTR including the TMV omega fragment to maximise translation efficiency, a 35S polyadenylation/transcription termination sequence, and encoded a MTP-Su9::NifK polypeptide having the wild-type C-terminus (SEQ ID NO:58). The coding region used codon optimisation for *N. benthamiana* rather than the human codon optimisation in pRA25. The SN46 construct was compared to pRA25 for effectiveness in increasing NifD fusion polypeptide accumulation after co-infiltration with a NifD construct. It was observed that SN46 was at least as effective as pRA25 in enhancing NifD fusion polypeptide accumulation, but also resulted in accumulation of the ~48 kDa polypeptide product. A representative Western blot is shown in FIG. 6.

Since the ~48 kDa polypeptide was detected using the HA-antibody, it corresponded to the C-terminal product of a protease cleavage of the translated fusion polypeptide. These results indicated that the ~48 kDa C-terminal polypeptide was produced in plant cells from the wild-type *K. oxytoca* NifD fusion polypeptide irrespective of the promoter or MTP sequence used for its expression. The ~48 kDa polypeptide is referred to herein as the NifD "secondary cleavage product" or as the NifD "degradation product".

TABLE 8

Genetic constructs for testing production and processing of MTP-NifD fusion polypeptides in plant cells. Each construct encoded a fusion polypeptide including an MTP as listed fused to the N-terminus of the wild-type *K. oxytoca* NifD sequence.

| Construct ID | Promoter | MTP | SEQ ID NO of MTP |
|---|---|---|---|
| SN4 | e35S | CPN60 No GG linker | SEQ ID NO: 29 |
| SN6 | SCSV-S4 | FAγ51 | SEQ ID NO: 21 |
| SN7 | SCSV-S4v2 | FAγ51 | SEQ ID NO: 21 |
| SN8 | SCSV-S7 | FAγ51 | SEQ ID NO: 21 |
| SN9 | 35S | FAγ51 | SEQ ID NO: 21 |
| SN10 | e35S | FAγ51 | SEQ ID NO: 21 |
| SN11 | e35S | CPN60 | SEQ ID NO: 28 |
| SN12 | e35S | SOD | SEQ ID NO: 30 |
| SN13 | e35S | 2SOD | SEQ ID NO: 31 |
| SN14 | e35S | SU9 | SEQ ID NO: 35 |
| SN15 | e35S | SODmod | SEQ ID NO: 32 |
| SN16 | e35S | 2SODmod | SEQ ID NO: 33 |
| SN17 | e35S | L29 | SEQ ID NO: 34 |
| SN19 | e35S | CoxIV twin strep | SEQ ID NO: 37 |

Is the Secondary Cleavage Due to Mitochondrial Targeting?

The inventors aimed to determine the cause of NifD secondary cleavage/degradation, firstly whether it was occurring before or after mitochondrial import. To test this, a NifD construct (SN34) was made which was identical to SN10 except that the MTP-FAγ51 sequence was replaced with a HA epitope tag, so encoding a HA::NifD::HA fusion polypeptide. That polypeptide, lacking a MTP, would not be targeted to mitochondria but instead was expected to be localised in the cytoplasm of the plant cells. Having an HA epitope at both ends of the translation product, any internal protease cleavage was expected to produce a N-terminal product and a C-terminal product that could both be detected with the HA-antibody if they were not further degraded. A second genetic construct was made where the C-terminal HA tag was removed from SN34. That construct (SN33) encoded a HA:NifD fusion polypeptide which was almost identical in size to the MPP-processed MTP-FAγ51::NifD polypeptide, each possessing only one HA epitope tag, and so making the comparison more direct.

After co-infiltration of SN75 and SN46 into *N. benthamiana* and Western blot analysis of protein extracts from the infiltrated leaf cells, it was observed that SN33 and SN34 both produced discrete, strong bands corresponding in size to the full-length fusion polypeptides translated from these constructs. The main polypeptide band for SN34 was slightly larger than the polypeptide band for SN33, understood to be due to the presence of the additional C-terminal HA epitope in SN34. These SN33 and SN34 NifD specific bands were considerably stronger in intensity than the corresponding full-length band produced from cells infiltrated with SN10. Importantly, there was no 48 kDa C-terminal cleavage/degradation product observed after introduction of SN34 and SN33. Similarly, there was no N-terminal cleavage product observed for SN34.

A further construct designated SN66 was made which had a mutated MTP sequence in order to test whether production of the 48 kDa polypeptide required a first cleavage in the MTP sequence by MPP. For this, the MTP-FAγ51 encoded in SN10 was modified with a sequence of identical length that contained a region of 5 consecutive alanine substitutions in the MTP and a second region of 8 substitutions that would render it resistant to mitochondrial processing by MPP. The specific substitutions are shown in FIG. 7. The second alanine scanned region encompassed the recognition and cleavage site for MPP and therefore MPP-processing was predicted be abolished due to these substitutions. It was not known if this fusion polypeptide would be transported to the mitochondria. When this construct was introduced into *N. benthamiana* leaf cells, protein extracts from the cells were observed to contain the 48 kDa product by Western blot analysis.

A second construct designated SN64 was made having a similarly mutated MTP sequence having alanine substitutions compared to the MTP-CPN60 sequence (SEQ ID NO:28). When this construct was tested in *N. benthamiana* leaf cells, the 48 kDa secondary cleavage product was again observed (FIG. 6).

Together these results demonstrated that the secondary cleavage/degradation of the MTP::NifD fusion polypeptides was a consequence of the mitochondrial targeting and was presumed to be caused by a mitochondrial protease. However, the secondary cleavage was not dependent on a prior cleavage of the MTP sequence by MPP in the mitochondria.

Detection of an N-Terminal NifD Cleavage Product Demonstrated that Secondary Cleavage was at a Specific Site by an Endoprotease As the 48 kDa C-terminal cleavage/degradation product was clearly produced in the plant cells after introduction of SN10 and other constructs encoding the MTP::NifD fusion polypeptides, the inventors wanted to see whether a corresponding N-terminal NifD cleavage product could be observed in the plant cells or whether the degradation occurred by exo-protease activity from the N-terminus. Accordingly, another construct (SN75) was made which was identical to SN10 except that a Gly-Gly linked HA tag was also included directly after the MTP-FAγ51 and before the NifD coding region, and SEQ ID NO:36 was used as the MTP-FAγ51. It was predicted that if the fusion polypeptide produced from this construct was cleaved at the same specific location within NifD, two HA-tagged products would be produced—the longer ~48 kDa C-terminal product seen previously in MTP::NifD extracts and a shorter ~13 kDa N-terminal product. However, given that a specific peptidase in mitochondria degrades N-terminal cleaved pre-sequences after MPP cleavage (Kmiec et al, 2013), the inventors did not know whether any N-terminal cleavage/degradation product would be observed.

After infiltration of SN75 into *N. benthamiana* leaves and Western blotting analysis of protein extracts, a shorter N-terminal product of approximately 15 kDa was detected as well as the longer C-terminal product of approximately 48 kDa. Although the sum of the sizes of these two products was slightly greater than the predicted size of the MPP-processed MTP-FAγ51::HA::NifD::HA polypeptide (57.6 kDa), this difference was likely a result of overestimating band sizes relative to the markers which may have been due to the surface charges of the polypeptides affecting the migration rate in the gel electrophoresis. Nevertheless, this result demonstrated that the secondary cleavage of the NifD part of the fusion polypeptide was specific and discrete, occurring at a specific site in the NifD polypeptide, and not a result of sequential degradation from the N-terminus.

Does the Secondary Cleavage/Degradation of Mitochondrially-Targeted NifD Occur in Yeast?

Burén et al. (2017b) reported that targeting an *Azotobacter vinelandii* NifD polypeptide to yeast mitochondria produced a faster migrating ~50 kDa band detectable by NifD antibodies. The present inventors wanted to determine if the plant-optimised *K. oxytoca* NifD sequences also exhibited a similar cleavage when expressed in yeast. For this purpose, a yeast expression vector was made which included the MTP-FAγ51::NifD::HA coding sequence from SN10 with flanking KpnI/SacI restriction sites to allow cloning into the yeast expression vector pYES2. This construct was designated SNY10. As a control for non-mitochondrial localisation, a second yeast NifD construct designated SNY196 was made where the MTP-FAγ51 of SNY10 was replaced with a 6×His epitope tag. This second construct was designed to express a cytoplasmically-localised NifD polypeptide of almost the same size as the processed polypeptides from SN10 or SNY10, thereby enabling visualisation of the expected size on the Western blots. A plant orthologue of SNY196 was also made (SN196) where the GAL1 promoter was replaced with the e35S promoter. This construct was identical to SN10 except the 6×His tag substituted for the MTP-FAγ51 of SN10.

Yeast cells containing either the SNY10 (MTP-FAγ51::NifD::HA) or the SNY196 (6×His::NifD::HA) constructs were grown as described in Example 1 for expression of the genes encoding the fusion polypeptides. Proteins were extracted from the transformed cells after induction of transgene expression and analysed by Western blotting with HA-antibody. The results are shown in FIG. 8. In the lane for SNY10, a less intense band was observed of the size expected (~58 kDa) for a MPP-processed MTP-FAγ51::NifD::HA polypeptide. This polypeptide was of the same size as the plant expressed MTP-FAγ51::NifD::HA polypeptide after MPP processing and the polypeptide from SN196. Importantly, a much more intense polypeptide band at ~48 kDa band was observed from SNY10 which was of the same size as the plant expressed cleavage/degradation product from SN10. That is, most of the yeast expressed MTP-FAγ51::NifD::HA was cleaved in a similar fashion to the cleavage in plant cells, indeed even more efficiently in the yeast cells. The fact that the C-terminal cleavage products from the yeast and plant cells were of the same size indicated that the protease cleavage was occurring at the same site in both yeast and plant cell mitochondria. In contrast, the protein extract from yeast cells containing SNY196 produced a single, discrete band of the expected size for non-mitochondrially targeted NifD. No specific, C-terminal NifD::HA polypeptide band was detected from SNY196 at ~48 kDa that would have indicated non-mitochondrial cleavage at the same site.

Remarkably, no MTP::NifD fusion polypeptide that was not processed by MPP was detected in protein extracts from the yeast cells containing SNY10, in contrast to the observation that in *N. benthamiana* cells producing the same MTP-FAγ51::NifD polypeptide, both unprocessed and MPP-processed forms of the polypeptide were observed. That is, in yeast the MTP sequence was fully processed by MPP. This was thought to reflect differences in processing machinery and efficiencies between the two organisms. It might also have come from the fact that the yeast cells were stably transformed cells in contrast to the plant cells which were only transiently transformed.

Together these results indicated that the wild-type NifD polypeptide from *K. oxytoca*, expressed as an MTP-fusion polypeptide, was cleaved at the same specific site when targeted to yeast or plant mitochondria and that the cleavage was dependent on mitochondrial targeting.

Example 7. Identification of the Secondary Cleavage Site in Wild-Type NifD

The results of the experiments described in Example 6 indicated that the secondary cleavage of the MTP::NifD fusion polypeptide occurred at a specific site within the wild-type NifD sequence and was a consequence of mitochondrial targeting. As the cleavage was considered to be undesirable for several reasons, the inventors wanted to modify the region of NifD in an attempt to prevent the cleavage in plant cells. From the sizes of the N-terminal and C-terminal cleavage products, the cleavage site was thought to lay in the region of amino acids 80-120 of the wild-type NifD sequence (SEQ ID NO:18). However, the possibility existed that cleavage at the specific site was influenced by distal sequences, not just the amino acids adjacent to the cleavage site. For this reason, the inventors took a broader approach to identifying the specific site of secondary cleavage and the surrounding amino acids and possible further regions which could influence the cleavage.

As an initial attempt to identify the cleavage site within NifD or at least predict its location, both the unprocessed and MPP-processed amino acid sequences were entered into Mitofate software (Fukusawa et al., 2015) to see whether any MPP sites were predicted. The Mitofate software predicts sites for cleavage by MPP by incorporating amino acid sequence features including positively charged amphiphilicity and presequence motifs as well as amino acid composition and physico-chemical properties. The software also predicts presequence cleavage sites by MPP by generation of a consensus position weight matrix between amino acid residues −4 and +5 of aligned cleavage sites of a yeast training data set. This tool also incorporates information on the distance from the N-terminus, as MTPs are generally between 10-90aa long, with a minority being longer than 110aa (Huang et al., 2009).

Assuming that MPP might recognise the secondary cleavage site after an initial cleavage within the MTP as the preprotein travelled through the outer and inner mitochondrial membranes, the amino acid sequences resulting from the initial MPP processing event were entered into the Mitofates software for two lengths of the MTP-FAγ, namely FAγ-scar37-NifD (35aa FAγ scar plus GG) and FAγ-scar11-nifD (9aa FAγ51 scar plus GG). The analysis by Mitofates using the sequence FAγ-scar37-NifD returned a predicted cleavage site immediately after amino acid G62 within the sequence VRGCAY (SEQ ID NO:60) relative to the N-terminus of NifD, and the sequence FAγ-scant 1-NifD returned a predicted cleavage site immediately after $N_{99}$ in the sequence RAGRRNYYTG (SEQ ID NO:61). The Mitofate analysis therefore showed that the NifD sequence in this area appeared to possess characteristics of one or even two MPP processing sites. As described below, the second of these predicted sites turned out to be correct for the secondary cleavage.

In a different approach to identify regions in NifD that were involved in the secondary cleavage, a series of genetic constructs were made each with a block of 5 consecutive amino acid substitutions within the approximate region of secondary cleavage of NifD, where non-alanine amino acids were replaced with alanines and native alanine amino acids were replaced with glycines. That is, alanine was used for all substitutions except that the native alanine residues were replaced with glycine. The series of substitution mutants spanned about 6 kDa of the presumptive cleavage site from amino acid 49 to amino acid 108 of SEQ ID NO:18. These constructs were designated NifD-Var 1 to 6 and Var 9 to 14 (Table 9). Two other variants were made with discrete substitutions based on the Mitofates prediction of a possible cleavage site within the sequence VRGCAY (SEQ ID NO:60), designated NifD-Var 7 and Var 8. In all other respects these constructs encoding NifD variants were identical to SN10 in that the polypeptides had the MTP-FAγ51 translationally fused to a NifD protein coding region and a C-terminal HA epitope tag that would allow detection of any NifD C-terminal cleavage product.

These 14 constructs were introduced from *A. tumefaciens* individually into *N. benthamiana* leaf cells together with SN46 (MTP-Su9::NifK). Protein extracts were prepared from infiltrated leaf spots and subjected to SDS-PAGE and Western blotting using HA-antibody. Of the 14 variants tested, 12 still produced the 48 kDa cleavage product and were indistinguishable in their banding pattern compared to the bands derived from SN10 having the wild-type NifD sequence. However, NifD-Var 13 (genetic construct SN100) was conspicuous in showing no 48 kDa cleavage product and, from the size and intensity of the band on the Western blot, a relatively higher ratio of processed to unprocessed FAγ51::NifD than the other variants. For NifD-Var 12 (SN99), a faint band was detected at 48 kDa, considerably less in intensity than for the wild-type. Again, the ratio of MPP-processed NifD to unprocessed NifD was greater for NifD-Var 12 compared to the wild-type and the variants other than NifD-Var13. Based on the amino acids substituted in NifD-Var 12 and 13, it was concluded that a specific region of the NifD polypeptide including at least some amino acids within the amino acid sequence RAGRRNYYTG (SEQ ID NO:61) corresponding to amino acids 94-103 of SEQ ID NO:18 was required for the secondary cleavage of NifD in mitochondria.

Based on that experiment and the conclusion drawn, genetic constructs encoding a second set of amino acid variants of NifD were made in which one, two or three of the amino acids within the RAGRRNYYTG (SEQ ID NO:61) sequence were substituted. In this set of variants, alanines were not used instead of the wild-type amino acids but rather changes based on phylogenetic analysis of a large set of naturally occurring NifD sequences (see below) and modelling of NifD-NifK structures was used to identify replacement amino acids at each particular position. The concept here was that naturally occurring variants of the RAGRRNYYTG (SEQ ID NO:61) sequence might be more likely to maintain NifD function and that rational design of variations was possible to avoid secondary cleavage and maintain function. Each construct was identical to SN10 except for the amino acid substitution(s), so encoding a polypeptide having the MTP-FAγ51 fused to NifD and then a C-terminal HA epitope tag to enable detection of a 48 kDa C-terminal cleavage product. The substitutions in this set of NifD variants, designated NifD-Var 15 to 36, are listed in Table 10 and a representative Western blot is shown in FIG. 9.

The 19 individual genetic constructs (SN108-SN126), each encoding one of the variant NifD sequences, were introduced into *N. benthamiana* cells via *A. tumefaciens* and, after 5 days for expression of the chimeric genes, proteins were extracted and subjected to SDS-PAGE and Western blotting using HA-antibody. As was done previously, the genetic construct SN46 encoding MTP-Su9::NifK was co-infiltrated with each NifD variant in order to increase the level of NifD accumulation. From the Western blot data, three groups of variants were observed: (1) Those that showed an identical banding pattern to that obtained with SN10, comprising the wild-type NifD sequence, namely SN108, SN109, SN111-113, SN115, SN116 and SN121. For these, the ratio of the intensities of the 48 kDa band to the MPP-processed NifD (primary cleavage) was essentially the same as for SN10, indicating that the secondary cleavage was not affected by the amino acid substitution(s). (2) Those that showed a 48 kDa product, but the ratio of the intensities of the 48 kDa product to the MPP-processed NifD was noticeably reduced compared to the ratio for SN10 (SN110, SN122 and SN123). (3) Variants that showed no 48 kDa secondary cleavage/degradation product (SN114, SN117, SN118, SN119, SN120, SN124, SN125 and SN126), that is, the secondary cleavage was eliminated or reduced to the extent that it was not detected, by 1-3 specific amino acid substitutions. Most remarkably, two of this last set, namely NifD-Var 21 having a Y100Q substitution (encoded by SN114) and NifD-Var29 having a Y100K substitution (SN119) had single amino acid substitutions, and another variant Var 24 encoded by SN117 had two amino acid substitutions YY100-101QT. That these specific amino acid substitutions would have had this effect could not possibly have been predicted beforehand.

From this set of variants, it appeared that substitution of the arginine at position 98 alone did not prevent the secondary cleavage (NifD-Var 19 and Var 32). Likewise, single amino acid substitutions of the asparagine at position 99 (NifD-Var20), the tyrosine at position 101 (NifD-Var 15 and Var 22), the threonine at position 102 (NifD-Var 16 and Var 23) or 2 or 3 substitutions at positions 101-103 alone did not prevent the secondary cleavage. However, the single, double or triple substitutions that were tested including the tyrosine at position 100 (NifD-Var 21, 24, 26, 29 and 30) all abolished the secondary cleavage of NifD. Cleavage was also abolished by double or triple substitutions of amino acids not including the tyrosine at position 100 (NifD-Var 34, 35 and 36). It was clear that multiple variants could be readily identified having amino acid substitutions at positions selected from amino acid positions 98-102 which were resistant to the secondary cleavage, for example through using the approach exemplified here.

Abolition of Secondary Cleavage of MTP::NifD in Yeast

Given the data in Example 6 that cleavage of the MTP::NifD fusion polypeptide occurred at the same region in yeast cells as in plant mitochondria, the variant having the Y100Q substitution was tested in yeast mitochondria. For this purpose, the protein coding region from SN114 (MTP-FAγ51::NifD(Y100Q)::HA) was amplified by PCR to provide flanking KpnI and SacI restriction enzyme sites and these were used to insert the gene into the yeast expression vector pYES2. This construct for yeast expression was designated SNY114. Protein extracts were obtained from yeast transformants containing SNY114 and analysed by Western blotting. Remarkably, the extracts from cells containing SNY114 produced a strong band at the same size as the NifD-Var 29 construct in plant cells, with a much reduced amount of secondary cleavage occurring. This contrasted strongly with the result in FIG. 8 with the wild-type NifD sequence which when expressed in yeast produced an intense 48 kDa cleavage/degradation product. Although there were some protein bands of other sizes observed from SNY114, these were less intense than the predominant full length band corresponding to the desired MPP-processed MTP::NifD::HA polypeptide. It was concluded that the full length, correctly processed NifD polypeptide was expressed as the predominant MTP::NifD polypeptide in yeast mitochondria, as in plant mitochondria, when amino acid substitutions were included at positions 98-102 of NifD with reference to SEQ ID NO:18, for example at position 100.

TABLE 9

Alanine-substitution variants of FAγ51-NifD fusion polypeptide and effect on secondary cleavage/degradation in plant cells.

| Vari-ant | Con-struct No | Wild-type sequence | Modified sequence | Position in SEQ ID NO: 18 | Secondary cleavage efficiency |
|---|---|---|---|---|---|
| 1 | SN52 | SNRKS (SEQ ID NO: 62) | AAAAA (SEQ ID NO: 63) | 49-53 | ++ |
| 2 | SN53 | QPGVM (SEQ ID NO: 64) | AAAAA (SEQ ID NO: 63) | 54-58 | ++ |
| 3 | SN54 | TVRGC (SEQ ID NO: 65) | AAAAA (SEQ ID NO: 63) | 59-63 | ++ |
| 4 | SN55 | AYAGS (SEQ ID NO: 66) | GAGAA (SEQ ID NO: 67) | 64-68 | ++ |
| 5 | SN56 | KGVVF (SEQ ID NO: 68) | AAAAA (SEQ ID NO: 63) | 69-73 | ++ |
| 6 | SN57 | GPIKD (SEQ ID NO: 69) | AAAAA (SEQ ID NO: 63) | 74-78 | ++ |
| 7 | SN58 | TVRGCAYAGS (SEQ ID NO: 70) | TARACGYGGS (SEQ ID NO: 71) | 59-68 | ++ |
| 8 | SN59 | AYAG (SEQ ID NO: 72) | GAGG (SEQ ID NO: 73) | 64-67 | ++ |
| 9 | SN96 | MAHIS (SEQ ID NO: 74) | AGAAA (SEQ ID NO: 75) | 79-83 | ++ |
| 10 | SN97 | HGPVG (SEQ ID NO: 76) | AAAAA (SEQ ID NO: 63) | 84-88 | ++ |
| 11 | SN98 | CGQYS (SEQ ID NO: 77) | AAAAA (SEQ ID NO: 63) | 89-93 | ++ |
| 12 | SN99 | RAGRR (SEQ ID NO: 78) | AGAAA (SEQ ID NO: 75) | 94-98 | + |
| 13 | SN100 | NYYTG (SEQ ID NO: 79) | AAAAA (SEQ ID NO: 63) | 99-103 | - |
| 14 | SN101 | VSGVD (SEQ ID NO: 80) | AAAAA (SEQ ID NO: 63) | 104-108 | ++ |

TABLE 10

Second set of amino acid substitution variants of FAγ51-NifD fusion polypeptide and effect on secondary cleavage/degradation and impact on function in ARA bacterial assays. The wild-type sequence RAGRRNYYTG (SEQ ID NO: 61) was replaced with the indicated modified sequence. Nt = not tested.

| Variant | Construct No. | Modified sequence | Secondary cleavage efficiency | NifD function |
|---|---|---|---|---|
| 15 | SN108 | RAGRRNY**F**TG (SEQ ID NO: 81) | ++ | Nt |
| 16 | SN109 | RAGRRNYY**A**G (SEQ ID NO: 82) | ++ | Nt |
| 17 | SN110 | RAGRRNY**FA**G (SEQ ID NO: 83) | + | Nt |
| 18 | SN111 | RAGRRNYY**AA** (SEQ ID NO: 84) | ++ | Nt |
| 19 | SN112 | RAGR**A**NYYTG (SEQ ID NO: 85) | ++ | Nt |
| 20 | SN113 | RAGRR**H**YYTG (SEQ ID NO: 86) | ++ | Nt |
| 21 | SN114 | RAGRRN**Q**YTG (SEQ ID NO: 87) | - | 147% |
| 22 | SN115 | RAGRRNY**T**TG (SEQ ID NO: 88) | ++ | Nt |
| 23 | SN116 | RAGRRNYY**V**G (SEQ ID NO: 89) | ++ | Nt |
| 24 | SN117 | RAGRRN**QT**TG (SEQ ID NO: 90) | - | 107% |
| 26 | SN118 | RAGRR**HKG**TG (SEQ ID NO: 91) | - | 33% |
| 29 | SN119 | RAGRRN**K**YTG (SEQ ID NO: 92) | - | 94% |
| 30 | SN120 | RAGRRN**KA**TG (SEQ ID NO: 93) | - | 67% |
| 31 | SN121 | RAGRRNY**A**TG (SEQ ID NO: 94) | ++ | Nt |
| 32 | SN122 | RAGR**K**NYYTG (SEQ ID NO: 95) | + | Nt |

TABLE 10-continued

Second set of amino acid substitution variants of FAγ51-NifD fusion polypeptide and effect on secondary cleavage/degradation and impact on function in ARA bacterial assays. The wild-type sequence RAGRRNYYTG (SEQ ID NO: 61) was replaced with the indicated modified sequence. Nt = not tested.

| Variant | Construct No. | Modified sequence | Secondary cleavage efficiency | NifD function |
|---|---|---|---|---|
| 33 | SN123 | RAGR**K**NY**F**TG (SEQ ID NO: 96) | + | 4% |
| 34 | SN124 | RAGR**K**NYY**A**G (SEQ ID NO: 97) | - | 1% |
| 35 | SN125 | RAGR**K**NY**FA**G (SEQ ID NO: 98) | - | 2% |
| 36 | SN126 | RAGR**K**NY**AA**G (SEQ ID NO: 99) | - | Nt |

Demonstration of the Secondary Cleavage Site by Mass Spectrometry

Protein extracts from *N. benthamiana* leaves infiltrated with SN14 (MTP-Su9::NifD::HA) were run on SDS-PAGE using a gel having a polyacrylamide concentration of 4-20% (Invitrogen). The gel was stained with Aqua stain (Bulldog Bio). After destaining in water, 5 slices were cut from the gel for the region spanning the molecular weights 37-50 kDa. The slices were numbered 1 to 5 from the smaller molecular weights to the larger. Each gel slice was cut into approximately 1 mm cubes and soaked in 150 μl 30% methanol for 15 minutes. To reduce proteins that may have oxidised, the buffer was removed and replaced with 100 μl of fresh 25 mM ammonium bicarbonate (ABC) buffer with 5 μl of 15% dithiothreitol and incubated at room temperature for an hour. Cysteine residues were inactivated by the addition of 5 μl of 40% acrylamide and incubation at room temperature for 1 hour, after which the buffers were carefully removed. Three wash steps were carried out, each of 50 μl of ABC buffer and 50 μl acetonitrile and incubation at room temperature. The gel pieces were dried by the addition of 100 μl of 100% acetonitrile for 2 min, which was then discarded. The proteins in the dried gel pieces were then digested with 0.1 μg trypsin (Promega) in 20 μl ABC with incubation overnight at 37° C. The tryptic digest was stopped with 1 μl of a 50% (v/v) formic acid solution and sonication for 15 min. The samples were filtered after the addition of 10 μl of water before transfer into LCMS vials.

The resulting tryptic digest from each gel slice was injected onto a Dionex Nanomate 3000 (ThermoFisher) nano liquid chromatography (LC) system directly coupled to an Orbitrap Fusion Tribrid Mass Spectrometer. The peptides were desalted for 5 min on an Acclaim PepMap C18 (300 Å, 5 mm×300 μm) trap column at a flow rate of 10 μL/min with loading solvent, and separated on an Acclaim PepMap C18 (100 Å, 150 mm×0.075 mm) column at a flow rate of 0.3 μL/min at 35 C. A linear gradient from 5% to 40% solvent B over 60 min was employed followed by a wash and re-equilibration with 40-99% B over 5 min, a 5 min hold at 99% B, return to 5% B over 6 min, and held for 7 min. The solvents used were: (A) 0.1% formic acid, 99.9% water; (B) 0.08% formic acid, 80% acetonitrile, 19.92% water. The nano-LC was directly coupled to the Nanospray Flex Ion source of the Orbitrap Fusion MS. The ion spray voltage was set to 2400 V, the sweep gas was set to 1 Arb and the ion transfer tube temperature was set to 300° C. Data were acquired in data-dependent acquisition mode consisting of a Orbitap-MS survey scan followed by parallel acquisition of a high resolution Orbitrap scan at 120,000 resolution and multiple MS/MS events in the linear ion trap, over a 3 second period. First stage MS analysis was performed in positive ion mode over the mass range of m/z 400-1500 with an AGC target of $4\times10^5$ and a maximum injection time of 50 ms. Tandem mass spectra were acquired in the ion trap on precursor ions that exceeded an intensity threshold of 1000 counts with charge state 2-7. Spectra were acquired using quadrupole isolation with a 1.6 m/z isolation window and (Higher energy Collisional Dissociation) HCD set at 28% based on the size and charge of the precursor ion for optimum peptide fragmentation. Ion trap scan rate was set to rapid with an AGC target of $4\times10^3$ and a maximum injection time of 300 ms, the instrument was set to utilise the maximum parallelizable time for injecting ions into the trap during a 3 second window whilst the orbitrap was collecting high resolution MS spectra. Dynamic exclusion was set to exclude precursor ions after one occurrence with a 15 sec interval and a mass tolerance of 10 ppm.

Analysis of the data for protein identification was conducted using the Sequest algorithm in Proteome Discoverer v2.2 (ThermoFisher). Carbamidomethyl was selected as the alkylating agent and trypsin was selected as the digestion enzyme. Dynamic modifications were selected for oxidation on NifD with a maximum of three modifications. Tandem mass spectrometry data were searched against a database of tryptic peptides for NifD derived from the fusion polypeptide amino acid sequence encoded by SN14 and the *N. benthamiana* proteome, common contaminants and organism specific databases annotated from UniProt. The database search results were curated to yield the protein identifications using a 1% global false discovery rate (FDR) determined by the in-built FDR tool within Proteome Discoverer software.

Of the five samples submitted to mass spectrometry, no NifD peptides were identified in the sample coming from the gel slice for the highest molecular weight, sample 5. In contrast, NifD peptides were identified in the other samples 1-4. The greatest coverage was for sample 2, the second lowest band excised from the gel, with 17 specific tryptic peptides derived from the NifD sequence being identified in that sample. Six to 11 specific NifD peptides were identified in samples 1, 3 and 4. Importantly, the peptide YYTGVSGVDSFGTLNFTSDFQER (SEQ ID NO:100) was positively identified in sample 2. The XCorr score was sufficiently high for that peptide and the posterior error probability (PEP) score was sufficiently low to confirm the positive identification, indicating that the peptide fragment ions were not the product of a similarly sized but different peptide. It was concluded that this peptide must have arisen from SN14 by a specific cleavage of the NifD sequence within the RRNY sequence (SEQ ID NO:101) between the asparagine (N) and tyrosine (Y) residues in the plant cells, followed by the tryptic digestion in the analysis. The positive identification of the cleavage site by this MS analysis was in complete agreement with the mutational approach described above.

Example 8. Phylogenetic Analysis of NifD Around the Secondary Cleavage Site

Nitrogenase enzymes including NifD polypeptides are naturally produced in numerous bacterial and archaeal phyla. A set of 1751 naturally occurring NifD amino acid sequences from a very wide range of bacterial and archaeal sources was extracted from the InterPro database on 12 Dec. 2018. All of the sequences were listed as members of the family IPR005972, defined as Nitrogenase molybdenum-iron protein alpha chain which are all NifD polypeptides of the molybdenum-iron type. The sequences were from 21 different phyla. The majority of sequences were from Proteobacteria (63.0%) followed by *Firmicutes* (12.3%) and Cyanobacteria (12.3%). Others at lower numbers were from the phyla Actinobacteria, Aquificae, Bacteroidetes, *Candidatus margulisbacteria, Candidatus sumerlaeota,* Chlorobi, Chloroflexi, *chordata*, Chrysiogenetes, Deferribacteres, Elusimicrobia, Euryarchaeota, Fusobacteria, Lentisphaerae, Nitrospirae, Planctomycetes, Spirochaetes and Verrucomicrobia.

The set of 1751 sequences contained 275 duplicate sequences. The duplicate sequences were removed, which resulted in a set of 1476 unique sequences. These were examined to understand the diversity of amino acid sequences at positions corresponding to the RAGRRNYYTG sequence (SEQ ID NO:61) of *K. oxytoca*. The sequences were aligned using the multiple sequence alignment program Mafft version 7 using the FFT-NS-2 strategy with default parameters, i.e using the default "fast and progressive" settings (Katoh et al., 2013). The aligned sequences were visualised using the ALVIS software (interactive non-aggregative visualization and explorative analysis of multiple sequence alignments) (Schwarz et al., 2016). The NifD sequences were between 362 and 592 residues long. The multiple sequence alignment ('mega-alignment') contained 907 positions, taking into account the numerous gaps in the individual sequences that were introduced by the alignment program. In the mega-alignment, the proposed secondary cleavage site was found between positions 270 to 275, corresponding to residues 97 to 102 in the *K. oxytoca* sequence (SEQ ID NO:18). Sixty-eight sequences were identified that contained the same 10 amino acids sequence as amino acids 94-103 of *K. oxytoca* (RAGRRNYYTG; SEQ ID NO:61).

A protein similarity network was generated for the 1476 members of the InterPro family IPR005972, showing clusters of related sequences from different phyla of diazotrophs. Representative sequences were chosen from different clusters (Table 11) and aligned in the region corresponding to amino acids 49-108 of the *K. oxytoca* NifD sequence. The alignment for that region is shown in FIG. 10. A high degree of sequence conservation was noted, including 19 amino acids that were completely conserved and many others that were highly conserved. Not shown in FIG. 10, the sequences from *Desulfotomaculum ferrireducens, Halanaerobium saccharolyticum, Clostridium ljungdahlii, Methanosarcina barkeri, Desulfovibrio vulgaris* and *Chlorobium tepidum* and the related sequences in their clusters contained a 50-60 residue insertion further towards the C-terminus, therefore forming a subgroup of NifD sequences.

The frequency distribution of residues was calculated around the predicted secondary cleavage site, taken as being immediately after the RRN amino acids, for positions −3, −2, −1, +1, +2 and +3 (Table 12). The arginine (R) in position −3 was completely conserved except for two sequences in the set that showed a "gap" for both positions −3 and −2. However, these two sequences were only fragments, not complete NifD sequences (A0A2N4YT47—*Klebsiella variicola*, A0A2N5A8Y2—*Klebsiella variicola*) and therefore were uncertain and could be excluded from further analysis. The arginine at position −2 was almost completely conserved. There were only two sequences out of the 1476 that contained a residue other than arginine at that position: NifD from *Paenibacillus fujiensis* (B9X2A1) contained a cysteine residue and NifD from *Alcaligenes faecalis* (Q44045) contained a glycine residue. It was not known whether these sequences were active for NifD. Asparagine (N) was highly conserved at position −1, present in 97.83% of the 1476 sequences. About 1.9% of the 1476 sequences contained a histidine, phenylalanine, alanine or serine residue at that position instead of asparagine. The most frequent residue at position +1 was tyrosine (Y, 71.54%), followed by glutamine, leucine and lysine, each of those three at a frequency in the range of 7-11%. As there were substantial numbers of naturally occurring NifD sequences having one of these amino acids other than tyrosine at that position, it was concluded that those amino acids at position +1 provided for NifD activity. Phenylalanine, methionine and glutamic acid were also represented in that position at lesser frequencies. The most frequent residue at position +2 was tyrosine (64.43%), followed by alanine and threonine, and then any of six other amino acids at lower frequencies. Again, it was concluded that those amino acids at position +2 provided for NifD activity. The most frequent residue at position +3 was valine (V, 27.24%), followed by isoleucine, threonine and lysine, then any of 11 other amino acids. Clearly, the degree of conservation of the amino acids in the six positions corresponding to residues 97-102 of the *K. oxytoca* NifD sequence decreased along that sequence, from the two arginines which were considered to be essential to NifD function through to position +3 which showed wide variability.

The 1474 NifD amino acid sequences (excluding the two partial sequences mentioned above) were then examined at the positions corresponding to amino acids 97-101 of SEQ ID NO:18 for the presence of the sequence RRNY (SEQ ID NO:101) and more specifically within that set RRNYY (SEQ ID NO:102). There were 1045 sequences (70.90%) that comprised RRNY (SEQ ID NO:101) and, of those, 935 sequences comprising RRNYY (SEQ ID NO:102) corresponding to amino acids 97-101 of SEQ ID NO:18. On the basis of the secondary cleavage data described above, it was concluded that the 1045 naturally occurring NifD polypeptides having the sequence RRNY (SEQ ID NO:101) would be subject to secondary cleavage within that sequence upon entry into eukaryotic cell mitochondria, whereas NifD polypeptides having the sequence RRNX (SEQ ID NO:154) where X was any amino acid other than tyrosine (Y) would be less subject to secondary cleavage within that sequence. Those NifD sequences were therefore not preferred on the basis of their propensity to secondary cleavage. On the contrary, NifD sequences comprising any amino acid other than tyrosine (Y) at the position corresponding to Y100 of the *K. oxytoca* NifD (SEQ ID NO:18) were preferred, on the basis that they were likely to be resistant to cleavage upon introduction into eukaryotic cell mitochondria. Such sequences can readily be tested to confirm their resistance to cleavage within this region when expressed within plant cells as a MTP-NifD fusion polypeptide.

On further examination of the 1474 sequences, there were 155 sequences (10.51%) having the sequence RRNQ (SEQ ID NO:103) and 95 sequences (6.45%) having the sequence RRNK (SEQ ID NO:104), both of which were considered to not be subject to secondary cleavage and therefore more preferred than the sequences not having glutamine or lysine in the fourth position. These NifD polypeptides were considered more preferred than NifD polypeptides having the sequence RRNF (SEQ ID NO:220). It was then noticed that 141 of the 155 of the NifD sequences comprising the sequence RRNQ (SEQ ID NO:103) had a threonine (T) immediately after, i.e. comprised the sequence RRNQT (SEQ ID NO:105). On the basis that the polypeptide encoded by Var 24 (SN117) comprising the sequence RRNQT (SEQ ID NO:105) was not cleaved at that position and that the sequence was relatively frequent in naturally occurring NifD polypeptides, it was concluded that NifD polypeptides comprising the sequence RRNQT (SEQ ID NO:105) were highly preferred for use in eukaryotic cell mitochondria.

TABLE 11

Representative NifD sequences from a wide range of diazotrophic organisms.

| UniProt accession | Organism | Length | Phylum |
|---|---|---|---|
| A0A1S6IX91 | *Desulfotomaculum ferrireducens* | 539 | Firmicutes |
| Q1K0I7 | *Desulfuromonas acetoxidans* (strain DSM 684/11070) | 480 | Proteobacteria |
| C6E9A1 | *Geobacter* sp. (strain M21) | 480 | Proteobacteria |
| B0TAP4 | *Heliobacterium modesticaldum* (strain ATCC 51547/Ice1) | 486 | Firmicutes |
| Q0RAV5 | *Frankia alni* (strain ACN14a) | 486 | Actinobacteria |
| A0A089HSS3 | *Paenibacillus durus* (*Paenibacillus azotofixans*) | 485 | Firmicutes |
| A0A166T5M1 | *Leptolyngbya valderiana* BDU 20041 | 481 | Cyanobacteria |
| P00464 | *Nostoc* sp. (strain PCC 7120/SAG 25.82/UTEX 2576) | 497 | Cyanobacteria |
| A0A060DN91 | *Azospirillum brasilense* | 479 | Proteobacteria |
| P19066 | *Sinorhizobium fredii* (strain NBRC 101917/NGR234) | 504 | Proteobacteria |
| C1DGZ7 | *Azotobacter vinelandii* (strain DJ/ATCC BAA-1303) | 492 | Proteobacteria |
| A0A378D475 | *Klebsiella oxytoca* | 483 | Proteobacteria |
| A0A2J817Q6 | *Vibrio diazotrophicus* | 488 | Proteobacteria |
| A0A1D7TJ51 | *Sulfurospirillum halorespirans* DSM 13726 | 484 | Proteobacteria |
| E4TZQ3 | *Sulfuricurvum kujiense* (strain ATCC BAA-921/DSM 16994/JCM 11577/YK-1) | 489 | Proteobacteria |
| B8DR77 | *Desulfovibrio vulgaris* (strain Miyazaki F/DSM 19637) | 544 | Proteobacteria |
| A0A0E3R6R4 | *Methanosarcina barkeri* 227 | 532 | Euryarchaeota |
| A0A0W1JIT9 | *Desulfitobacterium hafniense* (*Desulfitobacterium frappieri*) | 493 | Firmicutes |
| Q8KC89 | *Chlorobaculum tepidum* (strain ATCC 49652/DSM 12025/NBRC 103806/TLS) (*Chlorobium tepidum*) | 543 | Chlorobi |
| A0A327XSU0 | *Halanaerobium saccharolyticum* | 539 | Firmicutes |
| A0A162KU04 | *Clostridium ljungdahlii* | 536 | Firmicutes |

TABLE 12

Frequency distribution of amino acid residues in the 1476 naturally occurring NifD sequences around the secondary cleavage site.

| | *K. oxytoca* amino acid | | | | | |
|---|---|---|---|---|---|---|
| | R97 | R98 | N99 | Y100 | Y101 | T102 |
| | Position relative to cleavage site | | | | | |
| | −3 | −2 | −1 | 1 | 2 | 3 |
| most common | R, 1474 (99.86%) | R, 1472 (99.73%) | N, 1444 (97.83%) | Y, 1056 (71.54%) | Y, 951 (64.43%) | V, 402 (27.24%) |
| 2nd most common | Gap, 2 (0.14%) | Gap, 2 (0.14%) | H, 17 (1.15%) | Q, 159 (10.77%) | A, 240 (16.26%) | I, 374 (25.34%) |
| 3rd most common | | C, 1 (0.07%) | F, 7 (0.47%) | L, 114 (7.72%) | T, 148 (10.03%) | T, 147 (9.97%) |
| 4th most common | | G, 1 (0.07%) | A, 3 (0.20%) | K, 108 (7.32%) | M, 44 (2.98%) | K, 135 (9.15%) |
| 5th most common | | | X, 2 (0.14%) * | F, 27 (1.83%) | F, 38 (2.57%) | R, 113 (7.66%) |
| 6th most common | | | Gap, 2 (0.14%) | M, 10 (0.68%) | G, 27 (1.83%) | N, 96 (6.50%) |
| 7th most common | | | S, 1 (0.07%) | E, 1 (0.07%) | S, 14 (0.95%) | D, 68 (4.61%) |
| 8th most common | | | | Gap, 1 (0.07%) | V, 12 (0.81%) | S 40 (2.71%) |
| 9th most common | | | | | N, 1 (0.07%) | E, 27 (1.83%) |
| 10th most common | | | | | Gap, 1 (0.07%) | Q, 23 (1.56%) |
| 11th most common | | | | | | L, 20 (1.36%) |
| 12th most common | | | | | | A, 12 (0.81%) |
| 13th most common | | | | | | H, 9 (0.81%) |

TABLE 12-continued

Frequency distribution of amino acid residues in the 1476 naturally occurring NifD sequences around the secondary cleavage site.

| | *K. oxytoca* amino acid | | | | | |
|---|---|---|---|---|---|---|
| | R97 | R98 | N99 | Y100 | Y101 | T102 |
| | Position relative to cleavage site | | | | | |
| | −3 | −2 | −1 | 1 | 2 | 3 |
| 14th most common | | | | | | M, 8 (0.61%) |
| 15th most common | | | | | | Y, 2 (0.14%) |

* "X" meaning an unknown amino acid is present in the sequences *Methylocella palustris* (Q6KCQ3) and *Methylosinus trichosporium* (Q6KCQ2).

Example 9. Functional Testing of NifD Variants Around the Secondary Cleavage Site The MTP-FAγ51::NifD variants that did not show cleavage at the presumed site between residues 99 and 100 were tested for NifD function in the MIT2.1 system in *E. coli*, as follows. In order to introduce the mutations encoding the amino acid substitutions into the NifD gene in pMIT2.1 and to allow for easier cloning, restriction sites for the enzymes AgeI and SalI were introduced into the NifD coding region spanning the sites for the amino acid changes. This was done by PCR-mediated mutagenesis using oligonucleotide primer combinations 5'-CTAATGCTACCGGTGAACGTAACCTGGCACTGATTCAAGAAGTACTGGAAG TGTTC-3' (SEQ ID NO:108) and 5'-GTTACGTTCACCGGTAGCATTAGTCATCATCCGG CTCCTCCGCTAGATAAAAATGTG-3' (SEQ ID NO:109) for AgeI insertion, and 5'-GTTTCTGGCGTCGACTCTTTCGGCACGCTGAACTTCACCTCTGACTTCCAGG AAC-3' (SEQ ID NO:110) and 5'-CGAAAGAGTCGACGCCA GAAACGCCCGTGTAGTAGTTA CGACGTCCCGCGCG-3' (SEQ ID NO:111) for SalI insertion into the NifD gene of the pTopoH-J construct (Example 4). This AgeI to SalI fragment was codon optimised for *N. benthamiana* expression. The resulting vector was digested with SbfI, and ligated with SbfI digested B-ori, creating the positive control vector designated pSO043, encoding wild-type NifD as well as the other Nif polypeptides.

The AgeI-SalI region of NifD containing each of the amino acid substitutions was amplified by PCR in order to add AgeI and SalI restriction sites at the same positions as in pSO043. This used primers 5'-GACCAATGCTACCGGTGAGAGGAACC-3' (SEQ ID NO:112) and 5'-GTTAAGAGTCCCGAAAGAGTCGACACCAG-3' (SEQ ID NO:113) and DNA from the constructs SN114, SN118, SN119, SN120, SN123, SN124 and SN125 as template, each encoding a different variant NifD sequence. The amplified AgeI-SalI NifD variant fragments were then ligated into pSO043 digested with AgeI and SalI, resulting in the series of constructs designated pSO044-050. These constructs thereby contained the AgeI-SalI region which was codon optimised for expression in plant cells whereas the rest of the NifD gene was codon optimised for expression in *E. coli*. Two other NifD vectors were also constructed in a similar manner using SN100 (NifD-Var13 having amino acid residues 99 and 103 substituted with five alanine residues) and EC38014, having a *N. benthamiana* codon optimised NifD gene, as DNA templates, resulting in pSO052 and pSO053, respectively.

The bacterial expression constructs having variant NifD genes were introduced into *E. coli* strain JM109 along with the expression induction vector pN249 and tested for nitrogenase function using the acetylene reduction assay (ARA). The bacteria co-transformed with pSO053 (positive control, wild-type NifD) and the NifD variants encoded by pSO052 (alanine substitutions of residues 99 to 103), pSO044 (Y100Q), pSO045 (NYY99-101HKG), pSO046 (Y100K), and pSO047 (YY100-101KA) each produced ethylene to some extent. The amount of ethylene produced by pSO044, pSO045, pSO046 and pSO047 was 147%, 33%, 94%, and 67%, respectively, compared to the positive control. pSO052 also produced ethylene at 14% of the positive control. However, the *E. coli* cells containing pSO048, pSO049 and pSO050, all including the substitution R98K, produced only traces of ethylene at rates greater than the negative control, indicating that those NifD mutants were almost inactive for nitrogenase. In analogous fashion, a construct having the YY100-101QT double substitution yielded 107% ARA activity relative to the wild-type NifD control (Table 10). Therefore, both the Y100Q and YY100-101QT substitutions yielded increased NifD activity relative to the wild-type NifD sequence. It was concluded that arginine at position 98 was required for NifD function, consistent with its complete conservation in naturally occurring NifD sequences where activity could be assumed.

It was concluded more generally that NifD variants had been identified which retained substantial NifD function, indeed full or even increased NifD function for some variants, which were not subject to the secondary cleavage observed with the wild-type *K. oxytoca* NifD sequence. It was also concluded that the resistance of the NifD polypeptides to the secondary cleavage in plant mitochondria was combinable with increased nitrogenase activity, the latter being demonstrated for the modified NifD sequence in a bacterial system. It was also concluded that other NifD variants could be identified which were not subject to the secondary cleavage but which had lost NifD function.

Example 10. Other NifD Polypeptides

Modelling of the NifD-NifK Structure Around the Secondary Cleavage Site in NifD.

The protein structure of NifD polypeptide from *K. oxytoca* provided in PDB: 1QGU was visualised using PyMOL software, in particular focusing on the structure around the secondary cleavage site when NifD was bound with NifK polypeptide from *K. oxytoca*. The secondary cleavage site was observed to be located at the interface of NifD and NifK polypeptides, internally in the complex, and in close proximity to the essential cofactor FeMoco (FIG. 11). In the resting state, the Arg97 residue of NifD was coordinated to the bridging sulfido ligand (S5) located between Fe3 and Fe7 of FeMoco, explaining why Arg97 was entirely conserved in functional NifD polypeptides. It was thought to play an important role in stabilising the negative charges of the more reduced edge of the cluster (Fe1-Fe3-Fe7) (Spatzal et al., 2016). The hydroxyl group of Tyr100 in NifD formed hydrogen bonds to the amino group in Arg98 in NifD, the hydroxyl group in Ser515 in NifK and the carboxy group of Asp517 in NifK from *K. oxytoca*, also showing its importance for NifD function.

Homology models for the NifD variants having the Y100Q and Y100K substitutions were prepared using the SWISS-MODEL server (Waterhouse et al., 2018). The sequence of NifD Y100Q or NifD Y100K was used as target sequence. The sequence of NifK from *K. oxytoca* was again added to the model as a hetero target. For the Y100Q variant, the model predicted that the amino group of Gln100 of the NifD polypeptide formed a hydrogen bond to the carboxy group of Asp517 in NifK and the backbone carbonyl oxygen atom of Tyr514 in NifK. For the Y100K variant the model predicted that the amino group of Lys100 also forms hydrogen bonds to Asp517 and Tyr514 in NifK. The interaction of Tyr100 with Ser515 in NifK was replaced by an interaction of Gln100 or Lys100 with the backbone oxygen atom of Tyr514 in NifK. These observations were consistent with the retention of NifD activity for the Y100Q and Y100K substitutions.

The observations that (i) the sequence around the secondary cleavage site was internal in the NifD polypeptide when folded in its active conformation and (ii) that the NifD-linker-NifK polypeptide including the wild-type *K. oxytoca* NifD sequence was cleaved suggested that the secondary cleavage was occurring while the polypeptide was unfolded or being unfolded in the mitochondria.

The phylogenetic analysis described above (Example 8) showing that the amino acid residues leucine, phenylalanine, methionine and glutamic acid were also represented in naturally occurring NifD polypeptides at the position corresponding to Y100 in *K. oxytoca* NifD i.e. the +1 position relative to the secondary cleavage site and those NifD polypeptides were presumed to be functional. In those polypeptides, the amino acid Leu at the position corresponding to amino acid 100 was followed at position 101 by alanine (53 sequences), methionine (41 sequences), valine (10 sequences), threonine (4 sequences), phenylalanine (4 sequences) or tyrosine (2 sequences). When the amino acid corresponding to position 100 was Phe, the following amino acid was usually alanine (23 sequences) and in a few cases serine (2 sequences) or tyrosine (2 sequences). Met at position 100 was followed by alanine (3 sequences), methionine (3 sequences), glycine (2 sequences), valine (1 sequence) or threonine. Glu at position 100 was followed by threonine (1 sequence). However, the presence of Phe, Leu or Met at position 100 would not provide the hydrogen bonds that Y100 had with amino acids Ser515 and Asp517 in NifK from *K. oxytoca.*

To test their function, genetic constructs comprising the Y100L, Y100F and Y100M substitutions were made to the NifD sequence of *K. oxytoca* in an analogous fashion to the substitutions described above. These constructs encoding NifD variants were tested for the secondary cleavage phenotype after introduction into *N. benthamiana* leaf cells and for NifD function in *E. coli* using the pMIT2.1 system, in analogous fashion to that described in Example 8. All three of these NifD polypeptides having substitutions Y100L, Y100F and Y100M were still subject to secondary cleavage, showing that the amino acid sequences at the site were still recognised by MPP in the plant mitochondria. The other 14 possible substitutions at position 100 are readily tested in analogous fashion.

Prediction and Testing of Naturally Occurring NifD Sequences for Cleavage

On the basis of the mutational and phylogenetic analyses, predictions were made about different naturally occurring NifD sequences, whether they would be cleaved or not cleaved, or less cleaved, in the region corresponding to amino acids 97-102 of the *K. oxytoca* NifD (SEQ ID NO:18). To test these predictions, one sequence was selected from each of the three clusters of NifD sequences that contained the highest number of members having the RRNYY sequence (SEQ ID NO:102), predicted to be cleaved. These selected NifD sequences were from *Azotobacter vinelandii, Azospirillum brasilense*, and *Sinorhizobium fredii*. These sequences are provided as SEQ ID NOs:148-150. Three other NifD amino acid sequences were identified which did not have the RRNY sequence (SEQ ID NO:101), instead having RRNQ (SEQ ID NO:103), RRNK (SEQ ID NO:104) or RRFK (SEQ ID NO:106) at the corresponding sequence (Table 13). These selected NifD sequences were from *Clorobium tepidum, Desulfotomaculum ferrireducens* and *Desulfovibrio vulgaris*, contained either a glutamine or lysine residue rather than tyrosine in the equivalent of position 100. These sequences are provided as SEQ ID NOs:151-153. It was predicted these three polypeptides would be less subject to cleavage within those sequences.

These selected sequences were aligned with the *K. oxytoca* sequence using Emboss Needle Pairwise Alignment Tool to determine the extent of identity, also shown in Table 13. It was noted that SEQ ID Nos:151-153 that did not have the RRNY sequence (SEQ ID NO:101) were less than 40% identical to SEQ ID NO:18.

To test the prediction in each case about the extent of secondary cleavage, genetic constructs (SN221-226) were made encoding MTP-FAγ51::NifD::HA fusion polypeptides where the NifD sequence was the same as the naturally occurring sequence, for introduction into *N. benthamiana* leaves. Protein extracts were prepared 5 days after infiltration and subjected to SDS-PAGE and Western blotting. It was observed that the fusion polypeptides comprising the RRNYY sequence (SEQ ID NO:102) from *A. vinelandii* and *S. fredii* NifD yielded intense secondary cleavage bands in the Western blots, with much more than 50% of the polypeptides cleaved at the secondary site, whereas the NifD polypeptide from *D. vulgaris* not having RRNYY (SEQ ID NO:102) showed little secondary cleavage. Polypeptides from *C. tepidum* and *D. ferrireducens* showed some secondary cleavage but less than for *A. vinelandii* and *S. fredii* NifD The experiment was repeated, including genetic constructs as controls which encoded fusion polypeptides that would not be cleaved with MPP due to alanine substitutions in the MTP-FAγ51 sequence (lanes marked A in FIG. 12) or that lacked the MTP sequence but had a 6×His motif instead (lanes marked C), equal in size to the MPP-processed forms. The Western blot analysis (FIG. 12) again showed that the ratio of full-length NifD and the secondary cleavage product varied for all six of the NifD fusion polypeptides. Burén et al. (2017b) observed, in yeast mitochondria, a degradation product of NifD from *A. vinelandii* of approx. 48 kDa. The size of that polypeptide was in line with the predicted secondary cleavage by MPP at the RRNYY (SEQ ID NO:102) site. In the repeat experiment, a degradation product of this size was observed for the *A. vinelandii* NifD polypeptide. A second degradation product was also observed at approximately 40 kDa molecular weight, suggesting the presence of a second cryptic cleavage site. The two degradation products were not observed for the genetic construct encoding the cytoplasmically localised fusion polypeptide 6×His::NifD::HA, indicating that the second degradation product also arose from mitochondrial protease activity. A difference was also noted between the processing in plant mitochondria compared to the yeast mitochondria. Further studies are required to determine the origin of the second degradation product of the *A. vinelandii* AvNifD fusion polypeptide in plant cells.

The fusion polypeptide including the NifD sequence from *A. brasilense* was mainly present in the unprocessed form, indicating that the import efficiency of the AbNifD fusion polypeptide into the mitochondria was low. For this reason, it was difficult to assess the amount of MPP cleavage for that one. Significantly, this time only a faint degradation product was observed for the fusion polypeptide including the SfNifD sequence from *S. fredii.*

The relative abundance of the MTP51::NifD::HA polypeptides varied extensively even though the same promotor was used in all of the genetic constructs. The abundance of the NifD fusion polypeptides from *A. brasilense, A. vinelandii* and *D. vulgaris* was low compared to the NifD fusion polypeptides from *C. tepidum* and *S. fredii.*

The experiment was extended by fractionating the protein extracts into soluble and insoluble fractions as described in Example 1. It was observed that the NifD fusion polypeptides from *C. tepidum, D. ferrireducens* and *S. fredii* were soluble to some extent, up to about 50% for *D. ferrireducens* NifD.

It was concluded that naturally occurring NifD sequences having the RRNYY sequence (SEQ ID NO:102) were less preferred due to their tendency for secondary cleavage within that sequence in plant mitochondria, but that exceptions such as the *S. fredii* NifD can be found.

Example 11. NifD Variants in the Context of NifD-NifK Fusion Polypeptides

The effect of the Y100Q substitution on NifD processing and function in the context of a NifD-linker-NifK fusion polypeptide was also tested. To do this, the pMIT2.1 vector was first modified to translationally fuse the otherwise wild-type NifD and NifK coding regions, as follows. The operon structure between the NifD and NifK genes in pMIT2.1, encoding separate NifD and NifK polypeptides, was replaced with a nucleotide sequence to provide for a translational fusion of the NifD and NifK polypeptides, joined by a 30 amino acid linker (ATPPPGSTTTAYPYDVPDYATPPPGSTTTA, SEQ ID NO:116) which included a HA epitope tag (YPYDVPDYA, SEQ ID NO:115). The DNA fragment encoding this NifD::linker (HA)::NifK polypeptide was from the NifD::FLAGlinker::NifKs gene (Allen et al., 2017) except that the nucleotide sequence coding for the amino acids of the FLAG epitope was replaced with a sequence encoding the HA epitope, forming a vector herein designated as pTopoH-J-DHAK. After that, the second, unmodified half of pMIT2.1 (NifB-ori) digested with SbfI was ligated with pTopoH-J-DHAK after digestion with SbfI, resulting in pSO018. This construct therefore encoded the translational fusion of NifD::linker(HA)::NifK with all of the other Nif genes as in pMIT2.1, the NifD amino acid sequence being unmodified with respect to the wild-type *K. oxytoca* sequence.

Introduction of the Y100Q mutation in the NifD coding region in pTopoH-J and pTopoH-J-DHAK was achieved by mutagenesis using primers 5'-GTCGTAACCAATACACGGGCGTTTCTGGCGTCGACTCTTTCGGCACG-3' (SEQ ID NO:117) and 5'-GCCCGTGTATTGGTTACGACGTCCCGCGCGAGAG TACTGGC-3' (SEQ ID

TABLE 13

Wild-type NifD polypeptide sequences at the sequence corresponding to *K. oxytoca* amino acids 97-102. The % amino acid sequence identity to SEQ ID NO: 18 is shown. The first three sequences comprising RRNYY (SEQ ID NO: 102) were predicted to be cleaved whereas the last three sequences were predicted to not be cleaved within this region.

| Organism | Genbank Accession No. | Length | % identity | Sequence at site |
|---|---|---|---|---|
| *Azospirillum brasilense* | WP_014239785 (SEQ ID NO: 148) | 479 | 69.7 | RRNYY (SEQ ID NO: 102) |
| *Azotobacter vinelandii* | WP_012698832 (SEQ ID NO: 149) | 492 | 71.8 | RRNYY (SEQ ID NO: 102) |
| *Sinorhizobium fredii* | WP_010875129 (SEQ ID NO: 150) | 504 | 63.8 | RRNYY (SEQ ID NO: 102) |
| *Chlorobium tepidum* | WP_010933201 (SEQ ID NO: 151) | 543 | 39.9 | RRNQT (SEQ ID NO: 105) |
| *Desulfovibrio vulgaris* | WP_015946243 (SEQ ID NO: 152) | 544 | 35.3 | RRNQT (SEQ ID NO: 105) |
| *Desulfotomaculum ferriducens* | WP_077714465 (SEQ ID NO: 153) | 539 | 38.4 | RRNKA (SEQ ID NO: 107) |

NO:118) to make the nucleotide substitutions T298C and C300A, changing the tyrosine (Y) codon TAC to the glutamine (Q) codon CAA. The resulting pTopoH-J vectors encoding unfused or fused NifD(Y100Q) were digested with SbfI and ligated with NifB-ori also digested with SbfI, creating pSO054 which was the reformed pMIT2.1 encoding NifD(Y100Q) and pSO055 which was the reformed pMIT2.1 encoding the NifD(Y100Q)::linker(HA)::NifK translational fusion polypeptide.

These genetic constructs were tested with the acetylene reduction assay in *E. coli*. pSO054 (encoding unfused NifD (Y100Q)) and pSO055 (encoding the fused NifD(Y100Q)::linker(HA)::NifK) produced ethylene at between 80% and 90% compared to their respective positive controls pSO005 and pSO018. This demonstrated that the Y100Q mutation did not compromise NifD activity in the context of the NifD::linker::NifK fusion polypeptide, with the activity being reduced only slightly.

Example 12. Solubility of Wild-Type NifD and Sequence Variants in Plant Mitochondria Example 3 describes experiments showing that many of the Nif polypeptides expressed in the form of an MTP::Nif fusion polypeptide for mitochondrial localisation were essentially insoluble or only sparingly soluble when expressed as a single polypeptide. The data also demonstrated that the process of targeting Nif fusion polypeptides to the mitochondria or the mitochondrial environment itself, or both, negatively influenced Nif polypeptide solubility for at least NifD, NifH and NifK, relative to cytoplasmic localisation. As solubility of nitrogenase protein components in the mitochondrial matrix is considered to be a prerequisite for functional reconstitution of nitrogenase in the mitochondria of eukaryotic cells, the inventors sought to determine the reasons for these observations on Nif polypeptide solubility. In particular, considering the importance of NifD, NifK and NifH, several approaches were tested to increase the solubility of these crucial polypeptides as described below. Insolubility in the mitochondria could be a consequence of incorrect protein folding, improper glycosylation or other post-translational modification, formation of aggregates or association with cell membranes, or a combination of these or other reasons.

Solubility of NifD Fusion Polypeptides—Effect of Promoter, MTP and NifD Sequences Initially, a set of plant expressed MTP::NifD polypeptides were tested for solubility, including whether N- and C-terminal modifications might influence solubility of the MPP-processed and unprocessed forms. For this purpose, a range of MTP::NifD constructs including some described above were infiltrated into *N. benthamiana* leaves via *A. tumefaciens* (Table 14). These constructs varied in the promoter for expression (e35S or SCSV S4 promoters) or in the encoded MTP or NifD polypeptide sequences (cleaved or non-cleaved at the secondary site). All of them contained a HA epitope tag fused to the C-terminus of the NifD polypeptide except for the polypeptide encoded by SN75 which had a HA epitope sequence fused to each of the N-terminus and C-terminus of NifD, thus flanking the NifD polypeptide. As a positive control for a soluble NifD polypeptide, the genetic construct SN33 (Example 3) encoding the non-mitochondrial targeted version of NifD was also infiltrated. In each case, the construct SN46 encoding the MTP-Su9::NifK was co-infiltrated with the NifD construct to enhance NifD accumulation. For each infiltration, proteins were extracted from each leaf spot and fractionated into soluble and insoluble fractions as described in Example 1, as well as retaining some unfractionated samples ("total protein"). Samples were analysed by loading them in adjacent lanes on SDS-PAGE gels and Western blotting using anti-HA to detect the MPP-processed and unprocessed MTP::NifD::HA and MTP::HA::NifD::HA polypeptides.

From the Western blots, the non-mitochondrially targeted HA::NifD polypeptide produced from SN33 was almost completely soluble (solubility score of 4, Table 14). In contrast the MTP-FAγ::NifD::HA polypeptide encoded by SN10 and its MPP-processed derivative were either not detected or barely detected in the soluble fraction, so were essentially insoluble. Modifying the promoter by substituting the SCSV S4 promoter (SN06) for the e35S promoter appeared to slightly increase the amount of soluble NifD::HA polypeptide. Changing the MTP by replacing the FAγ51 sequence with the CPN60 or Su9 MTP sequences (SN04, SN14) did not noticeably increase NifD solubility. A slight increase in solubility was observed when the Y100Q amino acid substitution was incorporated into the NifD amino acid sequence (SN114). None of these modifications had a major effect. However, the standout change in both NifD expression level and solubility occurred with SN75. At least 50% of the fusion polypeptide encoded by SN75, containing a HA epitope tag between the MTP-FAγ51 and the NifD sequence as well as a second, C-terminal HA epitope tag, was in the soluble fraction. Curiously, a different N-terminal epitope located between the MTP and NifD produced a different result—the construct encoding the MTP-CoxIV::TwinStrep::NifD:HA polypeptide (SN19) yielded mostly insoluble NifD polypeptide.

In view of the result with SN75, a similar construct was made (SN140) for NifK expression, having a Gly-Gly linked HA epitope tag placed between the MTP-FAγ51 (SEQ ID NO:36) and the NifK sequences. After infiltration of SN140 into *N. benthamiana* leaf cells, soluble, insoluble and total protein fractions were prepared. However in contrast to SN75, SDS-PAGE and Western blotting showed that the NifK fusion polypeptide remained insoluble. This result demonstrated that the insertion of the HA linker-GG into the fusion polypeptide had different effects on protein solubility depending on its Nif polypeptide, in this case NifD vs NifK.

Overall, these results confirmed that the process of targeting NifD polypeptides to the mitochondria or the mitochondrial environment itself negatively affected NifD solubility. They also showed that a N-terminal modification could overcome this problem at least in part.

TABLE 14

Solubility of MTP::NifD fusion polypeptides after expression in plant cells and processing of the MTP by MPP, as determined by SDS-PAGE and Western blot analysis of soluble and insoluble fractions. Solubility scores were given for each fusion polypeptide: 0, no soluble full length NifD polypeptide detected; 1, soluble polypeptide only just detected; 2, soluble polypeptide detected but <50% of total polypeptide; 3, soluble polypeptide detected at >50% of total polypeptide; 4, at least 90% of total polypeptide detected as soluble polypeptide.

| Construct ID | Promoter | MTP | Secondary cleavage | Epitope tag(s) | Solubility score |
|---|---|---|---|---|---|
| SN33 | e35S | None | Yes | 5'HA | 4 |
| SN10 | e35S | FAγ51 | Yes | 3'HA | 1 |
| SN06 | S4V2 | FAγ51 | Yes | 3'HA | 2 |
| SN04 | e35S | CPN60 | Yes | 3'HA | 0 |
| SN14 | e35S | Su9 | Yes | 3'HA | 0 |
| SN19 | e35S | CoxIV | Yes | 5'TwinStrep 3'HA | 0 |

TABLE 14-continued

Solubility of MTP::NifD fusion polypeptides after expression in plant cells and processing of the MTP by MPP, as determined by SDS-PAGE and Western blot analysis of soluble and insoluble fractions. Solubility scores were given for each fusion polypeptide: 0, no soluble full length NifD polypeptide detected; 1, soluble polypeptide only just detected; 2, soluble polypeptide detected but <50% of total polypeptide; 3, soluble polypeptide detected at >50% of total polypeptide; 4, at least 90% of total polypeptide detected as soluble polypeptide.

| Construct ID | Promoter | MTP | Secondary cleavage | Epitope tag(s) | Solubility score |
|---|---|---|---|---|---|
| SN53 | e35S | FAγ51 | Yes | 3'HA | 0 |
| SN58 | e35S | FAγ51 | Yes | 3'HA | 0 |
| SN75 | e35S | FAγ51 | Yes | 5'HA + 3'HA | 3 |
| SN114 | e35S | FAγ51 | No (Y100Q) | 3'HA | 2 |
| SN100 | e35S | FAγ51 | No | 3'HA | 0 |
| SN96 | e35S | FAγ51 | Yes | 3'HA | 2 |
| SN97 | e35S | FAγ51 | Yes | 3'HA | 2 |
| SN99 | e35S | FAγ51 | Yes (reduced) | 3'HA | 1 |

Solubility of NifD::Linker::NifK Fusion Polypeptides

Given these results, the effect on NifD solubility of another C-terminal extension was tested, namely the addition of a NifK sequence to provide a MTP::NifD::linker (HA)::NifK translational fusion (Allen et al., 2017). For this, the genetic construct SN68 was made that, like SN10, contained the strong e35S promoter for expression and a TMV-omega 5'-UTR region for efficient translation (Gallie et al., 1987). SN68 encoded a fusion polypeptide that had the MTP-FAγ51 with a Gly-Gly linker fused to the NifD N-terminus, then a 30 amino acid linker comprising the HA epitope tag sequence as previously used in pRA20, followed by the NifK sequence. This is shown schematically in FIG. 13. The NifD amino acid sequence was according to SEQ ID NO:18. The protein coding region was codon-optimised for expression in *N. benthamiana.*

This polypeptide was tested for solubility by infiltration of SN68 into *N. benthamiana* and isolation of soluble, insoluble and total protein fractions. SDS-PAGE with Western blot analysis was performed on the protein fractions. Two bands appeared on the blots (FIG. 14) which were slightly smaller than expected and probably represented cleavage at the secondary cleavage site within the NifD sequence. However, despite this, it was observed that most of the fusion polypeptides comprising the HA epitope and the NifK sequence were in the soluble fraction and only a small amount in the insoluble fraction (FIG. 14). This was the first time that the inventors had observed a mostly soluble NifK polypeptide.

Since the SN68-encoded polypeptide included the amino acid sequence that was susceptible to the secondary cleavage between amino acids 97-102 of NifD, a second, corresponding construct was made that contained the Y100Q amino acid substitution that had been shown to protect NifD from the secondary cleavage in mitochondria (Example 6). This genetic construct was designated SN159. In order to distinguish processed and unprocessed fusion polypeptides on the SDS-PAGE gels and thereby establish whether the fusion polypeptide encoded by SN159 was cleaved by MPP within the MTP sequence, a third construct was made identical to SN159 except that the MTP-FAγ51 sequence was modified with alanine substitutions that would render it resistant to mitochondrial processing by MPP. The same alanine substitutions within MTP were made as in the SN66 polypeptide. The third construct, SN160, was thus designed to produce a mMTP::NifD::linker(HA)::NifK fusion polypeptide which would not be processed by MPP and therefore yield a larger size product than a processed product from SN159. Further, a fourth, control construct was made, designated SN176, encoding a fusion polypeptide that lacked an MTP sequence and therefore was not targeted to the mitochondria but rather would be cytoplasmically located. For this construct, the MTP-FAγ51 sequence of SN159 was replaced with a 6×His tag linked by two glycine's to the NifD start codon. The 6×His+Gly-Gly sequence was very similar in size to the scar sequence predicted to be produced from MTP-FAγ51 after MPP-processing. It was predicted that if SN159 was processed correctly, the protein products from SN176 and SN159 would be of virtually identical length (1040 residues/116,251 Da for SN176, 1042 residues/ 116,317 Da for processed SN159).

These constructs SN68, SN159, SN160 and SN176 were infiltrated separately into *N. benthamiana* leaves and, after 5 days, three protein fractions were prepared from each infiltrated leaf region: total protein, soluble protein and insoluble protein, as described in Examples 1 and 3. The fractions were analysed by SDS-PAGE and Western blotting with HA-antibody. The SDS-PAGE gels were run for longer than normal in view of the large sizes of the polypeptides, to provide for better resolution.

Both SN159 and SN160 yielded a distinct polypeptide band having a molecular weight of approximately 120 kDa, with the main polypeptide from SN160 noticeably larger than that from SN159. The polypeptide from SN159 appeared to be the same size as that produced from SN176 which lacked the MTP sequence. From this, it was concluded that the polypeptide produced from SN159 was efficiently processed by MPP. In contrast, the polypeptides produced from SN68 were smaller and therefore were presumed to include a product from secondary cleavage within the NifD sequence. It was predicted that the polypeptide produced from SN68, not having the Y100Q substitution, would be subject to secondary cleavage and therefore produce a product of 933 residues/104,403 Da. A polypeptide band of that size was observed.

Most gratifying, and surprising to the inventors, was the result from the solubility analysis for the polypeptides produced from these constructs. More of the polypeptide produced from SN159 was observed in the soluble fraction than in the insoluble fraction. This was the first time the inventors had seen this for a mitochondrially targeted NifD polypeptide. Moreover, the processed MTP::NifD::linker (HA)::NifK polypeptide had been shown to function for NifD and NifK in the bacterial assay system (Example 11). Therefore, the inventors concluded that they had successfully modified the Nif polypeptides to produce a soluble, functional polypeptide having both NifD and NifK functions which was resistant to the secondary cleavage of the NifD sequence within the RRNYY sequence (SEQ ID NO:102).

Besides solubility, there were some important processing differences between the individually expressed NifD and the NifD::linker::NifK polypeptides. Firstly, unlike the NifD polypeptide from SN10 and its substitution variants (Example 6), the MTP::NifD::linker::NifK polypeptide that contained wild-type NifD sequence (SN68) was fully processed by MPP. Even though the ~48 kDa secondary cleavage product predominated from SN10 and some other NifD variant constructs, full length NifD polypeptide that had not been cleaved at the RRNYY (SEQ ID NO:102) site was always detected. Secondly, despite the use of the same MTP-FAγ51 for SN159, SN10 and other NifD variants, processing by MPP appeared complete for SN159, whereas both processed and unprocessed MTP-FAγ51::NifD were always observed when NifD was expressed on its own. Therefore, fortuitously, the fusion polypeptide from SN159 not only had resistance to the secondary cleavage in mitochondria and was predominantly soluble, it also appeared to be completely processed at the canonical site within the MTP sequence.

Isolation of the NifD-Linker-NifK Fusion Polypeptide

The NifD::linker(HA)::NifK fusion polypeptide encoded by SN159 was isolated from *N. benthamiana* leaf samples by the following immuno-selective method. Twelve leaf pieces each approximately 2 cm 2 in size that had been infiltrated with SN159 were ground in 10 mL solubility buffer. The solubility buffer contained: 100 mM Tris pH 8.0, 150 mM NaCl, 0.25 M mannitol, 5% (v/v) glycerol, 1% (w/v) PVP40, 0.1% (v/v) Tween 20, 2 mM TCEP, 0.2 mM PMSF and 10 μM leupeptin. The use of the low level of detergent (0.1% Tween20) was expected to result in extraction of only soluble proteins. The ground mixture was centrifuged at 5500×g for 15 min at 4° C. and the supernatant transferred to a clean tube. Anti-HA agarose beads (Sigma) were washed once with buffer containing 50 mM Tris pH 8.0 and 75 mM NaCl (TN buffer) and the beads then added to the supernatant to immuno-precipitate polypeptides having the HA epitope. The mixture was incubated for 1 h at 4° C. with slow rotation and the beads allowed to settle. A sample of the supernatant was retained as the "unbound proteins". The beads were washed 5 times with 1 mL of TN buffer each time, centrifuging each time at 1000×g for 2 min at RT to settle the beads. Finally, 60 μL of Laemmli buffer was added to the beads and the mixture heated at 95° C. for 5 min to release the bound proteins and denature them. Samples were loaded onto duplicate SDS-PAGE gels.

One of the gels was blotted onto a membrane and treated as a Western blot. An intense polypeptide band of the size expected for a MPP-processed NifD::linker(HA)::NifK polypeptide was observed as well as two less intense bands for smaller polypeptides that were considered to be degradation products, probably caused by protease cleavage at cryptic sites within NifD. Since the NifD sequence within the polypeptide had the Y100Q amino acid substitution, it was unlikely that the further protease cleavage/degradation was occurring at that site in NifD but rather at one or more new sites. The Western blot also showed two intense bands which were thought to represent the mouse Ig 50 kDa and 25 kDa polypeptides present in the anti-HA agarose beads used in the immuno-precipitation.

The second SDS-PAGE gel was stained with Coomassie stain and used to excise gel slices in the regions corresponding to the NifD::linker(HA)::NifK band (Sample 1) and the smaller degradation products (Sample 2). Proteins in these gel slices were digested with trypsin and analysed by LC-MS as described in Example 1. The extracted tryptic peptides were dried and resuspended in 30 μL of 1% formic acid. Initially, 5 μL of the tryptic peptides from each of the digests were injected on the 6600 Triple TOF MS using an Eksigent microHPLC (55 min). Residual tryptic peptides were stored at −20° C.

Data were processed using ProteinPilot against the species-specific UniProt Knowledgebase (UniProtKB) databases appended with the custom and adventitious databases: Uniprot-Nbenth+Custom Nif database+Common Repository of Adventitious Protein. Several specific peptides from the target polypeptide were positively identified in Sample 1, with 2 peptides from within the NifD sequence identified at the >95% confidence level and one other peptide from NifD and two other peptides within the NifK sequence identified with 94.9, 93.3 and 55.3% confidence levels. Two scar peptides derived from cleavage by MPP within the MTP sequence, ISTQVVR (SEQ ID NO:119) and SISTQVVR (SEQ ID NO:120), were not detected in the discovery data but were detected using the more sensitive targeted MRM on the 6500 Q-trap with 6 transition ions/peptide, at retentions times of 2.83 min and 3.15 min, respectively. Assessment of the dominant transition ions (+2y6) indicated that the peptide SISTQVVR (SEQ ID NO:120) was slightly more abundant than ISTQVVR (SEQ ID NO:119) in Sample 1.

It was concluded that Sample 1 indeed contained the MPP-processed NifD::linker(HA)::NifK polypeptide and that the polypeptide had been extracted from the *N. benthamiana* cells in a soluble form.

Sample 2 had a lower protein content and therefore the analysis was more difficult. Nevertheless, a single tryptic peptide was identified from within the NifD sequence and evidence for a second peptide from within NifD. The two scar peptides ISTQVVR (SEQ ID NO:119) and SISTQVVR (SEQ ID NO:120) were not detected in the discovery data and the more sensitive MRM on the 650 Q-trap. These data were consistent with the polypeptides in Sample 2 having resulted from an additional cleavage within the NifD sequence.

Enhancement of Solubility of NifK Polypeptide

The inventors tested whether the co-expression of NifD and NifK polypeptides from separate constructs would enhance the solubility of the NifK polypeptide relative to expression of NifK without NifD. The experiments described above with SN140 (MTP-HA::NifK) had shown that the polypeptide was essentially insoluble when expressed alone. Therefore, *N. benthamiana* leaves were infiltrated with a mixture of *A. tumefaciens* strains separately transformed with SN140 and either SN10, SN114 or SN117. SN10 encoded the wild-type NifD sequence whereas SN114 and SN117 contained amino acid substitutions in NifD to reduce the secondary cleavage. Protein extracts containing soluble and insoluble fractions as well as non-fractionated proteins were analysed by SDS-PAGE and Western blotting, as before.

The blots showed that there was a substantial increase in the solubility of the NifK fusion polypeptide expressed from SN140 when co-introduced with any of the NifD constructs. In the absence of NifD, NifK was barely detectable in the soluble fraction, whereas, in the presence of NifD, about equal amounts of NifK were found in the soluble and insoluble fractions. It was concluded that solubility of MTP::NifK polypeptide was increased by co-expression of NifD together in the same plant cell, even when expressed as separate polypeptides. This added to the observation described above that the MTP-NifD-linker-NifK fusion polypeptide provided for a more soluble form of NifK polypeptide. It was also concluded that both observations pointed to an association of the NifD and NifK polypeptides in the mitochondrial matrix—necessarily for the NifD-linker-NifK fusion polypeptide, but also when expressed as separate polypeptides.

Example 13. Purification of Plant Mitochondria Using a Fusion Protein and Magnetic Beads The inventors conceived of a way to rapidly purify plant mitochondria in order to better investigate the localisation and function of exogenous polypeptides in mitochondria such as Nif polypeptides which they desired to introduce into that subcellular organelle. Traditional methods for isolation of highly enriched plant mitochondria typically require freshly harvested leaf material to be processed with various buffers followed by a sequence of centrifugation steps to remove non-mitochondrial components (Millar et al., 2007). Those methods required substantial amounts of starting material (e.g. 20 to 40 grams of plant material) and the entire process takes many hours before the purified mitochondria were ready for use or analysis. More rapid isolation methods starting with smaller amounts of plant material have been developed (Millar et al., 2007). However those methods are best considered as mitochondrial enrichments as the products usually still contain other cellular components (Carrari et al., 2003).

In the *N. benthamiana* leaf assays described herein, 8-10 or more "infiltration zones" can be applied to a single leaf with each zone capable of expressing single or multiple (up to about 8) transgenes introduced via a mixture of *A. tumefaciens* transformants. Such leaf assays were ideal for rapid-throughput testing of gene combinations and were generally predictive of metabolic pathways eventually designed for expression in stably transformed plants. Generally each infiltration zone was only 2-3 cm in diameter, resulting in an overall fresh weight of 50 to 100 mg per infiltration zone. Small amounts of fresh material such as these were not suitable for traditional plant mitochondrial preparations where the numerous steps result in substantial loss of mitochondria. Therefore the inventors established a protocol for one-step purification of plant mitochondria in less than 10 min from small samples such as 50-100 mg.

The outer membrane of plant mitochondria has various protein import and export machineries. Metaxin is a plant-specific protein of about 40 kDa found on the outer membrane of plant mitochondria and is possibly involved in the recognition of proteins prior to import into the mitochondria (Lister et al., 2004). The protein appears to be specifically located to mitochondria. Structurally, metaxin has a single membrane spanning region located towards the C-terminus of the protein with the N-terminus of the protein likely to be located in the plant cytoplasm. A fusion of GFP to the N-terminus of metaxin resulted in plant mitochondria with a fluorescent signal located to the outer membrane (Lister et al., 2004). The inventors considered that the N-terminus of metaxin, if indeed located within the cytoplasm, was likely to be accessible to antibody binding and might allow for an affinity tag based purification method. It was further considered that placing the epitope at the N-terminus of a reporter polypeptide such as the GFP variant mTurquoise would help push the epitope into the cytoplasm. The Twin-Strep-tag was selected as the tag to add to the N-terminus. The Twin-Strep-tag Strepavidin interaction provided a specific and tight, yet reversible, binding with applications reported in affinity-based protein purification (Schmidt et al., 2013; Schmidt and Skerra, 2007). The Twin-Strep-tag as a translational fusion provided tight yet reversible binding to the engineered binding substrate StrepTactinXT, although it can also bind to streptavidin.

The inventors conceived of a fusion polypeptide with several components, shown schematically in FIG. 15. A genetic construct was designed and made encoding this fusion polypeptide. A combination of gene synthesis and the GoldenGate cloning methods was used to generate a genetic construct having a 35S promoter for expression in plant cells and encoding a TwinStrep-mTurquoise-TEV recognition sequence-metaxin fusion polypeptide (construct SN197, SEQ ID NO:121). The N-terminal Twin-Strep-tag epitope was included to enable antibody-mediated affinity purification, the mTurquoise component allowed for monitoring of the purification using confocal microscopy and also extended the N-terminus of metaxin further into the plant cytosol, and the TEV protease recognition sequence allowed in vitro TEV protease mediated cleavage of the polypeptide in order to release the plant mitochondria from the magnetic beads. Since wild-type metaxin becomes embedded in the outer membrane of the plant mitochondria, expression of the gene from SN197 in plant cells was thought to enable purification of this organelle, provided that the fusion protein would localise to the outer membrane of mitochondria. That was unknown until tested as described below.

*A. tumefaciens* cells containing SN197 were infiltrated into *N. benthamiana* leaves, together as part of a mixture of cells containing separate constructs for expression of the p19 silencing suppressor, MTP-FAγ::GFP (construct pRA01) and a cytoplasmically localised NifU::HA (SN211), each at an OD of 0.1 and therefore with a total OD of 0.4. Appropriate control mixtures having some but not all of the components, each with p19, were also infiltrated. After four days, infiltration zones were excised, providing samples of about 100 mg fresh weight in a 4 cm×2 cm leaf piece. The following steps were performed at 4° C. Leaf material was ground by hand in a mortar and pestle using 500 μL KPBS buffer. That buffer contained 5.07 g KCl and 0.68 g $KH_2PO_4$ in 500 mL deionised water, adjusted to pH 7.25 using 1M KOH. The slurry was centrifuged at low speed, 1000 g for 5 min, to pellet cell wall debris but leaving most mitochondria in suspension. 300 μL of supernatant was applied to 50 μL of a slurry of magnetic beads coated with streptavidin (2.8 μm diameter, smooth coated beads, DynalBeads MyOne C1 product code 65002) in a 1.5 ml Eppendorf tube, after the beads had been washed once with KPBS buffer. At set times, the magnetic beads in the mixture were collected to the wall of the tube using a magnet and the remainder of the liquid was carefully removed. The magnetic beads were then washed twice with 1 mL of KPBS, each time collecting them as before with the magnet, and finally resuspended in 50 μL KPBS. As a control sample, the same bead purification protocol was applied to *N. benthamiana* leaf extracts expressing pRA01 (encoding MTP-FAγ77::GFP), SN211 (encoding cytoplasmic NifU::HA) and p19 but without SN197.

Several experiments were carried out to determine optimised conditions for mitochondrial purification using the magnetic beads. Firstly, various TwinStrep-binding bead products were compared. It was observed that MyOne C1 beads were superior to Dynalbeads MyWay T1, M-280 and M-270 and also to an IBT StreptaxtinXT-Agarose product. A time course of binding of the SN197 sample to C1-beads was conducted using 1, 5, 10, 30 or 60 min incubation, finding that maximal and saturated binding occurred after 5 min. No GFP signal was detected after the purification protocol for the samples where SN197 was omitted from the infiltration mixtures, indicating that there was no non-specific binding of mitochondria to the magnetic beads. Confocal microscopy showed that the fluorescent signals from mTurquoise (SN197) and GFP (MTP-FAγ77::GFP) was greatest in incubations with MyOne C1 beads. Different concentrations of C1 beads were incubated with the extracts. Recovery of TwinStrep::mTurquoise::TEV::Metaxin and MTP-FAγ::GFP was dependent upon bead concentration, saturating at 50 μl of MyOne C1 bead slurry, so that amount was subsequently used.

The steps in the purification process were analysed via confocal microscopy to assess the presence of GFP and mTurquoise polypeptides and autofluorescence from plant chloroplasts. GFP and mTurquoise were detected at excitation wavelengths of 488 nm and 434 nm, respectively. The samples coming from infiltrations with the combination SN197, pRA01 and p19, when ground with KPBS buffer and subjected to low speed centrifugation, were enriched for GFP-fluorescing mitochondria. Only a few intact subcellular organelles other than mitochondria, such as chloroplasts and nuclei, and few fragments of cellular debris were observed. After washing of the beads using 2 mL of KPBS buffer and magnetic pull-down, confocal microscopy of the resulting suspension showed that fluorescing mitochondria were physically attached to the beads. After this step in the purification, other organelles and cell debris were not observed.

The purification process was also analysed via Western blot assays. To do this, polypeptides bound to the magnetic beads were released and denatured by the addition of 100 μL of Laemmli buffer (Example 1) and heating the samples at 95° C. Samples of the plant extract after grinding but before purification, labelled the "input sample", were also included in the Western blot analysis using antibody binding to GFP to detect MTP-FAγ::GFP and mTurquoise:metaxin polypeptides and anti-HA to detect the NifU::HA polypeptide. The Western blots showed that the TwinStrep::mTurquiose::TEV::Metaxin polypeptide was readily detected at a molecular weight of about 80 kDa, consistent with a single, intact translational fusion protein. A band was observed at about 30 kDa with the antibody to GFP for samples including pRA01, consistent with expected size of the mitochondrially targeted MTP-FAγ::GFP. Furthermore, a band at about 42 kDa was observed with the HA antibody from extracts having SN211, consistent with the expected size for the NifU::HA polypeptide. To check for non-mitochondrial proteins as potential contaminants, the abundance of the cytoplasmic protein α-tubulin was assessed with a corresponding antibody (Sigma Catalog No. T6074, clone B-5-1-2 monoclonal antibody). A specific band for this protein at about 52 kDa was only observed in lanes having the input sample; no α-tubulin signal was found in purified mitochondrial extracts showing that the purification was very good. It was concluded that use of the metaxin fusion polypeptide such as the one encoded by SN197 enabled the efficient and rapid, small-scale isolation and purification of plant mitochondria. It was also concluded that the fusion polypeptide was capable of being embedded within the outer membrane of plant mitochondria after expression of the genetic construct in the plant cells, and that the N-terminal TwinStrep epitope tag was accessible to streptavidin-coated magnetic beads.

When the isolated and purified mitochondria were analysed by proteomics, the samples were highly enriched for mitochondrial proteins, with very low levels of the small subunit of Rubisco. This further confirmed the high degree of enrichment by using the method.

Example 14. Association of NifS and NifU Polypeptides in Mitochondria of Plant Cells Nitrogenase components contain several metalloclusters that are essential for function. The nitrogenase protein for the molybdenum-based enzyme that performs the catalysis, also known as the molybdenum-iron protein, is an $\alpha_2\beta_2$-tetramer of the NifD and NifK polypeptides. In the active state, the catalytic tetramer contains a $[Fe_8S_7]$ complex, referred to as a P-cluster, at each α/β subunit interface and also a FeMo-cofactor (FeMo-co) within each a subunit. The nitrogenase reductase component, also known as the iron protein, is a homodimer of NifH polypeptides which contains a subunit-bridging $[Fe_4S_4]$ cluster. These Fe—S and P-clusters as well as the FeMoco are essential for transfer of electrons for the reduction of $N_2$. The synthesis and structure of nitrogenase is reviewed in Rubio and Ludden (2005).

The correct assembly and maturation of these metalloclusters is a complicated process and involves several accessory proteins (Rubio and Ludden, 2008). The first step of the maturation process is the generation of basic Fe—S clusters. This is catalyzed by NifS and NifU. In bacteria, these two proteins are required for full nitrogenase activity. The Fe—S clusters are then transferred to NifH, NifB and possibly NifD-NifK. NifS and NifU are not only involved in the assembly of the Mo-dependent nitrogenase, but also in the assembly of VFe and FeFe nitrogenase for synthesis of their Fe—S metalloclusters (Kennedy and Dean, 1992).

These activities have been well studied in bacteria. NifS is a pyridoxal phosphate (PLP, vitamin B6) dependent cysteine desulfurase which generates the inorganic sulphide required for Fe—S cluster synthesis from cysteine. The reaction produces alanine as a byproduct. The sulphide is then provided to NifU for the sequential formation of $[Fe_2S_2]$ and $[Fe_4S_4]$ clusters. The NifS enzyme functions in bacteria as a homodimer.

NifU provides a scaffold for $[Fe_4S_4]$ cluster formation, functioning as a homodimer in bacteria. Its N-terminal domain can bind one $[Fe_2S_2]$ cluster per monomer. The $[Fe_2S_2]$ clusters in the monomers can be reductively fused to form one $[Fe_4S_4]$ cluster per NifU dimer. The C-terminal domain of NifU can hold one $[Fe_4S_4]$ cluster per monomer. NifU then donates $[Fe_4S_4]$ clusters to NifB for processing into an 8Fe core on NifB, which is subsequently used for the synthesis of FeMoco. In a divergent pathway for the Fe—S clusters, one $[Fe_4S_4]$ cluster bound to the N-terminal or C-terminal scaffolding domains of NifU is transferred to apo-NifH for maturation of nitrogenase reductase, the NifH protein (Smith et al., 2005). It has been proposed that NifU also donates two $[Fe_4S_4]$ clusters to the NifD-NifK and that NifH condenses that pair of clusters into a mature P-cluster $[Fe_8—S_7]$ (Dos Santos et al., 2004).

It has been reported that NifS and NifU form a transient complex in bacteria, but not a tight complex (Yuvaniyama et al., 2000). NifU did not co-purify with NifS when NifS was purified from crude extracts prepared from *A. vinelandii* (Dos Santos et al., 2012). Furthermore, specific immunoprecipitation of either NifU or NifS did not result in co-precipitation of the other polypeptide. However, when isolated and purified NifU and NifS were combined in vitro and the mixture subjected to size exclusion chromatography, a heterotetrameric complex was detected. However, that experiment used purified proteins. No one has reported co-expressing NifS and NifU in plant cells and showing that they bind to each other, and NifS has not previously been co-purified with NifU from crude extracts.

As described in Examples 2-4, a NifU fusion polypeptide targeted to mitochondria was processed efficiently and accurately by MPP and a NifS fusion polypeptide was processed partially when produced from the genetic constructs SN32 and SN31, respectively. The fusion polypeptides had the MTP-FAγ51 for the mitochondrial targeting and a C-terminal HA epitope for detection by Western blotting. In one experiment, at least 90% of the processed NifU polypeptide accumulated in a soluble form in the plant mitochondria, although the amount varied somewhat from experiment to experiment, and some (<50%) of the processed NifS polypeptide accumulated in a soluble form (FIG. 3). Moreover, NifS and NifU polypeptides that retained the FAγ-scar9 motif at the N-terminus were demonstrated to be functional in *E. coli* for supporting nitrogenase activity, so both NifS and NifU remained active with a 9-amino acid N-terminal extension (Example 4).

Based on these successes, the inventors designed and carried out further experiments to test the production, processing, solubility and function of NifS and NifU when introduced into mitochondria in plant cells, as follows.

Construction of Plasmids Encoding Fusion Polypeptides with TwinStrep Epitopes.

Two genetic constructs were designed and made for expression of the encoded fusion polypeptides in plant cells, with mitochondrial targeting, one encoding a MTP-FAγ51::NifU::TwinStrep fusion polypeptide (SEQ ID NO:160) and the other a MTP-FAγ51::NifS::TwinStrep fusion polypeptide (SEQ ID NO:161). The amino acid sequences of the NifS and NifU regions of the fusion polypeptides were based on the amino acid sequences of the *Klebsiella oxytoca* proteins. The TwinStrep epitope (or tag) is abbreviated herein as "TS". The TwinStrep epitope was chosen as it has a high affinity for binding to StrepTactinXT resin under essentially physiological conditions and was thus ideally suited to the purification of proteins comprising the epitope, even at low concentrations. Furthermore, the elution conditions were gentle, which allowed the purification of protein complexes. The nucleotide sequences of the protein coding regions were codon optimized for improved expression in plant cells. Each genetic construct contained a 35S CaMV promoter sequence (Accession No. EC51288) for expression in the plant cells and a region coding for the 51 amino acids of MTP-FAγ51 fused 5' to the Nif coding region. These constructs were made using the GoldenGate assembly strategy (Weber et al., 2011; Engler et al., 2014), using analogous methods to those described above. These constructs were designated as SN166 for NifU and SN231 for NifS.

Another construct was made (SN167) which was the same as SN166 except that the MTP-FAγ51 region was mutated so that the encoded fusion polypeptide had alanine substitutions in the MTP sequence that would not allow for processing by MPP in mitochondria—the mutated region was designated mFAγ51.

Production of the Fusion Polypeptides in Plant Cells, their Processing and Solubility These genetic constructs along with others were tested for production and processing of the encoded polypeptides in plant cells and their solubility. As described in Examples 2 and 3, the construct SN31 encoding the MTP-FAγ51::NifS::HA fusion polypeptide was infiltrated into *N. benthamiana* leaves and protein extracts analysed by Western blotting with anti-HA antibody. Two polypeptide bands were observed on the blots. These corresponded in size with the unprocessed and MPP-processed polypeptides (Example 3). The processed and unprocessed NifS polypeptides were present in both the soluble and the insoluble protein fractions, indicating partial solubility. In contrast, when SN166 was introduced separately into *N. benthamiana* leaves, the MTP-FAγ51::NifU::TS fusion polypeptide was efficiently processed by MPP and the resultant scar9-NifU::TS polypeptide was almost fully soluble, where the scar9 included the Gly-Gly linker resulting from the cloning procedure used. As described in Example 4, NifS and NifU polypeptides having a N-terminal extension of 9 amino acids were active in providing nitrogenase function to *E. coli* when combined with the wild-type *K. oxytoca* proteins for the other Nifs. It has also been shown that a His-tag on the C-terminus of NifS in *A. vinelandii* does not interfere with diazotrophic growth and assembly of the FeS clusters on NifH (Smith et al., 2005).

The genetic constructs SN166 and SN167 were introduced separately into *N. benthamiana* leaves to confirm the effectiveness of the MTP sequence in the SN166-encoded polypeptide and the effects of the mitochondrial targeting on solubility and purification on a StrepTactinXT column. Proteins were extracted from the leaf tissues under non-denaturing conditions. The extraction buffer contained 100 mM Tris-HCl pH 8.0, 150 mM NaCl, 5% (v/v) glycerol, 2 mM TCEP, 1% (w/v) PVP (average MW 40 kDa) and 0.1% Tween 20. A 2 ml StrepTactinXT column was washed with buffer containing 100 mM Tris pH 8.0, 150 mM NaCl and 2 mM TCEP (wash buffer) and then loaded with the protein extract from SN166 or, separately, from SN167. After washing the column to remove unbound proteins, the bound proteins were eluted with wash buffer containing 50 mM biotin. Samples containing protein were concentrated to a volume of 200-500 μl using a 4 mL Amicon Ultra 10 kD MWCO concentrator. Aliquots of 20 μl were subjected to SDS-PAG electrophoresis and Western blotting using the antibody Streptactin HRP. Duplicate gels were stained with Coomassie blue to stain proteins.

The Western blots (FIG. 16, upper panel) showed that the NifU::TwinStrep fusion polypeptide had indeed been purified from the SN166 infiltrated tissues through the use of the StrepTactinXT column. The extract from the SN167 infiltrated tissues yielded a small amount of purified NifU::TwinStrep protein which appeared to be mostly of the unprocessed form. The corresponding gels stained with Coomassie blue (FIG. 16, lower panel) confirmed that a high degree of enrichment had occurred in the purification process.

Gel slices were cut out of the Coomassie stained gel and the polypeptides in those slices subjected to N-terminal amino acid analysis. This confirmed that the MTP-FAγ51::NifU::TwinStrep fusion polypeptide encoded by SN166 had been cleaved by MPP at the intended site in the MTP sequence, since the purified polypeptide had the N-terminal sequence resulting from the intended processing.

It was concluded from these data that the NifS and NifU fusion polypeptides that were targeted to the mitochondria were indeed expressed in the plant cells and processed in the mitochondria and were sufficiently in a soluble form to allow for purification.

Co-Expression of MTP::NifU::TwinStrep and MTP::NifS::HA in Plant Cells—NifS and NifU Associate in Plant Mitochondria To assess the expression, processing, solubility and stability, and to test for possible association of NifS and NifU fusion polypeptides when produced together in plant mitochondria, the genetic constructs SN31 (Example 2) encoding the MTP-FAγ51::NifS::HA polypeptide and SN166 encoding the MTP-FAγ51::NifU::TS polypeptide were co-infiltrated into *N. benthamiana* leaves using the method as described in Example 1. Protein extracts from the leaves were prepared and examined for the presence of NifS-NifU complexes by, first of all, performing affinity purification of NifU using a StrepTactinXT column and then testing for the co-purification of NifS polypeptide, using the method described in Example 1. Briefly, in a first experiment 12 g fresh weight of leaf material was processed under anaerobic conditions using an extraction buffer which was non-denaturing. A second, repeat purification started with 16.6 g fresh weight of leaf material. A third purification was carried out using 23 g fresh weight leaf material, where the buffer used was slightly different in that $Fe^{2+}$ and L-cysteine were added to 2 mM and 0.5 mM, respectively. In each experiment, the filtered lysate was passed through a StreptactinXT column (IBA Lifesciences) to retain the NifU polypeptide by its TS epitope. After washing the column, bound proteins were eluted with a buffer containing biotin and then concentrated as described above. Samples were retained at each step of the purification process, specifically samples from: (i) the total extractable protein at the start of the experiment, (ii) the pelleted cell debris after the first centrifugation, (iii) the input protein solution which was the fraction soluble in extraction buffer prior to passage over the column, (iv) the flowthrough fraction which did not bind to the column and (v) the concentrated eluate after elution with biotin. Samples were treated with SDS and heating to 95° C. before SDS-PAG electrophoresis and Western blotting.

The purified and concentrated NifU sample from the third purification contained some visible brown colour, indicating the presence of Fe—S clusters.

Duplicate aliquots of these samples were subjected to Western blot analysis with immunodetection using anti-Strep antibody or anti-HA antibody. Western blots from the first and third purification experiments are shown in FIGS. 17 and 18. The third purification experiment was done in the presence of 0.5 mM L-cysteine and 2 mM $Fe^{2+}$ supplementation in the extraction buffer. The Western analysis showed that both proteins were present in the soluble fraction after extraction from the leaf material. For NifS, both the processed and the unprocessed forms were present in the soluble fraction, while for NifU only the processed form was present, indicating efficient processing. The anti-Strep antibody detected a scar9-NifU-TwinStrep polypeptide in the crude samples as well as in the sample eluted from the column. The intensity of the signal from the eluate was very strong, indicating that the scar9-NifU-TwinStrep polypeptide had been purified and concentrated from the plant extracts. The mobility of the polypeptide in the gels upon electrophoresis was consistent with mitochondrial processing within the MTP sequence and the processing appeared to be almost complete.

When the membrane was exposed to the anti-HA antibody, which was approximately 20× more sensitive than the anti-strep antibody, a HA-tagged polypeptide was revealed at a size consistent with mitochondrial processing of the NifS polypeptide, i.e. scar9-NifS::HA. No unprocessed form of the NifS fusion polypeptide was detected in the sample. Since the NifS polypeptide used in this experiment did not contain a strep-tag, these results indicated that NifS and NifU formed a complex and that the NifS polypeptide was co-purified through its interaction with NifU. Significantly, it was observed that the processed form, scar9-NifS::HA, was greatly enriched in the eluate from the column relative to the unprocessed form when compared to the ratio of the two forms in the input sample prior to column purification. These observations were surprising to the inventors on the basis of reports from bacteria expressing NifS and NifU which had not demonstrated association of the polypeptides. They concluded that, under the anaerobic, non-denaturing conditions used in the experiment for protein extraction: (i) the NifS fusion polypeptide was co-purified with the scar9-NifU::TS polypeptide, indicating an association of the two polypeptides when co-expressed in the plant cells with mitochondrial targeting, (ii) the MPP-processed form of the NifS polypeptide, scar9-NifS::HA was the form that associated with the NifU polypeptide, and (iii) that both the processed NifU and the processed NifS polypeptides were produced in at least partly soluble form in the mitochondria to allow for the observed association. There were at least three possible explanations for observation (ii). Firstly, unprocessed MTP-FAγ51::NifS might not have been able to interact with NifU due to steric hindrance or misfolding. Secondly, the unprocessed form might not have been imported into the mitochondria where the NifU polypeptide was localized, and thirdly, the unprocessed form of NifS might not have been sufficiently soluble and was thus not able to interact with NifU, or any combination of these reasons.

The inventors were not aware of any previous reports of a NifS-NifU complex being isolated from plant mitochondria, or indeed from any cell.

The samples from the first purification were again subjected to denaturing SDS-PAGE. This time, the gels were stained with Coomassie blue (FIG. 18, panel C) and regions of the gel corresponding to the processed NifU and NifS polypeptides were analysed by proteomics to identify both the introduced polypeptides and any endogenous proteins that were co-purified on the column. The gel slices were treated as described in Example 1, including with trypsin digestion and analysed by LC-MS/MS. The analysis identified the presence of peptide ISTQVVR (SEQ ID NO:119) predicted for tryptic digestion of the scar peptide (SEQ ID NO:42) at the N-terminus, showing that both NifS and NifU were processed exactly at the predicted MPP-cleavage site within the MTP. Targeted MRM confirmed the identity of the tryptic peptides and thereby confirmed the presence of the cleaved polypeptides at the regions expected in the SDS-PAGE gel.

Size Exclusion Chromatography

To further confirm that a protein complex was formed between NifS and NifU, a sample of the concentrated eluate was applied to a high-resolution size exclusion chromatography using as a Superdex 200 Increase 3.2/300 column. Calibration of the column was carried out with native protein size markers (Biorad Gel Filtration Standard Cat. #151-1901). Fractions from the column were further analysed by electrophoresing samples on denaturing SDS-PAGE. The chromatogram and Western blot analysis showed that NifS and NifU formed a complex, as the NifS protein eluted at a higher molecular weight than expected for NifS. This indicated that a heterotetramer formed by association of 2 NifS and 2 NifU polypeptides.

UV/Visible Spectroscopy Detected Iron-Sulfur Clusters on NifU

Eluate containing StreptactinXT column-purified NifU and NifS from a fourth experiment was applied to a PD10 column (GE Healthcare) equilibrated in 50 mM Tris-HCl pH 8.0 and 300 mM NaCl to remove biotin and excess $Fe^{2+}$ and cysteine. A spectrum was obtained using an anaerobic cuvette with a screw cap and septum with a 1 cm pathway on a Cary 100 Bio UV/visible spectrophotometer. The spectrum showed one main peak at 280 nm, as expected for proteins due to the absorption from tryptophan, phenylalanine and cysteine. Additionally, a second peak was observed at 325 nm and a shoulder at 420 nm and 460 nm, which indicated the presence of Fe—S clusters on NifU.

Further Tests for Association of NifS and NifU Polypeptides by Purification First of All of NifS.

As described above, a genetic construct was designed and made that encoded a MTP-FAγ51::NifS::TS fusion polypeptide, designated SN231, for transient expression in plant cells. This construct was analogous to SN166 that encoded the MTP-FAγ51::NifU::TS fusion polypeptide except that it had the NifS sequence rather than the NifU sequence. SN231 and SN32 were co-infiltrated into *N. benthamiana* leaves as for the SN31/SN166 combination described above, and protein extracts are prepared as described above. The supernatant was passed through a StrepTactinXT column to purify NifS fusion polypeptide containing the TwinStrep epitope. Samples of the eluted and concentrated proteins were analysed by Western blotting and are probed with anti-Strep and anti-HA antibodies. The blot (FIG. 19) showed the presence of a processed scar9::NifU::HA polypeptide in the eluate as well as the scar9::NifS::TS polypeptide, again indicating the association of processed NifS and NifU polypeptides in the extracts from the plant cells.

The eluate from this purification was also subjected to size exclusion chromatography as described above, and the fractions were analysed by Western blot using anti-strep antibody and anti-HA antibody. The Western blot analysis confirmed that NifU and NifS formed a complex.

In the future, the purified NifS and NifU polypeptides will be analysed by Inductively Coupled Plasma Mass Spectrometry (ICP-MS) to determine the iron content of the protein, and with Mossbauer spectroscopy to confirm the presence and the type and redox status of Fe—S clusters bound to the polypeptides.

Cluster formation can be shown in in vitro reactions with added $Fe^{2+}$ and L-cysteine. In one experiment, wild-type NifH polypeptide is purified from *A. vinelandii* and the Fe—S clusters removed by chelation to produce apo-NifH polypeptide. Wild-type NifD-NifK complex is also purified from *A. vinelandii*. In vitro ARA assays show that the purified NifU polypeptide purified from *N. benthamiana* cells as described above is able to donate Fe—S clusters to the apo-NifH polypeptide, thereby reconstituting NifH activity as the nitrogenase reductase for ARA activity.

Example 15. Production of Homocitrate by Expression of NifV in Plant Cells

Introduction (R)-2-hydroxy-1,2,4-butane-tricarboxylic acid, referred to herein and commonly known as homocitrate, is required for the activity of all known nitrogenases, namely the molybdenum (Mo—Fe), vanadium (V—Fe) and iron (Fe—Fe) nitrogenases respectively (Hu and Ribbe, 2016). The nitrogenase protein for the Mo-based enzyme that performs the reduction of nitrogen is an $\alpha_2\beta_2$-tetramer of the NifD and NifK polypeptides that contains a FeMo cofactor (FeMoco) within each a subunit as well as a $[Fe_8S_7]$ complex, referred to as a P-cluster, at each $\alpha/\beta$ subunit interface. The FeMoco which comprises a homocitrate molecule is essential for the reduction of $N_2$.

Homocitrate (HC) forms part of the essential nitrogenase cofactors FeMoco, FeVco and FeFeco in bacteria expressing nitrogenase, binding to the Mo, V or Fe atoms of the cofactor through its 2-hydroxy and 2-carboxy groups. FeMoco, FeVco and FeFeco are at the sites of catalysis and the three cofactors are thought to bind, activate, and reduce $N_2$ in largely the same way. FeMoco, also known as the M-cluster of the Mo-nitrogenase, contains $[Fe_4S_3]$ and $[MoFe_3S_3]$ subclusters joined through three bridging inorganic sulfide atoms referred to as "belt sulphides" and one interstitial carbide atom (Hu and Ribbe, 2016) to form the cofactor having the chemical formula HC—Mo—$Fe_7$—$S_9$—C. The vanadium-nitrogenase including its cofactor FeVco has recently been crystallised (Sippel and Einsle, 2017; Sippel et al., 2018). FeVco has a nearly identical metal-sulfur core to FeMoco except for the substitution of a vanadium atom for the molybdenum atom and a carbonate ion instead of one of the belt sulfides. FeVco is therefore a [HC—V—$Fe_7$—$S_8CO_3$—C] cluster with the homocitrate molecule liganded to the vanadium atom. In the case of the *Azotobacter vinelandii* VnfD polypeptide that is part of the catalytic V-nitrogenase enzyme (VnfDGK), the homocitrate of the metallocluster is coordinated to amino acids C257 and H423 of VnfD. These ligand amino acids are highly conserved relative to NifD of the Mo-nitrogenase. The Mo- and V-nitrogenases differ in reactivity to carbon monoxide (CO) which inhibits the former but is converted to hydrocarbons by the latter (Sippel et al., 2018). Homocitrate similarly forms part of FeFeco and the cofactor binds to the AnfD polypeptide in analogous fashion. The Fe-nitrogenase has lower $N_2$-reducing activity compared to the V-nitrogenase which in turn is less active than Mo-nitrogenase, suggesting that organisms that are equipped with all three systems resort to a preferential expression that depends on relative Mo, V and Fe bioavailability. For example, the bacterium *A. vinelandii* can express each of the Mo-, V- and Fe-nitrogenases, but each one under different nutrient conditions, the V-nitrogenase only under molybdenum-limited conditions, and the Fe-nitrogenase only when both Mo and V are limiting.

In free-living nitrogen-fixing bacteria, homocitrate is produced by the NifV gene product, an enzyme that condenses acetyl-CoA and α-ketoglutarate (αKG) to make the homocitrate (Zheng et al., 1997). NifV is the only gene product required for homocitrate synthesis in these bacteria. The homocitrate synthase activity can be measured by enzyme assays as described in Zheng et al. (1997). *A. vinelandii* nifV mutants are unable to produce any form of fully-active nitrogenase, but the activity of all three nitrogenases was restored by the addition of homocitrate to the growth medium (Zheng et al., 1997). In the absence of added homocitrate, the mutant nifV bacteria exhibited abnormal nitrogenase-mediated reactions including altered substrate specificity and inhibitor specificity. The mutant bacteria reduced acetylene and evolved $H_2$, but did not reduce $N_2$ (McLean and Dixon, 1981). These altered activities were due to the incorporation of endogenous molecules related to homocitrate such as citrate within the metallocluster (Hoover et al., 1988). It is thought that homocitrate is unique in its ability to correctly place the substrate $N_2$ within the active site and is therefore required for fully and properly functional nitrogenases.

The *A. vinelandii* NifV is the best studied NifV (Zheng et al., 1997; SEQ ID NO:163), referred to herein as AvNifV. Over-expression of the AvNifV polypeptide in *E. coli* generated a dimeric protein having a molecular weight of approximately 89 kDa, with the monomer having a molecular weight of 44 kDa. The enzyme was oxygen labile, losing approximately 50% of its activity after two hours exposure to air having 21% oxygen. This oxygen sensitivity of its condensing activity was not impacted by addition of $MoO_4^{-2}$, $Fe^{2+}$ or $Mg^{2+}$ to the reaction medium. Reaction kinetics indicated that AvNifV had a Km of 0.06 mM for acetyl-CoA and 2.24 mM for αKG. NifV can also condense acetyl-CoA to other keto-acid substrates such as oxaloacetate and α-ketoadipate (Zheng et al., 1997).

In legume-*Rhizobia* symbioses such as between *Lotus japonicus* and *Mesorhizobium loti*, the bacterial partner does not have homocitrate synthase activity encoded by a NifV gene. Instead, the host plant *L. japonicus* expresses a homocitrate synthase, LjFEN1, to supply this essential organic acid for nitrogen fixation by the *Rhizobia* in the nodules (Hakoyama et al., 2009). The LjFEN1 polypeptide is rather distantly related to *A. vinelandii* NifV, the two polypeptides having about 36% amino acid identity. LjFEN1 has 540 amino acid residues and a molecular weight of approximately 58.6 kDa. No signal peptide sequence was found in the gene encoding LjFEN1, indicating that it was probably a cytosolic protein. *L. japonicus* has two orthologues of FEN1, namely Accession Nos. AK339695 and AK339656, which are 81% and 71% identical in amino acid sequence to LjFEN1, respectively. Phylogenetic analysis suggested LjFEN1 evolved from AK339695. In symbioses between *L. japonicus* plants mutated in LjFEN1 and *M. loti*, fully functional nodules with detectable nitrogenase activity were produced if the microsymbiont carried a heterologous copy of the AvNifV or the FEN1 gene.

In contrast to many other eukaryotes, fungi such as the yeast *Saccharomyces cerevisiae* produce homocitrate as an intermediate in the lysine biosynthesis pathway through a NifV-like enzyme (Thomas et al., 1966; Verhasselt et al., 1995). Yeast mutants in the gene ORF D1298 encoding the NifV-like enzyme which functions in that pathway were complemented by over-expression of LjFEN1.

Genomic analyses of numerous plant species indicate that only those plants involved in symbiotic relationships with bacteria express an active homocitrate synthase, such as LjFEN1, and that NifV-like genes are not found non-leguminous plants (Hakoyama et al., 2009). Additionally, no metabolic pathway has been identified in higher plants for synthesis of lysine through homocitrate as an intermediate. Consistent with these reports, examination of the genome sequence of *N. benthamiana* (Naim et al., 2012) did not identify any homologues of NifV or FEN1. The closest gene identified in terms of homology was a gene (QUT *N. benthamiana* Genome and Transcriptome DB Accession No. P72026) that was homologous to a gene encoding the enzyme 2-isopropylmalate synthase (EC. 2.3.3.13) involved in leucine biosynthesis but not in homocitrate synthesis. The inventors concluded that *N. benthamiana* did not normally produce homocitrate by NifV or FEN1-like enzymes. Other than a single report related to vanilla pods (Palama et al., 2009), the inventors are not aware of any report of homocitrate being produced in non-legumes, including no reports for tobacco, cotton and cereals. There are no known reports of FEN1 or NifV being used to produce homocitrate in non-legumes.

Results

As described in Examples 2-4 above, a NifV fusion polypeptide based on the *K. oxytoca* amino acid sequence (KoNifV; SEQ ID NO:13) and targeted to mitochondria in plant cells was processed efficiently (>90%) and accurately by MPP when produced from the genetic construct SN142. The fusion polypeptide as translated upon expression of the genetic construct had an N-terminal MTP-FAγ51 for mitochondrial targeting and a C-terminal HA epitope for detection by Western blotting. Moreover, the NifV polypeptide based on the *K. oxytoca* amino acid sequence with the FAγ-scar9 motif fused at the N-terminus was demonstrated to be functional in *E. coli* for supporting near wild-type levels of nitrogenase activity, providing about 90% of activity in the MIT2.1 system relative to wild-type, so the NifV fusion polypeptide remained active with a 9-amino acid N-terminal extension (Example 4). However, the processed KoNifV polypeptide accumulated in an insoluble form in the plant mitochondria (FIG. 3).

The insolubility of the *K. oxytoca* NifV fusion polypeptide in *N. benthamiana* cells was considered by the inventors to be a problem for constituting nitrogenase function in plant cells since an essentially insoluble polypeptide was unlikely to provide sufficient enzymatic function for the synthesis of homocitrate. Therefore, the inventors sought more soluble NifV polypeptides by expression of natural NifV and other HCS-like variants fused to the same MTP and HA epitope sequences for mitochondrial localisation and detection.

Selection of Variant NifV Sequences

Sequence databases were searched for NifV variant sequences and other homocitrate synthase (HCS) enzymes related to the KoNifV amino acid sequence. The sequences were from a wide variety of bacteria and yeasts, including some from thermotolerant bacteria. NifV polypeptide sequences were extracted from the UniProt database using NifV as the query, accessing the database on 14/09/2018. 2044 NifV/HCS-like amino acid sequences were identified and extracted from the database. To select and test representative sequences, a protein network was established based on protein similarity, resulting in the clustering of NifV?HCS-like polypeptides based on sequence similarity. To do this, the amino acid sequences were aligned with MAFFT—Multiple alignment program for amino acid or nucleotide sequences—software, version 7 using the server mafft.cbrc.jp/alignment/server/large.html?aug31. The strategy G-large-INS-1 for less than 10000 sequences, shorter than 5000 sites, was used. The output was converted from .pir to .phy format using an online sequence converter (www.hiv.lanl.gov/content/sequence/FORMAT_CONVERSION/form.html).

Cytoscape (https://cytoscape.org) software was used to visualize clusters of sequences that were related to each other. In order to calculate distance matrices and prepare the data in the input files for Cytoscape, the PHYLIP/protdist program was used to calculate the Kimura distance matrix for the NifV sequences. The output file was modified using Notepad to prepare an appropriate input format for the aMATReader in Cytoscape. The distance matrix was then modified in Excel to decrease file size and define subgroups: all values that were greater than 0.1 were removed, thereby creating subgroups, redundant sequences were removed.

A representative HCS-like amino acid sequence was selected from each of six clusters of HCS and related sequences. Additionally, three *Methanocaldococcus infernus* HCS-like sequences were selected because they were considered more likely to be thermotolerant and possibly remain stable and soluble, as well as NifV sequences from *K. oxytoca* (KoNifV) and *A. vinelandii* (AvNifV) as comparisons. A variant of KoNifV (Accession No. WP_004138778; SEQ ID NO:164) was also identified, based on the amino acid sequence in the bacterial expression construct MIT2.1. The amino acid sequences of KoNifV in EC38020 and NifV in MIT2.1 differed in amino acids 155-157 and 232-236 relative to SEQ ID NO:13 but were otherwise identical. A *Saccharomyces cerevisiae* HCS (ScHCS) sequence was also selected, corresponding to the *S. cerevisiae* gene Lys21p, referred to as D1298 in Verhasselt et al. (1995). A homologous enzyme in *S. cerevisiae*, Lys20, appeared to be more active and less negatively regulated by lysine.

The selected sequences are listed in Table 15 along with the percentage identity to KoNifV from EC38020 (SEQ ID NO:13). A sequence alignment for the amino acid sequences is shown as FIG. 20, which shows highly conserved amino acids. Clearly the selected sequences covered a wide range of NifV/HCS-like sequences.

TABLE 15

NifV and NifV/HCS-like sequences selected for testing.

| Sequence ID | Genbank accession | Organism | Sequence identity (%) | SEQ ID NO |
|---|---|---|---|---|
| KoNifV | AFI71011 | *Klebsiella oxytoca* | 100 | 13 |
| KoNifV (MIT2.1) | WP_004138778 | *Klebsiella oxytoca*, variant NifV in pMITv2.1 | 98 | 164 |
| AvNifV | CP001157 | *Azotobacter vinelandii* | 42 | 163 |
| TbHCS | CP002466 | *Thermoanaerobacter brockii* | 56 | 206 |
| TpHCS | CP002028 | *Thermincola potens* | 65 | 207 |
| ScHCS | CP036483 | *Saccharomyces cerevisiae* | 43 | 208 |
| NsHCS | CP007203 | *Nodularia spumigena* | 43 | 209 |
| MaHCS | AE010299 | *Methanosarcina acetivorans* | 55 | 210 |
| CtHCS | AE006470 | *Chlorobaculum tepidum* | 27 | 211 |
| MiHCS1 | ADG13125 | *Methanocaldococcus infernus* | 44 | 212 |
| MiHCS2 | ADG13175 | *Methanocaldococcus infernus* | 42 | 213 |
| MiHCS3 | ADG14004 | *Methanocaldococcus infernus* | 40 | 214 |
| LjFEN1 | BAI49592 | *Lotus japonicus* | 30 | 215 |

Construction of Plasmids Encoding Fusion Polypeptides with NifV and NifV/HCS-Like Sequences.

Fusion polypeptides having the selected NifV and NifV/HC S-like sequences, listed in Table 15, and having MTP-FAγ51 at each N-terminus were then tested for their ability to be expressed in plant cells, their processing by MPP in the mitochondria and their production of homocitrate. The solubility of each mitochondrially-targeted polypeptide was also tested using the method described in Example 1. These experiments were done by generating genetic constructs encoding these sequences and expressing them in the *N. benthamiana* leaf system. Each encoded fusion polypeptide had an identical HA epitope for detection with anti-HA antibody, located between the MTP and NifV/HCS-like sequence, except for the KoNifV fusion polypeptide encoded by SN142 which had the HA epitope at its C-terminus (Table 15). This experiment was therefore designed to test whether the N- or C-terminal extensions to each NifV/HCS-like sequence would still allow for production of homocitrate in the plant cells. A parallel set of genetic constructs (Table 15) was made to express cytoplasmically-targeted polypeptides lacking the MTP-FAγ51 sequence at the N-termini but instead having a N-terminal HA epitope. Each fusion polypeptide was thereby compared for its expression and function to its corresponding cytoplasmic polypeptide lacking the MTP sequence.

A DNA sequence for each fusion polypeptide was synthesised using codon optimisation for plant expression and compatible with GoldenGate cloning protocols. The genetic constructs were made using a modular cloning system by the GoldenGate protocol. Except for SN142, the DNA components were, in the 5' to 3' order for assembly: the 35S CaMV promoter (EC51288), a chimeric sequence coding for the MTP-FAγ51 and HA epitope followed by a GG linker (EC38095), a codon-optimised coding regions for the NifV/HCS-like variant, and finally a CaMV 3' polyadenylation region/transcription terminator (EC41414). The components were assembled into the desired genetic constructs and inserted into expression vectors using Type IIS restriction cloning according to GoldenGate assembly (Weber et al., 2011). The resultant constructs are listed in Table 16. Molecular weights of the encoded fusion polypeptides before and after MPP-processing were calculated using ExPASy compute pI/Mw (web.expasy.org/compute_pi/) with monoisotopic setting.

TABLE 16

Genetic constructs for transient expression of NifV/HCS-like fusion polypeptides in *N. benthamiana* leaves or in stably transformed plants. MTP, FAγ51 mitochondrial targeting peptide; Mw, molecular weight; na, not applicable.

| Construct ID | Fusion polypeptide | Length (amino acids) | Mw (Da) | Processed length (amino acids) | Mw (Da) |
|---|---|---|---|---|---|
| SN142 | MTP::KoNifV::HA | 445 | 48088 | 403 | 43529 |
| SN248 | MTP::HA::TbHCS | 447 | 49336 | 405 | 44777 |
| SN249 | MTP::HA::TpHCS | 442 | 48521 | 400 | 43963 |
| SN250 | MTP::HA::ScHCS | 504 | 55488 | 462 | 50929 |
| SN251 | MTP::HA::NsHCS | 440 | 47715 | 398 | 43156 |
| SN252 | MTP::HA::MaHCS | 440 | 48316 | 398 | 43758 |
| SN253 | MTP::HA::CtHCS | 440 | 47931 | 398 | 43372 |
| SN254 | MTP::HA::AvNifV | 448 | 48395 | 406 | 43836 |
| SN255 | MTP::HA::MiHCS1 | 575 | 62818 | 533 | 58259 |
| SN256 | MTP::HA::MiHCS2 | 554 | 60106 | 512 | 55548 |
| SN257 | MTP::HA::MiHCS3 | 460 | 50986 | 418 | 46428 |
| Cytoplasmic constructs | | | | | |
| SN212 | KoNifV::HA | 392 | 42362 | na | na |
| SN258 | HA::TbHCS | 395 | 43741 | na | na |
| SN259 | HA::TpHCS | 390 | 42926 | na | na |
| SN260 | HA::ScHCS | 452 | 49892 | na | na |
| SN261 | HA::NsHCS | 388 | 42120 | na | na |
| SN262 | HA::MaHCS | 388 | 42721 | na | na |
| SN263 | HA::CtHCS | 388 | 42336 | na | na |
| SN264 | HA::AvNifV | 396 | 42800 | na | na |
| SN265 | HA::MiHCS1 | 523 | 57223 | na | na |
| SN266 | HA::MiHCS2 | 502 | 54511 | na | na |
| SN267 | HA::MiHCS3 | 408 | 45391 | na | na |
| SN70 | HA::LjFen1 | 552 | 59962 | na | na |

Expression in *N. benthamiana* Leaves and Testing for Solubility and Homocitrate Production Each genetic construct was introduced into *N. benthamiana* leaves via *Agrobacterium* using the methods as described in Example 1. Leaf samples were harvested 5 days post-infiltration and protein extracts made and analysed by Western blot methods using anti-HA antibody (FIGS. 21 and 22). Parallel leaf samples were harvested for metabolite extraction and measurement of homocitrate levels by a GC-MS/MS technique as described below.

All of the tested fusion polypeptides were readily detected by the Western blotting analysis and so were expressed efficiently in the plant cells, for both the mitochondrially-targeted and the cytoplasmically-targeted polypeptides. As observed previously (Example 3), the mitochondrially-targeted *K. oxytoca* NifV fusion polypeptide was produced at good levels and processed efficiently by MPP but was essentially insoluble in the plant cells. In similar fashion, the mitochondrially-targeted MiHCS2, MiHCS3 and MaHCS fusion polypeptides were also expressed at good levels and appeared to be processed but insoluble. The NsHCS and MiHCS1 fusion polypeptides appeared to be processed but were only partially soluble. In contrast, the TbHCS, TpHCS and CtHCS fusion polypeptides appeared to be processed and essentially soluble when targeted to the mitochondria. The mitochondrially-targeted *S. cerevisiae* HCS (ScHCS) appeared to be expressed at a lower level than the other polypeptides but was efficiently processed and soluble. The *Azotobacter vinelandii* NifV (AvNifV) fusion polypeptide was expressed at a good level, efficiently processed and was partly soluble (~50%) when targeted to plant mitochondria using MTP-FAγ51. Likewise, the *Chlorobaculum tepidum* HCS (CtHCS) was well expressed, efficiently processed and soluble when targeted to plant mitochondria using MTP-FAγ51.

In contrast to the mitochondrially-targeted polypeptides, most of the cytoplasmically-targeted polypeptides were soluble or at least partially soluble, including the KoNifV polypeptide (FIG. 22). The inventors concluded that the insolubility was due in some cases to the mitochondrial localisation, and that polypeptides could show different levels of solubility in the two locations. In general, the signal intensities of the cytoplasmically targeted polypeptides were lower compared to the corresponding mitochondrially targeted polypeptides. The exceptions were ScHCS, MiHCS1 and KoNifV, where the cytoplasmically targeted polypeptides appeared to have better expression levels compared to the counterparts that were targeted to the mitochondria.

Gas Chromatography-Tandem Mass Spectrometry (GC-MS/MS) Analysis to Measure Homocitrate Levels To measure homocitrate levels in the leaf samples after gene introduction and thereby demonstrate HCS activity for either the mitochondrially-targeted or cytoplasmically-targeted fusion polypeptides, a GC-MS/MS method was developed and validated, as follows. Polar metabolites including any homocitrate were extracted into 10 volumes per wet leaf weight (v/w) of extraction solution which contained in methanol:$H_2O$ (1:1 v/v): 22 μM D4 citric acid (Cambridge Isotope Laboratories Inc., cat. no. DLM-3487), 36 μM 13C fumaric acid (Cambridge Isotope Laboratories Inc., cat. no. CLM-1529), 23 μM 13C sorbitol (Cambridge Isotope Laboratories Inc., cat. no. CLM-1565), 31 μM D3 aspartic acid (Cambridge Isotope Laboratories Inc., cat. no. DLM-832), and 54 μM D5 glycine (Cambridge Isotope Laboratories Inc., cat. no. DLM-280) as internal standards. The leaf samples were homogenised with the extraction solution in 1.5 ml microfuge tubes using a Qiagen tissue lyser and 3 mm tungsten carbide beads. The leaf samples were homogenised at 1/20 rpm twice for three minutes while rotating the tube positions within racks that were pre-chilled to −80° C. After homogenisation, the samples were centrifuged at 10,000×g for 30 minutes at 4° C. to remove solid matter, and the resulting supernatant containing the metabolites was collected and stored at −80° C. until analysis. Thirty μl of each supernatant was dried in a vacuum concentrator for metabolite derivatization, which was carried out manually as follows. To each dried sample, 10 μl of 20 mg/ml methoxyamine hydrochloride in pyridine was added. The solutions were incubated at 37° C. for 90 min with vortexing at 15 min intervals, then 15 μl of N,O-bis(trimethylsilyl) trifluoroacetamide+trimethylchlorosilane (BSTFA+TMCS) (99:1) was added and the solution again incubated at 37° C. for 30 min with vortexing at 15 min intervals, then 5 μl of alkane mix (n-dodecane, n-pentadecane, n-octadecane, n-eicosane, n-pentacosane, n-heptacosane, n-dotriacontane at 0.029% w/v each) was added and mixed. Each derivatization mix was left at ambient temperature for 60 min before GC-MS analysis.

The GC-MS metabolite analysis was conducted on a Shimadzu TQ8050 gas chromatography tandem mass spectrometer fitted with a DB-5 capillary column (30 m×0.25 mm ID×1 μm film thickness). One μl was injected at 1:10 split mode onto the column with the inlet heated to 280° C. and helium as carrier gas. The oven temperature was set to 100° C., held for 4 min, then increased to 320° C. at 10° C./minute, and held for 11 min. The mass spectrometer interface was heated to 280° C., ion source at 200° C. Masses between 45 and 600 were measured in full-scan mode. For multiple reaction monitoring (MRM) mode, the Shimadzu MRM library containing 467 compounds with target and qualifier ions between particular retention time windows, set for each metabolite derivative, was used for detection with the same GC and MS parameters. Multiple reaction monitoring (MRM) parameters were developed for homocitric acid 4TMS and included in the MRM analysis protocol by scanning m/z=287, 243, 147, and 73 across collision energies 3-45 V. Based on the scan, the following two fragmentation patterns were used for detection at retention index 1931: target ions m/z=287>73 at 21 volts, and reference ions m/z=287/243 at 9 volts. To prevent contamination of the injection syringe from one sample to the next, the syringe was washed five times each with hexane followed by a 1:1 v/v solution of ethylacetate and acetone, followed by a rinse with pyridine to remove any residual homocitric acid 4TMS from the previous sample. Putative compounds identified in MRM mode were crosschecked against the chromatogram obtained in full-scan mode, where the mass spectrum at the particular retention time was searched against the NIST 17 library and Golm metabolome database (Hummel et al., 2007).

Results for Homocitrate Production in Plant Cells

Homocitrate was readily detected and measured by this method in many of the samples. The control *N. benthamiana* leaf samples which had been infiltrated with the p19 construct alone without a NifV/HCS sequence showed low, background levels of homocitrate. The GC-MS/MS method was exceedingly sensitive, so it was not surprising that a low level of homocitrate was identified. The signal in the control plants was considered genuine since the method used two diagnostic ions and retention time against an authentic commercial standard. There was no background noise for those particular ions in quality control (QC) standard mixes or extraction buffer only.

Non-infiltrated leaf samples and leaves inoculated with a gene encoding GFP also showed low, background levels of homocitrate. A baseline peak area was selected which had the highest amount of peak area of the three negative controls (GFP, p19, wild-type). For each sample infiltrated with a NifV/HCS gene, the baseline homocitrate target ion peak area was subtracted from the peak area for the test sample. The normalised peak areas were converted to a login scale and the data is presented in FIG. 23.

The data showed that the NifV/HCS polypeptides from *K. oxytoca* (KoNifV) and all three from *Methanocaldococcus infernus* (MiHCS1, MiHCS2 and MiHCS3) did not produce detectable homocitrate above the baseline level for both the mitochondrially-targeted and cytoplasmically-targeted polypeptides. These data were consistent with the observed insolubility of KoNifV and the MiHCSs for the mitochondrially-targeted polypeptides (FIGS. 20 and 21) but the lack of HCS activity for the cytoplasmically-targeted polypeptides was a mystery. The *M. infernus* polypeptides may have been inactive at the growth temperature of *N. benthamiana*. In contrast, both the mitochondrially-targeted and the cytoplasmically-targeted fusion polypeptides comprising seven of the other NifV/HCS sequences were clearly active in producing homocitrate in the leaf cells.

Several specific observations were particularly noteworthy. The *S. cerevisiae* HCS (ScHCS) polypeptides were the most active of the tested polypeptides in producing homocitrate, being 10- to 100-fold more active than the other polypeptides, regardless of the mitochondrial or cytoplasmic localisation. The 22 amino acid N-terminal extension (scar sequence) having the sequence ISTQVVRNRGGYPYDVPDYAGG (SEQ ID NO:166) including the HA epitope sequence on the N terminus of ScHCS was clearly tolerated for HCS function. A shorter, 12 amino acid scar sequence MYPYDVPDYAGG (SEQ ID NO:165) on the N terminus of ScHCS was also tolerated for function. Most surprisingly, the AvNifV fusion polypeptide of 406 amino acids from SN254 (encoding MTP::HA::AvNifV, processed to scar9-HA::AvNifV) produced 27-fold more homocitrate when it was targeted to plant mitochondria relative to the cytoplasmically-targeted polypeptide. This was also true, but less in extent, for the *Chlorobaculumtepidum* HCS (CtHCS) produced from SN253. The likely reason for these observations was that the AvNifV and CtHCS polypeptides were both somewhat oxygen sensitive, the mitochondrial location being more protected from oxygen and so yielding greater activity. At the same time, the definite homocitrate production when AvNifV and CtHCS were located in the cytoplasm suggested that those two polypeptides could tolerate oxygen to some extent. Oxygen sensitivity of AvNifV has been reported by Zheng et al. (1997). In similar fashion, the *Thermincola potens, Thermoanaerobacter brockii* and *Methanosarcina acetivorans* HCSs also produced homocitrate regardless of where they were located. Notably, these three HCSs were more active when located to the cytoplasm, indicating they were not as oxygen sensitive. As was observed with ScHCS, the 22 amino acid extension having the sequence ISTQVVRNRGGYPYDVPDYAGG (SEQ ID NO:166) on the N-terminus of AvNifV was tolerated for function.

ScHCS had the highest level of homocitrate production and therefore was considered by the inventors to be the most suitable NifV/HCS for use as part of a recombinant Nif pathway in plant mitochondria if high-level homocitrate production was desired. However, any of the other HCS sequences could be used for FeMoco synthesis since homocitrate forms part of a cofactor which is not used up in the nitrogenase reaction, so not much would be needed. The optimal level of NifV function can be determined empirically, as further described in the Examples below.

FeMoco synthesis and subsequent nitrogenase activity can be achieved in vitro by combining NifB, NifX, NifE, NifN, NifH, apoNifD-NifK, NafY, Mo, Fe, S, s-adenosylmethionine, ATP regenerating mixture (ATP, phosphocreatine, creatine phosphokinase) and R-homocitrate as reported by Curatti et al. (2007), which suggests that NifV does not need to interact physically with the other Nif components if the combination mixture is provided with sufficient homocitrate. It is thought that NifH, in particular, functions as an ATP-dependent Mo-homocitrate insertase to deliver Mo-homocitrate to the NifE-NifN complex for FeMoco assembly (Hu et al., 2013). The inventors considered that, if there was a possibly detrimental effect of producing high levels of homocitrate by ScHCS in plant mitochondria, then AvNifV would be more suited as part of a recombinant Nif pathway than ScHCS as the AvNifV enzyme was more likely to deliver the homocitrate it produced to NifH by physical association.

Measurement of α-Ketoglutarate and Pyruvate in the *N. benthamiana* Cells.

The GC-MS metabolite analysis also detected the derivatives α-ketoglutaric acid (αKG) 1MEOX 2TMS and pyruvic acid 1MEOX 1TMS, derivatives of αKG and pyruvic acid, respectively. αKG and acetyl-Coenzyme A (Ac-CoA), which is produced from oxidation of pyruvate by pyruvate dehydrogenase, are the two substrates that NifV/HCS enzymes use to synthesise homocitrate. When ScHCS was expressed in *N. benthamiana* leaves, it reduced the level of αKG and pyruvate compared to when *A. vinelandii* NifV was targeted to the mitochondria, which were essentially the same levels as in the negative control leaves lacking NifV/HCS. Since αKG and pyruvate are key intermediates of the TCA cycle in the mitochondrial matrix, a decrease in their levels may have a detrimental effect on overall mitochondrial function, so over-expression of NifV/HCS to deleterious levels should be avoided. Therefore, it was concluded that AvNifV would be better suited for FeMoco, FeVco or FeFeco assembly than ScHCS if the homocitrate that was produced by AvNifV could be delivered to NifH via protein-protein interaction, rather than via diffusion that possibly requires a higher concentration of homocitrate.

Example 16. Solubility of NifH Variants when Expressed in Plant Cells

Introduction

The NifH polypeptide from *Klebsiella oxytoca* (KoNifH; SEQ ID NO:1) was found to be mostly insoluble, or in some experiments entirely insoluble, in plant mitochondria when expressed as a fusion polypeptide with an MTP sequence and a HA epitope sequence in a transient leaf expression system (Example 3). It was concluded that the NifH fusion polypeptide did not fold correctly in the *N. benthamiana* mitochondria or remained associated with the membranes, even though the MTP sequence had been cleaved correctly by MPP, and thus was unlikely to function properly as a NifH protein in that situation. In contrast, a corresponding NifH fusion polypeptide including the *K. oxytoca* NifH sequence but lacking the MTP sequence at the N-terminus, directed to the cytoplasm rather than the mitochondria, was soluble in the transient leaf expression system. The insolubility of the fusion polypeptide was therefore related to the mitochondrial localisation. Previously, Lopez-Torrejon et al. (2016) reported that NifH from *Azotobacter vinelandii* retained the electron transport function of NifH and was soluble in yeast mitochondria. However, it was also reported at a conference in Stockholm, Sweden, that NifH from *A. vinelandii* accumulated only at low levels when expressed in plant mitochondria in a transient leaf expression system, presumably due to low solubility (Xi Jiang at ENFC in Stockholm, 2018). It therefore appeared to the inventors that yeast cells and plant cells might differ with respect to the solubility and/or function of any one specific NifH polypeptide.

Results

In an attempt to circumvent the problem of the apparent insolubility of the KoNifH fusion polypeptides that had been tested for high level expression in *N. benthamiana*, the inventors searched for homologues of NifH proteins from other organisms that might be soluble as fusion polypeptides in plant mitochondria, using the process described as follows.

NifH polypeptide sequences were extracted from the InterPro database using family IPR005977—Nitrogenase iron protein NifH—as the query, accessing the database on 23 Apr. 2018. 4183 NifH amino acid sequences were identified and extracted from the database. To select and test representative sequences, a protein network was established based on protein similarity, resulting in the clustering of NifH polypeptides based on sequence similarity. To do this, the amino acid sequences were aligned with MAFFT—Multiple alignment program for amino acid or nucleotide sequences—software, version 7 using the server mafft.cbrc.jp/alignment/server/large.html?aug31. The strategy G-large-INS-1 for less than 10,000 sequences, shorter than 5,000 sites, was used. The output was converted from .pir to .phy format using an online sequence converter (www.hiv.lanl.gov/content/sequence/FORMAT_CONVERSION/form.html). In order to calculate distance matrices and prepare the data in the input files for Cytoscape, the PHYLIP/protdist program was used to calculate the Kimura distance matrix for the NifH sequences. The output file was modified using Notepad++ to prepare an appropriate input format for the aMATReader in Cytoscape. The distance matrix was then modified in Excel to decrease file size and define subgroups: all values that were greater than 0.1 were removed, thereby creating subgroups, redundant sequences were removed, zero values were removed, and values were rounded to three decimal places.

This distance matrix was imported into Cytoscape using the aMATReader app as an undirected network, using delimiter: tab, deselect rows for import. At this stage, the network contained 3,114 nodes and 450,489 edges. The network was visualized using the prefuse force directed layout (unweighted). Additional information was extracted from the UniProt knowledgebase including entry name, status, protein names, gene names, organism, length and taxonomic lineage (PHYLUM) and imported into Cytoscape. Nodes were coloured by phylum and nodes representing sequences that were selected for biochemical analysis are displayed as larger nodes. Protein sequences that were longer than 700 amino acids were removed from the network—eleven protein sequences were removed as the length of these sequences (731-804 amino acid residues) was not in agreement with the length of a typical NifH protein at 260-300 amino acid residues. Nine of the 11 sequences were from *Methanosarcina* species, one was from *Anaerovirgula multivorans* and one from *Treponema azotonutricium*. These proteins were typically annotated as “NifEH”. The first part of each NifEH had a sequence that was similar to NifH including a P-loop, a $[Fe_4S_4]$-cluster binding site, and the second part of each sequence was related to NifE or NifD, respectively. In *Methanosarcina*, there is a gene coding for a NifD or a similar polypeptide located next to the gene for NifEH, but there is no NifK equivalent located in close proximity. These NifEH polypeptides might have a different function even though they were structurally related to the nitrogenase proteins. To the inventors’ knowledge, such proteins have not been mentioned in the scientific literature and no experimental data is available.

The final network contained 3,103 nodes and 450,486 edges. The Cytoscape versions used for network generation and visualisation were 3.6.1 and 3.7.0. The InterPro database did not contain separate families for AnfH or VnfH proteins; therefore these were included in the NifH group. The contributing signatures from the InterPro member databases, namely CDD, TIGRFAMs and HAMAP, did not discriminate between NifH, AnfH and VnfH. The AnfH and VnfH sequences were therefore also included in the alignment. A subset of AnfH sequences was identified from the NifH sequences.

Sequence Selection

A representative of each clustered group that containing more than 13 sequences was selected for biochemical analysis, for comparison to *K. oxytoca* NifH. This included NifH sequences from thermophilic nitrogen-fixing organisms to be tested for solubility and functional analysis (Table 17). The column for temperature in Table 17 indicated the optimal growth temperature for some of the organisms. The extent of sequence identity of each of the selected NifH sequences to SEQ ID NO:1 is shown in Table 18. The amino acid sequences of the fusion polypeptides comprising the selected NifH polypeptides other than KoNifH, fused at the C-terminus of the MTP-CoxIV-TwinStrep sequence, are provided in SEQ ID NOs:168 to 181.

TABLE 17

NifH sequences from nitrogen-fixing and related organisms, tested for solubility when expressed as fusion polypeptides in *N. benthamiana* leaves.

| Source Organism | Temperature [° C.] | SEQ ID NO | Genetic Construct | Reference |
|---|---|---|---|---|
| *K. oxytoca* | | 1 | SN41 | |
| *Azospirillum brasilense* | | 168 | SN178 | |
| *Mastigocladus laminosus* (*Fischerella*) | 45-50 | 169 | SN179 | Miyamoto et al. (1979); Khumanthem et al. (2007). |
| *Frankia casurinae* | | 170 | SN180 | |
| *Marichromatium gracile* biotype *thermosufidiphilum* | max 44 | 171 | SN181 | Serrano et al. (2009). |
| *Methanocaldococcus infernus* | | 172 | SN182 | Mehta and Baross, (2006). |
| *Heliobacterium modesticaldum* | 50 (max 56) | 173 | SN183 | Kimble et al. (1995). |
| *Chlorobaculum tepidum* (*Chlorobium tepidum*) | 48-50 | 174 | SN184 | Wahlund and Madigan, (1993). |
| *Geobacter* sp. M21 | | 175 | SN185 | |

TABLE 17-continued

NifH sequences from nitrogen-fixing and related organisms, tested for solubility when expressed as fusion polypeptides in *N. benthamiana* leaves.

| Source Organism | Temperature [° C.] | SEQ ID NO | Genetic Construct | Reference |
|---|---|---|---|---|
| *Bradyrhizobium. diazoefficans* | | 176 | SN186 | |
| *Methanobacterium thermoautotrophicum* | 40-70 (opt 65) | 177 | SN187 | Smith et al. (1997). |
| *Methanosarcina* | | 178 | SN188 | |
| *Desulfotomaculum acetoxidans* | 36 | 179 | SN189 | |
| *Carboxydothermus pertinax* | carboxydotrophic 50-70 (opt 65) | 180 | SN190 | Yoneda et al. (2012). |
| *Nostoc calcicola* | | 181 | SN191 | |

The *Carboxydothermus pertinax* strain was probably not capable of nitrogen fixation since the NifD protein coding region in that organism had an internal stop codon. Therefore, the NifH sequence might also not have been functional.

TABLE 18

Amino acid sequence identity to NifH from *K. oxytoca* (SEQ ID NO: 1).

| NifH from: source organism | % sequence identity |
|---|---|
| *Azospirillum brasilense* | 72.4 |
| *Mastigocladus laminosus* (*Fischerella* sp.) | 72.1 |
| *Frankia casuarinae* (strain DSM 45818/CECT 9043/CcI3) | 75.1 |
| *Marichromatium gracile* (*Chromatium gracile*) | 85.0 |
| *Methanocaldococcus infernus* (strain DSM 11812/JCM 15783/ME) | 56.8 |
| *Heliobacterium modesticaldum* (strain ATCC 51547/Ice1) | 74.9 |
| *Chlorobaculum tepidum* (strain ATCC 49652/DSM 12025/NBRC 103806/TLS) (*Chlorobium tepidum*) | 65.8 |
| *Geobacter* sp. (strain M21) | 79.9 |
| *Bradyrhizobium diazoefficiens* (strain JCM 10833/IAM 13628/NBRC 14792/USDA 110) | 74.6 |
| *Methanothermobacter thermautotrophicus*(strain ATCC 29096/DSM 1053/JCM 10044/NBRC 100330/Delta H) (*Methanobacterium thermoautotrophicum*) | 59.5 |
| *Methanosarcina barkeri* | 61.4 |
| *Desulfotomaculum acetoxidans* (strain ATCC 49208/DSM 771/VKM B-1644) | 64.8 |
| *Carboxydothermus pertinax* | 61.0 |
| *Nostoc calcicola* FACHB-389 | 56.3 |

Solubility Testing for NifH Proteins in Transient Leaf Expression System

The solubility of the different NifH polypeptides when expressed as MTP-CoxIV::TwinStrep::NifH fusions for plant mitochondrial localisation was assessed by the Western blot method using a strep-antibody. The TwinStrep sequence was placed between the MTP and NifH sequences. This epitope was used to allow for the subsequent purification of the NifH fusion polypeptides, if desired. Protein extracts were made from the infiltrated leaf tissues and fractionated under aerobic conditions for soluble and insoluble fractions. The solubility of each NifH fusion polypeptide was assessed when it was co-expressed with *K. oxytoca* NifM expressed from the genetic construct SN44 (encoding MTP-FAγ51::NifM::HA), to see if the co-expression with NifM might increase the solubility. NifM is thought to be involved in maturation of NifH in *K. oxytoca*. It was not known if the NifH polypeptides from the other species tested required a NifM-like protein for full activity. Most of those organisms other than the proteobacteria do not contain a NifM homologue in their genome, but other non-homologous proteins might perform a similar function instead of NifM.

The Western blot analysis (FIG. 24) showed that soluble, or at least partly soluble, NifH protein was detected for the fusion polypeptides including the NifH sequences from *M. laminosus, M. infernus, H. modesticaldum, C. tepdium, Geobacter* sp. M21 and *M. thermoautotrophicus*. There was little or no NifH fusion polypeptide detected in the soluble fraction for those including NifH from *K. oxytoca, A. brasilense, F. casurinae, M. gracile* and *B. diazoefficans*. It was concluded that most of the NifH polypeptides that were at least partially soluble in plant cell mitochondria were derived from thermophilic bacteria, possibly because such polypeptides were inherently more stable than those from mesophilic bacteria and so would more readily able to fold into, and maintain, their native conformations.

It was also observed that there was no significant increase in the solubility when NifH fusion polypeptide was co-expressed with *K. oxytoca* NifM, including for the *K. oxytoca* NifH (FIG. 24). As mentioned above, it was not known whether the NifH proteins in most of the bacterial species tested required a NifM-like activity for maturation and production of a fully functional NifH.

Purification of *M. infernus* NifH and *M. laminosus* NifH from *N. benthamiana* Leaves The Twin Strep::NifH fusion polypeptides for NifH from *M. infernus* and *M. laminosus* were successfully purified from the infiltrated *N. benthamiana* leaf samples after extraction under non-denaturing conditions and then using a StrepTactinXT column. This confirmed that the MPP-processed NifH fusion polypeptides from these two species were indeed soluble in the mitochondria of the leaf cells. The purified proteins are used for biochemical analysis, such as analysis for the presence of FeS clusters and the ability of the NifH polypeptides to donate electrons to purified NifD-NifK isolated from *A. vinelandii.*

Testing of Variant NifH Polypeptides in a Bacterial Nitrogenase System

The NifH candidates that were found to be soluble when targeted to leaf mitochondria were tested for NifH function in *E. coli* using the MIT2.1 system. A XhoI site was introduced into the 3' end of the NifH protein coding region in MIT2.1 by site directed mutagenesis. This newly introduced XhoI restriction site along with an existing XhoI site upstream of NifH was used to separately replace the wild-type *K. oxytoca* NifH sequence in MIT2.1 with seven selected NifH variant sequences that were synthesised with XhoI restriction sites flanking each open reading frame: *M. laminosus* NifH (MlNifH; Genbank Accession No. Q47917), *M. infernus* NifH (MiNifH; Genbank Accession No. WP_013099459), *H. modesticaldum* NifH (HmNifH; Genbank Accession No. WP_012282218), *C. tepidum* NifH (CtNifH; Genbank Accession No. WP_010933198), *Geobacter* sp. NifH (GspNifH; Genbank Accession No. WP_015837436), *M. thermautotrophicus* NifH (MtNifH; Genbank Accession No. AAB86034), and *Carboxydothermus pertinax* NifH (CpNifH; Genbank Accession No. WP_075859892). Replacement of the NifH variants were done with pHJ-TOPO containing *K. oxytoca* NifHDKYENJ, then pB-ori containing the latter half of MIT2.1 of *K. oxytoca* NifBQFUSVWZM was ligated to the modified pHJ-TOPO after both plasmids were digested with SbfI.

The resulting modified MIT2.1 plasmids containing the NifH variants were used to transform *E. coli* strain JM109 and the transformants tested in the acetylene reduction assay. Compared to JM109 with the original MIT2.1 as positive control in the ARA, none of the JM109 strains carrying the modified MIT2.1 plasmids with the NifH variants reduced acetylene, instead showing the same background level of ethylene production as JM109 carrying the negative control plasmid pB-ori. Based on this result, the inventors concluded that the NifH variants would not function with the NifD-NifK proteins from *K. oxytoca* but would function with their corresponding NifDK heterotetramer, for example *C. tepidum* NifH with *C. tepidum* NifD-NifK. The compatibility of each NifH with NifD-NifK can therefore be determined empirically.

Example 17. Expression of NifH and NifM in Stably Transformed Plants

Introduction

A functional NifH protein, also known as the Fe protein, is essential for nitrogenase activity. It has several known functions for nitrogenase activity: it is required for donation of electrons to the nitrogenase enzyme, for maturation of the metalloclusters including the P-cluster and is involved in the synthesis of the cofactors FeMoco, FeVco and FeFeco for the Mo-nitrogenase, V-nitrogenase and Fe-nitrogenase, respectively. Previously Rubio and colleagues have co-expressed *Azotobacter vinelandii* NifH and NifM within yeast with targeting to the mitochondria. Purified NifH protein from the yeast cells was capable of electron donation in vitro to a holo-NifD-NifK complex (Lopez-Torrejon 2016) but the other functions of the NifH polypeptide were not tested in that in vitro system, which was not designed for that. The introduction of a fully functional NifH within an organelle such as plant mitochondria will be essential for engineering nitrogenase into plants.

The inventors have previously shown using a transient system in *N. benthamiana* leaves that *Klebsiella oxytoca* NifH (KoNifH) could be targeted to the plant mitochondria by translationally fusing an MTP sequence to the N-terminus of the KoNifH polypeptide (Allen et al 2017). The fusion polypeptide was well expressed and processed by cleavage within the MTP sequence, demonstrating mitochondrial localisation of the expressed fusion polypeptide. When translationally fused at the N-terminus of KoNifH, two different mitochondrial targeting peptides MTP-FAγ77 and MTP-FAγ51 were efficiently and specifically cleaved at the expected site within the MTP. The abundance of the processed NifH fusion polypeptide was relatively high compared to other mitochondrially-targeted Nif proteins. Furthermore, the experiments described in Example 4 herein demonstrated that the 9 amino acid "scar sequence" from the C-terminus of the MTP sequence left after cleavage by mitochondrial matrix protease (MPP) with an additional Gly-Gly linker, 11 amino acids in total, at the N-terminus of KoNifH did not reduce acetylene reduction activity when assayed in a bacterial complementation format.

However, in the case of the MTP-FAγ51::KoNifH::HA fusion polypeptide (SEQ ID NO:25) encoded by the vectors SN18 and SN27, the MPP-cleaved polypeptide scar9::KoNifH::HA was found almost exclusively within the insoluble protein fraction (Examples 2 and 3). To assess whether the insolubility of NifH might be due to the targeting peptide, another genetic construct (SN42) was made and tested using a different MTP sequence, encoding a MTP-CoxIV::TwinStrep::KoNifH::HA (SEQ ID NO:128). Although a correctly processed form derived from MTP-CoxIV::TwinStrep::KoNifH::HA was readily detected in the transient leaf assays after cleavage at the expected site within the MTP, this scar32::KoNifH::HA product was also found predominantly in the insoluble protein fraction.

As insoluble proteins are likely to be misfolded or remain bound to membranes and therefore non-functional, the inventors sought various alternative methods to improve the solubility of NifH, described as follows. The functional consequences of a 32 amino acid N-terminal extension to KoNifH was also tested, corresponding to the polypeptide produced after cleavage of the MTP-CoxIV::TwinStrep::KoNifH::HA fusion polypeptide by the MPP in plant mitochondria.

Genetic and biochemical studies with *Azotobacter vinelandii* and *Klebsiella oxytoca* showed that NifM was required for the production of a functional and mature NifH protein in those nitrogen fixing bacteria. As shown in Examples 2-4 herein, a mitochondrially targeted version of *K. oxytoca* NifM, MTP-FAγ51::KoNifM::HA (SEQ ID NO:123) was expressed, cleaved accurately and efficiently within the plant mitochondria, and detected in the soluble fraction. However, the 9 amino acid scar sequence at the N-terminus of KoNifM reduced acetylene reduction activity to only 10-20% of the wild-type level in the *E. coli* MIT2.1 system (Table 4). Proteomic analysis of the bacterial strains producing the processed scar9::NifM::HA polypeptide showed that this N-terminal addition to NifM resulted in about a 50-fold increase in the accumulation of the modified NifM polypeptide relative to the wild-type NifM. As it is known that nitrogenase activity is sensitive to changes in expression levels of the various Nif proteins (Temme et al., 2012), it is plausible that the excess of scar9::NifM in that bacterial assay format reduced the nitrogenase function to 10-20% of the wild-type level.

Co-Expression of NifH and NifM in *N. benthamiana* Leaves

In order to test whether the solubility of NifH within plant mitochondria might be increased by co-expression with a NifM fusion polypeptide that was also targeted to that organelle, a mixture of Agrobacterial strains each containing a different vector was infiltrated into *N. benthamiana* leaves as described in Example 1. A first strain that comprised either a vector encoding MTP-FAγ51::KoNifH::HA (SN18) or the vector encoding the MTP-CoxIV::TwinStrep::KoNifH::HA fusion polypeptide (SN42) and a second strain that comprised SN30 encoding the MTP-FAγ51::KoNifM::HA fusion polypeptide were mixed and infiltrated. Five days after infiltration, total, soluble and insoluble protein fractions were prepared from the leaf tissues and subjected to Western blot analysis. There was no consistent increase in the solubility of the NifH polypeptide in these combinations relative to infiltrations with a single vector.

As a further attempt, another vector was constructed which had two genes on the same T-DNA, one gene encoding the MTP-CoxIV::TwinStrep::KoNifH::HA fusion polypeptide (SEQ ID NO:128) and the other encoding a MTP-FAγ51::HA::KoNifM polypeptide (SEQ ID NO:167). The first gene had a TwinStrep epitope between the MTP and NifH sequences and a HA epitope at the C-terminus. The second gene had a HA epitope between the MTP and NifM sequences. The genetic construct with the two genes was designated SL6. It was constructed using the modular DNA assembly system referred to as the GoldenGate method, as described above. The gene encoding the KoNifH fusion polypeptide was under the control of the enhanced 35S promoter, while the gene encoding the KoNifM polypeptide was the SCSV S4 promoter (Accession No. AY181084).

*Agrobacterium* cultures transformed with SL6 were infiltrated into *N. benthamiana* leaves. Samples were harvested five days after infiltration and total, soluble and insoluble protein fractions were prepared. Western blot analysis of the protein extracts indicated that the co-expression of both the NifH and NifM fusion polypeptides from the same vector did not consistently increase the solubility of NifH, although at least one experiment appeared to show an increase in the amount of soluble NifH polypeptide.

It was then decided to use SL6 to transform *N. tabacum* (tobacco) and *N. benthamiana* to produce stably-transformed plants with the T-DNA integrated into the plant nuclear genome.

Plant Transformation Protocol

To transform *N. benthamiana* plants, plants were grown aseptically in tissue culture as a source of plant material for transformation. The source plants were established from surface sterilised seeds. To do this, seeds were rinsed with 70% ethanol, then surface sterilised with 5% sodium hypochlorite for 10 mins with agitation, followed by rinsing in several changes of water. The seeds were then germinated on plates containing MSO medium at 4.43 g/L (M519, PhytoTechnology Laboratories) containing 3% sucrose and 0.8% agar, at pH 5.8. Plants were grown in a growth room at 26° C. using a 16/8 hour photoperiod. After approximately 2 weeks, developing seedlings were transferred and thinned out to 4 seedlings per deep tissue culture plate and cultured on the same medium and growth conditions. About 2 weeks later, single well-established plants were cultured in tissue culture pots. Leaves from 6-week-old *N. benthamiana* plants were used for *Agrobacterium*-mediated transformation.

Cultures of *A. tumefaciens* strain AGL1 containing the genetic constructs in binary vectors such as SL6 were grown at 28° C. in MG/L medium with antibiotics to maintain selection for the genetic constructs. Cultures having an optical density of between 0.25-0.5 at 600 nm were used to inoculate the *N. benthamiana* tissues, as follows. Upper leaves from the tissue-culture grown plants were excised and floated on MG/L medium to maintain turgidity until used, and cut into pieces about 1 $cm^2$, including leaf midribs. The *Agrobacterium* culture containing the genetic construct was added to the leaf pieces, ensuring the explants were completely wet, and left for 20-30 mins with occasional shaking to allow the bacteria to bind to the plant cells along the cut edges. The inoculated explants were then lightly blotted on sterile filter paper to remove excess Agrobacteria and transferred adaxial side down to Co-cultivation Medium MS9 without antibiotics. MS9 contained MSO medium with 3% sucrose, 0.8% agar at pH 5.8, sterilised by autoclaving, and the plant hormones IBA at 1 mg/L and IAA at 0.5 mg/L added after the autoclaving and cooling of the MSO-agar medium to 55° C. The inoculated explants were co-cultivated at 26° C. for 48 h in the dark. Following the co-cultivation period, the explants were transferred to shoot regeneration medium (MS9 and the plant hormones IBA at 1 mg/L and IAA at 0.5 mg/L plus kanamycin at 100 mg/L and Timentin at 150 mg/L), adaxial side up, plating about 10 explants per plate. These were incubated at 26° C. under lighting with a 16/8-hour photoperiod. The explants were transferred to fresh shoot regeneration medium every 2-3 weeks until shoot development occurred. After 6-8 weeks, shoots that had developed to sufficient size were transferred to root initiation medium (⅓ MSO+100 mg/L kanamycin+150 mg/L Timentin+1 mg/L IBA). Once individual plants had developed strong roots, small leaf samples were harvested for DNA extraction and testing by PCR for the presence of the selectable marker gene and the desired transgenes. Confirmed transgenic plants were then planted in soil and grown in a glasshouse, allowing the plants to acclimatise gradually.

*Nicotiana tabacum* plants of cultivar Wisconsin 38 (Wi38) were transformed by standard methods (Borsch et al., 1985).

Twelve independently transformed plants were generated with SL6 in *N. benthamiana*, designated SL6-1 to 12, and another twelve generated in *N. tabacum*, SL6-13 to 24. These initial transgenic plants were referred to as the TO generation. The presence of the T-DNA in each of the plants was confirmed using PCR on DNA prepared from leaf samples from the plants, confirming that all of the plants were transgenic. These independently transformed plants were grown to maturity and T1 seeds harvested after self-fertilisation of each plant. To test segregation of the transgene in one line, 60 T1 seeds from the plant designated SL6-13 were sown into soil and grown for four weeks under standard glasshouse conditions. The presence of transgenes was assessed using PCR. Twenty plants lacked the transgene (null segregants) and 40 plants were PCR positive, indicating a low copy number transgenic event, probably having one T-DNA insertion in plant SL6-13. Several null segregants were identified and maintained as negative controls.

The production of the NifH and NifM fusion polypeptides in the transgenic plants was assessed by extraction of total protein and detection using either anti-Strep antibody or anti-HA antibody in Western blots. The level of NifH fusion polypeptide in the stably transformed tobacco plants was much lower than the levels observed previously in transient expression in *N. benthamiana* leaves. Surprisingly and unexpectedly in view of the earlier results from those experiments, the tobacco plants including a plant designated SL6-13 produced detectable levels of correctly processed NifH that was found exclusively within the soluble fraction. Likewise, *N. benthamiana* plants stably transformed with SL6 produced significantly less NifH polypeptide, but the polypeptide had been processed efficiently and was also found in the soluble fraction.

Analysis of Progeny Transgenic Plants

Leaves of various ages were harvested from progeny plants to see if there was any effect of leaf age on the accumulation, processing and solubility of the NifH and NifM fusion polypeptides. Samples were taken from two *N. tabacum* plants that were progeny from SL6-13, taking a young leaf, a "middle aged" leaf and an older leaf from each plant. The NifH fusion polypeptide was detected by Western blotting using anti-Strep antibody and the NifM polypeptide with anti-HA antibody in each of the leaves. The level of accumulation of the NifH fusion polypeptide increased with the age of the leaves.

Purification of the NifH Fusion Polypeptide from the Stably Transformed Plants

Given that the TwinStrep tagged NifH polypeptide was soluble and that sufficient plant material was available, this polypeptide was purified using the StreptactinXT affinity media. Approximately 90 g of SL6-13 plant leaf material was extracted by homogenising the material in a non-denaturing buffer, centrifugation to remove cellular debris, filtration through 0.22 μm filters and passage through a StreptactinXT column. After elution from the column using biotin, fractions containing the NifH polypeptide were collected and concentrated. Samples were analysed by proteomics and subjected to Western blot analysis with anti-Strep antibody to detect the NifH polypeptide and anti-HA antibody to detect both the NifH and NifM polypeptides (FIG. 25). The purified protein was subjected to N-terminal analysis to determine the amino acid sequence at the N-terminus. These analyses confirmed that the CoxIV MTP was cleaved at the predicted MPP cleavage site. Purification of NifH by binding to the StreptactinXT column also supported the conclusion that the TwinStrep::KoNifH extracted from the stably transformed plants was soluble. Overall, these results indicated that the scar32::TwinStrep::KoNifH::HA protein isolated from stably transformed *N. tabacum* plants had been correctly processed within the mitochondria and was fully soluble, fulfilling two major requirements for NifH function within plants.

Co-Expression of NifS and NifU with NifH and NifM in the Transformed *N. benthamiana* Plants Genetic constructs encoding NifS (SN31) and NifU (SN32) fusion polypeptides were infiltrated into the *N. benthamiana* plants transformed with SL6, to see whether co-expression of the NifS and NifU fusion polypeptides might increase the level of NifH polypeptide accumulation.

Example 18. Expression of Anf Polypeptides in Plant Cells

Introduction

The iron-only nitrogenase system is found in some diazotrophic bacteria, for example in *A. vinelandii* which has three nitrogenase systems based on molybdenum (Mo), vanadium (V) and iron-only (Fe), using the cofactors FeMoco, FeVco and FeFeco, respectively (Davis et al., 1996; Robson et al., 1986). Both the molybdenum (Mo-nitrogenase) and the vanadium nitrogenase (V-nitrogenase) enzymes that actually catalyse the reduction of dinitrogen have known crystal structures. While the iron-only nitrogenase (Fe-nitrogenase) crystal structure is yet to be established, it is thought to have a similar structure to that of the vanadium nitrogenase (Sippel & Einsle, 2017). All organisms recorded to date that contain one or both of the V- or Fe-nitrogenases also contain the Mo-nitrogenase. Generally, the V- and Fe-nitrogenases are repressed by the expression of the Mo-nitrogenase and are expressed only when the availability of Mo becomes limiting. To distinguish between the molybdenum-type nitrogenase and alternative nitrogenase, the Isotopic Acetylene Reduction Assay (ISARA) can be used which measures $^{13}C$ isotopes in the acetylene reduction assay (Zhang et al., 2016).

The Fe-nitrogenase is the least studied of the three systems. It has the lowest nitrogenase catalytic activity of the three systems but its biogenesis appears to be simpler, requiring less proteins for nitrogenase activity. There are 6 known Fe-nitrogenase proteins from the well-studied organism *Azotobacter vinelandii*, namely AnfD, AnfK, AnfH, AnfG, AnfO and AnfR, which are distinct for Fe-nitrogenase. Of these 6 proteins, the first 4 are known to be required and to contribute to the activity of the nitrogenase enzyme. Each nitrogenase system requires catalytic proteins designated as Nif (or Vnf or Anf) D, K and H, and the Fe-nitrogenase uses the AnfD, AnfK and AnfH proteins. The V- and Fe-nitrogenases also require the additional structural protein designated VnfG or AnfG, respectively, which is not required by the Mo-nitrogenase. The anfO and anfR genes are located downstream from the other structural anf genes but their function is not known and they have been shown to not affect the activity of the Fe-nitrogenase when expressed in an *E. coli* system (Yang et al., 2014). The remaining minimal accessory genes required for activity of the Fe-nitrogenase are common to the Mo-nitrogenase pathway, namely NifS, NifU, NifB, NifV, NifJ and NifF (Yang et al., 2014). The iron-only nitrogenase therefore has a minimal set of 4 Anf and 6 accessory Nif polypeptides required for heterologous function within *E. coli* (Yang et al., 2014).

In the Fe-nitrogenase system, the dinitrogenase enzyme which is the site of dinitrogen reduction is a heterohexamer made up of two AnfD polypeptides as the α unit, two AnfK polypeptides as the β unit and two AnfG polypeptides as the δ unit, so in a $\alpha_2\beta_2\delta_2$ conformation. The dinitrogenase reductase enzyme, the obligate electron donor to the dinitrogenase enzyme, is a homodimer with 2 identical AnfH polypeptides. Dinitrogenase reductase is also known as the Fe protein and contains a single $[Fe_4S_4]$ cluster at the interface of its subunits (Burén, Young, et al., 2017). The AnfH protein is also predicted to have two other functions including being required for the maturation of the dinitrogenase enzyme in analogous fashion to the NifH and VnfH gene products in the Mo- and V-nitrogenases.

As for the Mo- and V-nitrogenases, the engineering of plants to express the Fe-nitrogenase is considered to be exceedingly difficult. All of the key nitrogenase enzymes require a specific biochemical environment, being extremely oxygen sensitive, and require large quantities of ATP, a source of reductant, and elements such as Fe, Mo, V and S must be available in sufficient quantities in the correct cellular compartment. In particular, the Anf enzymes quickly become irreversibly inactivated when exposed to oxygen. As mentioned above, a minimal set of 4 Anf and 6 accessory Nif polypeptides would need to be introduced into a plant, which is very difficult to do from a technical viewpoint.

Experiments were therefore carried out seeking to express Anf genes in plant cells, aiming for mitochondrial localisation of the Anf gene products, as described below. Since the 4 key Anf proteins are the AnfD, AnfK, AnfH and AnfG proteins, the inventors first tested 4 genetic constructs each expressing an individual Anf gene, and then combined the 4 genes into one T-DNA in one vector.

Single Gene Constructs to Express Anf Fusion Polypeptides in Plant Cells

A first series of genetic constructs was designed and made to separately express the AnfD, AnfK, AnfH and AnfG polypeptides in plant cells such as *N. benthamiana* leaf cells. Each synthetic gene was under the control of the strong 35S promoter and a CaMV 3' polyadenylation region/transcriptional terminator which flanked the protein coding region. The Anf sequences from *A. vinelandii* were used to design the encoded amino acid sequences, and the nucleotide sequences were codon-optimised for expression in plant cells. For mitochondrial localisation, the constructs encoded fusion polypeptides having the MTP-FAγ51 fused to the N-terminus and either a HA- or a TwinStrep-epitope for detection of the polypeptides by Western blotting with anti-HA or anti-Strep antibodies, respectively. The HA epitope was fused translationally either C-terminally or, in most cases, between the MTP and Anf sequences, whereas the TwinStrep epitope was fused to the C-terminus of the Anf sequences. For each genetic construct that encoded a mitochondrially-targeted fusion polypeptide, two corresponding control constructs were also made. The first encoded a polypeptide which lacked the MTP sequence and therefore expressed a smaller, cytoplasmically-targeted polypeptide that provided a molecular weight comparator on the Western blots for an MPP-processed polypeptide from the MTP-Anf polypeptides (processed Anf), with the qualification that the MPP-processed polypeptide in each case included a "scar sequence" of about 9 amino acids and so the sizes were not identical. The second control construct in each case encoded a fusion polypeptide which had 13 amino acids in the MTP sequence substituted with alanines (Allen et al., 2017), designed to prevent processing by MPP. These second control polypeptides therefore provided a molecular weight comparator for the unprocessed polypeptide from the corresponding MTP-Anf construct. The alanine-mutated MTP sequence was designated herein as mFAγ51. When protein extracts from the infiltrated plant tissues were analysed, the sample from each MTP-Anf construct and its two corresponding control constructs were loaded onto adjacent lanes for gel electrophoresis, so allowing for the best detection of processing of the MTP-Anf polypeptide. Subsequently, the expected site of cleavage within the MTP motif was confirmed by mass spectrometry.

Where retention of AnfK function was desired for fusion polypeptides having the AnfK sequence, C-terminal extensions relative to the wild-type polypeptide were avoided. The desirability of using the wild-type C-terminal sequence for AnfK was analogous to the use of the wild-type C-terminus for NifK from *K. oxytoca* (WO2018/141030), since C-terminal extensions abolished function (Yang et al., 2017).

The single gene constructs are listed in Table 19, which also lists the predicted molecular weight (kDa) of each polypeptide before and after processing in the mitochondria by MPP. Table 19 also lists the SEQ ID NOs for the unprocessed fusion polypeptides. The genetic constructs were made using the GoldenGate assembly methods in analogous fashion to the constructs described in the earlier Examples.

As per Table 19, the control constructs for the AnfD constructs (SN81 and SN161) were SN82 which produced a polypeptide corresponding in approximate size to the processed form and SN158 which produced a polypeptide having the size of the unprocessed form. Protein extracts from these constructs were therefore run in adjacent lanes in the gel electrophoresis step of the Western blot analysis. For the AnfK construct SN129, the controls were SN152 and SN155. For the AnfH construct SN130, the controls were SN153 and SN156. For the AnfG construct SN131, the controls were SN154 and SN157.

Aside from varying the position of the HA epitope at either the C-terminus or toward the N-terminus, another variation that was made in one construct (SN195) was to use a CoxIV MTP sequence (Burén et al., 2017) rather than the MTP-FAγ51 sequence.

TABLE 19

Single gene constructs for expression of Anf fusion polypeptides in plant cells. (NA: not applicable)

| Plasmid | Expressed polypeptide | Predicted molecular weight (kDa) Unprocessed | Processed | SEQ ID NO for Unprocessed |
|---|---|---|---|---|
| SN81 | MTP-FAγ51::AnfD::HA | 65.4 | 60.7 | 182 |
| SN82 | HA::AnfD | 59.7 | NA | 183 |
| SN129 | MTP-FAγ51::HA::AnfK | 58.1 | 53.5 | 184 |
| SN130 | MTP-FAγ51::HA::AnfH | 36.9 | 32.4 | 185 |
| SN131 | MTP-FAγ51::HA::AnfG | 22.2 | 17.7 | 186 |
| SN152 | HA::AnfK | 52.5 | NA | 187 |
| SN153 | HA::AnfH | 31.3 | NA | 188 |
| SN154 | HA::AnfG | 16.6 | NA | 189 |
| SN155 | mFAγ51::HA::AnfK | 57.4 | NA | 190 |
| SN156 | mFAγ51::HA::AnfH | 36.3 | NA | 191 |
| SN157 | mFAγ51::HA::AnfG | 21.6 | NA | 192 |
| SN158 | mFAγ51::HA::AnfD | 64.6 | NA | 193 |
| SN161 | MTP-FAγ51::HA::AnfD | 65.3 | 60.7 | 194 |
| SN177 | MTP-FAγ51::AnfD::Twin Strep | 69.2 | 64.5 | 195 |
| SN195 | MTP-CoxIV::Twin Strep::AnfK | 57.7 | 54.7 | 196 |

Expression of Anf Fusion Polypeptides in *N. benthamiana* Leaf Cells

Each of the constructs was separately introduced into *N. benthamiana* plants by *Agrobacterium*-mediated methods as described in Example 1. Leaf samples were harvested 4-5 days post-infiltration and protein extracts prepared and analysed by SDS-polyacrylamide gel electrophoresis (PAGE) and Western blot as described in the earlier Examples. The expressed polypeptides were thereby tested for mitochondrial matrix import by virtue of the processing of the MTP leader sequences by MPP. In further experiments, protein extracts were fractionated into soluble and insoluble fractions using the method described in Example 1.

When the crude protein extracts were analysed by Western blotting using the anti-HA antibody, polypeptide bands were readily detected which matched the predicted sizes of the Anf polypeptides (FIG. 26). All of the individual mitochondrially-targeted polypeptides comprising the AnfD, AnfK, AnfH and AnfG sequences were expressed well and were seen after a short exposure (2 min) in the Western blot procedure. Each of the constructs SN161, SN130 and SN131 for the AnfD, AnfH and AnfG fusion polypeptides, respectively, each having the MTP-FAγ51 sequence, yielded a single dominant band on the blot at the molecular weight expected for a polypeptide processed by MPP within the MTP sequence. The bands in the adjacent lanes for the control polypeptides in each case confirmed that these bands were for processed polypeptides. It was concluded that these three fusion polypeptides were well expressed and processed efficiently in the mitochondria. The processing was subsequently confirmed by mass spectrometry. The sample from SN130 encoding MTP-FAγ51::HA::AnfH also showed a less distinct but nevertheless definite band at a higher molecular weight, at a size appropriate for a dimer of the polypeptide, despite the protein denaturation conditions used during the gel electrophoresis step.

The lanes for two of the AnfK constructs were more complicated with multiple bands. The AnfK cytoplasmic- and mitochondrially-targeted polypeptides produced from SN152 and SN129, respectively, showed additional bands detected by the HA antibody that were smaller than expected for cleavage within the MTP sequence, indicating that the AnfK polypeptide appeared to undergo additional proteolytic cleavage. The smaller polypeptides, about 4-6 kDa less in size, may also have arisen from premature transcription or translation termination. Despite this observation for AnfK, it was concluded that all four of the genetic constructs including the N-terminal MTP sequence had expressed the intended fusion polypeptide with processing, partially in the case of AnfK, to provide the desired mitochondrially localised Anf polypeptides.

Expression and Processing of Anf Fusion Polypeptides in Plant Cells from Multi-Gene Constructs The first experiment described above had used single gene constructs for production of the individual Anf fusion polypeptides. The inventors now decided to test the expression of all four of the AnfD, AnfK, AnfH and AnfG fusion polypeptides from a single vector, with each of the Anf genes having its own 35S promoter and transcription terminator. This experiment aimed to test whether there were any interactions between the four Anf polypeptides when they were expressed together in the same plant cells, in particular looking for changes in the levels of accumulation of individual polypeptides or in their processing by MPP. To do this, a genetic construct was assembled having all four of the genes in a single T-DNA of the binary vector, with each gene having the MTP-FAγ51 sequence fused translationally to a HA epitope and followed by the Anf sequence. The same nucleotide sequences and amino acid sequences were used as for the single gene vectors SN161, SN129, SN130 and SN131. The resultant genetic construct was designated SL26. Two control constructs were also made, SL31 which encoded the four Anf fusion polypeptides each with the alanine-mutated MTP sequence for producing size markers for the unprocessed polypeptides (mFAγ51::HA::Anf), and SL36 which encoded the four fusion polypeptides lacking the MTP sequence (HA::Anf) as the size marker for processed polypeptides. Additionally, to aid in the identification of the multiple polypeptide bands in the Western blots, three additional vectors were made by stepwise deletion of one, two or three genes from SL26: SL27 had the AnfG gene deleted, SL28 had the AnfH and AnfG genes deleted, and SL29 had the AnfK, AnfH and AnfG genes deleted leaving only the AnfD gene. The multi-gene vectors and their constituent genes are listed in Table 20.

All of these multi-gene vectors were separately introduced into *N. benthamiana* leaves by the method described in Example 1. Proteins were extracted from the leaf tissues 4 or 5 days post-infiltration and analysed by Western blotting, as before. The results (FIG. 27) showed that all four of the Anf polypeptides fused to the MTP-FAγ51 and HA sequences were readily detected, being well expressed as single, strong bands. Furthermore, the AnfD, AnfH and AnfG fusion polypeptides having the N-terminal MTP-FAγ51 leader sequences were efficiently processed within the MTP sequence and the AnfK fusion polypeptide was partially processed, as evidenced by the comparison with the sizes of the corresponding polypeptides expressed from SL31 in the adjacent lane. This was confirmed in a separate experiment using the multi-gene construct SL36 which encoded the 4 HA::Anf polypeptides that did not have the MTP sequence, and so providing size markers in the Western blot procedure for the processed polypeptides from SL26. The Western blot for the extracts arising from the series of vectors SL26, SL27, SL28 and SL29 (FIG. 27, panel C) assisted in identifying the four polypeptides in the mixture, confirming their identity, as did a mixture of the four single gene vectors in the lane labelled Mix.

The levels of accumulation of the four Anf polypeptides could be compared when expressed from the multi-gene construct relative to the mixture of the single gene constructs. For the multi-gene construct, the AnfD fusion polypeptide accumulated at a greater level than the other three Anf polypeptides (FIG. 27, panel A), which was surprising considering that the NifD gene was the most difficult to express of the corresponding NifD, NifK and NifH genes for the Mo-nitrogenase (Allen et al., 2017). Furthermore, the AnfD polypeptide appeared to be full-length and there was no evidence of a secondary, cryptic cleavage site in AnfD, contrary to the observations with NifD from *K. oxytoca* (Examples 6 and 7).

TABLE 20

Listing of multi-gene vectors and the encoded polypeptides for expression of Anf fusion polypeptides in plant cells.

| Plasmid | Encoded fusion polypeptides | Predicted molecular weight (kDa) Unprocessed | Processed |
|---|---|---|---|
| SL23 | MTP-FAγ51::AnfD::HA | 65.4 | 60.7 |
| | MTP-FAγ51::HA::AnfK | 58.1 | 53.5 |
| | MTP-FAγ51::HA::AnfH | 36.9 | 32.4 |
| | MTP-FAγ51::HA::AnfG | 22.2 | 17.7 |
| SL26 | MTP-FAγ51::HA::AnfG | 22.2 | 17.7 |
| | MTP-FAγ51::HA::AnfD | 65.3 | 60.7 |
| | MTP-FAγ51::HA::AnfK | 58.1 | 53.5 |
| | MTP-FAγ51::HA::AnfH | 36.9 | 32.4 |
| SL27 | MTP-FAγ51::HA::AnfD | 65.3 | 60.7 |
| | MTP-FAγ51::HA::AnfK | 58.1 | 53.5 |
| | MTP-FAγ51::HA::AnfH | 36.9 | 32.4 |
| SL28 | MTP-FAγ51::HA::AnfD | 65.3 | 60.7 |
| | MTP-FAγ51::HA::AnfK | 58.1 | 53.5 |
| SL29 | MTP-FAγ51::HA::AnfD | 65.3 | 60.7 |
| SL30 | MTP-FAγ51::HA::AnfG | 22.2 | 17.7 |
| | MTP-FAγ51::AnfD::Twin Strep | 69.2 | 64.5 |
| | MTP-FAγ51::HA::AnfK | 58.1 | 53.5 |
| | MTP-FAγ51::HA::AnfH | 36.9 | 32.4 |
| SL31 | mFAγ51::HA::AnfD | 64.6 | NA |
| | mFAγ51::HA::AnfK | 57.4 | NA |
| | mFAγ51::HA::AnfH | 36.3 | NA |
| | mFAγ51::HA::AnfG | 21.6 | NA |
| SL34 | MTP-FAγ51::HA::AnfG | 22.2 | 17.7 |
| | MTP-FAγ51::HA::AnfD | 65.3 | 60.7 |
| | CoxIV::Twin Strep::AnfK | 57.7 | 54.7 |
| | MTP-FAγ51::HA::AnfH | 36.9 | 32.4 |
| SL36 | HA::AnfD | 59.7 | NA |
| | HA::AnfK | 52.5 | NA |
| | HA::AnfH | 31.3 | NA |
| | HA::AnfG | 16.6 | NA |
| SL37 | MTP-FAγ51::HA::AnfG | 22.2 | 17.7 |
| | MTP-FAγ51::AnfD::HA | 65.4 | 60.7 |
| | CoxIV::Twin Strep::AnfK | 57.7 | 54.7 |
| | MTP-FAγ51::HA::AnfH | 36.9 | 32.4 |

Confirmation of the Mitochondrial Localisation and MPP Processing

The processing of the MTP-FAγ51::HA::Anf fusion polypeptides was a clear indication to the inventors of the mitochondrial localisation of the four, processed Anf polypeptides expressed from SL26. This was further confirmed by enrichment of mitochondrial fractions obtained from the infiltrated leaf tissues, using the metaxin-mediated method as described in Example 13. This involved the addition of the genetic construct SN197 encoding a TwinStrep-mTurquoise-TEV recognition sequence-metaxin fusion polypeptide (SEQ ID NO:121) in *A. tumefaciens* to a mixture with the *Agrobacterium* containing SL26. The metaxin region of the polypeptide from SN197, when expressed transiently in the plant cells, was localised to the outer membrane of mitochondria (Lister et al., 2007). This exposed the N-terminal TwinStrep motif to the cytosol, allowing for the rapid purification of the marked mitochondria under gentle conditions using beads coated with anti-Strep antibody. This resulted in a considerable enrichment of mitochondrial proteins relative to non-mitochondrial proteins in the same cell.

To test this, a mixture of *A. tumefaciens* cultures containing SN197 in one strain and SL26 in another strain was introduced into *N. benthamiana* leaves. Infiltrated tissues were harvested 5 days later. These tissues were processed for mitochondrial isolation as described in Example 13. Proteins in the isolated mitochondria were then analysed by SDS-PAGE and Western blotting using the HA antibody for detection. All of the Anf polypeptides were readily detected in the mitochondrial fraction. The bands detected on the Western blot were consistent with the sizes of the processed AnfD, AnfK, AnfH and AnfG polypeptides from SL26, indicating once again that the Anf polypeptides were localised to the plant mitochondria. A smaller band from the AnfK fusion polypeptide that was probably formed by an additional proteolytic cleavage (see above) was also enriched in the mitochondrial fraction, suggesting that the secondary cleavage was occurring in the mitochondria. The observation that the Anf polypeptides were processed was evidence that they were localised to the mitochondrial matrix.

The processing by cleavage within the MTP sequence was confirmed by LC-MS methods after tryptic digestion of proteins, using the methods described in Example 1. Protein bands were isolated from Coomassie stained gels after electrophoresis of protein extracts expressed from SL26. The protein identity in gel slices was confirmed through LC-MS and targeted MRM. The protein identities matched to Metaxin, AnfD, AnfK and AnfH with at least 95% confidence. The AnfG protein was not identified in the Coomassie gel that underwent LC-MS detection, probably due to its low-level accumulation. All of the Anf proteins except for AnfK were detected with the intended N-terminus after efficient cleavage of the MTP. For the AnfK polypeptide, two N-terminal FAγ51 MTP targeted peptides were detected by the MRM at a low signal level indicating that partial MPP cleavage of the AnfK fusion polypeptide was occurring. This was consistent with the observations made with the Western blot analysis and confirmed that partial cleavage was occurring at the intended site within the MTP sequence by MPP.

Solubility of Mitochondrial Anf Fusion Polypeptides after Expression in Plant Cells The inventors considered that, to be functional, the Fe-nitrogenase proteins should be produced in a soluble form to allow for the necessary protein to protein interactions and stability in the Fe-nitrogenase enzyme, as well as allowing the enzymes to interact with their substrates and cofactors. If the proteins were not in a soluble form, it could be an indication of improper protein folding or tight binding to the mitochondrial membranes and thereby detrimental to nitrogenase activity. Therefore, experiments were carried out to test whether the expressed Anf polypeptides were in a soluble form when produced in plant mitochondria. This was done by fractionating protein extracts into soluble (supernatant) and insoluble (pellet) forms using the method as described in Example 1.

This was first done using the single gene constructs in *N. benthamiana* leaves, as before. Protein extracts for the soluble and insoluble proteins were prepared from leaves inoculated with the genetic constructs and analysed by Western blotting (FIG. 28). The Western blot showed that when the AnfD fusion polypeptide was targeted to the mitochondria in *N. benthamiana* leaves, it was essentially insoluble with only a very faint band visible in the soluble fraction (FIG. 28). The processed and unprocessed AnfK polypeptides were essentially present only in the soluble fraction, whereas the processed AnfH polypeptide was only partially soluble. The mitochondrially-targeted AnfG polypeptide was only present in the soluble fraction, indicating that the processed AnfG fusion polypeptide was in a soluble form when expressed with the mitochondrial matrix of *N. benthamiana.*

The solubility of mitochondrially-targeted AnfD, AnfK, AnfH and AnfG when co-expressed was tested in the following manner. The solubilities of the AnfD, AnfK, AnfH and AnfG fusion polypeptides expressed from the multi-gene vector SL26 were compared to the solubilities of the polypeptides expressed from SL31. A mixture of *Agrobacterium* strains each containing a single-gene construct was also used to infiltrate the plants. The Western blot is shown in FIG. 27, panel B.

A surprising and unexpected result was observed with the multi-gene vector SL26. This time, some of the processed AnfD fusion polypeptide was clearly observed in the soluble fraction, indicating that the co-expression of the other Anf polypeptides had increased the solubility of at least some of the AnfD polypeptide. This suggested that either some of the AnfD polypeptide was being stabilised, perhaps through a protein to protein association of the AnfD polypeptide with one or more of the other Anf polypeptides, or increased folding was occurring of the AnfD polypeptide into its proper conformation. The possibility of protein-protein association was tested as described in the following Example.

The series of vectors SL26, SL27, SL28 and SL29 were used in a similar experiment to compare the solubility of the AnfD polypeptide when co-expressed with one, two or all three of the other Anf polypeptides. The fusion polypeptides expressed from multi-gene vectors SL26, SL27 and SL28 and the single gene vector SL29 were tested for polypeptide accumulation levels and for soluble and insoluble AnfD polypeptides. The results from the transient *N. benthamiana* leaf assay indicated that as the number of Anf genes reduced, so did the solubility of the AnfD polypeptide, especially in the absence of AnfK. Therefore, it was concluded that the presence of AnfK, in particular, enhanced the solubility of the AnfD polypeptide.

Further confirmation of the solubility of the mitochondrially-localised Anf polypeptides was obtained by an affinity purification experiment using beads linked to anti-HA antibody. When the crude extracts were contacted with the beads and unbound proteins washed away before analysing the bound proteins, each of the AnfD (both processed and unprocessed forms), AnfK (both processed and unprocessed forms), AnfH (processed) and AnfG (processed) fusion polypeptides were recovered from the beads. The HA-enriched polypeptide bands observed on the Coomassie stained gels were excised and the polypeptides in the gel slices were analysed by LC-MS mass spectrometry. The bands present in the gels were of the correct sizes for both processed and unprocessed AnfD, AnfK and AnfG polypeptides. The polypeptides identified for AnfG included a potentially partially processed polypeptide having an extra amino acid at the N-terminal MTP cleavage site. This was consistent with the observation of two close migrating bands present for AnfG in the Western blot for extracts from SL26 (See FIG. 27, panel C). The band present for AnfH was for the processed size only, indicating efficient processing within the MTP sequence. The identity of the polypeptide bands was confirmed through the LC-MS analysis.

Several other multi-gene vectors were designed and made to test whether the position of the Anf gene on the multi-gene vector or the position of the HA epitope affected the protein expression, solubility or both. These vectors included constructs designated SL23, SL30, SL34 and SL37. The different positioning of the genes on the multi-gene vector did not appear to significantly impact the protein expression and solubility.

The vector SL26 is used to transform tobacco (*N. tabacum*), *N. benthamiana* and *Arabidopsis thaliana* plants, producing stably transformed plants which express the AnfD, AnfK, AnfH and AnfG polypeptides.

Discussion

These experiments demonstrated that it was possible to express Anf genes encoding AnfD, AnfK, AnfG and AnfH fusion polypeptides and have them processed and localised in the mitochondria of plant cells. The polypeptides were proved to be cleaved at the intended site within the MTP sequence, in each case leaving a 9 amino acid "scar sequence" at the N-terminus of the fusion polypeptide. Mitochondrial localisation was also demonstrated in several different ways. Single and multi-gene constructs were introduced and expressed using a leaf assay with the plant *N. benthamiana*. The solubility of mitochondrially-localised Anf polypeptides was also tested. Solubility of AnfD increased with the use of multi-gene constructs to co-express AnfK, AnfH and AnfG.

Example 19. Synergistic Interaction of Fe-Nitrogenase Polypeptides within Plant Leaf Mitochondria In diazotrophic bacteria, the AnfD, AnfK and AnfG proteins form a heterohexamer complex that, with the required cofactors, constitutes the dinitrogenase enzyme (Davis et al., 1996; Zheng et al., 2018). This complex is the catalytic enzyme for reduction of dinitrogen. In order to be an active enzyme, this complex requires the FeFeco-factor and multiple Fe—S clusters.

The inventors designed and carried out several experiments to detect protein-protein interactions of the Anf polypeptides within plant mitochondria after expression from a multi-gene vector. To test this in a first experiment, a vector designated SL30 (Table 20) was designed and made that contained anfD, anfK, anfH and anfG genes, each expressed from its own 35S promoter and with the same transcription terminators as for SL26. The important modification relative to SL26 was that the AnfD fusion polypeptide of SL30 had a TwinStrep epitope fused to the C-terminus of AnfD to provide for purification of the AnfD polypeptide under gentle, non-denaturing conditions. SL30 still had the MTP-FAγ51 sequence fused to the N-terminus of AnfD for mitochondrial localisation. The AnfK, AnfH and AnfG fusion polypeptides encoded by SL30 had the MTP-FAγ51 sequence translationally fused at the N-terminus of the polypeptides followed by a HA epitope and then the Anf sequence, as for SL26. Each individual gene in SL30 retained its own 35S promoter and terminator, again as for SL26.

SL30 was introduced into *A. tumefaciens* and cultures of the transformed Agrobacteria were infiltrated into *N. benthamiana* leaves as before. Five days later, leaf samples were harvested and processed under ambient air conditions for extraction of soluble proteins into extraction buffer, using the same extraction buffer as in Example 14. The crude protein mixture was passed through a Strep-tactin XT affinity column under aerobic conditions. After washing the column with 10 column volumes of wash buffer (as per Example 14) to remove unbound proteins, the bound proteins were eluted with wash buffer containing 50 mM biotin, pH 7.2, and analysed by SDS-PAGE and Western blotting using Strep-tactin antibody for detection of the AnfD polypeptide and anti-HA antibody to detect any co-purifying Anf polypeptides having the HA epitope.

Extracted proteins were assessed by the Western blot method using Strep-tactin antibody. The analysis showed that purified AnfD polypeptide was present in the eluate and that it migrated at the molecular weight for the processed form (FIG. 26), indicating that the mitochondrially-targeted AnfD was processed, soluble and interacted with the Strep-tactin affinity media. When the Western blot was probed with the HA antibody, a faint but clearly visible band corresponding to the AnfK fusion polypeptide was observed, migrating at a speed consistent with a correctly MPP-processed isoform of AnfK. This indicated that the AnfK fusion polypeptide had been co-purified through association with the AnfD polypeptide. The AnfG polypeptide was not visible in the Western blot. There were also several bands of lower molecular weight on the Western blot that may have represented breakdown products of AnfD, which may have occurring post-extraction.

A second, analogous experiment was carried out in the same manner except that a new multi-gene construct, SL34, was made and used. With this construct, the TwinStrep epitope was fused to the AnfK sequence, between the MTP and AnfK sequences, and the AnfD polypeptide was the same as the one encoded by SL26 (Table 20) i.e with a HA epitope. This configuration was designed to test for the reverse capture and detection compared to the experiment with SL26, in that the AnfK polypeptide could be purified on the Strep-tactin column and the bound proteins analysed with the HA antibody for the presence of the other Anf polypeptides. The AnfK polypeptide encoded by SL34 contained a CoxIV MTP leader sequence with a fused Twin-strep at the N-terminus of AnfK, rather than the MTP-FAγ51. The AnfD, AnfH and AnfG fusion polypeptides encoded by SL34 each had the MTP-FAγ51 sequence translationally fused at the N-terminus of the polypeptide followed by the HA epitope. The CoxIV MTP has previously been shown to correctly target proteins to the mitochondrial matrix within *N. benthamiana* (Burén et al., 2017).

An *A. tumefaciens* culture containing SL34 was infiltrated into *N. benthamiana* leaves and leaf samples harvested 5 days later. The tissue samples were processed using the same experimental conditions for SL30 under ambient air, and the resultant crude protein extracts passed through the Strep-tactin column to purify the AnfK polypeptide containing the TwinStrep sequence. The eluate from the column was again analysed by SDS-PAGE and Western blotting using both the HA and Strep-tactin antibodies for detection of polypeptides having the HA- and TwinStrep-epitopes, respectively. The Western blot that was probed with Strep-tactin antibody showed the presence of purified AnfK polypeptide in the eluate, as intended, and the molecular weight of the polypeptide was consistent with it being the MPP-processed isoform. When the Western blot was further probed with the HA antibody, the presence of AnfD polypeptide was observed, indicating that the AnfD polypeptide had been co-purified with the AnfK polypeptide. The molecular weight of the AnfD was consistent with it being the MPP-processed isoform. AnfG was again not observed in the Western blot but was later detected at low signal intensities by LC-MS mass spectrometry. This experiment, like the previous experiment with SL30, demonstrated that the MPP-processed AnfD and AnfK polypeptides targeted to the mitochondrial matrix of the plant cells were associating together.

Another multi-gene vector was assembled, SL37 (Table 20), which encoded a fusion polypeptide having MTP-CoxIV and Twin-strep sequences fused at the N-terminus of AnfK, and AnfH and AnfG fusion polypeptides having the MTP-FAγ51 sequence translationally fused followed by a HA epitope at the N-terminus of the other Anf polypeptides. The AnfD polypeptide also had the MTP-FAγ51 MTP translationally fused to the N-terminus whereas the HA epitope was translationally fused at the C-terminus of the AnfD sequence. This construct was designed to test whether the AnfK polypeptide was associating with the full-length, processed AnfD polypeptide or possibly with a truncated AnfD product. This time, the protein extraction and processing were conducted under anaerobic conditions. The protein extract was passed through a Strep-tactin XT affinity column and then eluted, all under anaerobic conditions. The eluate was then analysed by SDS-PAGE and Western blotting with the HA and strep-tactin antibodies for detection.

The Western blot probed with the Strep-tactin antibody showed the presence of the processed AnfK polypeptide in the eluate. Furthermore, the Western blot probed with the HA antibody showed polypeptide bands corresponding in size to both processed and unprocessed AnfD polypeptides, with bands at lower molecular weights representing smaller AnfD products which were likely produced post-extraction. Polypeptide bands of the sizes for the AnfH and AnfG polypeptides were also observed in the eluate but at a much lower intensity than for AnfK or AnfD (FIG. 26).

The eluates produced from the SL34 and SL37 samples were analysed by LC-MS mass spectrometry and targeted MRM. Peptides from the AnfK, AnfD and AnfG polypeptides were detected in both eluates, with peptides from AnfH detected but only after anaerobic extraction.

As a negative control for the above experiments, to test the specificity of the detection, SL26, which encoded the AnfD, AnfK, AnfG and AnfH polypeptides, all fused to MTP-FAγ51 and having a HA epitope at the N-terminus (Table 20), was introduced into the *N. benthamiana* leaves. Leaf tissues were processed in the same manner as for SL30 and SL34 in aerobic conditions as described above. The only polypeptide band observed in the Strep-tactin probed Western blot of the protein extracts from SL26 was a relatively faint background band. There were no Anf polypeptide bands present in the eluate for either Strep-tactin or the HA probed Western blots. This control experiment demonstrated that the polypeptides containing the HA epitope observed on the Western blots were specifically from association of the AnfD and AnfK polypeptides.

Another multi-gene vector was assembled, SL93 (Table 22), having four genes encoding fusion polypeptides: one having MTP-CoxIV and Twin-strep sequences fused at the N-terminus of AnfG (MTP-CoxIV::TS::AnfG), and the other three separately encoding AnfH, AnfD and AnfK fusion polypeptides each having the MTP-FAγ51 sequence translationally fused followed by a HA epitope at the N-terminus. This construct was designed and made to test whether the AnfG polypeptide was associating with the AnfD polypeptide and/or with the AnfK polypeptide, by purification of the AnfG fusion polypeptide first of all by the Twin-Strep tag. In this experiment, the protein extraction and processing of the samples were conducted under anaerobic conditions. Following infiltration of *N. benthamiana* leaves with SL93 from *Agrobacterium* and preparation of extracts five days later, the protein extract from SL93 was passed through a Strep-tactin XT affinity column and then bound proteins eluted with biotin, all under anaerobic conditions. The eluate was then analysed by SDS-PAGE and Western blotting with the HA and Strep-tactin antibodies for detection, as before.

The Western blot probed with the Strep-tactin antibody showed the presence of the correctly processed AnfG polypeptide in the eluate. Furthermore, the Western blot of the same eluate probed with the HA antibody showed polypeptide bands corresponding in size to both processed and unprocessed AnfD and AnfK polypeptides after a 20 min exposure, although at a much lower intensity than for AnfG. Polypeptide bands of the sizes for the AnfH, AnfD and AnfK polypeptides were also observed in the total protein prior to the AnfG purification process. The eluate produced from the SL93 sample was analysed by LC-MS mass spectrometry and targeted MRM. Peptides from AnfG, AnfD and AnfK were detected within the eluate. Clearly, the AnfG fusion polypeptide was associating with the AnfD and AnfK polypeptides in the plant mitochondria, indicating that they were all in sufficiently soluble form to be able to form a complex.

Discussion

These experiments demonstrated for the first time the production of the distinct Fe-nitrogenase (Anf) proteins within a eukaryotic environment, specifically in plant mitochondria. The multi-gene constructs and differential epitope tagging in these experiments were used to show an association between AnfD and AnfK fusion polypeptides targeted to the plant mitochondrial matrix, and furthermore with AnfG fusion polypeptide. These results demonstrated that it was possible to produce multiple Anf polypeptides and localise them within the plant mitochondria in a soluble form to allow protein complexes. Moreover, co-expression of multiple Anf genes (AnfK, AnfH, AnfG) from a single vector led to an increase in AnfD polypeptide solubility, even though it was still only partially soluble.

When processed under aerobic conditions, some of the purified AnfD polypeptide co-purified with the AnfK polypeptide. A reverse experiment was conducted under aerobic conditions where AnfK was translationally fused to the TwinStrep epitope, where the other Anf polypeptides were all fused to a HA epitope. Some AnfD protein co-purified with the AnfK polypeptide as well as low amounts of the AnfG protein. When an analogous experiment was conducted under anaerobic conditions, again only low amounts of the AnfG protein were detected, indicating that the AnfD, AnfK and AnfG polypeptides were interacting within the soluble fraction of the mitochondria to form a complex. The detection of AnfG and AnfD along with AnfK as it was being purified indicated a three-way association. It was also demonstrated that AnfG co-purified with AnfD-AnfK under anaerobic conditions. The predicted structure of the FeFe nitrogenase has the AnfG polypeptide physically interacting with the surface of AnfD (Sippel and Einsle, 2017; Zheng et al., 2018). Interestingly, in one experiment when the extraction was conducted under anaerobic conditions, small amounts of the AnfH protein were also found within the eluate.

The AnfG protein was observed at a lower abundance in the pull-down experiments relative to AnfD and AnfK A band at the correct size for AnfG was visible after a longer exposure. The lesser abundance of AnfG may indicate that the optimal ratio of the subunits for the Fe-nitrogenase heterohexamer has not yet been achieved.

The inventors concluded from these experiments that the association of the AnfD and AnfK polypeptides and the three-way association of AnfD, AnfK and AnfG demonstrated the potential for using these Fe-nitrogenase components in plant mitochondria for nitrogenase engineering.

Example 20. Production of a Translational Fusion Between AnfD and AnfK Targeted to Plant Mitochondria Although a crystal structure for the Fe-nitrogenase has not been reported, it has been predicted that the AnfD, AnfK and AnfG subunits of the Fe-dinitrogenase in nitrogen fixing bacteria that have the Fe-nitrogenase are in a 1:1:1 stoichiometric ratio (Hu & Ribbe, 2015; Zheng et al., 2018). That ratio for the AnfD, AnfK and AnfG polypeptides may be important for the optimal function of the Fe-nitrogenase and may influence solubility of the AnfD component. As described in this Example, a predicted structural model for the Fe-nitrogenase was developed. The model was used to design an oligopeptide linker of an appropriate length to join the C-terminus of AnfD to the N-terminus of AnfK and thereby generate a translational fusion of AnfD and AnfK. The length of the linker was designed to allow for the correct folding of the protein complex, based on the predicted structural model. Genetic constructs to express the fusion polypeptide were made and tested. The fusion polypeptide had an MTP sequence to localise it to the mitochondrial matrix.

Generation of a Structural Model for the Fe-Nitrogenase

To design an AnfD::linker::AnfK fusion polypeptide, a homology model was created for the AnfDKHG complex based on the *A. vinelandii* V-nitrogenase crystal structure PDB ID: 5N6Y (Sippel and Einsle, 2017). This was used since no Fe-nitrogenase crystal structure had been reported, and the V-nitrogenase was thought to be the nearest in sequence homology. Homology models were constructed using SWISS-MODEL (swissmodel.expasy.org/) for each of the wild-type *A. vinelandii* AnfD and AnfK polypeptides (SEQ ID NOs:216 and 217) using the respective monomers from the PDB ID: 5N6Y $\alpha_2\beta_2$-heterodimer as templates. The AnfD model had the C-terminal 31 residues of the wild-type sequence missing (NSETLRQYTGGYDSVSKLREREYPAFERKVG, SEQ ID NO:197), and the AnfK model had two N-terminal amino acids missing (PH). The full heterodimer was constructed using the matchmaker function in Chimera to superpose the AnfD and AnfK homology models onto the native 5N6Y $\alpha_2\beta_2$-heterodimer, after which the above-mentioned missing residues were manually added to the model using Discovery Studio 2018 (Dassault Systèmes BIOVIA, San Diego). The 31 amino acid residues at the C-terminus of the AnfD monomer were added as α-helices, so as to take a conservative approach to the overall length of this section. AnfD was 36 residues longer at the C-terminus than the VnfD structure upon which it was built, so it is not possible to say with certainty what conformation this additional sequence would take. Therefore, the modelling took the shortest option available for the 31 amino acids that were not initially constructed during the generation of the homology model.

The entire $\alpha_2\beta_2$ heterodimer model, without cofactors, was prepared for molecular dynamics using the Xleap module of AMBER18 by solvating in a periodic water box (TIP3P, truncated octahedron, 12.0 Å minimum boundary distance from the solute) and neutralising with $Na^+$ ions (frcmod.ionsjc tip3p). The system was subjected to energy minimisation with Amber18 using 25,000 steps of steepest descent followed by 25,000 steps of conjugate gradient, followed by 20 ns of molecular dynamics using AMBER18. The protein was treated with the ff14SB forcefield and the simulation was conducted at 298 K (NVT ensemble) using a 12.0 Å cutoff with long range interactions treated with the particle mesh Ewald summation. The purpose of the simulation was to identify potential regions of high strain and any other potentially detrimental features, hence 20 ns was sufficient for this task. The trajectory was analysed using VMD (hwww.ks.uiuc.edu/). The α-helices constructed for the 31 residues added at the C-terminus of AnfD retained their structure over the course of the trajectory, suggesting this could possibly be their native conformation, although more extensive dynamics simulations would be required for further corroboration. The added residues and linkers relaxed early in the simulation with no apparent adverse interactions with the rest of the structure.

It was predicted from the model that a peptide linker joining the C-terminus of AnfD to the N-terminus of AnfK could create a fusion protein that retained its overall structure and therefore keep its function. An initial linker peptide sequence of 16 amino acids designated linker16 was used for modelling, having the amino acid sequence GGGSGGGSGGGSGGGS (SEQ ID NO:198), expected to provide a disordered linker. The homology models predicted that an oligopeptide of at least 16 amino acids in length could span the required distance. The linker of 16 amino acids was therefore added in extended conformation and then relaxed with a series of rough geometry optimisations in Discovery Studio.

Coordinates of the AnfDK fusion dimer were generated from the final frame of the 20 ns molecular dynamics simulation and this structure was superposed with PDB ID: 5N6Y in order to generate starting positions for a homology model of AnfG, which was generated with SWISS-MODEL using a VnfG monomer from 5N6Y as a template. Once the $Anf(DKG)_2$ model was constructed, it was superposed with the NifDKH model from PDB ID: 1N2C to generate starting positions for the AnfH homology models, which were constructed in SWISS-MODEL using a NifH monomer from PDB ID: 1N2C as a template. Prior to molecular dynamics, conducted as described above, the AnfG and AnfH dimer structures were manually positioned slightly away from their interfaces with the AnfD-AnfK fusion structures to relieve steric clashes that arose from artefacts of the superposition.

The amino acid sequence of the synthetic fusion polypeptide with the linker16 is provided as SEQ ID NO:199. The modelled structure is represented in FIG. 29.

For detection purposes, a HA epitope having the sequence YPYDVPDYA (SEQ ID NO:115) was added into the middle of the 16 amino acid linker, to provide a 26-amino acid sequence GGGGSGGGSYPYDVPDYAGGGSGGGS (SEQ ID NO:200), designated herein as "linker26(HA)". The HA epitope was not included in the minimisation or the molecular dynamics. The fusion polypeptide with this linker26(HA) between and joining the AnfD and AnfK sequences and with no N-terminal MTP sequence (SEQ ID NO:201), or MTP-FAγ51 (SEQ ID NO:202), MTP-CoxIV (SEQ ID NO:203), mFAγ51 (SEQ ID NO:204) or a 6×His sequence (SEQ ID NO:205) fused to the N-terminus of the fusion polypeptide was in each case predicted to allow the AnfD, AnfK, AnfG and AnfH polypeptides to associate properly with no predicted adverse effects on the native structure. In these designs, the AnfG protein was not included in this linker design as both N- and C-terminals of AnfG were buried close to the surface of AnfD and seemed unlikely to tolerate any linker extensions. It has also been demonstrated that both AnfG and AnfK do not tolerate a C-terminal amino acid extension (Yang et al., 2018), which was consistent with the homology-based model of the Fe-nitrogenase developed as described above.

Constructs used in this Example are summarised in Table 21.

SN273 is provided as SEQ ID NO:203. To provide molecular weight markers to detect processing of the translation product within mitochondria, two genetic constructs were made as controls. The first (SN274) lacked the MTP-FAγ51 sequence and therefore would be targeted to the cytoplasm. The second (SN275) had a mutated MTP-FAγ51 sequence that prevented cleavage by MPP, designated mFAγ51. The amino acid sequences of the fusion polypeptides encoded by SN274 and SN275 are provided as SEQ ID NOs:204 and 205.

These vectors were separately introduced into *N. benthamiana* leaves using the *Agrobacterium*-mediated methods described in Example 1. As further controls, vectors expressing individual Anf proteins in various combinations, SL26, SL28, SN161 and SN129, were also infiltrated into *N. benthamiana* leaves. Leaf tissues were harvested 4 days post-infiltration and processed for total, soluble and insoluble protein fractions as described in Example 1. The resulting protein fractions were analysed by SDS-PAGE and Western blotting using the HA epitope for detection.

TABLE 21

Listing of genetic constructs used in this Example.

| Plasmid | Encoded polypeptide | Predicted molecular weight (kDa) Unprocessed | Processed* |
|---|---|---|---|
| SN272 | MTP-FAγ51::HA::AnfD::Linker26(HA)::AnfK | 118 | 113 |
| SN273 | MTP-CoxIV::TwinStrep::AnfD::Linker26(HA)::AnfK | 118 | 115 |
| SN274 | mFAγ51::HA::AnfD::Linker26(HA)::AnfK | 117 | NA |
| SN275 | HIS::AnfD::Linker26(HA)::AnfK | 112 | NA |
| SN161 | MTP-FAγ51::HA::AnfD | 65.3 | 60.7 |
| SN129 | MTP-FAγ51::HA::AnfK | 58.1 | 53.5 |
| SL26 | MTP-FAγ51::HA::AnfG | 22.2 | 17.7 |
| | MTP-FAγ51::HA::AnfD | 65.3 | 60.7 |
| | MTP-FAγ51::HA::AnfK | 58.1 | 53.5 |
| | MTP-FAγ51::HA::AnfH | 36.9 | 32.4 |
| SL28 | MTP-FAγ51::HA::AnfD | 65.3 | 60.7 |
| | MTP-FAγ51::HA::AnfK | 58.1 | 53.5 |
| SN129 | MTP-FAγ51::HA::AnfK | 58.1 | 53.5 |
| SN161 | MTP-FAγ51::HA::AnfD | 65.3 | 60.7 |

Synthesis and Testing of Genetic Constructs to Express the AnfD-Linker-AnfK Polypeptide in Plant Cells A DNA sequence encoding the AnfD::Linker26(HA)::AnfK protein coding region was chemically synthesised and used to make a set of genetic constructs through GoldenGate protocols, using the *A. vinelandii* amino acid sequences for AnfD and AnfK The protein coding region was codon-optimised for plant expression. Expression of the gene encoding the fusion polypeptide in plant cells was under the control of the 35S promoter and Nos3' polyadenylation region/transcription terminator (Table 21). For mitochondrial targeting, a sequence encoding MTP-FAγ51::HA was added upstream of the AnfD::Linker26(HA)::AnfK protein coding region so that, when transcribed and translated, the MTP and HA amino acid sequences were translationally fused to the AnfD::linker26(HA)::AnfK polypeptide as a single translational product. The genetic construct encoding this fusion polypeptide was designated SN272. The amino acid sequence of the full-length fusion polypeptide encoded by SN272 is provided as SEQ ID NO:202. A second vector designated SN273 was made which encoded an identical polypeptide except that an MTP sequence from a CoxIV gene with a TwinStrep sequence (Burén et al., 2017) was substituted for the MTP-FAγ51 sequence. The amino acid sequence of the full-length fusion polypeptide encoded by The Western blots revealed that all of the AnfD::linker26(HA)::AnfK fusion polypeptides were readily detected in the total protein fractions isolated from the *N. benthamiana* leaves (FIG. 30). The molecular weight of the main polypeptide band from each construct was consistent with the predicted size of the polypeptides in the range 110-120 kDa (see Table 21). The predicted size of the full-length (unprocessed) MTP-FAγ51::HA::AnfD::Linker26(HA)::AnfK fusion polypeptide was approximately 118 kDa. The processed polypeptide after cleavage was predicted to be approximately 113 kDa, which could be distinguished from the unprocessed polypeptide by their different mobilities on the SDS-PAGE gels and in the Western blots. The molecular weight of the polypeptide detected on the Western blots (FIG. 30) matched the control polypeptide encoded by SN275 which represented the processed form, indicating that the MTP-FAγ51::HA::AnfD::Linker26(HA)::AnfK polypeptide from SN272 had been efficiently imported into the mitochondria import and cleaved within the *N. benthamiana* cells. Likewise, the polypeptide band generated from the construct SN273 encoding the MTP-CoxIV::TwinStrep::AnfD::Linker26(HA)::AnfK fusion polypeptide also appeared to be efficiently and correctly processed. The MTP-FAγ51::HA::AnfD::Linker26(HA)::AnfK fusion polypeptide from SN272 had two HA epitopes whereas the MTP-CoxIV::TwinStrep::AnfD::Linker26(HA)::AnfK fusion polypeptide from SN273 had only one, so the former polypeptide may have been detected more efficiently per polypeptide in these Western blots.

The Western blots of the soluble and insoluble fractions indicated that expression of mitochondrially-targeted AnfD by itself from SN161 resulted in a predominantly insoluble polypeptide (FIG. 31, panel A), with only very faint bands visible. However, the solubility of the AnfD polypeptide was increased when the same AnfD gene was co-expressed with AnfK from SL28 and further improved when the AnfD gene was co-expressed with AnfK, AnfH and AnfG from SL26. In each case where the AnfD and AnfK genes were co-expressed, the AnfD and AnfK polypeptides were detected in different abundances in the soluble fraction, despite the genes being expressed from the same T-DNA. In contrast, the translational fusion of AnfD and AnfK in the form of a MTP::HA::AnfD::Linker26(HA)::AnfK fusion polypeptide, targeted to the mitochondria as in SN272 and SN273, necessarily provided the ideal stoichiometric ratio for AnfD and AnfK polypeptides as 1:1. The inventors concluded that the fusion polypeptide using the linker sequence had at least this advantage relative to expression of the polypeptides from separate genes, even when the two genes were linked on one T-DNA.

The polypeptides resulting from processing of the MTP::HA::AnfD::Linker26(HA)::AnfK polypeptides expressed from SN272 and SN273 were detected in both the soluble and insoluble fractions of the plant extracts (FIG. 31, panels A) and B)). Since the addition of genes expressing AnfH and AnfG targeted to the mitochondria increased the solubility of mitochondrially-targeted AnfD, further experiments co-expressed mitochondrially-targeted MTP::HA::AnfD::Linker26(HA)::AnfK together with mitochondrially-targeted AnfH and AnfG, see below.

The polypeptide resulting from processing of the MTP-FAγ51::HA::AnfD::Linker26(HA)::AnfK fusion polypeptide was purified after expression of the gene from SN272, using the HA epitope in an affinity based purification method. The purified protein is subjected to proteomics analysis to confirm that the N-terminal sequence is as expected for the cleavage by MPP.

The genetic construct SN272 was a binary vector suitable for producing stably transformed plants by *Agrobacterium*-mediated transformation with the addition of a selectable marker gene. The gene encoding the fusion polypeptide was therefore excised and inserted into a binary vector containing a suitable selectable marker gene, resulting in the binary vector SL79. That vector was used to produce stably transformed *Arabidopsis thaliana* plants and can be used to transform other plants, for example tobacco and *N. benthamiana* plants. The fusion polypeptide was demonstrated to be expressed, cleaved within the MTP sequence at the intended site by MPP, and demonstrated to be present in the mitochondria (see below). At least some of the processed fusion polypeptide is present in the soluble fraction.

Example 21. Production of Anf and Nif Proteins Required for the Fe-Nitrogenase within Plant Cells with Mitochondrial Targeting Introduction A minimum of ten genes encoding Anf and Nif proteins was reported to be required to constitute Fe-nitrogenase in the bacterium *E. coli* (Yang et al., 2014), namely 4 structural Anf genes encoding the AnfD, AnfK, AnfH and AnfG polypeptides and 6 so-called accessory Nif genes encoding the NifV, NifS, NifU, NifJ, NifF and NifB polypeptides. The sequences for the Anf polypeptides were based on the nitrogen fixing bacterium *A. vinelandii* and, for the other Nif polypeptides, on the bacterium *K. oxytoca*. Expression of the set of ten genes in *E. coli* produced a functional Fe-nitrogenase although with low activity (Yang et al., 2014).

Based on the data described in the earlier Examples herein showing the production of Anf and Nif fusion polypeptides in plant mitochondria in soluble form, the present inventors decided to attempt to engineer plant cells to produce the minimum set of genes for producing Fe-nitrogenase, targeting the gene products to the mitochondrial matrix in the plant cells.

Results

The set of gene products that was selected for a series of experiments included AnfD, AnfK, AnfG and AnfH polypeptides based on the diazotroph *A. vinelandii* (Av), and 6 Nif proteins, namely NifF, NifJ, NifS and NifU based on *K. oxytoca* (Ko), NifV from *A. vinelandii* (AvNifV) and NifB from *Methanocaldococcus infernus* (MiNifB). Genetic constructs were designed and made to express the polypeptides in *N. benthamiana* leaves with targeting to the mitochondrial matrix through translational fusion of N-terminal MTP sequences, in analogous fashion to the genetic constructs described in the earlier Examples. The nucleotide sequences for expressing the fusion polypeptides were codon optimised for expression in plant cells, as before. Two different MTP sequences were used, namely MTP-FAγ51 and MTP-CoxIV, for mitochondrial targeting of the fusion polypeptides. The polypeptides that had MTP-FAγ51 had a HA epitope fused at either the N- or C-terminus, whereas the polypeptides that had MTP-CoxIV had a TwinStrep epitope inserted between it and the Anf/Nif polypeptide. For expression in *N. benthamiana*, each gene was under the control of a 35S promoter and nos 3' polyadenylation region/transcriptional terminator. These nucleotide sequences were upstream and downstream of each protein coding region, respectively. The constructs were assembled using the Golden Gate methods, as before.

The multi-gene constructs SL42 and SL43 were made using these principles and methods. The vectors each had five different, separate genes linked in one T-DNA (Table 22). SL42 had genes encoding fusion polypeptides which included the KoNifS, KoNifU, KoNifJ, KoNifF and MiNifB sequences, each with its own MTP and epitope sequences translationally fused. SL43 had genes encoding fusion polypeptides which included AvAnfD, AvAnfK, AvAnfH, AvAnfG and AvNifV sequences, again each having its own MTP and epitope sequences. The AvNifV sequence was selected out of the many available NifV sequences on the basis of the expression, processing and solubility data and evidence of homocitrate production by AvNifV targeted to plant mitochondria as described in Example 15.

TABLE 22

Single and multi-gene genetic constructs encoding components of Fe-nitrogenase for expression in plant cells.

| Plasmid | Encoded fusion polypeptides | Predicted molecular weight (kDa) | |
|---|---|---|---|
| | | Unprocessed | Processed |
| SL42 | MTP-FAγ51::KoNifF::HA | 26.1 | 21 |
| | MTP-FAγ51::KoNifJ::HA | 135 | 130 |
| | MTP-FAγ51::KoNifS::HA | 50.3 | 45 |
| | MTP-FAγ51::KoNifU::HA | 36 | 31 |
| | MTP-CoxIV::TwinStrep::MiNifB | 41.6 | 38 |
| SL43 | MTP-FAγ51::HA::AvAnfG | 22.2 | 17.7 |
| | MTP-FAγ51::HA::AvAnfD | 65.3 | 60.7 |
| | MTP-CoxIV::TwinStrep::AvAnfK | 57.7 | 54.7 |
| | MTP-FAγ51::HA::AvAnfH | 36.9 | 32.4 |
| | MTP-FAγ51::HA::AvNifV | 48.4 | 43.8 |
| SL48 | MTP-FAγ51::HA::AvAnfG | 22.2 | 17.7 |
| | MTP-CoxIV::TwinStrep::AvAnfD::Linker26(HA)::AvAnfK | 118 | 115 |
| | MTP-FAγ51::HA::AvAnfH | 36.9 | 32.4 |
| | MTP-FAγ51::HA::AvNifV | 48.4 | 43.8 |
| SL49 | MTP-FAγ51::KoNifF::HA | 26.1 | 21 |
| | MTP-FAγ51::KoNifJ::HA | 135 | 130 |
| | MTP-FAγ51::KoNifU::HA | 36 | 31 |
| | MTP-FAγ51::HA::MiNifB | 41.9 | 37.3 |
| SN254 | MTP-FAγ51::HA::AvNifV | 48.4 | 43.8 |
| SL50 | MTP-FAγ51::HA::AvAnfG | 22.2 | 17.7 |
| | MTP-CoxIV::TwinStrep::AvAnfD::Linker26(HA)::AvAnfK | 118 | 115 |
| | MTP-FAγ51::HA::AvAnfH | 36.9 | 32.4 |
| | MTP-FAγ51::HA::AvNifV | 48.4 | 43.8 |
| | MTP-FAγ51::HA::AvFdxN | 16.4 | 11.9 |
| SL54 | MTP-FAγ51::KoNifF::HA | 26.1 | 21 |
| | MTP-FAγ51::KoNifJ::HA | 135 | 130 |
| | MTP-FAγ51::KoNifS::HA | 50.3 | 45 |
| | MTP-FAγ51::KoNifU::HA | 36 | 31 |
| | MTP-FAγ51::KoNifB::HA | 58 | 53 |
| SN192 | MTP-FAγ51::KoNifB::HA | 58 | 53 |
| SL78 | MTP-FAγ51::KoNifF::HA | 26.1 | 21 |
| | MTP-FAγ51::KoNifJ::HA | 135 | 130 |
| | MTP-FAγ51::KoNifS::HA | 50.3 | 45 |
| | MTP-FAγ51::KoNifU::HA | 36 | 31 |
| | MTP-FAγ51::HA::MiNifB | 41.9 | 37.3 |
| SL79 | MTP-CoxIV::TwinStrep::AvAnfD::Linker26(HA)::AvAnfK | 118 | 115 |
| | MTP-FAγ51::HA::AvAnfG | 22.2 | 17.7 |
| | MTP-FAγ51::HA::AvAnfH | 36.9 | 32.4 |
| | MTP-FAγ51::HA::AvNifV | 48.4 | 43.8 |
| | MTP-FAγ51::HA::FdxN | 16.4 | 11.9 |
| SL29 | MTP-FAγ51::HA::AvAnfD | 65.3 | 60.7 |
| SL93 | MTP-CoxIV::TwinStrep::AvAnfG | 21.9 | 18.9 |
| | MTP-FAγ51::HA::AvAnfD | 65.3 | 60.7 |
| | MTP-FAγ51::HA::AvAnfK | 58.1 | 53.5 |
| | MTP-FAγ51::HA::AvAnfH | 36.9 | 32.4 |

Production of the Fusion Polypeptides in Plant Cells

Cultures of *A. tumefaciens* containing SL42 were infiltrated into 5-week-old *N. benthamiana* leaves as described in Example 1. Four to five days post infiltration, leaf samples were harvested. Total, soluble and insoluble protein fractions were extracted, as follows. For testing the solubility of plant-expressed polypeptides, the leaf tissue was ground in ice-cold extraction buffer (100 mM Tris pH 8.0, 150 mM NaCl, 0.25 M mannitol, 5% (v/v) glycerol, 1% (v/v) Tween 20, 1% (w/v) PVP, freshly-added 2 mM TCEP, 0.2 mM PMSF and 10 μM leupeptin) and transferred to a microfuge tube. The sample was centrifuged at 20,000×g for 5 min to divide the sample into soluble (supernatant) and insoluble (pellet) fractions. The supernatant was transferred to a fresh microfuge tube and centrifuged again at 20,000×g for 5 min to remove any remaining insoluble material. The insoluble fraction was washed by resuspension of the pellet in 300 μl extraction buffer, with dispersal by repeated strokes of the pipette, and centrifuged at 20,000×g for 5 min, discarding the supernatant. This washing step was repeated twice more, removing any remaining soluble protein from the insoluble fraction. Samples were then analysed by SDS-PAGE and Western blotting using anti-HA and anti-Strep antibodies. The anti-HA antibody (Monoclonal Anti-HA, Sigma) was used at 1:5000 dilution, and the anti-Strep/HRP conjugate antibody (Strep-MAB-conjugate HRP, IBA) was used at 1:10,000 dilution.

The Western blot analysis for SL42 (FIG. 32) showed that all five polypeptides were readily detected with the appropriate antibodies, each showing polypeptide bands present in the soluble protein fraction. The NifJ fusion polypeptide appeared to be entirely processed by MPP, whereas the NifU, NifS and NifF polypeptides were present as both processed and unprocessed forms, indicating less efficient cleavage by MPP. The NifJ, NifU, NifS, NifF and NifB polypeptides were present in both the soluble and insoluble fractions. The NifB polypeptide, which was translationally fused at the N-terminus with the MTP-CoxIV-Twin-strep sequence, was visible when the anti-Strep antibody was used for detection (FIG. 31, Panel B).

The Western blot analysis for SL43 (FIG. 33) also showed that all five of the encoded polypeptides were readily detected with the appropriate antibodies, each showing polypeptide bands present in the soluble protein fraction. Importantly, the processed AnfD, AnfK and AnfH fusion polypeptides were all observed in the soluble fraction. They were also observed in the insoluble fraction, indicating partial solubility for these three fusion polypeptides. This result was significantly better than had been observed with the expression of the corresponding genes from single-gene vectors. The AnfD, AnfG, AnfH and NifV fusion polypeptides all appeared to be partially cleaved by MPP, each showing bands for the processed and unprocessed forms. The AnfK fusion polypeptide appeared to be efficiently processed.

Next, the *A. tumefaciens* cultures containing SL42 and SL43 were mixed and infiltrated into *N. benthamiana* leaves as described before. This experiment therefore introduced all 4 AvAnf genes and all six of the Nif genes, 10 genes in combination. The surprising and significant result observed in the Western blot (FIG. 34) was that all 10 polypeptides were readily detected. Moreover, all 10 polypeptides were present in the soluble fraction, some exhibiting efficient processing by MPP. Several of the polypeptides were visible with 2 bands, with the upper band representing unprocessed polypeptide and the lower band representing the MPP-cleaved polypeptide and demonstrating mitochondrial import. The unprocessed polypeptide band was visible for the proteins AnfD, NifV, NifU and NifF as well as a band present at the predicted size for cleaved polypeptides.

Association of AnfD and AnfK in Plant Cells

The multi-gene vectors, SL43 and SL49 (Table 22) were infiltrated into 5-week-old *N. benthamiana* plants, separately and in combination. SL43 encoded a fusion polypeptide having four separate genes encoding AnfD, AnfH, AnfG and NifV polypeptides each with the MTP-FAγ51 sequence translationally fused followed by a HA epitope at the N-terminus of the Nif polypeptides, and a fifth gene encoding MTP-CoxIV and Twin-strep sequences fused at the N-terminus of AnfK SL49 encoded NifJ, NifF and NifU fusion polypeptides with the MTP-FAγ51 sequence translationally fused at the N-terminus of the Nif polypeptides followed by a HA epitope at the C-terminus, and a NifB fusion polypeptide having MTP-FAγ51 and HA fused at the N-terminus. The constructs were designed to enable purification of the AnfK polypeptide product using the Twin-Strep epitope and to test the possibility of co-purification of other Anf or Nif proteins.

Protein extraction and processing from the co-infiltrated plant samples were conducted under anaerobic conditions. The protein extract was passed through a StrepTactin XT affinity column and then eluted. Samples collected along the polypeptide purification process were analysed by SDS-PAGE and Western blotting with the HA and Strep-tactin antibodies for detection.

The Western blot probed with the Strep-tactin antibody showed the presence of processed AnfK fusion polypeptide in each of the total, input, pellet and eluate fractions, with bands at lower molecular weights potentially representing smaller AnfK-derived products, which were likely produced by post-extraction degradation by protease contamination. The purified AnfK fusion polypeptide was greatly concentrated in the eluate fraction compared to the input fraction as shown by the intensity of the AnfK band on the blot. When the Western blot was re-probed with the HA antibody, all of the encoded Anf and Nif fusion polypeptides were detected within the input sample, although the band for AnfG was visible only after exposure of the blot for 20 min rather than 1 min. Significantly, the HA antibody also showed the presence of the processed AnfD polypeptide within the eluate sample. The presence of AnfD and AnfK within the eluate sample indicated that when the AnfK fusion polypeptide was purified, the MPP-processed AnfD polypeptide was co-purified, indicating protein-protein interaction of these two fusion polypeptides.

Homocitrate Production in the Infiltrated Plant Cells

As described in Example 15, the plant codon optimised *A. vinelandii* NifV fusion polypeptide (AvNifV) exhibited homocitrate synthase activity when expressed individually from the genetic construct SN254. The leaf samples infiltrated with either SL42 or SL43, or both vectors in combination, were assayed for the presence of homocitrate using the GC-MS/MS method as described in Example 15. Homocitrate was detected in the samples infiltrated with SL43, either alone or in combination with SL42, but not with SL42 alone. This was consistent with the presence of the AvNifV gene on SL43.

Further Constructs for Combinations of Anf and Nif Genes

As shown in Example 20, a fusion polypeptide with mitochondrial targeting that had joined AnfD with AnfK through an oligopeptide linker was expressed, efficiently processed, and was observed to be predominantly present in the soluble protein fraction after introduction of the genetic construct into plant cells. Therefore, a genetic construct was made which substituted the AnfD and AnfK genes on SL43 with a hybrid gene that encoded a MTP-CoxIV::TwinStrep::AnfD::Linker26(HA)::AnfK fusion polypeptide (SEQ ID NO:203). This new vector was designated SL48.

When SL48 and SL49 were introduced separately into *N. benthamiana* leaves, all of the encoded polypeptides were observed by Western blot analysis to be present in the soluble protein extracts to at least some extent (FIGS. 35 and 36). When the combination of SL48 and SL49 was introduced into *N. benthamiana* leaves, all eight of the encoded polypeptides were observed by Western blot analysis to be present in the soluble protein extracts, including the processed scar::TwinStrep::AvAnfD::Linker26(HA)::AvAnfK fusion polypeptide (labelled as AnfDK in FIG. 37).

Another construct SL78 (Table 22) was made which was the same as SL49 except with addition of a fifth gene, encoding MTP-FAγ51::NifS::HA. SL48 and SL78 were infiltrated into *N. benthamiana* leaves, separately or in combination. Western blots of total, soluble and insoluble protein fractions showed the presence of all of the encoded fusion polypeptides in the soluble fraction as well as the total protein sample. That is, all 9 fusion polypeptides encoded by the combination of the two vectors could be detected, including the MPP-processed scar9::TwinStrep::AvAnfD::Linker26(HA)::AvAnfK fusion polypeptide from SL48. Therefore, all ten of the Anf and Nif proteins reported to be required as a minimum set to constitute Fe-nitrogenase in the bacterium *E. coli* (Yang et al., 2014) were produced in the plant cells, targeted to the mitochondria and present at least partially in soluble form.

Homocitrate production was detected in the infiltrated cells which had received SL48, indicating that the AvNifV gene on SL48 produced an active homocitrate synthase.

Protein Purification from Plant Cells Producing Anf and Nif Fusion Polypeptides.

Since the processed polypeptide encoded by the MTP-CoxIV::TwinStrep::AnfD::Linker26(HA)::AnfK gene on SL48 had a TwinStrep epitope translationally fused after the MTP sequence at its N-terminal end, the StrepTactinXT column purification method could be used to purify this fusion polypeptide from *N. benthamiana* cells that had been infiltrated with SL48 and SL49. Purification was carried out using the methods described above, and the purified scar::TwinStrep::AnfD::Linker26(HA)::AnfK polypeptide was concentrated using the method as described in Example 14.

The solution containing the purified polypeptide was seen to have a small amount of brown colour at the base of the sample. The inventors considered that this colour was due to the presence of Fe—S clusters bound to the scar::TwinStrep::AnfD::Linker26(HA)::AnfK polypeptide, indicating activity of at least the NifS, NifU and AnfH fusion polypeptides in the plant cells in providing the Fe—S clusters to the AnfD-linker-AnfK fusion polypeptide. This will be confirmed by measurement of the $Fe^{2+}$ and S content in the isolated polypeptide using, for example, inductively coupled plasma mass spectrometry (TCPMS). Electroparamagnetic resonance (EPR) measurements are expected to detect specific wavelength shifts indicating the presence and structure of the Fe—S clusters bound to the polypeptide.

Increases in the amount of bound Fe—S clusters are expected by the addition of another gene to the Anf+Nif gene combinations described above, namely a gene encoding a ferredoxin such as FdxN from *A. vinelandii* or other nitrogen fixing organism (Example 22).

Example 22. Expression of FdxN in Plant Cells with Mitochondrial Targeting

Introduction

A FdxN gene is important for optimal function of nitrogenase in many diazotrophs, for example in *A. vinelandii* (Jimenez-Vicente et al., 2014; Burén et al., 2019). The genome of *A. vinelandii* strain CA (Setubal et al., 2009; www.ncbi.nlm.nih.gov/nuccore/NC_021149.1) has 16 ferredoxin-like genes including FdxN which belong to a class of 2x[4Fe-4S] cluster ferredoxins (Jimenez-Vicente et al., 2014). This class of ferredoxins contains two conserved motifs, Cys-X2-Cys-X2-Cys-X3-Cys and Cys-X2-Cys-X7~9-Cys-X3-Cys-X3~5-Cys, which are conserved in *A. vinelandii* FdxN except for the last Cys residue in the second motif (Matsubara and Saeki, 1992). FdxN genes functioning for nitrogenase in bacteria are often but not always found as part of an operon transcribed with other genes involved in nitrogenase, including Nif genes. For example, FdxN in *A. vinelandii* is part of a single operon containing NifB, FdxN, NifO-NifQ, RhdN and $Grx5^{nif}$ protein coding regions. FdxN was transcribed at about the same level as NifB under diazotrophic growth conditions (Rodriguez-Quinones et al., 1993). When the nitrogenase enzymes were expressed in a ΔFdxN deletion mutant of *A. vinelandii*, a 5-fold reduction in NifB-co synthesis and consequently in nitrogenase activity was observed. The FdxN gene from *A. vinelandii* therefore encodes a ferredoxin protein which is involved in the synthesis of NifB-co that is required for all three of the Mo-, V- and Fe-nitrogenases. Deletion of FdxN also reduced the growth rate of *A. vinelandii* under diazotrophic conditions to about 50% of wild-type, indicating that the complete absence of FdxN was tolerated for growth and nitrogenase activity but needed for optimal growth and nitrogenase activity. FdxN in *A. vinelandii* is thought to act either as a ferredoxin in donating electrons to the NifB protein during the production of NifB-co or as an intermediate carrier of [4Fe-4S] to NifB, or both (Burén et al., 2019).

In contrast, FdxN in *Rhizobium meliloti* was demonstrated to be necessary for symbiotic nitrogen fixation, since fdxN mutants were unable to fix nitrogen. The function was restored by introducing a plasmid encoding FdxN (Klipp et al., 1988). Purified *R. meliloti* FdxN polypeptide was able to mediate electron transport to *Rhodobacter capsulatus* nitrogenase in vitro (Riedel et al., 1995). However, this absolute requirement for FdxN in *R. meliloti* was not reflected in many other diazotrophs such as *R. capsulatus*.

Different again, in *K. oxytoca* a flavodoxin (NifF) and a pyruvate:flavodoxin oxidoreductase (NifJ) mediate electron transfer from pyruvate to nitrogenase, not FdxN (Shah et al., 1983). Consistent with this, a *K. oxytoca* Nif gene cluster that produced functional nitrogenase when transferred to *E. coli* had the NifJHDKTYENXUSVWZMFLABQ genes but did not include a FdxN or equivalent gene (Smanski et al., 2014; Yang et al., 2013; Temme et al., 2012). The synthetic vector pMIT v2.1 expressed functional nitrogenase in *E. coli* without including a FdxN gene, although endogenous ferredoxins in *E. coli* might have provided such function. Proteins other than ferredoxin might also have substituted for FdxN function in *E. coli*, for example flavodoxins. Nitrogenase in diazotrophic bacteria commonly makes use of one or more flavodoxin proteins such as NifF and NifJ as an electron donor, so NifF might have provided the function. In another study, Yang et al. (2017) replaced *K. oxytoca* NifF of the nitrogenase vector pKU7017 with *Chlamydomonas* or plant plastid ferredoxins from *Arabidopsis*, corn, rice and corn, all of which reduced acetylene at a rate of between 50-100% compared to control with NifF, showing that these ferredoxins could substitute for NifF at least for the function of electron donation to the NifH and NifD-NifK nitrogenase proteins. The vector pKU7017 did not include a *K. oxytoca* ferredoxin gene but does have a NifF gene, so the NifF protein or an endogenous *E. coli* ferredoxin might have provided electrons to NifH/NifD-NifK or to NifB for the formation of NifB-co, or both. In contrast, Yates 1972 found purified *A. chromococcum* flavodoxin, but not ferredoxin, could donate electrons to mature dinitrogenase. Jimenez-Vincente et al. (2014) confirmed the lack of electron donation of FdxN to NifD-NifK. The function of FdxN protein and its requirement for nitrogenase function is therefore not clear for different bacteria, let alone for nitrogenase when expressed in plants and targeted to mitochondria.

The structure and diversity of ferredoxins and related proteins has been reviewed by Matsubara and Saeki (1992).

Phylogenetic Analysis of FdxN Polypeptides

A search of the NCBI non-redundant protein database using the *A. vinelandii* FdxN (SEQ ID NO:232) returned a hit to the protein family PRK13795 (hypothetical protein, provisional), which was the only member of the superfamily cl36298. The 627 amino acid sequences in PRK13795 however coded for enzymes related to phosphoadenosine phosphosulfate reductase found in Archaea which were 400-800 amino acids in length and contained a [4Fe-4S] binding site, but no ferredoxin-like proteins. The protein information for FdxN from *A. vinelandii* strains DJ (Accession No. ACO81189.1) and CA (WP_012703542.1) was annotated as belonging to family pfam12838. The region name of this domain was called "Fer4_7 4 Fe-4S dicluster domain" and pfam12838 was the only family member of the superfamily cl38378. The description of pfam12838 was "Superfamily includes proteins containing domains which bind to iron-sulfur clusters". Members include bacterial ferredoxins, various dehydrogenases, and various reductases. The structure of the domain was an alpha-beta sandwich and the domain contained two $Fe_4S_4$ clusters. There were 206 representative amino acid sequences listed in protein family pfam12838, of which 26 amino acid sequences were shorter than 160aa, used as a size cutoff since the longest sequence of the 16 *A. vinelandii* sequences annotated as a ferredoxin was 156 residues. The 26 amino acid sequences in pfam12838 of 93-156 amino acids in length were aligned using NCBI Global alignment (blast.ncbi.nlm.nih.gov/Blast) and the percentage identity to SEQ ID NO:232 (WP_012703542.1) determined. The percentage identity of the 26 sequences to SEQ ID NO:232 ranged between 10-22%, showing the diversity of FdxN sequences. The 26 sequences used in this analysis were from Accession Nos: Q8KG02_CHLTE, Q3ATN2_CHLCH, Q8KG03_CHLTE, Q9X2D5_THEMA, Q2JP81_SYNJB, Q9I1H8_PSEAE, Q01ZR2_SOLUS, ESU39497, WP_043013856, WP_012106131, WP_018723072, EKY12520, WP_012422852, ABG77170.1, EEX22670, WP_015853105, WP_012455913, WP_020095796, WP_012235387, WP_011973256, WP_015758977, WP_012302957, WP_012301895, WP_036081271, WP_004845399 and Q39V82_GEOMG.

Single Gene Constructs to Express FdxN Fusion Polypeptides in Plant Cells

The inventors sought to express a gene encoding an *A. vinelandii* FdxN fusion polypeptide in plant cells, aiming for mitochondrial localisation of the FdxN gene product, as follows. Two genetic constructs (SN291, SN292) were first tested which expressed a MTP-FdxN fusion polypeptide on its own. Subsequent experiments combined the FdxN gene in a 5 gene construct together with genes encoding AnfD-Linker(HA)-AnfK, AnfH, AnfG and NifV fusion polypeptides, with the 5 genes on one T-DNA vector and each fusion polypeptide having an MTP sequence for mitochondrial targeting. A further experiment included a co-expression experiment with two 5 gene constructs, namely the vector encoding AnfD-Linker(HA)-AnfK, AnfH, AnfG, NifV and FdxN fusion polypeptides into one T-DNA vector, designated SL50, and SL49 (Example 21).

The two genetic constructs SN291 and SN292 were designed and made to express the FdxN fusion polypeptides (SEQ ID NO:233, SEQ ID NO:234) on its own in plant cells such as *N. benthamiana* leaf cells, and two control constructs SN299 and SN300 (Table 23). The synthetic genes were each under the control of the strong CaMV 35S promoter and a nos 3' polyadenylation region/transcriptional terminator which flanked the protein coding region. The FdxN amino acid sequence from *A. vinelandii* (SEQ ID NO:232) with an added Ala residue at the C-terminus was used to design the nucleotide sequence of the protein coding region in each construct, with codon-optimisation for expression in plant cells. For mitochondrial localisation, SN291 encoded a fusion polypeptide having the MTP-FAγ51 fused to the N-terminus and a C-terminal HA-epitope for detection of the polypeptide by Western blotting with the anti-HA antibody. The HA epitope was fused translationally either C-terminally (SN291) or between the MTP and FdxN sequence (SN292). One control construct (SN300) encoded a polypeptide which lacked the MTP sequence and therefore expressed a smaller, cytoplasmically targeted polypeptide that provided a molecular weight comparator on the Western blots for an MPP-processed polypeptide from the MTP-FdxN polypeptides (processed FdxN), with the qualification that the MPP-processed polypeptide in each case included a "scar sequence" of about 9 amino acids and so the sizes were close but not identical. The second control construct (SN299) encoded a fusion polypeptide which had 13 amino acids in the MTP sequence substituted with alanines (Allen et al., 2017), designed to prevent processing by MPP. These second control polypeptides therefore provided a molecular weight comparator for the unprocessed polypeptide from the corresponding MTP-FdxN constructs. The alanine-mutated MTP sequence was designated mFAγ51. When protein extracts from the infiltrated plant tissues were analysed, the sample from each MTP-FdxN construct and its two corresponding control constructs were loaded onto adjacent lanes for gel electrophoresis, so allowing for the best detection of processing of the MTP-FdxN polypeptide.

TABLE 23

Single and multi-gene genetic constructs encoding FdxN and components of Fe-nitrogenase for expression in plant cells.

| Plasmid | Expressed polypeptide | Predicted molecular weight (kDa) Unprocessed | Predicted molecular weight (kDa) Processed | SEQ ID NO for Unprocessed |
|---|---|---|---|---|
| SN291 | MTP-FAγ51::FdxN::HA | 16.6 | 11.9 | 233 |
| SN292 | MTP-FAγ51::HA::FdxN | 16.4 | 11.9 | 234 |
| SN299 | mFAγ51::HA::FdxN | 15.8 | NA | 235 |
| SN300 | HA::FdxN | NA | 10.8 | 236 |
| SL50 | MTP-FAγ51::HA::AnfG | 22.2 | 17.7 | 186 |
| | MTP-CoxIV::TwinStrep::AnfD::Linker26(HA)::AnfK | 118 | 115 | 203 |
| | MTP-FAγ51::HA::AnfH | 36.9 | 32.4 | 185 |
| | MTP-FAγ51::HA::NifV | 48.4 | 43.8 | 237 |
| | MTP-FAγ51::HA::FdxN | 16.4 | 11.9 | 233 |
| SL54 | MTP-FAγ51::NifF::HA | 26.1 | 21 | 137 |
| | MTP-FAγ51::NifJ::HA | 135 | 130 | 138 |
| | MTP-FAγ51::NifS::HA | 50.3 | 45 | 124 |
| | MTP-FAγ51::NifU::HA | 36 | 31 | 125 |
| | MTP-FAγ51::KoNifB::HA | 58 | 53 | 147 |

Production of the Fusion Polypeptides in Plant Cells

Cultures of *A. tumefaciens* containing SN291 were infiltrated into 5-week-old *N. benthamiana* leaves as described in Example 1. Four to five days post infiltration, leaf samples were harvested. Total, soluble and insoluble protein fractions were extracted, as follows. For testing the solubility of plant-expressed polypeptides, the leaf tissue was ground in ice-cold extraction buffer (100 mM Tris pH 8.0, 150 mM NaCl, 0.25 M mannitol, 5% (v/v) glycerol, 1% (v/v) Tween 20, 1% (w/v) PVP, freshly-added 2 mM TCEP, 0.2 mM PMSF and 10 μM leupeptin) and transferred to a microfuge tube. The sample was centrifuged at 20,000×g for 5 min to divide the sample into soluble (supernatant) and insoluble (pellet) fractions. The supernatant was transferred to a fresh microfuge tube and centrifuged again at 20,000×g for 5 min to remove any remaining insoluble material. The insoluble fraction was washed by resuspension of the pellet in 300 μL extraction buffer, with dispersal by repeated strokes of the pipette, and centrifuged at 20,000×g for 5 min, discarding the supernatant. This washing step was repeated twice more, removing any remaining soluble protein from the insoluble fraction. Samples were then analysed by SDS-PAGE and Western blotting using anti-HA antibody. The anti-HA antibody (Monoclonal Anti-HA, Sigma) was used at 1:5000 dilution.

The Western blot analysis for SN291 (FIG. 38) showed that the FdxN polypeptide was readily detected in the total protein fraction with the HA-antibody, showing a faint polypeptide present in both the soluble and insoluble protein fractions, requiring longer exposures in the Western procedure to be visible, indicating the AvFdxN fusion polypeptide was partially soluble. The FdxN fusion polypeptide appeared to be partially processed by MPP, with both processed and unprocessed forms, indicating inefficient cleavage by MPP. The bands in the adjacent lanes for the control polypeptides in each case confirmed that these bands were for processed and unprocessed polypeptides.

Cultures of *A. tumefaciens* containing SN292 were infiltrated into 5-week-old *N. benthamiana* leaves as described in Example 1. Four to five days post infiltration, leaf samples were harvested. Total, soluble and insoluble protein fractions were extracted, using the same method as for SN291. The Western blot analysis for SN292 showed that the FdxN polypeptide was readily detected in the total protein fraction with the HA-antibody, indicating that the position of the HA epitope in the fusion polypeptide, either C-terminal or towards the N-terminus, did not affect the level of expression of the polypeptide. Again, the FdxN fusion polypeptide appeared to be partially processed by MPP, with the majority of the protein at the correct size for the processed forms. The bands in the adjacent lanes for the control polypeptides in each case confirmed that these bands were for processed polypeptides.

Production of Combinations of Fusion Polypeptides Including FdxN in Plant Cells

A new genetic construct was designed and made using the GoldenGate synthesis method, designated SL50 (Table 22), and tested separately (FIG. 40) and in combination with SL49 or SL54 (FIG. 41). One gene on SL50 encoded the MTP-CoxIV::TwinStrep::AnfD::Linker26(HA)::AnfK fusion polypeptide and the other four genes encoded AnfH, AnfG, NifV and FdxN fusion polypeptides, with each having the MTP-FAγ51 sequence followed by a HA epitope translationally fused at the N-terminus of the polypeptides. The genetic constructs SL49 and SL50 were introduced into *N. benthamiana* cells separately and protein expression analysed by Western blot. All five of the encoded fusion polypeptides from SL50 were detected with the appropriate antibodies, each showing polypeptide bands present in the soluble protein fraction, with exception of the FdxN polypeptide which was not visible within either the soluble or insoluble fractions (FIG. 40). Importantly, the processed AnfD-linker-AnfK, NifV and AnfH fusion polypeptides were all observed in the soluble fraction as well as the insoluble fraction, so all three were at least partially soluble. The AnfG, AnfH and NifV polypeptides all appeared to be partially cleaved, each showing bands for the processed and unprocessed forms. The AnfD-linker-AnfK polypeptide appeared to be efficiently processed. The FdxN polypeptide was only visible after a long exposure time and could only be seen at the processed size within the total protein.

Next, the *Agrobacterium* cultures containing SL50 and SL49 were mixed and the mixture infiltrated into *N. benthamiana* leaves as before. This experiment therefore introduced 3 Anf genes encoding the AnfH and AnfG polypeptides and the fused AnfD-linker-AnfK polypeptide, 5 of the Nif genes, encoding NifF, NifJ, NifU, NifB and NifV polypeptides, and the FdxN gene, i.e. 9 genes in combination. The surprising result observed in the Western blot (FIG. 41) was that all 9 polypeptides were readily detected. Several of the polypeptides were visible with 2 bands, with the upper band representing unprocessed polypeptide and the lower band representing the cleaved polypeptide upon mitochondrial import. The unprocessed polypeptide band was visible for the NifV, NifU and NifF fusion polypeptides as well as a band present at the predicted size for cleaved polypeptides. All of the polypeptides with the exception of the FdxN polypeptide were present within the soluble fraction, which was not visible within either the soluble or insoluble fractions due to its low level of accumulation.

Another genetic construct was designed and made using the GoldenGate synthesis method, designated SL54 (Table 23), and tested separately and in combination with SL50. SL54 had a gene encoding a MTP-FAγ51::NifB::HA fusion polypeptide (SEQ ID NO:147) which used the sequence from *K. oxytoca*, but otherwise SL54 was identical to SL42 (Table 22) for expression of NifS, NifU, NifJ and NifF fusion polypeptides. This experiment also tested whether the NifB fusion polypeptide based on the *K. oxytoca* sequence, previously shown to be mostly insoluble when expressed on its own, might be improved in its solubility when expressed in combination with the other polypeptides.

SL50 and SL54 were first of all introduced separately into *N. benthamiana* leaves and soluble and insoluble protein fractions prepared and analysed by Western blot analysis as well as the total protein fractions. All of the encoded polypeptides were observed to be present in the soluble protein extracts to at least some extent as well as in the total protein fractions, with the exceptions of the NifB and FdxN polypeptides which were either not visible or obscured by other protein bands of a similar size. The least intense polypeptide was the FdxN polypeptide which was only visible in the total protein sample after a longer exposure.

SL50 and SL54 were also introduced together into *N. benthamiana* leaves. The AnfH, AnfG, NifV, NifJ, NifS, NifU and NifF polypeptides as well as the processed AnfD-linker-AnfK polypeptide were all observed by the Western blot analysis to be present in the soluble protein extracts to at least some extent. Again, the FdxN polypeptide was not visible in either the soluble or insoluble fractions due to its low level of accumulation. The presence of the NifB polypeptide within the soluble fraction could not be confirmed due to its size which coincided in the SDS-polyacrylamide gels with the unprocessed NifS polypeptide (FIG. 39).

As a size and solubility control, a single gene vector (SN192) encoding the *K. oxytoca* NifB polypeptide was separately infiltrated into *N. benthamiana* leaves. When the Western blot was probed with the HA antibody, the NifB polypeptide was visible as both the unprocessed and processed forms and was visible within the total protein and insoluble fractions, with no NifB visible within the soluble fraction (FIG. 39).

In further experiments, the TwinStrep-AnfD-linker-AnfK polypeptide expressed from SL50 will be purified. In further experiments, combinations of SL50 with variants of SL54 will be tested, the variants having NifB polypeptides originating from organisms other than *K. oxytoca.*

Generation of Plants Stably Transformed with Anf and Nif Genes

Each set of genes in SL49 and SL50 were transferred separately to a binary vector having a selectable marker gene. The resultant constructs were used to generate transformed *A. thaliana* plants by the floral dip method. After initial selection with kanamycin, nine T1 transformants were obtained for SL49 and two T1 transformants obtained for SL50. These transgenic plants are expected to express all of the encoded polypeptides, incorporate Fe—S clusters such as P-cluster into the AnfD-linker-AnfK and AnfH polypeptides and produce homocitrate in increased amounts relative to corresponding wild-type plants or plants lacking the NifV gene. The constructs are also used to transform other plants, for example tobacco (*N. tabacum*) and *N. benthamiana.*

When leaf samples of the 9 plants transformed with the T-DNA from SL49 were analysed by Western blot, 2 of the plants (SL49-1 and SL49-2) were observed to be producing all four of the encoded Nif fusion polypeptides: NifB, NifF, NifJ and NifU (FIG. 43). Four of the plants (SL49-3 to 6) were expressing only the NifF polypeptide and were assumed to represent plants in which only part of the T-DNA had been integrated into the genome, namely encoding NifF, or if the other Nif genes had been incorporated they were not expressed. One plant (SL49-9) was expressing the NifB and NifU polypeptides, possibly NifJ as well, but not the NifF polypeptide, and again were assumed to have a partial T-DNA integrated. In each of the plants expressing Nif polypeptides, the fusion polypeptides appeared to be efficiently processed by MPP to produce the scar::Nif::HA or scar::HA::Nif polypeptides, based on comparison with the same polypeptides expressed transiently in *N. benthamiana*. It was concluded that the polypeptides produced in the stably transformed plants were processed by MPP more efficiently, indeed even completely, than when expressed transiently in the *N. benthamiana* leaves.

The DNA region including the set of genes in SL79, namely genes for AnfD-linker-AnfK, AnfH, AnfG, NifV and FdxN fusion polypeptides, all having a HA or TS epitope (Table 22) and in SL29 encoding the MTP-FAγ51::HA::AvAnfD fusion polypeptide were separately transferred to a binary vector having a selectable marker gene for kanamycin resistance. The resultant constructs were used to generate transformed *A. thaliana* plants by a standard floral dip method. Seeds (T1) were obtained from the treated plants and plated onto selective media to select transgenic (T1) plants. After the selection with the antibiotic kanamycin, five T1 transformants were obtained for SL29 and two T1 transformants obtained for SL79. Plant samples were collected for measurement of homocitrate production. These transgenic plants were expected to express all of the encoded polypeptides, incorporate Fe—S clusters such as P-cluster into the AnfH polypeptides as well as the AnfD-AnfK protein complex or the AnfD-linker-AnfK polypeptides and produce homocitrate in increased amounts relative to corresponding wild-type plants or plants lacking the NifV gene.

Of the 5 plants transgenic for the T-DNA from SL29, four were observed by Western blotting to be producing the scar::HA::AnfD polypeptide. The 2 plants transgenic for the T-DNA from SL79, namely SL79-1 and SL79-2, were observed by Western blotting to be producing the scar-AnfD-linker-AnfK, scar-AnfH, scar-AnfG, scar-NifV and scar-FdxN fusion polypeptides.

To produce stably transformed plants expressing nine of the Nif/Anf/Fdx fusion polypeptides, the SL79-1 plants are crossed with SL49-1 plants to produce F1 and F2 plants containing both T-DNAs. To produce plants stably transformed with an additional NifS gene, the experiment is repeated with SL78 rather than SL49, so producing plants expressing the combination of nine Nif/Anf genes as the expected minimal set for expressing functional Fe-nitrogenase as well as FdxN.

Example 23. Analysis of Anf Polypeptides

As described herein, an AnfH polypeptide is a NifH polypeptide which is a member of the nitrogenase conserved superfamily cl25403 containing the PRK13233 conserved domain and having at least 69% amino acid sequence identity to the *Azotobacter vinelandii* AnfH polypeptide (SEQ ID NO:218) when measured along the full length of 275 amino acid residues of SEQ ID NO:218. The inventors analysed AnfH polypeptide sequences present in databases and aligned these and compared them to a representative molybdenum-type NifH.

Databases were searched for AnfH amino acid sequences. These were identified as having the PRK13233 conserved domain and at least 69% identity to SEQ ID NO:218. This identified 314 such sequences. These were aligned with NCBI COBALT and a consensus sequence developed which had 300 residue positions including gaps. This consensus sequence was 89% identical to SEQ ID NO:218. The aligned AnfH amino acid sequences remarkably had 137 amino acids of the 300 positions that were identical in all of the 314 naturally occurring AnfH polypeptides and many other amino acids that were conserved in many of the AnfH polypeptides. Since the 137 conserved amino acids within the PRK13233 domain spanned most of the AnfH sequences, it was concluded that the PRK13233 domain covered most of the AnfH sequences and that PRK13233 was indicative of a family of sequences, not of one particular sequence. The 137 conserved amino acids included the sequence motifs YGKGGIGKSTTXQNT (motif I, SEQ ID NO:225), IHGCDPKAD (motif II, SEQ ID NO:226), CVESGGPEPGVGCAGRG (motif III, SEQ ID NO:227), DVLGDVVCGGFAMP (motif IV, SEQ ID NO:228), VASGEMMAXYAANNI (motif V, SEQ ID NO:229), QSGVR (motif VI, SEQ ID NO:230) and CNSRXVD (motif VII, SEQ ID NO:231), where X represents any amino acid. All of the motifs I-VII were present in all 314 AnfH sequences analysed.

The 137 amino acids that were fully conserved were as follows, with the number referring to the amino acid position in SEQ ID NO:218 and the letter to the amino acid at that position: 3R, 4K, 6A, 8Y, 9G, 10K, 11G, 12G, 13I, 14G, 15K, 16S, 17T, 18T, 20Q, 21N, 22T, 25A, 36I, 37H, 38G, 39C, 40D, 41P, 42K, 43A, 44D, 46T, 47R, 50L, 52G, 55Q, 60D, 63R, 75V, 79G, 85C, 86V, 87E, 88S, 89G, 90G, 91P, 92E, 93P, 94G, 95V, 96G, 97C, 98A, 99G, 100R, 101G, 103I, 104T, 106I, 108L, 109M, 110E, 115Y, 119L, 120D, 125D, 126V, 127L, 128G, 129D, 130V, 131V, 132C, 133G, 134G, 135F, 136A, 137M, 138P, 140R, 142G, 143K, 144A, 146E, 148Y, 150V, 151A, 152S, 153G, 154E, 155M, 156M, 157A, 159Y, 160A, 161A, 162N, 163N, 164I, 167G, 170K, 172A, 174Q, 175S, 176G, 177V, 178R, 180G, 181G, 184C, 185N, 186S, 187R, 189V, 190D, 192E, 198E, 199F, 204G, 212P, 213R, 215N, 217V, 218Q, 220A, 221E, 222F, 227V, 236Q, 239E, 240Y, 243L, 247I, 250N, 254V, 255I, 256P, 258P, 265E, 272G. When aligned with the *A. vinelandii* NifH sequence (AvNifH; SEQ ID NO:224), 121 of the 137 fully conserved amino acids from AnfH sequences were also present in the corresponding positions of AvNifH. The 16 amino acids that were conserved in all of the AnfH sequences but not in AvNifH were: 4K, 22T, 37H, 52G, 60D, 63R, 108L, 109M, 142G, 151A, 174Q, 189V, 198E, 199F, 222F and 247I with reference to SEQ ID NO:218. These 16 amino acids were therefore characteristic of AnfH relative to the molybdenum-type NifH sequence of AvNifH and can be used to distinguish AnfH polypeptides from other NifH sequences which do not have all 16 amino acids in common. AvNifH, KoNifH (SEQ ID NO:1) and other molybdenum type NifH sequences had motifs III and IV but did not have motifs I, II, V-VII, and therefore these motifs could also be used to distinguish the AnfH subset from other NifH polypeptides.

Example 24. Co-Expression of Additional Nif Polypeptides Improves Abundance of NifD-NifK Complex and NifY A mature and catalytically active Mo-nitrogenase includes two metallofactors, the P-cluster and the FeMo-co cluster. These metalloclusters are assembled in several steps in an order reported in Burén et al. (2019), based largely on studies with *A. vinelandii* nitrogenase. For the synthesis of the P-cluster, a NafH polypeptide interacts with a protein complex referred to as pre-apo-NifD-NifK and aids the placement of 2 separate [$Fe_4$—$S_4$] clusters, donated from NifU, onto positions within the NifD and NifK polypeptides. The NafH-NifD-NifK interaction is then replaced by a NifW-NifD-NifK interaction. The NifW polypeptide is then displaced by a mature NifH and NifZ, and at this stage the [$Fe_4$—$S_4$] clusters are condensed into the [$Fe_8$—$S_7$] cluster on the interface of NifD and NifK, the so-called P-cluster, with elimination of one sulfur atom. The formation of the P-cluster converts pre-apo-NifD-NifK to one, perhaps two, 'apo-NifD-NifK' intermediates which bind to NafY (also referred to as a γ protein) and/or NifY. In the case of NafY, structural studies have shown that a N-terminal domain on NafY binds to apo-NifD-NifK and a C-terminal domain binds to binds to FeMo-co. FeMo-co is formed elsewhere on NifE-NifN and NifX is thought to be involved in shuttling the metallofactor between the proteins.

This sequential assembly pathway and its putative protein interactions are based on studies of *A. vinelandii* nitrogenase and some of these steps are likely different or use different proteins in other organisms. For example, *Klebsiella oxytoca* does not have genes encoding NafH or NafY and its NifY is more similar to NafY than NifY in *A. vinelandii*. NifX in *K. oxytoca* was not needed for diazotrophy (Temme et al., 2012). Only functional FeProtein (NifH) is required for the formation of P-clusters in *Klebsiella* as deletion of the NifH gene disrupted P-cluster formation and diazotrophic growth. In contrast, deletion separately of genes encoding NafY, NifY, NifW or NifZ in *A. vinelandii* slowed but did not stop diazotrophic growth, indicating that these components were partially redundant or that a lack of a particular protein could be compensated by other factors in *A. vinelandii.*

The present inventors decided to test the effect on a NifD-NifK fusion polypeptide of co-expression of NifW, NifX, NifY and NifZ polypeptides in plant cells with mitochondrial targeting. To do this, a plant expression construct designated SL55 was made using Golden Gate cloning methods. SL55 had four Nif genes encoding KoNifW, KoNifX, KoNifY and KoNifZ fusion polypeptides, each based on the *K. oxytoca* sequence and having an N-terminal fusion to the MTP-FAγ51 sequence. Each polypeptide also had a HA epitope fused at the C-terminus for detection in Western blots. Components used for construction of SL55 were from SN340 (MTP-KoNifW-HA), SN144 (MTP-KoNifX-HA), SN145 (MTP-KoNifY-HA) and SN146 (MTP-KoNifZ-HA). Each individual gene was flanked by a 35S-promoter and a 3' polyadenylation region/transcription terminator for expression in plant cells. The second genetic construct used in the co-infiltration experiment was SL47, encoding mitochondrially targeted MTP-FAγ51::KoNifDY100Q::linker26(HA)::KoNifK, as encoded by SN159. This translational fusion had the NifD sequence based on the *K. oxytoca* sequence with Y100Q substitution within the NifD sequence. The constructs SL55 and SL47 were infiltrated either separately or together into *N. benthamiana* leaves and samples taken 4 or 5 days after infiltration for Western blot analysis. Proteins were extracted under aerobic conditions, resolved on a 4-20% gradient gel (SDS-PAGE) and probed with anti-HA antibody and HRP secondary antibody as before.

Leaves infiltrated with SL47 alone produced a relatively weak signal for a polypeptide of ~110 kDa, expected for the size of the scar::NifD::linker26(HA)::NifK polypeptide (FIG. 42). Leaves expressing the four MTP-Nif fusion genes on SL55 either alone or co-infiltrated with SL47 produced strong signals for correctly MPP-processed NifW, NifX, NifY and NifZ polypeptides, as described in Examples 2 and 3. Surprisingly and significantly, the leaves co-infiltrated with SL55 and SL47 resulted in a much greater intensity of the band corresponding to correctly processed scar::NifD::linker26(HA)::NifK polypeptide (FIG. 42). It was also noted that a weaker band produced from SL55 at about 100 kDa, possibly arising from secondary degradation of scar::NifD::linker26(HA)::NifK polypeptide within the mitochondria, was less abundant when SL47 was co-infiltrated with SL55. This reduced abundance of the putative degradation product occurred despite the greater abundance of the correctly processed scar::NifD::linker26(HA)::NifK polypeptide.

Additionally, co-expression of a combination of single-gene vectors SN340, SN144, SN145 and SN146 resulted in greater intensity of the band for correctly processed NifY relative to expression from SN145 alone. This result suggested that the combination of SN340, SN144, and SN146 (NifW, NifX and NifZ fusion polypeptides) improved the expression and/or the stability of the NifY fusion polypeptide in the plant mitochondria. The inventors concluded that one or more than one or the combination of mitochondrially targeted NifW, NifX, NifY and NifZ improved the abundance of the translational fusion of NifD and NifK polypeptides. This experiment also showed that co-expression of NifW, NifX, and NifZ polypeptides improves the abundance of NifY in plant cells.

Another construct (SN229) was made encoding a similar NifD-NifK fusion polypeptide but including a Twin-strep epitope to provide for purification of the MPP-processed polypeptide from plant cells. SN229 was co-infiltrated into *N. benthamiana* leaves with SL55. Protein extracts are prepared and passed through a Strep-tactinXR column under aerobic or anaerobic conditions. The eluate from the column contains purified scar::TS::NifD::linker26(HA)::NifK polypeptide and is analysed for the presence of NifW and NifZ fusion polypeptide, one or both of which are expected to co-purify with the NifD-NifK protein.

The constructs SN299, SL55 and a third construct encoding separate NifH, NifM, NifS and NifU fusion polypeptides, all of them mitochondrially targeted by fusion with an MTP, are co-infiltrated into *N. benthamiana* leaves. Protein extracts are again prepared and passed through a Strep-tactinXR column under aerobic or anaerobic conditions. The resulting eluate is expected to contain purified scar::TS::NifD::linker26(HA)::NifK polypeptide which has properly formed P-cluster bound to it, available for receiving FeMoco, i.e. an apo-NifD-NifK polypeptide. The level of P-cluster is measured using ICP-MS.

Example 25. Cysteine Desulfurase Activity of NifS Expressed in Plant Cells and Targeted to Mitochondria As described in Example 14, wild-type NifS polypeptide is a cysteine desulfurase which in diazotrophic bacteria generates the inorganic sulphide required for Fe—S cluster synthesis from cysteine, producing alanine as a byproduct after removal of the sulphur from the cysteine substrate. To test directly for this activity, the plant expression construct SN231, encoding MTP-FAγ51::NifS::TS, was infiltrated into *N. benthamiana* leaves and NifS fusion protein comprising the TwinStrep epitope purified using a StrepTactinXT column as described in Example 14. The elution buffer used to purify the protein was replaced with an assay buffer containing 25 mM Tris-HCl, pH 8.0, and 1 mM DTT by three rounds of passing the purified protein through a 4 mL Amicon Ultra kDa MWCO concentrator, then resuspending the concentrated protein in the assay buffer. The total dilution factor of the elution buffer by this method was approximately 1:5600. The final protein concentration in the assay buffer was estimated to be 0.46 mg/ml. The substrate cysteine was added to the purified protein at a final concentration of 0.5 mM and the reaction mixture incubated in the anaerobic hood at ambient temperature for 2.5 h, after which the reaction was stopped by adding methanol to a final concentration of 86% of the assay solution.

To measure conversion of cysteine and production of alanine in the reactions, GC tandem mass spectrometry (GC-MSMS) was used as follows. Each reaction mixture was dried in a vacuum concentrator prior to metabolite derivatization, which was carried out as follows. To each dried sample, 10 μl of 20 mg/ml methoxyamine hydrochloride in pyridine was added. The solutions were incubated at 37° C. for 90 min with vortexing at 15 min intervals, then 15 μl of a mixture of N,O-bis(trimethylsilyl)trifluoroacetamide and trimethylchlorosilane (BSTFA+TMCS) (99:1) was added and the solution incubated at 37° C. for 30 min with vortexing at 15 min intervals. 5 μl of alkane mix (n-dodecane, n-pentadecane, n-octadecane, n-eicosane, n-pentacosane, n-heptacosane, n-dotriacontane at 0.029% w/v each) was added as molecular weight markers and mixed. Each derivatization mix was left at ambient temperature for 60 min before GC-MSMS analysis.

The GC-MSMS analysis was conducted on a Shimadzu TQ8050 gas chromatography tandem mass spectrometer fitted with a DB-5 capillary column (30 m×0.25 mm ID×1 μm film thickness). One μl was injected at 1:10 split mode onto the column with the inlet heated to 280° C. and helium as carrier gas. The oven temperature was set to 100° C., held for 4 min, then increased to 320° C. at 10° C./minute, and held for 11 min. The mass spectrometer interface was heated to 280° C., ion source at 200° C. Masses between 45 and 600 were measured in full-scan mode. For multiple reaction monitoring (MRM) mode, the Shimadzu MRM library containing 467 compounds with target and qualifier ions between particular retention time windows, set for each metabolite derivative, was used for detection with the same GC and MS parameters. Multiple reaction monitoring (MRM) parameters for alanine 2TMS and cysteine 3TMS were as follows. Alanine 2TMS was measured by detection of two fragmentation patterns at retention index 1105: target ions m/z=116>73 at 15 volts, and reference ions m/z=190/147 at 9 volts. Cysteine 3TMS was measured by detection of two fragmentation patterns at retention index 1564: target ions m/z=220>73 at 24 volts, and reference ions m/z=218/73 at 24 volts.

The results of the assays are provided in Table 24. The reaction mixtures having water, assay buffer-only and assay buffer containing NifS without added cysteine did not have detectable amounts of cysteine. When cysteine was added as substrate to the assay containing NifS, the peak area of cysteine (measured as the cysteine 3TMS derivative) decreased by three-fold compared to when it was added to buffer-only, showing that the cysteine was being consumed. A low level of alanine 2TMS was detected in the reaction mixtures for buffer-only and buffer-only with added cysteine—this low level of alanine was considered to be a contaminant. In contrast, in the assay containing NifS the peak area of alanine increased by 18.5-fold. The consumption of cysteine and concomitant increase in alanine in the assay containing NifS and cysteine was definitive evidence that the NifS that was expressed, targeted to the mitochondrial matrix and processed in *N. benthamiana* leaf cells was functional as a cysteine desulphurase. It was noteworthy that the NifS polypeptide assayed was a processed fusion polypeptide that had a nine amino acid scar (scar9) plus two glycines at the N-terminus and a 28 amino acid TS tag plus two glycines at the C-terminus, yet it was able to convert cysteine to alanine.

TABLE 24

Peak areas of alanine 2TMS and cysteine 3TMS of water, assay buffer-only, and assay containing NifS purified from *N. benthamiana* leaf, with and without cysteine. +cys, with added cysteine.

| Compound Name | water | buffer | buffer + cys | NifS | NifS + cys |
|---|---|---|---|---|---|
| Cysteine 3TMS | 0 | 0 | 208920 | 0 | 70116 |
| Alanine 2TMS | 0 | 30564 | 30632 | 8870 | 164965 |

The present application claims priority from AU 2019903818 filed 10 Oct. 2019 and AU 2020900689 filed 5 Mar. 2020, the entire contents of all of which are incorporated herein by reference.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abe et al. (2000). Cell 100:551-560.

Abdullah et al. (1986). Biotechnology 4(12):1087.

Allen et al. (1994). Crit. Rev. Biotechnol. 14:225-249.

Allen et al. (1995). J. Biol. Chem. 270:26890-26896.

Allen et al. (2017). Front. Plant Sci., 8:287. doi: 10.3389/fpls.2017.00287

Arnold et al. (1988). Tree physiology, 4:291-300.

Altschul et al. (1997). Nucleic Acids Res. 25:3389-3402.
Balk and Pilon (2011). Trends Plant Sci 16:218-226.
Barker et al. (1983). Plant Molecular Biology, 2(6):335-350.
Becker et al. (2012). Trends in Biochemical Sciences 37:85-91.
Bevan et al. (1983). Nature 304:184-187.
Boison et al. (2006). Arch. Microbiol. 186:367-376.
Boyd et al. (2011) Geobiology 9:221-232
Boyd and Peters (2013). Front. Microbiol. 4:201. doi: 10.3389/fmicb.2013.00201.
Brigle et al. (1987). J. Bacterial. 169:1547-1553.
Bruce (2001). Biochimica et Biophysica Acta (BBA)—Molecular Cell Research 1541:2-21.
Burén et al. (2017a). Front Plant Sci 8:1567.
Burén et al. (2017b). ACS Synthetic Biology 6(6):1043-1055.
Burén and Rubio (2018) Fems Microbiol Lett 365:fnx274; doi: 10.1093/femsle/fnx274.
Burén et al. (2019). Proc. Nat. Acad. Sci. USA 116:25078-25086.
Burén et al. (2020). Chemical Reviews doi.org/10.1021/acs.chemrev.9b00489.
Cannon et al. (1988) Nucleic Acids Res. 16:11379.
Capecchi. (1980). Cell, 22(2): 479-488.
Carrari et al. (2003). Metab. Eng. 5:191-200.
Carrie et al. (2010). Journal of Biological Chemistry 285: 36138-36148.
Carter et al. (1980). J. Biol. Chem. 255:4213-4223.
Chacinska et al. (2009). Cell 138:628-644.
Chen et al. (2013). Advanced Drug Delivery Reviews 65:1357-1369.
Cheng et al. (1996). Proceedings of the National Academy of Sciences, 93(8):3636-3641.
Cheng et al. (2005). Biochemical and Biophysical Research Communications 329:966-975.
Chiu et al. (2001). Biochemistry 40:641-650.
Christiansen et al. (1998) Biochemistry-Us 37: 12611-12623.
Clapp (1993). Clinics in perinatology, 20(1):155-168.
Clausen et al. (2000). Proc. Natl. Acad. Sci. U.S.A. 97:3856-361.
Cotton (2009). J. Am. Chem. Soc. 131: 4558-4559.
Cui et al. (2013). Proceedings of the National Academy of Sciences 110, 2052-2057.
Curatti et al. (2006). Proc. Natl. Acad. Sci. U.S.A. 103:5297-5301.
Curatti et al. (2007). Proceedings of the National Academy of Sciences 104(45): 17626-17631.
Curatti and Rubio (2014). Plant Sci 225:130-137.
Curiel et al. (1992). Am J Respir Cell Mol Biol, 6(3): 247-252.
Darshi et al. (2012). Journal of Biological Chemistry 287: 39480-39491.
Davis et al. (1996). J. Bacteriol. 178:1445-1450.
De'ath et al. (2012). Proc. Natl. Acad. Sci. USA 109:17995-17999.
de Bruijn (2015). In: Biological Nitrogen Fixation pp. 1087-1101. John Wiley & Sons, Inc.
de Kok et al. (2014). ACS Synth. Biol. 3:97-106.
Dilworth et al. (1988). Biochem. J. 249:745-751.
Dilworth et al. (1993). Biochem. J. 289:395-400.
Dos Santos et al. (2004). Chem Rev. 104:1159-73.
Dos Santos et al. (2012). BMC Genomics 13:162.
Drummond (1985). Biochem. J. 232:891-896.
Dyer et al. (2003). J. Biol. Chem. 278:32150-32156.
Eady (1996). Chem. Rev. 96:3013-3030.
Eglitis et al. (1988). Advances in Experimental Medicine and Biology 241:19-27.
Emerich and Burris, (1978). J. Bacteriol. 134:936-943.
Engler et al. (2014) ACS Synthetic Biology 3(11):839-843.
Fani et al. (2000). J. Mol. Evol. 51:1-11.
Fay et al. (2015) Proc Natl Acad Sci USA 112: 14829-14833.
Fay et al. (2016). Proc. Natl. Acad. Sci. U.S.A. 2016:9504-9508.
Fujimura et al. (1985). Plant Tissue Cult Lett. 2:74-75.
Fukusawa et al. (2015). Molecular and Cellular Proteomics 14:10.1074/mcp.M114.043083, 1113-1126.
Gallie et al. (1987). Nucleic Acids Res. 15:3257-73.
Garfinkel et al. (1983). Cell 27:143-153.
Gavini et al. (1998). Biochemical and Biophysical Research Communications. 244:498-504.
Gavini et al. (2006). Journal of Bacteriology 188:6020-6025.
Geddes et al. (2015). Curr Opin Biotech 32:216-222.
Geigenberger and Fernie (2014). Antioxid Redox Sign 21:1389-1421.
Glaser and Deshi (1999). J Bioenerg Biomembr 31:259-274.
Glibert et al. (2014). Environ Res Lett 9:e105001; doi.org/10.1088/1748-9326/9/10/105001.
Glick et al. (1992). Cell 69:809-822.
Goodwin et al. (1998) Biochemistry-Us 37: 10420-10428.
Good and Beatty (2011). PLoS Biol 9, e1001124.
Graham et al. (1973). Virology 52(2) 456-467.
Grant et al. (1995). J. Agric. Sci., 124 (3): 437-445
Guo et al. (2016). Angewandete Chemie 55:12764-12767
Fu et al. (1994). Biochemistry 1994 33:13455-63.
Hakoyama et al. (2009). Nature 462(7272): 514.
Hellinga (1997). Proc Natl Acad Sci USA. 94:19 10015-10017.
Hernandez et al. (2007). Mol. Microbiol. 63:177-192.
Hirel et al. (1989). Proc. Natl. Acad. Sci. USA 86:8247-8251.
Hinchee et al. (1988).
Homer et al. (1993). J. Bacteriol. 175:4907-4910.
Homer et al. (1995). J. Biol. Chem. 270:24745-24752.
Hoover et al. (1988). Biochemistry 27: 3647-3652.
Horsch et al. (1985). Cold Spring Harbor Symposia on Quantitative Biology 50:433-437.
Howard et al. (1986). J Biol. Chem. 261:772-778
Hu et al. (2004). J. Biol. Chem. 279:54963-54971.
Hu et al. (2005). Proc. Natl. Acad. Sci. U.S.A. 102:3236-3241.
Hu et al, (2006). Proc. Natl. Acad. Sci. U.S.A. 103:17119-17124.
Hu et al. (2008). Biochemistry 47:3973-3981.
Hu and Ribbe (2013). Bba-Bioenergetics 1827:1112-1122.
Hu and Ribbe, (2015). Journal of Biological Inorganic Chemistry 20(2):435-445. doi:10.1007/s00775-014-1225-3
Hu and Ribbe (2016). Annual Review of Biochemistry 85:455-483.
Huang et al. (2009). Plant Physiology 150(3):1272-1285.
Hummel et al. (2007). Metabolomics 75-95.
Hwang et al. (1996). J. Mol. Evol. November; 43:536-540.
Igarashi and Seefeldt (2003). Crit. Rev. Biochem. Mol. Biol. 38:351-384.
Jasniewski et al. (2018). Inorganics 6(1):25.
Jiménez-Vicente et al. (2014) FEBS Letters 588:512-516.
Johnson et al. (2005). Biochem. Soc. Trans. 33:90-93.
Joshi (1987). Nucleic Acids Res. 15:6643-6653.
Jouanneau et al. (1995). Biochim. Biophys. Acta 1232:33-42.

Katoh et al. (2013). Mol Biol Evol. 4:772-80.
Kay et al. (1987). Science 236:1299-1302.
Kennedy and Dean, (1992). Mol Gen Genet. 231:494-498.
Kerscher et al. (1997). The Journal of Cell Biology 139: 1663-1675.
Khumanthem et al. (2007). Indian Journal of Microbiology, 47:345-352.
Kim and Rees (1994). Biochemistry 33:389-397.
Kimble et al. (1995). Archives of Microbiology 163:259-267.
Klipp et al. (1988). Mol. Gen. Genet. 216:293-302.
Kmiec et al. (2013). PNAS 110: 40 E3761-E3769.
Koon et al. (2004). Proc Natl Acad Sci USA 10:8295-8300.
Lawson and Smith (2002). Met Ions Biol Syst; 39:75-119.
Lee et al. (1998). Biochemical and Biophysical Research Communications 244: 2 498-504.
Lee et al. (2000). J. Bacteriol. 182:7088-7091.
Lee et al. (2012). Plant Cell 24:5037-5057.
Lei et al. (1999). Biochem Biophys Res Commun. 264:186-90.
Lill and Mühlenhoff (2008). Annual Review of Biochemistry 77:669-700.
Lister et al. (2004). 134:777-789.
Lister et al. (2007). Plant Cell, 19:3739-3759.
Lopez-Torrejon et al. (2016). Nature Communications 7:11426.
Lu et al. (1993). Sci China B. 36: 11 1342-51.
Mackenzie and McIntosh (1999). Plant Cell 11:571-585.
Marques et al. (2014). Acta Crystallographica Section F 70(5):669-672.
Masukawa et al. (2007). Appl. Environ. Microbiol. 73:7562-7570.
Matsubara and Saeki (1992). Adv. Inorganic Chem. 38:223-280.
Mayer et al. (1999). J. Mol. Biol. 292:871-891.
McLean and Dixon (1981). Nature, 292:655.
McRose et al. (2017). Frontiers Microbiol. 8:267 doi: 10.3389/fmicb.2017.00267.
Medberry et al. (1992). The Plant Cell 4: 2 185-192.
Medberry et al. (1993). Plant J. 1993 3: 4 619-26.
Merrick and Dixon (1984). Trends Biotechnol 2:162-166.
Mehta and Baross (2006). Science 314:1783-1786.
Millar et al. (2007). Methods Cell Biol 80:65-90.
Miller and Eady (1988). Biochem. J. 256:429-432.
Miyamoto et al. (1979). Applied and Environmental Microbiology, 37:454-458.
Mueller et al. (2012). Nature 490:254-257.
Mühlenhoff et al. (2003). EMBO J. 22:4815-4825.
Murcha et al. (2004). J Mol Biol 344:443-454.
Murcha et al. (2014). Bba-Gen Subjects 1840:1233-1245.
Niedz et al. (1995). Plant Cell Reports 14: 7 403-6.
Naim et al. (2012). PLoS One 7(12):e52717.
Oldroyd and Dixon (2014) Curr Opin Biotechnol 26:19-24.
Olson et al. (2000). Biochemistry; 39:16213-16219.
Ouzounis et al. (1994). Trends Biochem. Sci. 19:199-200.
Ow et al. (1986). Science 234:856-859.
Paul and Merrick (1987) Eur. J. Biochem. 170:259-265.
Paustian et al. (1990). Biochemistry 29:3515-3522.
Petrova et al. (2000). Biochem. Biophys. Res. Commun. 270:863-867.
Pfanner and Geissler (2001) Nat. Rev. Mol. Cell Biol. 2:339-349.
Prasad et al. (1992). Plant Molecular Biology 18(5):873-885.
Prasher et al. (1985). Trends in Genetics 11: 8 320-3.
Pratte et al. (2006). J. Bacteriol. 188:5806-5811.
Riedel et al. (1995). Eur. J. Biochem. 231:742-746.
Robson and Postgate (1980). Annual Review of Microbiology 34:183-207.
Robson et al. (1986). Nature, 322:388-390.
Robson et al. (1989). EMBO J. 8:1217-1224.
Rockstrom et al. (2009). Nature 461:472-475.
Rodriguez-Quinones et al. (1993). J. Bacteriol. 175:2926-2935.
Roise et al. (1986) The EMBO Journal 5:1327-1334.
Roise and Schatz (1988). J. Biol. Chem. 263:4509-4511.
Rubio et al. (2002). J. Biol. Chem. 277:14299-14305.
Rubio et al. (2004) J Biol Chem 279: 19739-19746.
Rubio and Ludden (2005). J. Bacteriol. 187:405-414.
Rubio and Ludden (2008). Annu Rev Microbiol 62:93-111.
Salomon et al. (1984). EMBO 3:1 141-146.
Santi et al. (2013). Ann Bot 111:743-767.
Schleiff and Soll (2000) Planta 211:449-456.
Schmidt and Skerra (2007). Nat. Protoc. 2:1528-1535
Schmidt et al. (2013). Protein Expr. Purif. 92:54-61.
Schmitz et al. (2001). FEMS Microbiol Lett. 195:97-102.
Schwarz et al. (2016). Nucleic acids research 44(8): e77-e77.
Seefeldt et al. (2009). Annu Rev Biochem 78:701-722.
Serrano et al. (2009). Systematic and Applied Microbiology, 32:1-7.
Shah et al. (1983) J. Biol. Chem. 258:12064-12068.
Shah et al. (1999). J. Bacteriol. 181:2797-2801.
Siddavattam et al. (1993). Mol. Gen. Genet. 239:435-440.
Sippel and Einsle, (2017). Nature Chemical Biology, 13:956. doi:10.1038/nchembio.2428
Sippel et al. (2018). Journal of Biological Inorganic Chemistry 23(7): 1049-1056
Sirrenberg et al. (1996). Nature 384: 6609 582-5.
Smil (2002). Ambio 31:126-131.
Smith et al. (1997). J. Bacteriol. 179:7135-7155.
Smith et al. (2005). Annu. Rev. Biochem. 74:247-281.
Smanski et al. (2014). Nature Biotechnology 32:1241-1249.
Spatzal et al. (2016). Nature communications 7 (2016): 10902.
Stalker et al. (1988). J. Biol. Chem. 263(13):6310-6314.
Staples et al. (2007). J. Bacteriol. 189:7392-7398.
Suh et al. (2003). Journal of Biological Chemistry 278:5353-5360.
Sutton et al. (2008). Environ Pollut 156:583-604.
Temme et al. (2012). Proc. Natl. Acad. Sci. U.S.A. 109(18): 7085-7090.
Tezcan et al. (2005). Science 309:1377-1380.
Thiel et al. (1995) Proc Natl Acad Sci USA 92: 9358-9362.
Thiel et al. (1997). J. Bacteriol. 179:5222-5225.
Thillet et al. (1988). J. Biol. Chem 263(25):12500-12508
Thomas et al. (1966). Biochemistry 5(8):2513-2516.
Toriyama et al. (1986). Theor. Appl. Genet. 73:16-19
Verhasselt et al. (1995). Yeast 11(10):961-966.
von Heijne (1986). EMBO J. 5:1335-1342.
Wagner et al. (1992). Proc. Natl. Acad. Sci. U.S.A. 89:6099-6103
Wahlund and Madigan, (1993). J. Bacteriol. 175: 474-478.
Wang et al. (2013). PLoS Genet 9, e1003865.
Waterhouse et al. (2018). Nucleic Acids Res. 46(W1), W296-W303.
Weber et al. (2011) PloS one. 6(2), pp.e16765.
Wiig et al. (2011) Proc Natl Acad Sci USA 108: 8623-8627.
Wisniewski et al. (2011) Anal Biochem. 410:307-9.
Wood et al. (2009). Plant Biotechnol J. 7:914-924.
Xia et al. (2009). Nucleic acids research 37(suppl_2): W652-W660.
Xiao et al. (2010). Biochemistry 49:5588-5599.

Yang et al. (2014). Proc. Natl. Acad. Sci. U.S.A. 111:E3718-E3725.
Yang et al. (2010). BMC Plant Biology, 10. doi:10.1186/1471-2229-10-231.
Yang et al. (2017). Proc Natl Acad Sci USA 114:E2460-E2465.
Yang et al. (2018) Proc Natl Acad Sci USA doi/10.1073/pnas.1804992115
Yates (1972) FEBS Lett 27:63-67.
Yoneda et al. (2012). Int. J. Systematic Evol. Biol. 62:1692-1697.
Yuvaniyama et al. (2000) Proc. Natl. Acad. Sci. USA 97:599-604.
Zhang and Glaser (2002). Trends Plant Sci 7:14-21.
Zhang et al. (2009). Progress in Natural Science 19:1197-1200.
Zhang et al. (2016). Biogeochemistry 127, 189-198. doi:10.1007/s10533-016-0188-6.
Zhang and Wang (2013). PLoS One 8(7). doi:10.1371/journal.pone.0068491.
Zheng et al. (1994)
Zheng et al. (1997). J. Bacteriol. 179:5963-5966.
Zheng et al. (2018). Nature Microbiology, 3:281-286. doi:10.1038/s41564-017-0091-5.

SEQUENCE LISTING

```
<160> NUMBER OF SEQ ID NOS: 248

<210> SEQ ID NO 1
<211> LENGTH: 293
<212> TYPE: PRT
<213> ORGANISM: Klebsiella oxytoca

<400> SEQUENCE: 1

Met Thr Met Arg Gln Cys Ala Ile Tyr Gly Lys Gly Gly Ile Gly Lys
1               5                   10                  15

Ser Thr Thr Thr Gln Asn Leu Val Ala Ala Leu Ala Glu Met Gly Lys
            20                  25                  30

Lys Val Met Ile Val Gly Cys Asp Pro Lys Ala Asp Ser Thr Arg Leu
        35                  40                  45

Ile Leu His Ala Lys Ala Gln Asn Thr Ile Met Glu Met Ala Ala Glu
    50                  55                  60

Val Gly Ser Val Glu Asp Leu Glu Leu Glu Asp Val Leu Gln Ile Gly
65                  70                  75                  80

Tyr Gly Asp Val Arg Cys Ala Glu Ser Gly Gly Pro Glu Pro Gly Val
                85                  90                  95

Gly Cys Ala Gly Arg Gly Val Ile Thr Ala Ile Asn Phe Leu Glu Glu
            100                 105                 110

Glu Gly Ala Tyr Glu Asp Asp Leu Asp Phe Val Phe Tyr Asp Val Leu
        115                 120                 125

Gly Asp Val Val Cys Gly Gly Phe Ala Met Pro Ile Arg Glu Asn Lys
    130                 135                 140

Ala Gln Glu Ile Tyr Ile Val Cys Ser Gly Glu Met Met Ala Met Tyr
145                 150                 155                 160

Ala Ala Asn Asn Ile Ser Lys Gly Ile Val Lys Tyr Ala Lys Ser Gly
                165                 170                 175

Lys Val Arg Leu Gly Gly Leu Ile Cys Asn Ser Arg Gln Thr Asp Arg
            180                 185                 190

Glu Asp Glu Leu Ile Ile Ala Leu Ala Glu Lys Leu Gly Thr Gln Met
        195                 200                 205

Ile His Phe Val Pro Arg Asp Asn Ile Val Gln Arg Ala Glu Ile Arg
    210                 215                 220

Arg Met Thr Val Ile Glu Tyr Asp Pro Ala Cys Lys Gln Ala Asn Glu
225                 230                 235                 240

Tyr Arg Thr Leu Ala Gln Lys Ile Val Asn Asn Thr Met Lys Val Val
                245                 250                 255

Pro Thr Pro Cys Thr Met Asp Glu Leu Glu Ser Leu Leu Met Glu Phe
            260                 265                 270

Gly Ile Met Glu Glu Glu Asp Thr Ser Ile Ile Gly Lys Thr Ala Ala
        275                 280                 285
```

Glu Glu Asn Ala Ala
290

<210> SEQ ID NO 2
<211> LENGTH: 483
<212> TYPE: PRT
<213> ORGANISM: Klebsiella oxytoca

<400> SEQUENCE: 2

Met Met Thr Asn Ala Thr Gly Glu Arg Asn Leu Ala Leu Ile Gln Glu
1 5 10 15

Val Leu Glu Val Phe Pro Glu Thr Ala Arg Lys Glu Arg Arg Lys His
20 25 30

Met Met Val Ser Asp Pro Lys Met Lys Ser Val Gly Lys Cys Ile Ile
35 40 45

Ser Asn Arg Lys Ser Gln Pro Gly Val Met Thr Val Arg Gly Cys Ala
50 55 60

Tyr Ala Gly Ser Lys Gly Val Val Phe Gly Pro Ile Lys Asp Met Ala
65 70 75 80

His Ile Ser His Gly Pro Ala Gly Cys Gly Gln Tyr Ser Arg Ala Glu
85 90 95

Arg Arg Asn Tyr Tyr Thr Gly Val Ser Gly Val Asp Ser Phe Gly Thr
100 105 110

Leu Asn Phe Thr Ser Asp Phe Gln Glu Arg Asp Ile Val Phe Gly Gly
115 120 125

Asp Lys Lys Leu Ser Lys Leu Ile Glu Glu Met Glu Leu Leu Phe Pro
130 135 140

Leu Thr Lys Gly Ile Thr Ile Gln Ser Glu Cys Pro Val Gly Leu Ile
145 150 155 160

Gly Asp Asp Ile Ser Ala Val Ala Asn Ala Ser Ser Lys Ala Leu Asp
165 170 175

Lys Pro Val Ile Pro Val Arg Cys Glu Gly Phe Arg Gly Val Ser Gln
180 185 190

Ser Leu Gly His His Ile Ala Asn Asp Val Val Arg Asp Trp Ile Leu
195 200 205

Asn Asn Arg Glu Gly Gln Pro Phe Glu Thr Thr Pro Tyr Asp Val Ala
210 215 220

Ile Ile Gly Asp Tyr Asn Ile Gly Gly Asp Ala Trp Ala Ser Arg Ile
225 230 235 240

Leu Leu Glu Glu Met Gly Leu Arg Val Val Ala Gln Trp Ser Gly Asp
245 250 255

Gly Thr Leu Val Glu Met Glu Asn Thr Pro Phe Val Lys Leu Asn Leu
260 265 270

Val His Cys Tyr Arg Ser Met Asn Tyr Ile Ala Arg His Met Glu Glu
275 280 285

Lys His Gln Ile Pro Trp Met Glu Tyr Asn Phe Phe Gly Pro Thr Lys
290 295 300

Ile Ala Glu Ser Leu Arg Lys Ile Ala Asp Gln Phe Asp Asp Thr Ile
305 310 315 320

Arg Ala Asn Ala Glu Ala Val Ile Ala Arg Tyr Glu Gly Gln Met Ala
325 330 335

Ala Ile Ile Ala Lys Tyr Arg Pro Arg Leu Glu Gly Arg Lys Val Leu
340 345 350

Leu Tyr Ile Gly Gly Leu Arg Pro Arg His Val Ile Gly Ala Tyr Glu

```
        355                 360                 365

Asp Leu Gly Met Glu Ile Ile Ala Ala Gly Tyr Glu Phe Ala His Asn
    370                 375                 380

Asp Asp Tyr Asp Arg Thr Leu Pro Asp Leu Lys Glu Gly Thr Leu Leu
385                 390                 395                 400

Phe Asp Asp Ala Ser Ser Tyr Glu Leu Glu Ala Phe Val Lys Ala Leu
                405                 410                 415

Lys Pro Asp Leu Ile Gly Ser Gly Ile Lys Glu Lys Tyr Ile Phe Gln
            420                 425                 430

Lys Met Gly Val Pro Phe Arg Gln Met His Ser Trp Asp Tyr Ser Gly
        435                 440                 445

Pro Tyr His Gly Tyr Asp Gly Phe Ala Ile Phe Ala Arg Asp Met Asp
    450                 455                 460

Met Thr Leu Asn Asn Pro Ala Trp Asn Glu Leu Thr Ala Pro Trp Leu
465                 470                 475                 480

Lys Ser Ala


<210> SEQ ID NO 3
<211> LENGTH: 520
<212> TYPE: PRT
<213> ORGANISM: Klebsiella oxytoca

<400> SEQUENCE: 3

Met Ser Gln Thr Ile Asp Lys Ile Asn Ser Cys Tyr Pro Leu Phe Glu
1               5                   10                  15

Gln Asp Glu Tyr Gln Glu Leu Phe Arg Asn Lys Arg Gln Leu Glu Glu
            20                  25                  30

Ala His Asp Ala Gln Arg Val Gln Glu Val Phe Ala Trp Thr Thr Thr
        35                  40                  45

Ala Glu Tyr Glu Ala Leu Asn Phe Gln Arg Glu Ala Leu Thr Val Asp
    50                  55                  60

Pro Ala Lys Ala Cys Gln Pro Leu Gly Ala Val Leu Cys Ser Leu Gly
65                  70                  75                  80

Phe Ala Asn Thr Leu Pro Tyr Val His Gly Ser Gln Gly Cys Val Ala
                85                  90                  95

Tyr Phe Arg Thr Tyr Phe Asn Arg His Phe Lys Glu Pro Ile Ala Cys
            100                 105                 110

Val Ser Asp Ser Met Thr Glu Asp Ala Ala Val Phe Gly Gly Asn Asn
        115                 120                 125

Asn Met Asn Leu Gly Leu Gln Asn Ala Ser Ala Leu Tyr Lys Pro Glu
    130                 135                 140

Ile Ile Ala Val Ser Thr Thr Cys Met Ala Glu Val Ile Gly Asp Asp
145                 150                 155                 160

Leu Gln Ala Phe Ile Ala Asn Ala Lys Lys Asp Gly Phe Val Asp Ser
                165                 170                 175

Ser Ile Ala Val Pro His Ala His Thr Pro Ser Phe Ile Gly Ser His
            180                 185                 190

Val Thr Gly Trp Asp Asn Met Phe Glu Gly Phe Ala Lys Thr Phe Thr
        195                 200                 205

Ala Asp Tyr Gln Gly Gln Pro Gly Lys Leu Pro Lys Leu Asn Leu Val
    210                 215                 220

Thr Gly Phe Glu Thr Tyr Leu Gly Asn Phe Arg Val Leu Lys Arg Met
225                 230                 235                 240

Met Glu Gln Met Ala Val Pro Cys Ser Leu Leu Ser Asp Pro Ser Glu
```

```
                245                 250                 255

Val Leu Asp Thr Pro Ala Asp Gly His Tyr Arg Met Tyr Ser Gly Gly
            260                 265                 270

Thr Thr Gln Gln Glu Met Lys Glu Ala Pro Asp Ala Ile Asp Thr Leu
        275                 280                 285

Leu Leu Gln Pro Trp Gln Leu Leu Lys Ser Lys Lys Val Val Gln Glu
    290                 295                 300

Met Trp Asn Gln Pro Ala Thr Glu Val Ala Ile Pro Leu Gly Leu Ala
305                 310                 315                 320

Ala Thr Asp Glu Leu Leu Met Thr Val Ser Gln Leu Ser Gly Lys Pro
                325                 330                 335

Ile Ala Asp Ala Leu Thr Leu Glu Arg Gly Arg Leu Val Asp Met Met
            340                 345                 350

Leu Asp Ser His Thr Trp Leu His Gly Lys Lys Phe Gly Leu Tyr Gly
        355                 360                 365

Asp Pro Asp Phe Val Met Gly Leu Thr Arg Phe Leu Leu Glu Leu Gly
    370                 375                 380

Cys Glu Pro Thr Val Ile Leu Ser His Asn Ala Asn Lys Arg Trp Gln
385                 390                 395                 400

Lys Ala Met Asn Lys Met Leu Asp Ala Ser Pro Tyr Gly Arg Asp Ser
                405                 410                 415

Glu Val Phe Ile Asn Cys Asp Leu Trp His Phe Arg Ser Leu Met Phe
            420                 425                 430

Thr Arg Gln Pro Asp Phe Met Ile Gly Asn Ser Tyr Gly Lys Phe Ile
        435                 440                 445

Gln Arg Asp Thr Leu Ala Lys Gly Lys Ala Phe Glu Val Pro Leu Ile
    450                 455                 460

Arg Leu Gly Phe Pro Leu Phe Asp Arg His His Leu His Arg Gln Thr
465                 470                 475                 480

Thr Trp Gly Tyr Glu Gly Ala Met Asn Ile Val Thr Thr Leu Val Asn
                485                 490                 495

Ala Val Leu Glu Lys Leu Asp Ser Asp Thr Ser Gln Leu Gly Lys Thr
            500                 505                 510

Asp Tyr Ser Phe Asp Leu Val Arg
        515                 520


<210> SEQ ID NO 4
<211> LENGTH: 468
<212> TYPE: PRT
<213> ORGANISM: Klebsiella oxytoca

<400> SEQUENCE: 4

Met Thr Ser Cys Ser Ser Phe Ser Gly Gly Lys Ala Cys Arg Pro Ala
1               5                   10                  15

Asp Asp Ser Ala Leu Thr Pro Leu Val Ala Asp Lys Ala Ala Ala His
            20                  25                  30

Pro Cys Tyr Ser Arg His Gly His His Arg Phe Ala Arg Met His Leu
        35                  40                  45

Pro Val Ala Pro Ala Cys Asn Leu Gln Cys Asn Tyr Cys Asn Arg Lys
    50                  55                  60

Phe Asp Cys Ser Asn Glu Ser Arg Pro Gly Val Ser Ser Thr Leu Leu
65                  70                  75                  80

Thr Pro Glu Gln Ala Val Val Lys Val Arg Gln Val Ala Gln Ala Ile
                85                  90                  95
```

-continued

Pro Gln Leu Ser Val Val Gly Ile Ala Gly Pro Gly Asp Pro Leu Ala
100 105 110

Asn Ile Ala Arg Thr Phe Arg Thr Leu Glu Leu Ile Arg Glu Gln Leu
115 120 125

Pro Asp Leu Lys Leu Cys Leu Ser Thr Asn Gly Leu Val Leu Pro Asp
130 135 140

Ala Val Asp Arg Leu Leu Asp Val Gly Val Asp His Val Thr Val Thr
145 150 155 160

Ile Asn Thr Leu Asp Ala Glu Ile Ala Ala Gln Ile Tyr Ala Trp Leu
165 170 175

Trp Leu Asp Gly Glu Arg Tyr Ser Gly Arg Glu Ala Gly Glu Ile Leu
180 185 190

Ile Ala Arg Gln Leu Glu Gly Val Arg Arg Leu Thr Ala Lys Gly Val
195 200 205

Leu Val Lys Ile Asn Ser Val Leu Ile Pro Gly Ile Asn Asp Ser Gly
210 215 220

Met Ala Gly Val Ser Arg Ala Leu Arg Ala Ser Gly Ala Phe Ile His
225 230 235 240

Asn Ile Met Pro Leu Ile Ala Arg Pro Glu His Gly Thr Val Phe Gly
245 250 255

Leu Asn Gly Gln Pro Glu Pro Asp Ala Glu Thr Leu Ala Ala Thr Arg
260 265 270

Ser Arg Cys Gly Glu Val Met Pro Gln Met Thr His Cys His Gln Cys
275 280 285

Arg Ala Asp Ala Ile Gly Met Leu Gly Glu Asp Arg Ser Gln Gln Phe
290 295 300

Thr Gln Leu Pro Ala Pro Glu Ser Leu Pro Ala Trp Leu Pro Ile Leu
305 310 315 320

His Gln Arg Ala Gln Leu His Ala Ser Ile Ala Thr Arg Gly Glu Ser
325 330 335

Glu Ala Asp Asp Ala Cys Leu Val Ala Val Ala Ser Ser Arg Gly Asp
340 345 350

Val Ile Asp Cys His Phe Gly His Ala Asp Arg Phe Tyr Ile Tyr Ser
355 360 365

Leu Ser Ala Ala Gly Met Val Leu Val Asn Glu Arg Phe Thr Pro Lys
370 375 380

Tyr Cys Gln Gly Arg Asp Asp Cys Glu Pro Gln Asp Asn Ala Ala Arg
385 390 395 400

Phe Ala Ala Ile Leu Glu Leu Leu Ala Asp Val Lys Ala Val Phe Cys
405 410 415

Val Arg Ile Gly His Thr Pro Trp Gln Gln Leu Glu Gln Glu Gly Ile
420 425 430

Glu Pro Cys Val Asp Gly Ala Trp Arg Pro Val Ser Glu Val Leu Pro
435 440 445

Ala Trp Trp Gln Gln Arg Arg Gly Ser Trp Pro Ala Ala Leu Pro His
450 455 460

Lys Gly Val Ala
465

<210> SEQ ID NO 5
<211> LENGTH: 457
<212> TYPE: PRT
<213> ORGANISM: Klebsiella oxytoca

<400> SEQUENCE: 5

```
Met Lys Gly Asn Glu Ile Leu Ala Leu Leu Asp Glu Pro Ala Cys Glu
1               5                   10                  15

His Asn His Lys Gln Lys Ser Gly Cys Ser Ala Pro Lys Pro Gly Ala
            20                  25                  30

Thr Ala Ala Gly Cys Ala Phe Asp Gly Ala Gln Ile Thr Leu Leu Pro
        35                  40                  45

Ile Ala Asp Val Ala His Leu Val His Gly Pro Ile Gly Cys Ala Gly
    50                  55                  60

Ser Ser Trp Asp Asn Arg Gly Ser Ala Ser Ser Gly Pro Thr Leu Asn
65                  70                  75                  80

Arg Leu Gly Phe Thr Thr Asp Leu Asn Glu Gln Asp Val Ile Met Gly
                85                  90                  95

Arg Gly Glu Arg Arg Leu Phe His Ala Val Arg His Ile Val Thr Arg
            100                 105                 110

Tyr His Pro Ala Ala Val Phe Ile Tyr Asn Thr Cys Val Pro Ala Met
        115                 120                 125

Glu Gly Asp Asp Leu Glu Ala Val Cys Gln Ala Ala Gln Thr Ala Thr
    130                 135                 140

Gly Val Pro Val Ile Ala Ile Asp Ala Ala Gly Phe Tyr Gly Ser Lys
145                 150                 155                 160

Asn Leu Gly Asn Arg Pro Ala Gly Asp Val Met Val Lys Arg Val Ile
                165                 170                 175

Gly Gln Arg Glu Pro Ala Pro Trp Pro Glu Ser Thr Leu Phe Ala Pro
            180                 185                 190

Glu Gln Arg His Asp Ile Gly Leu Ile Gly Glu Phe Asn Ile Ala Gly
        195                 200                 205

Glu Phe Trp His Ile Gln Pro Leu Leu Asp Glu Leu Gly Ile Arg Val
    210                 215                 220

Leu Gly Ser Leu Ser Gly Asp Gly Arg Phe Ala Glu Ile Gln Thr Met
225                 230                 235                 240

His Arg Ala Gln Ala Asn Met Leu Val Cys Ser Arg Ala Leu Ile Asn
                245                 250                 255

Val Ala Arg Ala Leu Glu Gln Arg Tyr Gly Thr Pro Trp Phe Glu Gly
            260                 265                 270

Ser Phe Tyr Gly Ile Arg Ala Thr Ser Asp Ala Leu Arg Gln Leu Ala
        275                 280                 285

Ala Leu Leu Gly Asp Asp Asp Leu Arg Gln Arg Thr Glu Ala Leu Ile
    290                 295                 300

Ala Arg Glu Glu Gln Ala Ala Glu Leu Ala Leu Gln Pro Trp Arg Glu
305                 310                 315                 320

Gln Leu Arg Gly Arg Lys Ala Leu Leu Tyr Thr Gly Gly Val Lys Ser
                325                 330                 335

Trp Ser Val Val Ser Ala Leu Gln Asp Leu Gly Met Thr Val Val Ala
            340                 345                 350

Thr Gly Thr Arg Lys Ser Thr Glu Glu Asp Lys Gln Arg Ile Arg Glu
        355                 360                 365

Leu Met Gly Glu Glu Ala Val Met Leu Glu Glu Gly Asn Ala Arg Thr
    370                 375                 380

Leu Leu Asp Val Val Tyr Arg Tyr Gln Ala Asp Leu Met Ile Ala Gly
385                 390                 395                 400

Gly Arg Asn Met Tyr Thr Ala Tyr Lys Ala Arg Leu Pro Phe Leu Asp
                405                 410                 415
```

```
Ile Asn Gln Glu Arg Glu His Ala Phe Ala Gly Tyr Gln Gly Ile Val
            420                 425                 430

Thr Leu Ala Arg Gln Leu Cys Gln Thr Ile Asn Ser Pro Ile Trp Pro
        435                 440                 445

Gln Thr His Ser Arg Ala Pro Trp Arg
    450                 455


<210> SEQ ID NO 6
<211> LENGTH: 176
<212> TYPE: PRT
<213> ORGANISM: Klebsiella oxytoca

<400> SEQUENCE: 6

Met Ala Asn Ile Gly Ile Phe Phe Gly Thr Asp Thr Gly Lys Thr Arg
1               5                   10                  15

Lys Ile Ala Lys Met Ile His Lys Gln Leu Gly Glu Leu Ala Asp Ala
            20                  25                  30

Pro Val Asn Ile Asn Arg Thr Thr Leu Asp Asp Phe Met Ala Tyr Pro
        35                  40                  45

Val Leu Leu Leu Gly Thr Pro Thr Leu Gly Asp Gly Gln Leu Pro Gly
    50                  55                  60

Leu Glu Ala Gly Cys Glu Ser Glu Ser Trp Ser Glu Phe Ile Ser Gly
65                  70                  75                  80

Leu Asp Asp Ala Ser Leu Lys Gly Lys Thr Val Ala Leu Phe Gly Leu
                85                  90                  95

Gly Asp Gln Arg Gly Tyr Pro Asp Asn Phe Val Ser Gly Met Arg Pro
            100                 105                 110

Leu Phe Asp Ala Leu Ser Ala Arg Gly Ala Gln Met Ile Gly Ser Trp
        115                 120                 125

Pro Asn Glu Gly Tyr Glu Phe Ser Ala Ser Ser Ala Leu Glu Gly Asp
    130                 135                 140

Arg Phe Val Gly Leu Val Leu Asp Gln Asp Asn Gln Phe Asp Gln Thr
145                 150                 155                 160

Glu Ala Arg Leu Ala Ser Trp Leu Glu Glu Ile Lys Arg Thr Val Leu
                165                 170                 175


<210> SEQ ID NO 7
<211> LENGTH: 1171
<212> TYPE: PRT
<213> ORGANISM: Klebsiella oxytoca

<400> SEQUENCE: 7

Met Ser Gly Lys Met Lys Thr Met Asp Gly Asn Ala Ala Ala Ala Trp
1               5                   10                  15

Ile Ser Tyr Ala Phe Thr Glu Val Ala Ala Ile Tyr Pro Ile Thr Pro
            20                  25                  30

Ser Thr Pro Met Ala Glu Asn Val Asp Glu Trp Ala Ala Gln Gly Lys
        35                  40                  45

Lys Asn Leu Phe Gly Gln Pro Val Arg Leu Met Glu Met Gln Ser Glu
    50                  55                  60

Ala Gly Ala Ala Gly Ala Val His Gly Ala Leu Gln Ala Gly Ala Leu
65                  70                  75                  80

Thr Thr Thr Tyr Thr Ala Ser Gln Gly Leu Leu Leu Met Ile Pro Asn
                85                  90                  95

Met Tyr Lys Ile Ala Gly Glu Leu Leu Pro Gly Val Phe His Val Ser
            100                 105                 110
```

```
Ala Arg Ala Leu Ala Thr Asn Ser Leu Asn Ile Phe Gly Asp His Gln
        115                 120                 125

Asp Val Met Ala Val Arg Gln Thr Gly Cys Ala Met Leu Ala Glu Asn
    130                 135                 140

Asn Val Gln Gln Val Met Asp Leu Ser Ala Val Ala His Leu Ala Ala
145                 150                 155                 160

Ile Lys Gly Arg Ile Pro Phe Val Asn Phe Phe Asp Gly Phe Arg Thr
                165                 170                 175

Ser His Glu Ile Gln Lys Ile Glu Val Leu Glu Tyr Glu Gln Leu Ala
            180                 185                 190

Thr Leu Leu Asp Arg Pro Ala Leu Asp Ser Phe Arg Arg Asn Ala Leu
        195                 200                 205

His Pro Asp His Pro Val Ile Arg Gly Thr Ala Gln Asn Pro Asp Ile
    210                 215                 220

Tyr Phe Gln Glu Arg Glu Ala Gly Asn Arg Phe Tyr Gln Ala Leu Pro
225                 230                 235                 240

Asp Ile Val Glu Ser Tyr Met Thr Gln Ile Ser Ala Leu Thr Gly Arg
                245                 250                 255

Glu Tyr His Leu Phe Asn Tyr Thr Gly Ala Ala Asp Ala Glu Arg Val
            260                 265                 270

Ile Ile Ala Met Gly Ser Val Cys Asp Thr Val Gln Glu Val Val Asp
        275                 280                 285

Thr Leu Asn Ala Ala Gly Glu Lys Val Gly Leu Leu Ser Val His Leu
    290                 295                 300

Phe Arg Pro Phe Ser Leu Ala His Phe Phe Ala Gln Leu Pro Lys Thr
305                 310                 315                 320

Val Gln Arg Ile Ala Val Leu Asp Arg Thr Lys Glu Pro Gly Ala Gln
                325                 330                 335

Ala Glu Pro Leu Cys Leu Asp Val Lys Asn Ala Phe Tyr His His Asp
            340                 345                 350

Asp Ala Pro Leu Ile Val Gly Gly Arg Tyr Ala Leu Gly Gly Lys Asp
        355                 360                 365

Val Leu Pro Asn Asp Ile Ala Ala Val Phe Asp Asn Leu Asn Lys Pro
    370                 375                 380

Leu Pro Met Asp Gly Phe Thr Leu Gly Ile Val Asp Asp Val Thr Phe
385                 390                 395                 400

Thr Ser Leu Pro Pro Arg Gln Gln Thr Leu Ala Val Ser His Asp Gly
                405                 410                 415

Ile Thr Ala Cys Lys Phe Trp Gly Met Gly Ser Asp Gly Thr Val Gly
            420                 425                 430

Ala Asn Lys Ser Ala Ile Lys Ile Ile Gly Asp Lys Thr Pro Leu Tyr
        435                 440                 445

Ala Gln Ala Tyr Phe Ser Tyr Asp Ser Lys Lys Ser Gly Gly Ile Thr
    450                 455                 460

Val Ser His Leu Arg Phe Gly Asp Arg Pro Ile Asn Ser Pro Tyr Leu
465                 470                 475                 480

Ile His Arg Ala Asp Phe Ile Ser Cys Ser Gln Gln Ser Tyr Val Glu
                485                 490                 495

Arg Tyr Asp Leu Leu Asp Gly Leu Lys Pro Gly Gly Thr Phe Leu Leu
            500                 505                 510

Asn Cys Ser Trp Ser Asp Ala Glu Leu Glu Gln His Leu Pro Val Gly
        515                 520                 525

Phe Lys Arg Tyr Leu Ala Arg Glu Asn Ile His Phe Tyr Thr Leu Asn
```

```
    530                 535                 540

Ala Val Asp Ile Ala Arg Glu Leu Gly Leu Gly Gly Arg Phe Asn Met
545                 550                 555                 560

Leu Met Gln Ala Ala Phe Phe Lys Leu Ala Ala Ile Ile Asp Pro Gln
                565                 570                 575

Thr Ala Ala Asp Tyr Leu Lys Gln Ala Val Glu Lys Ser Tyr Gly Ser
            580                 585                 590

Lys Gly Ala Ala Val Ile Glu Met Asn Gln Arg Ala Ile Glu Leu Gly
        595                 600                 605

Met Ala Ser Leu His Gln Val Thr Ile Pro Ala His Trp Ala Thr Leu
    610                 615                 620

Asp Glu Pro Ala Ala Gln Ala Ser Ala Met Met Pro Asp Phe Ile Arg
625                 630                 635                 640

Asp Ile Leu Gln Pro Met Asn Arg Gln Cys Gly Asp Gln Leu Pro Val
                645                 650                 655

Ser Ala Phe Val Gly Met Glu Asp Gly Thr Phe Pro Ser Gly Thr Ala
            660                 665                 670

Ala Trp Glu Lys Arg Gly Ile Ala Leu Glu Val Pro Val Trp Gln Pro
        675                 680                 685

Glu Gly Cys Thr Gln Cys Asn Gln Cys Ala Phe Ile Cys Pro His Ala
    690                 695                 700

Ala Ile Arg Pro Ala Leu Leu Asn Gly Glu Glu His Asp Ala Ala Pro
705                 710                 715                 720

Val Gly Leu Leu Ser Lys Pro Ala Gln Gly Ala Lys Glu Tyr His Tyr
                725                 730                 735

His Leu Ala Ile Ser Pro Leu Asp Cys Ser Gly Cys Gly Asn Cys Val
            740                 745                 750

Asp Ile Cys Pro Ala Arg Gly Lys Ala Leu Lys Met Gln Ser Leu Asp
        755                 760                 765

Ser Gln Arg Gln Met Ala Pro Val Trp Asp Tyr Ala Leu Ala Leu Thr
    770                 775                 780

Pro Lys Ser Asn Pro Phe Arg Lys Thr Thr Val Lys Gly Ser Gln Phe
785                 790                 795                 800

Glu Thr Pro Leu Leu Glu Phe Ser Gly Ala Cys Ala Gly Cys Gly Glu
                805                 810                 815

Thr Pro Tyr Ala Arg Leu Ile Thr Gln Leu Phe Gly Asp Arg Met Leu
            820                 825                 830

Ile Ala Asn Ala Thr Gly Cys Ser Ser Ile Trp Gly Ala Ser Ala Pro
        835                 840                 845

Ser Ile Pro Tyr Thr Thr Asn His Arg Gly His Gly Pro Ala Trp Ala
    850                 855                 860

Asn Ser Leu Phe Glu Asp Asn Ala Glu Phe Gly Leu Gly Met Met Leu
865                 870                 875                 880

Gly Gly Gln Ala Val Arg Gln Gln Ile Ala Asp Asp Met Thr Ala Ala
                885                 890                 895

Leu Ala Leu Pro Val Ser Asp Glu Leu Ser Asp Ala Met Arg Gln Trp
            900                 905                 910

Leu Ala Lys Gln Asp Glu Gly Glu Gly Thr Arg Glu Arg Ala Asp Arg
        915                 920                 925

Leu Ser Glu Arg Leu Ala Ala Glu Lys Glu Gly Val Pro Leu Leu Glu
    930                 935                 940

Gln Leu Trp Gln Asn Arg Asp Tyr Phe Val Arg Arg Ser Gln Trp Ile
945                 950                 955                 960
```

```
Phe Gly Gly Asp Gly Trp Ala Tyr Asp Ile Gly Phe Gly Gly Leu Asp
                965                 970                 975

His Val Leu Ala Ser Gly Glu Asp Val Asn Ile Leu Val Phe Asp Thr
            980                 985                 990

Glu Val Tyr Ser Asn Thr Gly Gly  Gln Ser Ser Lys Ser  Thr Pro Val
        995                 1000                1005

Ala Ala  Ile Ala Lys Phe Ala  Ala Gln Gly Lys Arg  Thr Arg Lys
    1010                 1015                 1020

Lys Asp  Leu Gly Met Met Ala  Met Ser Tyr Gly Asn  Val Tyr Val
    1025                 1030                 1035

Ala Gln  Val Ala Met Gly Ala  Asp Lys Asp Gln Thr  Leu Arg Ala
    1040                 1045                 1050

Ile Ala  Glu Ala Glu Ala Trp  Pro Gly Pro Ser Leu  Val Ile Ala
    1055                 1060                 1065

Tyr Ala  Ala Cys Ile Asn His  Gly Leu Lys Ala Gly  Met Arg Cys
    1070                 1075                 1080

Ser Gln  Arg Glu Ala Lys Arg  Ala Val Glu Ala Gly  Tyr Trp His
    1085                 1090                 1095

Leu Trp  Arg Tyr His Pro Gln  Arg Glu Ala Glu Gly  Lys Thr Pro
    1100                 1105                 1110

Phe Met  Leu Asp Ser Glu Glu  Pro Glu Glu Ser Phe  Arg Asp Phe
    1115                 1120                 1125

Leu Leu  Gly Glu Val Arg Tyr  Ala Ser Leu His Lys  Thr Thr Pro
    1130                 1135                 1140

His Leu  Ala Asp Ala Leu Phe  Ser Arg Thr Glu Glu  Asp Ala Arg
    1145                 1150                 1155

Ala Arg  Phe Ala Gln Tyr Arg  Arg Leu Ala Gly Glu  Glu
    1160                 1165                 1170
```

<210> SEQ ID NO 8
<211> LENGTH: 266
<212> TYPE: PRT
<213> ORGANISM: Klebsiella oxytoca

<400> SEQUENCE: 8

```
Met Asn Pro Trp Gln Arg Phe Ala Arg Gln Arg Leu Ala Arg Ser Arg
1               5                   10                  15

Trp Asn Arg Asp Pro Ala Ala Leu Asp Pro Ala Asp Thr Pro Ala Phe
            20                  25                  30

Glu Gln Ala Trp Gln Arg Gln Cys His Met Glu Gln Thr Ile Val Ala
        35                  40                  45

Arg Val Pro Glu Gly Asp Ile Pro Ala Ala Leu Leu Glu Asn Ile Ala
    50                  55                  60

Ala Ser Leu Ala Ile Trp Leu Asp Glu Gly Asp Phe Ala Pro Pro Glu
65                  70                  75                  80

Arg Ala Ala Ile Val Arg His His Ala Arg Leu Glu Leu Ala Phe Ala
                85                  90                  95

Asp Ile Ala Arg Gln Ala Pro Gln Pro Asp Leu Ser Thr Val Gln Ala
            100                 105                 110

Trp Tyr Leu Arg His Gln Thr Gln Phe Met Arg Pro Glu Gln Arg Leu
        115                 120                 125

Thr Arg His Leu Leu Leu Thr Val Asp Asn Asp Arg Glu Ala Val His
    130                 135                 140

Gln Arg Ile Leu Gly Leu Tyr Arg Gln Ile Asn Ala Ser Arg Asp Ala
```

```
145                 150                 155                 160

Phe Ala Pro Leu Ala Gln Arg His Ser His Cys Pro Ser Ala Leu Glu
                165                 170                 175

Glu Gly Arg Leu Gly Trp Ile Ser Arg Gly Leu Leu Tyr Pro Gln Leu
            180                 185                 190

Glu Thr Ala Leu Phe Ser Leu Ala Glu Asn Ala Leu Ser Leu Pro Ile
        195                 200                 205

Ala Ser Glu Leu Gly Trp His Leu Leu Trp Cys Glu Ala Ile Arg Pro
    210                 215                 220

Ala Ala Pro Met Glu Pro Gln Gln Ala Leu Glu Ser Ala Arg Asp Tyr
225                 230                 235                 240

Leu Trp Gln Gln Ser Gln Gln Arg His Gln Arg Gln Trp Leu Glu Gln
                245                 250                 255

Met Ile Ser Arg Gln Pro Gly Leu Cys Gly
            260                 265


<210> SEQ ID NO 9
<211> LENGTH: 461
<212> TYPE: PRT
<213> ORGANISM: Klebsiella oxytoca

<400> SEQUENCE: 9

Met Ala Asp Ile Phe Arg Thr Asp Lys Pro Leu Ala Val Ser Pro Ile
1               5                   10                  15

Lys Thr Gly Gln Pro Leu Gly Ala Ile Leu Ala Ser Leu Gly Ile Glu
            20                  25                  30

His Ser Ile Pro Leu Val His Gly Ala Gln Gly Cys Ser Ala Phe Ala
        35                  40                  45

Lys Val Phe Phe Ile Gln His Phe His Asp Pro Val Pro Leu Gln Ser
    50                  55                  60

Thr Ala Met Asp Pro Thr Ser Thr Ile Met Gly Ala Asp Gly Asn Ile
65                  70                  75                  80

Phe Thr Ala Leu Asp Thr Leu Cys Gln Arg Asn Asn Pro Gln Ala Ile
                85                  90                  95

Val Leu Leu Ser Thr Gly Leu Ser Glu Ala Gln Gly Ser Asp Ile Ser
            100                 105                 110

Arg Val Val Arg Gln Phe Arg Glu Glu Tyr Pro Arg His Lys Gly Val
        115                 120                 125

Ala Ile Leu Thr Val Asn Thr Pro Asp Phe Tyr Gly Ser Met Glu Asn
    130                 135                 140

Gly Phe Ser Ala Val Leu Glu Ser Val Ile Glu Gln Trp Val Pro Pro
145                 150                 155                 160

Ala Pro Arg Pro Ala Gln Arg Asn Arg Arg Val Asn Leu Leu Val Ser
                165                 170                 175

His Leu Cys Ser Pro Gly Asp Ile Glu Trp Leu Arg Arg Cys Val Glu
            180                 185                 190

Ala Phe Gly Leu Gln Pro Ile Ile Leu Pro Asp Leu Ala Gln Ser Met
        195                 200                 205

Asp Gly His Leu Ala Gln Gly Asp Phe Ser Pro Leu Thr Gln Gly Gly
    210                 215                 220

Thr Pro Leu Arg Gln Ile Glu Gln Met Gly Gln Ser Leu Cys Ser Phe
225                 230                 235                 240

Ala Ile Gly Val Ser Leu His Arg Ala Ser Ser Leu Leu Ala Pro Arg
                245                 250                 255
```

Cys Arg Gly Glu Val Ile Ala Leu Pro His Leu Met Thr Leu Glu Arg
260 265 270

Cys Asp Ala Phe Ile His Gln Leu Ala Lys Ile Ser Gly Arg Ala Val
275 280 285

Pro Glu Trp Leu Glu Arg Gln Arg Gly Gln Leu Gln Asp Ala Met Ile
290 295 300

Asp Cys His Met Trp Leu Gln Gly Gln Arg Met Ala Ile Ala Ala Glu
305 310 315 320

Gly Asp Leu Leu Ala Ala Trp Cys Asp Phe Ala Asn Ser Gln Gly Met
325 330 335

Gln Pro Gly Pro Leu Val Ala Pro Thr Gly His Pro Ser Leu Arg Gln
340 345 350

Leu Pro Val Glu Arg Val Val Pro Gly Asp Leu Glu Asp Leu Gln Thr
355 360 365

Leu Leu Cys Ala His Pro Ala Asp Leu Leu Val Ala Asn Ser His Ala
370 375 380

Arg Asp Leu Ala Glu Gln Phe Ala Leu Pro Leu Val Arg Ala Gly Phe
385 390 395 400

Pro Leu Phe Asp Lys Leu Gly Glu Phe Arg Arg Val Arg Gln Gly Tyr
405 410 415

Ser Gly Met Arg Asp Thr Leu Phe Glu Leu Ala Asn Leu Ile Arg Glu
420 425 430

Arg His His His Leu Ala His Tyr Arg Ser Pro Leu Arg Gln Asn Pro
435 440 445

Glu Ser Ser Leu Ser Thr Gly Gly Ala Tyr Ala Ala Asp
450 455 460

<210> SEQ ID NO 10
<211> LENGTH: 167
<212> TYPE: PRT
<213> ORGANISM: Artificial Sequence
<220> FEATURE:
<223> OTHER INFORMATION: Klebsiella sp. RCB570

<400> SEQUENCE: 10

Met Pro Pro Leu Asp Trp Leu Arg Arg Leu Trp Leu Leu Tyr His Ala
1 5 10 15

Gly Lys Gly Ser Phe Pro Leu Arg Met Gly Leu Ser Pro Arg Asp Trp
20 25 30

Gln Ala Leu Arg Arg Arg Leu Gly Glu Val Glu Thr Pro Leu Asp Gly
35 40 45

Glu Thr Leu Thr Arg Arg Arg Leu Met Ala Glu Leu Asn Ala Thr Arg
50 55 60

Glu Glu Glu Arg Gln Gln Leu Gly Ala Trp Leu Ala Gly Trp Met Gln
65 70 75 80

Gln Asp Ala Gly Pro Met Ala Gln Ile Ile Ala Glu Val Ser Leu Ala
85 90 95

Phe Asn His Leu Trp Gln Asp Leu Gly Leu Ala Ser Arg Ala Glu Leu
100 105 110

Arg Leu Leu Met Ser Asp Cys Phe Pro Gln Leu Val Val Met Asn Glu
115 120 125

His Asn Met Arg Trp Lys Lys Phe Phe Tyr Arg Gln Arg Cys Leu Leu
130 135 140

Gln Gln Gly Glu Val Ile Cys Arg Ser Pro Ser Cys Asp Glu Cys Trp
145 150 155 160

```
Glu Arg Ser Ala Cys Phe Glu
                165


<210> SEQ ID NO 11
<211> LENGTH: 400
<212> TYPE: PRT
<213> ORGANISM: Klebsiella oxytoca

<400> SEQUENCE: 11

Met Lys Gln Val Tyr Leu Asp Asn Asn Ala Thr Thr Arg Leu Asp Pro
1               5                   10                  15

Met Val Leu Glu Ala Met Met Pro Phe Leu Thr Asp Phe Tyr Gly Asn
            20                  25                  30

Pro Ser Ser Ile His Asp Phe Gly Ile Pro Ala Gln Ala Ala Leu Glu
        35                  40                  45

Arg Ala His Gln Gln Ala Ala Ala Leu Leu Gly Ala Glu Tyr Pro Ser
    50                  55                  60

Glu Ile Ile Phe Thr Ser Cys Ala Thr Glu Ala Thr Ala Thr Ala Ile
65                  70                  75                  80

Ala Ser Ala Ile Ala Leu Leu Pro Glu Arg Arg Glu Ile Ile Thr Ser
                85                  90                  95

Val Val Glu His Pro Ala Thr Leu Ala Ala Cys Glu His Met Glu Arg
            100                 105                 110

Glu Gly Tyr Arg Ile His Arg Ile Ala Val Asp Gly Glu Gly Ala Leu
        115                 120                 125

Asp Met Ala Gln Phe Arg Ala Ala Leu Ser Pro Arg Val Ala Leu Val
    130                 135                 140

Ser Val Met Trp Ala Asn Asn Glu Thr Gly Val Leu Phe Pro Ile Gly
145                 150                 155                 160

Glu Met Ala Glu Leu Ala His Glu Gln Gly Ala Leu Phe His Cys Asp
                165                 170                 175

Ala Val Gln Val Val Gly Lys Ile Pro Ile Ala Val Gly Gln Thr Arg
            180                 185                 190

Ile Asp Met Leu Ser Cys Ser Ala His Lys Phe His Gly Pro Lys Gly
        195                 200                 205

Val Gly Cys Leu Tyr Leu Arg Arg Gly Thr Arg Phe Arg Pro Leu Leu
    210                 215                 220

Arg Gly Gly His Gln Glu Tyr Gly Arg Arg Ala Gly Thr Glu Asn Ile
225                 230                 235                 240

Cys Gly Ile Val Gly Met Gly Ala Ala Cys Glu Leu Ala Asn Ile His
                245                 250                 255

Leu Pro Gly Met Thr His Ile Gly Gln Leu Arg Asn Arg Leu Glu His
            260                 265                 270

Arg Leu Leu Ala Ser Val Pro Ser Val Met Val Met Gly Gly Gly Gln
        275                 280                 285

Pro Ala Val Pro Gly Thr Val Asn Leu Ala Phe Glu Phe Ile Glu Gly
    290                 295                 300

Glu Ala Ile Leu Leu Leu Leu Asn Gln Ala Gly Ile Ala Ala Ser Ser
305                 310                 315                 320

Gly Ser Ala Cys Thr Ser Gly Ser Leu Glu Pro Ser His Val Met Arg
                325                 330                 335

Ala Met Asn Ile Pro Tyr Thr Ala Ala His Gly Thr Ile Arg Phe Ser
            340                 345                 350

Leu Ser Arg Tyr Thr Arg Glu Lys Glu Ile Asp Tyr Val Val Ala Thr
        355                 360                 365
```

Leu Pro Pro Ile Ile Asp Arg Leu Arg Ala Leu Ser Pro Tyr Trp Gln
    370                 375                 380

Asn Gly Lys Pro Arg Pro Ala Asp Ala Val Phe Thr Pro Val Tyr Gly
385                 390                 395                 400

<210> SEQ ID NO 12
<211> LENGTH: 548
<212> TYPE: PRT
<213> ORGANISM: Klebsiella oxytoca

<400> SEQUENCE: 12

Met Trp Asn Tyr Ser Glu Lys Val Lys Asp His Phe Phe Asn Pro Arg
1               5                   10                  15

Asn Ala Arg Val Val Asp Asn Ala Asn Ala Val Gly Asp Val Gly Ser
            20                  25                  30

Leu Ser Cys Gly Asp Ala Leu Arg Leu Met Leu Arg Val Asp Pro Gln
        35                  40                  45

Ser Glu Ile Ile Glu Glu Ala Gly Phe Gln Thr Phe Gly Cys Gly Ser
    50                  55                  60

Ala Ile Ala Ser Ser Ser Ala Leu Thr Glu Leu Ile Ile Gly His Thr
65                  70                  75                  80

Leu Ala Glu Ala Gly Gln Ile Thr Asn Gln Gln Ile Ala Asp Tyr Leu
                85                  90                  95

Asp Gly Leu Pro Pro Glu Lys Met His Cys Ser Val Met Gly Gln Glu
            100                 105                 110

Ala Leu Arg Ala Ala Ile Ala Asn Phe Arg Gly Glu Ser Leu Glu Glu
        115                 120                 125

Glu His Asp Glu Gly Lys Leu Ile Cys Lys Cys Phe Gly Val Asp Glu
    130                 135                 140

Gly His Ile Arg Arg Ala Val Gln Asn Asn Gly Leu Thr Thr Leu Ala
145                 150                 155                 160

Glu Val Ile Asn Tyr Thr Lys Ala Gly Gly Gly Cys Thr Ser Cys His
                165                 170                 175

Glu Lys Ile Glu Leu Ala Leu Ala Glu Ile Leu Ala Gln Gln Pro Gln
            180                 185                 190

Thr Thr Pro Ala Val Ala Ser Gly Lys Asp Pro His Trp Gln Ser Val
        195                 200                 205

Val Asp Thr Ile Ala Glu Leu Arg Pro His Ile Gln Ala Asp Gly Gly
    210                 215                 220

Asp Met Ala Leu Leu Ser Val Thr Asn His Gln Val Thr Val Ser Leu
225                 230                 235                 240

Ser Gly Ser Cys Ser Gly Cys Met Met Thr Asp Met Thr Leu Ala Trp
                245                 250                 255

Leu Gln Gln Lys Leu Met Glu Arg Thr Gly Cys Tyr Met Glu Val Val
            260                 265                 270

Ala Ala Met Trp Asn Tyr Ser Glu Lys Val Lys Asp His Phe Phe Asn
        275                 280                 285

Pro Arg Asn Ala Arg Val Val Asp Asn Ala Asn Ala Val Gly Asp Val
    290                 295                 300

Gly Ser Leu Ser Cys Gly Asp Ala Leu Arg Leu Met Leu Arg Val Asp
305                 310                 315                 320

Pro Gln Ser Glu Ile Ile Glu Glu Ala Gly Phe Gln Thr Phe Gly Cys
                325                 330                 335

Gly Ser Ala Ile Ala Ser Ser Ser Ala Leu Thr Glu Leu Ile Ile Gly

```
            340                 345                 350

His Thr Leu Ala Glu Ala Gly Gln Ile Thr Asn Gln Gln Ile Ala Asp
        355                 360                 365

Tyr Leu Asp Gly Leu Pro Pro Glu Lys Met His Cys Ser Val Met Gly
    370                 375                 380

Gln Glu Ala Leu Arg Ala Ala Ile Ala Asn Phe Arg Gly Glu Ser Leu
385                 390                 395                 400

Glu Glu Glu His Asp Glu Gly Lys Leu Ile Cys Lys Cys Phe Gly Val
                405                 410                 415

Asp Glu Gly His Ile Arg Arg Ala Val Gln Asn Asn Gly Leu Thr Thr
            420                 425                 430

Leu Ala Glu Val Ile Asn Tyr Thr Lys Ala Gly Gly Gly Cys Thr Ser
        435                 440                 445

Cys His Glu Lys Ile Glu Leu Ala Leu Ala Glu Ile Leu Ala Gln Gln
    450                 455                 460

Pro Gln Thr Thr Pro Ala Val Ala Ser Gly Lys Asp Pro His Trp Gln
465                 470                 475                 480

Ser Val Val Asp Thr Ile Ala Glu Leu Arg Pro His Ile Gln Ala Asp
                485                 490                 495

Gly Gly Asp Met Ala Leu Leu Ser Val Thr Asn His Gln Val Thr Val
            500                 505                 510

Ser Leu Ser Gly Ser Cys Ser Gly Cys Met Met Thr Asp Met Thr Leu
        515                 520                 525

Ala Trp Leu Gln Gln Lys Leu Met Glu Arg Thr Gly Cys Tyr Met Glu
    530                 535                 540

Val Val Ala Ala
545
```

<210> SEQ ID NO 13
<211> LENGTH: 381
<212> TYPE: PRT
<213> ORGANISM: Klebsiella oxytoca

<400> SEQUENCE: 13

```
Met Glu Arg Val Leu Ile Asn Asp Thr Thr Leu Arg Asp Gly Glu Gln
1               5                   10                  15

Ser Pro Gly Val Ala Phe Arg Thr Ser Glu Lys Val Ala Ile Ala Glu
            20                  25                  30

Ala Leu Tyr Ala Ala Gly Ile Thr Ala Met Glu Val Gly Thr Pro Ala
        35                  40                  45

Met Gly Asp Glu Glu Ile Ala Arg Ile Gln Leu Val Arg Arg Gln Leu
    50                  55                  60

Pro Asp Ala Thr Leu Met Thr Trp Cys Arg Met Asn Ala Leu Glu Ile
65                  70                  75                  80

Arg Gln Ser Ala Asp Leu Gly Ile Asp Trp Val Asp Ile Ser Ile Pro
                85                  90                  95

Ala Ser Asp Lys Leu Arg Gln Tyr Lys Leu Arg Glu Pro Leu Ala Val
            100                 105                 110

Leu Leu Glu Arg Leu Ala Met Phe Ile His Leu Ala His Thr Leu Gly
        115                 120                 125

Leu Lys Val Cys Ile Gly Cys Glu Asp Ala Ser Arg Ala Ser Gly Gln
    130                 135                 140

Thr Leu Arg Ala Ile Ala Glu Val Ala Gln Asn Ala Pro Ala Ala Arg
145                 150                 155                 160
```

```
Leu Arg Tyr Ala Asp Thr Val Gly Leu Leu Asp Pro Phe Thr Thr Ala
                165                 170                 175

Ala Gln Ile Ser Ala Leu Arg Asp Val Trp Ser Gly Glu Ile Glu Met
            180                 185                 190

His Ala His Asn Asp Leu Gly Met Ala Thr Ala Asn Thr Leu Ala Ala
        195                 200                 205

Val Ser Ala Gly Ala Thr Ser Val Asn Thr Thr Val Leu Gly Leu Gly
    210                 215                 220

Glu Arg Ala Gly Asn Ala Ala Ala Trp Lys Pro Ser Ala Leu Gly Leu
225                 230                 235                 240

Glu Arg Cys Leu Gly Val Glu Thr Gly Val His Phe Ser Ala Leu Pro
                245                 250                 255

Ala Leu Cys Gln Arg Val Ala Glu Ala Ala Gln Arg Ala Ile Asp Pro
            260                 265                 270

Gln Gln Pro Leu Val Gly Glu Leu Val Phe Thr His Glu Ser Gly Val
        275                 280                 285

His Val Ala Ala Leu Leu Arg Asp Ser Glu Ser Tyr Gln Ser Ile Ala
    290                 295                 300

Pro Ser Leu Met Gly Arg Ser Tyr Arg Leu Val Leu Gly Lys His Ser
305                 310                 315                 320

Gly Arg Gln Ala Val Asn Gly Val Phe Asp Gln Met Gly Tyr His Leu
                325                 330                 335

Asn Ala Ala Gln Ile Asn Gln Leu Leu Pro Ala Ile Arg Arg Phe Ala
            340                 345                 350

Glu Asn Trp Lys Arg Ser Pro Lys Asp Tyr Glu Leu Val Ala Ile Tyr
        355                 360                 365

Asp Glu Leu Cys Gly Glu Ser Ala Leu Arg Ala Arg Gly
    370                 375                 380


<210> SEQ ID NO 14
<211> LENGTH: 156
<212> TYPE: PRT
<213> ORGANISM: Klebsiella oxytoca

<400> SEQUENCE: 14

Met Pro Pro Ile Asn Arg Gln Phe Asp Met Val His Ser Asp Glu Trp
1               5                   10                  15

Ser Met Lys Val Ala Phe Ala Ser Ser Asp Tyr Arg His Val Asp Gln
            20                  25                  30

His Phe Gly Ala Thr Pro Arg Leu Val Val Tyr Gly Val Lys Ala Asp
        35                  40                  45

Arg Val Thr Leu Ile Arg Val Val Asp Phe Ser Val Glu Asn Gly His
    50                  55                  60

Gln Thr Glu Lys Ile Ala Arg Arg Ile His Ala Leu Glu Asp Cys Val
65                  70                  75                  80

Thr Leu Phe Cys Val Ala Ile Gly Asp Ala Val Phe Arg Gln Leu Leu
                85                  90                  95

Gln Val Gly Val Arg Ala Glu Arg Val Pro Ala Asp Thr Thr Ile Val
            100                 105                 110

Gly Leu Leu Gln Glu Ile Gln Leu Tyr Trp Tyr Asp Lys Gly Gln Arg
        115                 120                 125

Lys Asn Gln Arg Gln Arg Asp Pro Glu Arg Phe Thr Arg Leu Leu Gln
    130                 135                 140

Glu Gln Glu Trp His Gly Asp Pro Asp Pro Arg Arg
145                 150                 155
```

<210> SEQ ID NO 15
<211> LENGTH: 220
<212> TYPE: PRT
<213> ORGANISM: Klebsiella oxytoca

<400> SEQUENCE: 15

```
Met Ser Asp Asn Asp Thr Leu Phe Trp Arg Met Leu Ala Leu Phe Gln
1               5                   10                  15

Ser Leu Pro Asp Leu Gln Pro Ala Gln Ile Val Asp Trp Leu Ala Gln
            20                  25                  30

Glu Ser Gly Glu Thr Leu Thr Pro Glu Arg Leu Ala Thr Leu Thr Gln
        35                  40                  45

Pro Gln Leu Ala Ala Ser Phe Pro Ser Ala Thr Ala Val Met Ser Pro
    50                  55                  60

Ala Arg Trp Ser Arg Val Met Ala Ser Leu Gln Gly Ala Leu Pro Ala
65                  70                  75                  80

His Leu Arg Ile Val Arg Pro Ala Gln Arg Thr Pro Gln Leu Leu Ala
                85                  90                  95

Ala Phe Cys Ser Gln Asp Gly Leu Val Ile Asn Gly His Phe Gly Gln
            100                 105                 110

Gly Arg Leu Phe Phe Ile Tyr Ala Phe Asp Glu Gln Gly Gly Trp Leu
        115                 120                 125

Tyr Asp Leu Arg Arg Tyr Pro Ser Ala Pro His Gln Gln Glu Ala Asn
    130                 135                 140

Glu Val Arg Ala Arg Leu Ile Glu Asp Cys Gln Leu Leu Phe Cys Gln
145                 150                 155                 160

Glu Ile Gly Gly Pro Ala Ala Ala Arg Pro Ile Arg His Arg Ile His
                165                 170                 175

Pro Met Lys Ala Gln Pro Gly Thr Thr Ile Gln Ala Gln Cys Glu Ala
            180                 185                 190

Ile Asn Thr Leu Leu Ala Gly Arg Leu Pro Pro Trp Leu Ala Lys Arg
        195                 200                 205

Leu Asn Arg Asp Asn Pro Leu Glu Glu Arg Val Phe
    210                 215                 220
```

<210> SEQ ID NO 16
<211> LENGTH: 148
<212> TYPE: PRT
<213> ORGANISM: Klebsiella oxytoca

<400> SEQUENCE: 16

```
Met Arg Pro Lys Phe Thr Phe Ser Glu Glu Val Arg Val Val Arg Ala
1               5                   10                  15

Ile Arg Asn Asp Gly Thr Val Ala Gly Phe Ala Pro Gly Ala Leu Leu
            20                  25                  30

Val Arg Arg Gly Ser Thr Gly Phe Val Arg Asp Trp Gly Val Phe Leu
        35                  40                  45

Gln Asp Gln Ile Ile Tyr Gln Ile His Phe Pro Glu Thr Asp Arg Ile
    50                  55                  60

Ile Gly Cys Arg Glu Gln Glu Leu Ile Pro Ile Thr Gln Pro Trp Leu
65                  70                  75                  80

Ala Gly Asn Leu Gln Tyr Arg Asp Ser Val Thr Cys Gln Met Ala Leu
                85                  90                  95

Ala Val Asn Gly Asp Val Val Val Ser Ala Gly Gln Arg Gly Arg Val
            100                 105                 110
```

Glu Ala Thr Asp Arg Gly Glu Leu Gly Asp Ser Tyr Thr Val Asp Phe
115 120 125

Ser Gly Arg Trp Phe Arg Val Pro Val Gln Ala Ile Ala Leu Ile Glu
130 135 140

Glu Arg Glu Glu
145

<210> SEQ ID NO 17
<211> LENGTH: 88
<212> TYPE: PRT
<213> ORGANISM: Klebsiella oxytoca

<400> SEQUENCE: 17

Met Met Glu Trp Phe Tyr Gln Ile Pro Gly Val Asp Glu Leu Arg Ser
1 5 10 15

Ala Glu Ser Phe Phe Gln Phe Phe Ala Val Pro Tyr Gln Pro Glu Leu
20 25 30

Leu Gly Arg Cys Ser Leu Pro Val Leu Ala Thr Phe His Arg Lys Leu
35 40 45

Arg Ala Glu Val Pro Leu Gln Asn Arg Leu Glu Asp Asn Asp Arg Ala
50 55 60

Pro Trp Leu Leu Ala Arg Arg Leu Leu Ala Glu Ser Tyr Gln Gln Gln
65 70 75 80

Phe Gln Glu Ser Gly Thr Gly Gly
85

<210> SEQ ID NO 18
<211> LENGTH: 483
<212> TYPE: PRT
<213> ORGANISM: Klebsiella oxytoca

<400> SEQUENCE: 18

Met Met Thr Asn Ala Thr Gly Glu Arg Asn Leu Ala Leu Ile Gln Glu
1 5 10 15

Val Leu Glu Val Phe Pro Glu Thr Ala Arg Lys Glu Arg Arg Lys His
20 25 30

Met Met Val Ser Asp Pro Glu Met Glu Ser Val Gly Lys Cys Ile Ile
35 40 45

Ser Asn Arg Lys Ser Gln Pro Gly Val Met Thr Val Arg Gly Cys Ala
50 55 60

Tyr Ala Gly Ser Lys Gly Val Val Phe Gly Pro Ile Lys Asp Met Ala
65 70 75 80

His Ile Ser His Gly Pro Val Gly Cys Gly Gln Tyr Ser Arg Ala Gly
85 90 95

Arg Arg Asn Tyr Tyr Thr Gly Val Ser Gly Val Asp Ser Phe Gly Thr
100 105 110

Leu Asn Phe Thr Ser Asp Phe Gln Glu Arg Asp Ile Val Phe Gly Gly
115 120 125

Asp Lys Lys Leu Ser Lys Leu Ile Glu Glu Met Glu Leu Leu Phe Pro
130 135 140

Leu Thr Lys Gly Ile Thr Ile Gln Ser Glu Cys Pro Val Gly Leu Ile
145 150 155 160

Gly Asp Asp Ile Ser Ala Val Ala Asn Ala Ser Ser Lys Ala Leu Asp
165 170 175

Lys Pro Val Ile Pro Val Arg Cys Glu Gly Phe Arg Gly Val Ser Gln
180 185 190

Ser Leu Gly His His Ile Ala Asn Asp Val Val Arg Asp Trp Ile Leu
195 200 205

Asn Asn Arg Glu Gly Gln Pro Phe Glu Thr Thr Pro Tyr Asp Val Ala
210 215 220

Ile Ile Gly Asp Tyr Asn Ile Gly Gly Asp Ala Trp Ala Ser Arg Ile
225 230 235 240

Leu Leu Glu Glu Met Gly Leu Arg Val Val Ala Gln Trp Ser Gly Asp
245 250 255

Gly Thr Leu Val Glu Met Glu Asn Thr Pro Phe Val Lys Leu Asn Leu
260 265 270

Val His Cys Tyr Arg Ser Met Asn Tyr Ile Ala Arg His Met Glu Glu
275 280 285

Lys His Gln Ile Pro Trp Met Glu Tyr Asn Phe Phe Gly Pro Thr Lys
290 295 300

Ile Ala Glu Ser Leu Arg Lys Ile Ala Asp Gln Phe Asp Asp Thr Ile
305 310 315 320

Arg Ala Asn Ala Glu Ala Val Ile Ala Arg Tyr Glu Gly Gln Met Ala
325 330 335

Ala Ile Ile Ala Lys Tyr Arg Pro Arg Leu Glu Gly Arg Lys Val Leu
340 345 350

Leu Tyr Met Gly Gly Leu Arg Pro Arg His Val Ile Gly Ala Tyr Glu
355 360 365

Asp Leu Gly Met Glu Ile Ile Ala Ala Gly Tyr Glu Phe Ala His Asn
370 375 380

Asp Asp Tyr Asp Arg Thr Leu Pro Asp Leu Lys Glu Gly Thr Leu Leu
385 390 395 400

Phe Asp Asp Ala Ser Ser Tyr Glu Leu Glu Ala Phe Val Lys Ala Leu
405 410 415

Lys Pro Asp Leu Ile Gly Ser Gly Ile Lys Glu Lys Tyr Ile Phe Gln
420 425 430

Lys Met Gly Val Pro Phe Arg Gln Met His Ser Trp Asp Tyr Ser Gly
435 440 445

Pro Tyr His Gly Tyr Asp Gly Phe Ala Ile Phe Ala Arg Asp Met Asp
450 455 460

Met Thr Leu Asn Asn Pro Ala Trp Asn Glu Leu Thr Ala Pro Trp Leu
465 470 475 480

Lys Ser Ala

<210> SEQ ID NO 19
<211> LENGTH: 400
<212> TYPE: PRT
<213> ORGANISM: Klebsiella oxytoca

<400> SEQUENCE: 19

Met Lys Gln Val Tyr Leu Asp Asn Asn Ala Thr Thr Arg Leu Asp Pro
1 5 10 15

Met Val Leu Glu Ala Met Met Pro Phe Leu Thr Asp Phe Tyr Gly Asn
20 25 30

Pro Ser Ser Ile His Asp Phe Gly Ile Pro Ala Gln Ala Ala Leu Glu
35 40 45

Arg Ala His Gln Gln Ala Ala Ala Leu Leu Gly Ala Glu Tyr Pro Ser
50 55 60

Glu Ile Ile Phe Thr Ser Cys Ala Thr Glu Ala Thr Ala Thr Ala Ile
65 70 75 80

```
Ala Ser Ala Ile Ala Leu Leu Pro Glu Arg Arg Glu Ile Ile Thr Ser
                85                  90                  95

Val Val Glu His Pro Ala Thr Leu Ala Ala Cys Glu His Leu Glu Arg
            100                 105                 110

Gln Gly Tyr Arg Ile His Arg Ile Ala Val Asp Ser Glu Gly Ala Leu
        115                 120                 125

Asp Met Ala Gln Phe Arg Ala Ala Leu Ser Pro Arg Val Ala Leu Val
    130                 135                 140

Ser Val Met Trp Ala Asn Asn Glu Thr Gly Val Leu Phe Pro Ile Gly
145                 150                 155                 160

Glu Met Ala Glu Leu Ala His Glu Gln Gly Ala Leu Phe His Cys Asp
                165                 170                 175

Ala Val Gln Val Val Gly Lys Ile Pro Ile Ala Val Gly Gln Thr Arg
            180                 185                 190

Ile Asp Met Leu Ser Cys Ser Ala His Lys Phe His Gly Pro Lys Gly
        195                 200                 205

Val Gly Cys Leu Tyr Leu Arg Arg Gly Thr Arg Phe Arg Pro Leu Leu
    210                 215                 220

Arg Gly Gly His Gln Glu Tyr Gly Arg Arg Ala Gly Thr Glu Asn Ile
225                 230                 235                 240

Cys Gly Ile Val Gly Met Gly Ala Ala Cys Glu Leu Ala Asn Ile His
                245                 250                 255

Leu Pro Gly Met Thr His Ile Gly Gln Leu Arg Asn Arg Leu Glu His
            260                 265                 270

Arg Leu Leu Ala Ser Val Pro Ser Val Met Val Met Gly Gly Gly Gln
        275                 280                 285

Pro Arg Val Pro Gly Thr Val Asn Leu Ala Phe Glu Phe Ile Glu Gly
    290                 295                 300

Glu Ala Ile Leu Leu Leu Leu Asn Gln Ala Gly Ile Ala Ala Ser Ser
305                 310                 315                 320

Gly Ser Ala Cys Thr Ser Gly Ser Leu Glu Pro Ser His Val Met Arg
                325                 330                 335

Ala Met Asn Ile Pro Tyr Thr Ala Ala His Gly Thr Ile Arg Phe Ser
            340                 345                 350

Leu Ser Arg Tyr Thr Arg Glu Lys Glu Ile Asp Tyr Val Val Ala Thr
        355                 360                 365

Leu Pro Pro Ile Ile Asp Arg Leu Arg Ala Leu Ser Pro Tyr Trp Gln
    370                 375                 380

Asn Gly Lys Pro Arg Pro Ala Asp Ala Val Phe Thr Pro Val Tyr Gly
385                 390                 395                 400
```

<210> SEQ ID NO 20
<211> LENGTH: 80
<212> TYPE: PRT
<213> ORGANISM: Artificial Sequence
<220> FEATURE:
<223> OTHER INFORMATION: Amino acid sequence of the N-terminal extension comprising the pFA MTP (amino acids 1-77) and the amino acid triplet GAP (78-80). Cleavage by MPP occurs between amino acid residues 42 and 43

<400> SEQUENCE: 20

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30
```

Gln Glu Glu Gly Leu Leu Gly Val Arg Ser Ile Ser Thr Gln Val Val
35 40 45

Arg Asn Arg Met Lys Ser Val Lys Asn Ile Gln Lys Ile Thr Lys Ala
50 55 60

Met Lys Met Val Ala Ala Ser Lys Leu Arg Ala Val Gln Gly Ala Pro
65 70 75 80

<210> SEQ ID NO 21
<211> LENGTH: 54
<212> TYPE: PRT
<213> ORGANISM: Artificial Sequence
<220> FEATURE:
<223> OTHER INFORMATION: Amino acid sequence of the MTP-FAγ51 polypeptide with additional N-terminal Met and C-terminal GG. Cleavage by MPP occurs between amino acid residues 43 and 44.

<400> SEQUENCE: 21

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly
50

<210> SEQ ID NO 22
<211> LENGTH: 9
<212> TYPE: PRT
<213> ORGANISM: Artificial Sequence
<220> FEATURE:
<223> OTHER INFORMATION: Amino acid sequence of the FAv-scar9 polypeptide.

<400> SEQUENCE: 22

Ile Ser Thr Gln Val Val Arg Asn Arg
1 5

<210> SEQ ID NO 23
<211> LENGTH: 389
<212> TYPE: PRT
<213> ORGANISM: Artificial Sequence
<220> FEATURE:
<223> OTHER INFORMATION: Amino acid sequence of the MTP-FA 77::NifH::HA fusion polypeptide encoded by pRA10. Amino acids 1-77 correspond to MTP-FA 77, amino acids 78-80 are the GAP, amino acids 81-372 were the K. oxytoca NifH amino acids) and amino acids 373-389 include the HA

<400> SEQUENCE: 23

Met Ala Met Ala Val Phe Arg Arg Glu Gly Arg Arg Leu Leu Pro Ser
1 5 10 15

Ile Ala Ala Arg Pro Ile Ala Ala Ile Arg Ser Pro Leu Ser Ser Asp
20 25 30

Gln Glu Glu Gly Leu Leu Gly Val Arg Ser Ile Ser Thr Gln Val Val
35 40 45

Arg Asn Arg Met Lys Ser Val Lys Asn Ile Gln Lys Ile Thr Lys Ala
50 55 60

Met Lys Met Val Ala Ala Ser Lys Leu Arg Ala Val Gln Gly Ala Pro
65 70 75 80

Thr Met Arg Gln Cys Ala Ile Tyr Gly Lys Gly Gly Ile Gly Lys Ser
85 90 95

```
Thr Thr Thr Gln Asn Leu Val Ala Ala Leu Ala Glu Met Gly Lys Lys
            100                 105                 110

Val Met Ile Val Gly Cys Asp Pro Lys Ala Asp Ser Thr Arg Leu Ile
        115                 120                 125

Leu His Ala Lys Ala Gln Asn Thr Ile Met Glu Met Ala Ala Glu Val
    130                 135                 140

Gly Ser Val Glu Asp Leu Glu Leu Glu Asp Val Leu Gln Ile Gly Tyr
145                 150                 155                 160

Gly Asp Val Arg Cys Ala Glu Ser Gly Gly Pro Glu Pro Gly Val Gly
                165                 170                 175

Cys Ala Gly Arg Gly Val Ile Thr Ala Ile Asn Phe Leu Glu Glu Glu
            180                 185                 190

Gly Ala Tyr Glu Asp Asp Leu Asp Phe Val Phe Tyr Asp Val Leu Gly
        195                 200                 205

Asp Val Val Cys Gly Gly Phe Ala Met Pro Ile Arg Glu Asn Lys Ala
    210                 215                 220

Gln Glu Ile Tyr Ile Val Cys Ser Gly Glu Met Met Ala Met Tyr Ala
225                 230                 235                 240

Ala Asn Asn Ile Ser Lys Gly Ile Val Lys Tyr Ala Lys Ser Gly Lys
                245                 250                 255

Val Arg Leu Gly Gly Leu Ile Cys Asn Ser Arg Gln Thr Asp Arg Glu
            260                 265                 270

Asp Glu Leu Ile Ile Ala Leu Ala Glu Lys Leu Gly Thr Gln Met Ile
        275                 280                 285

His Phe Val Pro Arg Asp Asn Ile Val Gln Arg Ala Glu Ile Arg Arg
    290                 295                 300

Met Thr Val Ile Glu Tyr Asp Pro Ala Cys Lys Gln Ala Asn Glu Tyr
305                 310                 315                 320

Arg Thr Leu Ala Gln Lys Ile Val Asn Asn Thr Met Lys Val Val Pro
                325                 330                 335

Thr Pro Cys Thr Met Asp Glu Leu Glu Ser Leu Leu Met Glu Phe Gly
            340                 345                 350

Ile Met Glu Glu Glu Asp Thr Ser Ile Ile Gly Lys Thr Ala Ala Glu
        355                 360                 365

Glu Asn Ala Ala Ala Gly Gly Gly Gly Gly Tyr Pro Tyr Asp Val Pro
    370                 375                 380

Asp Tyr Ala Pro Gly
385
```

<210> SEQ ID NO 24
<211> LENGTH: 363
<212> TYPE: PRT
<213> ORGANISM: Artificial Sequence
<220> FEATURE:
<223> OTHER INFORMATION: Amino acid sequence of the MTP-FA 51::NifH::HA fusion polypeptide encoded by pRA34. Amino acids 1-51 correspond to MTP-FA 51, amino acids 52-54 are the GAP, amino acids 55-346 were the K. oxytoca NifH amino acids and amino acids 347-363 include the HA

<400> SEQUENCE: 24

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
```

```
        35                  40                  45

Arg Asn Arg Gly Ala Pro Thr Met Arg Gln Cys Ala Ile Tyr Gly Lys
    50                  55                  60

Gly Gly Ile Gly Lys Ser Thr Thr Thr Gln Asn Leu Val Ala Ala Leu
65                  70                  75                  80

Ala Glu Met Gly Lys Lys Val Met Ile Val Gly Cys Asp Pro Lys Ala
                85                  90                  95

Asp Ser Thr Arg Leu Ile Leu His Ala Lys Ala Gln Asn Thr Ile Met
            100                 105                 110

Glu Met Ala Ala Glu Val Gly Ser Val Glu Asp Leu Glu Leu Glu Asp
        115                 120                 125

Val Leu Gln Ile Gly Tyr Gly Asp Val Arg Cys Ala Glu Ser Gly Gly
    130                 135                 140

Pro Glu Pro Gly Val Gly Cys Ala Gly Arg Gly Val Ile Thr Ala Ile
145                 150                 155                 160

Asn Phe Leu Glu Glu Glu Gly Ala Tyr Glu Asp Asp Leu Asp Phe Val
                165                 170                 175

Phe Tyr Asp Val Leu Gly Asp Val Val Cys Gly Gly Phe Ala Met Pro
            180                 185                 190

Ile Arg Glu Asn Lys Ala Gln Glu Ile Tyr Ile Val Cys Ser Gly Glu
        195                 200                 205

Met Met Ala Met Tyr Ala Ala Asn Asn Ile Ser Lys Gly Ile Val Lys
    210                 215                 220

Tyr Ala Lys Ser Gly Lys Val Arg Leu Gly Gly Leu Ile Cys Asn Ser
225                 230                 235                 240

Arg Gln Thr Asp Arg Glu Asp Glu Leu Ile Ile Ala Leu Ala Glu Lys
                245                 250                 255

Leu Gly Thr Gln Met Ile His Phe Val Pro Arg Asp Asn Ile Val Gln
            260                 265                 270

Arg Ala Glu Ile Arg Arg Met Thr Val Ile Glu Tyr Asp Pro Ala Cys
        275                 280                 285

Lys Gln Ala Asn Glu Tyr Arg Thr Leu Ala Gln Lys Ile Val Asn Asn
    290                 295                 300

Thr Met Lys Val Val Pro Thr Pro Cys Thr Met Asp Glu Leu Glu Ser
305                 310                 315                 320

Leu Leu Met Glu Phe Gly Ile Met Glu Glu Glu Asp Thr Ser Ile Ile
                325                 330                 335

Gly Lys Thr Ala Ala Glu Glu Asn Ala Ala Ala Gly Gly Gly Gly Gly
            340                 345                 350

Tyr Pro Tyr Asp Val Pro Asp Tyr Ala Pro Gly
        355                 360


<210> SEQ ID NO 25
<211> LENGTH: 358
<212> TYPE: PRT
<213> ORGANISM: Artificial Sequence
<220> FEATURE:
<223> OTHER INFORMATION: Amino acid sequence of the MTP-FAv51::NifH::HA
      fusion polypeptide encoded by SN18. Amino acids 1-54 correspond to
      the MTP-FA 51 with GG, amino acids 55-347 were the K. oxytoca NifH
      amino acids and amino acids 348-358 include the HA epitope

<400> SEQUENCE: 25

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
```

```
            20                  25                  30

Asp Gln Glu Glu Gly Leu Leu Gly Val Arg Ser Ile Ser Thr Gln Val
        35                  40                  45

Val Arg Asn Arg Gly Gly Met Thr Met Arg Gln Cys Ala Ile Tyr Gly
    50                  55                  60

Lys Gly Gly Ile Gly Lys Ser Thr Thr Thr Gln Asn Leu Val Ala Ala
65                  70                  75                  80

Leu Ala Glu Met Gly Lys Lys Val Met Ile Val Gly Cys Asp Pro Lys
                85                  90                  95

Ala Asp Ser Thr Arg Leu Ile Leu His Ala Lys Ala Gln Asn Thr Ile
            100                 105                 110

Met Glu Met Ala Ala Glu Val Gly Ser Val Glu Asp Leu Glu Leu Glu
        115                 120                 125

Asp Val Leu Gln Ile Gly Tyr Gly Asp Val Arg Cys Ala Glu Ser Gly
    130                 135                 140

Gly Pro Glu Pro Gly Val Gly Cys Ala Gly Arg Gly Val Ile Thr Ala
145                 150                 155                 160

Ile Asn Phe Leu Glu Glu Glu Gly Ala Tyr Glu Asp Asp Leu Asp Phe
                165                 170                 175

Val Phe Tyr Asp Val Leu Gly Asp Val Val Cys Gly Gly Phe Ala Met
            180                 185                 190

Pro Ile Arg Glu Asn Lys Ala Gln Glu Ile Tyr Ile Val Cys Ser Gly
        195                 200                 205

Glu Met Met Ala Met Tyr Ala Ala Asn Asn Ile Ser Lys Gly Ile Val
    210                 215                 220

Lys Tyr Ala Lys Ser Gly Lys Val Arg Leu Gly Gly Leu Ile Cys Asn
225                 230                 235                 240

Ser Arg Gln Thr Asp Arg Glu Asp Glu Leu Ile Ile Ala Leu Ala Glu
                245                 250                 255

Lys Leu Gly Thr Gln Met Ile His Phe Val Pro Arg Asp Asn Ile Val
            260                 265                 270

Gln Arg Ala Glu Ile Arg Arg Met Thr Val Ile Glu Tyr Asp Pro Ala
        275                 280                 285

Cys Lys Gln Ala Asn Glu Tyr Arg Thr Leu Ala Gln Lys Ile Val Asn
    290                 295                 300

Asn Thr Met Lys Val Val Pro Thr Pro Cys Thr Met Asp Glu Leu Glu
305                 310                 315                 320

Ser Leu Leu Met Glu Phe Gly Ile Met Glu Glu Glu Asp Thr Ser Ile
                325                 330                 335

Ile Gly Lys Thr Ala Ala Glu Glu Asn Ala Ala Gly Gly Tyr Pro Tyr
            340                 345                 350

Asp Val Pro Asp Tyr Ala
        355
```

<210> SEQ ID NO 26
<211> LENGTH: 371
<212> TYPE: PRT
<213> ORGANISM: Artificial Sequence
<220> FEATURE:
<223> OTHER INFORMATION: Amino acid sequence of the MTP-FAv51::HA::NifH fusion polypeptide encoded by SN29. Amino acids 1-53 correspond to the MTP-FA 51 with GG, amino acids 54-64 include the HA epitope, amino acids 65-357 correspond to K. oxytoca NifH and amino acids 358-371

<400> SEQUENCE: 26

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Thr Met Arg Gln Cys Ala Ile Tyr Gly Lys Gly Gly Ile Gly Lys
65                  70                  75                  80

Ser Thr Thr Thr Gln Asn Leu Val Ala Ala Leu Ala Glu Met Gly Lys
                85                  90                  95

Lys Val Met Ile Val Gly Cys Asp Pro Lys Ala Asp Ser Thr Arg Leu
            100                 105                 110

Ile Leu His Ala Lys Ala Gln Asn Thr Ile Met Glu Met Ala Ala Glu
        115                 120                 125

Val Gly Ser Val Glu Asp Leu Glu Leu Glu Asp Val Leu Gln Ile Gly
    130                 135                 140

Tyr Gly Asp Val Arg Cys Ala Glu Ser Gly Gly Pro Glu Pro Gly Val
145                 150                 155                 160

Gly Cys Ala Gly Arg Gly Val Ile Thr Ala Ile Asn Phe Leu Glu Glu
                165                 170                 175

Glu Gly Ala Tyr Glu Asp Asp Leu Asp Phe Val Phe Tyr Asp Val Leu
            180                 185                 190

Gly Asp Val Val Cys Gly Gly Phe Ala Met Pro Ile Arg Glu Asn Lys
        195                 200                 205

Ala Gln Glu Ile Tyr Ile Val Cys Ser Gly Glu Met Met Ala Met Tyr
    210                 215                 220

Ala Ala Asn Asn Ile Ser Lys Gly Ile Val Lys Tyr Ala Lys Ser Gly
225                 230                 235                 240

Lys Val Arg Leu Gly Gly Leu Ile Cys Asn Ser Arg Gln Thr Asp Arg
                245                 250                 255

Glu Asp Glu Leu Ile Ile Ala Leu Ala Glu Lys Leu Gly Thr Gln Met
            260                 265                 270

Ile His Phe Val Pro Arg Asp Asn Ile Val Gln Arg Ala Glu Ile Arg
        275                 280                 285

Arg Met Thr Val Ile Glu Tyr Asp Pro Ala Cys Lys Gln Ala Asn Glu
    290                 295                 300

Tyr Arg Thr Leu Ala Gln Lys Ile Val Asn Asn Thr Met Lys Val Val
305                 310                 315                 320

Pro Thr Pro Cys Thr Met Asp Glu Leu Glu Ser Leu Leu Met Glu Phe
                325                 330                 335

Gly Ile Met Glu Glu Glu Asp Thr Ser Ile Ile Gly Lys Thr Ala Ala
            340                 345                 350

Glu Glu Asn Ala Ala Ala Ser Leu Ala Arg Val Asp Arg Gln Ala Arg
        355                 360                 365

Val Ser Pro
    370
```

<210> SEQ ID NO 27
<211> LENGTH: 9
<212> TYPE: PRT
<213> ORGANISM: Artificial Sequence
<220> FEATURE:
<223> OTHER INFORMATION: 6xHis sequence used instead of the MTP, with N-terminal Met and C-terminal GG

<400> SEQUENCE: 27

Met His His His His His His Gly Gly
1 5

<210> SEQ ID NO 28
<211> LENGTH: 33
<212> TYPE: PRT
<213> ORGANISM: Artificial Sequence
<220> FEATURE:
<223> OTHER INFORMATION: Amino acid sequence of the CPN60 MTP

<400> SEQUENCE: 28

Met Tyr Arg Phe Ala Ser Asn Leu Ala Ser Lys Ala Arg Ile Ala Gln
1 5 10 15

Asn Ala Arg Gln Val Ser Ser Arg Met Ser Trp Ser Arg Asn Tyr Gly
20 25 30

Gly

<210> SEQ ID NO 29
<211> LENGTH: 31
<212> TYPE: PRT
<213> ORGANISM: Artificial Sequence
<220> FEATURE:
<223> OTHER INFORMATION: Amino acid sequence of the CPN60/No GGlinker MTP

<400> SEQUENCE: 29

Met Tyr Arg Phe Ala Ser Asn Leu Ala Ser Lys Ala Arg Ile Ala Gln
1 5 10 15

Asn Ala Arg Gln Val Ser Ser Arg Met Ser Trp Ser Arg Asn Tyr
20 25 30

<210> SEQ ID NO 30
<211> LENGTH: 31
<212> TYPE: PRT
<213> ORGANISM: Artificial Sequence
<220> FEATURE:
<223> OTHER INFORMATION: Amino acid sequence of the Superoxide dismutase (SOD) MTP

<400> SEQUENCE: 30

Met Ala Ile Arg Cys Val Ala Ser Arg Lys Thr Leu Ala Gly Leu Lys
1 5 10 15

Glu Thr Ser Ser Arg Leu Leu Arg Ile Arg Gly Ile Gln Gly Gly
20 25 30

<210> SEQ ID NO 31
<211> LENGTH: 60
<212> TYPE: PRT
<213> ORGANISM: Artificial Sequence
<220> FEATURE:
<223> OTHER INFORMATION: Amino acid sequence of the Superoxide dismutase doubled (2SOD) MTP

<400> SEQUENCE: 31

Met Ala Ile Arg Cys Val Ala Ser Arg Lys Thr Leu Ala Gly Leu Lys
1 5 10 15

Glu Thr Ser Ser Arg Leu Leu Arg Ile Arg Gly Ile Gln Met Ala Ile
20 25 30

Arg Cys Val Ala Ser Arg Lys Thr Leu Ala Gly Leu Lys Glu Thr Ser
35 40 45

```
Ser Arg Leu Leu Arg Ile Arg Gly Ile Gln Gly Gly
    50                  55                  60


<210> SEQ ID NO 32
<211> LENGTH: 29
<212> TYPE: PRT
<213> ORGANISM: Artificial Sequence
<220> FEATURE:
<223> OTHER INFORMATION: Amino acid sequence of the Superoxide
      dismutase, modified (SODmod) MTP

<400> SEQUENCE: 32

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Gly Gly
            20                  25


<210> SEQ ID NO 33
<211> LENGTH: 56
<212> TYPE: PRT
<213> ORGANISM: Artificial Sequence
<220> FEATURE:
<223> OTHER INFORMATION: Amino acid sequence of the Superoxide
      dismutase, modified (2SODmod) doubled MTP

<400> SEQUENCE: 33

Met Ala Ile Arg Cys Val Ala Ser Arg Lys Thr Leu Ala Gly Leu Lys
1               5                   10                  15

Glu Thr Ser Ser Arg Leu Leu Arg Ile Arg Gly Met Ala Ile Arg Cys
            20                  25                  30

Val Ala Ser Arg Lys Thr Leu Ala Gly Leu Lys Glu Thr Ser Ser Arg
        35                  40                  45

Leu Leu Arg Ile Arg Gly Gly Gly
    50                  55


<210> SEQ ID NO 34
<211> LENGTH: 34
<212> TYPE: PRT
<213> ORGANISM: Artificial Sequence
<220> FEATURE:
<223> OTHER INFORMATION: Amino acid sequence of the L29 MTP (At1G07830)

<400> SEQUENCE: 34

Met Phe Leu Thr Arg Phe Val Gly Arg Arg Phe Leu Ala Ala Ala Ser
1               5                   10                  15

Ala Arg Ser Glu Ser Thr Thr Ala Ala Ala Ala Ala Ser Thr Ile Arg
            20                  25                  30

Gly Gly


<210> SEQ ID NO 35
<211> LENGTH: 70
<212> TYPE: PRT
<213> ORGANISM: Neurospora crassa

<400> SEQUENCE: 35

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
```

```
    50                  55                  60

Arg Ala Tyr Ser Gly Gly
65                  70


<210> SEQ ID NO 36
<211> LENGTH: 53
<212> TYPE: PRT
<213> ORGANISM: Artificial Sequence
<220> FEATURE:
<223> OTHER INFORMATION: Amino acid sequence of the gATPase gamma
      subunit (FAv51) MTP, without the additional N-terminal Met. SEQ ID
      NO:21 has an additional N-terminal Met. Cleavage by MPP occurs
      between amino acid residues 42 and 43.

<400> SEQUENCE: 36

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly
    50


<210> SEQ ID NO 37
<211> LENGTH: 61
<212> TYPE: PRT
<213> ORGANISM: Artificial Sequence
<220> FEATURE:
<223> OTHER INFORMATION: Amino acid sequence of the CoxIV twin strep
      (ABM97483) MTP

<400> SEQUENCE: 37

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly
    50                  55                  60


<210> SEQ ID NO 38
<211> LENGTH: 43
<212> TYPE: PRT
<213> ORGANISM: Artificial Sequence
<220> FEATURE:
<223> OTHER INFORMATION: Amino acid sequence of the CoxIV 10xHis
      (ABM97483) MTP

<400> SEQUENCE: 38

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Gly Gly His
            20                  25                  30

His His His His His His His His His Gly Gly
        35                  40


<210> SEQ ID NO 39
<211> LENGTH: 4
<212> TYPE: PRT
<213> ORGANISM: Artificial Sequence
<220> FEATURE:
```

<223> OTHER INFORMATION: Amino acid sequence of the predicted scar for the Superoxide dismutase (SOD) MTP with GG

<400> SEQUENCE: 39

Ile Gln Gly Gly
1

<210> SEQ ID NO 40
<211> LENGTH: 15
<212> TYPE: PRT
<213> ORGANISM: Artificial Sequence
<220> FEATURE:
<223> OTHER INFORMATION: Amino acid sequence of the predicted scar for Superoxide dismutase, doubled (2SOD) MTP with GG

<400> SEQUENCE: 40

```
Glu Ser Thr Thr Ala Ala Ala Ala Ala Ser Thr Ile Arg Gly Gly
1               5                   10                  15
```

<210> SEQ ID NO 41
<211> LENGTH: 4
<212> TYPE: PRT
<213> ORGANISM: Neurospora crassa

<400> SEQUENCE: 41

Tyr Ser Gly Gly
1

<210> SEQ ID NO 42
<211> LENGTH: 11
<212> TYPE: PRT
<213> ORGANISM: Artificial Sequence
<220> FEATURE:
<223> OTHER INFORMATION: Amino acid sequence of the predicted scar for the gATPase gamma subunit (FAγ51) MTP with GG

<400> SEQUENCE: 42

```
Ile Ser Thr Gln Val Val Arg Asn Arg Gly Gly
1               5                   10
```

<210> SEQ ID NO 43
<211> LENGTH: 36
<212> TYPE: PRT
<213> ORGANISM: Artificial Sequence
<220> FEATURE:
<223> OTHER INFORMATION: Amino acid sequence of the predicted scar for the CoxIV twin strep MTP with GG

<400> SEQUENCE: 43

```
Gln Gln Lys Pro Ser Ala Trp Ser His Pro Gln Phe Glu Lys Gly Gly
1               5                   10                  15

Gly Ser Gly Gly Gly Ser Gly Gly Ser Ala Trp Ser His Pro Gln Phe
            20                  25                  30

Glu Lys Gly Gly
        35
```

<210> SEQ ID NO 44
<211> LENGTH: 18
<212> TYPE: PRT
<213> ORGANISM: Artificial Sequence
<220> FEATURE:
<223> OTHER INFORMATION: Amino acid sequence of the predicted scar for the CoxIV 10xHis MTP with GG

<400> SEQUENCE: 44

```
Gln Gln Lys Pro Gly Gly His His His His His His His His His His
```

1 5 10 15

Gly Gly

<210> SEQ ID NO 45
<211> LENGTH: 40
<212> TYPE: DNA
<213> ORGANISM: Artificial Sequence
<220> FEATURE:
<223> OTHER INFORMATION: Oligonucleotide primer MIT_V2.1_SbfInifH_FW2

<400> SEQUENCE: 45
aacctgcagg tgacgtctaa gaaaaggaat attcagcaat 40

<210> SEQ ID NO 46
<211> LENGTH: 39
<212> TYPE: DNA
<213> ORGANISM: Artificial Sequence
<220> FEATURE:
<223> OTHER INFORMATION: Oligonucleotide primer MIT_V2.1_SbfInifJ_RV2

<400> SEQUENCE: 46
aacctgcagg gctaactaac taaccacgga caaaaaacc 39

<210> SEQ ID NO 47
<211> LENGTH: 35
<212> TYPE: DNA
<213> ORGANISM: Artificial Sequence
<220> FEATURE:
<223> OTHER INFORMATION: Oligonucleotide primer MIT_V2.1_SbfInifB_FW

<400> SEQUENCE: 47
aacctgcagg tactctaacc ccatcggccg tctta 35

<210> SEQ ID NO 48
<211> LENGTH: 35
<212> TYPE: DNA
<213> ORGANISM: Artificial Sequence
<220> FEATURE:
<223> OTHER INFORMATION: Oligonucleotide primer MIT_V2.1_SbfIori_RV

<400> SEQUENCE: 48
aacctgcagg tacgtagcaa tcaactcact ggctc 35

<210> SEQ ID NO 49
<211> LENGTH: 9
<212> TYPE: PRT
<213> ORGANISM: Artificial Sequence
<220> FEATURE:
<223> OTHER INFORMATION: Amino acid sequence of mscar9 from MTP-FAv51 having substitution of the N-terminal Ile residue with a Met for translation initiation

<400> SEQUENCE: 49

Met Ser Thr Gln Val Val Arg Asn Arg
1 5

<210> SEQ ID NO 50
<211> LENGTH: 6
<212> TYPE: PRT
<213> ORGANISM: Artificial Sequence
<220> FEATURE:
<223> OTHER INFORMATION: Tryptic peptide

<400> SEQUENCE: 50

Ser Thr Gln Val Val Arg
1 5

<210> SEQ ID NO 51
<211> LENGTH: 9
<212> TYPE: PRT
<213> ORGANISM: Artificial Sequence
<220> FEATURE:
<223> OTHER INFORMATION: Amino acid sequence of MTP-FAv9 scar without N-terminal Met and with C-terminal Met

<400> SEQUENCE: 51

Ser Thr Gln Val Val Arg Asn Arg Met
1 5

<210> SEQ ID NO 52
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 52
atgtcaactc aagtggtgcg taaccgcatg acctcttgtt cgtcgtt 47

<210> SEQ ID NO 53
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 53
tttagccctc ctatgattga tttgatgtat tacagagagg 40

<210> SEQ ID NO 54
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 54
ggttacgcac cacttgagtt gacattttag ccctcctatg attgatttga tg 52

<210> SEQ ID NO 55
<211> LENGTH: 7
<212> TYPE: PRT
<213> ORGANISM: Artificial Sequence
<220> FEATURE:
<223> OTHER INFORMATION: Tryptic peptide

<400> SEQUENCE: 55

Met Ser Thr Gln Val Val Arg
1 5

<210> SEQ ID NO 56
<211> LENGTH: 8
<212> TYPE: PRT
<213> ORGANISM: Artificial Sequence
<220> FEATURE:
<223> OTHER INFORMATION: Tryptic peptide

<400> SEQUENCE: 56

Ser Thr Gln Val Val Arg Asn Arg
1 5

<210> SEQ ID NO 57

<211> LENGTH: 599
<212> TYPE: PRT
<213> ORGANISM: Artificial Sequence
<220> FEATURE:
<223> OTHER INFORMATION: Amino acid sequence of the MTP-FA 77::NifK fusion polypeptide (pRA25), lacking any C-terminal extension. Amino acids 1-77 correspond to the MTP-FA 77, amino acids 78-80 are GAP, and amino acids 81-599 correspond to K. oxytoca NifK without the initiator

<400> SEQUENCE: 57

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Met Lys Ser Val Lys Asn Ile Gln Lys Ile Thr Lys Ala
    50                  55                  60

Met Lys Met Val Ala Ala Ser Lys Leu Arg Ala Val Gln Gly Ala Pro
65                  70                  75                  80

Ser Gln Thr Ile Asp Lys Ile Asn Ser Cys Tyr Pro Leu Phe Glu Gln
                85                  90                  95

Asp Glu Tyr Gln Glu Leu Phe Arg Asn Lys Arg Gln Leu Glu Glu Ala
            100                 105                 110

His Asp Ala Gln Arg Val Gln Glu Val Phe Ala Trp Thr Thr Thr Ala
        115                 120                 125

Glu Tyr Glu Ala Leu Asn Phe Arg Arg Glu Ala Leu Thr Val Asp Pro
    130                 135                 140

Ala Lys Ala Cys Gln Pro Leu Gly Ala Val Leu Cys Ser Leu Gly Phe
145                 150                 155                 160

Ala Asn Thr Leu Pro Tyr Val His Gly Ser Gln Gly Cys Val Ala Tyr
                165                 170                 175

Phe Arg Thr Tyr Phe Asn Arg His Phe Lys Glu Pro Ile Ala Cys Val
            180                 185                 190

Ser Asp Ser Met Thr Glu Asp Ala Ala Val Phe Gly Gly Asn Asn Asn
        195                 200                 205

Met Asn Leu Gly Leu Gln Asn Ala Ser Ala Leu Tyr Lys Pro Glu Ile
    210                 215                 220

Ile Ala Val Ser Thr Thr Cys Met Ala Glu Val Ile Gly Asp Asp Leu
225                 230                 235                 240

Gln Ala Phe Ile Ala Asn Ala Lys Lys Asp Gly Phe Val Asp Ser Ser
                245                 250                 255

Ile Ala Val Pro His Ala His Thr Pro Ser Phe Ile Gly Ser His Val
            260                 265                 270

Thr Gly Trp Asp Asn Met Phe Glu Gly Phe Ala Lys Thr Phe Thr Ala
        275                 280                 285

Asp Tyr Gln Gly Gln Pro Gly Lys Leu Pro Lys Leu Asn Leu Val Thr
    290                 295                 300

Gly Phe Glu Thr Tyr Leu Gly Asn Phe Arg Val Leu Lys Arg Met Met
305                 310                 315                 320

Glu Gln Met Ala Val Pro Cys Ser Leu Leu Ser Asp Pro Ser Glu Val
                325                 330                 335

Leu Asp Thr Pro Ala Asp Gly His Tyr Arg Met Tyr Ser Gly Gly Thr
            340                 345                 350

Thr Gln Gln Glu Met Lys Glu Ala Pro Asp Ala Ile Asp Thr Leu Leu
```

355 360 365

Leu Gln Pro Trp Gln Leu Leu Lys Ser Lys Lys Val Val Gln Glu Met
370 375 380

Trp Asn Gln Pro Ala Thr Glu Val Ala Ile Pro Leu Gly Leu Ala Ala
385 390 395 400

Thr Asp Glu Leu Leu Met Thr Val Ser Gln Leu Ser Gly Lys Pro Ile
405 410 415

Ala Asp Ala Leu Thr Leu Glu Arg Gly Arg Leu Val Asp Met Met Leu
420 425 430

Asp Ser His Thr Trp Leu His Gly Lys Lys Phe Gly Leu Tyr Gly Asp
435 440 445

Pro Asp Phe Val Met Gly Leu Thr Arg Phe Leu Leu Glu Leu Gly Cys
450 455 460

Glu Pro Thr Val Ile Leu Ser His Asn Ala Asn Lys Arg Trp Gln Lys
465 470 475 480

Ala Met Asn Lys Met Leu Asp Ala Ser Pro Tyr Gly Arg Asp Ser Glu
485 490 495

Val Phe Ile Asn Cys Asp Leu Trp His Phe Arg Ser Leu Met Phe Thr
500 505 510

Arg Gln Pro Asp Phe Met Ile Gly Asn Ser Tyr Gly Lys Phe Ile Gln
515 520 525

Arg Asp Thr Leu Ala Lys Gly Lys Ala Phe Glu Val Pro Leu Ile Arg
530 535 540

Leu Gly Phe Pro Leu Phe Asp Arg His His Leu His Arg Gln Thr Thr
545 550 555 560

Trp Gly Tyr Glu Gly Ala Met Asn Ile Val Thr Thr Leu Val Asn Ala
565 570 575

Val Leu Glu Lys Leu Asp Ser Asp Thr Ser Gln Leu Gly Lys Thr Asp
580 585 590

Tyr Ser Phe Asp Leu Val Arg
595

<210> SEQ ID NO 58
<211> LENGTH: 4
<212> TYPE: PRT
<213> ORGANISM: Klebsiella oxytoca

<400> SEQUENCE: 58

Asp Leu Val Arg
1

<210> SEQ ID NO 59
<211> LENGTH: 60
<212> TYPE: PRT
<213> ORGANISM: Artificial Sequence
<220> FEATURE:
<223> OTHER INFORMATION: Amino acid sequence of the mutant MTP-FAv51 polypeptide

<400> SEQUENCE: 59

Met Met Ala Met Ala Val Phe Arg Arg Glu Gly Arg Arg Leu Leu Pro
1 5 10 15

Ser Ile Ala Ala Arg Pro Ile Ala Ala Ala Ala Ala Ala Ala Ser Ser
20 25 30

Asp Gln Glu Glu Gly Leu Leu Ala Ala Ala Ala Ala Ala Ala Ala Val
35 40 45

Val Arg Asn Arg Gly Gly Met Met Thr Asn Ala Thr 50 55 60

<210> SEQ ID NO 60
<211> LENGTH: 6
<212> TYPE: PRT
<213> ORGANISM: Artificial Sequence
<220> FEATURE:
<223> OTHER INFORMATION: peptide

<400> SEQUENCE: 60

Val Arg Gly Cys Ala Tyr
1 5

<210> SEQ ID NO 61
<211> LENGTH: 10
<212> TYPE: PRT
<213> ORGANISM: Artificial Sequence
<220> FEATURE:
<223> OTHER INFORMATION: peptide

<400> SEQUENCE: 61

Arg Ala Gly Arg Arg Asn Tyr Tyr Thr Gly
1 5 10

<210> SEQ ID NO 62
<211> LENGTH: 5
<212> TYPE: PRT
<213> ORGANISM: Artificial Sequence
<220> FEATURE:
<223> OTHER INFORMATION: peptide

<400> SEQUENCE: 62

Ser Asn Arg Lys Ser
1 5

<210> SEQ ID NO 63
<211> LENGTH: 5
<212> TYPE: PRT
<213> ORGANISM: Artificial Sequence
<220> FEATURE:
<223> OTHER INFORMATION: peptide

<400> SEQUENCE: 63

Ala Ala Ala Ala Ala
1 5

<210> SEQ ID NO 64
<211> LENGTH: 5
<212> TYPE: PRT
<213> ORGANISM: Artificial Sequence
<220> FEATURE:
<223> OTHER INFORMATION: peptide

<400> SEQUENCE: 64

Gln Pro Gly Val Met
1 5

<210> SEQ ID NO 65
<211> LENGTH: 5
<212> TYPE: PRT
<213> ORGANISM: Artificial Sequence
<220> FEATURE:
<223> OTHER INFORMATION: peptide

<400> SEQUENCE: 65

Thr Val Arg Gly Cys
1 5

<210> SEQ ID NO 66
<211> LENGTH: 5
<212> TYPE: PRT
<213> ORGANISM: Artificial Sequence
<220> FEATURE:
<223> OTHER INFORMATION: peptide

<400> SEQUENCE: 66

Ala Tyr Ala Gly Ser
1               5

<210> SEQ ID NO 67
<211> LENGTH: 5
<212> TYPE: PRT
<213> ORGANISM: Artificial Sequence
<220> FEATURE:
<223> OTHER INFORMATION: peptide

<400> SEQUENCE: 67

Gly Ala Gly Ala Ala
1               5

<210> SEQ ID NO 68
<211> LENGTH: 5
<212> TYPE: PRT
<213> ORGANISM: Artificial Sequence
<220> FEATURE:
<223> OTHER INFORMATION: peptide

<400> SEQUENCE: 68

Lys Gly Val Val Phe
1               5

<210> SEQ ID NO 69
<211> LENGTH: 5
<212> TYPE: PRT
<213> ORGANISM: Artificial Sequence
<220> FEATURE:
<223> OTHER INFORMATION: peptide

<400> SEQUENCE: 69

Gly Pro Ile Lys Asp
1               5

<210> SEQ ID NO 70
<211> LENGTH: 10
<212> TYPE: PRT
<213> ORGANISM: Artificial Sequence
<220> FEATURE:
<223> OTHER INFORMATION: peptide

<400> SEQUENCE: 70

Thr Val Arg Gly Cys Ala Tyr Ala Gly Ser
1               5                   10

<210> SEQ ID NO 71
<211> LENGTH: 10
<212> TYPE: PRT
<213> ORGANISM: Artificial Sequence
<220> FEATURE:
<223> OTHER INFORMATION: peptide

<400> SEQUENCE: 71

Thr Ala Arg Ala Cys Gly Tyr Gly Gly Ser
1               5                   10

<210> SEQ ID NO 72
<211> LENGTH: 4
<212> TYPE: PRT
<213> ORGANISM: Artificial Sequence
<220> FEATURE:
<223> OTHER INFORMATION: peptide

<400> SEQUENCE: 72

Ala Tyr Ala Gly
1

<210> SEQ ID NO 73
<211> LENGTH: 4
<212> TYPE: PRT
<213> ORGANISM: Artificial Sequence
<220> FEATURE:
<223> OTHER INFORMATION: peptide

<400> SEQUENCE: 73

Gly Ala Gly Gly
1

<210> SEQ ID NO 74
<211> LENGTH: 5
<212> TYPE: PRT
<213> ORGANISM: Artificial Sequence
<220> FEATURE:
<223> OTHER INFORMATION: peptide

<400> SEQUENCE: 74

Met Ala His Ile Ser
1 5

<210> SEQ ID NO 75
<211> LENGTH: 5
<212> TYPE: PRT
<213> ORGANISM: Artificial Sequence
<220> FEATURE:
<223> OTHER INFORMATION: peptide

<400> SEQUENCE: 75

Ala Gly Ala Ala Ala
1 5

<210> SEQ ID NO 76
<211> LENGTH: 5
<212> TYPE: PRT
<213> ORGANISM: Artificial Sequence
<220> FEATURE:
<223> OTHER INFORMATION: peptide

<400> SEQUENCE: 76

His Gly Pro Val Gly
1 5

<210> SEQ ID NO 77
<211> LENGTH: 5
<212> TYPE: PRT
<213> ORGANISM: Artificial Sequence
<220> FEATURE:
<223> OTHER INFORMATION: peptide

<400> SEQUENCE: 77

Cys Gly Gln Tyr Ser
1 5

<210> SEQ ID NO 78
<211> LENGTH: 5
<212> TYPE: PRT
<213> ORGANISM: Artificial Sequence
<220> FEATURE:
<223> OTHER INFORMATION: peptide

<400> SEQUENCE: 78

Arg Ala Gly Arg Arg
1               5

<210> SEQ ID NO 79
<211> LENGTH: 5
<212> TYPE: PRT
<213> ORGANISM: Artificial Sequence
<220> FEATURE:
<223> OTHER INFORMATION: peptide

<400> SEQUENCE: 79

Asn Tyr Tyr Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: peptide

<400> SEQUENCE: 80

Val Ser Gly Val Asp
1               5

<210> SEQ ID NO 81
<211> LENGTH: 10
<212> TYPE: PRT
<213> ORGANISM: Artificial Sequence
<220> FEATURE:
<223> OTHER INFORMATION: peptide

<400> SEQUENCE: 81

Arg Ala Gly Arg Arg Asn Tyr Phe Thr Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: peptide

<400> SEQUENCE: 82

Arg Ala Gly Arg Arg Asn Tyr Tyr Ala Gly
1               5                   10

<210> SEQ ID NO 83
<211> LENGTH: 10
<212> TYPE: PRT
<213> ORGANISM: Artificial Sequence
<220> FEATURE:
<223> OTHER INFORMATION: peptide

<400> SEQUENCE: 83

Arg Ala Gly Arg Arg Asn Tyr Phe Ala Gly
1               5                   10

<210> SEQ ID NO 84

<211> LENGTH: 10
<212> TYPE: PRT
<213> ORGANISM: Artificial Sequence
<220> FEATURE:
<223> OTHER INFORMATION: peptide

<400> SEQUENCE: 84

Arg Ala Gly Arg Arg Asn Tyr Tyr Ala Ala
1 5 10

<210> SEQ ID NO 85
<211> LENGTH: 10
<212> TYPE: PRT
<213> ORGANISM: Artificial Sequence
<220> FEATURE:
<223> OTHER INFORMATION: peptide

<400> SEQUENCE: 85

Arg Ala Gly Arg Ala Asn Tyr Tyr Thr Gly
1 5 10

<210> SEQ ID NO 86
<211> LENGTH: 10
<212> TYPE: PRT
<213> ORGANISM: Artificial Sequence
<220> FEATURE:
<223> OTHER INFORMATION: peptide

<400> SEQUENCE: 86

Arg Ala Gly Arg Arg His Tyr Tyr Thr Gly
1 5 10

<210> SEQ ID NO 87
<211> LENGTH: 10
<212> TYPE: PRT
<213> ORGANISM: Artificial Sequence
<220> FEATURE:
<223> OTHER INFORMATION: peptide

<400> SEQUENCE: 87

Arg Ala Gly Arg Arg Asn Gln Tyr Thr Gly
1 5 10

<210> SEQ ID NO 88
<211> LENGTH: 10
<212> TYPE: PRT
<213> ORGANISM: Artificial Sequence
<220> FEATURE:
<223> OTHER INFORMATION: peptide

<400> SEQUENCE: 88

Arg Ala Gly Arg Arg Asn Tyr Thr Thr Gly
1 5 10

<210> SEQ ID NO 89
<211> LENGTH: 10
<212> TYPE: PRT
<213> ORGANISM: Artificial Sequence
<220> FEATURE:
<223> OTHER INFORMATION: peptide

<400> SEQUENCE: 89

Arg Ala Gly Arg Arg Asn Tyr Tyr Val Gly
1 5 10

<210> SEQ ID NO 90
<211> LENGTH: 10

<212> TYPE: PRT
<213> ORGANISM: Artificial Sequence
<220> FEATURE:
<223> OTHER INFORMATION: peptide

<400> SEQUENCE: 90

Arg Ala Gly Arg Arg Asn Gln Thr Thr Gly
1               5                   10

<210> SEQ ID NO 91
<211> LENGTH: 10
<212> TYPE: PRT
<213> ORGANISM: Artificial Sequence
<220> FEATURE:
<223> OTHER INFORMATION: peptide

<400> SEQUENCE: 91

Arg Ala Gly Arg Arg His Lys Gly Thr Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: peptide

<400> SEQUENCE: 92

Arg Ala Gly Arg Arg Asn Lys Tyr Thr Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: peptide

<400> SEQUENCE: 93

Arg Ala Gly Arg Arg Asn Lys Ala Thr Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: peptide

<400> SEQUENCE: 94

Arg Ala Gly Arg Arg Asn Tyr Ala Thr Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: peptide

<400> SEQUENCE: 95

Arg Ala Gly Arg Lys Asn Tyr Tyr Thr Gly
1               5                   10

<210> SEQ ID NO 96
<211> LENGTH: 10
<212> TYPE: PRT

<213> ORGANISM: Artificial Sequence
<220> FEATURE:
<223> OTHER INFORMATION: peptide

<400> SEQUENCE: 96

Arg Ala Gly Arg Lys Asn Tyr Phe Thr Gly
1 5 10

<210> SEQ ID NO 97
<211> LENGTH: 10
<212> TYPE: PRT
<213> ORGANISM: Artificial Sequence
<220> FEATURE:
<223> OTHER INFORMATION: peptide

<400> SEQUENCE: 97

Arg Ala Gly Arg Lys Asn Tyr Tyr Ala Gly
1 5 10

<210> SEQ ID NO 98
<211> LENGTH: 10
<212> TYPE: PRT
<213> ORGANISM: Artificial Sequence
<220> FEATURE:
<223> OTHER INFORMATION: peptide

<400> SEQUENCE: 98

Arg Ala Gly Arg Lys Asn Tyr Phe Ala Gly
1 5 10

<210> SEQ ID NO 99
<211> LENGTH: 10
<212> TYPE: PRT
<213> ORGANISM: Artificial Sequence
<220> FEATURE:
<223> OTHER INFORMATION: peptide

<400> SEQUENCE: 99

Arg Ala Gly Arg Lys Asn Tyr Ala Ala Gly
1 5 10

<210> SEQ ID NO 100
<211> LENGTH: 23
<212> TYPE: PRT
<213> ORGANISM: Artificial Sequence
<220> FEATURE:
<223> OTHER INFORMATION: peptide

<400> SEQUENCE: 100

Tyr Tyr Thr Gly Val Ser Gly Val Asp Ser Phe Gly Thr Leu Asn Phe
1 5 10 15

Thr Ser Asp Phe Gln Glu Arg
20

<210> SEQ ID NO 101
<211> LENGTH: 4
<212> TYPE: PRT
<213> ORGANISM: Artificial Sequence
<220> FEATURE:
<223> OTHER INFORMATION: peptide

<400> SEQUENCE: 101

Arg Arg Asn Tyr
1

<210> SEQ ID NO 102

<211> LENGTH: 5
<212> TYPE: PRT
<213> ORGANISM: Artificial Sequence
<220> FEATURE:
<223> OTHER INFORMATION: peptide

<400> SEQUENCE: 102

Arg Arg Asn Tyr Tyr
1               5

<210> SEQ ID NO 103
<211> LENGTH: 4
<212> TYPE: PRT
<213> ORGANISM: Artificial Sequence
<220> FEATURE:
<223> OTHER INFORMATION: peptide

<400> SEQUENCE: 103

Arg Arg Asn Gln
1

<210> SEQ ID NO 104
<211> LENGTH: 4
<212> TYPE: PRT
<213> ORGANISM: Artificial Sequence
<220> FEATURE:
<223> OTHER INFORMATION: peptide

<400> SEQUENCE: 104

Arg Arg Asn Lys
1

<210> SEQ ID NO 105
<211> LENGTH: 5
<212> TYPE: PRT
<213> ORGANISM: Artificial Sequence
<220> FEATURE:
<223> OTHER INFORMATION: peptide

<400> SEQUENCE: 105

Arg Arg Asn Gln Thr
1               5

<210> SEQ ID NO 106
<211> LENGTH: 4
<212> TYPE: PRT
<213> ORGANISM: Artificial Sequence
<220> FEATURE:
<223> OTHER INFORMATION: peptide

<400> SEQUENCE: 106

Arg Arg Phe Lys
1

<210> SEQ ID NO 107
<211> LENGTH: 5
<212> TYPE: PRT
<213> ORGANISM: Artificial Sequence
<220> FEATURE:
<223> OTHER INFORMATION: peptide

<400> SEQUENCE: 107

Arg Arg Asn Lys Ala
1               5

<210> SEQ ID NO 108
<211> LENGTH: 56

<212> TYPE: DNA
<213> ORGANISM: Artificial Sequence
<220> FEATURE:
<223> OTHER INFORMATION: Oligonucleotide primer

<400> SEQUENCE: 108
ctaatgctac cggtgaacgt aacctggcac tgattcaaga agtactggaa gtgttc 56

<210> SEQ ID NO 109
<211> LENGTH: 57
<212> TYPE: DNA
<213> ORGANISM: Artificial Sequence
<220> FEATURE:
<223> OTHER INFORMATION: Oligonucleotide primer

<400> SEQUENCE: 109
gttacgttca ccggtagcat tagtcatcat ccggctcctc cgctagataa aaatgtg 57

<210> SEQ ID NO 110
<211> LENGTH: 55
<212> TYPE: DNA
<213> ORGANISM: Artificial Sequence
<220> FEATURE:
<223> OTHER INFORMATION: Oligonucleotide primer

<400> SEQUENCE: 110
gtttctggcg tcgactcttt cggcacgctg aacttcacct ctgacttcca ggaac 55

<210> SEQ ID NO 111
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 111
cgaaagagtc gacgccagaa acgcccgtgt agtagttacg acgtcccgcg cg 52

<210> SEQ ID NO 112
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 112
gaccaatgct accggtgaga ggaacc 26

<210> SEQ ID NO 113
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 113
gttaagagtc ccgaaagagt cgacaccag 29

<210> SEQ ID NO 114
<211> LENGTH: 11
<212> TYPE: PRT
<213> ORGANISM: Artificial Sequence
<220> FEATURE:
<223> OTHER INFORMATION: Amino acid sequence of an 11-residue section from a known unstructured linker region from Hypocrea jecorina cellobiohydrolase II (Accession no. AAG39980.1).

<400> SEQUENCE: 114

Ala Thr Pro Pro Pro Gly Ser Thr Thr Thr Arg
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Amino acid sequence of 9-residue HA epitope

<400> SEQUENCE: 115

Tyr Pro Tyr Asp Val Pro Asp Tyr Ala
1               5

<210> SEQ ID NO 116
<211> LENGTH: 30
<212> TYPE: PRT
<213> ORGANISM: Artificial Sequence
<220> FEATURE:
<223> OTHER INFORMATION: Amino acid sequence of linker for the NifD::linker::NifK fusion polypeptide.

<400> SEQUENCE: 116

Ala Thr Pro Pro Pro Gly Ser Thr Thr Thr Ala Tyr Pro Tyr Asp Val
1               5                   10                  15

Pro Asp Tyr Ala Thr Pro Pro Pro Gly Ser Thr Thr Thr Ala
            20                  25                  30

<210> SEQ ID NO 117
<211> LENGTH: 47
<212> TYPE: DNA
<213> ORGANISM: Artificial Sequence
<220> FEATURE:
<223> OTHER INFORMATION: Oligonucleotide primer

<400> SEQUENCE: 117
gtcgtaacca atacacgggc gtttctggcg tcgactcttt cggcacg 47

<210> SEQ ID NO 118
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 118
gcccgtgtat tggttacgac gtcccgcgcg agagtactgg c 41

<210> SEQ ID NO 119
<211> LENGTH: 7
<212> TYPE: PRT
<213> ORGANISM: Artificial Sequence
<220> FEATURE:
<223> OTHER INFORMATION: peptide sequence

<400> SEQUENCE: 119

Ile Ser Thr Gln Val Val Arg
1               5

<210> SEQ ID NO 120
<211> LENGTH: 8
<212> TYPE: PRT
<213> ORGANISM: Artificial Sequence
<220> FEATURE:
<223> OTHER INFORMATION: peptide sequence

<400> SEQUENCE: 120

Ser Ile Ser Thr Gln Val Val Arg
1 5

<210> SEQ ID NO 121
<211> LENGTH: 603
<212> TYPE: PRT
<213> ORGANISM: Artificial Sequence
<220> FEATURE:
<223> OTHER INFORMATION: Amino acid sequence of the metaxin fusion polypeptide encoded by construct SN197. The TwinStrep epitope corresponds to amino acids 1-31, mTurquoise to amino acids 32-273, a TEV cleavage site to amino acids 274-282 and the metaxin sequence to amino acids

<400> SEQUENCE: 121

Met Trp Ser His Pro Gln Phe Glu Lys Gly Gly Gly Ser Gly Gly Gly
1 5 10 15

Ser Gly Gly Ser Ala Trp Ser His Pro Gln Phe Glu Lys Gly Met Val
20 25 30

Ser Lys Gly Glu Glu Leu Phe Thr Gly Val Val Pro Ile Leu Val Glu
35 40 45

Leu Asp Gly Asp Val Asn Gly His Lys Phe Ser Val Ser Gly Glu Gly
50 55 60

Glu Gly Asp Ala Thr Tyr Gly Lys Leu Thr Leu Lys Phe Ile Cys Thr
65 70 75 80

Thr Gly Lys Leu Pro Val Pro Trp Pro Thr Leu Val Thr Thr Leu Ser
85 90 95

Trp Gly Val Gln Cys Phe Ala Arg Tyr Pro Asp His Met Lys Gln His
100 105 110

Asp Phe Phe Lys Ser Ala Met Pro Glu Gly Tyr Val Gln Glu Arg Thr
115 120 125

Ile Phe Phe Lys Asp Asp Gly Asn Tyr Lys Thr Arg Ala Glu Val Lys
130 135 140

Phe Glu Gly Asp Thr Leu Val Asn Arg Ile Glu Leu Lys Gly Ile Asp
145 150 155 160

Phe Lys Glu Asp Gly Asn Ile Leu Gly His Lys Leu Glu Tyr Asn Tyr
165 170 175

Phe Ser Asp Asn Val Tyr Ile Thr Ala Asp Lys Gln Lys Asn Gly Ile
180 185 190

Lys Ala Asn Phe Lys Ile Arg His Asn Ile Glu Asp Gly Gly Val Gln
195 200 205

Leu Ala Asp His Tyr Gln Gln Asn Thr Pro Ile Gly Asp Gly Pro Val
210 215 220

Leu Leu Pro Asp Asn His Tyr Leu Ser Thr Gln Ser Lys Leu Ser Lys
225 230 235 240

Asp Pro Asn Glu Lys Arg Asp His Met Val Leu Leu Glu Phe Val Thr
245 250 255

Ala Ala Gly Ile Thr Leu Gly Met Asp Glu Leu Tyr Lys Gly Gly Gly
260 265 270

Gly Glu Asn Leu Tyr Phe Gln Gly Gly Gly Met Glu Glu Ala Lys Glu
275 280 285

Arg Glu Lys Leu Thr Leu Val Thr Arg Lys Ser Ser Phe Gly Leu Pro
290 295 300

Thr Ser Cys Pro Asn Cys Leu Pro Val Tyr Leu Tyr Leu Lys Phe Ser
305 310 315 320

```
Lys Thr Pro Phe Asp Leu Ala Phe Asn Leu Ile Asn Pro Asp Phe Gly
                325                 330                 335

Gln Ile Pro Tyr Val Glu Ser Gly Thr Tyr Val Ala Tyr Asn Asn Glu
            340                 345                 350

Lys Gly Gly Val Ile Arg Ser Leu Ile Glu Asp Gly Phe Val Asp Leu
        355                 360                 365

Asp Ser Gln Val His Gly Ile Pro Glu Trp Val Ser Thr Lys Ala Met
    370                 375                 380

Val Asp Ser Trp Leu Ala Asp Ala Ile Leu Tyr Glu Leu Trp Val Gly
385                 390                 395                 400

Ser Asp Gly Ser Ser Ala His Lys Ile Tyr Phe Ser Asp Leu Pro Trp
                405                 410                 415

Pro Leu Gly Lys Leu Leu Tyr Leu Lys Gln Val His Val Ala Lys Gln
            420                 425                 430

Ile Leu Asp Ile Thr Lys Asp Asn Ala Glu Arg Arg Glu Glu Glu Ile
        435                 440                 445

Tyr Arg Asn Ala Asn Asp Ala Phe Ser Ala Leu Ser Thr Arg Leu Gly
    450                 455                 460

Glu Gln Ala Tyr Leu Phe Asp Asn Arg Pro Thr Ser Leu Asp Ala Val
465                 470                 475                 480

Phe Leu Gly His Ala Leu Phe Thr Leu Tyr Ala Leu Pro Glu Asn Ser
                485                 490                 495

Val Leu Arg Asn Lys Leu Leu Glu His Asp Asn Leu Val Arg Tyr Thr
            500                 505                 510

Glu Lys His Lys Leu Glu Leu Val Asp Ser Ser Ala Ser Ser Ser Ser
        515                 520                 525

Gly Thr Gln Ser Gln Ser Asp Pro Ser Ser Val Pro Arg Arg Pro Ser
    530                 535                 540

Gln Trp Ser Ser Lys Pro Lys Ser Lys Pro Lys Arg Glu Lys Thr Glu
545                 550                 555                 560

Glu Glu Lys Lys Phe Arg Arg Arg Ala Lys Tyr Phe Leu Val Thr Gln
                565                 570                 575

Leu Val Ala Val Leu Val Phe Leu Ser Leu Leu Gly Gly Ser Gly Asp
            580                 585                 590

Ala Glu Val Glu Leu Asp Glu Asp Asp Tyr Glu
        595                 600
```

<210> SEQ ID NO 122
<211> LENGTH: 547
<212> TYPE: PRT
<213> ORGANISM: Artificial Sequence
<220> FEATURE:
<223> OTHER INFORMATION: Amino acid sequence of the MTP-FA 51::NifD::HA fusion polypeptide encoded by SN10. Amino acids 1-54 correspond to the MTP-FA 51 with GG at its C-terminus, amino acids 55-536 were the K. oxytoca NifD amino acids (SEQ ID NO:18) with its initiator Met, and amino

<400> SEQUENCE: 122

```
Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Met Thr Asn Ala Thr Gly Glu Arg Asn
```

```
    50                  55                  60

Leu Ala Leu Ile Gln Glu Val Leu Glu Val Phe Pro Glu Thr Ala Arg
65                  70                  75                  80

Lys Glu Arg Arg Lys His Met Met Val Ser Asp Pro Glu Met Glu Ser
                85                  90                  95

Val Gly Lys Cys Ile Ile Ser Asn Arg Lys Ser Gln Pro Gly Val Met
            100                 105                 110

Thr Val Arg Gly Cys Ala Tyr Ala Gly Ser Lys Gly Val Val Phe Gly
        115                 120                 125

Pro Ile Lys Asp Met Ala His Ile Ser His Gly Pro Val Gly Cys Gly
    130                 135                 140

Gln Tyr Ser Arg Ala Gly Arg Arg Asn Tyr Tyr Thr Gly Val Ser Gly
145                 150                 155                 160

Val Asp Ser Phe Gly Thr Leu Asn Phe Thr Ser Asp Phe Gln Glu Arg
                165                 170                 175

Asp Ile Val Phe Gly Gly Asp Lys Lys Leu Ser Lys Leu Ile Glu Glu
            180                 185                 190

Met Glu Leu Leu Phe Pro Leu Thr Lys Gly Ile Thr Ile Gln Ser Glu
        195                 200                 205

Cys Pro Val Gly Leu Ile Gly Asp Asp Ile Ser Ala Val Ala Asn Ala
    210                 215                 220

Ser Ser Lys Ala Leu Asp Lys Pro Val Ile Pro Val Arg Cys Glu Gly
225                 230                 235                 240

Phe Arg Gly Val Ser Gln Ser Leu Gly His His Ile Ala Asn Asp Val
                245                 250                 255

Val Arg Asp Trp Ile Leu Asn Asn Arg Glu Gly Gln Pro Phe Glu Thr
            260                 265                 270

Thr Pro Tyr Asp Val Ala Ile Ile Gly Asp Tyr Asn Ile Gly Gly Asp
        275                 280                 285

Ala Trp Ala Ser Arg Ile Leu Leu Glu Glu Met Gly Leu Arg Val Val
    290                 295                 300

Ala Gln Trp Ser Gly Asp Gly Thr Leu Val Glu Met Glu Asn Thr Pro
305                 310                 315                 320

Phe Val Lys Leu Asn Leu Val His Cys Tyr Arg Ser Met Asn Tyr Ile
                325                 330                 335

Ala Arg His Met Glu Glu Lys His Gln Ile Pro Trp Met Glu Tyr Asn
            340                 345                 350

Phe Phe Gly Pro Thr Lys Ile Ala Glu Ser Leu Arg Lys Ile Ala Asp
        355                 360                 365

Gln Phe Asp Asp Thr Ile Arg Ala Asn Ala Glu Ala Val Ile Ala Arg
    370                 375                 380

Tyr Glu Gly Gln Met Ala Ala Ile Ile Ala Lys Tyr Arg Pro Arg Leu
385                 390                 395                 400

Glu Gly Arg Lys Val Leu Leu Tyr Met Gly Gly Leu Arg Pro Arg His
                405                 410                 415

Val Ile Gly Ala Tyr Glu Asp Leu Gly Met Glu Ile Ile Ala Ala Gly
            420                 425                 430

Tyr Glu Phe Ala His Asn Asp Asp Tyr Asp Arg Thr Leu Pro Asp Leu
        435                 440                 445

Lys Glu Gly Thr Leu Leu Phe Asp Asp Ala Ser Ser Tyr Glu Leu Glu
    450                 455                 460

Ala Phe Val Lys Ala Leu Lys Pro Asp Leu Ile Gly Ser Gly Ile Lys
465                 470                 475                 480
```

Glu Lys Tyr Ile Phe Gln Lys Met Gly Val Pro Phe Arg Gln Met His
485 490 495

Ser Trp Asp Tyr Ser Gly Pro Tyr His Gly Tyr Asp Gly Phe Ala Ile
500 505 510

Phe Ala Arg Asp Met Asp Met Thr Leu Asn Asn Pro Ala Trp Asn Glu
515 520 525

Leu Thr Ala Pro Trp Leu Lys Ser Gly Gly Tyr Pro Tyr Asp Val Pro
530 535 540

Asp Tyr Ala
545

<210> SEQ ID NO 123
<211> LENGTH: 331
<212> TYPE: PRT
<213> ORGANISM: Artificial Sequence
<220> FEATURE:
<223> OTHER INFORMATION: Amino acid sequence of the MTP-FA 51::NifM::HA fusion polypeptide encoded by SN30. Amino acids 1-54 correspond to the MTP-FA 51 with GG at its C-terminus, amino acids 55-320 correspond to K. oxytoca NifM (SEQ ID NO:8) with its initiator Met, and amino

<400> SEQUENCE: 123

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Asn Pro Trp Gln Arg Phe Ala Arg Gln
50 55 60

Arg Leu Ala Arg Ser Arg Trp Asn Arg Asp Pro Ala Ala Leu Asp Pro
65 70 75 80

Ala Asp Thr Pro Ala Phe Glu Gln Ala Trp Gln Arg Gln Cys His Met
85 90 95

Glu Gln Thr Ile Val Ala Arg Val Pro Glu Gly Asp Ile Pro Ala Ala
100 105 110

Leu Leu Glu Asn Ile Ala Ala Ser Leu Ala Ile Trp Leu Asp Glu Gly
115 120 125

Asp Phe Ala Pro Pro Glu Arg Ala Ala Ile Val Arg His His Ala Arg
130 135 140

Leu Glu Leu Ala Phe Ala Asp Ile Ala Arg Gln Ala Pro Gln Pro Asp
145 150 155 160

Leu Ser Thr Val Gln Ala Trp Tyr Leu Arg His Gln Thr Gln Phe Met
165 170 175

Arg Pro Glu Gln Arg Leu Thr Arg His Leu Leu Leu Thr Val Asp Asn
180 185 190

Asp Arg Glu Ala Val His Gln Arg Ile Leu Gly Leu Tyr Arg Gln Ile
195 200 205

Asn Ala Ser Arg Asp Ala Phe Ala Pro Leu Ala Gln Arg His Ser His
210 215 220

Cys Pro Ser Ala Leu Glu Glu Gly Arg Leu Gly Trp Ile Ser Arg Gly
225 230 235 240

Leu Leu Tyr Pro Gln Leu Glu Thr Ala Leu Phe Ser Leu Ala Glu Asn
245 250 255

Ala Leu Ser Leu Pro Ile Ala Ser Glu Leu Gly Trp His Leu Leu Trp

```
            260                 265                 270

Cys Glu Ala Ile Arg Pro Ala Ala Pro Met Glu Pro Gln Gln Ala Leu
        275                 280                 285

Glu Ser Ala Arg Asp Tyr Leu Trp Gln Gln Ser Gln Gln Arg His Gln
    290                 295                 300

Arg Gln Trp Leu Glu Gln Met Ile Ser Arg Gln Pro Gly Leu Cys Gly
305                 310                 315                 320

Gly Gly Tyr Pro Tyr Asp Val Pro Asp Tyr Ala
                325                 330


<210> SEQ ID NO 124
<211> LENGTH: 465
<212> TYPE: PRT
<213> ORGANISM: Artificial Sequence
<220> FEATURE:
<223> OTHER INFORMATION: Amino acid sequence of the MTP-FA 51::NifS::HA
      fusion polypeptide encoded by SN31.  Amino acids 1-54 correspond
      to the MTP-FA 51 with GG at its C-terminus, amino acids 55-454
      correspond to K. oxytoca NifS (SEQ ID NO:19) with its initiator
      Met, according to

<400> SEQUENCE: 124

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Lys Gln Val Tyr Leu Asp Asn Asn Ala
    50                  55                  60

Thr Thr Arg Leu Asp Pro Met Val Leu Glu Ala Met Met Pro Phe Leu
65                  70                  75                  80

Thr Asp Phe Tyr Gly Asn Pro Ser Ser Ile His Asp Phe Gly Ile Pro
                85                  90                  95

Ala Gln Ala Ala Leu Glu Arg Ala His Gln Gln Ala Ala Ala Leu Leu
            100                 105                 110

Gly Ala Glu Tyr Pro Ser Glu Ile Ile Phe Thr Ser Cys Ala Thr Glu
        115                 120                 125

Ala Thr Ala Thr Ala Ile Ala Ser Ala Ile Ala Leu Leu Pro Glu Arg
    130                 135                 140

Arg Glu Ile Ile Thr Ser Val Val Glu His Pro Ala Thr Leu Ala Ala
145                 150                 155                 160

Cys Glu His Leu Glu Arg Gln Gly Tyr Arg Ile His Arg Ile Ala Val
                165                 170                 175

Asp Ser Glu Gly Ala Leu Asp Met Ala Gln Phe Arg Ala Ala Leu Ser
            180                 185                 190

Pro Arg Val Ala Leu Val Ser Val Met Trp Ala Asn Asn Glu Thr Gly
        195                 200                 205

Val Leu Phe Pro Ile Gly Glu Met Ala Glu Leu Ala His Glu Gln Gly
    210                 215                 220

Ala Leu Phe His Cys Asp Ala Val Gln Val Val Gly Lys Ile Pro Ile
225                 230                 235                 240

Ala Val Gly Gln Thr Arg Ile Asp Met Leu Ser Cys Ser Ala His Lys
                245                 250                 255

Phe His Gly Pro Lys Gly Val Gly Cys Leu Tyr Leu Arg Arg Gly Thr
            260                 265                 270
```

```
Arg Phe Arg Pro Leu Leu Arg Gly Gly His Gln Glu Tyr Gly Arg Arg
        275                 280                 285

Ala Gly Thr Glu Asn Ile Cys Gly Ile Val Gly Met Gly Ala Ala Cys
    290                 295                 300

Glu Leu Ala Asn Ile His Leu Pro Gly Met Thr His Ile Gly Gln Leu
305                 310                 315                 320

Arg Asn Arg Leu Glu His Arg Leu Leu Ala Ser Val Pro Ser Val Met
                325                 330                 335

Val Met Gly Gly Gly Gln Pro Arg Val Pro Gly Thr Val Asn Leu Ala
            340                 345                 350

Phe Glu Phe Ile Glu Gly Glu Ala Ile Leu Leu Leu Leu Asn Gln Ala
        355                 360                 365

Gly Ile Ala Ala Ser Ser Gly Ser Ala Cys Thr Ser Gly Ser Leu Glu
    370                 375                 380

Pro Ser His Val Met Arg Ala Met Asn Ile Pro Tyr Thr Ala Ala His
385                 390                 395                 400

Gly Thr Ile Arg Phe Ser Leu Ser Arg Tyr Thr Arg Glu Lys Glu Ile
                405                 410                 415

Asp Tyr Val Val Ala Thr Leu Pro Pro Ile Ile Asp Arg Leu Arg Ala
            420                 425                 430

Leu Ser Pro Tyr Trp Gln Asn Gly Lys Pro Arg Pro Ala Asp Ala Val
        435                 440                 445

Phe Thr Pro Val Tyr Gly Gly Gly Tyr Pro Tyr Asp Val Pro Asp Tyr
    450                 455                 460

Ala
465


<210> SEQ ID NO 125
<211> LENGTH: 339
<212> TYPE: PRT
<213> ORGANISM: Artificial Sequence
<220> FEATURE:
<223> OTHER INFORMATION: Amino acid sequence of the MTP-FA 51::NifU::HA
      fusion polypeptide encoded by SN32.  Amino acids 1-54 correspond
      to the MTP-FA 51 with GG at its C-terminus, amino acids 55-328
      correspond to K. oxytoca NifU (SEQ ID NO:12) with its initiator
      Met, and amino

<400> SEQUENCE: 125

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Trp Asn Tyr Ser Glu Lys Val Lys Asp
    50                  55                  60

His Phe Phe Asn Pro Arg Asn Ala Arg Val Val Asp Asn Ala Asn Ala
65                  70                  75                  80

Val Gly Asp Val Gly Ser Leu Ser Cys Gly Asp Ala Leu Arg Leu Met
                85                  90                  95

Leu Arg Val Asp Pro Gln Ser Glu Ile Ile Glu Glu Ala Gly Phe Gln
            100                 105                 110

Thr Phe Gly Cys Gly Ser Ala Ile Ala Ser Ser Ser Ala Leu Thr Glu
        115                 120                 125

Leu Ile Ile Gly His Thr Leu Ala Glu Ala Gly Gln Ile Thr Asn Gln
    130                 135                 140
```

Gln Ile Ala Asp Tyr Leu Asp Gly Leu Pro Pro Glu Lys Met His Cys
145 150 155 160

Ser Val Met Gly Gln Glu Ala Leu Arg Ala Ala Ile Ala Asn Phe Arg
165 170 175

Gly Glu Ser Leu Glu Glu Glu His Asp Glu Gly Lys Leu Ile Cys Lys
180 185 190

Cys Phe Gly Val Asp Glu Gly His Ile Arg Arg Ala Val Gln Asn Asn
195 200 205

Gly Leu Thr Thr Leu Ala Glu Val Ile Asn Tyr Thr Lys Ala Gly Gly
210 215 220

Gly Cys Thr Ser Cys His Glu Lys Ile Glu Leu Ala Leu Ala Glu Ile
225 230 235 240

Leu Ala Gln Gln Pro Gln Thr Thr Pro Ala Val Ala Ser Gly Lys Asp
245 250 255

Pro His Trp Gln Ser Val Val Asp Thr Ile Ala Glu Leu Arg Pro His
260 265 270

Ile Gln Ala Asp Gly Gly Asp Met Ala Leu Leu Ser Val Thr Asn His
275 280 285

Gln Val Thr Val Ser Leu Ser Gly Ser Cys Ser Gly Cys Met Met Thr
290 295 300

Asp Met Thr Leu Ala Trp Leu Gln Gln Lys Leu Met Glu Arg Thr Gly
305 310 315 320

Cys Tyr Met Glu Val Val Ala Ala Gly Gly Tyr Pro Tyr Asp Val Pro
325 330 335

Asp Tyr Ala

<210> SEQ ID NO 126
<211> LENGTH: 522
<212> TYPE: PRT
<213> ORGANISM: Artificial Sequence
<220> FEATURE:
<223> OTHER INFORMATION: Amino acid sequence of the MTP-FA 51::NifE::HA fusion polypeptide encoded by SN38. Amino acids 1-54 correspond to the MTP-FA 51 with GG at its C-terminus, amino acids 55-511 correspond to K. oxytoca NifE with its initiator Met according to Temme et al.,

<400> SEQUENCE: 126

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Lys Gly Asn Glu Ile Leu Ala Leu Leu
50 55 60

Asp Glu Pro Ala Cys Glu His Asn His Lys Gln Lys Ser Gly Cys Ser
65 70 75 80

Ala Pro Lys Pro Gly Ala Thr Ala Gly Gly Cys Ala Phe Asp Gly Ala
85 90 95

Gln Ile Thr Leu Leu Pro Ile Ala Asp Val Ala His Leu Val His Gly
100 105 110

Pro Ile Gly Cys Ala Gly Ser Ser Trp Asp Asn Arg Gly Ser Ala Ser
115 120 125

Ser Gly Pro Thr Leu Asn Arg Leu Gly Phe Thr Thr Asp Leu Asn Glu
130 135 140

```
Gln Asp Val Ile Met Gly Arg Gly Glu Arg Arg Leu Phe His Ala Val
145                 150                 155                 160

Arg His Ile Val Thr Arg Tyr His Pro Ala Ala Val Phe Ile Tyr Asn
                165                 170                 175

Thr Cys Val Pro Ala Met Glu Gly Asp Asp Leu Glu Ala Val Cys Gln
            180                 185                 190

Ala Ala Gln Thr Ala Thr Gly Val Pro Val Ile Ala Ile Asp Ala Ala
        195                 200                 205

Gly Phe Tyr Gly Ser Lys Asn Leu Gly Asn Arg Leu Ala Gly Asp Val
    210                 215                 220

Met Val Lys Arg Val Ile Gly Gln Arg Glu Pro Ala Pro Trp Pro Glu
225                 230                 235                 240

Ser Thr Leu Phe Ala Pro Glu Gln Arg His Asp Ile Gly Leu Ile Gly
                245                 250                 255

Glu Phe Asn Ile Ala Gly Glu Phe Trp His Ile Gln Pro Leu Leu Asp
            260                 265                 270

Glu Leu Gly Ile Arg Val Leu Gly Ser Leu Ser Gly Asp Gly Arg Phe
        275                 280                 285

Ala Glu Ile Gln Thr Met His Arg Ala Gln Ala Asn Met Leu Val Cys
    290                 295                 300

Ser Arg Ala Leu Ile Asn Val Ala Arg Ala Leu Glu Gln Arg Tyr Gly
305                 310                 315                 320

Thr Pro Trp Phe Glu Gly Ser Phe Tyr Gly Ile Arg Ala Thr Ser Asp
                325                 330                 335

Ala Leu Arg Gln Leu Ala Ala Leu Leu Gly Asp Asp Asp Leu Arg Gln
            340                 345                 350

Arg Thr Glu Ala Leu Ile Ala Arg Glu Glu Gln Ala Ala Glu Leu Ala
        355                 360                 365

Leu Gln Pro Trp Arg Glu Gln Leu Arg Gly Arg Lys Ala Leu Leu Tyr
    370                 375                 380

Thr Gly Gly Val Lys Ser Trp Ser Val Val Ser Ala Leu Gln Asp Leu
385                 390                 395                 400

Gly Met Thr Val Val Ala Thr Gly Thr Arg Lys Ser Thr Glu Glu Asp
                405                 410                 415

Lys Gln Arg Ile Arg Glu Leu Met Gly Glu Glu Ala Val Met Leu Glu
            420                 425                 430

Glu Gly Asn Ala Arg Thr Leu Leu Asp Val Val Tyr Arg Tyr Gln Ala
        435                 440                 445

Asp Leu Met Ile Ala Gly Gly Arg Asn Met Tyr Thr Ala Tyr Lys Ala
    450                 455                 460

Arg Leu Pro Phe Leu Asp Ile Asn Gln Glu Arg Glu His Ala Phe Ala
465                 470                 475                 480

Gly Tyr Gln Gly Ile Val Thr Leu Ala Arg Gln Leu Cys Gln Thr Ile
                485                 490                 495

Asn Ser Pro Ile Trp Pro Gln Thr His Ser Arg Ala Pro Trp Arg Gly
            500                 505                 510

Gly Tyr Pro Tyr Asp Val Pro Asp Tyr Ala
        515                 520
```

<210> SEQ ID NO 127
<211> LENGTH: 526
<212> TYPE: PRT
<213> ORGANISM: Artificial Sequence
<220> FEATURE:

<223> OTHER INFORMATION: Amino acid sequence of the MTP-FA 51::NifN::HA fusion polypeptide encoded by SN39. Amino acids 1-54 correspond to the MTP-FA 51 with GG at its C-terminus, amino acids 55-515 correspond to K. oxytoca NifN (SEQ ID NO:9) with its initiator Met, and amino

<400> SEQUENCE: 127

```
Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Ala Asp Ile Phe Arg Thr Asp Lys Pro
    50                  55                  60

Leu Ala Val Ser Pro Ile Lys Thr Gly Gln Pro Leu Gly Ala Ile Leu
65                  70                  75                  80

Ala Ser Leu Gly Ile Glu His Ser Ile Pro Leu Val His Gly Ala Gln
                85                  90                  95

Gly Cys Ser Ala Phe Ala Lys Val Phe Phe Ile Gln His Phe His Asp
            100                 105                 110

Pro Val Pro Leu Gln Ser Thr Ala Met Asp Pro Thr Ser Thr Ile Met
        115                 120                 125

Gly Ala Asp Gly Asn Ile Phe Thr Ala Leu Asp Thr Leu Cys Gln Arg
    130                 135                 140

Asn Asn Pro Gln Ala Ile Val Leu Leu Ser Thr Gly Leu Ser Glu Ala
145                 150                 155                 160

Gln Gly Ser Asp Ile Ser Arg Val Val Arg Gln Phe Arg Glu Glu Tyr
                165                 170                 175

Pro Arg His Lys Gly Val Ala Ile Leu Thr Val Asn Thr Pro Asp Phe
            180                 185                 190

Tyr Gly Ser Met Glu Asn Gly Phe Ser Ala Val Leu Glu Ser Val Ile
        195                 200                 205

Glu Gln Trp Val Pro Pro Ala Pro Arg Pro Ala Gln Arg Asn Arg Arg
    210                 215                 220

Val Asn Leu Leu Val Ser His Leu Cys Ser Pro Gly Asp Ile Glu Trp
225                 230                 235                 240

Leu Arg Arg Cys Val Glu Ala Phe Gly Leu Gln Pro Ile Ile Leu Pro
                245                 250                 255

Asp Leu Ala Gln Ser Met Asp Gly His Leu Ala Gln Gly Asp Phe Ser
            260                 265                 270

Pro Leu Thr Gln Gly Gly Thr Pro Leu Arg Gln Ile Glu Gln Met Gly
        275                 280                 285

Gln Ser Leu Cys Ser Phe Ala Ile Gly Val Ser Leu His Arg Ala Ser
    290                 295                 300

Ser Leu Leu Ala Pro Arg Cys Arg Gly Glu Val Ile Ala Leu Pro His
305                 310                 315                 320

Leu Met Thr Leu Glu Arg Cys Asp Ala Phe Ile His Gln Leu Ala Lys
                325                 330                 335

Ile Ser Gly Arg Ala Val Pro Glu Trp Leu Glu Arg Gln Arg Gly Gln
            340                 345                 350

Leu Gln Asp Ala Met Ile Asp Cys His Met Trp Leu Gln Gly Gln Arg
        355                 360                 365

Met Ala Ile Ala Ala Glu Gly Asp Leu Leu Ala Ala Trp Cys Asp Phe
    370                 375                 380
```

```
Ala Asn Ser Gln Gly Met Gln Pro Gly Pro Leu Val Ala Pro Thr Gly
385                 390                 395                 400

His Pro Ser Leu Arg Gln Leu Pro Val Glu Arg Val Val Pro Gly Asp
                405                 410                 415

Leu Glu Asp Leu Gln Thr Leu Leu Cys Ala His Pro Ala Asp Leu Leu
            420                 425                 430

Val Ala Asn Ser His Ala Arg Asp Leu Ala Glu Gln Phe Ala Leu Pro
        435                 440                 445

Leu Val Arg Ala Gly Phe Pro Leu Phe Asp Lys Leu Gly Glu Phe Arg
    450                 455                 460

Arg Val Arg Gln Gly Tyr Ser Gly Met Arg Asp Thr Leu Phe Glu Leu
465                 470                 475                 480

Ala Asn Leu Ile Arg Glu Arg His His His Leu Ala His Tyr Arg Ser
                485                 490                 495

Pro Leu Arg Gln Asn Pro Glu Ser Ser Leu Ser Thr Gly Gly Ala Tyr
            500                 505                 510

Ala Ala Asp Gly Gly Tyr Pro Tyr Asp Val Pro Asp Tyr Ala
        515                 520                 525


<210> SEQ ID NO 128
<211> LENGTH: 365
<212> TYPE: PRT
<213> ORGANISM: Artificial Sequence
<220> FEATURE:
<223> OTHER INFORMATION: Amino acid sequence of the MTP-CoxIV-Twin-
      Strep::NifH::HA fusion polypeptide encoded by SN42.  Amino acids
      1-61 correspond to the MTP-CoxIV-Twin-Strep with GG at its
      C-terminus, amino acids 62-354 were the K. oxytoca NifH amino
      acids (SEQ ID NO:1) with

<400> SEQUENCE: 128

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Thr Met
    50                  55                  60

Arg Gln Cys Ala Ile Tyr Gly Lys Gly Gly Ile Gly Lys Ser Thr Thr
65                  70                  75                  80

Thr Gln Asn Leu Val Ala Ala Leu Ala Glu Met Gly Lys Lys Val Met
                85                  90                  95

Ile Val Gly Cys Asp Pro Lys Ala Asp Ser Thr Arg Leu Ile Leu His
            100                 105                 110

Ala Lys Ala Gln Asn Thr Ile Met Glu Met Ala Ala Glu Val Gly Ser
        115                 120                 125

Val Glu Asp Leu Glu Leu Glu Asp Val Leu Gln Ile Gly Tyr Gly Asp
    130                 135                 140

Val Arg Cys Ala Glu Ser Gly Gly Pro Glu Pro Gly Val Gly Cys Ala
145                 150                 155                 160

Gly Arg Gly Val Ile Thr Ala Ile Asn Phe Leu Glu Glu Glu Gly Ala
                165                 170                 175

Tyr Glu Asp Asp Leu Asp Phe Val Phe Tyr Asp Val Leu Gly Asp Val
            180                 185                 190

Val Cys Gly Gly Phe Ala Met Pro Ile Arg Glu Asn Lys Ala Gln Glu
```

```
        195                 200                 205

Ile Tyr Ile Val Cys Ser Gly Glu Met Met Ala Met Tyr Ala Ala Asn
    210                 215                 220

Asn Ile Ser Lys Gly Ile Val Lys Tyr Ala Lys Ser Gly Lys Val Arg
225                 230                 235                 240

Leu Gly Gly Leu Ile Cys Asn Ser Arg Gln Thr Asp Arg Glu Asp Glu
                245                 250                 255

Leu Ile Ile Ala Leu Ala Glu Lys Leu Gly Thr Gln Met Ile His Phe
            260                 265                 270

Val Pro Arg Asp Asn Ile Val Gln Arg Ala Glu Ile Arg Arg Met Thr
        275                 280                 285

Val Ile Glu Tyr Asp Pro Ala Cys Lys Gln Ala Asn Glu Tyr Arg Thr
    290                 295                 300

Leu Ala Gln Lys Ile Val Asn Asn Thr Met Lys Val Val Pro Thr Pro
305                 310                 315                 320

Cys Thr Met Asp Glu Leu Glu Ser Leu Leu Met Glu Phe Gly Ile Met
                325                 330                 335

Glu Glu Glu Asp Thr Ser Ile Ile Gly Lys Thr Ala Ala Glu Glu Asn
            340                 345                 350

Ala Ala Gly Gly Tyr Pro Tyr Asp Val Pro Asp Tyr Ala
        355                 360                 365


<210> SEQ ID NO 129
<211> LENGTH: 590
<212> TYPE: PRT
<213> ORGANISM: Artificial Sequence
<220> FEATURE:
<223> OTHER INFORMATION: Amino acid sequence of the MTP-Su9::NifK fusion
      polypeptide encoded by SN46.  Amino acids 1-70 correspond to the
      MTP-Su9 with GG at its C-terminus, amino acids 71-590 correspond
      to K. oxytoca NifK (SEQ ID NO:3) with its initiator Met.

<400> SEQUENCE: 129

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Gly Gly Met Ser Gln Thr Ile Asp Lys Ile Asn Ser
65                  70                  75                  80

Cys Tyr Pro Leu Phe Glu Gln Asp Glu Tyr Gln Glu Leu Phe Arg Asn
                85                  90                  95

Lys Arg Gln Leu Glu Glu Ala His Asp Ala Gln Arg Val Gln Glu Val
            100                 105                 110

Phe Ala Trp Thr Thr Thr Ala Glu Tyr Glu Ala Leu Asn Phe Gln Arg
        115                 120                 125

Glu Ala Leu Thr Val Asp Pro Ala Lys Ala Cys Gln Pro Leu Gly Ala
    130                 135                 140

Val Leu Cys Ser Leu Gly Phe Ala Asn Thr Leu Pro Tyr Val His Gly
145                 150                 155                 160

Ser Gln Gly Cys Val Ala Tyr Phe Arg Thr Tyr Phe Asn Arg His Phe
                165                 170                 175

Lys Glu Pro Ile Ala Cys Val Ser Asp Ser Met Thr Glu Asp Ala Ala
```

```
            180                 185                 190

Val Phe Gly Gly Asn Asn Asn Met Asn Leu Gly Leu Gln Asn Ala Ser
        195                 200                 205

Ala Leu Tyr Lys Pro Glu Ile Ile Ala Val Ser Thr Thr Cys Met Ala
    210                 215                 220

Glu Val Ile Gly Asp Asp Leu Gln Ala Phe Ile Ala Asn Ala Lys Lys
225                 230                 235                 240

Asp Gly Phe Val Asp Ser Ser Ile Ala Val Pro His Ala His Thr Pro
                245                 250                 255

Ser Phe Ile Gly Ser His Val Thr Gly Trp Asp Asn Met Phe Glu Gly
            260                 265                 270

Phe Ala Lys Thr Phe Thr Ala Asp Tyr Gln Gly Gln Pro Gly Lys Leu
        275                 280                 285

Pro Lys Leu Asn Leu Val Thr Gly Phe Glu Thr Tyr Leu Gly Asn Phe
    290                 295                 300

Arg Val Leu Lys Arg Met Met Glu Gln Met Ala Val Pro Cys Ser Leu
305                 310                 315                 320

Leu Ser Asp Pro Ser Glu Val Leu Asp Thr Pro Ala Asp Gly His Tyr
                325                 330                 335

Arg Met Tyr Ser Gly Gly Thr Thr Gln Gln Glu Met Lys Glu Ala Pro
            340                 345                 350

Asp Ala Ile Asp Thr Leu Leu Leu Gln Pro Trp Gln Leu Leu Lys Ser
        355                 360                 365

Lys Lys Val Val Gln Glu Met Trp Asn Gln Pro Ala Thr Glu Val Ala
    370                 375                 380

Ile Pro Leu Gly Leu Ala Ala Thr Asp Glu Leu Leu Met Thr Val Ser
385                 390                 395                 400

Gln Leu Ser Gly Lys Pro Ile Ala Asp Ala Leu Thr Leu Glu Arg Gly
                405                 410                 415

Arg Leu Val Asp Met Met Leu Asp Ser His Thr Trp Leu His Gly Lys
            420                 425                 430

Lys Phe Gly Leu Tyr Gly Asp Pro Asp Phe Val Met Gly Leu Thr Arg
        435                 440                 445

Phe Leu Leu Glu Leu Gly Cys Glu Pro Thr Val Ile Leu Ser His Asn
    450                 455                 460

Ala Asn Lys Arg Trp Gln Lys Ala Met Asn Lys Met Leu Asp Ala Ser
465                 470                 475                 480

Pro Tyr Gly Arg Asp Ser Glu Val Phe Ile Asn Cys Asp Leu Trp His
                485                 490                 495

Phe Arg Ser Leu Met Phe Thr Arg Gln Pro Asp Phe Met Ile Gly Asn
            500                 505                 510

Ser Tyr Gly Lys Phe Ile Gln Arg Asp Thr Leu Ala Lys Gly Lys Ala
        515                 520                 525

Phe Glu Val Pro Leu Ile Arg Leu Gly Phe Pro Leu Phe Asp Arg His
    530                 535                 540

His Leu His Arg Gln Thr Thr Trp Gly Tyr Glu Gly Ala Met Asn Ile
545                 550                 555                 560

Val Thr Thr Leu Val Asn Ala Val Leu Glu Lys Leu Asp Ser Asp Thr
                565                 570                 575

Ser Gln Leu Gly Lys Thr Asp Tyr Ser Phe Asp Leu Val Arg
            580                 585                 590
```

<210> SEQ ID NO 130

```
<211> LENGTH: 426
<212> TYPE: PRT
<213> ORGANISM: Artificial Sequence
<220> FEATURE:
<223> OTHER INFORMATION: Amino acid sequence of the MTP-L29::NifV::HA
      fusion polypeptide encoded by SN51.  Amino acids 1-34 correspond
      to the MTP-L29 with GG at its C-terminus, amino acids 35-415
      correspond to K. oxytoca NifV (SEQ ID NO:13) with its initiator
      Met, and amino acids 416-

<400> SEQUENCE: 130

Met Phe Leu Thr Arg Phe Val Gly Arg Arg Phe Leu Ala Ala Ala Ser
1               5                   10                  15

Ala Arg Ser Glu Ser Thr Thr Ala Ala Ala Ala Ala Ser Thr Ile Arg
            20                  25                  30

Gly Gly Met Glu Arg Val Leu Ile Asn Asp Thr Thr Leu Arg Asp Gly
        35                  40                  45

Glu Gln Ser Pro Gly Val Ala Phe Arg Thr Ser Glu Lys Val Ala Ile
    50                  55                  60

Ala Glu Ala Leu Tyr Ala Ala Gly Ile Thr Ala Met Glu Val Gly Thr
65                  70                  75                  80

Pro Ala Met Gly Asp Glu Glu Ile Ala Arg Ile Gln Leu Val Arg Arg
                85                  90                  95

Gln Leu Pro Asp Ala Thr Leu Met Thr Trp Cys Arg Met Asn Ala Leu
            100                 105                 110

Glu Ile Arg Gln Ser Ala Asp Leu Gly Ile Asp Trp Val Asp Ile Ser
        115                 120                 125

Ile Pro Ala Ser Asp Lys Leu Arg Gln Tyr Lys Leu Arg Glu Pro Leu
    130                 135                 140

Ala Val Leu Leu Glu Arg Leu Ala Met Phe Ile His Leu Ala His Thr
145                 150                 155                 160

Leu Gly Leu Lys Val Cys Ile Gly Cys Glu Asp Ala Ser Arg Ala Ser
                165                 170                 175

Gly Gln Thr Leu Arg Ala Ile Ala Glu Val Ala Gln Asn Ala Pro Ala
            180                 185                 190

Ala Arg Leu Arg Tyr Ala Asp Thr Val Gly Leu Leu Asp Pro Phe Thr
        195                 200                 205

Thr Ala Ala Gln Ile Ser Ala Leu Arg Asp Val Trp Ser Gly Glu Ile
    210                 215                 220

Glu Met His Ala His Asn Asp Leu Gly Met Ala Thr Ala Asn Thr Leu
225                 230                 235                 240

Ala Ala Val Ser Ala Gly Ala Thr Ser Val Asn Thr Thr Val Leu Gly
                245                 250                 255

Leu Gly Glu Arg Ala Gly Asn Ala Ala Ala Trp Lys Pro Ser Ala Leu
            260                 265                 270

Gly Leu Glu Arg Cys Leu Gly Val Glu Thr Gly Val His Phe Ser Ala
        275                 280                 285

Leu Pro Ala Leu Cys Gln Arg Val Ala Glu Ala Ala Gln Arg Ala Ile
    290                 295                 300

Asp Pro Gln Gln Pro Leu Val Gly Glu Leu Val Phe Thr His Glu Ser
305                 310                 315                 320

Gly Val His Val Ala Ala Leu Leu Arg Asp Ser Glu Ser Tyr Gln Ser
                325                 330                 335

Ile Ala Pro Ser Leu Met Gly Arg Ser Tyr Arg Leu Val Leu Gly Lys
            340                 345                 350

His Ser Gly Arg Gln Ala Val Asn Gly Val Phe Asp Gln Met Gly Tyr
```

```
        355                 360                 365

His Leu Asn Ala Ala Gln Ile Asn Gln Leu Leu Pro Ala Ile Arg Arg
    370                 375                 380

Phe Ala Glu Asn Trp Lys Arg Ser Pro Lys Asp Tyr Glu Leu Val Ala
385                 390                 395                 400

Ile Tyr Asp Glu Leu Cys Gly Glu Ser Ala Leu Arg Ala Arg Gly Gly
                405                 410                 415

Gly Tyr Pro Tyr Asp Val Pro Asp Tyr Ala
            420                 425


<210> SEQ ID NO 131
<211> LENGTH: 1085
<212> TYPE: PRT
<213> ORGANISM: Artificial Sequence
<220> FEATURE:
<223> OTHER INFORMATION: Amino acid sequence of the MTP-FA
      51::NifD::linker(HA)::NifK fusion polypeptide encoded by SN68.
      Amino acids 1-54 correspond to the MTP-FA 51 with GG at its
      C-terminus, amino acids 55-536 correspond to wild-type K. oxytoca
      NifD amino acids (SEQ ID NO:18

<400> SEQUENCE: 131

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Thr Asn Ala Thr Gly Glu Arg Asn Leu
    50                  55                  60

Ala Leu Ile Gln Glu Val Leu Glu Val Phe Pro Glu Thr Ala Arg Lys
65                  70                  75                  80

Glu Arg Arg Lys His Met Met Val Ser Asp Pro Glu Met Glu Ser Val
                85                  90                  95

Gly Lys Cys Ile Ile Ser Asn Arg Lys Ser Gln Pro Gly Val Met Thr
            100                 105                 110

Val Arg Gly Cys Ala Tyr Ala Gly Ser Lys Gly Val Val Phe Gly Pro
        115                 120                 125

Ile Lys Asp Met Ala His Ile Ser His Gly Pro Val Gly Cys Gly Gln
    130                 135                 140

Tyr Ser Arg Ala Gly Arg Arg Asn Tyr Tyr Thr Gly Val Ser Gly Val
145                 150                 155                 160

Asp Ser Phe Gly Thr Leu Asn Phe Thr Ser Asp Phe Gln Glu Arg Asp
                165                 170                 175

Ile Val Phe Gly Gly Asp Lys Lys Leu Ser Lys Leu Ile Glu Glu Met
            180                 185                 190

Glu Leu Leu Phe Pro Leu Thr Lys Gly Ile Thr Ile Gln Ser Glu Cys
        195                 200                 205

Pro Val Gly Leu Ile Gly Asp Asp Ile Ser Ala Val Ala Asn Ala Ser
    210                 215                 220

Ser Lys Ala Leu Asp Lys Pro Val Ile Pro Val Arg Cys Glu Gly Phe
225                 230                 235                 240

Arg Gly Val Ser Gln Ser Leu Gly His His Ile Ala Asn Asp Val Val
                245                 250                 255

Arg Asp Trp Ile Leu Asn Asn Arg Glu Gly Gln Pro Phe Glu Thr Thr
            260                 265                 270
```

```
Pro Tyr Asp Val Ala Ile Ile Gly Asp Tyr Asn Ile Gly Gly Asp Ala
        275                 280                 285

Trp Ala Ser Arg Ile Leu Leu Glu Glu Met Gly Leu Arg Val Val Ala
    290                 295                 300

Gln Trp Ser Gly Asp Gly Thr Leu Val Glu Met Glu Asn Thr Pro Phe
305                 310                 315                 320

Val Lys Leu Asn Leu Val His Cys Tyr Arg Ser Met Asn Tyr Ile Ala
                325                 330                 335

Arg His Met Glu Glu Lys His Gln Ile Pro Trp Met Glu Tyr Asn Phe
            340                 345                 350

Phe Gly Pro Thr Lys Ile Ala Glu Ser Leu Arg Lys Ile Ala Asp Gln
        355                 360                 365

Phe Asp Asp Thr Ile Arg Ala Asn Ala Glu Ala Val Ile Ala Arg Tyr
    370                 375                 380

Glu Gly Gln Met Ala Ala Ile Ile Ala Lys Tyr Arg Pro Arg Leu Glu
385                 390                 395                 400

Gly Arg Lys Val Leu Leu Tyr Met Gly Gly Leu Arg Pro Arg His Val
                405                 410                 415

Ile Gly Ala Tyr Glu Asp Leu Gly Met Glu Ile Ile Ala Ala Gly Tyr
            420                 425                 430

Glu Phe Ala His Asn Asp Asp Tyr Asp Arg Thr Leu Pro Asp Leu Lys
        435                 440                 445

Glu Gly Thr Leu Leu Phe Asp Asp Ala Ser Ser Tyr Glu Leu Glu Ala
    450                 455                 460

Phe Val Lys Ala Leu Lys Pro Asp Leu Ile Gly Ser Gly Ile Lys Glu
465                 470                 475                 480

Lys Tyr Ile Phe Gln Lys Met Gly Val Pro Phe Arg Gln Met His Ser
                485                 490                 495

Trp Asp Tyr Ser Gly Pro Tyr His Gly Tyr Asp Gly Phe Ala Ile Phe
            500                 505                 510

Ala Arg Asp Met Asp Met Thr Leu Asn Asn Pro Ala Trp Asn Glu Leu
        515                 520                 525

Thr Ala Pro Trp Leu Lys Ser Ala Ala Thr Pro Pro Pro Gly Ser Thr
    530                 535                 540

Thr Thr Ala Tyr Pro Tyr Asp Val Pro Asp Tyr Ala Thr Pro Pro Pro
545                 550                 555                 560

Gly Ser Thr Thr Thr Ala Ser Gln Thr Ile Asp Lys Ile Asn Ser Cys
                565                 570                 575

Tyr Pro Leu Phe Glu Gln Asp Glu Tyr Gln Glu Leu Phe Arg Asn Lys
            580                 585                 590

Arg Gln Leu Glu Glu Ala His Asp Ala Gln Arg Val Gln Glu Val Phe
        595                 600                 605

Ala Trp Thr Thr Thr Ala Glu Tyr Glu Ala Leu Asn Phe Gln Arg Glu
    610                 615                 620

Ala Leu Thr Val Asp Pro Ala Lys Ala Cys Gln Pro Leu Gly Ala Val
625                 630                 635                 640

Leu Cys Ser Leu Gly Phe Ala Asn Thr Leu Pro Tyr Val His Gly Ser
                645                 650                 655

Gln Gly Cys Val Ala Tyr Phe Arg Thr Tyr Phe Asn Arg His Phe Lys
            660                 665                 670

Glu Pro Ile Ala Cys Val Ser Asp Ser Met Thr Glu Asp Ala Ala Val
        675                 680                 685

Phe Gly Gly Asn Asn Asn Met Asn Leu Gly Leu Gln Asn Ala Ser Ala
```

```
    690                 695                 700

Leu Tyr Lys Pro Glu Ile Ile Ala Val Ser Thr Thr Cys Met Ala Glu
705                 710                 715                 720

Val Ile Gly Asp Asp Leu Gln Ala Phe Ile Ala Asn Ala Lys Lys Asp
                725                 730                 735

Gly Phe Val Asp Ser Ser Ile Ala Val Pro His Ala His Thr Pro Ser
            740                 745                 750

Phe Ile Gly Ser His Val Thr Gly Trp Asp Asn Met Phe Glu Gly Phe
        755                 760                 765

Ala Lys Thr Phe Thr Ala Asp Tyr Gln Gly Gln Pro Gly Lys Leu Pro
    770                 775                 780

Lys Leu Asn Leu Val Thr Gly Phe Glu Thr Tyr Leu Gly Asn Phe Arg
785                 790                 795                 800

Val Leu Lys Arg Met Met Glu Gln Met Ala Val Pro Cys Ser Leu Leu
                805                 810                 815

Ser Asp Pro Ser Glu Val Leu Asp Thr Pro Ala Asp Gly His Tyr Arg
            820                 825                 830

Met Tyr Ser Gly Gly Thr Thr Gln Gln Glu Met Lys Glu Ala Pro Asp
        835                 840                 845

Ala Ile Asp Thr Leu Leu Leu Gln Pro Trp Gln Leu Leu Lys Ser Lys
    850                 855                 860

Lys Val Val Gln Glu Met Trp Asn Gln Pro Ala Thr Glu Val Ala Ile
865                 870                 875                 880

Pro Leu Gly Leu Ala Ala Thr Asp Glu Leu Leu Met Thr Val Ser Gln
                885                 890                 895

Leu Ser Gly Lys Pro Ile Ala Asp Ala Leu Thr Leu Glu Arg Gly Arg
            900                 905                 910

Leu Val Asp Met Met Leu Asp Ser His Thr Trp Leu His Gly Lys Lys
        915                 920                 925

Phe Gly Leu Tyr Gly Asp Pro Asp Phe Val Met Gly Leu Thr Arg Phe
    930                 935                 940

Leu Leu Glu Leu Gly Cys Glu Pro Thr Val Ile Leu Ser His Asn Ala
945                 950                 955                 960

Asn Lys Arg Trp Gln Lys Ala Met Asn Lys Met Leu Asp Ala Ser Pro
                965                 970                 975

Tyr Gly Arg Asp Ser Glu Val Phe Ile Asn Cys Asp Leu Trp His Phe
            980                 985                 990

Arg Ser Leu Met Phe Thr Arg Gln  Pro Asp Phe Met Ile  Gly Asn Ser
        995                 1000                1005

Tyr Gly  Lys Phe Ile Gln Arg  Asp Thr Leu Ala Lys  Gly Lys Ala
    1010                1015                1020

Phe Glu  Val Pro Leu Ile Arg  Leu Gly Phe Pro Leu  Phe Asp Arg
    1025                1030                1035

His His  Leu His Arg Gln Thr  Thr Trp Gly Tyr Glu  Gly Ala Met
    1040                1045                1050

Asn Ile  Val Thr Thr Leu Val  Asn Ala Val Leu Glu  Lys Leu Asp
    1055                1060                1065

Ser Asp  Thr Ser Gln Leu Gly  Lys Thr Asp Tyr Ser  Phe Asp Leu
    1070                1075                1080

Val Arg
    1085
```

<210> SEQ ID NO 132

<211> LENGTH: 557
<212> TYPE: PRT
<213> ORGANISM: Artificial Sequence
<220> FEATURE:
<223> OTHER INFORMATION: Amino acid sequence of the MTP-FA 51::HA::NifD::HA fusion polypeptide encoded by SN75. Amino acids 1-53 correspond to the MTP-FA 51 with GG at its C-terminus, amino acids 54-64 correspond to the first HA epitope, amino acids 65-546 correspond to

<400> SEQUENCE: 132

```
Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Met Thr Asn Ala Thr Gly Glu Arg Asn Leu Ala Leu Ile Gln Glu
65                  70                  75                  80

Val Leu Glu Val Phe Pro Glu Thr Ala Arg Lys Glu Arg Arg Lys His
                85                  90                  95

Met Met Val Ser Asp Pro Glu Met Glu Ser Val Gly Lys Cys Ile Ile
            100                 105                 110

Ser Asn Arg Lys Ser Gln Pro Gly Val Met Thr Val Arg Gly Cys Ala
        115                 120                 125

Tyr Ala Gly Ser Lys Gly Val Val Phe Gly Pro Ile Lys Asp Met Ala
    130                 135                 140

His Ile Ser His Gly Pro Val Gly Cys Gly Gln Tyr Ser Arg Ala Gly
145                 150                 155                 160

Arg Arg Asn Tyr Tyr Thr Gly Val Ser Gly Val Asp Ser Phe Gly Thr
                165                 170                 175

Leu Asn Phe Thr Ser Asp Phe Gln Glu Arg Asp Ile Val Phe Gly Gly
            180                 185                 190

Asp Lys Lys Leu Ser Lys Leu Ile Glu Glu Met Glu Leu Leu Phe Pro
        195                 200                 205

Leu Thr Lys Gly Ile Thr Ile Gln Ser Glu Cys Pro Val Gly Leu Ile
    210                 215                 220

Gly Asp Asp Ile Ser Ala Val Ala Asn Ala Ser Ser Lys Ala Leu Asp
225                 230                 235                 240

Lys Pro Val Ile Pro Val Arg Cys Glu Gly Phe Arg Gly Val Ser Gln
                245                 250                 255

Ser Leu Gly His His Ile Ala Asn Asp Val Val Arg Asp Trp Ile Leu
            260                 265                 270

Asn Asn Arg Glu Gly Gln Pro Phe Glu Thr Thr Pro Tyr Asp Val Ala
        275                 280                 285

Ile Ile Gly Asp Tyr Asn Ile Gly Gly Asp Ala Trp Ala Ser Arg Ile
    290                 295                 300

Leu Leu Glu Glu Met Gly Leu Arg Val Val Ala Gln Trp Ser Gly Asp
305                 310                 315                 320

Gly Thr Leu Val Glu Met Glu Asn Thr Pro Phe Val Lys Leu Asn Leu
                325                 330                 335

Val His Cys Tyr Arg Ser Met Asn Tyr Ile Ala Arg His Met Glu Glu
            340                 345                 350

Lys His Gln Ile Pro Trp Met Glu Tyr Asn Phe Phe Gly Pro Thr Lys
```

```
        355                 360                 365

Ile Ala Glu Ser Leu Arg Lys Ile Ala Asp Gln Phe Asp Asp Thr Ile
    370                 375                 380

Arg Ala Asn Ala Glu Ala Val Ile Ala Arg Tyr Glu Gly Gln Met Ala
385                 390                 395                 400

Ala Ile Ile Ala Lys Tyr Arg Pro Arg Leu Glu Gly Arg Lys Val Leu
                405                 410                 415

Leu Tyr Met Gly Gly Leu Arg Pro Arg His Val Ile Gly Ala Tyr Glu
            420                 425                 430

Asp Leu Gly Met Glu Ile Ile Ala Ala Gly Tyr Glu Phe Ala His Asn
        435                 440                 445

Asp Asp Tyr Asp Arg Thr Leu Pro Asp Leu Lys Glu Gly Thr Leu Leu
    450                 455                 460

Phe Asp Asp Ala Ser Ser Tyr Glu Leu Glu Ala Phe Val Lys Ala Leu
465                 470                 475                 480

Lys Pro Asp Leu Ile Gly Ser Gly Ile Lys Glu Lys Tyr Ile Phe Gln
                485                 490                 495

Lys Met Gly Val Pro Phe Arg Gln Met His Ser Trp Asp Tyr Ser Gly
            500                 505                 510

Pro Tyr His Gly Tyr Asp Gly Phe Ala Ile Phe Ala Arg Asp Met Asp
        515                 520                 525

Met Thr Leu Asn Asn Pro Ala Trp Asn Glu Leu Thr Ala Pro Trp Leu
    530                 535                 540

Lys Ser Gly Gly Tyr Pro Tyr Asp Val Pro Asp Tyr Ala
545                 550                 555


<210> SEQ ID NO 133
<211> LENGTH: 547
<212> TYPE: PRT
<213> ORGANISM: Artificial Sequence
<220> FEATURE:
<223> OTHER INFORMATION: Amino acid sequence of the MTP-FA 51::NifD::HA
      fusion polypeptide encoded by SN99.  Amino acids 1-54 correspond
      to the MTP-FA 51 with GG at its C-terminus, amino acids 55-536
      correspond to K. oxytoca NifD comprising the alanine substitution
      mutations at

<400> SEQUENCE: 133

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Met Thr Asn Ala Thr Gly Glu Arg Asn
    50                  55                  60

Leu Ala Leu Ile Gln Glu Val Leu Glu Val Phe Pro Glu Thr Ala Arg
65                  70                  75                  80

Lys Glu Arg Arg Lys His Met Met Val Ser Asp Pro Glu Met Glu Ser
                85                  90                  95

Val Gly Lys Cys Ile Ile Ser Asn Arg Lys Ser Gln Pro Gly Val Met
            100                 105                 110

Thr Val Arg Gly Cys Ala Tyr Ala Gly Ser Lys Gly Val Val Phe Gly
        115                 120                 125

Pro Ile Lys Asp Met Ala His Ile Ser His Gly Pro Val Gly Cys Gly
    130                 135                 140
```

```
Gln Tyr Ser Ala Ala Ala Ala Ala Asn Tyr Tyr Thr Gly Val Ser Gly
145                 150                 155                 160

Val Asp Ser Phe Gly Thr Leu Asn Phe Thr Ser Asp Phe Gln Glu Arg
                165                 170                 175

Asp Ile Val Phe Gly Gly Asp Lys Lys Leu Ser Lys Leu Ile Glu Glu
            180                 185                 190

Met Glu Leu Leu Phe Pro Leu Thr Lys Gly Ile Thr Ile Gln Ser Glu
        195                 200                 205

Cys Pro Val Gly Leu Ile Gly Asp Asp Ile Ser Ala Val Ala Asn Ala
    210                 215                 220

Ser Ser Lys Ala Leu Asp Lys Pro Val Ile Pro Val Arg Cys Glu Gly
225                 230                 235                 240

Phe Arg Gly Val Ser Gln Ser Leu Gly His His Ile Ala Asn Asp Val
                245                 250                 255

Val Arg Asp Trp Ile Leu Asn Asn Arg Glu Gly Gln Pro Phe Glu Thr
            260                 265                 270

Thr Pro Tyr Asp Val Ala Ile Ile Gly Asp Tyr Asn Ile Gly Gly Asp
        275                 280                 285

Ala Trp Ala Ser Arg Ile Leu Leu Glu Glu Met Gly Leu Arg Val Val
    290                 295                 300

Ala Gln Trp Ser Gly Asp Gly Thr Leu Val Glu Met Glu Asn Thr Pro
305                 310                 315                 320

Phe Val Lys Leu Asn Leu Val His Cys Tyr Arg Ser Met Asn Tyr Ile
                325                 330                 335

Ala Arg His Met Glu Glu Lys His Gln Ile Pro Trp Met Glu Tyr Asn
            340                 345                 350

Phe Phe Gly Pro Thr Lys Ile Ala Glu Ser Leu Arg Lys Ile Ala Asp
        355                 360                 365

Gln Phe Asp Asp Thr Ile Arg Ala Asn Ala Glu Ala Val Ile Ala Arg
    370                 375                 380

Tyr Glu Gly Gln Met Ala Ala Ile Ile Ala Lys Tyr Arg Pro Arg Leu
385                 390                 395                 400

Glu Gly Arg Lys Val Leu Leu Tyr Met Gly Gly Leu Arg Pro Arg His
                405                 410                 415

Val Ile Gly Ala Tyr Glu Asp Leu Gly Met Glu Ile Ile Ala Ala Gly
            420                 425                 430

Tyr Glu Phe Ala His Asn Asp Asp Tyr Asp Arg Thr Leu Pro Asp Leu
        435                 440                 445

Lys Glu Gly Thr Leu Leu Phe Asp Asp Ala Ser Ser Tyr Glu Leu Glu
    450                 455                 460

Ala Phe Val Lys Ala Leu Lys Pro Asp Leu Ile Gly Ser Gly Ile Lys
465                 470                 475                 480

Glu Lys Tyr Ile Phe Gln Lys Met Gly Val Pro Phe Arg Gln Met His
                485                 490                 495

Ser Trp Asp Tyr Ser Gly Pro Tyr His Gly Tyr Asp Gly Phe Ala Ile
            500                 505                 510

Phe Ala Arg Asp Met Asp Met Thr Leu Asn Asn Pro Ala Trp Asn Glu
        515                 520                 525

Leu Thr Ala Pro Trp Leu Lys Ser Gly Gly Tyr Pro Tyr Asp Val Pro
    530                 535                 540

Asp Tyr Ala
545
```

<210> SEQ ID NO 134
<211> LENGTH: 547
<212> TYPE: PRT
<213> ORGANISM: Artificial Sequence
<220> FEATURE:
<223> OTHER INFORMATION: Amino acid sequence of the MTP-FA 51::NifD::HA fusion polypeptide encoded by SN100. Amino acids 1-54 correspond to the MTP-FA 51 with GG at its C-terminus, amino acids 55-536 correspond to K. oxytoca NifD amino acids comprising the alanine substitution

<400> SEQUENCE: 134

```
Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Met Thr Asn Ala Thr Gly Glu Arg Asn
    50                  55                  60

Leu Ala Leu Ile Gln Glu Val Leu Glu Val Phe Pro Glu Thr Ala Arg
65                  70                  75                  80

Lys Glu Arg Arg Lys His Met Met Val Ser Asp Pro Glu Met Glu Ser
                85                  90                  95

Val Gly Lys Cys Ile Ile Ser Asn Arg Lys Ser Gln Pro Gly Val Met
            100                 105                 110

Thr Val Arg Gly Cys Ala Tyr Ala Gly Ser Lys Gly Val Val Phe Gly
        115                 120                 125

Pro Ile Lys Asp Met Ala His Ile Ser His Gly Pro Val Gly Cys Gly
    130                 135                 140

Gln Tyr Ser Arg Ala Gly Arg Arg Ala Ala Ala Ala Ala Val Ser Gly
145                 150                 155                 160

Val Asp Ser Phe Gly Thr Leu Asn Phe Thr Ser Asp Phe Gln Glu Arg
                165                 170                 175

Asp Ile Val Phe Gly Gly Asp Lys Lys Leu Ser Lys Leu Ile Glu Glu
            180                 185                 190

Met Glu Leu Leu Phe Pro Leu Thr Lys Gly Ile Thr Ile Gln Ser Glu
        195                 200                 205

Cys Pro Val Gly Leu Ile Gly Asp Asp Ile Ser Ala Val Ala Asn Ala
    210                 215                 220

Ser Ser Lys Ala Leu Asp Lys Pro Val Ile Pro Val Arg Cys Glu Gly
225                 230                 235                 240

Phe Arg Gly Val Ser Gln Ser Leu Gly His His Ile Ala Asn Asp Val
                245                 250                 255

Val Arg Asp Trp Ile Leu Asn Asn Arg Glu Gly Gln Pro Phe Glu Thr
            260                 265                 270

Thr Pro Tyr Asp Val Ala Ile Ile Gly Asp Tyr Asn Ile Gly Gly Asp
        275                 280                 285

Ala Trp Ala Ser Arg Ile Leu Leu Glu Glu Met Gly Leu Arg Val Val
    290                 295                 300

Ala Gln Trp Ser Gly Asp Gly Thr Leu Val Glu Met Glu Asn Thr Pro
305                 310                 315                 320

Phe Val Lys Leu Asn Leu Val His Cys Tyr Arg Ser Met Asn Tyr Ile
                325                 330                 335

Ala Arg His Met Glu Glu Lys His Gln Ile Pro Trp Met Glu Tyr Asn
            340                 345                 350
```

Phe Phe Gly Pro Thr Lys Ile Ala Glu Ser Leu Arg Lys Ile Ala Asp
355 360 365

Gln Phe Asp Asp Thr Ile Arg Ala Asn Ala Glu Ala Val Ile Ala Arg
370 375 380

Tyr Glu Gly Gln Met Ala Ala Ile Ile Ala Lys Tyr Arg Pro Arg Leu
385 390 395 400

Glu Gly Arg Lys Val Leu Leu Tyr Met Gly Gly Leu Arg Pro Arg His
405 410 415

Val Ile Gly Ala Tyr Glu Asp Leu Gly Met Glu Ile Ile Ala Ala Gly
420 425 430

Tyr Glu Phe Ala His Asn Asp Asp Tyr Asp Arg Thr Leu Pro Asp Leu
435 440 445

Lys Glu Gly Thr Leu Leu Phe Asp Asp Ala Ser Ser Tyr Glu Leu Glu
450 455 460

Ala Phe Val Lys Ala Leu Lys Pro Asp Leu Ile Gly Ser Gly Ile Lys
465 470 475 480

Glu Lys Tyr Ile Phe Gln Lys Met Gly Val Pro Phe Arg Gln Met His
485 490 495

Ser Trp Asp Tyr Ser Gly Pro Tyr His Gly Tyr Asp Gly Phe Ala Ile
500 505 510

Phe Ala Arg Asp Met Asp Met Thr Leu Asn Asn Pro Ala Trp Asn Glu
515 520 525

Leu Thr Ala Pro Trp Leu Lys Ser Gly Gly Tyr Pro Tyr Asp Val Pro
530 535 540

Asp Tyr Ala
545

<210> SEQ ID NO 135
<211> LENGTH: 167
<212> TYPE: PRT
<213> ORGANISM: Artificial Sequence
<220> FEATURE:
<223> OTHER INFORMATION: Amino acid sequence of the MTP-Su9::NifW fusion polypeptide encoded by SN104. Amino acids 1-70 correspond to the MTP-Su9 with GG at its C-terminus, amino acids 71-158 correspond to K. oxytoca NifW (SEQ ID NO:17) with its initiator Met, and amino

<400> SEQUENCE: 135

Met Ala Ser Thr Arg Val Leu Ala Ser Arg Leu Ala Ser Gln Met Ala
1 5 10 15

Ala Ser Ala Lys Val Ala Arg Pro Ala Val Arg Val Ala Gln Val Ser
20 25 30

Lys Arg Thr Ile Gln Thr Gly Ser Pro Leu Gln Thr Leu Lys Arg Thr
35 40 45

Gln Met Thr Ser Ile Val Asn Ala Thr Thr Arg Gln Ala Phe Gln Lys
50 55 60

Arg Ala Tyr Ser Gly Gly Met Met Glu Trp Phe Tyr Gln Ile Pro Gly
65 70 75 80

Val Asp Glu Leu Arg Ser Ala Glu Ser Phe Phe Gln Phe Phe Ala Val
85 90 95

Pro Tyr Gln Pro Glu Leu Leu Gly Arg Cys Ser Leu Pro Val Leu Ala
100 105 110

Thr Phe His Arg Lys Leu Arg Ala Glu Val Pro Leu Gln Asn Arg Leu
115 120 125

Glu Asp Asn Asp Arg Ala Pro Trp Leu Leu Ala Arg Arg Leu Leu Ala
130 135 140

```
Glu Ser Tyr Gln Gln Gln Phe Gln Glu Ser Gly Thr Gly Gly Tyr Pro
145                 150                 155                 160

Tyr Asp Val Pro Asp Tyr Ala
                165


<210> SEQ ID NO 136
<211> LENGTH: 547
<212> TYPE: PRT
<213> ORGANISM: Artificial Sequence
<220> FEATURE:
<223> OTHER INFORMATION: Amino acid sequence of the MTP-FA 51::NifD::HA
      fusion polypeptide encoded by SN114.  Amino acids 1-54 correspond
      to the MTP-FA 51 with GG at its C-terminus, amino acids 55-536
      correspond to K. oxytoca NifD comprising the Y100Q substitution
      mutation at amino

<400> SEQUENCE: 136

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Met Thr Asn Ala Thr Gly Glu Arg Asn
    50                  55                  60

Leu Ala Leu Ile Gln Glu Val Leu Glu Val Phe Pro Glu Thr Ala Arg
65                  70                  75                  80

Lys Glu Arg Arg Lys His Met Met Val Ser Asp Pro Glu Met Glu Ser
                85                  90                  95

Val Gly Lys Cys Ile Ile Ser Asn Arg Lys Ser Gln Pro Gly Val Met
            100                 105                 110

Thr Val Arg Gly Cys Ala Tyr Ala Gly Ser Lys Gly Val Val Phe Gly
        115                 120                 125

Pro Ile Lys Asp Met Ala His Ile Ser His Gly Pro Val Gly Cys Gly
    130                 135                 140

Gln Tyr Ser Arg Ala Gly Arg Arg Asn Gln Tyr Thr Gly Val Ser Gly
145                 150                 155                 160

Val Asp Ser Phe Gly Thr Leu Asn Phe Thr Ser Asp Phe Gln Glu Arg
                165                 170                 175

Asp Ile Val Phe Gly Gly Asp Lys Lys Leu Ser Lys Leu Ile Glu Glu
            180                 185                 190

Met Glu Leu Leu Phe Pro Leu Thr Lys Gly Ile Thr Ile Gln Ser Glu
        195                 200                 205

Cys Pro Val Gly Leu Ile Gly Asp Asp Ile Ser Ala Val Ala Asn Ala
    210                 215                 220

Ser Ser Lys Ala Leu Asp Lys Pro Val Ile Pro Val Arg Cys Glu Gly
225                 230                 235                 240

Phe Arg Gly Val Ser Gln Ser Leu Gly His His Ile Ala Asn Asp Val
                245                 250                 255

Val Arg Asp Trp Ile Leu Asn Asn Arg Glu Gly Gln Pro Phe Glu Thr
            260                 265                 270

Thr Pro Tyr Asp Val Ala Ile Ile Gly Asp Tyr Asn Ile Gly Gly Asp
        275                 280                 285

Ala Trp Ala Ser Arg Ile Leu Leu Glu Glu Met Gly Leu Arg Val Val
    290                 295                 300

Ala Gln Trp Ser Gly Asp Gly Thr Leu Val Glu Met Glu Asn Thr Pro
```

```
305                 310                 315                 320

Phe Val Lys Leu Asn Leu Val His Cys Tyr Arg Ser Met Asn Tyr Ile
                325                 330                 335

Ala Arg His Met Glu Glu Lys His Gln Ile Pro Trp Met Glu Tyr Asn
            340                 345                 350

Phe Phe Gly Pro Thr Lys Ile Ala Glu Ser Leu Arg Lys Ile Ala Asp
        355                 360                 365

Gln Phe Asp Asp Thr Ile Arg Ala Asn Ala Glu Ala Val Ile Ala Arg
    370                 375                 380

Tyr Glu Gly Gln Met Ala Ala Ile Ile Ala Lys Tyr Arg Pro Arg Leu
385                 390                 395                 400

Glu Gly Arg Lys Val Leu Leu Tyr Met Gly Gly Leu Arg Pro Arg His
                405                 410                 415

Val Ile Gly Ala Tyr Glu Asp Leu Gly Met Glu Ile Ile Ala Ala Gly
            420                 425                 430

Tyr Glu Phe Ala His Asn Asp Asp Tyr Asp Arg Thr Leu Pro Asp Leu
        435                 440                 445

Lys Glu Gly Thr Leu Leu Phe Asp Asp Ala Ser Ser Tyr Glu Leu Glu
    450                 455                 460

Ala Phe Val Lys Ala Leu Lys Pro Asp Leu Ile Gly Ser Gly Ile Lys
465                 470                 475                 480

Glu Lys Tyr Ile Phe Gln Lys Met Gly Val Pro Phe Arg Gln Met His
                485                 490                 495

Ser Trp Asp Tyr Ser Gly Pro Tyr His Gly Tyr Asp Gly Phe Ala Ile
            500                 505                 510

Phe Ala Arg Asp Met Asp Met Thr Leu Asn Asn Pro Ala Trp Asn Glu
        515                 520                 525

Leu Thr Ala Pro Trp Leu Lys Ser Gly Gly Tyr Pro Tyr Asp Val Pro
    530                 535                 540

Asp Tyr Ala
545


<210> SEQ ID NO 137
<211> LENGTH: 241
<212> TYPE: PRT
<213> ORGANISM: Artificial Sequence
<220> FEATURE:
<223> OTHER INFORMATION: Amino acid sequence of the MTP-FA 51::NifF::HA
      fusion polypeptide encoded by SN138. Amino acids 1-54 correspond
      to the MTP-FA 51 with GG, amino acids 55-230 correspond to K.
      oxytoca NifF (SEQ ID NO:6) and amino acids 231-241 include the HA
      epitope.

<400> SEQUENCE: 137

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Ala Asn Ile Gly Ile Phe Phe Gly Thr
    50                  55                  60

Asp Thr Gly Lys Thr Arg Lys Ile Ala Lys Met Ile His Lys Gln Leu
65                  70                  75                  80

Gly Glu Leu Ala Asp Ala Pro Val Asn Ile Asn Arg Thr Thr Leu Asp
                85                  90                  95
```

```
Asp Phe Met Ala Tyr Pro Val Leu Leu Leu Gly Thr Pro Thr Leu Gly
            100                 105                 110

Asp Gly Gln Leu Pro Gly Leu Glu Ala Gly Cys Glu Ser Glu Ser Trp
        115                 120                 125

Ser Glu Phe Ile Ser Gly Leu Asp Asp Ala Ser Leu Lys Gly Lys Thr
    130                 135                 140

Val Ala Leu Phe Gly Leu Gly Asp Gln Arg Gly Tyr Pro Asp Asn Phe
145                 150                 155                 160

Val Ser Gly Met Arg Pro Leu Phe Asp Ala Leu Ser Ala Arg Gly Ala
                165                 170                 175

Gln Met Ile Gly Ser Trp Pro Asn Glu Gly Tyr Glu Phe Ser Ala Ser
            180                 185                 190

Ser Ala Leu Glu Gly Asp Arg Phe Val Gly Leu Val Leu Asp Gln Asp
        195                 200                 205

Asn Gln Phe Asp Gln Thr Glu Ala Arg Leu Ala Ser Trp Leu Glu Glu
    210                 215                 220

Ile Lys Arg Thr Val Leu Gly Gly Tyr Pro Tyr Asp Val Pro Asp Tyr
225                 230                 235                 240

Ala


<210> SEQ ID NO 138
<211> LENGTH: 1236
<212> TYPE: PRT
<213> ORGANISM: Artificial Sequence
<220> FEATURE:
<223> OTHER INFORMATION: Amino acid sequence of the MTP-FA 51::NifJ::HA
      fusion polypeptide encoded by SN139. Amino acids 1-54 correspond
      to the MTP-FA 51 with GG, amino acids 55-1225 correspond to K.
      oxytoca NifJ (SEQ ID NO:7), and amino acids 1226-1236 include the
      HA epitope.

<400> SEQUENCE: 138

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Ser Gly Lys Met Lys Thr Met Asp Gly
    50                  55                  60

Asn Ala Ala Ala Ala Trp Ile Ser Tyr Ala Phe Thr Glu Val Ala Ala
65                  70                  75                  80

Ile Tyr Pro Ile Thr Pro Ser Thr Pro Met Ala Glu Asn Val Asp Glu
                85                  90                  95

Trp Ala Ala Gln Gly Lys Lys Asn Leu Phe Gly Gln Pro Val Arg Leu
            100                 105                 110

Met Glu Met Gln Ser Glu Ala Gly Ala Ala Gly Ala Val His Gly Ala
        115                 120                 125

Leu Gln Ala Gly Ala Leu Thr Thr Thr Tyr Thr Ala Ser Gln Gly Leu
    130                 135                 140

Leu Leu Met Ile Pro Asn Met Tyr Lys Ile Ala Gly Glu Leu Leu Pro
145                 150                 155                 160

Gly Val Phe His Val Ser Ala Arg Ala Leu Ala Thr Asn Ser Leu Asn
                165                 170                 175

Ile Phe Gly Asp His Gln Asp Val Met Ala Val Arg Gln Thr Gly Cys
            180                 185                 190
```

```
Ala Met Leu Ala Glu Asn Asn Val Gln Gln Val Met Asp Leu Ser Ala
        195                 200                 205

Val Ala His Leu Ala Ala Ile Lys Gly Arg Ile Pro Phe Val Asn Phe
    210                 215                 220

Phe Asp Gly Phe Arg Thr Ser His Glu Ile Gln Lys Ile Glu Val Leu
225                 230                 235                 240

Glu Tyr Glu Gln Leu Ala Thr Leu Leu Asp Arg Pro Ala Leu Asp Ser
                245                 250                 255

Phe Arg Arg Asn Ala Leu His Pro Asp His Pro Val Ile Arg Gly Thr
            260                 265                 270

Ala Gln Asn Pro Asp Ile Tyr Phe Gln Glu Arg Glu Ala Gly Asn Arg
        275                 280                 285

Phe Tyr Gln Ala Leu Pro Asp Ile Val Glu Ser Tyr Met Thr Gln Ile
    290                 295                 300

Ser Ala Leu Thr Gly Arg Glu Tyr His Leu Phe Asn Tyr Thr Gly Ala
305                 310                 315                 320

Ala Asp Ala Glu Arg Val Ile Ile Ala Met Gly Ser Val Cys Asp Thr
                325                 330                 335

Val Gln Glu Val Val Asp Thr Leu Asn Ala Ala Gly Glu Lys Val Gly
            340                 345                 350

Leu Leu Ser Val His Leu Phe Arg Pro Phe Ser Leu Ala His Phe Phe
        355                 360                 365

Ala Gln Leu Pro Lys Thr Val Gln Arg Ile Ala Val Leu Asp Arg Thr
    370                 375                 380

Lys Glu Pro Gly Ala Gln Ala Glu Pro Leu Cys Leu Asp Val Lys Asn
385                 390                 395                 400

Ala Phe Tyr His His Asp Asp Ala Pro Leu Ile Val Gly Gly Arg Tyr
                405                 410                 415

Ala Leu Gly Gly Lys Asp Val Leu Pro Asn Asp Ile Ala Ala Val Phe
            420                 425                 430

Asp Asn Leu Asn Lys Pro Leu Pro Met Asp Gly Phe Thr Leu Gly Ile
        435                 440                 445

Val Asp Asp Val Thr Phe Thr Ser Leu Pro Pro Arg Gln Gln Thr Leu
    450                 455                 460

Ala Val Ser His Asp Gly Ile Thr Ala Cys Lys Phe Trp Gly Met Gly
465                 470                 475                 480

Ser Asp Gly Thr Val Gly Ala Asn Lys Ser Ala Ile Lys Ile Ile Gly
                485                 490                 495

Asp Lys Thr Pro Leu Tyr Ala Gln Ala Tyr Phe Ser Tyr Asp Ser Lys
            500                 505                 510

Lys Ser Gly Gly Ile Thr Val Ser His Leu Arg Phe Gly Asp Arg Pro
        515                 520                 525

Ile Asn Ser Pro Tyr Leu Ile His Arg Ala Asp Phe Ile Ser Cys Ser
    530                 535                 540

Gln Gln Ser Tyr Val Glu Arg Tyr Asp Leu Leu Asp Gly Leu Lys Pro
545                 550                 555                 560

Gly Gly Thr Phe Leu Leu Asn Cys Ser Trp Ser Asp Ala Glu Leu Glu
                565                 570                 575

Gln His Leu Pro Val Gly Phe Lys Arg Tyr Leu Ala Arg Glu Asn Ile
            580                 585                 590

His Phe Tyr Thr Leu Asn Ala Val Asp Ile Ala Arg Glu Leu Gly Leu
        595                 600                 605

Gly Gly Arg Phe Asn Met Leu Met Gln Ala Ala Phe Phe Lys Leu Ala
```

```
    610                 615                 620

Ala Ile Ile Asp Pro Gln Thr Ala Ala Asp Tyr Leu Lys Gln Ala Val
625                 630                 635                 640

Glu Lys Ser Tyr Gly Ser Lys Gly Ala Ala Val Ile Glu Met Asn Gln
                645                 650                 655

Arg Ala Ile Glu Leu Gly Met Ala Ser Leu His Gln Val Thr Ile Pro
            660                 665                 670

Ala His Trp Ala Thr Leu Asp Glu Pro Ala Ala Gln Ala Ser Ala Met
        675                 680                 685

Met Pro Asp Phe Ile Arg Asp Ile Leu Gln Pro Met Asn Arg Gln Cys
    690                 695                 700

Gly Asp Gln Leu Pro Val Ser Ala Phe Val Gly Met Glu Asp Gly Thr
705                 710                 715                 720

Phe Pro Ser Gly Thr Ala Ala Trp Glu Lys Arg Gly Ile Ala Leu Glu
                725                 730                 735

Val Pro Val Trp Gln Pro Glu Gly Cys Thr Gln Cys Asn Gln Cys Ala
            740                 745                 750

Phe Ile Cys Pro His Ala Ala Ile Arg Pro Ala Leu Leu Asn Gly Glu
        755                 760                 765

Glu His Asp Ala Ala Pro Val Gly Leu Leu Ser Lys Pro Ala Gln Gly
    770                 775                 780

Ala Lys Glu Tyr His Tyr His Leu Ala Ile Ser Pro Leu Asp Cys Ser
785                 790                 795                 800

Gly Cys Gly Asn Cys Val Asp Ile Cys Pro Ala Arg Gly Lys Ala Leu
                805                 810                 815

Lys Met Gln Ser Leu Asp Ser Gln Arg Gln Met Ala Pro Val Trp Asp
            820                 825                 830

Tyr Ala Leu Ala Leu Thr Pro Lys Ser Asn Pro Phe Arg Lys Thr Thr
        835                 840                 845

Val Lys Gly Ser Gln Phe Glu Thr Pro Leu Leu Glu Phe Ser Gly Ala
    850                 855                 860

Cys Ala Gly Cys Gly Glu Thr Pro Tyr Ala Arg Leu Ile Thr Gln Leu
865                 870                 875                 880

Phe Gly Asp Arg Met Leu Ile Ala Asn Ala Thr Gly Cys Ser Ser Ile
                885                 890                 895

Trp Gly Ala Ser Ala Pro Ser Ile Pro Tyr Thr Thr Asn His Arg Gly
            900                 905                 910

His Gly Pro Ala Trp Ala Asn Ser Leu Phe Glu Asp Asn Ala Glu Phe
        915                 920                 925

Gly Leu Gly Met Met Leu Gly Gly Gln Ala Val Arg Gln Gln Ile Ala
    930                 935                 940

Asp Asp Met Thr Ala Ala Leu Ala Leu Pro Val Ser Asp Glu Leu Ser
945                 950                 955                 960

Asp Ala Met Arg Gln Trp Leu Ala Lys Gln Asp Glu Gly Glu Gly Thr
                965                 970                 975

Arg Glu Arg Ala Asp Arg Leu Ser Glu Arg Leu Ala Ala Glu Lys Glu
            980                 985                 990

Gly Val Pro Leu Leu Glu Gln Leu  Trp Gln Asn Arg Asp  Tyr Phe Val
        995                 1000                1005

Arg Arg  Ser Gln Trp Ile Phe  Gly Gly Asp Gly Trp  Ala Tyr Asp
    1010                1015                1020

Ile Gly  Phe Gly Gly Leu Asp  His Val Leu Ala Ser  Gly Glu Asp
    1025                1030                1035
```

Val Asn Ile Leu Val Phe Asp Thr Glu Val Tyr Ser Asn Thr Gly
1040 1045 1050

Gly Gln Ser Ser Lys Ser Thr Pro Val Ala Ala Ile Ala Lys Phe
1055 1060 1065

Ala Ala Gln Gly Lys Arg Thr Arg Lys Lys Asp Leu Gly Met Met
1070 1075 1080

Ala Met Ser Tyr Gly Asn Val Tyr Val Ala Gln Val Ala Met Gly
1085 1090 1095

Ala Asp Lys Asp Gln Thr Leu Arg Ala Ile Ala Glu Ala Glu Ala
1100 1105 1110

Trp Pro Gly Pro Ser Leu Val Ile Ala Tyr Ala Ala Cys Ile Asn
1115 1120 1125

His Gly Leu Lys Ala Gly Met Arg Cys Ser Gln Arg Glu Ala Lys
1130 1135 1140

Arg Ala Val Glu Ala Gly Tyr Trp His Leu Trp Arg Tyr His Pro
1145 1150 1155

Gln Arg Glu Ala Glu Gly Lys Thr Pro Phe Met Leu Asp Ser Glu
1160 1165 1170

Glu Pro Glu Glu Ser Phe Arg Asp Phe Leu Leu Gly Glu Val Arg
1175 1180 1185

Tyr Ala Ser Leu His Lys Thr Thr Pro His Leu Ala Asp Ala Leu
1190 1195 1200

Phe Ser Arg Thr Glu Glu Asp Ala Arg Ala Arg Phe Ala Gln Tyr
1205 1210 1215

Arg Arg Leu Ala Gly Glu Glu Gly Gly Tyr Pro Tyr Asp Val Pro
1220 1225 1230

Asp Tyr Ala
1235

<210> SEQ ID NO 139
<211> LENGTH: 584
<212> TYPE: PRT
<213> ORGANISM: Artificial Sequence
<220> FEATURE:
<223> OTHER INFORMATION: Amino acid sequence of the MTP-FA 51::HA::NifK fusion polypeptide encoded by SN140. Amino acids 1-53 correspond to the MTP-FA 51 with GG, amino acids 54-64 include the HA epitope, and amino acids 65-584 correspond to K. oxytoca NifK (SEQ ID NO:3) with

<400> SEQUENCE: 139

Met Ala Met Ala Val Phe Arg Arg Glu Gly Arg Arg Leu Leu Pro Ser
1 5 10 15

Ile Ala Ala Arg Pro Ile Ala Ala Ile Arg Ser Pro Leu Ser Ser Asp
20 25 30

Gln Glu Glu Gly Leu Leu Gly Val Arg Ser Ile Ser Thr Gln Val Val
35 40 45

Arg Asn Arg Gly Gly Tyr Pro Tyr Asp Val Pro Asp Tyr Ala Gly Gly
50 55 60

Met Ser Gln Thr Ile Asp Lys Ile Asn Ser Cys Tyr Pro Leu Phe Glu
65 70 75 80

Gln Asp Glu Tyr Gln Glu Leu Phe Arg Asn Lys Arg Gln Leu Glu Glu
85 90 95

Ala His Asp Ala Gln Arg Val Gln Glu Val Phe Ala Trp Thr Thr Thr
100 105 110

Ala Glu Tyr Glu Ala Leu Asn Phe Gln Arg Glu Ala Leu Thr Val Asp

```
        115                 120                 125

Pro Ala Lys Ala Cys Gln Pro Leu Gly Ala Val Leu Cys Ser Leu Gly
    130                 135                 140

Phe Ala Asn Thr Leu Pro Tyr Val His Gly Ser Gln Gly Cys Val Ala
145                 150                 155                 160

Tyr Phe Arg Thr Tyr Phe Asn Arg His Phe Lys Glu Pro Ile Ala Cys
                165                 170                 175

Val Ser Asp Ser Met Thr Glu Asp Ala Ala Val Phe Gly Gly Asn Asn
            180                 185                 190

Asn Met Asn Leu Gly Leu Gln Asn Ala Ser Ala Leu Tyr Lys Pro Glu
        195                 200                 205

Ile Ile Ala Val Ser Thr Thr Cys Met Ala Glu Val Ile Gly Asp Asp
    210                 215                 220

Leu Gln Ala Phe Ile Ala Asn Ala Lys Lys Asp Gly Phe Val Asp Ser
225                 230                 235                 240

Ser Ile Ala Val Pro His Ala His Thr Pro Ser Phe Ile Gly Ser His
                245                 250                 255

Val Thr Gly Trp Asp Asn Met Phe Glu Gly Phe Ala Lys Thr Phe Thr
            260                 265                 270

Ala Asp Tyr Gln Gly Gln Pro Gly Lys Leu Pro Lys Leu Asn Leu Val
        275                 280                 285

Thr Gly Phe Glu Thr Tyr Leu Gly Asn Phe Arg Val Leu Lys Arg Met
    290                 295                 300

Met Glu Gln Met Ala Val Pro Cys Ser Leu Leu Ser Asp Pro Ser Glu
305                 310                 315                 320

Val Leu Asp Thr Pro Ala Asp Gly His Tyr Arg Met Tyr Ser Gly Gly
                325                 330                 335

Thr Thr Gln Gln Glu Met Lys Glu Ala Pro Asp Ala Ile Asp Thr Leu
            340                 345                 350

Leu Leu Gln Pro Trp Gln Leu Leu Lys Ser Lys Lys Val Val Gln Glu
        355                 360                 365

Met Trp Asn Gln Pro Ala Thr Glu Val Ala Ile Pro Leu Gly Leu Ala
    370                 375                 380

Ala Thr Asp Glu Leu Leu Met Thr Val Ser Gln Leu Ser Gly Lys Pro
385                 390                 395                 400

Ile Ala Asp Ala Leu Thr Leu Glu Arg Gly Arg Leu Val Asp Met Met
                405                 410                 415

Leu Asp Ser His Thr Trp Leu His Gly Lys Lys Phe Gly Leu Tyr Gly
            420                 425                 430

Asp Pro Asp Phe Val Met Gly Leu Thr Arg Phe Leu Leu Glu Leu Gly
        435                 440                 445

Cys Glu Pro Thr Val Ile Leu Ser His Asn Ala Asn Lys Arg Trp Gln
    450                 455                 460

Lys Ala Met Asn Lys Met Leu Asp Ala Ser Pro Tyr Gly Arg Asp Ser
465                 470                 475                 480

Glu Val Phe Ile Asn Cys Asp Leu Trp His Phe Arg Ser Leu Met Phe
                485                 490                 495

Thr Arg Gln Pro Asp Phe Met Ile Gly Asn Ser Tyr Gly Lys Phe Ile
            500                 505                 510

Gln Arg Asp Thr Leu Ala Lys Gly Lys Ala Phe Glu Val Pro Leu Ile
        515                 520                 525

Arg Leu Gly Phe Pro Leu Phe Asp Arg His His Leu His Arg Gln Thr
    530                 535                 540
```

Thr Trp Gly Tyr Glu Gly Ala Met Asn Ile Val Thr Thr Leu Val Asn
545 550 555 560

Ala Val Leu Glu Lys Leu Asp Ser Asp Thr Ser Gln Leu Gly Lys Thr
565 570 575

Asp Tyr Ser Phe Asp Leu Val Arg
580

<210> SEQ ID NO 140
<211> LENGTH: 232
<212> TYPE: PRT
<213> ORGANISM: Artificial Sequence
<220> FEATURE:
<223> OTHER INFORMATION: Amino acid sequence of the MTP-FA 51::NifQ::HA fusion polypeptide encoded by SN141. Amino acids 1-54 correspond to the MTP-FA 51 with GG, amino acids 55-221 correspond to K. oxytoca NifQ (SEQ ID NO:10) and amino acids 222-232 include the HA epitope.

<400> SEQUENCE: 140

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Pro Pro Leu Asp Trp Leu Arg Arg Leu
50 55 60

Trp Leu Leu Tyr His Ala Gly Lys Gly Ser Phe Pro Leu Arg Met Gly
65 70 75 80

Leu Ser Pro Arg Asp Trp Gln Ala Leu Arg Arg Arg Leu Gly Glu Val
85 90 95

Glu Thr Pro Leu Asp Gly Glu Thr Leu Thr Arg Arg Arg Leu Met Ala
100 105 110

Glu Leu Asn Ala Thr Arg Glu Glu Glu Arg Gln Gln Leu Gly Ala Trp
115 120 125

Leu Ala Gly Trp Met Gln Gln Asp Ala Gly Pro Met Ala Gln Ile Ile
130 135 140

Ala Glu Val Ser Leu Ala Phe Asn His Leu Trp Gln Asp Leu Gly Leu
145 150 155 160

Ala Ser Arg Ala Glu Leu Arg Leu Leu Met Ser Asp Cys Phe Pro Gln
165 170 175

Leu Val Val Met Asn Glu His Asn Met Arg Trp Lys Lys Phe Phe Tyr
180 185 190

Arg Gln Arg Cys Leu Leu Gln Gln Gly Glu Val Ile Cys Arg Ser Pro
195 200 205

Ser Cys Asp Glu Cys Trp Glu Arg Ser Ala Cys Phe Glu Gly Gly Tyr
210 215 220

Pro Tyr Asp Val Pro Asp Tyr Ala
225 230

<210> SEQ ID NO 141
<211> LENGTH: 446
<212> TYPE: PRT
<213> ORGANISM: Artificial Sequence
<220> FEATURE:
<223> OTHER INFORMATION: Amino acid sequence of the MTP-FA 51::NifV::HA fusion polypeptide encoded by SN142. Amino acids 1-54 correspond to the MTP-FA 51 with GG, amino acids 55-435 correspond to K. oxytoca NifV (SEQ ID NO:13) and amino acids 436-446 include the HA epitope.

<400> SEQUENCE: 141

```
Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Glu Arg Val Leu Ile Asn Asp Thr Thr
    50                  55                  60

Leu Arg Asp Gly Glu Gln Ser Pro Gly Val Ala Phe Arg Thr Ser Glu
65                  70                  75                  80

Lys Val Ala Ile Ala Glu Ala Leu Tyr Ala Ala Gly Ile Thr Ala Met
                85                  90                  95

Glu Val Gly Thr Pro Ala Met Gly Asp Glu Glu Ile Ala Arg Ile Gln
            100                 105                 110

Leu Val Arg Arg Gln Leu Pro Asp Ala Thr Leu Met Thr Trp Cys Arg
        115                 120                 125

Met Asn Ala Leu Glu Ile Arg Gln Ser Ala Asp Leu Gly Ile Asp Trp
    130                 135                 140

Val Asp Ile Ser Ile Pro Ala Ser Asp Lys Leu Arg Gln Tyr Lys Leu
145                 150                 155                 160

Arg Glu Pro Leu Ala Val Leu Leu Glu Arg Leu Ala Met Phe Ile His
                165                 170                 175

Leu Ala His Thr Leu Gly Leu Lys Val Cys Ile Gly Cys Glu Asp Ala
            180                 185                 190

Ser Arg Ala Ser Gly Gln Thr Leu Arg Ala Ile Ala Glu Val Ala Gln
        195                 200                 205

Asn Ala Pro Ala Ala Arg Leu Arg Tyr Ala Asp Thr Val Gly Leu Leu
    210                 215                 220

Asp Pro Phe Thr Thr Ala Ala Gln Ile Ser Ala Leu Arg Asp Val Trp
225                 230                 235                 240

Ser Gly Glu Ile Glu Met His Ala His Asn Asp Leu Gly Met Ala Thr
                245                 250                 255

Ala Asn Thr Leu Ala Ala Val Ser Ala Gly Ala Thr Ser Val Asn Thr
            260                 265                 270

Thr Val Leu Gly Leu Gly Glu Arg Ala Gly Asn Ala Ala Ala Trp Lys
        275                 280                 285

Pro Ser Ala Leu Gly Leu Glu Arg Cys Leu Gly Val Glu Thr Gly Val
    290                 295                 300

His Phe Ser Ala Leu Pro Ala Leu Cys Gln Arg Val Ala Glu Ala Ala
305                 310                 315                 320

Gln Arg Ala Ile Asp Pro Gln Gln Pro Leu Val Gly Glu Leu Val Phe
                325                 330                 335

Thr His Glu Ser Gly Val His Val Ala Ala Leu Leu Arg Asp Ser Glu
            340                 345                 350

Ser Tyr Gln Ser Ile Ala Pro Ser Leu Met Gly Arg Ser Tyr Arg Leu
        355                 360                 365

Val Leu Gly Lys His Ser Gly Arg Gln Ala Val Asn Gly Val Phe Asp
    370                 375                 380

Gln Met Gly Tyr His Leu Asn Ala Ala Gln Ile Asn Gln Leu Leu Pro
385                 390                 395                 400
```

Ala Ile Arg Arg Phe Ala Glu Asn Trp Lys Arg Ser Pro Lys Asp Tyr
405 410 415

Glu Leu Val Ala Ile Tyr Asp Glu Leu Cys Gly Glu Ser Ala Leu Arg
420 425 430

Ala Arg Gly Gly Gly Tyr Pro Tyr Asp Val Pro Asp Tyr Ala
435 440 445

<210> SEQ ID NO 142
<211> LENGTH: 151
<212> TYPE: PRT
<213> ORGANISM: Artificial Sequence
<220> FEATURE:
<223> OTHER INFORMATION: Amino acid sequence of the MTP-FA 51::NifW::HA fusion polypeptide encoded by SN143. Amino acids 1-54 correspond to the MTP-FA 51 with GG, amino acids 55-140 correspond to K. oxytoca NifW (SEQ ID NO:17), and amino acids 141-151 include the HA epitope.

<400> SEQUENCE: 142

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Met Glu Trp Phe Tyr Gln Ile Pro Gly
50 55 60

Val Asp Glu Leu Arg Ser Ala Glu Ser Phe Phe Gln Phe Phe Ala Val
65 70 75 80

Pro Tyr Gln Pro Glu Leu Leu Gly Arg Cys Ser Leu Pro Val Leu Ala
85 90 95

Thr Phe His Arg Lys Leu Arg Ala Glu Val Pro Leu Gln Asn Arg Leu
100 105 110

Glu Asp Asn Asp Arg Ala Pro Trp Leu Leu Ala Arg Arg Leu Leu Ala
115 120 125

Glu Ser Tyr Gln Gln Gln Phe Gln Glu Ser Gly Thr Gly Gly Tyr Pro
130 135 140

Tyr Asp Val Pro Asp Tyr Ala
145 150

<210> SEQ ID NO 143
<211> LENGTH: 221
<212> TYPE: PRT
<213> ORGANISM: Artificial Sequence
<220> FEATURE:
<223> OTHER INFORMATION: Amino acid sequence of the MTP-FA 51::NifX::HA fusion polypeptide encoded by SN144. Amino acids 1-54 correspond to the MTP-FA 51 with GG, amino acids 55-210 correspond to K. oxytoca NifX (SEQ ID NO:14), and amino acids 211-221 include the HA epitope.

<400> SEQUENCE: 143

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Pro Pro Ile Asn Arg Gln Phe Asp Met
50 55 60

```
Val His Ser Asp Glu Trp Ser Met Lys Val Ala Phe Ala Ser Ser Asp
65                  70                  75                  80

Tyr Arg His Val Asp Gln His Phe Gly Ala Thr Pro Arg Leu Val Val
                85                  90                  95

Tyr Gly Val Lys Ala Asp Arg Val Thr Leu Ile Arg Val Val Asp Phe
            100                 105                 110

Ser Val Glu Asn Gly His Gln Thr Glu Lys Ile Ala Arg Arg Ile His
        115                 120                 125

Ala Leu Glu Asp Cys Val Thr Leu Phe Cys Val Ala Ile Gly Asp Ala
    130                 135                 140

Val Phe Arg Gln Leu Leu Gln Val Gly Val Arg Ala Glu Arg Val Pro
145                 150                 155                 160

Ala Asp Thr Thr Ile Val Gly Leu Leu Gln Glu Ile Gln Leu Tyr Trp
                165                 170                 175

Tyr Asp Lys Gly Gln Arg Lys Asn Gln Arg Gln Arg Asp Pro Glu Arg
            180                 185                 190

Phe Thr Arg Leu Leu Gln Glu Gln Glu Trp His Gly Asp Pro Asp Pro
        195                 200                 205

Arg Arg Gly Gly Tyr Pro Tyr Asp Val Pro Asp Tyr Ala
    210                 215                 220
```

```
<210> SEQ ID NO 144
<211> LENGTH: 285
<212> TYPE: PRT
<213> ORGANISM: Artificial Sequence
<220> FEATURE:
<223> OTHER INFORMATION: Amino acid sequence of the MTP-FA 51::NifY::HA
      fusion polypeptide encoded by SN145. Amino acids 1-54 correspond
      to the MTP-FA 51 with GG, amino acids 55-274 correspond to K.
      oxytoca NifY according to Temme et al., (2012), and amino acids
      275-285

<400> SEQUENCE: 144

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Ser Asp Asn Asp Thr Leu Phe Trp Arg
    50                  55                  60

Met Leu Ala Leu Phe Gln Ser Leu Pro Asp Leu Gln Pro Ala Gln Ile
65                  70                  75                  80

Val Asp Trp Leu Ala Gln Glu Ser Gly Glu Thr Leu Thr Pro Glu Arg
                85                  90                  95

Leu Ala Thr Leu Thr Gln Pro Gln Leu Ala Ala Ser Phe Pro Ser Ala
            100                 105                 110

Thr Ala Val Met Ser Pro Ala Arg Trp Ser Arg Val Met Ala Ser Leu
        115                 120                 125

Gln Gly Ala Leu Pro Ala His Leu Arg Ile Val Arg Pro Ala Gln Arg
    130                 135                 140

Thr Pro Gln Leu Leu Ala Ala Phe Cys Ser Gln Asp Gly Leu Val Ile
145                 150                 155                 160

Asn Gly His Phe Gly Gln Gly Arg Leu Phe Phe Ile Tyr Ala Phe Asp
                165                 170                 175

Glu Gln Gly Gly Trp Leu Tyr Asp Leu Arg Arg Tyr Pro Ser Ala Pro
            180                 185                 190
```

His Gln Gln Glu Ala Asn Glu Val Arg Ala Arg Leu Ile Glu Asp Cys
195 200 205

Gln Leu Leu Phe Cys Gln Glu Ile Gly Gly Pro Ala Ala Ala Arg Leu
210 215 220

Ile Arg His Arg Ile His Pro Met Lys Ala Gln Pro Gly Thr Thr Ile
225 230 235 240

Gln Ala Gln Cys Glu Ala Ile Asn Thr Leu Leu Ala Gly Arg Leu Pro
245 250 255

Pro Trp Leu Ala Lys Arg Leu Asn Arg Asp Asn Pro Leu Glu Glu Arg
260 265 270

Val Phe Gly Gly Tyr Pro Tyr Asp Val Pro Asp Tyr Ala
275 280 285

<210> SEQ ID NO 145
<211> LENGTH: 213
<212> TYPE: PRT
<213> ORGANISM: Artificial Sequence
<220> FEATURE:
<223> OTHER INFORMATION: Amino acid sequence of the MTP-FA 51::NifZ::HA fusion polypeptide encoded by SN146. Amino acids 1-54 correspond to the MTP-FA 51 with GG, amino acids 55-202 correspond to K. oxytoca NifZ (SEQ ID NO:16), and amino acids 203-213 include the HA epitope.

<400> SEQUENCE: 145

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Arg Pro Lys Phe Thr Phe Ser Glu Glu
50 55 60

Val Arg Val Val Arg Ala Ile Arg Asn Asp Gly Thr Val Ala Gly Phe
65 70 75 80

Ala Pro Gly Ala Leu Leu Val Arg Arg Gly Ser Thr Gly Phe Val Arg
85 90 95

Asp Trp Gly Val Phe Leu Gln Asp Gln Ile Ile Tyr Gln Ile His Phe
100 105 110

Pro Glu Thr Asp Arg Ile Ile Gly Cys Arg Glu Gln Glu Leu Ile Pro
115 120 125

Ile Thr Gln Pro Trp Leu Ala Gly Asn Leu Gln Tyr Arg Asp Ser Val
130 135 140

Thr Cys Gln Met Ala Leu Ala Val Asn Gly Asp Val Val Val Ser Ala
145 150 155 160

Gly Gln Arg Gly Arg Val Glu Ala Thr Asp Arg Gly Glu Leu Gly Asp
165 170 175

Ser Tyr Thr Val Asp Phe Ser Gly Arg Trp Phe Arg Val Pro Val Gln
180 185 190

Ala Ile Ala Leu Ile Glu Glu Arg Glu Glu Gly Gly Tyr Pro Tyr Asp
195 200 205

Val Pro Asp Tyr Ala
210

<210> SEQ ID NO 146
<211> LENGTH: 1085
<212> TYPE: PRT

<213> ORGANISM: Artificial Sequence
<220> FEATURE:
<223> OTHER INFORMATION: Amino acid sequence of MTP-FA 51::NifD(Y100Q)::linker(HA)::NifK fusion polypeptide encoded by SN159. Amino acids 1-54 correspond to the MTP-FA 51 with GG at its C-terminus, amino acids 55-536 correspond to K. oxytoca NifD with the Y100Q substitution, amino

<400> SEQUENCE: 146

```
Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Thr Asn Ala Thr Gly Glu Arg Asn Leu
    50                  55                  60

Ala Leu Ile Gln Glu Val Leu Glu Val Phe Pro Glu Thr Ala Arg Lys
65                  70                  75                  80

Glu Arg Arg Lys His Met Met Val Ser Asp Pro Glu Met Glu Ser Val
                85                  90                  95

Gly Lys Cys Ile Ile Ser Asn Arg Lys Ser Gln Pro Gly Val Met Thr
            100                 105                 110

Val Arg Gly Cys Ala Tyr Ala Gly Ser Lys Gly Val Val Phe Gly Pro
        115                 120                 125

Ile Lys Asp Met Ala His Ile Ser His Gly Pro Val Gly Cys Gly Gln
    130                 135                 140

Tyr Ser Arg Ala Gly Arg Arg Asn Gln Tyr Thr Gly Val Ser Gly Val
145                 150                 155                 160

Asp Ser Phe Gly Thr Leu Asn Phe Thr Ser Asp Phe Gln Glu Arg Asp
                165                 170                 175

Ile Val Phe Gly Gly Asp Lys Lys Leu Ser Lys Leu Ile Glu Glu Met
            180                 185                 190

Glu Leu Leu Phe Pro Leu Thr Lys Gly Ile Thr Ile Gln Ser Glu Cys
        195                 200                 205

Pro Val Gly Leu Ile Gly Asp Asp Ile Ser Ala Val Ala Asn Ala Ser
    210                 215                 220

Ser Lys Ala Leu Asp Lys Pro Val Ile Pro Val Arg Cys Glu Gly Phe
225                 230                 235                 240

Arg Gly Val Ser Gln Ser Leu Gly His His Ile Ala Asn Asp Val Val
                245                 250                 255

Arg Asp Trp Ile Leu Asn Asn Arg Glu Gly Gln Pro Phe Glu Thr Thr
            260                 265                 270

Pro Tyr Asp Val Ala Ile Ile Gly Asp Tyr Asn Ile Gly Gly Asp Ala
        275                 280                 285

Trp Ala Ser Arg Ile Leu Leu Glu Glu Met Gly Leu Arg Val Val Ala
    290                 295                 300

Gln Trp Ser Gly Asp Gly Thr Leu Val Glu Met Glu Asn Thr Pro Phe
305                 310                 315                 320

Val Lys Leu Asn Leu Val His Cys Tyr Arg Ser Met Asn Tyr Ile Ala
                325                 330                 335

Arg His Met Glu Glu Lys His Gln Ile Pro Trp Met Glu Tyr Asn Phe
            340                 345                 350

Phe Gly Pro Thr Lys Ile Ala Glu Ser Leu Arg Lys Ile Ala Asp Gln
        355                 360                 365
```

```
Phe Asp Asp Thr Ile Arg Ala Asn Ala Glu Ala Val Ile Ala Arg Tyr
    370                 375                 380

Glu Gly Gln Met Ala Ala Ile Ile Ala Lys Tyr Arg Pro Arg Leu Glu
385                 390                 395                 400

Gly Arg Lys Val Leu Leu Tyr Met Gly Gly Leu Arg Pro Arg His Val
                405                 410                 415

Ile Gly Ala Tyr Glu Asp Leu Gly Met Glu Ile Ile Ala Ala Gly Tyr
            420                 425                 430

Glu Phe Ala His Asn Asp Asp Tyr Asp Arg Thr Leu Pro Asp Leu Lys
        435                 440                 445

Glu Gly Thr Leu Leu Phe Asp Asp Ala Ser Ser Tyr Glu Leu Glu Ala
    450                 455                 460

Phe Val Lys Ala Leu Lys Pro Asp Leu Ile Gly Ser Gly Ile Lys Glu
465                 470                 475                 480

Lys Tyr Ile Phe Gln Lys Met Gly Val Pro Phe Arg Gln Met His Ser
                485                 490                 495

Trp Asp Tyr Ser Gly Pro Tyr His Gly Tyr Asp Gly Phe Ala Ile Phe
            500                 505                 510

Ala Arg Asp Met Asp Met Thr Leu Asn Asn Pro Ala Trp Asn Glu Leu
        515                 520                 525

Thr Ala Pro Trp Leu Lys Ser Ala Ala Thr Pro Pro Pro Gly Ser Thr
    530                 535                 540

Thr Thr Ala Tyr Pro Tyr Asp Val Pro Asp Tyr Ala Thr Pro Pro Pro
545                 550                 555                 560

Gly Ser Thr Thr Thr Ala Ser Gln Thr Ile Asp Lys Ile Asn Ser Cys
                565                 570                 575

Tyr Pro Leu Phe Glu Gln Asp Glu Tyr Gln Glu Leu Phe Arg Asn Lys
            580                 585                 590

Arg Gln Leu Glu Glu Ala His Asp Ala Gln Arg Val Gln Glu Val Phe
        595                 600                 605

Ala Trp Thr Thr Thr Ala Glu Tyr Glu Ala Leu Asn Phe Gln Arg Glu
    610                 615                 620

Ala Leu Thr Val Asp Pro Ala Lys Ala Cys Gln Pro Leu Gly Ala Val
625                 630                 635                 640

Leu Cys Ser Leu Gly Phe Ala Asn Thr Leu Pro Tyr Val His Gly Ser
                645                 650                 655

Gln Gly Cys Val Ala Tyr Phe Arg Thr Tyr Phe Asn Arg His Phe Lys
            660                 665                 670

Glu Pro Ile Ala Cys Val Ser Asp Ser Met Thr Glu Asp Ala Ala Val
        675                 680                 685

Phe Gly Gly Asn Asn Asn Met Asn Leu Gly Leu Gln Asn Ala Ser Ala
    690                 695                 700

Leu Tyr Lys Pro Glu Ile Ile Ala Val Ser Thr Thr Cys Met Ala Glu
705                 710                 715                 720

Val Ile Gly Asp Asp Leu Gln Ala Phe Ile Ala Asn Ala Lys Lys Asp
                725                 730                 735

Gly Phe Val Asp Ser Ser Ile Ala Val Pro His Ala His Thr Pro Ser
            740                 745                 750

Phe Ile Gly Ser His Val Thr Gly Trp Asp Asn Met Phe Glu Gly Phe
        755                 760                 765

Ala Lys Thr Phe Thr Ala Asp Tyr Gln Gly Gln Pro Gly Lys Leu Pro
    770                 775                 780

Lys Leu Asn Leu Val Thr Gly Phe Glu Thr Tyr Leu Gly Asn Phe Arg
```

785 790 795 800

Val Leu Lys Arg Met Met Glu Gln Met Ala Val Pro Cys Ser Leu Leu
805 810 815

Ser Asp Pro Ser Glu Val Leu Asp Thr Pro Ala Asp Gly His Tyr Arg
820 825 830

Met Tyr Ser Gly Gly Thr Thr Gln Gln Glu Met Lys Glu Ala Pro Asp
835 840 845

Ala Ile Asp Thr Leu Leu Leu Gln Pro Trp Gln Leu Leu Lys Ser Lys
850 855 860

Lys Val Val Gln Glu Met Trp Asn Gln Pro Ala Thr Glu Val Ala Ile
865 870 875 880

Pro Leu Gly Leu Ala Ala Thr Asp Glu Leu Leu Met Thr Val Ser Gln
885 890 895

Leu Ser Gly Lys Pro Ile Ala Asp Ala Leu Thr Leu Glu Arg Gly Arg
900 905 910

Leu Val Asp Met Met Leu Asp Ser His Thr Trp Leu His Gly Lys Lys
915 920 925

Phe Gly Leu Tyr Gly Asp Pro Asp Phe Val Met Gly Leu Thr Arg Phe
930 935 940

Leu Leu Glu Leu Gly Cys Glu Pro Thr Val Ile Leu Ser His Asn Ala
945 950 955 960

Asn Lys Arg Trp Gln Lys Ala Met Asn Lys Met Leu Asp Ala Ser Pro
965 970 975

Tyr Gly Arg Asp Ser Glu Val Phe Ile Asn Cys Asp Leu Trp His Phe
980 985 990

Arg Ser Leu Met Phe Thr Arg Gln Pro Asp Phe Met Ile Gly Asn Ser
995 1000 1005

Tyr Gly Lys Phe Ile Gln Arg Asp Thr Leu Ala Lys Gly Lys Ala
1010 1015 1020

Phe Glu Val Pro Leu Ile Arg Leu Gly Phe Pro Leu Phe Asp Arg
1025 1030 1035

His His Leu His Arg Gln Thr Thr Trp Gly Tyr Glu Gly Ala Met
1040 1045 1050

Asn Ile Val Thr Thr Leu Val Asn Ala Val Leu Glu Lys Leu Asp
1055 1060 1065

Ser Asp Thr Ser Gln Leu Gly Lys Thr Asp Tyr Ser Phe Asp Leu
1070 1075 1080

Val Arg
1085

<210> SEQ ID NO 147
<211> LENGTH: 533
<212> TYPE: PRT
<213> ORGANISM: Artificial Sequence
<220> FEATURE:
<223> OTHER INFORMATION: Amino acid sequence of the MTP-FA 51::NifB::HA fusion polypeptide encoded by SN192. Amino acids 1-54 correspond to the MTP-FA 51 with GG, amino acids 55-522 correspond to K. oxytoca NifB according to Temme et al., (2012), and amino acids 523-533

<400> SEQUENCE: 147

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

-continued

```
Asp Gln Glu Glu Gly Leu Leu Gly Val Arg Ser Ile Ser Thr Gln Val
        35                  40                  45

Val Arg Asn Arg Gly Gly Met Thr Ser Cys Ser Ser Phe Ser Gly Gly
    50                  55                  60

Lys Ala Cys Arg Pro Ala Asp Asp Ser Ala Leu Thr Pro Leu Val Ala
65                  70                  75                  80

Asp Lys Ala Ala Ala His Pro Cys Tyr Ser Arg His Gly His His Arg
                85                  90                  95

Phe Ala Arg Met His Leu Pro Val Ala Pro Ala Cys Asn Leu Gln Cys
            100                 105                 110

Asn Tyr Cys Asn Arg Lys Phe Asp Cys Ser Asn Glu Ser Arg Pro Gly
        115                 120                 125

Val Ser Ser Thr Leu Leu Thr Pro Glu Gln Ala Val Val Lys Val Arg
    130                 135                 140

Gln Val Ala Gln Ala Ile Pro Gln Leu Ser Val Val Gly Ile Ala Gly
145                 150                 155                 160

Pro Gly Asp Pro Leu Ala Asn Ile Ala Arg Thr Phe Arg Thr Leu Glu
                165                 170                 175

Leu Ile Arg Glu Gln Leu Pro Asp Leu Lys Leu Cys Leu Ser Thr Asn
            180                 185                 190

Gly Leu Met Leu Pro Asp Ala Val Asp Arg Leu Leu Asp Val Gly Val
        195                 200                 205

Asp His Val Thr Val Thr Ile Asn Thr Leu Asp Ala Glu Ile Ala Ala
    210                 215                 220

Gln Ile Tyr Ala Trp Leu Trp Leu Asp Gly Glu Arg Tyr Ser Gly Arg
225                 230                 235                 240

Glu Ala Gly Glu Ile Leu Ile Ala Arg Gln Leu Glu Gly Val Arg Arg
                245                 250                 255

Leu Thr Ala Lys Gly Val Leu Val Lys Ile Asn Ser Val Leu Ile Pro
            260                 265                 270

Gly Ile Asn Asp Ser Gly Met Ala Asp Val Ser Arg Ala Leu Arg Ala
        275                 280                 285

Ser Gly Ala Phe Ile His Asn Ile Met Pro Leu Ile Ala Arg Pro Glu
    290                 295                 300

His Gly Thr Val Phe Gly Leu Asn Gly Gln Pro Glu Pro Asp Ala Glu
305                 310                 315                 320

Thr Leu Ala Ala Thr Arg Ser Arg Cys Gly Glu Val Met Pro Gln Met
                325                 330                 335

Thr His Cys His Gln Cys Arg Ala Asp Ala Ile Gly Met Leu Gly Glu
            340                 345                 350

Asp Arg Ser Gln Gln Phe Thr Gln Leu Pro Ala Pro Glu Ser Leu Pro
        355                 360                 365

Ala Trp Leu Pro Ile Leu His Gln Arg Ala Gln Leu His Ala Ser Ile
    370                 375                 380

Ala Thr Arg Gly Glu Ser Glu Ala Asp Asp Ala Cys Leu Val Ala Val
385                 390                 395                 400

Ala Ser Ser Arg Gly Asp Val Ile Asp Cys His Phe Gly His Ala Asp
                405                 410                 415

Arg Phe Tyr Ile Tyr Ser Leu Ser Ala Ala Gly Met Val Leu Val Asn
            420                 425                 430

Glu Arg Phe Thr Pro Lys Tyr Cys Gln Gly Arg Asp Asp Cys Glu Pro
        435                 440                 445

Gln Asp Asn Ala Ala Arg Phe Ala Ala Ile Leu Glu Leu Leu Ala Asp
```

450 455 460

Val Lys Ala Val Phe Cys Val Arg Ile Gly His Thr Pro Trp Gln Gln
465 470 475 480

Leu Glu Gln Glu Gly Ile Glu Pro Cys Val Asp Gly Ala Trp Arg Pro
485 490 495

Val Ser Glu Val Leu Pro Ala Trp Trp Gln Gln Arg Arg Gly Ser Trp
500 505 510

Pro Ala Ala Leu Pro His Lys Gly Val Ala Gly Gly Tyr Pro Tyr Asp
515 520 525

Val Pro Asp Tyr Ala
530

<210> SEQ ID NO 148
<211> LENGTH: 479
<212> TYPE: PRT
<213> ORGANISM: Azospirillum brasilense

<400> SEQUENCE: 148

Met Ser Leu Ser Val Asn Glu Gly Val Asp Val Lys Gly Leu Val Asp
1 5 10 15

Lys Val Leu Glu Ala Tyr Pro Glu Lys Ser Arg Lys Arg Arg Ala Lys
20 25 30

His Leu Asn Val Leu Glu Ala Glu Ala Lys Asp Cys Gly Val Lys Ser
35 40 45

Asn Ile Lys Ser Ile Pro Gly Val Met Thr Ile Arg Gly Cys Ala Tyr
50 55 60

Ala Gly Ser Lys Gly Val Val Trp Gly Pro Ile Lys Asp Met Ile His
65 70 75 80

Ile Ser His Gly Pro Val Gly Cys Gly Tyr Tyr Ser Trp Ser Gly Arg
85 90 95

Arg Asn Tyr Tyr Val Gly Asp Thr Gly Val Asp Ser Trp Gly Thr Met
100 105 110

His Phe Thr Ser Asp Phe Gln Glu Lys Asp Ile Val Phe Gly Gly Asp
115 120 125

Lys Lys Leu His Lys Val Ile Glu Glu Ile Asn Glu Leu Phe Pro Leu
130 135 140

Val Asn Gly Ile Ser Ile Gln Ser Glu Cys Pro Ile Gly Leu Ile Gly
145 150 155 160

Asp Asp Ile Glu Ala Val Ala Arg Ala Lys Ser Glu Glu Leu Gly Lys
165 170 175

Pro Val Val Pro Val Arg Cys Glu Gly Phe Arg Gly Val Ser Gln Ser
180 185 190

Leu Gly His His Ile Ala Asn Asp Val Ile Arg Asp Trp Ile Phe Glu
195 200 205

Lys Thr Glu Pro Lys Glu Gly Phe Val Ser Thr Pro Tyr Asp Val Thr
210 215 220

Ile Ile Gly Asp Tyr Asn Ile Gly Gly Asp Ala Trp Ala Ser Arg Ile
225 230 235 240

Leu Leu Glu Glu Ile Gly Leu Arg Val Ile Ala Gln Trp Ser Gly Asp
245 250 255

Gly Thr Leu Ala Glu Leu Glu Asn Thr Pro Lys Ala Lys Val Asn Leu
260 265 270

Ile His Cys Tyr Arg Ser Met Asn Tyr Ile Ala Arg His Met Glu Glu
275 280 285

Lys Phe Gly Ile Pro Trp Met Glu Tyr Asn Phe Phe Gly Pro Ser Gln
290 295 300

Ile Ala Glu Ser Leu Arg Lys Ile Ala Ala Leu Phe Asp Asp Thr Ile
305 310 315 320

Lys Glu Asn Ala Glu Lys Val Ile Ala Lys Tyr Gln Pro Met Val Asp
325 330 335

Ala Val Ile Ala Lys Phe Lys Pro Arg Leu Glu Gly Lys Lys Val Met
340 345 350

Ile Tyr Val Gly Gly Leu Arg Pro Arg His Val Val Asp Ala Tyr His
355 360 365

Asp Leu Gly Met Glu Ile Val Gly Thr Gly Tyr Glu Phe Ala His Asn
370 375 380

Asp Asp Tyr Gln Arg Thr Gln His Tyr Val Lys Glu Gly Thr Leu Ile
385 390 395 400

Tyr Asp Asp Val Thr Ala Phe Glu Leu Glu Lys Phe Val Glu Val Met
405 410 415

Arg Pro Asp Leu Val Ala Ser Gly Ile Lys Glu Lys Tyr Val Phe Gln
420 425 430

Lys Met Gly Leu Pro Phe Arg Gln Met His Ser Trp Asp Tyr Ser Gly
435 440 445

Pro Tyr His Gly Tyr Asp Gly Phe Ala Ile Phe Ala Arg Asp Met Asp
450 455 460

Leu Ala Ile Asn Asn Pro Val Trp Gly Ile Met Lys Ala Pro Phe
465 470 475

<210> SEQ ID NO 149
<211> LENGTH: 492
<212> TYPE: PRT
<213> ORGANISM: Azotobacter vinelandii

<400> SEQUENCE: 149

Met Thr Gly Met Ser Arg Glu Glu Val Glu Ser Leu Ile Gln Glu Val
1 5 10 15

Leu Glu Val Tyr Pro Glu Lys Ala Arg Lys Asp Arg Asn Lys His Leu
20 25 30

Ala Val Asn Asp Pro Ala Val Thr Gln Ser Lys Lys Cys Ile Ile Ser
35 40 45

Asn Lys Lys Ser Gln Pro Gly Leu Met Thr Ile Arg Gly Cys Ala Tyr
50 55 60

Ala Gly Ser Lys Gly Val Val Trp Gly Pro Ile Lys Asp Met Ile His
65 70 75 80

Ile Ser His Gly Pro Val Gly Cys Gly Gln Tyr Ser Arg Ala Gly Arg
85 90 95

Arg Asn Tyr Tyr Ile Gly Thr Thr Gly Val Asn Ala Phe Val Thr Met
100 105 110

Asn Phe Thr Ser Asp Phe Gln Glu Lys Asp Ile Val Phe Gly Gly Asp
115 120 125

Lys Lys Leu Ala Lys Leu Ile Asp Glu Val Glu Thr Leu Phe Pro Leu
130 135 140

Asn Lys Gly Ile Ser Val Gln Ser Glu Cys Pro Ile Gly Leu Ile Gly
145 150 155 160

Asp Asp Ile Glu Ser Val Ser Lys Val Lys Gly Ala Glu Leu Ser Lys
165 170 175

Thr Ile Val Pro Val Arg Cys Glu Gly Phe Arg Gly Val Ser Gln Ser
180 185 190

Leu Gly His His Ile Ala Asn Asp Ala Val Arg Asp Trp Val Leu Gly
195 200 205

Lys Arg Asp Glu Asp Thr Thr Phe Ala Ser Thr Pro Tyr Asp Val Ala
210 215 220

Ile Ile Gly Asp Tyr Asn Ile Gly Gly Asp Ala Trp Ser Ser Arg Ile
225 230 235 240

Leu Leu Glu Glu Met Gly Leu Arg Cys Val Ala Gln Trp Ser Gly Asp
245 250 255

Gly Ser Ile Ser Glu Ile Glu Leu Thr Pro Lys Val Lys Leu Asn Leu
260 265 270

Val His Cys Tyr Arg Ser Met Asn Tyr Ile Ser Arg His Met Glu Glu
275 280 285

Lys Tyr Gly Ile Pro Trp Met Glu Tyr Asn Phe Phe Gly Pro Thr Lys
290 295 300

Thr Ile Glu Ser Leu Arg Ala Ile Ala Ala Lys Phe Asp Glu Ser Ile
305 310 315 320

Gln Lys Lys Cys Glu Glu Val Ile Ala Lys Tyr Lys Pro Glu Trp Glu
325 330 335

Ala Val Val Ala Lys Tyr Arg Pro Arg Leu Glu Gly Lys Arg Val Met
340 345 350

Leu Tyr Ile Gly Gly Leu Arg Pro Arg His Val Ile Gly Ala Tyr Glu
355 360 365

Asp Leu Gly Met Glu Val Val Gly Thr Gly Tyr Glu Phe Ala His Asn
370 375 380

Asp Asp Tyr Asp Arg Thr Met Lys Glu Met Gly Asp Ser Thr Leu Leu
385 390 395 400

Tyr Asp Asp Val Thr Gly Tyr Glu Phe Glu Glu Phe Val Lys Arg Ile
405 410 415

Lys Pro Asp Leu Ile Gly Ser Gly Ile Lys Glu Lys Phe Ile Phe Gln
420 425 430

Lys Met Gly Ile Pro Phe Arg Gln Met His Ser Trp Asp Tyr Ser Gly
435 440 445

Pro Tyr His Gly Phe Asp Gly Phe Ala Ile Phe Ala Arg Asp Met Asp
450 455 460

Met Thr Leu Asn Asn Pro Cys Trp Lys Lys Leu Gln Ala Pro Trp Glu
465 470 475 480

Ala Ser Glu Gly Ala Glu Lys Val Ala Ala Ser Ala
485 490

<210> SEQ ID NO 150
<211> LENGTH: 504
<212> TYPE: PRT
<213> ORGANISM: Sinorhizobium fredii

<400> SEQUENCE: 150

Met Ser Leu Asp Tyr Glu Asn Asp Ser Ala Leu His Gln Glu Leu Ile
1 5 10 15

Thr Gln Val Leu Ser Gln Tyr Pro His Lys Ala Ala Lys Arg Arg Gln
20 25 30

Lys His Leu Ser Val Ala Ser Asp Arg Glu Ala Val Gly Glu Glu Gly
35 40 45

Glu Thr Leu Ser Glu Cys Asp Val Lys Ser Asn Ile Lys Ser Ile Pro
50 55 60

Gly Val Met Thr Ile Arg Gly Cys Ala Tyr Ala Gly Ser Lys Gly Val

```
65                  70                  75                  80

Val Trp Gly Pro Val Lys Asp Met Val His Ile Ser His Gly Pro Val
                85                  90                  95

Gly Cys Gly Gln Tyr Ser Trp Ser Gln Arg Arg Asn Tyr Tyr Val Gly
            100                 105                 110

Thr Thr Gly Val Asp Thr Phe Val Thr Met Gln Phe Thr Ser Asp Phe
        115                 120                 125

Gln Glu Lys Asp Ile Val Phe Gly Gly Asp Lys Lys Leu Glu Gln Val
    130                 135                 140

Ile Asp Glu Ile Glu Glu Leu Phe Pro Leu Asn Asn Gly Ile Thr Ile
145                 150                 155                 160

Gln Ser Glu Cys Pro Ile Gly Leu Ile Gly Asp Asp Ile Glu Ala Val
                165                 170                 175

Ser Arg Lys Lys Ala Ala Glu His Glu Thr Thr Ile Val Pro Val Arg
            180                 185                 190

Cys Glu Gly Phe Arg Gly Val Ser Gln Ser Leu Gly His His Ile Ala
        195                 200                 205

Asn Asp Ala Ile Arg Asp Trp Val Phe Asp Lys Ala Asp Gly Lys Thr
    210                 215                 220

Asp Val Glu Phe Glu Thr Gly Pro Tyr Asp Val Asn Val Ile Gly Asp
225                 230                 235                 240

Tyr Asn Ile Gly Gly Asp Ala Trp Ala Ser Arg Ile Leu Leu Glu Glu
                245                 250                 255

Ile Gly Leu Arg Val Val Gly Asn Trp Ser Gly Asp Ala Thr Leu Ala
            260                 265                 270

Glu Val Glu Arg Ala Pro Arg Ala Lys Leu Asn Leu Ile His Cys Tyr
        275                 280                 285

Arg Ser Met Asn Tyr Ile Cys Arg His Met Glu Glu Arg Tyr Ala Ile
    290                 295                 300

Pro Trp Met Glu Tyr Asn Phe Phe Gly Pro Ser Gln Ile Glu Ala Ser
305                 310                 315                 320

Leu Arg Lys Ile Ala Arg His Phe Gly Pro Thr Ile Glu Glu Arg Ala
                325                 330                 335

Glu Arg Val Ile Ala Lys Tyr Arg Pro Leu Val Asp Ala Val Ile Asp
            340                 345                 350

Lys Tyr Trp Pro Arg Leu Gln Gly Lys Arg Val Met Leu Tyr Val Gly
        355                 360                 365

Gly Leu Arg Pro Arg His Val Ile Thr Ala Tyr Glu Asp Leu Gly Met
    370                 375                 380

Gln Ile Val Gly Thr Gly Tyr Glu Phe Ala His Asn Asp Asp Tyr Gln
385                 390                 395                 400

Arg Thr Gly His Tyr Val Lys Thr Gly Thr Leu Ile Tyr Asp Asp Ala
                405                 410                 415

Thr Ser Tyr Glu Leu Asp Thr Phe Ile Glu Arg Ile Arg Pro Asp Leu
            420                 425                 430

Val Gly Ser Gly Ile Lys Glu Lys Tyr Pro Val Gln Lys Met Gly Ile
        435                 440                 445

Pro Phe Arg Gln Met His Ser Trp Asp Tyr Ser Gly Pro Tyr His Gly
    450                 455                 460

Tyr Asp Gly Phe Ala Ile Phe Ala Arg Asp Met Asp Leu Ala Ile Asn
465                 470                 475                 480

Asn Pro Val Trp Asp Leu Tyr Asp Ala Pro Trp Lys Lys Met Thr Val
                485                 490                 495
```

```
Pro Thr Ala Ala Val Ala Ala Glu
            500


<210> SEQ ID NO 151
<211> LENGTH: 543
<212> TYPE: PRT
<213> ORGANISM: Chlorobium tepidum

<400> SEQUENCE: 151

Met Glu Ala Lys Val Leu Ile Pro Asp Pro Ser Lys Ile Lys Glu Glu
1               5                   10                  15

Leu Ile Asn Lys Tyr Pro Ala Lys Val Ala Lys Lys Arg Ser Lys Ser
            20                  25                  30

Ile Val Val Asn Asp Pro Glu Ile Val Pro Glu Val Gln Ala Asn Val
        35                  40                  45

Arg Thr Val Pro Gly Ile Ile Thr Gln Arg Gly Cys Ala Tyr Ala Gly
    50                  55                  60

Cys Lys Gly Val Val Leu Gly Pro Thr Arg Asp Ile Val Asn Ile Val
65                  70                  75                  80

His Gly Pro Ile Gly Cys Ser Phe Tyr Ala Trp Leu Thr Arg Arg Asn
                85                  90                  95

Gln Thr Arg Pro Glu Thr Pro Glu His Glu Asn Tyr Ile Thr Tyr Cys
            100                 105                 110

Phe Ser Thr Asp Met Gln Glu Glu His Val Val Phe Gly Gly Glu Lys
        115                 120                 125

Lys Leu Lys Val Ala Ile Gln Glu Ala Tyr Asp Leu Phe His Pro Lys
    130                 135                 140

Ala Ile Ala Ile Phe Ser Thr Cys Pro Val Gly Leu Ile Gly Asp Asp
145                 150                 155                 160

Val His Ala Val Ala Arg Glu Met Lys Glu Lys Leu Gly Asp Cys Asn
                165                 170                 175

Val Phe Gly Phe Ser Cys Glu Gly Tyr Arg Gly Val Ser Gln Ser Ala
            180                 185                 190

Gly His His Ile Ala Asn Asn Gly Val Phe Lys His Met Val Gly Asn
        195                 200                 205

Asn Asn Glu Val Lys Pro Gly Lys Phe Lys Leu Asn Leu Leu Gly Glu
    210                 215                 220

Tyr Asn Ile Gly Gly Asp Ala Phe Glu Ile Glu Arg Leu Leu Glu Lys
225                 230                 235                 240

Cys Gly Ile Thr Leu Val Ala Ser Phe Ser Gly Asn Ser Thr Val Gly
                245                 250                 255

Ala Ile Glu Asn Ala His Thr Ala Asp Leu Asn Val Ile Met Cys His
            260                 265                 270

Arg Ser Ile Asn Tyr Met Gly Asp Met Met Glu Thr Lys Tyr Gly Ile
        275                 280                 285

Pro Trp Met Lys Val Asn Phe Val Gly Ala Glu Ser Thr Ala Lys Ser
    290                 295                 300

Leu Arg Lys Ile Ala Glu Tyr Phe Gly Asp Glu Glu Leu Lys Ala Lys
305                 310                 315                 320

Val Glu Glu Val Ile Ala Glu Glu Val Pro Ala Val Lys Ala Ile Ile
                325                 330                 335

Asp Glu Ile Arg Pro Arg Thr Glu Gly Lys Thr Ala Met Leu Phe Val
            340                 345                 350

Gly Gly Ser Arg Ala His His Tyr Gln Asp Leu Phe Ser Glu Leu Gly
```

```
        355                 360                 365

Met Thr Thr Ile Ala Ala Gly Tyr Glu Phe Ala His Arg Asp Asp Tyr
    370                 375                 380

Glu Gly Arg Glu Val Leu Pro Lys Ile Lys Ile Asp Ala Asp Ser Lys
385                 390                 395                 400

Asn Ile Glu Glu Leu Lys Val Thr Ala Asp Pro Glu Leu Tyr Asn Pro
                405                 410                 415

Arg Lys Ser Lys Ala Glu Leu Glu Glu Leu Lys Ala Lys Gly Leu Glu
            420                 425                 430

Ile Asn Gly Tyr Glu Gly Met Met Lys Gln Met Met Lys Lys Thr Leu
        435                 440                 445

Val Val Asp Asp Ile Ser His Tyr Glu Ser Glu Lys Leu Ile Glu Met
    450                 455                 460

Tyr Lys Pro Asp Ile Phe Cys Ala Gly Ile Lys Glu Lys Tyr Val Val
465                 470                 475                 480

Gln Lys Met Gly Val Pro Leu Lys Gln Leu His Ser Tyr Asp Tyr Gly
                485                 490                 495

Gly Pro Tyr Thr Gly Phe Lys Gly Ala Val Asn Phe Tyr Lys Asp Ile
            500                 505                 510

Asp Arg Met Val Asn Asn Pro Val Trp Lys Met Ile Lys Ala Pro Trp
        515                 520                 525

Glu Lys Ser Glu Pro Glu Ser Leu Glu Ala Ser Tyr Val Ala Ser
    530                 535                 540


<210> SEQ ID NO 152
<211> LENGTH: 544
<212> TYPE: PRT
<213> ORGANISM: Desulfovibrio vulgaris

<400> SEQUENCE: 152

Met Ala Leu Lys His Lys Ser Ile Pro Asp Val Ala Thr Val Lys Glu
1               5                   10                  15

Glu Leu Leu Lys Lys Tyr Pro Thr Lys Val Ala Arg Lys Arg Ala Lys
            20                  25                  30

Gln Ile Val Ile Asn Asp Val Lys Asp Gly Asp Val Val Pro Glu Val
        35                  40                  45

Gln Ala Asn Val Arg Thr Thr Pro Gly Ile Ile Thr Met Arg Gly Cys
    50                  55                  60

Thr Tyr Ala Gly Cys Lys Gly Val Ile Leu Gly Pro Thr Arg Asp Ile
65                  70                  75                  80

Val Asn Ile Thr His Gly Pro Ile Gly Cys Gly Phe Tyr Ser Trp Leu
                85                  90                  95

Thr Arg Arg Asn Gln Thr Lys Ala Pro Leu Glu Ser Ser Glu Asn Phe
            100                 105                 110

Met Pro Tyr Ala Phe Ser Thr Asp Met Gln Asp Glu Asp Ile Ile Phe
        115                 120                 125

Gly Gly Glu Lys Lys Leu Ile Ala Ala Ile Gln Glu Ala Tyr Asp Thr
    130                 135                 140

Phe His Pro Lys Ala Ile Ala Ile Phe Ala Thr Cys Pro Val Gly Leu
145                 150                 155                 160

Ile Gly Asp Asp Ile His Ala Val Ala Arg Lys Met Lys Glu Lys Leu
                165                 170                 175

Gly Ile Asn Ile Phe Ala Phe Ser Cys Glu Gly Tyr Lys Gly Val Ser
            180                 185                 190
```

```
Gln Ser Ala Gly His His Ile Ala Asn Asn Gln Ile Phe Thr His Val
        195                 200                 205

Val Gly Glu Asp Asp Thr Pro Lys Leu Gly Glu Tyr Lys Ile Asn Met
    210                 215                 220

Leu Gly Glu Tyr Asn Ile Gly Gly Asp Ala Phe Glu Leu Glu Arg Val
225                 230                 235                 240

Leu Glu Lys Cys Gly Ile Thr Leu Val Ser Thr Phe Ser Gly Asn Ser
                245                 250                 255

Thr Tyr Glu His Phe Ala Thr Ala His Gln Ala Asp Leu Asn Ala Val
            260                 265                 270

Met Cys His Arg Ser Ile Asn Tyr Val Ala Glu Met Met Glu Thr Lys
        275                 280                 285

Tyr Gly Ile Pro Trp Ile Lys Val Asn Phe Ile Gly Ala Glu Ser Ser
    290                 295                 300

Ala Lys Ser Leu Arg Lys Ile Ala Gln Tyr Phe Gly Asp Lys Lys Leu
305                 310                 315                 320

Ile Asp Arg Val Glu Glu Val Ile Ala Glu Glu Met Pro Ala Val His
                325                 330                 335

Ala Ala Leu Glu Asp Val Lys Pro Phe Thr Glu Gly Lys Thr Ala Met
            340                 345                 350

Leu Phe Val Gly Gly Ser Arg Ala His His Tyr Gln Asp Leu Phe Thr
        355                 360                 365

Glu Met Gly Met Lys Thr Ile Ala Ala Gly Tyr Glu Phe Ala His Arg
    370                 375                 380

Asp Asp Tyr Glu Gly Arg Lys Val Met Pro Thr Ile Lys Val Asp Ala
385                 390                 395                 400

Asp Ser Arg Asn Ile Glu Glu Ile Glu Val Thr Pro Asp Ser Thr Arg
                405                 410                 415

Phe Val Pro Arg Lys Ser Asp Glu Asp Leu Lys Arg Leu Ala Glu Ala
            420                 425                 430

Gly Phe Thr Phe Lys Asp Tyr Glu Gly Met Met Pro Gln Met Glu Ser
        435                 440                 445

Asp Thr Leu Val Ile Asp Asp Leu Asn Gln Tyr Glu Ala Asp Lys Leu
    450                 455                 460

Ile Glu Leu Leu Lys Pro Asp Val Phe Cys Ala Gly Ile Lys Glu Lys
465                 470                 475                 480

Phe Ser Val Gln Lys Met Gly Val Pro Met Lys Gln Leu His Ser Tyr
                485                 490                 495

Asp Tyr Gly Gly Pro Tyr Ala Gly Phe Lys Gly Ala Val Asn Phe Tyr
            500                 505                 510

Thr Glu Ile Lys Arg Leu Val Thr Ser Lys Val Trp Ser Asp Leu Lys
        515                 520                 525

Ala Pro Trp Glu Glu Asn Pro Glu Leu Ser Ala Thr Tyr Val Trp Glu
    530                 535                 540
```

<210> SEQ ID NO 153
<211> LENGTH: 538
<212> TYPE: PRT
<213> ORGANISM: Artificial Sequence
<220> FEATURE:
<223> OTHER INFORMATION: Amino acid sequence of wild-type Desulfotomaculum ferrireducens NifD polypeptide, 539aa

<400> SEQUENCE: 153

```
Met Ala Ile Asn Glu Lys Val Leu Asp Glu Ile Leu Ser Gln Tyr Pro
1               5                   10                  15
```

```
Thr Lys Val Lys Lys Asn Arg Lys Lys His Ile Ile Ile Lys Asp Pro
            20                  25                  30

Asn Gln Ala Arg Gln Glu Ile Glu Ala Asn Thr Arg Thr Ile Pro Gly
        35                  40                  45

Ile Ile Thr Asn Arg Gly Cys Ala Tyr Ala Gly Cys Lys Gly Val Val
    50                  55                  60

Leu Gly Pro Leu Lys Asp Val Val His Ile Thr His Gly Pro Ile Gly
65                  70                  75                  80

Cys Gly Tyr Tyr Ser Trp Leu Thr Arg Arg Asn Lys Ala Ala Ser Ser
                85                  90                  95

Asp Pro Thr Lys Asn Phe Ile Ser Tyr Cys Phe Ser Thr Asp Met Gln
            100                 105                 110

Glu Ser Asp Ile Val Phe Gly Gly Glu Lys Lys Leu Ala Arg Met Ile
        115                 120                 125

Asp Glu Val Met Glu Ile Phe Lys Pro Asn Ala Ile Thr Ile Ser Ala
    130                 135                 140

Thr Cys Pro Val Gly Leu Ile Gly Asp Asp Leu Gly Ala Val Ala Lys
145                 150                 155                 160

Ala Ala Glu Gln Lys His Gly Ile Thr Val Met His Phe Asn Cys Glu
                165                 170                 175

Gly Tyr Lys Gly Val Ser Gln Ser Ala Gly His His Ile Ala Asn Asn
            180                 185                 190

Thr Leu Met Glu Arg Val Ile Gly Ala Gly Glu Leu Glu Ala Ala Pro
        195                 200                 205

Gly Arg Tyr Pro Ile Asn Ile Leu Gly Glu Tyr Asn Ile Gly Gly Asp
    210                 215                 220

Ser Trp Glu Ile Glu Arg Ile Leu Arg Glu Ile Gly Tyr Thr Val Leu
225                 230                 235                 240

Ser Val Met Thr Gly Asp Gly Ser Tyr Glu Glu Leu Lys Asn Ala His
                245                 250                 255

Val Ala Glu Leu Asn Leu Val Gln Cys His Arg Ser Ile Asn Tyr Ile
            260                 265                 270

Ala Glu Met Leu Glu Thr Lys Tyr Gly Thr Pro Trp Leu Lys Val Asn
        275                 280                 285

Phe Ile Gly Ile Gln Ser Thr Ile Asp Ser Leu Arg Asn Met Ala Ile
    290                 295                 300

Tyr Phe Gly Asp Pro Glu Leu Thr Arg Arg Thr Glu Glu Val Ile Ala
305                 310                 315                 320

Lys Glu Leu Ala Glu Val Glu Pro Val Met Glu Gln Tyr Lys Lys Ile
                325                 330                 335

Cys Gln Gly Lys Thr Ala Phe Cys Phe Val Gly Gly Ser Arg Gly His
            340                 345                 350

His Tyr Gln Gly Leu Phe Ala Glu Leu Gly Met Glu Thr Val Leu Ala
        355                 360                 365

Gly Tyr Glu Phe Ala His Arg Asp Asp Tyr Glu Gly Arg Asp Val Leu
    370                 375                 380

Pro Gln Ile Lys Leu Asp Ala Asp Asn Lys Asn Ile Pro Glu Leu His
385                 390                 395                 400

Val Glu Pro Asp Gln Arg Arg Phe Lys Leu Lys Val Pro Arg Glu Arg
                405                 410                 415

Met Glu Glu Leu Lys Lys Lys Ile Pro Leu Ser Tyr Tyr Ala Gly Met
            420                 425                 430
```

Met Val Asp Met Lys Gly Gly His Val Val Val Asp Asp Leu Asn His
435 440 445

Tyr Glu Thr Glu Gln Phe Ile Lys Leu Leu Lys Pro Asp Ile Phe Ala
450 455 460

Ser Gly Ile Lys Asp Lys Tyr Val Val Gln Lys Met Gly Ile Pro Ala
465 470 475 480

Lys Gln Leu His Ser Tyr Asp Tyr Ser Gly Pro Tyr Ala Gly Phe Lys
485 490 495

Gly Ala Val Lys Phe Ala Glu Asp Ile Thr Met Ser Phe Ile Ser Pro
500 505 510

Thr Trp Asn Phe Ile Thr Pro Pro Trp Lys Asn Gln Pro Ile Leu Glu
515 520 525

Gly Glu Ile Val Glu Gly Gly Cys Ser Thr
530 535

<210> SEQ ID NO 154
<211> LENGTH: 4
<212> TYPE: PRT
<213> ORGANISM: Artificial Sequence
<220> FEATURE:
<223> OTHER INFORMATION: peptide sequence
<220> FEATURE:
<221> NAME/KEY: X
<222> LOCATION: (4)..(4)
<223> OTHER INFORMATION: any amino acid other than Y

<400> SEQUENCE: 154

Arg Arg Asn Xaa
1

<210> SEQ ID NO 155
<211> LENGTH: 9
<212> TYPE: PRT
<213> ORGANISM: Artificial Sequence
<220> FEATURE:
<223> OTHER INFORMATION: Tryptic peptide sequence from NifM

<400> SEQUENCE: 155

Asp Ala Phe Ala Pro Leu Ala Gln Arg
1 5

<210> SEQ ID NO 156
<211> LENGTH: 10
<212> TYPE: PRT
<213> ORGANISM: Artificial Sequence
<220> FEATURE:
<223> OTHER INFORMATION: Tryptic peptide sequence from NifM

<400> SEQUENCE: 156

Asp Tyr Leu Trp Gln Gln Ser Gln Gln Arg
1 5 10

<210> SEQ ID NO 157
<211> LENGTH: 14
<212> TYPE: PRT
<213> ORGANISM: Artificial Sequence
<220> FEATURE:
<223> OTHER INFORMATION: Tryptic peptide sequence from CAT polypeptide

<400> SEQUENCE: 157

Ile Thr Gly Tyr Thr Thr Val Asp Ile Ser Gln Trp His Arg
1 5 10

<210> SEQ ID NO 158

<211> LENGTH: 9
<212> TYPE: PRT
<213> ORGANISM: Artificial Sequence
<220> FEATURE:
<223> OTHER INFORMATION: Tryptic peptide sequence from CAT polypeptide

<400> SEQUENCE: 158

Leu Met Asn Ala His Pro Glu Phe Arg
1 5

<210> SEQ ID NO 159
<211> LENGTH: 7
<212> TYPE: PRT
<213> ORGANISM: Artificial Sequence
<220> FEATURE:
<223> OTHER INFORMATION: Tryptic peptide sequence from CAT polypeptide

<400> SEQUENCE: 159

Tyr Tyr Thr Gln Gly Asp Lys
1 5

<210> SEQ ID NO 160
<211> LENGTH: 358
<212> TYPE: PRT
<213> ORGANISM: Artificial Sequence
<220> FEATURE:
<223> OTHER INFORMATION: Amino acid sequence of the MTP-FAγ51::NifU::TwinStrep fusion polypeptide encoded by SN166. Amino acids 1-54 are the MTP-FAγ51 sequence with an additional methionine translational start and C-terminal GG, amino acids 55-328 are the NifU sequence, and

<400> SEQUENCE: 160

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Trp Asn Tyr Ser Glu Lys Val Lys Asp
50 55 60

His Phe Phe Asn Pro Arg Asn Ala Arg Val Val Asp Asn Ala Asn Ala
65 70 75 80

Val Gly Asp Val Gly Ser Leu Ser Cys Gly Asp Ala Leu Arg Leu Met
85 90 95

Leu Arg Val Asp Pro Gln Ser Glu Ile Ile Glu Glu Ala Gly Phe Gln
100 105 110

Thr Phe Gly Cys Gly Ser Ala Ile Ala Ser Ser Ser Ala Leu Thr Glu
115 120 125

Leu Ile Ile Gly His Thr Leu Ala Glu Ala Gly Gln Ile Thr Asn Gln
130 135 140

Gln Ile Ala Asp Tyr Leu Asp Gly Leu Pro Pro Glu Lys Met His Cys
145 150 155 160

Ser Val Met Gly Gln Glu Ala Leu Arg Ala Ala Ile Ala Asn Phe Arg
165 170 175

Gly Glu Ser Leu Glu Glu Glu His Asp Glu Gly Lys Leu Ile Cys Lys
180 185 190

Cys Phe Gly Val Asp Glu Gly His Ile Arg Arg Ala Val Gln Asn Asn
195 200 205

Gly Leu Thr Thr Leu Ala Glu Val Ile Asn Tyr Thr Lys Ala Gly Gly
210 215 220

Gly Cys Thr Ser Cys His Glu Lys Ile Glu Leu Ala Leu Ala Glu Ile
225 230 235 240

Leu Ala Gln Gln Pro Gln Thr Thr Pro Ala Val Ala Ser Gly Lys Asp
245 250 255

Pro His Trp Gln Ser Val Val Asp Thr Ile Ala Glu Leu Arg Pro His
260 265 270

Ile Gln Ala Asp Gly Gly Asp Met Ala Leu Leu Ser Val Thr Asn His
275 280 285

Gln Val Thr Val Ser Leu Ser Gly Ser Cys Ser Gly Cys Met Met Thr
290 295 300

Asp Met Thr Leu Ala Trp Leu Gln Gln Lys Leu Met Glu Arg Thr Gly
305 310 315 320

Cys Tyr Met Glu Val Val Ala Ala Gly Gly Trp Ser His Pro Gln Phe
325 330 335

Glu Lys Gly Gly Gly Ser Gly Gly Gly Ser Gly Gly Ser Ala Trp Ser
340 345 350

His Pro Gln Phe Glu Lys
355

<210> SEQ ID NO 161
<211> LENGTH: 484
<212> TYPE: PRT
<213> ORGANISM: Artificial Sequence
<220> FEATURE:
<223> OTHER INFORMATION: Amino acid sequence of the MTP-FAγ51::NifS::TwinStrep fusion polypeptide encoded by SN231. Amino acids 1-54 are the MTP-FAγ51 sequence with an additional methionine translational start and C-terminal GG, amino acids 55-454 are the NifS sequence, and

<400> SEQUENCE: 161

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Met Lys Gln Val Tyr Leu Asp Asn Asn Ala
50 55 60

Thr Thr Arg Leu Asp Pro Met Val Leu Glu Ala Met Met Pro Phe Leu
65 70 75 80

Thr Asp Phe Tyr Gly Asn Pro Ser Ser Ile His Asp Phe Gly Ile Pro
85 90 95

Ala Gln Ala Ala Leu Glu Arg Ala His Gln Gln Ala Ala Ala Leu Leu
100 105 110

Gly Ala Glu Tyr Pro Ser Glu Ile Ile Phe Thr Ser Cys Ala Thr Glu
115 120 125

Ala Thr Ala Thr Ala Ile Ala Ser Ala Ile Ala Leu Leu Pro Glu Arg
130 135 140

Arg Glu Ile Ile Thr Ser Val Val Glu His Pro Ala Thr Leu Ala Ala
145 150 155 160

Cys Glu His Leu Glu Arg Gln Gly Tyr Arg Ile His Arg Ile Ala Val
165 170 175

Asp Ser Glu Gly Ala Leu Asp Met Ala Gln Phe Arg Ala Ala Leu Ser
180 185 190

Pro Arg Val Ala Leu Val Ser Val Met Trp Ala Asn Asn Glu Thr Gly

```
        195                 200                 205

Val Leu Phe Pro Ile Gly Glu Met Ala Glu Leu Ala His Glu Gln Gly
    210                 215                 220

Ala Leu Phe His Cys Asp Ala Val Gln Val Val Gly Lys Ile Pro Ile
225                 230                 235                 240

Ala Val Gly Gln Thr Arg Ile Asp Met Leu Ser Cys Ser Ala His Lys
                245                 250                 255

Phe His Gly Pro Lys Gly Val Gly Cys Leu Tyr Leu Arg Arg Gly Thr
            260                 265                 270

Arg Phe Arg Pro Leu Leu Arg Gly Gly His Gln Glu Tyr Gly Arg Arg
        275                 280                 285

Ala Gly Thr Glu Asn Ile Cys Gly Ile Val Gly Met Gly Ala Ala Cys
    290                 295                 300

Glu Leu Ala Asn Ile His Leu Pro Gly Met Thr His Ile Gly Gln Leu
305                 310                 315                 320

Arg Asn Arg Leu Glu His Arg Leu Leu Ala Ser Val Pro Ser Val Met
                325                 330                 335

Val Met Gly Gly Gly Gln Pro Arg Val Pro Gly Thr Val Asn Leu Ala
            340                 345                 350

Phe Glu Phe Ile Glu Gly Glu Ala Ile Leu Leu Leu Leu Asn Gln Ala
        355                 360                 365

Gly Ile Ala Ala Ser Ser Gly Ser Ala Cys Thr Ser Gly Ser Leu Glu
    370                 375                 380

Pro Ser His Val Met Arg Ala Met Asn Ile Pro Tyr Thr Ala Ala His
385                 390                 395                 400

Gly Thr Ile Arg Phe Ser Leu Ser Arg Tyr Thr Arg Glu Lys Glu Ile
                405                 410                 415

Asp Tyr Val Val Ala Thr Leu Pro Pro Ile Ile Asp Arg Leu Arg Ala
            420                 425                 430

Leu Ser Pro Tyr Trp Gln Asn Gly Lys Pro Arg Pro Ala Asp Ala Val
        435                 440                 445

Phe Thr Pro Val Tyr Gly Gly Gly Trp Ser His Pro Gln Phe Glu Lys
    450                 455                 460

Gly Gly Gly Ser Gly Gly Gly Ser Gly Gly Ser Ala Trp Ser His Pro
465                 470                 475                 480

Gln Phe Glu Lys


<210> SEQ ID NO 162
<211> LENGTH: 9
<212> TYPE: PRT
<213> ORGANISM: Artificial Sequence
<220> FEATURE:
<223> OTHER INFORMATION: Peptide sequence

<400> SEQUENCE: 162

Ile Ser Thr Gln Val Val Arg Asn Met
1               5


<210> SEQ ID NO 163
<211> LENGTH: 384
<212> TYPE: PRT
<213> ORGANISM: Artificial Sequence
<220> FEATURE:
<223> OTHER INFORMATION: Amino acid sequence of the NifV polypeptide
      from A. vinelandii (AvNifV; Accession No. CP001157); 384aa.

<400> SEQUENCE: 163
```

```
Met Ala Ser Val Ile Ile Asp Asp Thr Thr Leu Arg Asp Gly Glu Gln
1               5                   10                  15

Ser Ala Gly Val Ala Phe Asn Ala Asp Glu Lys Ile Ala Ile Ala Arg
            20                  25                  30

Ala Leu Ala Glu Leu Gly Val Pro Glu Leu Glu Ile Gly Ile Pro Ser
        35                  40                  45

Met Gly Glu Glu Glu Arg Glu Val Met His Ala Ile Ala Gly Leu Gly
    50                  55                  60

Leu Ser Ser Arg Leu Leu Ala Trp Cys Arg Leu Cys Asp Val Asp Leu
65                  70                  75                  80

Ala Ala Ala Arg Ser Thr Gly Val Thr Met Val Asp Leu Ser Leu Pro
                85                  90                  95

Val Ser Asp Leu Met Leu His His Lys Leu Asn Arg Asp Arg Asp Trp
            100                 105                 110

Ala Leu Arg Glu Val Ala Arg Leu Val Gly Glu Ala Arg Met Ala Gly
        115                 120                 125

Leu Glu Val Cys Leu Gly Cys Glu Asp Ala Ser Arg Ala Asp Leu Glu
    130                 135                 140

Phe Val Val Gln Val Gly Glu Val Ala Gln Ala Ala Gly Ala Arg Arg
145                 150                 155                 160

Leu Arg Phe Ala Asp Thr Val Gly Val Met Glu Pro Phe Gly Met Leu
                165                 170                 175

Asp Arg Phe Arg Phe Leu Ser Arg Arg Leu Asp Met Glu Leu Glu Val
            180                 185                 190

His Ala His Asp Asp Phe Gly Leu Ala Thr Ala Asn Thr Leu Ala Ala
        195                 200                 205

Val Met Gly Gly Ala Thr His Ile Asn Thr Thr Val Asn Gly Leu Gly
    210                 215                 220

Glu Arg Ala Gly Asn Ala Ala Leu Glu Glu Cys Val Leu Ala Leu Lys
225                 230                 235                 240

Asn Leu His Gly Ile Asp Thr Gly Ile Asp Thr Arg Gly Ile Pro Ala
                245                 250                 255

Ile Ser Ala Leu Val Glu Arg Ala Ser Gly Arg Gln Val Ala Trp Gln
            260                 265                 270

Lys Ser Val Val Gly Ala Gly Val Phe Thr His Glu Ala Gly Ile His
        275                 280                 285

Val Asp Gly Leu Leu Lys His Arg Arg Asn Tyr Glu Gly Leu Asn Pro
    290                 295                 300

Asp Glu Leu Gly Arg Ser His Ser Leu Val Leu Gly Lys His Ser Gly
305                 310                 315                 320

Ala His Met Val Arg Asn Thr Tyr Arg Asp Leu Gly Ile Glu Leu Ala
                325                 330                 335

Asp Trp Gln Ser Gln Ala Leu Leu Gly Arg Ile Arg Ala Phe Ser Thr
            340                 345                 350

Arg Thr Lys Arg Ser Pro Gln Pro Ala Glu Leu Gln Asp Phe Tyr Arg
        355                 360                 365

Gln Leu Cys Glu Gln Gly Asn Pro Glu Leu Ala Ala Gly Gly Met Ala
    370                 375                 380
```

<210> SEQ ID NO 164
<211> LENGTH: 380
<212> TYPE: PRT
<213> ORGANISM: Artificial Sequence
<220> FEATURE:
<223> OTHER INFORMATION: Amino acid sequence of the KoNifV variant sequence

<400> SEQUENCE: 164

Met Glu Arg Val Leu Ile Asn Asp Thr Thr Leu Arg Asp Gly Glu Gln
1               5                   10                  15

Ser Pro Gly Val Ala Phe Arg Thr Ser Glu Lys Val Ala Ile Ala Glu
            20                  25                  30

Ala Leu Tyr Ala Ala Gly Ile Thr Ala Met Glu Val Gly Thr Pro Ala
        35                  40                  45

Met Gly Asp Glu Glu Ile Ala Arg Ile Gln Leu Val Arg Arg Gln Leu
    50                  55                  60

Pro Asp Ala Thr Leu Met Thr Trp Cys Arg Met Asn Ala Leu Glu Ile
65                  70                  75                  80

Arg Gln Ser Ala Asp Leu Gly Ile Asp Trp Val Asp Ile Ser Ile Pro
                85                  90                  95

Ala Ser Asp Lys Leu Arg Gln Tyr Lys Leu Arg Glu Pro Leu Ala Val
            100                 105                 110

Leu Leu Glu Arg Leu Ala Met Phe Ile His Leu Ala His Thr Leu Gly
        115                 120                 125

Leu Lys Val Cys Ile Gly Cys Glu Asp Ala Ser Arg Ala Ser Gly Gln
    130                 135                 140

Thr Leu Arg Ala Ile Ala Glu Val Ala Gln Gln Cys Ala Ala Ala Arg
145                 150                 155                 160

Leu Arg Tyr Ala Asp Thr Val Gly Leu Leu Asp Pro Phe Thr Thr Ala
                165                 170                 175

Ala Gln Ile Ser Ala Leu Arg Asp Val Trp Ser Gly Glu Ile Glu Met
            180                 185                 190

His Ala His Asn Asp Leu Gly Met Ala Thr Ala Asn Thr Leu Ala Ala
        195                 200                 205

Val Ser Ala Gly Ala Thr Ser Val Asn Thr Thr Val Leu Gly Leu Gly
    210                 215                 220

Glu Arg Ala Gly Asn Ala Ala Leu Glu Thr Val Ala Leu Gly Leu Glu
225                 230                 235                 240

Arg Cys Leu Gly Val Glu Thr Gly Val His Phe Ser Ala Leu Pro Ala
                245                 250                 255

Leu Cys Gln Arg Val Ala Glu Ala Ala Gln Arg Ala Ile Asp Pro Gln
            260                 265                 270

Gln Pro Leu Val Gly Glu Leu Val Phe Thr His Glu Ser Gly Val His
        275                 280                 285

Val Ala Ala Leu Leu Arg Asp Ser Glu Ser Tyr Gln Ser Ile Ala Pro
    290                 295                 300

Ser Leu Met Gly Arg Ser Tyr Arg Leu Val Leu Gly Lys His Ser Gly
305                 310                 315                 320

Arg Gln Ala Val Asn Gly Val Phe Asp Gln Met Gly Tyr His Leu Asn
                325                 330                 335

Ala Ala Gln Ile Asn Gln Leu Leu Pro Ala Ile Arg Arg Phe Ala Glu
            340                 345                 350

Asn Trp Lys Arg Ser Pro Lys Asp Tyr Glu Leu Val Ala Ile Tyr Asp
        355                 360                 365

Glu Leu Cys Gly Glu Ser Ala Leu Arg Ala Arg Gly
    370                 375                 380

<210> SEQ ID NO 165
<211> LENGTH: 12

<212> TYPE: PRT
<213> ORGANISM: Artificial Sequence
<220> FEATURE:
<223> OTHER INFORMATION: N-terminal extension (scar sequence).

<400> SEQUENCE: 165

Met Tyr Pro Tyr Asp Val Pro Asp Tyr Ala Gly Gly
1 5 10

<210> SEQ ID NO 166
<211> LENGTH: 22
<212> TYPE: PRT
<213> ORGANISM: Artificial Sequence
<220> FEATURE:
<223> OTHER INFORMATION: N-terminal AvNifV extension (scar sequence)

<400> SEQUENCE: 166

Ile Ser Thr Gln Val Val Arg Asn Arg Gly Gly Tyr Pro Tyr Asp Val
1 5 10 15

Pro Asp Tyr Ala Gly Gly
20

<210> SEQ ID NO 167
<211> LENGTH: 330
<212> TYPE: PRT
<213> ORGANISM: Artificial Sequence
<220> FEATURE:
<223> OTHER INFORMATION: Amino acid sequence of the MTP-FAγ51::HA::KoNifM polypeptide encoded by SN43. Amino acids 1-53 correspond to the MTP-FAγ51 sequence including a GG at its C-terminus, amino acids 54-64 correspond to the HA epitope including a GG at its C-terminus,

<400> SEQUENCE: 167

Met Ala Met Ala Val Phe Arg Arg Glu Gly Arg Arg Leu Leu Pro Ser
1 5 10 15

Ile Ala Ala Arg Pro Ile Ala Ala Ile Arg Ser Pro Leu Ser Ser Asp
20 25 30

Gln Glu Glu Gly Leu Leu Gly Val Arg Ser Ile Ser Thr Gln Val Val
35 40 45

Arg Asn Arg Gly Gly Tyr Pro Tyr Asp Val Pro Asp Tyr Ala Gly Gly
50 55 60

Met Asn Pro Trp Gln Arg Phe Ala Arg Gln Arg Leu Ala Arg Ser Arg
65 70 75 80

Trp Asn Arg Asp Pro Ala Ala Leu Asp Pro Ala Asp Thr Pro Ala Phe
85 90 95

Glu Gln Ala Trp Gln Arg Gln Cys His Met Glu Gln Thr Ile Val Ala
100 105 110

Arg Val Pro Glu Gly Asp Ile Pro Ala Ala Leu Leu Glu Asn Ile Ala
115 120 125

Ala Ser Leu Ala Ile Trp Leu Asp Glu Gly Asp Phe Ala Pro Pro Glu
130 135 140

Arg Ala Ala Ile Val Arg His His Ala Arg Leu Glu Leu Ala Phe Ala
145 150 155 160

Asp Ile Ala Arg Gln Ala Pro Gln Pro Asp Leu Ser Thr Val Gln Ala
165 170 175

Trp Tyr Leu Arg His Gln Thr Gln Phe Met Arg Pro Glu Gln Arg Leu
180 185 190

Thr Arg His Leu Leu Leu Thr Val Asp Asn Asp Arg Glu Ala Val His
195 200 205

```
Gln Arg Ile Leu Gly Leu Tyr Arg Gln Ile Asn Ala Ser Arg Asp Ala
    210                 215                 220

Phe Ala Pro Leu Ala Gln Arg His Ser His Cys Pro Ser Ala Leu Glu
225                 230                 235                 240

Glu Gly Arg Leu Gly Trp Ile Ser Arg Gly Leu Leu Tyr Pro Gln Leu
                245                 250                 255

Glu Thr Ala Leu Phe Ser Leu Ala Glu Asn Ala Leu Ser Leu Pro Ile
            260                 265                 270

Ala Ser Glu Leu Gly Trp His Leu Leu Trp Cys Glu Ala Ile Arg Pro
        275                 280                 285

Ala Ala Pro Met Glu Pro Gln Gln Ala Leu Glu Ser Ala Arg Asp Tyr
    290                 295                 300

Leu Trp Gln Gln Ser Gln Gln Arg His Gln Arg Gln Trp Leu Glu Gln
305                 310                 315                 320

Met Ile Ser Arg Gln Pro Gly Leu Cys Gly
                325                 330


<210> SEQ ID NO 168
<211> LENGTH: 354
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN178. Amino
      acids 1-31 correspond to the MTP-CoxIV sequence, amino acids 32-61
      correspond to the TwinStrep sequence including a GG at its
      C-terminus, and amino acids 62-354

<400> SEQUENCE: 168

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Ser Leu
    50                  55                  60

Arg Gln Ile Ala Phe Tyr Gly Lys Gly Gly Ile Gly Lys Ser Thr Thr
65                  70                  75                  80

Ser Gln Asn Thr Leu Ala Ala Leu Val Glu Leu Asp Gln Lys Ile Leu
                85                  90                  95

Ile Val Gly Cys Asp Pro Lys Ala Asp Ser Thr Arg Leu Ile Leu His
            100                 105                 110

Ala Lys Ala Gln Asp Thr Val Leu His Leu Ala Ala Glu Ala Gly Ser
        115                 120                 125

Val Glu Asp Leu Glu Leu Glu Asp Val Leu Lys Ile Gly Tyr Lys Gly
    130                 135                 140

Ile Lys Cys Val Glu Ser Gly Gly Pro Glu Pro Gly Val Gly Cys Ala
145                 150                 155                 160

Gly Arg Gly Val Ile Thr Ser Ile Asn Phe Leu Glu Glu Asn Gly Ala
                165                 170                 175

Tyr Asp Asp Val Asp Tyr Val Ser Tyr Asp Val Leu Gly Asp Val Val
            180                 185                 190

Cys Gly Gly Phe Ala Met Pro Ile Arg Glu Asn Lys Ala Gln Glu Ile
        195                 200                 205

Tyr Ile Val Met Ser Gly Glu Met Met Ala Leu Tyr Ala Ala Asn Asn
    210                 215                 220
```

Ile Ala Lys Gly Ile Leu Lys Tyr Ala His Ser Gly Gly Val Arg Leu
225 230 235 240

Gly Gly Leu Ile Cys Asn Glu Arg Gln Thr Asp Lys Glu Ile Asp Leu
245 250 255

Ala Ser Ala Leu Ala Ala Arg Leu Gly Thr Gln Leu Ile His Phe Val
260 265 270

Pro Arg Asp Asn Ile Val Gln His Ala Glu Leu Arg Arg Met Thr Val
275 280 285

Ile Glu Tyr Ala Pro Asp Ser Gln Gln Ala Gln Glu Tyr Arg Gln Leu
290 295 300

Ala Asn Lys Val His Ala Asn Lys Gly Lys Gly Thr Ile Pro Thr Pro
305 310 315 320

Ile Thr Met Glu Glu Leu Glu Glu Met Leu Met Asp Phe Gly Ile Met
325 330 335

Lys Ser Glu Glu Gln Gln Leu Ala Glu Leu Gln Ala Lys Glu Ala Ala
340 345 350

Lys Ala

<210> SEQ ID NO 169
<211> LENGTH: 356
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN179. Amino acids 1-31 correspond to the MTP-CoxIV sequence, amino acids 32-61 correspond to the TwinStrep sequence including a GG at its C-terminus, and amino acids 62-356

<400> SEQUENCE: 169

Met Leu Ser Leu Arg Gln Ser Ile Arg Phe Phe Lys Pro Ala Thr Arg
1 5 10 15

Thr Leu Cys Ser Ser Arg Tyr Leu Leu Gln Gln Lys Pro Ser Ala Trp
20 25 30

Ser His Pro Gln Phe Glu Lys Gly Gly Gly Ser Gly Gly Gly Ser Gly
35 40 45

Gly Ser Ala Trp Ser His Pro Gln Phe Glu Lys Gly Gly Met Thr Glu
50 55 60

Asn Ile Arg Gln Ile Ala Phe Tyr Gly Lys Gly Gly Ile Gly Lys Ser
65 70 75 80

Thr Thr Ser Gln Asn Thr Leu Ala Ala Met Ala Glu Met Gly Gln Arg
85 90 95

Ile Met Ile Val Gly Cys Asp Pro Lys Ala Asp Ser Thr Arg Leu Met
100 105 110

Leu His Ser Lys Ala Gln Thr Thr Val Leu His Leu Ala Ala Glu Arg
115 120 125

Gly Ala Val Glu Asp Leu Glu Leu Glu Glu Val Met Leu Thr Gly Phe
130 135 140

Arg Gly Val Lys Cys Val Glu Ser Gly Gly Pro Glu Pro Gly Val Gly
145 150 155 160

Cys Ala Gly Arg Gly Ile Ile Thr Ala Ile Asn Phe Leu Glu Glu Asn
165 170 175

Gly Ala Tyr Gln Asp Leu Asp Phe Val Ser Tyr Asp Val Leu Gly Asp
180 185 190

Val Val Cys Gly Gly Phe Ala Met Pro Ile Arg Glu Gly Lys Ala Gln
195 200 205

```
Glu Ile Tyr Ile Val Thr Ser Gly Glu Met Met Ala Met Tyr Ala Ala
    210                 215                 220

Asn Asn Ile Ala Arg Gly Ile Leu Lys Tyr Ala His Ser Gly Gly Val
225                 230                 235                 240

Arg Leu Gly Gly Leu Ile Cys Asn Ser Arg Lys Val Asp Arg Glu Ala
                245                 250                 255

Glu Leu Ile Glu Asn Leu Ala Glu Arg Leu Asn Thr Gln Met Ile His
            260                 265                 270

Phe Val Pro Arg Asp Asn Ile Val Gln His Ala Glu Leu Arg Arg Met
        275                 280                 285

Thr Val Asn Glu Tyr Ala Pro Asp Ser Asn Gln Ser Gln Glu Tyr Arg
    290                 295                 300

Ala Leu Ala Lys Lys Ile Ile Asn Asn Thr Lys Leu Thr Ile Pro Thr
305                 310                 315                 320

Pro Met Glu Met Asp Glu Leu Glu Ala Leu Leu Ile Glu Tyr Gly Ile
                325                 330                 335

Leu Asp Asp Asp Thr Lys His Ala Asp Ile Ile Gly Lys Pro Ala Glu
            340                 345                 350

Ala Ser Ala Lys
        355


<210> SEQ ID NO 170
<211> LENGTH: 348
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN180. Amino
      acids 1-31 correspond to the MTP-CoxIV sequence, amino acids 32-61
      correspond to the TwinStrep sequence including a GG at its
      C-terminus, and amino acids 62-338

<400> SEQUENCE: 170

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Gln
    50                  55                  60

Ile Ala Phe Tyr Gly Lys Gly Gly Ile Gly Lys Ser Thr Thr Gln Gln
65                  70                  75                  80

Asn Thr Met Ala Ala Met Ala Glu Met Gly Lys Lys Val Met Ile Val
                85                  90                  95

Gly Cys Asp Pro Lys Ala Asp Ser Thr Arg Leu Ile Leu His Ser Lys
            100                 105                 110

Ala Gln Thr Ser Val Ile Gln Leu Ala Ala Glu Lys Gly Ser Val Glu
        115                 120                 125

Asp Leu Glu Leu Asp Glu Val Leu Val Glu Gly Gln Trp Gly Ile Lys
    130                 135                 140

Cys Val Glu Ser Gly Gly Pro Glu Pro Gly Val Gly Cys Ala Gly Arg
145                 150                 155                 160

Gly Val Ile Thr Ser Ile Ser Tyr Leu Glu Glu Ala Gly Ala Tyr Glu
                165                 170                 175

Asp Leu Asp Phe Val Thr Tyr Asp Val Leu Gly Asp Val Val Cys Gly
```

```
            180                 185                 190

Gly Phe Ala Met Pro Ile Arg Gln Gly Lys Ala Gln Glu Ile Tyr Ile
        195                 200                 205

Val Thr Ser Gly Glu Met Met Ala Met Tyr Ala Ala Asn Asn Ile Ala
    210                 215                 220

Arg Gly Ile Leu Lys Tyr Ala His Ser Gly Gly Val Arg Leu Gly Gly
225                 230                 235                 240

Leu Ile Cys Asn Ser Arg Asn Thr Asp Arg Glu Asp Glu Leu Ile Ile
                245                 250                 255

Glu Leu Ala Arg Arg Leu Asn Thr Gln Met Ile His Phe Ile Pro Arg
            260                 265                 270

Asn Asn Val Val Gln His Ala Glu Leu Arg Arg Met Thr Val Ile Glu
        275                 280                 285

Tyr Asp Pro Lys Asn Glu Gln Ala Asp Gln Tyr Arg Gln Leu Ala Lys
    290                 295                 300

Lys Ile Val Asp Asn Asp Met Lys Thr Ile Pro Thr Pro Ile Thr Met
305                 310                 315                 320

Asp Glu Leu Glu Glu Leu Leu Ile Glu Phe Gly Ile Met Glu Gln Glu
                325                 330                 335

Asp Glu Ser Ile Ile Gly Lys Ala Ala Ala Val Ala
            340                 345


<210> SEQ ID NO 171
<211> LENGTH: 354
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN181. Amino
      acids 1-31 correspond to the MTP-CoxIV sequence, amino acids 32-61
      correspond to the TwinStrep sequence including a GG at its
      C-terminus, and amino acids 62-338

<400> SEQUENCE: 171

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Ala Thr
    50                  55                  60

Arg Gln Cys Ala Ile Tyr Gly Lys Gly Gly Ile Gly Lys Ser Thr Thr
65                  70                  75                  80

Thr Gln Asn Leu Val Ala Gly Leu Ala Glu Leu Gly Lys Arg Val Met
                85                  90                  95

Ile Val Gly Cys Asp Pro Lys Ala Asp Ser Thr Arg Leu Ile Leu His
            100                 105                 110

Ser Lys Ala Gln Glu Thr Ile Met Gln Met Ala Ala Asp Ala Gly Ser
        115                 120                 125

Val Glu Asp Leu Glu Leu Glu Asp Val Leu Lys Val Gly Phe Gly Asp
    130                 135                 140

Ile Lys Cys Val Glu Ser Gly Gly Pro Glu Pro Gly Val Gly Cys Ala
145                 150                 155                 160

Gly Arg Gly Val Ile Thr Ala Ile Asn Phe Leu Glu Glu Glu Gly Ala
                165                 170                 175
```

```
Tyr Glu Glu Asp Leu Asp Phe Val Phe Tyr Asp Val Leu Gly Asp Val
            180                 185                 190

Val Cys Gly Gly Phe Ala Met Pro Ile Arg Glu Asn Lys Ala Gln Glu
        195                 200                 205

Ile Tyr Ile Val Cys Ser Gly Glu Met Met Ala Met Tyr Ala Ala Asn
    210                 215                 220

Asn Ile Ala Lys Gly Ile Val Lys Tyr Ala Ser Ser Gly Gly Val Arg
225                 230                 235                 240

Leu Ala Gly Leu Ile Cys Asn Ser Arg Asn Thr Ala Arg Glu Asp Glu
                245                 250                 255

Leu Ile Met Glu Leu Ala Arg Gln Leu Gly Thr Gln Met Ile His Phe
            260                 265                 270

Val Pro Arg Asp Asn Ile Val Gln Arg Ala Glu Ile Arg Arg Met Thr
        275                 280                 285

Val Ile Glu Tyr Asp Pro Lys Ser Gly Gln Ala Asp Glu Tyr Arg Thr
    290                 295                 300

Leu Ala Gln Lys Ile Ile Asp Asn Lys Met Phe Val Val Pro Thr Pro
305                 310                 315                 320

Ile Ser Met Asp Ala Leu Glu Asp Leu Leu Met Glu Phe Gly Val Leu
                325                 330                 335

Glu Glu Glu Asp Glu Ser Ile Val Gly Lys Thr Ala Ala Glu Glu Ala
            340                 345                 350

Val Ala


<210> SEQ ID NO 172
<211> LENGTH: 345
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN182. Amino
      acids 1-31 correspond to the MTP-CoxIV sequence, amino acids 32-61
      correspond to the TwinStrep sequence including a GG at its
      C-terminus, and amino acids 62-345

<400> SEQUENCE: 172

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Ser Phe
    50                  55                  60

Asp Glu Ile Ala Pro Asn Ala Lys Lys Val Ala Ile Tyr Gly Lys Gly
65                  70                  75                  80

Gly Ile Gly Lys Ser Thr Thr Thr Gln Asn Thr Ala Ala Ala Leu Ala
                85                  90                  95

Tyr Tyr Tyr Lys Leu Lys Gly Met Ile His Gly Cys Asp Pro Lys Ala
            100                 105                 110

Asp Ser Thr Arg Met Ile Leu His Gly Lys Pro Gln Glu Thr Val Met
        115                 120                 125

Asp Val Leu Arg Glu Glu Gly Glu Glu Gly Val Thr Leu Glu Lys Val
    130                 135                 140

Arg Lys Val Gly Phe Cys Gly Ile Tyr Cys Val Glu Ser Gly Gly Pro
145                 150                 155                 160
```

```
Glu Pro Gly Val Gly Cys Ala Gly Arg Gly Val Ile Thr Ala Val Asn
                165                 170                 175

Leu Met Lys Glu Leu Gly Gly Tyr Pro Asp Asp Leu Asp Phe Leu Phe
            180                 185                 190

Phe Asp Val Leu Gly Asp Val Val Cys Gly Gly Phe Ala Met Pro Leu
        195                 200                 205

Arg Asp Gly Leu Ala Lys Glu Ile Tyr Ile Val Ser Ser Gly Glu Met
    210                 215                 220

Met Ala Leu Tyr Ala Ala Asn Asn Ile Ala Lys Gly Ile Leu Lys Tyr
225                 230                 235                 240

Ala Glu Gln Ser Gly Val Arg Leu Gly Gly Ile Ile Cys Asn Ser Arg
                245                 250                 255

Asn Val Asp Gly Glu Arg Glu Leu Met Glu Glu Phe Cys Asp Lys Leu
            260                 265                 270

Gly Thr Lys Leu Ile His Phe Ile Pro Arg Asp Asn Ile Val Gln Lys
        275                 280                 285

Ala Glu Phe Asn Lys Met Thr Val Val Glu Phe Ala Pro Asp His Pro
    290                 295                 300

Gln Ala Leu Glu Tyr Lys Lys Leu Gly Lys Lys Ile Met Asp Asn Asp
305                 310                 315                 320

Glu Leu Val Ile Pro Thr Pro Leu Ser Met Asp Glu Leu Glu Lys Leu
                325                 330                 335

Val Glu Lys Tyr Gly Leu Tyr Asp Lys
            340                 345
```

<210> SEQ ID NO 173
<211> LENGTH: 345
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN183. Amino acids 1-31 correspond to the MTP-CoxIV sequence, amino acids 32-61 correspond to the TwinStrep sequence including a GG at its C-terminus, and amino acids 62-345

<400> SEQUENCE: 173

```
Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Gln
    50                  55                  60

Ile Ala Ile Tyr Gly Lys Gly Gly Ile Gly Lys Ser Thr Thr Thr Gln
65                  70                  75                  80

Asn Thr Val Ser Ala Leu Ala Glu Met Gly Lys Lys Val Met Ile Val
                85                  90                  95

Gly Cys Asp Pro Lys Ala Asp Ser Thr Arg Leu Ile Leu His Ser Lys
            100                 105                 110

Ala Gln Ala Thr Val Met Asp Leu Ala Arg Glu Lys Gly Thr Val Glu
        115                 120                 125

Asp Leu Glu Leu Ser Asp Val Leu Leu Thr Gly Phe Ala Asp Ile Arg
    130                 135                 140

Cys Ala Glu Ser Gly Gly Pro Glu Pro Gly Val Gly Cys Ala Gly Arg
145                 150                 155                 160
```

Gly Val Ile Thr Ala Ile Asn Phe Leu Glu Glu Asn Gly Ala Tyr Thr
165 170 175

Pro Asp Leu Asp Tyr Val Phe Tyr Asp Val Leu Gly Asp Val Val Cys
180 185 190

Gly Gly Phe Ala Met Pro Ile Arg Glu Asn Lys Ala Gln Glu Ile Tyr
195 200 205

Ile Val Thr Ser Gly Glu Met Met Ala Met Tyr Ala Ala Asn Asn Ile
210 215 220

Ala Arg Gly Ile Leu Lys Tyr Ala Ser Ser Gly Lys Val Arg Leu Gly
225 230 235 240

Gly Leu Ile Cys Asn Ser Arg Lys Val Asp Lys Glu Tyr Glu Leu Ile
245 250 255

Asp Glu Leu Ala Thr Arg Leu Gly Thr Gln Met Ile His Phe Leu Pro
260 265 270

Arg Asp Asn Gln Val Gln Arg Ala Glu Leu Arg Arg Met Thr Val Ile
275 280 285

Glu Tyr Ser Pro Asp His Pro Gln Ala Asp Glu Tyr Arg Ala Leu Ala
290 295 300

Lys Lys Ile Asp Glu Asn Lys Lys Leu Val Ile Pro Thr Pro Leu Thr
305 310 315 320

Met Asp Glu Leu Glu Asp Leu Leu Ile Gln Tyr Gly Ile Leu Glu Asp
325 330 335

Glu Glu Thr Ala Ala Ala Lys Leu Gly
340 345

<210> SEQ ID NO 174
<211> LENGTH: 335
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN184. Amino acids 1-31 correspond to the MTP-CoxIV sequence, amino acids 32-61 correspond to the TwinStrep sequence including a GG at its C-terminus, and amino acids 62-335

<400> SEQUENCE: 174

Met Leu Ser Leu Arg Gln Ser Ile Arg Phe Phe Lys Pro Ala Thr Arg
1 5 10 15

Thr Leu Cys Ser Ser Arg Tyr Leu Leu Gln Gln Lys Pro Ser Ala Trp
20 25 30

Ser His Pro Gln Phe Glu Lys Gly Gly Gly Ser Gly Gly Gly Ser Gly
35 40 45

Gly Ser Ala Trp Ser His Pro Gln Phe Glu Lys Gly Gly Met Arg Lys
50 55 60

Val Ala Ile Tyr Gly Lys Gly Gly Ile Gly Lys Ser Thr Thr Thr Gln
65 70 75 80

Asn Thr Val Ala Gly Leu Ala Glu Ala Gly Lys Lys Val Met Val Val
85 90 95

Gly Cys Asp Pro Lys Ala Asp Ser Thr Arg Leu Leu Leu Gly Gly Leu
100 105 110

Gln Gln Lys Thr Val Leu Asp Thr Leu Arg Glu Glu Gly Glu Glu Val
115 120 125

Glu Leu Glu Asp Ile Ile Lys Glu Gly Tyr Arg Asn Thr Arg Cys Thr
130 135 140

Glu Ser Gly Gly Pro Glu Pro Gly Val Gly Cys Ala Gly Arg Gly Ile

```
145                 150                 155                 160

Ile Thr Ser Val Asn Leu Leu Glu Gln Leu Gly Ala Tyr Asp Asp Glu
                165                 170                 175

Trp Glu Leu Asp Tyr Val Phe Tyr Asp Val Leu Gly Asp Val Val Cys
            180                 185                 190

Gly Gly Phe Ala Met Pro Ile Arg Asp Gly Lys Ala Glu Glu Ile Tyr
        195                 200                 205

Ile Val Cys Ser Gly Glu Met Met Ala Met Tyr Ala Ala Asn Asn Ile
    210                 215                 220

Cys Lys Gly Ile Leu Lys Tyr Ala Asp Ala Gly Gly Val Arg Leu Gly
225                 230                 235                 240

Gly Leu Ile Cys Asn Ser Arg Lys Val Asp Asn Glu Arg Glu Met Ile
                245                 250                 255

Glu Glu Leu Ala Arg Arg Leu Gly Thr Gln Met Ile His Phe Val Pro
            260                 265                 270

Arg Asp Asn Phe Val Gln Arg Ala Glu Ile Asn Arg Lys Thr Val Ile
        275                 280                 285

Asp Phe Asp Pro Thr His Pro Gln Ala Asp Glu Tyr Arg Ala Leu Ala
    290                 295                 300

Lys Lys Ile Asp Glu Asn Lys Met Phe Val Ile Pro Lys Pro Leu Glu
305                 310                 315                 320

Ile Asp Glu Leu Glu Ser Leu Leu Ile Glu Phe Gly Ile Ala Asn
                325                 330                 335


<210> SEQ ID NO 175
<211> LENGTH: 350
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN185. Amino
      acids 1-31 correspond to the MTP-CoxIV sequence, amino acids 32-61
      correspond to the TwinStrep sequence including a GG at its
      C-terminus, and amino acids 62-350

<400> SEQUENCE: 175

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Gln
    50                  55                  60

Ile Ala Ile Tyr Gly Lys Gly Gly Ile Gly Lys Ser Thr Thr Thr Gln
65                  70                  75                  80

Asn Thr Val Ala Gly Leu Ala Ser Ile Gly Lys Lys Val Met Ile Val
                85                  90                  95

Gly Cys Asp Pro Lys Ala Asp Ser Thr Arg Leu Ile Leu His Ala Lys
            100                 105                 110

Ala Gln Ser Thr Val Met Asp Leu Val Arg Glu Leu Gly Thr Val Glu
        115                 120                 125

Asp Leu Glu Leu Glu Asp Val Met Lys Val Gly Tyr Gly Asp Val Lys
    130                 135                 140

Cys Val Glu Ser Gly Gly Pro Glu Pro Gly Val Gly Cys Ala Gly Arg
145                 150                 155                 160
```

Gly Val Ile Thr Ala Ile Asn Phe Leu Glu Glu Asn Gly Ala Tyr Thr
165 170 175

Pro Asp Leu Asp Phe Val Phe Tyr Asp Val Leu Gly Asp Val Val Cys
180 185 190

Gly Gly Phe Ala Met Pro Ile Arg Glu Gly Lys Ala Glu Glu Ile Tyr
195 200 205

Ile Val Cys Ser Gly Glu Met Met Ala Met Tyr Ala Ala Asn Asn Ile
210 215 220

Ala Lys Gly Ile Leu Lys Tyr Ala Thr Ser Gly Lys Val Arg Leu Ala
225 230 235 240

Gly Leu Ile Cys Asn Ala Arg Lys Thr Asp Lys Glu Tyr Glu Leu Ile
245 250 255

Asp Ala Leu Ala Lys Lys Leu Gly Thr Gln Met Ile His Phe Val Pro
260 265 270

Arg Asp Asn Gln Val Gln Arg Ala Glu Leu Arg Arg Met Thr Val Ile
275 280 285

Glu Tyr Ser Pro Glu His Pro Gln Ala Gln Glu Tyr Arg Thr Leu Ala
290 295 300

Gln Lys Ile Ala Asp Asn Lys Met Leu Val Val Pro Thr Pro Leu Glu
305 310 315 320

Met Glu Glu Leu Glu Asp Leu Leu Met Glu Phe Gly Ile Met Glu Ala
325 330 335

Glu Asp Glu Ser Ile Val Gly Val Ala Glu Ala Ala Ala Val
340 345 350

<210> SEQ ID NO 176
<211> LENGTH: 355
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN186. Amino acids 1-31 correspond to the MTP-CoxIV sequence, amino acids 32-61 correspond to the TwinStrep sequence including a GG at its C-terminus, and amino acids 62-355

<400> SEQUENCE: 176

Met Leu Ser Leu Arg Gln Ser Ile Arg Phe Phe Lys Pro Ala Thr Arg
1 5 10 15

Thr Leu Cys Ser Ser Arg Tyr Leu Leu Gln Gln Lys Pro Ser Ala Trp
20 25 30

Ser His Pro Gln Phe Glu Lys Gly Gly Gly Ser Gly Gly Gly Ser Gly
35 40 45

Gly Ser Ala Trp Ser His Pro Gln Phe Glu Lys Gly Gly Met Ala Ser
50 55 60

Leu Arg Gln Ile Ala Phe Tyr Gly Lys Gly Gly Ile Gly Lys Ser Thr
65 70 75 80

Thr Ser Gln Asn Thr Leu Ala Ala Leu Ala Glu Met Gly Gln Lys Ile
85 90 95

Leu Ile Val Gly Cys Asp Pro Lys Ala Asp Ser Thr Arg Leu Ile Leu
100 105 110

His Ala Lys Ala Gln Asp Thr Ile Leu Ser Leu Ala Ala Ser Ala Gly
115 120 125

Ser Val Glu Asp Leu Glu Leu Glu Asp Val Met Lys Val Gly Tyr Gln
130 135 140

Asp Ile Arg Cys Val Glu Ser Gly Gly Pro Glu Pro Gly Val Gly Cys
145 150 155 160

Ala Gly Arg Gly Val Ile Thr Ser Ile Asn Phe Leu Glu Glu Asn Gly
165 170 175

Ala Tyr Glu Asn Ile Asp Tyr Val Ser Tyr Asp Val Leu Gly Asp Val
180 185 190

Val Cys Gly Gly Phe Ala Met Pro Ile Arg Glu Asn Lys Ala Gln Glu
195 200 205

Ile Tyr Ile Val Met Ser Gly Glu Met Met Ala Met Tyr Ala Ala Asn
210 215 220

Asn Ile Ser Lys Gly Ile Leu Lys Tyr Ala Asn Ser Gly Gly Val Arg
225 230 235 240

Leu Gly Gly Leu Ile Cys Asn Glu Arg Gln Thr Asp Lys Glu Leu Glu
245 250 255

Leu Ala Glu Ala Leu Ala Lys Lys Leu Gly Thr Gln Leu Ile Tyr Phe
260 265 270

Val Pro Arg Asp Asn Val Val Gln His Ala Glu Leu Arg Arg Met Thr
275 280 285

Val Leu Glu Tyr Ala Pro Asp Ser Lys Gln Ala Asp His Tyr Arg Lys
290 295 300

Leu Ala Ala Lys Val His Asn Asn Gly Gly Lys Gly Ile Ile Pro Thr
305 310 315 320

Pro Ile Ser Met Asp Glu Leu Glu Asp Met Leu Met Glu His Gly Ile
325 330 335

Ile Lys Ala Val Asp Glu Ser Ile Ile Gly Lys Thr Ala Ala Glu Leu
340 345 350

Ala Ala Ser
355

<210> SEQ ID NO 177
<211> LENGTH: 336
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN187. Amino acids 1-31 correspond to the MTP-CoxIV sequence, amino acids 32-61 correspond to the TwinStrep sequence including a GG at its C-terminus, and amino acids 62-336

<400> SEQUENCE: 177

Met Leu Ser Leu Arg Gln Ser Ile Arg Phe Phe Lys Pro Ala Thr Arg
1 5 10 15

Thr Leu Cys Ser Ser Arg Tyr Leu Leu Gln Gln Lys Pro Ser Ala Trp
20 25 30

Ser His Pro Gln Phe Glu Lys Gly Gly Gly Ser Gly Gly Gly Ser Gly
35 40 45

Gly Ser Ala Trp Ser His Pro Gln Phe Glu Lys Gly Gly Met Val Arg
50 55 60

Lys Ile Ala Ile Tyr Gly Lys Gly Gly Ile Gly Lys Ser Thr Thr Gln
65 70 75 80

Gln Asn Thr Ala Ala Ala Met Ser Tyr Phe His Gly Lys Asn Val Met
85 90 95

Ile His Gly Cys Asp Pro Lys Ala Asp Ser Thr Arg Leu Ile Leu Gly
100 105 110

Gly Lys Met Gln Thr Thr Met Met Asp Thr Leu Arg Glu Leu Gly Glu
115 120 125

Val Ala Cys Thr Pro Asp Lys Val Ile Glu Thr Gly Phe Gly Gly Ile

```
    130                 135                 140

Lys Cys Val Glu Ser Gly Gly Pro Glu Pro Gly Val Gly Cys Ala Gly
145                 150                 155                 160

Arg Gly Val Ile Thr Ala Ile Thr Leu Met Glu Arg His Gly Val Tyr
                165                 170                 175

Glu Lys Asp Leu Asp Phe Val Phe Phe Asp Val Leu Gly Asp Val Val
            180                 185                 190

Cys Gly Gly Phe Ala Met Pro Val Arg Asp Gly Lys Ala Glu Glu Ile
        195                 200                 205

Tyr Ile Val Ala Ser Gly Glu Met Met Ala Leu Tyr Ala Ala Asn Asn
    210                 215                 220

Ile Cys Lys Gly Met Val Lys Tyr Ala Arg Gln Ser Gly Val Arg Leu
225                 230                 235                 240

Gly Gly Ile Ile Cys Asn Ser Arg Asn Val Asp Gly Glu Lys Glu Leu
                245                 250                 255

Leu Glu Glu Phe Cys Glu Arg Ile Gly Thr Gln Met Ile His Phe Val
            260                 265                 270

Pro Arg Asp Asn Ile Val Gln Lys Ala Glu Phe Asn Lys Lys Ser Val
        275                 280                 285

Ile Glu Phe Asp Pro Glu Cys Asn Gln Ser Gln Glu Tyr Arg Glu Leu
    290                 295                 300

Ala Arg Lys Ile Ile Glu Asn Lys Asp Phe Val Ile Pro Glu Pro Met
305                 310                 315                 320

Thr Met Asp Glu Met Glu Glu Leu Val Val Lys Tyr Gly Val Met Asp
                325                 330                 335
```

<210> SEQ ID NO 178
<211> LENGTH: 334
<212> TYPE: PRT
<213> ORGANISM: Artificial Sequence
<220> FEATURE:
<223> OTHER INFORMATION: Amino acid sequence of the MTP-CoxIV::TwinStrep::NifH polypeptide encoded by SN188. Amino acids 1-31 correspond to the MTP-CoxIV sequence, amino acids 32-61 correspond to the TwinStrep sequence including a GG at its C-terminus, and amino acids 62-334

<400> SEQUENCE: 178

```
Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Gln
    50                  55                  60

Ile Ala Ile Tyr Gly Lys Gly Gly Ile Gly Lys Ser Thr Thr Thr Gln
65                  70                  75                  80

Asn Leu Thr Ala Ser Leu Ser Thr Met Gly Asn Lys Ile Met Leu Val
                85                  90                  95

Gly Cys Asp Pro Lys Ala Asp Ser Thr Arg Met Leu Leu Gly Gly Leu
            100                 105                 110

Asn Gln Lys Thr Val Leu Asp Thr Leu Arg Ser Glu Gly Asp Glu Gly
        115                 120                 125

Val Asp Leu Asp Val Val Met Gln Arg Gly Phe Gly Asp Ile Lys Cys
    130                 135                 140
```

```
Val Glu Ser Gly Gly Pro Glu Pro Gly Val Gly Cys Ala Gly Arg Gly
145                 150                 155                 160

Ile Ile Thr Ser Ile Gly Leu Leu Glu Asn Leu Gly Ala Tyr Thr Asp
                165                 170                 175

Asp Leu Asp Tyr Val Phe Tyr Asp Val Leu Gly Asp Val Val Cys Gly
            180                 185                 190

Gly Phe Ala Met Pro Ile Arg Glu Gly Lys Ala Lys Glu Ile Tyr Ile
        195                 200                 205

Val Ala Ser Gly Glu Leu Met Ala Ile Tyr Ala Ala Asn Asn Ile Cys
    210                 215                 220

Lys Gly Leu Ala Lys Phe Ala Lys Gly Gly Ala Arg Leu Gly Gly Ile
225                 230                 235                 240

Ile Cys Asn Ser Arg Asn Val Asp Gly Glu Arg Glu Leu Leu Asp Ala
                245                 250                 255

Phe Ala Lys Lys Leu Gly Ser His Leu Ile His Phe Ile Pro Arg Asp
            260                 265                 270

Asn Ile Val Gln Arg Ala Glu Ile Asn Arg Lys Thr Val Ile Asp Phe
        275                 280                 285

Asp Pro Glu Ser Asn Gln Ala Lys Glu Tyr Leu Thr Leu Ala His Asn
    290                 295                 300

Val Gln Asn Asn Asp Lys Leu Val Val Pro Thr Pro Leu Pro Met Glu
305                 310                 315                 320

Glu Leu Glu Ala Met Met Val Glu Phe Gly Ile Val Asp Leu
                325                 330


<210> SEQ ID NO 179
<211> LENGTH: 336
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN189. Amino
      acids 1-31 correspond to the MTP-CoxIV sequence, amino acids 32-61
      correspond to the TwinStrep sequence including a GG at its
      C-terminus, and amino acids 62-336

<400> SEQUENCE: 179

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Gln
    50                  55                  60

Ile Ala Ile Tyr Gly Lys Gly Gly Ile Gly Lys Ser Thr Thr Thr Gln
65                  70                  75                  80

Asn Thr Val Ala Ala Leu Ala Asp Ala Gly Lys Lys Ile Met Val Val
                85                  90                  95

Gly Cys Asp Pro Lys Ala Asp Ser Thr Arg Leu Leu Leu Asn Gly Leu
            100                 105                 110

Asn Gln Lys Thr Val Leu Asp Thr Leu Arg Asp Glu Gly Glu Asp Val
        115                 120                 125

Ile Leu Glu Asp Val Leu Arg Thr Gly Phe Lys Asp Val Lys Cys Val
    130                 135                 140

Glu Ser Gly Gly Pro Glu Pro Gly Val Gly Cys Ala Gly Arg Gly Ile
145                 150                 155                 160
```

```
Ile Thr Ser Ile Asn Leu Leu Glu Ser Leu Gly Ala Tyr Thr Asp Asp
                165                 170                 175

Leu Asp Tyr Val Phe Tyr Asp Val Leu Gly Asp Val Val Cys Gly Gly
            180                 185                 190

Phe Ala Met Pro Ile Arg Glu Gly Lys Ala Arg Glu Ile Tyr Ile Val
        195                 200                 205

Ala Ser Gly Glu Leu Met Ala Leu Tyr Ala Ala Asn Asn Ile Cys Lys
    210                 215                 220

Gly Val Gln Lys Tyr Ala Lys Thr Gly Gly Val Arg Met Gly Gly Ile
225                 230                 235                 240

Ile Cys Asn Ser Arg Lys Val Asp Lys Glu Tyr Asp Leu Leu Lys Ala
                245                 250                 255

Phe Ala Glu Glu Ile Gly Thr Gln Leu Ile His Phe Leu Pro Arg Asp
            260                 265                 270

Asn Val Val Gln Arg Ala Glu Ile Lys Lys Lys Thr Val Ile Asp Tyr
        275                 280                 285

Asp Pro Thr Val Ala Gln Ala Asp Glu Tyr Arg Lys Leu Ala Lys Asn
    290                 295                 300

Ile Asp Glu Asn Thr Met Phe Val Ile Pro Asn Pro Met Thr Gln Asp
305                 310                 315                 320

Arg Leu Glu Glu Leu Met Met Glu His Gly Phe Met Glu Gly Leu Asp
                325                 330                 335


<210> SEQ ID NO 180
<211> LENGTH: 336
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN190. Amino
      acids 1-31 correspond to the MTP-CoxIV sequence, amino acids 32-61
      correspond to the TwinStrep sequence including a GG at its
      C-terminus, and amino acids 62-336

<400> SEQUENCE: 180

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Thr Arg
    50                  55                  60

Lys Ile Ala Ile Tyr Gly Lys Gly Gly Ile Gly Lys Ser Thr Thr Gln
65                  70                  75                  80

Gln Asn Thr Ala Ala Ala Leu Ala Tyr Phe Tyr Gly Lys Lys Val Leu
                85                  90                  95

Ile His Gly Cys Asp Pro Lys Ala Asp Cys Thr Arg Leu Ile Leu Gly
            100                 105                 110

Gly Lys Pro Gln Glu Thr Val Met Asp Thr Met Arg Glu Leu Gly Glu
        115                 120                 125

Asp Ala Val Thr Ile Asp Arg Val Val Lys Thr Gly Phe Cys Gly Ile
    130                 135                 140

Lys Cys Val Glu Ser Gly Gly Pro Glu Pro Gly Val Gly Cys Ala Gly
145                 150                 155                 160

Arg Gly Val Ile Thr Ala Ile Ser Leu Met Glu Glu Leu Gly Ala Tyr
```

```
                165                 170                 175

Thr Pro Asp Leu Asp Phe Ile Phe Phe Asp Val Leu Gly Asp Val Val
            180                 185                 190

Cys Gly Gly Phe Ala Met Pro Val Arg Glu Gly Lys Ala Gln Glu Ile
        195                 200                 205

Tyr Ile Val Ala Ser Gly Glu Met Met Ala Leu Tyr Ala Ala Asn Asn
    210                 215                 220

Ile Cys Arg Gly Met Val Lys Tyr Ala Glu Gln Ser Gly Val Arg Leu
225                 230                 235                 240

Gly Gly Ile Ile Cys Asn Ser Arg Asn Val Asp Gly Glu Arg Glu Leu
                245                 250                 255

Met Glu Glu Phe Cys Ser Lys Ile Gly Thr Gln Met Ile His Phe Ile
            260                 265                 270

Pro Arg Asp Asn Ile Val Gln Lys Ala Glu Phe Asn Arg Gln Thr Val
        275                 280                 285

Thr Gln Phe Asp Pro Asn Cys Asn Gln Ala Gln Glu Tyr Arg Glu Leu
    290                 295                 300

Ala Arg Lys Ile Ile Glu Asn Asp Met Phe Val Ile Pro Lys Pro Met
305                 310                 315                 320

Thr Met Asp Glu Met Glu Asn Leu Val Ile Lys Tyr Gly Leu Leu Glu
                325                 330                 335


<210> SEQ ID NO 181
<211> LENGTH: 335
<212> TYPE: PRT
<213> ORGANISM: Artificial Sequence
<220> FEATURE:
<223> OTHER INFORMATION: Amino acid sequence of the
      MTP-CoxIV::TwinStrep::NifH polypeptide encoded by SN191. Amino
      acids 1-31 correspond to the MTP-CoxIV sequence, amino acids 32-61
      correspond to the TwinStrep sequence including a GG at its
      C-terminus, and amino acids 62-335

<400> SEQUENCE: 181

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Arg Lys
    50                  55                  60

Ile Ala Ile Tyr Gly Arg Gly Gly Val Gly Lys Ser Thr Thr Thr Gln
65                  70                  75                  80

Asn Val Val Ala Gly Leu Ser Glu Met Ser Arg Lys Val Met Val Val
                85                  90                  95

Gly Cys Asp Ser Lys Ala Asp Ser Thr Arg Leu Leu Leu Gly Gly Leu
            100                 105                 110

His Gln Lys Ile Val Leu Asp Thr Leu Arg Lys Glu Glu Asp Asp Val
        115                 120                 125

Asn Leu Glu Asp Phe Arg Leu Glu Gly Trp Gly Lys Thr Leu Cys Val
    130                 135                 140

Glu Ser Gly Gly Pro Glu Pro Gly Val Gly Cys Thr Gly Arg Gly Ile
145                 150                 155                 160

Leu Thr Ser Ile Gly Leu Leu Glu Gln Leu Gly Ala Tyr Asp Asp Ala
                165                 170                 175
```

```
Val Arg Leu Asp Tyr Thr Phe Tyr Asp Gly Leu Gly Asp Val Val Cys
            180                 185                 190

Ser Gly Phe Val Met Pro Ile Arg Glu Arg Lys Ala Gln Glu Ile Tyr
        195                 200                 205

Ile Val Thr Ser Gly Glu Ile Met Ala Met Tyr Thr Ala Asn Asn Ile
    210                 215                 220

Cys Arg Ser Leu Gln Lys Tyr Ala Pro Val Gly Gly Ile Arg Leu Gly
225                 230                 235                 240

Gly Leu Ile Cys Asn Ser Arg Lys Val Asp Arg Glu Asn Asp Leu Val
                245                 250                 255

Glu Ala Leu Ala Glu Lys Leu Gly Thr Gln Thr Ile Tyr Ser Ile Pro
            260                 265                 270

Arg Asp Asn Met Val Gln Arg Ala Glu Phe Tyr Arg Lys Thr Val Ile
        275                 280                 285

Glu Tyr Ala Pro Glu Cys Glu Gln Ala Gln His Tyr Arg Asn Leu Ala
    290                 295                 300

Ala Ala Ile Asp Gln Asn Thr Asp Phe Val Ile Pro Lys Ser Met Ser
305                 310                 315                 320

Ser Asp Arg Leu Glu Glu Leu Leu Val Lys Phe Gly Leu Phe Asp
                325                 330                 335


<210> SEQ ID NO 182
<211> LENGTH: 583
<212> TYPE: PRT
<213> ORGANISM: Artificial Sequence
<220> FEATURE:
<223> OTHER INFORMATION: MTP-FAγ51::AnfD::HA polypeptide

<400> SEQUENCE: 182

Met Met Ala Met Ala Val Phe Arg Arg Glu Gly Arg Arg Leu Leu Pro
1               5                   10                  15

Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Pro His His Glu Phe Glu Cys Ser Lys
    50                  55                  60

Val Ile Pro Glu Arg Lys Lys His Ala Val Ile Lys Gly Lys Gly Glu
65                  70                  75                  80

Thr Leu Ala Asp Ala Leu Pro Gln Gly Tyr Leu Asn Thr Ile Pro Gly
                85                  90                  95

Ser Ile Ser Glu Arg Gly Cys Ala Tyr Cys Gly Ala Lys His Val Ile
            100                 105                 110

Gly Thr Pro Met Lys Asp Val Ile His Ile Ser His Gly Pro Val Gly
        115                 120                 125

Cys Thr Tyr Asp Thr Trp Gln Thr Lys Arg Tyr Ile Ser Asp Asn Asp
    130                 135                 140

Asn Phe Gln Leu Lys Tyr Thr Tyr Ala Thr Asp Val Lys Glu Lys His
145                 150                 155                 160

Ile Val Phe Gly Ala Glu Lys Leu Leu Lys Gln Asn Ile Ile Glu Ala
                165                 170                 175

Phe Lys Ala Phe Pro Gln Ile Lys Arg Met Thr Ile Tyr Gln Thr Cys
            180                 185                 190

Ala Thr Ala Leu Ile Gly Asp Asp Ile Asn Ala Ile Ala Glu Glu Val
        195                 200                 205
```

```
Met Glu Glu Met Pro Glu Val Asp Ile Phe Val Cys Asn Ser Pro Gly
    210                 215                 220

Phe Ala Gly Pro Ser Gln Ser Gly Gly His His Lys Ile Asn Ile Ala
225                 230                 235                 240

Trp Ile Asn Gln Lys Val Gly Thr Val Glu Pro Glu Ile Thr Gly Asp
                245                 250                 255

His Val Ile Asn Tyr Val Gly Glu Tyr Asn Ile Gln Gly Asp Gln Glu
            260                 265                 270

Val Met Val Asp Tyr Phe Lys Arg Met Gly Ile Gln Val Leu Ser Thr
        275                 280                 285

Phe Thr Gly Asn Gly Ser Tyr Asp Gly Leu Arg Ala Met His Arg Ala
    290                 295                 300

His Leu Asn Val Leu Glu Cys Ala Arg Ser Ala Glu Tyr Ile Cys Asn
305                 310                 315                 320

Glu Leu Arg Val Arg Tyr Gly Ile Pro Arg Leu Asp Ile Asp Gly Phe
                325                 330                 335

Gly Phe Lys Pro Leu Ala Asp Ser Leu Arg Lys Ile Gly Met Phe Phe
            340                 345                 350

Gly Ile Glu Asp Arg Ala Lys Ala Ile Ile Asp Glu Glu Val Ala Arg
        355                 360                 365

Trp Lys Pro Glu Leu Asp Trp Tyr Lys Glu Arg Leu Met Gly Lys Lys
    370                 375                 380

Val Cys Leu Trp Pro Gly Gly Ser Lys Leu Trp His Trp Ala His Val
385                 390                 395                 400

Ile Glu Glu Glu Met Gly Leu Lys Val Val Ser Val Tyr Thr Lys Phe
                405                 410                 415

Gly His Gln Gly Asp Met Glu Lys Gly Ile Ala Arg Cys Gly Glu Gly
            420                 425                 430

Thr Leu Ala Ile Asp Asp Pro Asn Glu Leu Glu Gly Leu Glu Ala Leu
        435                 440                 445

Glu Met Leu Lys Pro Asp Ile Ile Leu Thr Gly Lys Arg Pro Gly Glu
    450                 455                 460

Val Ala Lys Lys Val Arg Val Pro Tyr Leu Asn Ala His Ala Tyr His
465                 470                 475                 480

Asn Gly Pro Tyr Lys Gly Phe Glu Gly Trp Val Arg Phe Ala Arg Asp
                485                 490                 495

Ile Tyr Asn Ala Ile Tyr Ser Pro Ile His Gln Leu Ser Gly Ile Asp
            500                 505                 510

Ile Thr Lys Asp Asn Ala Pro Glu Trp Gly Asn Gly Phe Arg Thr Arg
        515                 520                 525

Gln Met Leu Ser Asp Gly Asn Leu Ser Asp Ala Val Arg Asn Ser Glu
    530                 535                 540

Thr Leu Arg Gln Tyr Thr Gly Gly Tyr Asp Ser Val Ser Lys Leu Arg
545                 550                 555                 560

Glu Arg Glu Tyr Pro Ala Phe Glu Arg Lys Val Gly Gly Gly Tyr Pro
                565                 570                 575

Tyr Asp Val Pro Asp Tyr Ala
            580
```

<210> SEQ ID NO 183
<211> LENGTH: 530
<212> TYPE: PRT
<213> ORGANISM: Artificial Sequence
<220> FEATURE:
<223> OTHER INFORMATION: HA::AnfD polypeptide

<400> SEQUENCE: 183

Met Tyr Pro Tyr Asp Val Pro Asp Tyr Ala Gly Gly Met Pro His His
1 5 10 15

Glu Phe Glu Cys Ser Lys Val Ile Pro Glu Arg Lys Lys His Ala Val
20 25 30

Ile Lys Gly Lys Gly Glu Thr Leu Ala Asp Ala Leu Pro Gln Gly Tyr
35 40 45

Leu Asn Thr Ile Pro Gly Ser Ile Ser Glu Arg Gly Cys Ala Tyr Cys
50 55 60

Gly Ala Lys His Val Ile Gly Thr Pro Met Lys Asp Val Ile His Ile
65 70 75 80

Ser His Gly Pro Val Gly Cys Thr Tyr Asp Thr Trp Gln Thr Lys Arg
85 90 95

Tyr Ile Ser Asp Asn Asp Asn Phe Gln Leu Lys Tyr Thr Tyr Ala Thr
100 105 110

Asp Val Lys Glu Lys His Ile Val Phe Gly Ala Glu Lys Leu Leu Lys
115 120 125

Gln Asn Ile Ile Glu Ala Phe Lys Ala Phe Pro Gln Ile Lys Arg Met
130 135 140

Thr Ile Tyr Gln Thr Cys Ala Thr Ala Leu Ile Gly Asp Asp Ile Asn
145 150 155 160

Ala Ile Ala Glu Glu Val Met Glu Glu Met Pro Glu Val Asp Ile Phe
165 170 175

Val Cys Asn Ser Pro Gly Phe Ala Gly Pro Ser Gln Ser Gly Gly His
180 185 190

His Lys Ile Asn Ile Ala Trp Ile Asn Gln Lys Val Gly Thr Val Glu
195 200 205

Pro Glu Ile Thr Gly Asp His Val Ile Asn Tyr Val Gly Glu Tyr Asn
210 215 220

Ile Gln Gly Asp Gln Glu Val Met Val Asp Tyr Phe Lys Arg Met Gly
225 230 235 240

Ile Gln Val Leu Ser Thr Phe Thr Gly Asn Gly Ser Tyr Asp Gly Leu
245 250 255

Arg Ala Met His Arg Ala His Leu Asn Val Leu Glu Cys Ala Arg Ser
260 265 270

Ala Glu Tyr Ile Cys Asn Glu Leu Arg Val Arg Tyr Gly Ile Pro Arg
275 280 285

Leu Asp Ile Asp Gly Phe Gly Phe Lys Pro Leu Ala Asp Ser Leu Arg
290 295 300

Lys Ile Gly Met Phe Phe Gly Ile Glu Asp Arg Ala Lys Ala Ile Ile
305 310 315 320

Asp Glu Glu Val Ala Arg Trp Lys Pro Glu Leu Asp Trp Tyr Lys Glu
325 330 335

Arg Leu Met Gly Lys Lys Val Cys Leu Trp Pro Gly Gly Ser Lys Leu
340 345 350

Trp His Trp Ala His Val Ile Glu Glu Glu Met Gly Leu Lys Val Val
355 360 365

Ser Val Tyr Thr Lys Phe Gly His Gln Gly Asp Met Glu Lys Gly Ile
370 375 380

Ala Arg Cys Gly Glu Gly Thr Leu Ala Ile Asp Asp Pro Asn Glu Leu
385 390 395 400

Glu Gly Leu Glu Ala Leu Glu Met Leu Lys Pro Asp Ile Ile Leu Thr

```
                405                 410                 415

Gly Lys Arg Pro Gly Glu Val Ala Lys Lys Val Arg Val Pro Tyr Leu
            420                 425                 430

Asn Ala His Ala Tyr His Asn Gly Pro Tyr Lys Gly Phe Glu Gly Trp
        435                 440                 445

Val Arg Phe Ala Arg Asp Ile Tyr Asn Ala Ile Tyr Ser Pro Ile His
    450                 455                 460

Gln Leu Ser Gly Ile Asp Ile Thr Lys Asp Asn Ala Pro Glu Trp Gly
465                 470                 475                 480

Asn Gly Phe Arg Thr Arg Gln Met Leu Ser Asp Gly Asn Leu Ser Asp
                485                 490                 495

Ala Val Arg Asn Ser Glu Thr Leu Arg Gln Tyr Thr Gly Gly Tyr Asp
            500                 505                 510

Ser Val Ser Lys Leu Arg Glu Arg Glu Tyr Pro Ala Phe Glu Arg Lys
        515                 520                 525

Val Gly
    530


<210> SEQ ID NO 184
<211> LENGTH: 526
<212> TYPE: PRT
<213> ORGANISM: Artificial Sequence
<220> FEATURE:
<223> OTHER INFORMATION: MTP-FAγ51::HA::AnfK polypeptide

<400> SEQUENCE: 184

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Thr Cys Glu Val Lys Glu Lys Gly Arg Val Gly Thr Ile Asn Pro
65                  70                  75                  80

Ile Phe Thr Cys Gln Pro Ala Gly Ala Gln Phe Val Ser Ile Gly Ile
                85                  90                  95

Lys Asp Cys Ile Gly Ile Val His Gly Gly Gln Gly Cys Val Met Phe
            100                 105                 110

Val Arg Leu Ile Phe Ser Gln His Tyr Lys Glu Ser Phe Glu Leu Ala
        115                 120                 125

Ser Ser Ser Leu His Glu Asp Gly Ala Val Phe Gly Ala Cys Gly Arg
    130                 135                 140

Val Glu Glu Ala Val Asp Val Leu Leu Ser Arg Tyr Pro Asp Val Lys
145                 150                 155                 160

Val Val Pro Ile Ile Thr Thr Cys Ser Thr Glu Ile Ile Gly Asp Asp
                165                 170                 175

Val Asp Gly Val Ile Lys Lys Leu Asn Glu Gly Leu Leu Lys Glu Lys
            180                 185                 190

Phe Pro Asp Arg Glu Val His Leu Ile Ala Met His Thr Pro Ser Phe
        195                 200                 205

Val Gly Ser Met Ile Ser Gly Tyr Asp Val Ala Val Arg Asp Val Val
    210                 215                 220

Arg His Phe Ala Lys Arg Glu Ala Pro Asn Asp Lys Ile Asn Leu Leu
```

```
225                 230                 235                 240

Thr Gly Trp Val Asn Pro Gly Asp Val Lys Glu Leu Lys His Leu Leu
                245                 250                 255

Gly Glu Met Asp Ile Glu Ala Asn Val Leu Phe Glu Ile Glu Ser Phe
            260                 265                 270

Asp Ser Pro Ile Leu Pro Asp Gly Ser Ala Val Ser His Gly Asn Thr
        275                 280                 285

Thr Ile Glu Asp Leu Ile Asp Thr Gly Asn Ala Arg Ala Thr Phe Ala
    290                 295                 300

Leu Asn Arg Tyr Glu Gly Thr Lys Ala Ala Glu Tyr Leu Gln Lys Lys
305                 310                 315                 320

Phe Glu Ile Pro Ala Ile Ile Gly Pro Thr Pro Ile Gly Ile Arg Asn
                325                 330                 335

Thr Asp Ile Phe Leu Gln Asn Leu Lys Lys Ala Thr Gly Lys Pro Ile
            340                 345                 350

Pro Gln Ser Leu Ala His Glu Arg Gly Val Ala Ile Asp Ala Leu Ala
        355                 360                 365

Asp Leu Thr His Met Phe Leu Ala Glu Lys Arg Val Ala Ile Tyr Gly
    370                 375                 380

Ala Pro Asp Leu Val Ile Gly Leu Ala Glu Phe Cys Leu Asp Leu Glu
385                 390                 395                 400

Met Lys Pro Val Leu Leu Leu Leu Gly Asp Asp Asn Ser Lys Tyr Val
                405                 410                 415

Asp Asp Pro Arg Ile Lys Ala Leu Gln Glu Asn Val Asp Tyr Gly Met
            420                 425                 430

Glu Ile Val Thr Asn Ala Asp Phe Trp Glu Leu Glu Asn Arg Ile Lys
        435                 440                 445

Asn Glu Gly Leu Glu Leu Asp Leu Ile Leu Gly His Ser Lys Gly Arg
    450                 455                 460

Phe Ile Ser Ile Asp Tyr Asn Ile Pro Met Leu Arg Val Gly Phe Pro
465                 470                 475                 480

Thr Tyr Asp Arg Ala Gly Leu Phe Arg Tyr Pro Thr Val Gly Tyr Gly
                485                 490                 495

Gly Ala Ile Trp Leu Ala Glu Gln Met Ala Asn Thr Leu Phe Ala Asp
            500                 505                 510

Met Glu His Lys Lys Asn Lys Glu Trp Val Leu Asn Val Trp
        515                 520                 525


<210> SEQ ID NO 185
<211> LENGTH: 339
<212> TYPE: PRT
<213> ORGANISM: Artificial Sequence
<220> FEATURE:
<223> OTHER INFORMATION: MTP-FAγ51::HA::AnfH polypeptide

<400> SEQUENCE: 185

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Thr Arg Lys Val Ala Ile Tyr Gly Lys Gly Gly Ile Gly Lys Ser
```

```
65                  70                  75                  80

Thr Thr Thr Gln Asn Thr Ala Ala Ala Leu Ala Tyr Phe His Asp Lys
                85                  90                  95

Lys Val Phe Ile His Gly Cys Asp Pro Lys Ala Asp Ser Thr Arg Leu
            100                 105                 110

Ile Leu Gly Gly Lys Pro Gln Glu Thr Leu Met Asp Met Leu Arg Asp
        115                 120                 125

Lys Gly Ala Glu Lys Ile Thr Asn Asp Asp Val Ile Lys Lys Gly Phe
    130                 135                 140

Leu Asp Ile Gln Cys Val Glu Ser Gly Gly Pro Glu Pro Gly Val Gly
145                 150                 155                 160

Cys Ala Gly Arg Gly Val Ile Thr Ala Ile Asp Leu Met Glu Glu Asn
                165                 170                 175

Gly Ala Tyr Thr Asp Asp Leu Asp Phe Val Phe Phe Asp Val Leu Gly
            180                 185                 190

Asp Val Val Cys Gly Gly Phe Ala Met Pro Ile Arg Asp Gly Lys Ala
        195                 200                 205

Gln Glu Val Tyr Ile Val Ala Ser Gly Glu Met Met Ala Ile Tyr Ala
    210                 215                 220

Ala Asn Asn Ile Cys Lys Gly Leu Val Lys Tyr Ala Lys Gln Ser Gly
225                 230                 235                 240

Val Arg Leu Gly Gly Ile Ile Cys Asn Ser Arg Lys Val Asp Gly Glu
                245                 250                 255

Arg Glu Phe Leu Glu Glu Phe Thr Ala Ala Ile Gly Thr Lys Met Ile
            260                 265                 270

His Phe Val Pro Arg Asp Asn Ile Val Gln Lys Ala Glu Phe Asn Lys
        275                 280                 285

Lys Thr Val Thr Glu Phe Ala Pro Glu Glu Asn Gln Ala Lys Glu Tyr
    290                 295                 300

Gly Glu Leu Ala Arg Lys Ile Ile Glu Asn Asp Glu Phe Val Ile Pro
305                 310                 315                 320

Lys Pro Leu Thr Met Asp Gln Leu Glu Asp Met Val Val Lys Tyr Gly
                325                 330                 335

Ile Ala Asp


<210> SEQ ID NO 186
<211> LENGTH: 196
<212> TYPE: PRT
<213> ORGANISM: Artificial Sequence
<220> FEATURE:
<223> OTHER INFORMATION: MTP-FAγ51::HA::AnfG polypeptide

<400> SEQUENCE: 186

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Ser Thr Ala Ser Ala Ala Ala Val Val Lys Gln Lys Val Glu Ala
65                  70                  75                  80

Pro Val His Pro Met Asp Ala Arg Ile Asp Glu Leu Thr Asp Tyr Ile
                85                  90                  95
```

Met Lys Asn Cys Leu Trp Gln Phe His Ser Arg Ser Trp Asp Arg Glu
100 105 110

Arg Gln Asn Ala Glu Ile Leu Lys Lys Thr Lys Glu Leu Leu Cys Gly
115 120 125

Glu Pro Val Asp Leu Ser Thr Ser His Asp Arg Cys Tyr Trp Val Asp
130 135 140

Ala Val Cys Leu Ala Asp Asp Tyr Arg Glu His Tyr Pro Trp Ile Asn
145 150 155 160

Ser Met Ser Lys Glu Glu Ile Gly Ser Leu Met Gln Gly Leu Lys Asp
165 170 175

Arg Met Asp Tyr Leu Thr Ile Thr Gly Ser Leu Asn Glu Glu Leu Ser
180 185 190

Asp Lys His Tyr
195

<210> SEQ ID NO 187
<211> LENGTH: 474
<212> TYPE: PRT
<213> ORGANISM: Artificial Sequence
<220> FEATURE:
<223> OTHER INFORMATION: HA::AnfK polypeptide

<400> SEQUENCE: 187

Met Tyr Pro Tyr Asp Val Pro Asp Tyr Ala Gly Gly Met Thr Cys Glu
1 5 10 15

Val Lys Glu Lys Gly Arg Val Gly Thr Ile Asn Pro Ile Phe Thr Cys
20 25 30

Gln Pro Ala Gly Ala Gln Phe Val Ser Ile Gly Ile Lys Asp Cys Ile
35 40 45

Gly Ile Val His Gly Gly Gln Gly Cys Val Met Phe Val Arg Leu Ile
50 55 60

Phe Ser Gln His Tyr Lys Glu Ser Phe Glu Leu Ala Ser Ser Ser Leu
65 70 75 80

His Glu Asp Gly Ala Val Phe Gly Ala Cys Gly Arg Val Glu Glu Ala
85 90 95

Val Asp Val Leu Leu Ser Arg Tyr Pro Asp Val Lys Val Val Pro Ile
100 105 110

Ile Thr Thr Cys Ser Thr Glu Ile Ile Gly Asp Asp Val Asp Gly Val
115 120 125

Ile Lys Lys Leu Asn Glu Gly Leu Leu Lys Glu Lys Phe Pro Asp Arg
130 135 140

Glu Val His Leu Ile Ala Met His Thr Pro Ser Phe Val Gly Ser Met
145 150 155 160

Ile Ser Gly Tyr Asp Val Ala Val Arg Asp Val Val Arg His Phe Ala
165 170 175

Lys Arg Glu Ala Pro Asn Asp Lys Ile Asn Leu Leu Thr Gly Trp Val
180 185 190

Asn Pro Gly Asp Val Lys Glu Leu Lys His Leu Leu Gly Glu Met Asp
195 200 205

Ile Glu Ala Asn Val Leu Phe Glu Ile Glu Ser Phe Asp Ser Pro Ile
210 215 220

Leu Pro Asp Gly Ser Ala Val Ser His Gly Asn Thr Thr Ile Glu Asp
225 230 235 240

Leu Ile Asp Thr Gly Asn Ala Arg Ala Thr Phe Ala Leu Asn Arg Tyr
245 250 255

```
Glu Gly Thr Lys Ala Ala Glu Tyr Leu Gln Lys Lys Phe Glu Ile Pro
            260                 265                 270

Ala Ile Ile Gly Pro Thr Pro Ile Gly Ile Arg Asn Thr Asp Ile Phe
        275                 280                 285

Leu Gln Asn Leu Lys Lys Ala Thr Gly Lys Pro Ile Pro Gln Ser Leu
    290                 295                 300

Ala His Glu Arg Gly Val Ala Ile Asp Ala Leu Ala Asp Leu Thr His
305                 310                 315                 320

Met Phe Leu Ala Glu Lys Arg Val Ala Ile Tyr Gly Ala Pro Asp Leu
                325                 330                 335

Val Ile Gly Leu Ala Glu Phe Cys Leu Asp Leu Glu Met Lys Pro Val
            340                 345                 350

Leu Leu Leu Leu Gly Asp Asp Asn Ser Lys Tyr Val Asp Asp Pro Arg
        355                 360                 365

Ile Lys Ala Leu Gln Glu Asn Val Asp Tyr Gly Met Glu Ile Val Thr
    370                 375                 380

Asn Ala Asp Phe Trp Glu Leu Glu Asn Arg Ile Lys Asn Glu Gly Leu
385                 390                 395                 400

Glu Leu Asp Leu Ile Leu Gly His Ser Lys Gly Arg Phe Ile Ser Ile
                405                 410                 415

Asp Tyr Asn Ile Pro Met Leu Arg Val Gly Phe Pro Thr Tyr Asp Arg
            420                 425                 430

Ala Gly Leu Phe Arg Tyr Pro Thr Val Gly Tyr Gly Gly Ala Ile Trp
        435                 440                 445

Leu Ala Glu Gln Met Ala Asn Thr Leu Phe Ala Asp Met Glu His Lys
    450                 455                 460

Lys Asn Lys Glu Trp Val Leu Asn Val Trp
465                 470
```

<210> SEQ ID NO 188
<211> LENGTH: 287
<212> TYPE: PRT
<213> ORGANISM: Artificial Sequence
<220> FEATURE:
<223> OTHER INFORMATION: HA::AnfH polypeptide

<400> SEQUENCE: 188

```
Met Tyr Pro Tyr Asp Val Pro Asp Tyr Ala Gly Gly Met Thr Arg Lys
1               5                   10                  15

Val Ala Ile Tyr Gly Lys Gly Gly Ile Gly Lys Ser Thr Thr Thr Gln
            20                  25                  30

Asn Thr Ala Ala Ala Leu Ala Tyr Phe His Asp Lys Lys Val Phe Ile
        35                  40                  45

His Gly Cys Asp Pro Lys Ala Asp Ser Thr Arg Leu Ile Leu Gly Gly
    50                  55                  60

Lys Pro Gln Glu Thr Leu Met Asp Met Leu Arg Asp Lys Gly Ala Glu
65                  70                  75                  80

Lys Ile Thr Asn Asp Asp Val Ile Lys Lys Gly Phe Leu Asp Ile Gln
                85                  90                  95

Cys Val Glu Ser Gly Gly Pro Glu Pro Gly Val Gly Cys Ala Gly Arg
            100                 105                 110

Gly Val Ile Thr Ala Ile Asp Leu Met Glu Glu Asn Gly Ala Tyr Thr
        115                 120                 125

Asp Asp Leu Asp Phe Val Phe Phe Asp Val Leu Gly Asp Val Val Cys
    130                 135                 140
```

Gly Gly Phe Ala Met Pro Ile Arg Asp Gly Lys Ala Gln Glu Val Tyr
145 150 155 160

Ile Val Ala Ser Gly Glu Met Met Ala Ile Tyr Ala Ala Asn Asn Ile
165 170 175

Cys Lys Gly Leu Val Lys Tyr Ala Lys Gln Ser Gly Val Arg Leu Gly
180 185 190

Gly Ile Ile Cys Asn Ser Arg Lys Val Asp Gly Glu Arg Glu Phe Leu
195 200 205

Glu Glu Phe Thr Ala Ala Ile Gly Thr Lys Met Ile His Phe Val Pro
210 215 220

Arg Asp Asn Ile Val Gln Lys Ala Glu Phe Asn Lys Lys Thr Val Thr
225 230 235 240

Glu Phe Ala Pro Glu Glu Asn Gln Ala Lys Glu Tyr Gly Glu Leu Ala
245 250 255

Arg Lys Ile Ile Glu Asn Asp Glu Phe Val Ile Pro Lys Pro Leu Thr
260 265 270

Met Asp Gln Leu Glu Asp Met Val Val Lys Tyr Gly Ile Ala Asp
275 280 285

<210> SEQ ID NO 189
<211> LENGTH: 144
<212> TYPE: PRT
<213> ORGANISM: Artificial Sequence
<220> FEATURE:
<223> OTHER INFORMATION: HA::AnfG polypeptide

<400> SEQUENCE: 189

Met Tyr Pro Tyr Asp Val Pro Asp Tyr Ala Gly Gly Met Ser Thr Ala
1 5 10 15

Ser Ala Ala Ala Val Val Lys Gln Lys Val Glu Ala Pro Val His Pro
20 25 30

Met Asp Ala Arg Ile Asp Glu Leu Thr Asp Tyr Ile Met Lys Asn Cys
35 40 45

Leu Trp Gln Phe His Ser Arg Ser Trp Asp Arg Glu Arg Gln Asn Ala
50 55 60

Glu Ile Leu Lys Lys Thr Lys Glu Leu Leu Cys Gly Glu Pro Val Asp
65 70 75 80

Leu Ser Thr Ser His Asp Arg Cys Tyr Trp Val Asp Ala Val Cys Leu
85 90 95

Ala Asp Asp Tyr Arg Glu His Tyr Pro Trp Ile Asn Ser Met Ser Lys
100 105 110

Glu Glu Ile Gly Ser Leu Met Gln Gly Leu Lys Asp Arg Met Asp Tyr
115 120 125

Leu Thr Ile Thr Gly Ser Leu Asn Glu Glu Leu Ser Asp Lys His Tyr
130 135 140

<210> SEQ ID NO 190
<211> LENGTH: 526
<212> TYPE: PRT
<213> ORGANISM: Artificial Sequence
<220> FEATURE:
<223> OTHER INFORMATION: mFAγ51::HA::AnfK polypeptide

<400> SEQUENCE: 190

Met Ala Met Ala Val Phe Arg Arg Glu Ala Ala Ala Leu Leu Pro Ser
1 5 10 15

Ile Ala Ala Arg Pro Ile Ala Ala Ala Ala Ala Ala Ala Ser Ser Asp

```
            20                  25                  30

Gln Glu Glu Gly Leu Leu Ala Ala Ala Ala Ala Ala Ala Ala Val Val
        35                  40                  45

Arg Asn Arg Gly Gly Tyr Pro Tyr Asp Val Pro Asp Tyr Ala Gly Gly
    50                  55                  60

Met Thr Cys Glu Val Lys Glu Lys Gly Arg Val Gly Thr Ile Asn Pro
65                  70                  75                  80

Ile Phe Thr Cys Gln Pro Ala Gly Ala Gln Phe Val Ser Ile Gly Ile
                85                  90                  95

Lys Asp Cys Ile Gly Ile Val His Gly Gly Gln Gly Cys Val Met Phe
            100                 105                 110

Val Arg Leu Ile Phe Ser Gln His Tyr Lys Glu Ser Phe Glu Leu Ala
        115                 120                 125

Ser Ser Ser Leu His Glu Asp Gly Ala Val Phe Gly Ala Cys Gly Arg
    130                 135                 140

Val Glu Glu Ala Val Asp Val Leu Leu Ser Arg Tyr Pro Asp Val Lys
145                 150                 155                 160

Val Val Pro Ile Ile Thr Thr Cys Ser Thr Glu Ile Ile Gly Asp Asp
                165                 170                 175

Val Asp Gly Val Ile Lys Lys Leu Asn Glu Gly Leu Leu Lys Glu Lys
            180                 185                 190

Phe Pro Asp Arg Glu Val His Leu Ile Ala Met His Thr Pro Ser Phe
        195                 200                 205

Val Gly Ser Met Ile Ser Gly Tyr Asp Val Ala Val Arg Asp Val Val
    210                 215                 220

Arg His Phe Ala Lys Arg Glu Ala Pro Asn Asp Lys Ile Asn Leu Leu
225                 230                 235                 240

Thr Gly Trp Val Asn Pro Gly Asp Val Lys Glu Leu Lys His Leu Leu
                245                 250                 255

Gly Glu Met Asp Ile Glu Ala Asn Val Leu Phe Glu Ile Glu Ser Phe
            260                 265                 270

Asp Ser Pro Ile Leu Pro Asp Gly Ser Ala Val Ser His Gly Asn Thr
        275                 280                 285

Thr Ile Glu Asp Leu Ile Asp Thr Gly Asn Ala Arg Ala Thr Phe Ala
    290                 295                 300

Leu Asn Arg Tyr Glu Gly Thr Lys Ala Ala Glu Tyr Leu Gln Lys Lys
305                 310                 315                 320

Phe Glu Ile Pro Ala Ile Ile Gly Pro Thr Pro Ile Gly Ile Arg Asn
                325                 330                 335

Thr Asp Ile Phe Leu Gln Asn Leu Lys Lys Ala Thr Gly Lys Pro Ile
            340                 345                 350

Pro Gln Ser Leu Ala His Glu Arg Gly Val Ala Ile Asp Ala Leu Ala
        355                 360                 365

Asp Leu Thr His Met Phe Leu Ala Glu Lys Arg Val Ala Ile Tyr Gly
    370                 375                 380

Ala Pro Asp Leu Val Ile Gly Leu Ala Glu Phe Cys Leu Asp Leu Glu
385                 390                 395                 400

Met Lys Pro Val Leu Leu Leu Leu Gly Asp Asp Asn Ser Lys Tyr Val
                405                 410                 415

Asp Asp Pro Arg Ile Lys Ala Leu Gln Glu Asn Val Asp Tyr Gly Met
            420                 425                 430

Glu Ile Val Thr Asn Ala Asp Phe Trp Glu Leu Glu Asn Arg Ile Lys
        435                 440                 445
```

```
Asn Glu Gly Leu Glu Leu Asp Leu Ile Leu Gly His Ser Lys Gly Arg
    450                 455                 460

Phe Ile Ser Ile Asp Tyr Asn Ile Pro Met Leu Arg Val Gly Phe Pro
465                 470                 475                 480

Thr Tyr Asp Arg Ala Gly Leu Phe Arg Tyr Pro Thr Val Gly Tyr Gly
                485                 490                 495

Gly Ala Ile Trp Leu Ala Glu Gln Met Ala Asn Thr Leu Phe Ala Asp
            500                 505                 510

Met Glu His Lys Lys Asn Lys Glu Trp Val Leu Asn Val Trp
        515                 520                 525
```

<210> SEQ ID NO 191
<211> LENGTH: 339
<212> TYPE: PRT
<213> ORGANISM: Artificial Sequence
<220> FEATURE:
<223> OTHER INFORMATION: mFAγ51::HA::AnfH polypeptide

<400> SEQUENCE: 191

```
Met Ala Met Ala Val Phe Arg Arg Glu Ala Ala Ala Leu Leu Pro Ser
1               5                   10                  15

Ile Ala Ala Arg Pro Ile Ala Ala Ala Ala Ala Ala Ala Ser Ser Asp
            20                  25                  30

Gln Glu Glu Gly Leu Leu Ala Ala Ala Ala Ala Ala Ala Ala Val Val
        35                  40                  45

Arg Asn Arg Gly Gly Tyr Pro Tyr Asp Val Pro Asp Tyr Ala Gly Gly
    50                  55                  60

Met Thr Arg Lys Val Ala Ile Tyr Gly Lys Gly Gly Ile Gly Lys Ser
65                  70                  75                  80

Thr Thr Thr Gln Asn Thr Ala Ala Ala Leu Ala Tyr Phe His Asp Lys
                85                  90                  95

Lys Val Phe Ile His Gly Cys Asp Pro Lys Ala Asp Ser Thr Arg Leu
            100                 105                 110

Ile Leu Gly Gly Lys Pro Gln Glu Thr Leu Met Asp Met Leu Arg Asp
        115                 120                 125

Lys Gly Ala Glu Lys Ile Thr Asn Asp Asp Val Ile Lys Lys Gly Phe
    130                 135                 140

Leu Asp Ile Gln Cys Val Glu Ser Gly Gly Pro Glu Pro Gly Val Gly
145                 150                 155                 160

Cys Ala Gly Arg Gly Val Ile Thr Ala Ile Asp Leu Met Glu Glu Asn
                165                 170                 175

Gly Ala Tyr Thr Asp Asp Leu Asp Phe Val Phe Phe Asp Val Leu Gly
            180                 185                 190

Asp Val Val Cys Gly Gly Phe Ala Met Pro Ile Arg Asp Gly Lys Ala
        195                 200                 205

Gln Glu Val Tyr Ile Val Ala Ser Gly Glu Met Met Ala Ile Tyr Ala
    210                 215                 220

Ala Asn Asn Ile Cys Lys Gly Leu Val Lys Tyr Ala Lys Gln Ser Gly
225                 230                 235                 240

Val Arg Leu Gly Gly Ile Ile Cys Asn Ser Arg Lys Val Asp Gly Glu
                245                 250                 255

Arg Glu Phe Leu Glu Glu Phe Thr Ala Ala Ile Gly Thr Lys Met Ile
            260                 265                 270

His Phe Val Pro Arg Asp Asn Ile Val Gln Lys Ala Glu Phe Asn Lys
        275                 280                 285
```

Lys Thr Val Thr Glu Phe Ala Pro Glu Glu Asn Gln Ala Lys Glu Tyr
290 295 300

Gly Glu Leu Ala Arg Lys Ile Ile Glu Asn Asp Glu Phe Val Ile Pro
305 310 315 320

Lys Pro Leu Thr Met Asp Gln Leu Glu Asp Met Val Val Lys Tyr Gly
325 330 335

Ile Ala Asp

<210> SEQ ID NO 192
<211> LENGTH: 196
<212> TYPE: PRT
<213> ORGANISM: Artificial Sequence
<220> FEATURE:
<223> OTHER INFORMATION: mFAγ51::HA::AnfG polypeptide

<400> SEQUENCE: 192

Met Ala Met Ala Val Phe Arg Arg Glu Ala Ala Ala Leu Leu Pro Ser
1 5 10 15

Ile Ala Ala Arg Pro Ile Ala Ala Ala Ala Ala Ala Ala Ser Ser Asp
20 25 30

Gln Glu Glu Gly Leu Leu Ala Ala Ala Ala Ala Ala Ala Ala Val Val
35 40 45

Arg Asn Arg Gly Gly Tyr Pro Tyr Asp Val Pro Asp Tyr Ala Gly Gly
50 55 60

Met Ser Thr Ala Ser Ala Ala Ala Val Val Lys Gln Lys Val Glu Ala
65 70 75 80

Pro Val His Pro Met Asp Ala Arg Ile Asp Glu Leu Thr Asp Tyr Ile
85 90 95

Met Lys Asn Cys Leu Trp Gln Phe His Ser Arg Ser Trp Asp Arg Glu
100 105 110

Arg Gln Asn Ala Glu Ile Leu Lys Lys Thr Lys Glu Leu Leu Cys Gly
115 120 125

Glu Pro Val Asp Leu Ser Thr Ser His Asp Arg Cys Tyr Trp Val Asp
130 135 140

Ala Val Cys Leu Ala Asp Asp Tyr Arg Glu His Tyr Pro Trp Ile Asn
145 150 155 160

Ser Met Ser Lys Glu Glu Ile Gly Ser Leu Met Gln Gly Leu Lys Asp
165 170 175

Arg Met Asp Tyr Leu Thr Ile Thr Gly Ser Leu Asn Glu Glu Leu Ser
180 185 190

Asp Lys His Tyr
195

<210> SEQ ID NO 193
<211> LENGTH: 582
<212> TYPE: PRT
<213> ORGANISM: Artificial Sequence
<220> FEATURE:
<223> OTHER INFORMATION: mFAγ51::HA::AnfD polypeptide

<400> SEQUENCE: 193

Met Ala Met Ala Val Phe Arg Arg Glu Ala Ala Ala Leu Leu Pro Ser
1 5 10 15

Ile Ala Ala Arg Pro Ile Ala Ala Ala Ala Ala Ala Ala Ser Ser Asp
20 25 30

Gln Glu Glu Gly Leu Leu Ala Ala Ala Ala Ala Ala Ala Ala Val Val
35 40 45

```
Arg Asn Arg Gly Gly Tyr Pro Tyr Asp Val Pro Asp Tyr Ala Gly Gly
    50                  55                  60

Met Pro His His Glu Phe Glu Cys Ser Lys Val Ile Pro Glu Arg Lys
65                  70                  75                  80

Lys His Ala Val Ile Lys Gly Lys Gly Glu Thr Leu Ala Asp Ala Leu
                85                  90                  95

Pro Gln Gly Tyr Leu Asn Thr Ile Pro Gly Ser Ile Ser Glu Arg Gly
            100                 105                 110

Cys Ala Tyr Cys Gly Ala Lys His Val Ile Gly Thr Pro Met Lys Asp
        115                 120                 125

Val Ile His Ile Ser His Gly Pro Val Gly Cys Thr Tyr Asp Thr Trp
    130                 135                 140

Gln Thr Lys Arg Tyr Ile Ser Asp Asn Asp Asn Phe Gln Leu Lys Tyr
145                 150                 155                 160

Thr Tyr Ala Thr Asp Val Lys Glu Lys His Ile Val Phe Gly Ala Glu
                165                 170                 175

Lys Leu Leu Lys Gln Asn Ile Ile Glu Ala Phe Lys Ala Phe Pro Gln
            180                 185                 190

Ile Lys Arg Met Thr Ile Tyr Gln Thr Cys Ala Thr Ala Leu Ile Gly
        195                 200                 205

Asp Asp Ile Asn Ala Ile Ala Glu Glu Val Met Glu Glu Met Pro Glu
    210                 215                 220

Val Asp Ile Phe Val Cys Asn Ser Pro Gly Phe Ala Gly Pro Ser Gln
225                 230                 235                 240

Ser Gly Gly His His Lys Ile Asn Ile Ala Trp Ile Asn Gln Lys Val
                245                 250                 255

Gly Thr Val Glu Pro Glu Ile Thr Gly Asp His Val Ile Asn Tyr Val
            260                 265                 270

Gly Glu Tyr Asn Ile Gln Gly Asp Gln Glu Val Met Val Asp Tyr Phe
        275                 280                 285

Lys Arg Met Gly Ile Gln Val Leu Ser Thr Phe Thr Gly Asn Gly Ser
    290                 295                 300

Tyr Asp Gly Leu Arg Ala Met His Arg Ala His Leu Asn Val Leu Glu
305                 310                 315                 320

Cys Ala Arg Ser Ala Glu Tyr Ile Cys Asn Glu Leu Arg Val Arg Tyr
                325                 330                 335

Gly Ile Pro Arg Leu Asp Ile Asp Gly Phe Gly Phe Lys Pro Leu Ala
            340                 345                 350

Asp Ser Leu Arg Lys Ile Gly Met Phe Phe Gly Ile Glu Asp Arg Ala
        355                 360                 365

Lys Ala Ile Ile Asp Glu Glu Val Ala Arg Trp Lys Pro Glu Leu Asp
    370                 375                 380

Trp Tyr Lys Glu Arg Leu Met Gly Lys Lys Val Cys Leu Trp Pro Gly
385                 390                 395                 400

Gly Ser Lys Leu Trp His Trp Ala His Val Ile Glu Glu Glu Met Gly
                405                 410                 415

Leu Lys Val Val Ser Val Tyr Thr Lys Phe Gly His Gln Gly Asp Met
            420                 425                 430

Glu Lys Gly Ile Ala Arg Cys Gly Glu Gly Thr Leu Ala Ile Asp Asp
        435                 440                 445

Pro Asn Glu Leu Glu Gly Leu Glu Ala Leu Glu Met Leu Lys Pro Asp
    450                 455                 460
```

```
Ile Ile Leu Thr Gly Lys Arg Pro Gly Glu Val Ala Lys Lys Val Arg
465                 470                 475                 480

Val Pro Tyr Leu Asn Ala His Ala Tyr His Asn Gly Pro Tyr Lys Gly
                485                 490                 495

Phe Glu Gly Trp Val Arg Phe Ala Arg Asp Ile Tyr Asn Ala Ile Tyr
            500                 505                 510

Ser Pro Ile His Gln Leu Ser Gly Ile Asp Ile Thr Lys Asp Asn Ala
        515                 520                 525

Pro Glu Trp Gly Asn Gly Phe Arg Thr Arg Gln Met Leu Ser Asp Gly
    530                 535                 540

Asn Leu Ser Asp Ala Val Arg Asn Ser Glu Thr Leu Arg Gln Tyr Thr
545                 550                 555                 560

Gly Gly Tyr Asp Ser Val Ser Lys Leu Arg Glu Arg Glu Tyr Pro Ala
                565                 570                 575

Phe Glu Arg Lys Val Gly
            580


<210> SEQ ID NO 194
<211> LENGTH: 582
<212> TYPE: PRT
<213> ORGANISM: Artificial Sequence
<220> FEATURE:
<223> OTHER INFORMATION: MTP-FAγ51::HA::AnfD polypeptide

<400> SEQUENCE: 194

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Pro His His Glu Phe Glu Cys Ser Lys Val Ile Pro Glu Arg Lys
65                  70                  75                  80

Lys His Ala Val Ile Lys Gly Lys Gly Glu Thr Leu Ala Asp Ala Leu
                85                  90                  95

Pro Gln Gly Tyr Leu Asn Thr Ile Pro Gly Ser Ile Ser Glu Arg Gly
            100                 105                 110

Cys Ala Tyr Cys Gly Ala Lys His Val Ile Gly Thr Pro Met Lys Asp
        115                 120                 125

Val Ile His Ile Ser His Gly Pro Val Gly Cys Thr Tyr Asp Thr Trp
    130                 135                 140

Gln Thr Lys Arg Tyr Ile Ser Asp Asn Asp Asn Phe Gln Leu Lys Tyr
145                 150                 155                 160

Thr Tyr Ala Thr Asp Val Lys Glu Lys His Ile Val Phe Gly Ala Glu
                165                 170                 175

Lys Leu Leu Lys Gln Asn Ile Ile Glu Ala Phe Lys Ala Phe Pro Gln
            180                 185                 190

Ile Lys Arg Met Thr Ile Tyr Gln Thr Cys Ala Thr Ala Leu Ile Gly
        195                 200                 205

Asp Asp Ile Asn Ala Ile Ala Glu Glu Val Met Glu Glu Met Pro Glu
    210                 215                 220

Val Asp Ile Phe Val Cys Asn Ser Pro Gly Phe Ala Gly Pro Ser Gln
225                 230                 235                 240
```

```
Ser Gly Gly His His Lys Ile Asn Ile Ala Trp Ile Asn Gln Lys Val
                245                 250                 255

Gly Thr Val Glu Pro Glu Ile Thr Gly Asp His Val Ile Asn Tyr Val
            260                 265                 270

Gly Glu Tyr Asn Ile Gln Gly Asp Gln Glu Val Met Val Asp Tyr Phe
        275                 280                 285

Lys Arg Met Gly Ile Gln Val Leu Ser Thr Phe Thr Gly Asn Gly Ser
    290                 295                 300

Tyr Asp Gly Leu Arg Ala Met His Arg Ala His Leu Asn Val Leu Glu
305                 310                 315                 320

Cys Ala Arg Ser Ala Glu Tyr Ile Cys Asn Glu Leu Arg Val Arg Tyr
                325                 330                 335

Gly Ile Pro Arg Leu Asp Ile Asp Gly Phe Gly Phe Lys Pro Leu Ala
            340                 345                 350

Asp Ser Leu Arg Lys Ile Gly Met Phe Phe Gly Ile Glu Asp Arg Ala
        355                 360                 365

Lys Ala Ile Ile Asp Glu Glu Val Ala Arg Trp Lys Pro Glu Leu Asp
    370                 375                 380

Trp Tyr Lys Glu Arg Leu Met Gly Lys Lys Val Cys Leu Trp Pro Gly
385                 390                 395                 400

Gly Ser Lys Leu Trp His Trp Ala His Val Ile Glu Glu Glu Met Gly
                405                 410                 415

Leu Lys Val Val Ser Val Tyr Thr Lys Phe Gly His Gln Gly Asp Met
            420                 425                 430

Glu Lys Gly Ile Ala Arg Cys Gly Glu Gly Thr Leu Ala Ile Asp Asp
        435                 440                 445

Pro Asn Glu Leu Glu Gly Leu Glu Ala Leu Glu Met Leu Lys Pro Asp
    450                 455                 460

Ile Ile Leu Thr Gly Lys Arg Pro Gly Glu Val Ala Lys Lys Val Arg
465                 470                 475                 480

Val Pro Tyr Leu Asn Ala His Ala Tyr His Asn Gly Pro Tyr Lys Gly
                485                 490                 495

Phe Glu Gly Trp Val Arg Phe Ala Arg Asp Ile Tyr Asn Ala Ile Tyr
            500                 505                 510

Ser Pro Ile His Gln Leu Ser Gly Ile Asp Ile Thr Lys Asp Asn Ala
        515                 520                 525

Pro Glu Trp Gly Asn Gly Phe Arg Thr Arg Gln Met Leu Ser Asp Gly
    530                 535                 540

Asn Leu Ser Asp Ala Val Arg Asn Ser Glu Thr Leu Arg Gln Tyr Thr
545                 550                 555                 560

Gly Gly Tyr Asp Ser Val Ser Lys Leu Arg Glu Arg Glu Tyr Pro Ala
                565                 570                 575

Phe Glu Arg Lys Val Gly
            580
```

<210> SEQ ID NO 195
<211> LENGTH: 604
<212> TYPE: PRT
<213> ORGANISM: Artificial Sequence
<220> FEATURE:
<223> OTHER INFORMATION: MTP-FAγ51::AnfD::Twin Strep polypeptide

<400> SEQUENCE: 195

```
Met Met Ala Met Ala Val Phe Arg Arg Glu Gly Arg Arg Leu Leu Pro
1               5                   10                  15
```

```
Ser Ile Ala Ala Arg Pro Ile Ala Ala Ile Arg Ser Pro Leu Ser Ser
            20                  25                  30

Asp Gln Glu Glu Gly Leu Leu Gly Val Arg Ser Ile Ser Thr Gln Val
        35                  40                  45

Val Arg Asn Arg Gly Gly Met Pro His His Glu Phe Glu Cys Ser Lys
    50                  55                  60

Val Ile Pro Glu Arg Lys Lys His Ala Val Ile Lys Gly Lys Gly Glu
65                  70                  75                  80

Thr Leu Ala Asp Ala Leu Pro Gln Gly Tyr Leu Asn Thr Ile Pro Gly
                85                  90                  95

Ser Ile Ser Glu Arg Gly Cys Ala Tyr Cys Gly Ala Lys His Val Ile
            100                 105                 110

Gly Thr Pro Met Lys Asp Val Ile His Ile Ser His Gly Pro Val Gly
        115                 120                 125

Cys Thr Tyr Asp Thr Trp Gln Thr Lys Arg Tyr Ile Ser Asp Asn Asp
    130                 135                 140

Asn Phe Gln Leu Lys Tyr Thr Tyr Ala Thr Asp Val Lys Glu Lys His
145                 150                 155                 160

Ile Val Phe Gly Ala Glu Lys Leu Leu Lys Gln Asn Ile Ile Glu Ala
                165                 170                 175

Phe Lys Ala Phe Pro Gln Ile Lys Arg Met Thr Ile Tyr Gln Thr Cys
            180                 185                 190

Ala Thr Ala Leu Ile Gly Asp Asp Ile Asn Ala Ile Ala Glu Glu Val
        195                 200                 205

Met Glu Glu Met Pro Glu Val Asp Ile Phe Val Cys Asn Ser Pro Gly
    210                 215                 220

Phe Ala Gly Pro Ser Gln Ser Gly Gly His His Lys Ile Asn Ile Ala
225                 230                 235                 240

Trp Ile Asn Gln Lys Val Gly Thr Val Glu Pro Glu Ile Thr Gly Asp
                245                 250                 255

His Val Ile Asn Tyr Val Gly Glu Tyr Asn Ile Gln Gly Asp Gln Glu
            260                 265                 270

Val Met Val Asp Tyr Phe Lys Arg Met Gly Ile Gln Val Leu Ser Thr
        275                 280                 285

Phe Thr Gly Asn Gly Ser Tyr Asp Gly Leu Arg Ala Met His Arg Ala
    290                 295                 300

His Leu Asn Val Leu Glu Cys Ala Arg Ser Ala Glu Tyr Ile Cys Asn
305                 310                 315                 320

Glu Leu Arg Val Arg Tyr Gly Ile Pro Arg Leu Asp Ile Asp Gly Phe
                325                 330                 335

Gly Phe Lys Pro Leu Ala Asp Ser Leu Arg Lys Ile Gly Met Phe Phe
            340                 345                 350

Gly Ile Glu Asp Arg Ala Lys Ala Ile Ile Asp Glu Glu Val Ala Arg
        355                 360                 365

Trp Lys Pro Glu Leu Asp Trp Tyr Lys Glu Arg Leu Met Gly Lys Lys
    370                 375                 380

Val Cys Leu Trp Pro Gly Gly Ser Lys Leu Trp His Trp Ala His Val
385                 390                 395                 400

Ile Glu Glu Glu Met Gly Leu Lys Val Val Ser Val Tyr Thr Lys Phe
                405                 410                 415

Gly His Gln Gly Asp Met Glu Lys Gly Ile Ala Arg Cys Gly Glu Gly
            420                 425                 430

Thr Leu Ala Ile Asp Asp Pro Asn Glu Leu Glu Gly Leu Glu Ala Leu
```

```
        435                 440                 445

Glu Met Leu Lys Pro Asp Ile Ile Leu Thr Gly Lys Arg Pro Gly Glu
    450                 455                 460

Val Ala Lys Lys Val Arg Val Pro Tyr Leu Asn Ala His Ala Tyr His
465                 470                 475                 480

Asn Gly Pro Tyr Lys Gly Phe Glu Gly Trp Val Arg Phe Ala Arg Asp
                485                 490                 495

Ile Tyr Asn Ala Ile Tyr Ser Pro Ile His Gln Leu Ser Gly Ile Asp
            500                 505                 510

Ile Thr Lys Asp Asn Ala Pro Glu Trp Gly Asn Gly Phe Arg Thr Arg
        515                 520                 525

Gln Met Leu Ser Asp Gly Asn Leu Ser Asp Ala Val Arg Asn Ser Glu
    530                 535                 540

Thr Leu Arg Gln Tyr Thr Gly Gly Tyr Asp Ser Val Ser Lys Leu Arg
545                 550                 555                 560

Glu Arg Glu Tyr Pro Ala Phe Glu Arg Lys Val Gly Gly Gly Ser Ala
                565                 570                 575

Trp Ser His Pro Gln Phe Glu Lys Gly Gly Gly Ser Gly Gly Gly Ser
            580                 585                 590

Gly Gly Ser Ala Trp Ser His Pro Gln Phe Glu Lys
        595                 600


<210> SEQ ID NO 196
<211> LENGTH: 523
<212> TYPE: PRT
<213> ORGANISM: Artificial Sequence
<220> FEATURE:
<223> OTHER INFORMATION: MTP-CoxIV::Twin Strep::AnfK polypeptide

<400> SEQUENCE: 196

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Thr Cys
    50                  55                  60

Glu Val Lys Glu Lys Gly Arg Val Gly Thr Ile Asn Pro Ile Phe Thr
65                  70                  75                  80

Cys Gln Pro Ala Gly Ala Gln Phe Val Ser Ile Gly Ile Lys Asp Cys
                85                  90                  95

Ile Gly Ile Val His Gly Gly Gln Gly Cys Val Met Phe Val Arg Leu
            100                 105                 110

Ile Phe Ser Gln His Tyr Lys Glu Ser Phe Glu Leu Ala Ser Ser Ser
        115                 120                 125

Leu His Glu Asp Gly Ala Val Phe Gly Ala Cys Gly Arg Val Glu Glu
    130                 135                 140

Ala Val Asp Val Leu Leu Ser Arg Tyr Pro Asp Val Lys Val Val Pro
145                 150                 155                 160

Ile Ile Thr Thr Cys Ser Thr Glu Ile Ile Gly Asp Asp Val Asp Gly
                165                 170                 175

Val Ile Lys Lys Leu Asn Glu Gly Leu Leu Lys Glu Lys Phe Pro Asp
            180                 185                 190

Arg Glu Val His Leu Ile Ala Met His Thr Pro Ser Phe Val Gly Ser
```

```
        195                 200                 205

Met Ile Ser Gly Tyr Asp Val Ala Val Arg Asp Val Val Arg His Phe
    210                 215                 220

Ala Lys Arg Glu Ala Pro Asn Asp Lys Ile Asn Leu Leu Thr Gly Trp
225                 230                 235                 240

Val Asn Pro Gly Asp Val Lys Glu Leu Lys His Leu Leu Gly Glu Met
                245                 250                 255

Asp Ile Glu Ala Asn Val Leu Phe Glu Ile Glu Ser Phe Asp Ser Pro
            260                 265                 270

Ile Leu Pro Asp Gly Ser Ala Val Ser His Gly Asn Thr Thr Ile Glu
        275                 280                 285

Asp Leu Ile Asp Thr Gly Asn Ala Arg Ala Thr Phe Ala Leu Asn Arg
    290                 295                 300

Tyr Glu Gly Thr Lys Ala Ala Glu Tyr Leu Gln Lys Lys Phe Glu Ile
305                 310                 315                 320

Pro Ala Ile Ile Gly Pro Thr Pro Ile Gly Ile Arg Asn Thr Asp Ile
                325                 330                 335

Phe Leu Gln Asn Leu Lys Lys Ala Thr Gly Lys Pro Ile Pro Gln Ser
            340                 345                 350

Leu Ala His Glu Arg Gly Val Ala Ile Asp Ala Leu Ala Asp Leu Thr
        355                 360                 365

His Met Phe Leu Ala Glu Lys Arg Val Ala Ile Tyr Gly Ala Pro Asp
    370                 375                 380

Leu Val Ile Gly Leu Ala Glu Phe Cys Leu Asp Leu Glu Met Lys Pro
385                 390                 395                 400

Val Leu Leu Leu Leu Gly Asp Asp Asn Ser Lys Tyr Val Asp Asp Pro
                405                 410                 415

Arg Ile Lys Ala Leu Gln Glu Asn Val Asp Tyr Gly Met Glu Ile Val
            420                 425                 430

Thr Asn Ala Asp Phe Trp Glu Leu Glu Asn Arg Ile Lys Asn Glu Gly
        435                 440                 445

Leu Glu Leu Asp Leu Ile Leu Gly His Ser Lys Gly Arg Phe Ile Ser
    450                 455                 460

Ile Asp Tyr Asn Ile Pro Met Leu Arg Val Gly Phe Pro Thr Tyr Asp
465                 470                 475                 480

Arg Ala Gly Leu Phe Arg Tyr Pro Thr Val Gly Tyr Gly Gly Ala Ile
                485                 490                 495

Trp Leu Ala Glu Gln Met Ala Asn Thr Leu Phe Ala Asp Met Glu His
            500                 505                 510

Lys Lys Asn Lys Glu Trp Val Leu Asn Val Trp
        515                 520


<210> SEQ ID NO 197
<211> LENGTH: 31
<212> TYPE: PRT
<213> ORGANISM: Artificial Sequence
<220> FEATURE:
<223> OTHER INFORMATION: peptide sequence

<400> SEQUENCE: 197

Asn Ser Glu Thr Leu Arg Gln Tyr Thr Gly Gly Tyr Asp Ser Val Ser
1               5                   10                  15

Lys Leu Arg Glu Arg Glu Tyr Pro Ala Phe Glu Arg Lys Val Gly
            20                  25                  30
```

```
<210> SEQ ID NO 198
<211> LENGTH: 16
<212> TYPE: PRT
<213> ORGANISM: Artificial Sequence
<220> FEATURE:
<223> OTHER INFORMATION: peptide sequence

<400> SEQUENCE: 198

Gly Gly Gly Ser Gly Gly Gly Ser Gly Gly Gly Ser Gly Gly Gly Ser
1               5                   10                  15


<210> SEQ ID NO 199
<211> LENGTH: 984
<212> TYPE: PRT
<213> ORGANISM: Artificial Sequence
<220> FEATURE:
<223> OTHER INFORMATION: Amino acid sequence of AnfD::linker16::AnfK
      polypeptide used for modelling the structure (Example 20). Amino
      acids 1-509 correspond to the AnfD sequence (A. vinelandii)
      omitting the N-terminal methionine, amino acids 510-525 correspond
      to the

<400> SEQUENCE: 199

Pro His His Glu Phe Glu Cys Ser Lys Val Ile Pro Glu Arg Lys Lys
1               5                   10                  15

His Ala Val Ile Lys Gly Lys Gly Glu Thr Leu Ala Asp Ala Leu Pro
            20                  25                  30

Gln Gly Tyr Leu Asn Thr Ile Pro Gly Ser Ile Ser Glu Arg Gly Cys
        35                  40                  45

Ala Tyr Cys Gly Ala Lys His Val Ile Gly Thr Pro Met Lys Asp Val
    50                  55                  60

Ile His Ile Ser His Gly Pro Val Gly Cys Thr Tyr Asp Thr Trp Gln
65                  70                  75                  80

Thr Lys Arg Tyr Ile Ser Asp Asn Asp Asn Phe Gln Leu Lys Tyr Thr
                85                  90                  95

Tyr Ala Thr Asp Val Lys Glu Lys His Ile Val Phe Gly Ala Glu Lys
            100                 105                 110

Leu Leu Lys Gln Asn Ile Ile Glu Ala Phe Lys Ala Phe Pro Gln Ile
        115                 120                 125

Lys Arg Met Thr Ile Tyr Gln Thr Cys Ala Thr Ala Leu Ile Gly Asp
    130                 135                 140

Asp Ile Asn Ala Ile Ala Glu Glu Val Met Glu Glu Met Pro Glu Val
145                 150                 155                 160

Asp Ile Phe Val Cys Asn Ser Pro Gly Phe Ala Gly Pro Ser Gln Ser
                165                 170                 175

Gly Gly His His Lys Ile Asn Ile Ala Trp Ile Asn Gln Lys Val Gly
            180                 185                 190

Thr Val Glu Pro Glu Ile Thr Gly Asp His Val Ile Asn Tyr Val Gly
        195                 200                 205

Glu Tyr Asn Ile Gln Gly Asp Gln Glu Val Met Val Asp Tyr Phe Lys
    210                 215                 220

Arg Met Gly Ile Gln Val Leu Ser Thr Phe Thr Gly Asn Gly Ser Tyr
225                 230                 235                 240

Asp Gly Leu Arg Ala Met His Arg Ala His Leu Asn Val Leu Glu Cys
                245                 250                 255

Ala Arg Ser Ala Glu Tyr Ile Cys Asn Glu Leu Arg Val Arg Tyr Gly
            260                 265                 270

Ile Pro Arg Leu Asp Ile Asp Gly Phe Gly Phe Lys Pro Leu Ala Asp
        275                 280                 285
```

```
Ser Leu Arg Lys Ile Gly Met Phe Phe Gly Ile Glu Asp Arg Ala Lys
    290                 295                 300

Ala Ile Ile Asp Glu Glu Val Ala Arg Trp Lys Pro Glu Leu Asp Trp
305                 310                 315                 320

Tyr Lys Glu Arg Leu Met Gly Lys Lys Val Cys Leu Trp Pro Gly Gly
                325                 330                 335

Ser Lys Leu Trp His Trp Ala His Val Ile Glu Glu Glu Met Gly Leu
            340                 345                 350

Lys Val Val Ser Val Tyr Thr Lys Phe Gly His Gln Gly Asp Met Glu
        355                 360                 365

Lys Gly Ile Ala Arg Cys Gly Glu Gly Thr Leu Ala Ile Asp Asp Pro
    370                 375                 380

Asn Glu Leu Glu Gly Leu Glu Ala Leu Glu Met Leu Lys Pro Asp Ile
385                 390                 395                 400

Ile Leu Thr Gly Lys Arg Pro Gly Glu Val Ala Lys Lys Val Arg Val
                405                 410                 415

Pro Tyr Leu Asn Ala His Ala Tyr His Asn Gly Pro Tyr Lys Gly Phe
            420                 425                 430

Glu Gly Trp Val Arg Phe Ala Arg Asp Ile Tyr Asn Ala Ile Tyr Ser
        435                 440                 445

Pro Ile His Gln Leu Ser Gly Ile Asp Ile Thr Lys Asp Asn Ala Pro
    450                 455                 460

Glu Trp Gly Asn Gly Phe Arg Thr Arg Gln Met Leu Ser Asp Gly Asn
465                 470                 475                 480

Ser Glu Thr Leu Arg Gln Tyr Thr Gly Gly Tyr Asp Ser Val Ser Lys
                485                 490                 495

Leu Arg Glu Arg Glu Tyr Pro Ala Phe Glu Arg Lys Val Gly Gly Gly
            500                 505                 510

Gly Ser Gly Gly Gly Ser Gly Gly Gly Ser Gly Gly Gly Ser Val Lys
        515                 520                 525

Glu Lys Gly Arg Val Gly Thr Ile Asn Pro Ile Phe Thr Cys Gln Pro
    530                 535                 540

Ala Gly Ala Gln Phe Val Ser Ile Gly Ile Lys Asp Cys Ile Gly Ile
545                 550                 555                 560

Val His Gly Gly Gln Gly Cys Val Met Phe Val Arg Leu Ile Phe Ser
                565                 570                 575

Gln His Tyr Lys Glu Ser Phe Glu Leu Ala Ser Ser Ser Leu His Glu
            580                 585                 590

Asp Gly Ala Val Phe Gly Ala Cys Gly Arg Val Glu Glu Ala Val Asp
        595                 600                 605

Val Leu Leu Ser Arg Tyr Pro Asp Val Lys Val Val Pro Ile Ile Thr
    610                 615                 620

Thr Cys Ser Thr Glu Ile Ile Gly Asp Asp Val Asp Gly Val Ile Lys
625                 630                 635                 640

Lys Leu Asn Glu Gly Leu Leu Lys Glu Lys Phe Pro Asp Arg Glu Val
                645                 650                 655

His Leu Ile Ala Met His Thr Pro Ser Phe Val Gly Ser Met Ile Ser
            660                 665                 670

Gly Tyr Asp Val Ala Val Arg Asp Val Val Arg His Phe Ala Lys Arg
        675                 680                 685

Glu Ala Pro Asn Asp Lys Ile Asn Leu Leu Thr Gly Trp Val Asn Pro
    690                 695                 700
```

Gly Asp Val Lys Glu Leu Lys His Leu Leu Gly Glu Met Asp Ile Glu
705 710 715 720

Ala Asn Val Leu Phe Glu Ile Glu Ser Phe Asp Ser Pro Ile Leu Pro
725 730 735

Asp Gly Ser Ala Val Ser His Gly Asn Thr Thr Ile Glu Asp Leu Ile
740 745 750

Asp Thr Gly Asn Ala Arg Ala Thr Phe Ala Leu Asn Arg Tyr Glu Gly
755 760 765

Thr Lys Ala Ala Glu Tyr Leu Gln Lys Lys Phe Glu Ile Pro Ala Ile
770 775 780

Ile Gly Pro Thr Pro Ile Gly Ile Arg Asn Thr Asp Ile Phe Leu Gln
785 790 795 800

Asn Leu Lys Lys Ala Thr Gly Lys Pro Ile Pro Gln Ser Leu Ala His
805 810 815

Glu Arg Gly Val Ala Ile Asp Ala Leu Ala Asp Leu Thr His Met Phe
820 825 830

Leu Ala Glu Lys Arg Val Ala Ile Tyr Gly Ala Pro Asp Leu Val Ile
835 840 845

Gly Leu Ala Glu Phe Cys Leu Asp Leu Glu Met Lys Pro Val Leu Leu
850 855 860

Leu Leu Gly Asp Asp Asn Ser Lys Tyr Val Asp Asp Pro Arg Ile Lys
865 870 875 880

Ala Leu Gln Glu Asn Val Asp Tyr Gly Met Glu Ile Val Thr Asn Ala
885 890 895

Asp Phe Trp Glu Leu Glu Asn Arg Ile Lys Asn Glu Gly Leu Glu Leu
900 905 910

Asp Leu Ile Leu Gly His Ser Lys Gly Arg Phe Ile Ser Ile Asp Tyr
915 920 925

Asn Ile Pro Met Leu Arg Val Gly Phe Pro Thr Tyr Asp Arg Ala Gly
930 935 940

Leu Phe Arg Tyr Pro Thr Val Gly Tyr Gly Gly Ala Ile Trp Leu Ala
945 950 955 960

Glu Gln Met Ala Asn Thr Leu Phe Ala Asp Met Glu His Lys Lys Asn
965 970 975

Lys Glu Trp Val Leu Asn Val Trp
980

<210> SEQ ID NO 200
<211> LENGTH: 26
<212> TYPE: PRT
<213> ORGANISM: Artificial Sequence
<220> FEATURE:
<223> OTHER INFORMATION: Linker sequence

<400> SEQUENCE: 200

Gly Gly Gly Gly Ser Gly Gly Gly Ser Tyr Pro Tyr Asp Val Pro Asp
1 5 10 15

Tyr Ala Gly Gly Gly Ser Gly Gly Gly Ser
20 25

<210> SEQ ID NO 201
<211> LENGTH: 1004
<212> TYPE: PRT
<213> ORGANISM: Artificial Sequence
<220> FEATURE:
<223> OTHER INFORMATION: Amino acid sequence of AnfD::linker26(HA)::AnfK polypeptide used for modelling the structure. Amino acids 1-517 correspond to the AnfD sequence, amino acids 518-543 correspond to the 26-amino acid linker, and amino acids 544-1004 to AnfK

<400> SEQUENCE: 201

Met Pro His His Glu Phe Glu Cys Ser Lys Val Ile Pro Glu Arg Lys
1               5                   10                  15

Lys His Ala Val Ile Lys Gly Lys Gly Glu Thr Leu Ala Asp Ala Leu
            20                  25                  30

Pro Gln Gly Tyr Leu Asn Thr Ile Pro Gly Ser Ile Ser Glu Arg Gly
        35                  40                  45

Cys Ala Tyr Cys Gly Ala Lys His Val Ile Gly Thr Pro Met Lys Asp
    50                  55                  60

Val Ile His Ile Ser His Gly Pro Val Gly Cys Thr Tyr Asp Thr Trp
65                  70                  75                  80

Gln Thr Lys Arg Tyr Ile Ser Asp Asn Asp Asn Phe Gln Leu Lys Tyr
                85                  90                  95

Thr Tyr Ala Thr Asp Val Lys Glu Lys His Ile Val Phe Gly Ala Glu
            100                 105                 110

Lys Leu Leu Lys Gln Asn Ile Ile Glu Ala Phe Lys Ala Phe Pro Gln
        115                 120                 125

Ile Lys Arg Met Thr Ile Tyr Gln Thr Cys Ala Thr Ala Leu Ile Gly
    130                 135                 140

Asp Asp Ile Asn Ala Ile Ala Glu Glu Val Met Glu Glu Met Pro Glu
145                 150                 155                 160

Val Asp Ile Phe Val Cys Asn Ser Pro Gly Phe Ala Gly Pro Ser Gln
                165                 170                 175

Ser Gly Gly His His Lys Ile Asn Ile Ala Trp Ile Asn Gln Lys Val
            180                 185                 190

Gly Thr Val Glu Pro Glu Ile Thr Gly Asp His Val Ile Asn Tyr Val
        195                 200                 205

Gly Glu Tyr Asn Ile Gln Gly Asp Gln Glu Val Met Val Asp Tyr Phe
    210                 215                 220

Lys Arg Met Gly Ile Gln Val Leu Ser Thr Phe Thr Gly Asn Gly Ser
225                 230                 235                 240

Tyr Asp Gly Leu Arg Ala Met His Arg Ala His Leu Asn Val Leu Glu
                245                 250                 255

Cys Ala Arg Ser Ala Glu Tyr Ile Cys Asn Glu Leu Arg Val Arg Tyr
            260                 265                 270

Gly Ile Pro Arg Leu Asp Ile Asp Gly Phe Gly Phe Lys Pro Leu Ala
        275                 280                 285

Asp Ser Leu Arg Lys Ile Gly Met Phe Phe Gly Ile Glu Asp Arg Ala
    290                 295                 300

Lys Ala Ile Ile Asp Glu Glu Val Ala Arg Trp Lys Pro Glu Leu Asp
305                 310                 315                 320

Trp Tyr Lys Glu Arg Leu Met Gly Lys Lys Val Cys Leu Trp Pro Gly
                325                 330                 335

Gly Ser Lys Leu Trp His Trp Ala His Val Ile Glu Glu Glu Met Gly
            340                 345                 350

Leu Lys Val Val Ser Val Tyr Thr Lys Phe Gly His Gln Gly Asp Met
        355                 360                 365

Glu Lys Gly Ile Ala Arg Cys Gly Glu Gly Thr Leu Ala Ile Asp Asp
    370                 375                 380

Pro Asn Glu Leu Glu Gly Leu Glu Ala Leu Glu Met Leu Lys Pro Asp
385                 390                 395                 400

```
Ile Ile Leu Thr Gly Lys Arg Pro Gly Glu Val Ala Lys Lys Val Arg
                405                 410                 415

Val Pro Tyr Leu Asn Ala His Ala Tyr His Asn Gly Pro Tyr Lys Gly
            420                 425                 430

Phe Glu Gly Trp Val Arg Phe Ala Arg Asp Ile Tyr Asn Ala Ile Tyr
        435                 440                 445

Ser Pro Ile His Gln Leu Ser Gly Ile Asp Ile Thr Lys Asp Asn Ala
    450                 455                 460

Pro Glu Trp Gly Asn Gly Phe Arg Thr Arg Gln Met Leu Ser Asp Gly
465                 470                 475                 480

Asn Leu Ser Asp Ala Val Arg Asn Ser Glu Thr Leu Arg Gln Tyr Thr
                485                 490                 495

Gly Gly Tyr Asp Ser Val Ser Lys Leu Arg Glu Arg Glu Tyr Pro Ala
            500                 505                 510

Phe Glu Arg Lys Val Gly Gly Gly Gly Ser Gly Gly Gly Ser Tyr Pro
        515                 520                 525

Tyr Asp Val Pro Asp Tyr Ala Gly Gly Gly Ser Gly Gly Gly Ser Thr
    530                 535                 540

Cys Glu Val Lys Glu Lys Gly Arg Val Gly Thr Ile Asn Pro Ile Phe
545                 550                 555                 560

Thr Cys Gln Pro Ala Gly Ala Gln Phe Val Ser Ile Gly Ile Lys Asp
                565                 570                 575

Cys Ile Gly Ile Val His Gly Gly Gln Gly Cys Val Met Phe Val Arg
            580                 585                 590

Leu Ile Phe Ser Gln His Tyr Lys Glu Ser Phe Glu Leu Ala Ser Ser
        595                 600                 605

Ser Leu His Glu Asp Gly Ala Val Phe Gly Ala Cys Gly Arg Val Glu
    610                 615                 620

Glu Ala Val Asp Val Leu Leu Ser Arg Tyr Pro Asp Val Lys Val Val
625                 630                 635                 640

Pro Ile Ile Thr Thr Cys Ser Thr Glu Ile Ile Gly Asp Asp Val Asp
                645                 650                 655

Gly Val Ile Lys Lys Leu Asn Glu Gly Leu Leu Lys Glu Lys Phe Pro
            660                 665                 670

Asp Arg Glu Val His Leu Ile Ala Met His Thr Pro Ser Phe Val Gly
        675                 680                 685

Ser Met Ile Ser Gly Tyr Asp Val Ala Val Arg Asp Val Val Arg His
    690                 695                 700

Phe Ala Lys Arg Glu Ala Pro Asn Asp Lys Ile Asn Leu Leu Thr Gly
705                 710                 715                 720

Trp Val Asn Pro Gly Asp Val Lys Glu Leu Lys His Leu Leu Gly Glu
                725                 730                 735

Met Asp Ile Glu Ala Asn Val Leu Phe Glu Ile Glu Ser Phe Asp Ser
            740                 745                 750

Pro Ile Leu Pro Asp Gly Ser Ala Val Ser His Gly Asn Thr Thr Ile
        755                 760                 765

Glu Asp Leu Ile Asp Thr Gly Asn Ala Arg Ala Thr Phe Ala Leu Asn
    770                 775                 780

Arg Tyr Glu Gly Thr Lys Ala Ala Glu Tyr Leu Gln Lys Lys Phe Glu
785                 790                 795                 800

Ile Pro Ala Ile Ile Gly Pro Thr Pro Ile Gly Ile Arg Asn Thr Asp
                805                 810                 815

Ile Phe Leu Gln Asn Leu Lys Lys Ala Thr Gly Lys Pro Ile Pro Gln
```

```
            820                 825                 830

Ser Leu Ala His Glu Arg Gly Val Ala Ile Asp Ala Leu Ala Asp Leu
        835                 840                 845

Thr His Met Phe Leu Ala Glu Lys Arg Val Ala Ile Tyr Gly Ala Pro
    850                 855                 860

Asp Leu Val Ile Gly Leu Ala Glu Phe Cys Leu Asp Leu Glu Met Lys
865                 870                 875                 880

Pro Val Leu Leu Leu Leu Gly Asp Asp Asn Ser Lys Tyr Val Asp Asp
                885                 890                 895

Pro Arg Ile Lys Ala Leu Gln Glu Asn Val Asp Tyr Gly Met Glu Ile
            900                 905                 910

Val Thr Asn Ala Asp Phe Trp Glu Leu Glu Asn Arg Ile Lys Asn Glu
        915                 920                 925

Gly Leu Glu Leu Asp Leu Ile Leu Gly His Ser Lys Gly Arg Phe Ile
    930                 935                 940

Ser Ile Asp Tyr Asn Ile Pro Met Leu Arg Val Gly Phe Pro Thr Tyr
945                 950                 955                 960

Asp Arg Ala Gly Leu Phe Arg Tyr Pro Thr Val Gly Tyr Gly Gly Ala
                965                 970                 975

Ile Trp Leu Ala Glu Gln Met Ala Asn Thr Leu Phe Ala Asp Met Glu
            980                 985                 990

His Lys Lys Asn Lys Glu Trp Val  Leu Asn Val Trp
        995                 1000


<210> SEQ ID NO 202
<211> LENGTH: 1068
<212> TYPE: PRT
<213> ORGANISM: Artificial Sequence
<220> FEATURE:
<223> OTHER INFORMATION: Amino acid sequence of the
      MTP-FAγ51::AnfD::linker26(HA)::AnfK polypeptide encoded by SN272.
      Amino acids 1-64 correspond to the MTP-FAγ51 sequence including
      the GG at its C-terminus, amino acids 65-581 correspond to the
      AnfD sequence (A. vinelandii),

<400> SEQUENCE: 202

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Pro His His Glu Phe Glu Cys Ser Lys Val Ile Pro Glu Arg Lys
65                  70                  75                  80

Lys His Ala Val Ile Lys Gly Lys Gly Glu Thr Leu Ala Asp Ala Leu
                85                  90                  95

Pro Gln Gly Tyr Leu Asn Thr Ile Pro Gly Ser Ile Ser Glu Arg Gly
            100                 105                 110

Cys Ala Tyr Cys Gly Ala Lys His Val Ile Gly Thr Pro Met Lys Asp
        115                 120                 125

Val Ile His Ile Ser His Gly Pro Val Gly Cys Thr Tyr Asp Thr Trp
    130                 135                 140

Gln Thr Lys Arg Tyr Ile Ser Asp Asn Asp Asn Phe Gln Leu Lys Tyr
145                 150                 155                 160
```

-continued

```
Thr Tyr Ala Thr Asp Val Lys Glu Lys His Ile Val Phe Gly Ala Glu
                165                 170                 175

Lys Leu Leu Lys Gln Asn Ile Ile Glu Ala Phe Lys Ala Phe Pro Gln
            180                 185                 190

Ile Lys Arg Met Thr Ile Tyr Gln Thr Cys Ala Thr Ala Leu Ile Gly
        195                 200                 205

Asp Asp Ile Asn Ala Ile Ala Glu Glu Val Met Glu Glu Met Pro Glu
    210                 215                 220

Val Asp Ile Phe Val Cys Asn Ser Pro Gly Phe Ala Gly Pro Ser Gln
225                 230                 235                 240

Ser Gly Gly His His Lys Ile Asn Ile Ala Trp Ile Asn Gln Lys Val
                245                 250                 255

Gly Thr Val Glu Pro Glu Ile Thr Gly Asp His Val Ile Asn Tyr Val
            260                 265                 270

Gly Glu Tyr Asn Ile Gln Gly Asp Gln Glu Val Met Val Asp Tyr Phe
        275                 280                 285

Lys Arg Met Gly Ile Gln Val Leu Ser Thr Phe Thr Gly Asn Gly Ser
    290                 295                 300

Tyr Asp Gly Leu Arg Ala Met His Arg Ala His Leu Asn Val Leu Glu
305                 310                 315                 320

Cys Ala Arg Ser Ala Glu Tyr Ile Cys Asn Glu Leu Arg Val Arg Tyr
                325                 330                 335

Gly Ile Pro Arg Leu Asp Ile Asp Gly Phe Gly Phe Lys Pro Leu Ala
            340                 345                 350

Asp Ser Leu Arg Lys Ile Gly Met Phe Phe Gly Ile Glu Asp Arg Ala
        355                 360                 365

Lys Ala Ile Ile Asp Glu Glu Val Ala Arg Trp Lys Pro Glu Leu Asp
    370                 375                 380

Trp Tyr Lys Glu Arg Leu Met Gly Lys Lys Val Cys Leu Trp Pro Gly
385                 390                 395                 400

Gly Ser Lys Leu Trp His Trp Ala His Val Ile Glu Glu Glu Met Gly
                405                 410                 415

Leu Lys Val Val Ser Val Tyr Thr Lys Phe Gly His Gln Gly Asp Met
            420                 425                 430

Glu Lys Gly Ile Ala Arg Cys Gly Glu Gly Thr Leu Ala Ile Asp Asp
        435                 440                 445

Pro Asn Glu Leu Glu Gly Leu Glu Ala Leu Glu Met Leu Lys Pro Asp
    450                 455                 460

Ile Ile Leu Thr Gly Lys Arg Pro Gly Glu Val Ala Lys Lys Val Arg
465                 470                 475                 480

Val Pro Tyr Leu Asn Ala His Ala Tyr His Asn Gly Pro Tyr Lys Gly
                485                 490                 495

Phe Glu Gly Trp Val Arg Phe Ala Arg Asp Ile Tyr Asn Ala Ile Tyr
            500                 505                 510

Ser Pro Ile His Gln Leu Ser Gly Ile Asp Ile Thr Lys Asp Asn Ala
        515                 520                 525

Pro Glu Trp Gly Asn Gly Phe Arg Thr Arg Gln Met Leu Ser Asp Gly
    530                 535                 540

Asn Leu Ser Asp Ala Val Arg Asn Ser Glu Thr Leu Arg Gln Tyr Thr
545                 550                 555                 560

Gly Gly Tyr Asp Ser Val Ser Lys Leu Arg Glu Arg Glu Tyr Pro Ala
                565                 570                 575

Phe Glu Arg Lys Val Gly Gly Gly Gly Ser Gly Gly Gly Ser Tyr Pro
```

```
            580                 585                 590

Tyr Asp Val Pro Asp Tyr Ala Gly Gly Gly Ser Gly Gly Gly Ser Thr
        595                 600                 605

Cys Glu Val Lys Glu Lys Gly Arg Val Gly Thr Ile Asn Pro Ile Phe
    610                 615                 620

Thr Cys Gln Pro Ala Gly Ala Gln Phe Val Ser Ile Gly Ile Lys Asp
625                 630                 635                 640

Cys Ile Gly Ile Val His Gly Gly Gln Gly Cys Val Met Phe Val Arg
                645                 650                 655

Leu Ile Phe Ser Gln His Tyr Lys Glu Ser Phe Glu Leu Ala Ser Ser
            660                 665                 670

Ser Leu His Glu Asp Gly Ala Val Phe Gly Ala Cys Gly Arg Val Glu
        675                 680                 685

Glu Ala Val Asp Val Leu Leu Ser Arg Tyr Pro Asp Val Lys Val Val
    690                 695                 700

Pro Ile Ile Thr Thr Cys Ser Thr Glu Ile Ile Gly Asp Asp Val Asp
705                 710                 715                 720

Gly Val Ile Lys Lys Leu Asn Glu Gly Leu Leu Lys Glu Lys Phe Pro
                725                 730                 735

Asp Arg Glu Val His Leu Ile Ala Met His Thr Pro Ser Phe Val Gly
            740                 745                 750

Ser Met Ile Ser Gly Tyr Asp Val Ala Val Arg Asp Val Val Arg His
        755                 760                 765

Phe Ala Lys Arg Glu Ala Pro Asn Asp Lys Ile Asn Leu Leu Thr Gly
    770                 775                 780

Trp Val Asn Pro Gly Asp Val Lys Glu Leu Lys His Leu Leu Gly Glu
785                 790                 795                 800

Met Asp Ile Glu Ala Asn Val Leu Phe Glu Ile Glu Ser Phe Asp Ser
                805                 810                 815

Pro Ile Leu Pro Asp Gly Ser Ala Val Ser His Gly Asn Thr Thr Ile
            820                 825                 830

Glu Asp Leu Ile Asp Thr Gly Asn Ala Arg Ala Thr Phe Ala Leu Asn
        835                 840                 845

Arg Tyr Glu Gly Thr Lys Ala Ala Glu Tyr Leu Gln Lys Lys Phe Glu
    850                 855                 860

Ile Pro Ala Ile Ile Gly Pro Thr Pro Ile Gly Ile Arg Asn Thr Asp
865                 870                 875                 880

Ile Phe Leu Gln Asn Leu Lys Lys Ala Thr Gly Lys Pro Ile Pro Gln
                885                 890                 895

Ser Leu Ala His Glu Arg Gly Val Ala Ile Asp Ala Leu Ala Asp Leu
            900                 905                 910

Thr His Met Phe Leu Ala Glu Lys Arg Val Ala Ile Tyr Gly Ala Pro
        915                 920                 925

Asp Leu Val Ile Gly Leu Ala Glu Phe Cys Leu Asp Leu Glu Met Lys
    930                 935                 940

Pro Val Leu Leu Leu Leu Gly Asp Asp Asn Ser Lys Tyr Val Asp Asp
945                 950                 955                 960

Pro Arg Ile Lys Ala Leu Gln Glu Asn Val Asp Tyr Gly Met Glu Ile
                965                 970                 975

Val Thr Asn Ala Asp Phe Trp Glu Leu Glu Asn Arg Ile Lys Asn Glu
            980                 985                 990

Gly Leu Glu Leu Asp Leu Ile Leu  Gly His Ser Lys Gly  Arg Phe Ile
        995                 1000                1005
```

```
Ser Ile  Asp Tyr Asn Ile Pro  Met Leu Arg Val Gly  Phe Pro Thr
    1010                1015                1020

Tyr Asp  Arg Ala Gly Leu Phe  Arg Tyr Pro Thr Val  Gly Tyr Gly
    1025                1030                1035

Gly Ala  Ile Trp Leu Ala Glu  Gln Met Ala Asn Thr  Leu Phe Ala
    1040                1045                1050

Asp Met  Glu His Lys Lys Asn  Lys Glu Trp Val Leu  Asn Val Trp
    1055                1060                1065


<210> SEQ ID NO 203
<211> LENGTH: 1065
<212> TYPE: PRT
<213> ORGANISM: Artificial Sequence
<220> FEATURE:
<223> OTHER INFORMATION: Amino acid sequence of the
      MTP-CoxIV::AnfD::linker26(HA)::AnfK polypeptide encoded by SN273.
      Amino acids 1-61 correspond to the MTP-CoxIV sequence including
      the GG at its C-terminus, amino acids 62-578 correspond to the
      AnfD sequence (A. vinelandii),

<400> SEQUENCE: 203

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro Ser Ala Trp
            20                  25                  30

Ser His Pro Gln Phe Glu Lys Gly Gly Gly Ser Gly Gly Gly Ser Gly
        35                  40                  45

Gly Ser Ala Trp Ser His Pro Gln Phe Glu Lys Gly Gly Met Pro His
    50                  55                  60

His Glu Phe Glu Cys Ser Lys Val Ile Pro Glu Arg Lys Lys His Ala
65                  70                  75                  80

Val Ile Lys Gly Lys Gly Glu Thr Leu Ala Asp Ala Leu Pro Gln Gly
                85                  90                  95

Tyr Leu Asn Thr Ile Pro Gly Ser Ile Ser Glu Arg Gly Cys Ala Tyr
            100                 105                 110

Cys Gly Ala Lys His Val Ile Gly Thr Pro Met Lys Asp Val Ile His
        115                 120                 125

Ile Ser His Gly Pro Val Gly Cys Thr Tyr Asp Thr Trp Gln Thr Lys
    130                 135                 140

Arg Tyr Ile Ser Asp Asn Asp Asn Phe Gln Leu Lys Tyr Thr Tyr Ala
145                 150                 155                 160

Thr Asp Val Lys Glu Lys His Ile Val Phe Gly Ala Glu Lys Leu Leu
                165                 170                 175

Lys Gln Asn Ile Ile Glu Ala Phe Lys Ala Phe Pro Gln Ile Lys Arg
            180                 185                 190

Met Thr Ile Tyr Gln Thr Cys Ala Thr Ala Leu Ile Gly Asp Asp Ile
        195                 200                 205

Asn Ala Ile Ala Glu Glu Val Met Glu Glu Met Pro Glu Val Asp Ile
    210                 215                 220

Phe Val Cys Asn Ser Pro Gly Phe Ala Gly Pro Ser Gln Ser Gly Gly
225                 230                 235                 240

His His Lys Ile Asn Ile Ala Trp Ile Asn Gln Lys Val Gly Thr Val
                245                 250                 255

Glu Pro Glu Ile Thr Gly Asp His Val Ile Asn Tyr Val Gly Glu Tyr
            260                 265                 270

Asn Ile Gln Gly Asp Gln Glu Val Met Val Asp Tyr Phe Lys Arg Met
```

```
        275                 280                 285

Gly Ile Gln Val Leu Ser Thr Phe Thr Gly Asn Gly Ser Tyr Asp Gly
    290                 295                 300

Leu Arg Ala Met His Arg Ala His Leu Asn Val Leu Glu Cys Ala Arg
305                 310                 315                 320

Ser Ala Glu Tyr Ile Cys Asn Glu Leu Arg Val Arg Tyr Gly Ile Pro
                325                 330                 335

Arg Leu Asp Ile Asp Gly Phe Gly Phe Lys Pro Leu Ala Asp Ser Leu
            340                 345                 350

Arg Lys Ile Gly Met Phe Phe Gly Ile Glu Asp Arg Ala Lys Ala Ile
        355                 360                 365

Ile Asp Glu Glu Val Ala Arg Trp Lys Pro Glu Leu Asp Trp Tyr Lys
    370                 375                 380

Glu Arg Leu Met Gly Lys Lys Val Cys Leu Trp Pro Gly Gly Ser Lys
385                 390                 395                 400

Leu Trp His Trp Ala His Val Ile Glu Glu Glu Met Gly Leu Lys Val
                405                 410                 415

Val Ser Val Tyr Thr Lys Phe Gly His Gln Gly Asp Met Glu Lys Gly
            420                 425                 430

Ile Ala Arg Cys Gly Glu Gly Thr Leu Ala Ile Asp Asp Pro Asn Glu
        435                 440                 445

Leu Glu Gly Leu Glu Ala Leu Glu Met Leu Lys Pro Asp Ile Ile Leu
    450                 455                 460

Thr Gly Lys Arg Pro Gly Glu Val Ala Lys Lys Val Arg Val Pro Tyr
465                 470                 475                 480

Leu Asn Ala His Ala Tyr His Asn Gly Pro Tyr Lys Gly Phe Glu Gly
                485                 490                 495

Trp Val Arg Phe Ala Arg Asp Ile Tyr Asn Ala Ile Tyr Ser Pro Ile
            500                 505                 510

His Gln Leu Ser Gly Ile Asp Ile Thr Lys Asp Asn Ala Pro Glu Trp
        515                 520                 525

Gly Asn Gly Phe Arg Thr Arg Gln Met Leu Ser Asp Gly Asn Leu Ser
    530                 535                 540

Asp Ala Val Arg Asn Ser Glu Thr Leu Arg Gln Tyr Thr Gly Gly Tyr
545                 550                 555                 560

Asp Ser Val Ser Lys Leu Arg Glu Arg Glu Tyr Pro Ala Phe Glu Arg
                565                 570                 575

Lys Val Gly Gly Gly Gly Ser Gly Gly Gly Ser Tyr Pro Tyr Asp Val
            580                 585                 590

Pro Asp Tyr Ala Gly Gly Gly Ser Gly Gly Gly Ser Thr Cys Glu Val
        595                 600                 605

Lys Glu Lys Gly Arg Val Gly Thr Ile Asn Pro Ile Phe Thr Cys Gln
    610                 615                 620

Pro Ala Gly Ala Gln Phe Val Ser Ile Gly Ile Lys Asp Cys Ile Gly
625                 630                 635                 640

Ile Val His Gly Gly Gln Gly Cys Val Met Phe Val Arg Leu Ile Phe
                645                 650                 655

Ser Gln His Tyr Lys Glu Ser Phe Glu Leu Ala Ser Ser Ser Leu His
            660                 665                 670

Glu Asp Gly Ala Val Phe Gly Ala Cys Gly Arg Val Glu Glu Ala Val
        675                 680                 685

Asp Val Leu Leu Ser Arg Tyr Pro Asp Val Lys Val Val Pro Ile Ile
    690                 695                 700
```

Thr Thr Cys Ser Thr Glu Ile Ile Gly Asp Asp Val Asp Gly Val Ile
705 710 715 720

Lys Lys Leu Asn Glu Gly Leu Leu Lys Glu Lys Phe Pro Asp Arg Glu
725 730 735

Val His Leu Ile Ala Met His Thr Pro Ser Phe Val Gly Ser Met Ile
740 745 750

Ser Gly Tyr Asp Val Ala Val Arg Asp Val Val Arg His Phe Ala Lys
755 760 765

Arg Glu Ala Pro Asn Asp Lys Ile Asn Leu Leu Thr Gly Trp Val Asn
770 775 780

Pro Gly Asp Val Lys Glu Leu Lys His Leu Leu Gly Glu Met Asp Ile
785 790 795 800

Glu Ala Asn Val Leu Phe Glu Ile Glu Ser Phe Asp Ser Pro Ile Leu
805 810 815

Pro Asp Gly Ser Ala Val Ser His Gly Asn Thr Thr Ile Glu Asp Leu
820 825 830

Ile Asp Thr Gly Asn Ala Arg Ala Thr Phe Ala Leu Asn Arg Tyr Glu
835 840 845

Gly Thr Lys Ala Ala Glu Tyr Leu Gln Lys Lys Phe Glu Ile Pro Ala
850 855 860

Ile Ile Gly Pro Thr Pro Ile Gly Ile Arg Asn Thr Asp Ile Phe Leu
865 870 875 880

Gln Asn Leu Lys Lys Ala Thr Gly Lys Pro Ile Pro Gln Ser Leu Ala
885 890 895

His Glu Arg Gly Val Ala Ile Asp Ala Leu Ala Asp Leu Thr His Met
900 905 910

Phe Leu Ala Glu Lys Arg Val Ala Ile Tyr Gly Ala Pro Asp Leu Val
915 920 925

Ile Gly Leu Ala Glu Phe Cys Leu Asp Leu Glu Met Lys Pro Val Leu
930 935 940

Leu Leu Leu Gly Asp Asp Asn Ser Lys Tyr Val Asp Asp Pro Arg Ile
945 950 955 960

Lys Ala Leu Gln Glu Asn Val Asp Tyr Gly Met Glu Ile Val Thr Asn
965 970 975

Ala Asp Phe Trp Glu Leu Glu Asn Arg Ile Lys Asn Glu Gly Leu Glu
980 985 990

Leu Asp Leu Ile Leu Gly His Ser Lys Gly Arg Phe Ile Ser Ile Asp
995 1000 1005

Tyr Asn Ile Pro Met Leu Arg Val Gly Phe Pro Thr Tyr Asp Arg
1010 1015 1020

Ala Gly Leu Phe Arg Tyr Pro Thr Val Gly Tyr Gly Gly Ala Ile
1025 1030 1035

Trp Leu Ala Glu Gln Met Ala Asn Thr Leu Phe Ala Asp Met Glu
1040 1045 1050

His Lys Lys Asn Lys Glu Trp Val Leu Asn Val Trp
1055 1060 1065

<210> SEQ ID NO 204
<211> LENGTH: 1068
<212> TYPE: PRT
<213> ORGANISM: Artificial Sequence
<220> FEATURE:
<223> OTHER INFORMATION: Amino acid sequence of the
mFAγ51::AnfD::linker26(HA)::AnfK polypeptide encoded by SN274.
Amino acids 1-64 correspond to the mFAγ51 sequence including the alanine substitutions that don't allow for MPP-cleavage and the GG at its C-terminus, amino acids

<400> SEQUENCE: 204

Met Ala Met Ala Val Phe Arg Arg Glu Ala Ala Ala Leu Leu Pro Ser
1               5                   10                  15

Ile Ala Ala Arg Pro Ile Ala Ala Ala Ala Ala Ala Ala Ser Ser Asp
            20                  25                  30

Gln Glu Glu Gly Leu Leu Ala Ala Ala Ala Ala Ala Ala Ala Val Val
        35                  40                  45

Arg Asn Arg Gly Gly Tyr Pro Tyr Asp Val Pro Asp Tyr Ala Gly Gly
    50                  55                  60

Met Pro His His Glu Phe Glu Cys Ser Lys Val Ile Pro Glu Arg Lys
65                  70                  75                  80

Lys His Ala Val Ile Lys Gly Lys Gly Glu Thr Leu Ala Asp Ala Leu
                85                  90                  95

Pro Gln Gly Tyr Leu Asn Thr Ile Pro Gly Ser Ile Ser Glu Arg Gly
            100                 105                 110

Cys Ala Tyr Cys Gly Ala Lys His Val Ile Gly Thr Pro Met Lys Asp
        115                 120                 125

Val Ile His Ile Ser His Gly Pro Val Gly Cys Thr Tyr Asp Thr Trp
    130                 135                 140

Gln Thr Lys Arg Tyr Ile Ser Asp Asn Asp Asn Phe Gln Leu Lys Tyr
145                 150                 155                 160

Thr Tyr Ala Thr Asp Val Lys Glu Lys His Ile Val Phe Gly Ala Glu
                165                 170                 175

Lys Leu Leu Lys Gln Asn Ile Ile Glu Ala Phe Lys Ala Phe Pro Gln
            180                 185                 190

Ile Lys Arg Met Thr Ile Tyr Gln Thr Cys Ala Thr Ala Leu Ile Gly
        195                 200                 205

Asp Asp Ile Asn Ala Ile Ala Glu Glu Val Met Glu Glu Met Pro Glu
    210                 215                 220

Val Asp Ile Phe Val Cys Asn Ser Pro Gly Phe Ala Gly Pro Ser Gln
225                 230                 235                 240

Ser Gly Gly His His Lys Ile Asn Ile Ala Trp Ile Asn Gln Lys Val
                245                 250                 255

Gly Thr Val Glu Pro Glu Ile Thr Gly Asp His Val Ile Asn Tyr Val
            260                 265                 270

Gly Glu Tyr Asn Ile Gln Gly Asp Gln Glu Val Met Val Asp Tyr Phe
        275                 280                 285

Lys Arg Met Gly Ile Gln Val Leu Ser Thr Phe Thr Gly Asn Gly Ser
    290                 295                 300

Tyr Asp Gly Leu Arg Ala Met His Arg Ala His Leu Asn Val Leu Glu
305                 310                 315                 320

Cys Ala Arg Ser Ala Glu Tyr Ile Cys Asn Glu Leu Arg Val Arg Tyr
                325                 330                 335

Gly Ile Pro Arg Leu Asp Ile Asp Gly Phe Gly Phe Lys Pro Leu Ala
            340                 345                 350

Asp Ser Leu Arg Lys Ile Gly Met Phe Phe Gly Ile Glu Asp Arg Ala
        355                 360                 365

Lys Ala Ile Ile Asp Glu Glu Val Ala Arg Trp Lys Pro Glu Leu Asp
    370                 375                 380

Trp Tyr Lys Glu Arg Leu Met Gly Lys Lys Val Cys Leu Trp Pro Gly
385                 390                 395                 400

```
Gly Ser Lys Leu Trp His Trp Ala His Val Ile Glu Glu Glu Met Gly
                405                 410                 415

Leu Lys Val Val Ser Val Tyr Thr Lys Phe Gly His Gln Gly Asp Met
            420                 425                 430

Glu Lys Gly Ile Ala Arg Cys Gly Glu Gly Thr Leu Ala Ile Asp Asp
        435                 440                 445

Pro Asn Glu Leu Glu Gly Leu Glu Ala Leu Glu Met Leu Lys Pro Asp
    450                 455                 460

Ile Ile Leu Thr Gly Lys Arg Pro Gly Glu Val Ala Lys Lys Val Arg
465                 470                 475                 480

Val Pro Tyr Leu Asn Ala His Ala Tyr His Asn Gly Pro Tyr Lys Gly
                485                 490                 495

Phe Glu Gly Trp Val Arg Phe Ala Arg Asp Ile Tyr Asn Ala Ile Tyr
            500                 505                 510

Ser Pro Ile His Gln Leu Ser Gly Ile Asp Ile Thr Lys Asp Asn Ala
        515                 520                 525

Pro Glu Trp Gly Asn Gly Phe Arg Thr Arg Gln Met Leu Ser Asp Gly
    530                 535                 540

Asn Leu Ser Asp Ala Val Arg Asn Ser Glu Thr Leu Arg Gln Tyr Thr
545                 550                 555                 560

Gly Gly Tyr Asp Ser Val Ser Lys Leu Arg Glu Arg Glu Tyr Pro Ala
                565                 570                 575

Phe Glu Arg Lys Val Gly Gly Gly Gly Ser Gly Gly Gly Ser Tyr Pro
            580                 585                 590

Tyr Asp Val Pro Asp Tyr Ala Gly Gly Gly Ser Gly Gly Gly Ser Thr
        595                 600                 605

Cys Glu Val Lys Glu Lys Gly Arg Val Gly Thr Ile Asn Pro Ile Phe
    610                 615                 620

Thr Cys Gln Pro Ala Gly Ala Gln Phe Val Ser Ile Gly Ile Lys Asp
625                 630                 635                 640

Cys Ile Gly Ile Val His Gly Gly Gln Gly Cys Val Met Phe Val Arg
                645                 650                 655

Leu Ile Phe Ser Gln His Tyr Lys Glu Ser Phe Glu Leu Ala Ser Ser
            660                 665                 670

Ser Leu His Glu Asp Gly Ala Val Phe Gly Ala Cys Gly Arg Val Glu
        675                 680                 685

Glu Ala Val Asp Val Leu Leu Ser Arg Tyr Pro Asp Val Lys Val Val
    690                 695                 700

Pro Ile Ile Thr Thr Cys Ser Thr Glu Ile Ile Gly Asp Asp Val Asp
705                 710                 715                 720

Gly Val Ile Lys Lys Leu Asn Glu Gly Leu Leu Lys Glu Lys Phe Pro
                725                 730                 735

Asp Arg Glu Val His Leu Ile Ala Met His Thr Pro Ser Phe Val Gly
            740                 745                 750

Ser Met Ile Ser Gly Tyr Asp Val Ala Val Arg Asp Val Val Arg His
        755                 760                 765

Phe Ala Lys Arg Glu Ala Pro Asn Asp Lys Ile Asn Leu Leu Thr Gly
    770                 775                 780

Trp Val Asn Pro Gly Asp Val Lys Glu Leu Lys His Leu Leu Gly Glu
785                 790                 795                 800

Met Asp Ile Glu Ala Asn Val Leu Phe Glu Ile Glu Ser Phe Asp Ser
                805                 810                 815
```

```
Pro Ile Leu Pro Asp Gly Ser Ala Val Ser His Gly Asn Thr Thr Ile
            820                 825                 830

Glu Asp Leu Ile Asp Thr Gly Asn Ala Arg Ala Thr Phe Ala Leu Asn
        835                 840                 845

Arg Tyr Glu Gly Thr Lys Ala Ala Glu Tyr Leu Gln Lys Lys Phe Glu
    850                 855                 860

Ile Pro Ala Ile Ile Gly Pro Thr Pro Ile Gly Ile Arg Asn Thr Asp
865                 870                 875                 880

Ile Phe Leu Gln Asn Leu Lys Lys Ala Thr Gly Lys Pro Ile Pro Gln
                885                 890                 895

Ser Leu Ala His Glu Arg Gly Val Ala Ile Asp Ala Leu Ala Asp Leu
            900                 905                 910

Thr His Met Phe Leu Ala Glu Lys Arg Val Ala Ile Tyr Gly Ala Pro
        915                 920                 925

Asp Leu Val Ile Gly Leu Ala Glu Phe Cys Leu Asp Leu Glu Met Lys
    930                 935                 940

Pro Val Leu Leu Leu Leu Gly Asp Asp Asn Ser Lys Tyr Val Asp Asp
945                 950                 955                 960

Pro Arg Ile Lys Ala Leu Gln Glu Asn Val Asp Tyr Gly Met Glu Ile
                965                 970                 975

Val Thr Asn Ala Asp Phe Trp Glu Leu Glu Asn Arg Ile Lys Asn Glu
            980                 985                 990

Gly Leu Glu Leu Asp Leu Ile Leu  Gly His Ser Lys Gly  Arg Phe Ile
        995                 1000                1005

Ser Ile  Asp Tyr Asn Ile Pro  Met Leu Arg Val Gly  Phe Pro Thr
    1010                1015                1020

Tyr Asp  Arg Ala Gly Leu Phe  Arg Tyr Pro Thr Val  Gly Tyr Gly
    1025                1030                1035

Gly Ala  Ile Trp Leu Ala Glu  Gln Met Ala Asn Thr  Leu Phe Ala
    1040                1045                1050

Asp Met  Glu His Lys Lys Asn  Lys Glu Trp Val Leu  Asn Val Trp
    1055                1060                1065
```

<210> SEQ ID NO 205
<211> LENGTH: 1013
<212> TYPE: PRT
<213> ORGANISM: Artificial Sequence
<220> FEATURE:
<223> OTHER INFORMATION: Amino acid sequence of the HISx6::AnfD::linker26(HA)::AnfK polypeptide encoded by SN275, which does not have an MTP sequence and would be cytoplasmically located. Amino acids 1-9 correspond to the HISx6 sequence including the GG at its C-terminus, amino

<400> SEQUENCE: 205

```
Met His His His His His His Gly Gly Met Pro His His Glu Phe Glu
1               5                   10                  15

Cys Ser Lys Val Ile Pro Glu Arg Lys Lys His Ala Val Ile Lys Gly
            20                  25                  30

Lys Gly Glu Thr Leu Ala Asp Ala Leu Pro Gln Gly Tyr Leu Asn Thr
        35                  40                  45

Ile Pro Gly Ser Ile Ser Glu Arg Gly Cys Ala Tyr Cys Gly Ala Lys
    50                  55                  60

His Val Ile Gly Thr Pro Met Lys Asp Val Ile His Ile Ser His Gly
65                  70                  75                  80

Pro Val Gly Cys Thr Tyr Asp Thr Trp Gln Thr Lys Arg Tyr Ile Ser
                85                  90                  95
```

```
Asp Asn Asp Asn Phe Gln Leu Lys Tyr Thr Tyr Ala Thr Asp Val Lys
            100                 105                 110

Glu Lys His Ile Val Phe Gly Ala Glu Lys Leu Leu Lys Gln Asn Ile
        115                 120                 125

Ile Glu Ala Phe Lys Ala Phe Pro Gln Ile Lys Arg Met Thr Ile Tyr
    130                 135                 140

Gln Thr Cys Ala Thr Ala Leu Ile Gly Asp Asp Ile Asn Ala Ile Ala
145                 150                 155                 160

Glu Glu Val Met Glu Glu Met Pro Glu Val Asp Ile Phe Val Cys Asn
                165                 170                 175

Ser Pro Gly Phe Ala Gly Pro Ser Gln Ser Gly Gly His His Lys Ile
            180                 185                 190

Asn Ile Ala Trp Ile Asn Gln Lys Val Gly Thr Val Glu Pro Glu Ile
        195                 200                 205

Thr Gly Asp His Val Ile Asn Tyr Val Gly Glu Tyr Asn Ile Gln Gly
    210                 215                 220

Asp Gln Glu Val Met Val Asp Tyr Phe Lys Arg Met Gly Ile Gln Val
225                 230                 235                 240

Leu Ser Thr Phe Thr Gly Asn Gly Ser Tyr Asp Gly Leu Arg Ala Met
                245                 250                 255

His Arg Ala His Leu Asn Val Leu Glu Cys Ala Arg Ser Ala Glu Tyr
            260                 265                 270

Ile Cys Asn Glu Leu Arg Val Arg Tyr Gly Ile Pro Arg Leu Asp Ile
        275                 280                 285

Asp Gly Phe Gly Phe Lys Pro Leu Ala Asp Ser Leu Arg Lys Ile Gly
    290                 295                 300

Met Phe Phe Gly Ile Glu Asp Arg Ala Lys Ala Ile Ile Asp Glu Glu
305                 310                 315                 320

Val Ala Arg Trp Lys Pro Glu Leu Asp Trp Tyr Lys Glu Arg Leu Met
                325                 330                 335

Gly Lys Lys Val Cys Leu Trp Pro Gly Gly Ser Lys Leu Trp His Trp
            340                 345                 350

Ala His Val Ile Glu Glu Glu Met Gly Leu Lys Val Val Ser Val Tyr
        355                 360                 365

Thr Lys Phe Gly His Gln Gly Asp Met Glu Lys Gly Ile Ala Arg Cys
    370                 375                 380

Gly Glu Gly Thr Leu Ala Ile Asp Asp Pro Asn Glu Leu Glu Gly Leu
385                 390                 395                 400

Glu Ala Leu Glu Met Leu Lys Pro Asp Ile Ile Leu Thr Gly Lys Arg
                405                 410                 415

Pro Gly Glu Val Ala Lys Lys Val Arg Val Pro Tyr Leu Asn Ala His
            420                 425                 430

Ala Tyr His Asn Gly Pro Tyr Lys Gly Phe Glu Gly Trp Val Arg Phe
        435                 440                 445

Ala Arg Asp Ile Tyr Asn Ala Ile Tyr Ser Pro Ile His Gln Leu Ser
    450                 455                 460

Gly Ile Asp Ile Thr Lys Asp Asn Ala Pro Glu Trp Gly Asn Gly Phe
465                 470                 475                 480

Arg Thr Arg Gln Met Leu Ser Asp Gly Asn Leu Ser Asp Ala Val Arg
                485                 490                 495

Asn Ser Glu Thr Leu Arg Gln Tyr Thr Gly Gly Tyr Asp Ser Val Ser
            500                 505                 510
```

```
Lys Leu Arg Glu Arg Glu Tyr Pro Ala Phe Glu Arg Lys Val Gly Gly
        515                 520                 525

Gly Gly Ser Gly Gly Gly Ser Tyr Pro Tyr Asp Val Pro Asp Tyr Ala
    530                 535                 540

Gly Gly Gly Ser Gly Gly Gly Ser Thr Cys Glu Val Lys Glu Lys Gly
545                 550                 555                 560

Arg Val Gly Thr Ile Asn Pro Ile Phe Thr Cys Gln Pro Ala Gly Ala
                565                 570                 575

Gln Phe Val Ser Ile Gly Ile Lys Asp Cys Ile Gly Ile Val His Gly
            580                 585                 590

Gly Gln Gly Cys Val Met Phe Val Arg Leu Ile Phe Ser Gln His Tyr
        595                 600                 605

Lys Glu Ser Phe Glu Leu Ala Ser Ser Ser Leu His Glu Asp Gly Ala
    610                 615                 620

Val Phe Gly Ala Cys Gly Arg Val Glu Glu Ala Val Asp Val Leu Leu
625                 630                 635                 640

Ser Arg Tyr Pro Asp Val Lys Val Val Pro Ile Ile Thr Thr Cys Ser
                645                 650                 655

Thr Glu Ile Ile Gly Asp Asp Val Asp Gly Val Ile Lys Lys Leu Asn
            660                 665                 670

Glu Gly Leu Leu Lys Glu Lys Phe Pro Asp Arg Glu Val His Leu Ile
        675                 680                 685

Ala Met His Thr Pro Ser Phe Val Gly Ser Met Ile Ser Gly Tyr Asp
    690                 695                 700

Val Ala Val Arg Asp Val Val Arg His Phe Ala Lys Arg Glu Ala Pro
705                 710                 715                 720

Asn Asp Lys Ile Asn Leu Leu Thr Gly Trp Val Asn Pro Gly Asp Val
                725                 730                 735

Lys Glu Leu Lys His Leu Leu Gly Glu Met Asp Ile Glu Ala Asn Val
            740                 745                 750

Leu Phe Glu Ile Glu Ser Phe Asp Ser Pro Ile Leu Pro Asp Gly Ser
        755                 760                 765

Ala Val Ser His Gly Asn Thr Thr Ile Glu Asp Leu Ile Asp Thr Gly
    770                 775                 780

Asn Ala Arg Ala Thr Phe Ala Leu Asn Arg Tyr Glu Gly Thr Lys Ala
785                 790                 795                 800

Ala Glu Tyr Leu Gln Lys Lys Phe Glu Ile Pro Ala Ile Ile Gly Pro
                805                 810                 815

Thr Pro Ile Gly Ile Arg Asn Thr Asp Ile Phe Leu Gln Asn Leu Lys
            820                 825                 830

Lys Ala Thr Gly Lys Pro Ile Pro Gln Ser Leu Ala His Glu Arg Gly
        835                 840                 845

Val Ala Ile Asp Ala Leu Ala Asp Leu Thr His Met Phe Leu Ala Glu
    850                 855                 860

Lys Arg Val Ala Ile Tyr Gly Ala Pro Asp Leu Val Ile Gly Leu Ala
865                 870                 875                 880

Glu Phe Cys Leu Asp Leu Glu Met Lys Pro Val Leu Leu Leu Leu Gly
                885                 890                 895

Asp Asp Asn Ser Lys Tyr Val Asp Asp Pro Arg Ile Lys Ala Leu Gln
            900                 905                 910

Glu Asn Val Asp Tyr Gly Met Glu Ile Val Thr Asn Ala Asp Phe Trp
        915                 920                 925

Glu Leu Glu Asn Arg Ile Lys Asn Glu Gly Leu Glu Leu Asp Leu Ile
```

```
    930                 935                 940

Leu Gly His Ser Lys Gly Arg Phe Ile Ser Ile Asp Tyr Asn Ile Pro
945                 950                 955                 960

Met Leu Arg Val Gly Phe Pro Thr Tyr Asp Arg Ala Gly Leu Phe Arg
                965                 970                 975

Tyr Pro Thr Val Gly Tyr Gly Gly Ala Ile Trp Leu Ala Glu Gln Met
            980                 985                 990

Ala Asn Thr Leu Phe Ala Asp Met  Glu His Lys Lys Asn  Lys Glu Trp
        995                 1000                1005

Val Leu  Asn Val Trp
    1010


<210> SEQ ID NO 206
<211> LENGTH: 383
<212> TYPE: PRT
<213> ORGANISM: Thermoanaerobacter brockii

<400> SEQUENCE: 206

Met Thr Leu Lys Lys Gly Lys Lys Val Tyr Ile Val Asp Thr Thr Leu
1               5                   10                  15

Arg Asp Gly Glu Gln Thr Ala Gly Val Val Phe Ala Asn Asn Glu Lys
            20                  25                  30

Ile Arg Ile Ala Gln Met Leu Asp Glu Ile Gly Ile Asp Gln Leu Glu
        35                  40                  45

Val Gly Ile Pro Thr Met Gly Gly Asp Glu Lys Glu Thr Val Thr Lys
    50                  55                  60

Ile Ala Lys Leu Gly Leu Asn Ala Ser Ile Met Ala Trp Asn Arg Ala
65                  70                  75                  80

Val Val Lys Asp Val Gln Glu Ser Leu Glu Cys Gly Val Asp Ala Val
                85                  90                  95

Ala Ile Ser Val Ser Thr Ser Asp Ile His Ile Glu His Lys Leu Lys
            100                 105                 110

Lys Thr Arg Gln Trp Val Leu Asp Asn Met Thr Glu Ala Val Lys Phe
        115                 120                 125

Ala Lys Lys Glu Gly Val Tyr Val Ser Val Asn Ala Glu Asp Ala Ser
    130                 135                 140

Arg Thr Asp Met Asn Phe Leu Ile Glu Phe Ala Lys Cys Ala Lys Gln
145                 150                 155                 160

Ala Gly Ala Asp Arg Leu Arg Phe Cys Asp Thr Val Gly Phe Leu Asp
                165                 170                 175

Pro Phe Lys Thr Tyr Asp Met Val Lys Ala Ile Lys Glu Ala Val Asp
            180                 185                 190

Ile Asp Ile Glu Met His Thr His Asn Asp Phe Gly Met Ala Thr Ala
        195                 200                 205

Asn Ala Leu Ala Gly Met Arg Ala Gly Ala Asn Phe Ile Gly Val Thr
    210                 215                 220

Val Asn Gly Leu Gly Glu Arg Ala Gly Asn Ala Ala Leu Glu Glu Val
225                 230                 235                 240

Val Met Ala Leu Lys His Val Tyr Lys Ile Asp Leu Gly Ile Asp Thr
                245                 250                 255

Thr Arg Phe Arg Glu Ile Ser Glu Tyr Val Ala Leu Ala Ser Gly Arg
            260                 265                 270

Gln Leu Pro Ala Trp Lys Ala Ile Val Gly Thr Asn Val Phe Ala His
        275                 280                 285
```

Glu Ser Gly Ile His Val Asp Gly Ala Leu Lys Asn Pro His Thr Tyr
290 295 300

Glu Ile Phe Asn Pro Asp Glu Val Gly Leu Glu Arg Gln Ile Val Ile
305 310 315 320

Gly Lys His Ser Gly Thr Ala Ala Leu Ile Asn Lys Phe Lys Glu Tyr
325 330 335

Gly Arg Val Leu Thr Glu Glu Glu Ala Asn Leu Leu Leu Pro His Val
340 345 350

Arg Lys Leu Ala Ile Gln Leu Lys Arg Pro Leu Phe Asp Lys Glu Leu
355 360 365

Met Tyr Leu Tyr Glu Asp Val Ile Lys Asn Arg Glu Lys Ala Ile
370 375 380

<210> SEQ ID NO 207
<211> LENGTH: 378
<212> TYPE: PRT
<213> ORGANISM: Thermincola potens

<400> SEQUENCE: 207

Met Met Glu Lys Lys Ile Thr Ile Val Asp Thr Thr Leu Arg Asp Gly
1 5 10 15

Glu Gln Thr Ala Gly Val Val Phe Ala Asn Lys Glu Lys Val Arg Ile
20 25 30

Ala Gln Met Leu Asp Glu Leu Gly Val His Gln Ile Glu Ala Gly Ile
35 40 45

Pro Val Met Gly Gly Asp Glu Glu Lys Ala Val Lys Asp Ile Val Lys
50 55 60

Leu Gly Leu Lys Ala Ser Ile Met Gly Trp Asn Arg Ala Val Ile Ser
65 70 75 80

Asp Ile Glu Glu Thr Leu Arg Cys Gly Val Asp Ala Val Ala Ile Ser
85 90 95

Ile Ser Thr Ser Asp Ile His Ile Gln His Lys Leu Gln Thr Ser Arg
100 105 110

Glu Trp Val Leu Glu Asn Met Val Lys Ala Val Glu Phe Ala Lys Lys
115 120 125

Glu Gly Val Tyr Ile Ser Val Asn Ala Glu Asp Ala Ser Arg Ser Asp
130 135 140

Met Glu Phe Leu Ile Gln Phe Ala Arg Ala Ala Lys Glu Ala Gly Ala
145 150 155 160

Asp Arg Ile Arg Tyr Cys Asp Thr Ile Gly Ile Leu Asp Pro Phe Thr
165 170 175

Thr Tyr Glu Asn Ile Gln Thr Leu Lys Lys His Val Asp Ile Asp Ile
180 185 190

Glu Met His Thr His Asn Asp Phe Gly Met Ala Thr Ala Asn Ala Leu
195 200 205

Ala Gly Ile Lys Ala Gly Ala Ser His Val Gly Val Thr Val Met Gly
210 215 220

Leu Gly Glu Arg Ala Gly Asn Ala Ala Leu Glu Glu Val Val Met Ala
225 230 235 240

Leu Lys His Ile Trp Gln Ile Asp Leu Gly Phe Lys Thr Asn Met Phe
245 250 255

Arg Asp Leu Ala Glu Tyr Val Ser Leu Ala Ser Gly Arg Glu Leu Pro
260 265 270

Ala Trp Lys Ala Ile Val Gly Ser Asn Met Phe Ala His Glu Ser Gly
275 280 285

Ile His Ala Asp Gly Ala Ile Lys Asn Pro Ile Thr Tyr Glu Val Phe
    290                 295                 300

Ala Pro Glu Glu Val Gly Leu Glu Arg Gln Ile Val Ile Gly Lys His
305                 310                 315                 320

Ser Gly Ser Lys Ala Leu Met Met Lys Phe Ala Glu Tyr Gly Ile His
                325                 330                 335

Leu Ser Glu Ala Asp Ala Ala Gln Leu Leu Pro Lys Ile Arg Ser His
            340                 345                 350

Ala Val Ala Leu Lys Arg Ser Leu Phe Asp Lys Glu Leu Val Tyr Ile
        355                 360                 365

Tyr Glu Glu Val Phe Gly Lys Lys Pro Leu
    370                 375

<210> SEQ ID NO 208
<211> LENGTH: 440
<212> TYPE: PRT
<213> ORGANISM: Saccharomyces cerevisiae

<400> SEQUENCE: 208

Met Ser Glu Asn Asn Glu Phe Gln Ser Val Thr Glu Ser Thr Thr Ala
1               5                   10                  15

Pro Thr Thr Ser Asn Pro Tyr Gly Pro Asn Pro Ala Asp Tyr Leu Ser
            20                  25                  30

Asn Val Lys Asn Phe Gln Leu Ile Asp Ser Thr Leu Arg Glu Gly Glu
        35                  40                  45

Gln Phe Ala Asn Ala Phe Phe Asp Thr Glu Lys Lys Ile Glu Ile Ala
    50                  55                  60

Arg Ala Leu Asp Asp Phe Gly Val Asp Tyr Ile Glu Leu Thr Ser Pro
65                  70                  75                  80

Val Ala Ser Glu Gln Ser Arg Lys Asp Cys Glu Ala Ile Cys Lys Leu
                85                  90                  95

Gly Leu Lys Ala Lys Ile Leu Thr His Ile Arg Cys His Met Asp Asp
            100                 105                 110

Ala Arg Val Ala Val Glu Thr Gly Val Asp Gly Val Asp Val Val Ile
        115                 120                 125

Gly Thr Ser Lys Phe Leu Arg Gln Tyr Ser His Gly Lys Asp Met Asn
    130                 135                 140

Tyr Ile Ala Lys Ser Ala Val Glu Val Ile Glu Phe Val Lys Ser Lys
145                 150                 155                 160

Gly Ile Glu Ile Arg Phe Ser Ser Glu Asp Ser Phe Arg Ser Asp Leu
                165                 170                 175

Val Asp Leu Leu Asn Ile Tyr Lys Thr Val Asp Lys Ile Gly Val Asn
            180                 185                 190

Arg Val Gly Ile Ala Asp Thr Val Gly Cys Ala Asn Pro Arg Gln Val
        195                 200                 205

Tyr Glu Leu Ile Arg Thr Leu Lys Ser Val Val Ser Cys Asp Ile Glu
    210                 215                 220

Cys His Phe His Asn Asp Thr Gly Cys Ala Ile Ala Asn Ala Tyr Thr
225                 230                 235                 240

Ala Leu Glu Gly Gly Ala Arg Leu Ile Asp Val Ser Val Leu Gly Ile
                245                 250                 255

Gly Glu Arg Asn Gly Ile Thr Pro Leu Gly Gly Leu Met Ala Arg Met
            260                 265                 270

Ile Val Ala Ala Pro Asp Tyr Val Arg Ser Lys Tyr Lys Leu His Lys

```
        275                 280                 285

Ile Arg Asp Ile Glu Asn Leu Val Ala Asp Ala Val Glu Val Asn Ile
    290                 295                 300

Pro Phe Asn Asn Pro Ile Thr Gly Phe Cys Ala Phe Thr His Lys Ala
305                 310                 315                 320

Gly Ile His Ala Lys Ala Ile Leu Ala Asn Pro Ser Thr Tyr Glu Ile
                325                 330                 335

Leu Asp Pro His Asp Phe Gly Met Lys Arg Tyr Ile His Phe Ala Asn
            340                 345                 350

Arg Leu Thr Gly Trp Asn Ala Ile Lys Ser Arg Val Asp Gln Leu Asn
        355                 360                 365

Leu Asn Leu Thr Asp Asp Gln Ile Lys Glu Val Thr Ala Lys Ile Lys
    370                 375                 380

Lys Leu Gly Asp Val Arg Pro Leu Asn Ile Asp Asp Val Asp Ser Ile
385                 390                 395                 400

Ile Lys Asp Phe His Ala Glu Leu Ser Thr Pro Leu Leu Lys Pro Val
                405                 410                 415

Asn Lys Gly Thr Asp Asp Asp Asn Ile Asp Ile Ser Asn Gly His Val
            420                 425                 430

Ser Lys Lys Ala Lys Val Thr Lys
        435                 440


<210> SEQ ID NO 209
<211> LENGTH: 376
<212> TYPE: PRT
<213> ORGANISM: Nodularia spumigena

<400> SEQUENCE: 209

Met Asn Glu Ile Leu Ile Asn Asp Thr Thr Leu Arg Asp Gly Glu Gln
1               5                   10                  15

Ala Ala Gly Val Ala Phe Thr Phe Glu Glu Lys Val Ala Ile Ala Gln
            20                  25                  30

Phe Leu Asp Ala Ile Gly Val Pro Glu Leu Glu Val Gly Ile Pro Ala
        35                  40                  45

Met Gly Glu Ala Glu Thr His Ala Ile Leu Ala Ile Ser Asp Leu Gly
    50                  55                  60

Leu Gln Ala Ser Leu Leu Gly Trp Asn Arg Ala Val Leu Ser Asp Ile
65                  70                  75                  80

Lys Ala Ser Ile Thr Cys Gly Leu Lys Arg Val His Ile Ala Ile Pro
                85                  90                  95

Val Ser Gly Ile Gln Ile Ala Ala Lys Phe His Gly Gln Trp Arg Val
            100                 105                 110

Ser Leu Gln Arg Leu Lys Asp Cys Ile Ser Phe Ala Val Asp Gln Gly
        115                 120                 125

Leu Trp Val Ala Val Gly Gly Glu Asp Ser Ser Arg Ala Asp Pro Asn
    130                 135                 140

Phe Leu Leu Asp Val Ala Leu Asn Ala Gln Glu Trp Gly Ala Ser Arg
145                 150                 155                 160

Phe Arg Phe Cys Asp Thr Val Gly Val Leu Asp Pro Phe Ser Thr Tyr
                165                 170                 175

Ala Lys Val Lys Gln Leu Val Ser Ala Leu Ser Ile Pro Leu Glu Ile
            180                 185                 190

His Thr His Asn Asp Phe Gly Leu Ala Thr Ala Asn Ala Leu Ala Gly
        195                 200                 205
```

Ile Lys Ala Gly Ala Thr Ser Val Asn Thr Thr Val Asn Gly Val Gly
    210                 215                 220

Glu Arg Ala Gly Asn Ala Ala Leu Glu Glu Val Val Met Ser Ile Lys
225                 230                 235                 240

Arg Ile Tyr Gly Ile Asn Leu Gly Ile Asp Thr Arg Arg Leu Leu Glu
                245                 250                 255

Leu Ser Gln Leu Val Ala Ser Ala Ser Asn Cys His Val Pro Pro Trp
            260                 265                 270

Lys Ala Ile Val Gly Glu Asn Thr Phe Ala His Glu Ser Gly Ile His
        275                 280                 285

Ala His Gly Val Leu Gln Asn Pro Leu Thr Tyr Glu Pro Phe Ala Pro
    290                 295                 300

Glu Glu Val Gly Trp Glu Arg Arg Leu Val Val Gly Lys His Ser Gly
305                 310                 315                 320

Arg His Leu Val Thr Ser Leu Leu Gln Gln Asn Asp Ile Phe Leu Asn
                325                 330                 335

Pro Glu Glu Thr Gln Ser Val Leu Asp Ala Val Arg Gln Gln Ser Val
            340                 345                 350

Lys Gln Lys Arg Asn Leu Thr Val Glu Glu Leu Leu Asn Leu Val Arg
        355                 360                 365

Glu Gln Arg Tyr Ser His Ala Thr
    370                 375

<210> SEQ ID NO 210
<211> LENGTH: 376
<212> TYPE: PRT
<213> ORGANISM: Methanosarcina acetivorans

<400> SEQUENCE: 210

Met Lys Ala Asp Ile Lys Val Ser Ile Val Asp Gln Thr Ile Asn Glu
1               5                   10                  15

Val Val Arg Leu Gly Val Asn Asn Pro Ala Asp Val Arg Phe Met Leu
            20                  25                  30

Ser Val Leu Lys Lys Tyr Ser Phe Asp Ala Ala Asp Val Ser Leu Asn
        35                  40                  45

Asn Leu Glu Lys Asn Met Val Glu Phe Glu Ala Asp Glu Phe Ser Glu
    50                  55                  60

Ser Met Arg Cys Arg Val Lys Cys Ser Gly Gln Glu Ile Phe Arg Ala
65                  70                  75                  80

Lys Lys Leu Gly Phe Ser Lys Ile Val Ile Asn Thr Ser Leu Asn Pro
                85                  90                  95

Leu Thr Pro Ile Gln Asp Met Leu Glu Pro Val Leu Gln Met Ala Cys
            100                 105                 110

Ser Asn Asp Gln Glu Ile Tyr Leu Ser Ile Asp Asn Ala Leu Glu Phe
        115                 120                 125

Ser Ile Arg Asp Val Glu Thr Ile Tyr Pro Leu Ile Pro Lys Tyr Gly
    130                 135                 140

Ile Lys Arg Leu Ile Leu Gly Asp Arg Ser Gly Lys Ala Asp Pro Phe
145                 150                 155                 160

Thr Thr Tyr Asp Lys Leu Gly Phe Leu Gly Asn Thr Ile Gln Cys Pro
                165                 170                 175

Val Glu Tyr Val Gly Tyr Asn Asp Tyr Gly Thr Ala Thr Ala Asn Thr
            180                 185                 190

Leu Ser Ala Leu Arg Ala Gly Ile Glu Tyr Val Ala Thr Ala Val Ser
        195                 200                 205

Gly Ile Gly Ile Pro Gly Val Ala Ala Met Glu Glu Val Leu Met Ala
    210                 215                 220

Ala Arg His Leu Trp Lys Asn Glu Leu Val Pro Asp Gly Tyr Ser Ile
225                 230                 235                 240

Ala Ala Asp Cys Glu Asn Ile Leu Tyr Arg Ala Gly Ile Met Leu Pro
                245                 250                 255

Gly Glu Lys Ala Ile Ile Gly Lys Asn Val Phe Ala His Glu Ser Gly
            260                 265                 270

Ile His Val Asp Gly Val Leu Lys Asn Pro Asn Leu Tyr Glu Ala Ile
        275                 280                 285

Lys Pro Glu Glu Val Gly Leu Arg Arg Leu Leu Val Ile Gly Lys His
    290                 295                 300

Ser Gly Thr Ala Ser Leu Val Gln Lys Leu Arg His Leu Gly Leu Ser
305                 310                 315                 320

Leu Ser Pro Glu Lys Ala Ala Ala Leu Leu Glu Lys Val Arg Asn Thr
                325                 330                 335

Ala Ile Leu Gln Lys Lys Pro Leu Thr Asp Leu Gln Leu Lys Thr Leu
            340                 345                 350

Tyr Asp Leu Gln Met Glu Ser Val Lys Asp Pro Asn Ile His Leu Ser
        355                 360                 365

Gly Lys Gly Glu Met Pro Cys Asp
    370                 375

<210> SEQ ID NO 211
<211> LENGTH: 376
<212> TYPE: PRT
<213> ORGANISM: Chlorobaculum tepidum

<400> SEQUENCE: 211

Met Ile Arg Lys Pro Trp Ile Ile Asp Thr Thr Leu Arg Asp Gly Glu
1               5                   10                  15

Gln Ala Pro Gly Val Val Phe Ser Pro His Glu Lys Lys Arg Ile Ala
            20                  25                  30

Ala Met Leu Ala Glu Thr Gly Val Asp Glu Ile Glu Val Gly Tyr Pro
        35                  40                  45

Ala Ile Ser Ala Ala Glu Arg Lys Val Ile Arg Glu Ile Val Ala Met
    50                  55                  60

Lys Leu Pro Val Arg Leu Thr Ser Trp Ser Arg Ala Asn Met Ala Asp
65                  70                  75                  80

Ile Glu Leu Ala Ala Glu Cys Gly Thr Asp Ala Val His Ile Ser Phe
                85                  90                  95

Pro Ala Ser Arg Leu Tyr Leu Glu Leu Ile His Lys Lys Asp Asp Trp
            100                 105                 110

Ile Gln Glu Gln Leu His Ala Leu Val Ser Lys Ala Arg Glu Arg Phe
        115                 120                 125

Asp Phe Val Ser Val Gly Gly Gln Asp Ala Thr Arg Ser Ser Thr Asp
    130                 135                 140

Phe Leu Gln Arg Phe Met Leu Asp Ala Glu Ala Ala Gly Ala Lys Arg
145                 150                 155                 160

Phe Arg Ile Ala Asp Thr Val Gly Ile Ala Thr Pro Val Ser Val Met
                165                 170                 175

Ala Leu Gly Ala Ala Leu Arg Gln Ser Ser Ser Leu Pro Leu Glu Phe
            180                 185                 190

His Ala His Asn Asp Leu Gly Met Ala Thr Ala Asn Ala Phe Thr Ala

```
        195                 200                 205

Leu Asn Glu Gly Phe Glu Ala Val Ser Val Ser Val Thr Gly Leu Gly
    210                 215                 220

Glu Arg Ala Gly Asn Ala Ala Leu Glu Glu Leu Ala Met Ala Leu Ala
225                 230                 235                 240

Leu Asn Gly Asp Phe Asp Thr His Leu Asp Thr Ser Met Leu Ser Arg
                245                 250                 255

Leu Cys Asp Ala Val Ala Thr Ala Ser Gly Arg Ala Ile Gln Glu Gln
            260                 265                 270

Lys Pro Val Val Gly Arg Ser Ala Phe Gln His Glu Ser Gly Ile His
        275                 280                 285

Cys Ala Ala Leu Leu Gln Asp Pro Leu Ser Tyr Gln Pro Phe Leu Pro
    290                 295                 300

Ser Arg Val Gly Arg Ser Asp Phe Glu Ile Val Ile Gly Lys His Ser
305                 310                 315                 320

Gly Thr Ala Ala Ile Ile Ala His Phe Asn Arg Arg Gly Ile Thr Ile
                325                 330                 335

Ser Lys Lys Glu Ala Arg Glu Leu Leu Asp Leu Ile Arg Ser Gln Ser
            340                 345                 350

Asp Arg Leu Lys Arg Ala Leu Arg Thr Asp Glu Ile Asp Ala Leu Arg
        355                 360                 365

Glu Gln Asn Ser Val Lys His Ala
    370                 375


<210> SEQ ID NO 212
<211> LENGTH: 511
<212> TYPE: PRT
<213> ORGANISM: Methanocaldococcus infernus

<400> SEQUENCE: 212

Met Ile Leu Tyr Lys Glu Glu Asn Glu Ile Ile Lys Glu Ala Leu Lys
1               5                   10                  15

Gly Leu Lys Leu Pro Asp Arg Val Tyr Ile Phe Asp Thr Thr Leu Arg
            20                  25                  30

Asp Gly Glu Gln Thr Pro Gly Val Ser Leu Thr Val Asp Glu Lys Val
        35                  40                  45

Glu Ile Ala Ile Asn Leu Asp Lys Leu Gly Val Asp Ile Ile Glu Ala
    50                  55                  60

Gly Phe Pro Ile Ser Ser Ser Gly Glu Tyr Glu Ala Val Lys Lys Ile
65                  70                  75                  80

Ala Ser Leu Asn Leu Asp Ala Glu Ile Cys Ala Leu Ala Arg Ala Val
                85                  90                  95

Lys Glu Asp Ile Asp Arg Ala Ile Asp Cys Gly Val Asp Arg Ile His
            100                 105                 110

Thr Phe Ile Ala Thr Ser Pro Leu His Arg Lys Tyr Lys Leu Lys Met
        115                 120                 125

Ser Lys Glu Glu Ile Val Glu Lys Ala Val Asn Ala Ile Glu Tyr Ile
    130                 135                 140

Lys Glu His Gly Ile Lys Val Glu Phe Ser Ala Glu Asp Ala Thr Arg
145                 150                 155                 160

Thr Glu Ile Asp Tyr Leu Lys Glu Val Tyr Lys Lys Ala Val Glu Ala
                165                 170                 175

Gly Ala Asp Ile Ile Asn Val Pro Asp Thr Val Gly Val Met Ile Pro
            180                 185                 190
```

```
Arg Ala Thr Tyr Tyr Leu Ile Ser Glu Leu Arg Lys Glu Ile Asp Asn
        195                 200                 205

Ile Ser Val His Cys His Asn Asp Phe Gly Leu Ala Val Ala Asn Ser
    210                 215                 220

Leu Ala Ala Val Glu Ala Gly Ala Ile Gln Cys His Val Thr Val Asn
225                 230                 235                 240

Gly Leu Gly Glu Arg Gly Gly Asn Ala Ala Leu Glu Glu Val Val Thr
                245                 250                 255

Ser Leu His Phe Ile Tyr Gly Ile Lys Thr Lys Val Lys Thr Glu Glu
            260                 265                 270

Leu Tyr Asn Ile Ser Lys Leu Val Glu Lys Leu Thr Glu Val Lys Val
        275                 280                 285

Gln Pro Asn Lys Ala Val Val Gly Asp Asn Ala Phe Ala His Glu Ser
    290                 295                 300

Gly Ile His Ala His Gly Val Leu Ala His Ala Leu Thr Tyr Glu Pro
305                 310                 315                 320

Ile Pro Pro Glu Leu Val Gly Gln Arg Arg Arg Ile Ile Leu Gly Lys
                325                 330                 335

His Thr Gly Thr His Ala Ile Glu Ala Lys Leu Lys Glu Leu Gly Tyr
            340                 345                 350

Thr Asn Ile Asn Lys Glu Gln Phe Lys Glu Ile Val Lys Arg Ile Lys
        355                 360                 365

Ser Leu Gly Asp Lys Gly Lys Arg Val Thr Asp Lys Asp Val Glu Ala
    370                 375                 380

Ile Val Glu Asp Val Ile Gly Arg Val Ser Lys Arg Glu Arg Val Val
385                 390                 395                 400

Asp Leu Glu Gln Ile Ala Val Met Thr Gly Asn Lys Val Ile Pro Thr
                405                 410                 415

Ala Ser Val Ala Leu Lys Ile Asn Asp Asn Leu Ile Lys Thr Ser Ala
            420                 425                 430

Ile Gly Val Gly Pro Val Asp Ala Ala Val Lys Ala Ile Gln Lys Ala
        435                 440                 445

Ile Gly Glu Lys Ile Lys Ile Lys Glu Tyr His Ile Asp Ala Ile Thr
    450                 455                 460

Gly Gly Thr Asp Ala Leu Ala Glu Val Val Val Thr Leu Glu Gly Tyr
465                 470                 475                 480

Gly Lys Glu Ile Thr Thr Lys Ala Ala Arg Glu Asp Ile Val Arg Ala
                485                 490                 495

Ser Val Glu Ala Val Ile Asp Gly Ile Asn Lys Ile Leu Lys Lys
            500                 505                 510
```

<210> SEQ ID NO 213
<211> LENGTH: 490
<212> TYPE: PRT
<213> ORGANISM: Methanocaldococcus infernus

<400> SEQUENCE: 213

```
Met Lys Val Arg Val Phe Asp Thr Thr Leu Arg Asp Gly Glu Gln Thr
1               5                   10                  15

Pro Gly Val Ser Leu Thr Pro Ser Asp Lys Leu Glu Ile Ala Lys Ala
            20                  25                  30

Leu Asp Glu Leu Gly Val Asp Val Ile Glu Ala Gly Ser Ala Ile Thr
        35                  40                  45

Ser Lys Gly Glu Arg Glu Gly Ile Lys Leu Ile Thr Arg Glu Asn Leu
    50                  55                  60
```

```
Asn Ala Glu Ile Cys Ser Phe Val Arg Pro Leu Thr Val Asp Ile Asp
65                  70                  75                  80

Ala Ala Ile Glu Cys Glu Val Asp Ser Ile His Leu Val Val Pro Ser
                85                  90                  95

Ser Pro Ile His Ile Lys Tyr Lys Leu Lys Lys Ser Glu Asp Glu Val
            100                 105                 110

Leu Asp Leu Ala Val Asn Ala Ile Glu Tyr Ala Lys Asp His Gly Leu
        115                 120                 125

Ile Val Glu Leu Ser Ala Glu Asp Ala Thr Arg Ala Glu Leu Asn Phe
    130                 135                 140

Leu Ile Lys Leu Phe Lys Ala Gly Glu Asn Leu Ala Asp Arg Val Cys
145                 150                 155                 160

Val Cys Asp Thr Val Gly Val Leu Thr Pro Gln Lys Ser Glu Glu Leu
                165                 170                 175

Phe Lys Lys Ile Thr Ser Glu Ile Lys Leu Pro Val Ser Val His Cys
            180                 185                 190

His Asn Asp Phe Gly Met Ala Thr Ala Asn Thr Cys Ser Ala Ile Leu
        195                 200                 205

Gly Gly Ala Val Gln Cys His Val Thr Val Asn Gly Ile Gly Glu Arg
    210                 215                 220

Ala Gly Asn Ala Ala Leu Glu Glu Val Val Thr Ala Leu Lys Phe Leu
225                 230                 235                 240

Tyr Asn Ile Glu Thr Asn Ile Lys Leu Glu Lys Leu Tyr Glu Val Ser
                245                 250                 255

Arg Leu Val Ala Arg Leu Met Lys Leu Pro Val Pro Pro Asn Lys Ala
            260                 265                 270

Ile Val Gly Asp Asn Ala Phe Ala His Glu Ala Gly Ile His Val Asp
        275                 280                 285

Gly Leu Ile Lys Asn Thr Lys Thr Tyr Glu Pro Ile Ser Pro Glu Val
    290                 295                 300

Val Gly Asn Lys Arg Arg Ile Ile Leu Gly Lys His Ser Gly Arg Lys
305                 310                 315                 320

Ala Leu Ile Tyr Lys Leu Lys Leu Met Gly Ile Glu Ala Ser Glu Glu
                325                 330                 335

Gln Ile Asn Lys Ile Tyr Glu Lys Ile Lys Glu Leu Gly Asp Leu Gly
            340                 345                 350

Lys Tyr Val Ser Asp Ala Asp Leu Met Ala Ile Val Lys Asp Val Leu
        355                 360                 365

Gly Lys Asp Leu Glu Glu Lys Ile Glu Leu Asp Glu Leu Thr Val Val
    370                 375                 380

Ser Gly Asn Lys Ile Thr Pro Ile Ala Ser Val Lys Leu His Tyr Lys
385                 390                 395                 400

Gly Glu Asp Arg Leu Leu Ile Glu Thr Ala Tyr Gly Val Gly Pro Val
                405                 410                 415

Asp Ala Ala Ile Asn Ala Val Arg Lys Ala Ile Ser Gly Val Ala Asp
            420                 425                 430

Ile Lys Leu Glu Glu Tyr Lys Val Glu Ala Ile Gly Gly Gly Thr Asp
        435                 440                 445

Ala Ile Ile Glu Val Thr Val Lys Leu Arg Lys Gly Val Asn Thr Val
    450                 455                 460

Glu Val Lys Lys Ala Asp Ser Asp Ile Ile Arg Ala Ser Val Asn Ala
465                 470                 475                 480
```

Val Met Glu Gly Ile Asn Leu Leu Leu Gln
485 490

<210> SEQ ID NO 214
<211> LENGTH: 396
<212> TYPE: PRT
<213> ORGANISM: Methanocaldococcus infernus

<400> SEQUENCE: 214

Met Asp Leu Leu Tyr Glu Asn Thr Trp Lys Ala Pro Ser Pro Tyr Asn
1 5 10 15

Pro Lys Leu Lys Leu Lys Asp Ile Tyr Ile Tyr Asp Thr Thr Leu Arg
20 25 30

Asp Gly Glu Gln Thr Pro Gly Val Cys Phe Thr Lys Glu Gln Lys Leu
35 40 45

Glu Ile Ala Arg Ala Leu Asp Glu Leu Gly Val Ser Gln Ile Glu Ala
50 55 60

Gly Phe Pro Ile Val Ser Lys Arg Glu Ala Glu Ile Val Lys Ala Ile
65 70 75 80

Ala Ser Glu Asn Leu Asn Ala Asp Ile Leu Ala Leu Ser Arg Ile Arg
85 90 95

Lys Glu Asp Ile Asn Lys Ala Ile Asp Cys Asp Val Asp Gly Ile Ile
100 105 110

Thr Phe Ile Ala Thr Ser Pro Leu His Ile Lys Cys Lys Phe Lys Gly
115 120 125

Lys Arg Leu Glu Asp Phe Phe Asp Thr Ile Val Glu Cys Ile Glu Tyr
130 135 140

Ala Lys Ser His Gly Leu Phe Val Ala Phe Ser Ala Glu Asp Gly Thr
145 150 155 160

Arg Thr Pro Leu Glu Asp Leu Ile Arg Val His Lys Leu Ala Glu Glu
165 170 175

Ala Gly Ala Asp Arg Val His Val Ala Asp Thr Ala Gly Thr Ala Thr
180 185 190

Pro Gln Ala Met Glu Phe Ile Cys Lys Ala Leu Thr Cys Ser Leu Asn
195 200 205

Lys Ala His Val Gly Val His Cys His Asn Asp Phe Gly Leu Ala Val
210 215 220

Ile Asn Ser Ile Tyr Gly Leu Ile Gly Gly Ala Lys Ala Val Ser Thr
225 230 235 240

Thr Val Asn Gly Ile Gly Glu Arg Ala Gly Asn Thr Ser Leu Glu Glu
245 250 255

Leu Ile Met Ser Leu Ile Val Leu Tyr Asp Val Asp Leu Lys Leu Asn
260 265 270

Leu Glu Val Leu Pro Lys Leu Cys Arg Met Val Glu Glu Tyr Ser Gly
275 280 285

Ile Lys Asn Pro Lys Asn Lys Pro Ile Val Gly Glu Leu Val Phe Ser
290 295 300

His Glu Ser Gly Ile His Val Asp Ala Val Ile Glu Asn Pro Leu Thr
305 310 315 320

Tyr Glu Pro Phe Leu Pro Glu Lys Ile Gly Leu Lys Arg Asn Ile Ile
325 330 335

Leu Gly Lys His Ser Gly Lys Arg Ala Val Lys Tyr Lys Leu Lys Leu
340 345 350

Leu Gly Val Glu Val Glu Asp Lys Leu Leu Asp Lys Ile Val Glu Arg
355 360 365

Val Lys Glu Leu Arg Glu Lys Gly Glu Lys Ile Asp Asp Glu Lys Leu
370 375 380

Leu Glu Ile Val Glu Glu Ile Lys Arg Ile Lys Asp
385 390 395

<210> SEQ ID NO 215
<211> LENGTH: 540
<212> TYPE: PRT
<213> ORGANISM: Lotus japonicus

<400> SEQUENCE: 215

Met Ala Ser Lys Asn Ser Ile Ile Arg Asn Arg Pro Glu Tyr Ile Pro
1 5 10 15

Asn His Ile Pro Asn Pro Thr Tyr Val Arg Ile Leu Asp Thr Thr Leu
20 25 30

Arg Asp Gly Glu Gln Ser Pro Gly Ala Ala Met Thr Cys Val Gln Lys
35 40 45

Leu Glu Thr Ala Arg Gln Leu Ala Lys Leu Gly Val Asp Ile Ile Glu
50 55 60

Ala Gly Phe Pro Cys Ala Ser Lys Gln Asp Phe Met Ala Val Lys Met
65 70 75 80

Ile Ala Glu Glu Val Gly Asn Cys Val Asp Gly Asn Gly Tyr Val Pro
85 90 95

Val Ile Thr Gly Val Ser Arg Cys Asn Glu Lys Asp Ile Ala Thr Ala
100 105 110

Trp Glu Ala Leu Lys His Ala Lys Arg Pro Arg Leu Arg Thr Phe Ile
115 120 125

Ala Thr Ser Pro Ile His Met Glu Tyr Lys Leu Arg Lys Ser Lys Asp
130 135 140

Gln Val Leu Glu Thr Ala Arg Asn Met Val Lys Phe Ala Arg Ser Leu
145 150 155 160

Gly Cys Thr Asp Ile Gln Phe Gly Ala Glu Asp Ala Ala Arg Ser Asp
165 170 175

Lys Glu Phe Leu Tyr Gln Ile Phe Gly Glu Val Ile Lys Ala Gly Ala
180 185 190

Thr Thr Leu Thr Ile Pro Asp Thr Val Gly Ile Ala Met Pro Phe Glu
195 200 205

Tyr Gly Lys Leu Ile Ala Asp Ile Lys Ala Asn Thr Pro Gly Ile Glu
210 215 220

Asn Ala Ile Met Ala Thr His Cys His Asn Asp Leu Gly Leu Ala Thr
225 230 235 240

Ala Asn Thr Ile Glu Gly Ala Arg Tyr Gly Ala Arg Gln Leu Glu Val
245 250 255

Thr Ile Asn Gly Ile Gly Glu Arg Ala Gly Asn Ala Ser Phe Glu Glu
260 265 270

Val Val Met Ala Leu Thr Cys Arg Gly Ile Asp Ile Leu Gly Gly Leu
275 280 285

His Thr Gly Ile Asn Thr Arg His Ile Leu Lys Thr Ser Lys Met Val
290 295 300

Glu Lys Tyr Ser Gly Leu His Leu Gln Pro His Lys Ala Leu Val Gly
305 310 315 320

Ala Asn Ala Phe Leu His Glu Ser Gly Ile His Gln Asp Gly Met Leu
325 330 335

Lys His Arg Gly Thr Tyr Glu Ile Ile Ser Pro Glu Asp Ile Gly Leu

```
            340                 345                 350

Val Arg Ser Val Gly Asp Thr Ile Val Leu Gly Lys Leu Ser Gly Arg
        355                 360                 365

Gln Ala Leu Arg Asn Arg Leu Glu Glu Leu Gly Tyr Lys Leu Lys Asp
    370                 375                 380

Thr Glu Val Glu Gly Val Phe Trp Gln Phe Lys Ala Val Ala Glu Lys
385                 390                 395                 400

Lys Lys Arg Ile Thr Asp Thr Asp Leu Arg Ala Leu Val Ser Asn Glu
                405                 410                 415

Ala Phe Asn Glu Gln Pro Ile Trp Lys Leu Gly Asp Leu Gln Val Thr
            420                 425                 430

Cys Gly Thr Val Gly Phe Ser Thr Ala Thr Val Lys Leu Phe Ser Ile
        435                 440                 445

Asp Gly Ser Met His Val Ala Cys Ser Ile Gly Thr Gly Pro Val Asp
    450                 455                 460

Ser Ala Tyr Lys Ala Ile Asn His Ile Val Lys Glu Pro Ala Lys Leu
465                 470                 475                 480

Val Lys Tyr Thr Leu Gly Ala Ile Thr Glu Gly Ile Asp Ala Thr Ala
                485                 490                 495

Thr Thr Ser Val Glu Ile Ser Arg Gly Asp Thr Asn His Pro Val Phe
            500                 505                 510

Ser Gly Thr Gly Gly Gly Thr Asp Val Val Val Ser Ser Val Asp Ala
        515                 520                 525

Tyr Leu Ser Ala Leu Asn Asn Met Leu Arg Phe Tyr
    530                 535                 540


<210> SEQ ID NO 216
<211> LENGTH: 518
<212> TYPE: PRT
<213> ORGANISM: Azotobacter vinelandii

<400> SEQUENCE: 216

Met Pro His His Glu Phe Glu Cys Ser Lys Val Ile Pro Glu Arg Lys
1               5                   10                  15

Lys His Ala Val Ile Lys Gly Lys Gly Glu Thr Leu Ala Asp Ala Leu
            20                  25                  30

Pro Gln Gly Tyr Leu Asn Thr Ile Pro Gly Ser Ile Ser Glu Arg Gly
        35                  40                  45

Cys Ala Tyr Cys Gly Ala Lys His Val Ile Gly Thr Pro Met Lys Asp
    50                  55                  60

Val Ile His Ile Ser His Gly Pro Val Gly Cys Thr Tyr Asp Thr Trp
65                  70                  75                  80

Gln Thr Lys Arg Tyr Ile Ser Asp Asn Asp Asn Phe Gln Leu Lys Tyr
                85                  90                  95

Thr Tyr Ala Thr Asp Val Lys Glu Lys His Ile Val Phe Gly Ala Glu
            100                 105                 110

Lys Leu Leu Lys Gln Asn Ile Ile Glu Ala Phe Lys Ala Phe Pro Gln
        115                 120                 125

Ile Lys Arg Met Thr Ile Tyr Gln Thr Cys Ala Thr Ala Leu Ile Gly
    130                 135                 140

Asp Asp Ile Asn Ala Ile Ala Glu Glu Val Met Glu Glu Met Pro Glu
145                 150                 155                 160

Val Asp Ile Phe Val Cys Asn Ser Pro Gly Phe Ala Gly Pro Ser Gln
                165                 170                 175
```

Ser Gly Gly His His Lys Ile Asn Ile Ala Trp Ile Asn Gln Lys Val
180 185 190

Gly Thr Val Glu Pro Glu Ile Thr Gly Asp His Val Ile Asn Tyr Val
195 200 205

Gly Glu Tyr Asn Ile Gln Gly Asp Gln Glu Val Met Val Asp Tyr Phe
210 215 220

Lys Arg Met Gly Ile Gln Val Leu Ser Thr Phe Thr Gly Asn Gly Ser
225 230 235 240

Tyr Asp Gly Leu Arg Ala Met His Arg Ala His Leu Asn Val Leu Glu
245 250 255

Cys Ala Arg Ser Ala Glu Tyr Ile Cys Asn Glu Leu Arg Val Arg Tyr
260 265 270

Gly Ile Pro Arg Leu Asp Ile Asp Gly Phe Gly Phe Lys Pro Leu Ala
275 280 285

Asp Ser Leu Arg Lys Ile Gly Met Phe Phe Gly Ile Glu Asp Arg Ala
290 295 300

Lys Ala Ile Ile Asp Glu Glu Val Ala Arg Trp Lys Pro Glu Leu Asp
305 310 315 320

Trp Tyr Lys Glu Arg Leu Met Gly Lys Lys Val Cys Leu Trp Pro Gly
325 330 335

Gly Ser Lys Leu Trp His Trp Ala His Val Ile Glu Glu Glu Met Gly
340 345 350

Leu Lys Val Val Ser Val Tyr Thr Lys Phe Gly His Gln Gly Asp Met
355 360 365

Glu Lys Gly Ile Ala Arg Cys Gly Glu Gly Thr Leu Ala Ile Asp Asp
370 375 380

Pro Asn Glu Leu Glu Gly Leu Glu Ala Leu Glu Met Leu Lys Pro Asp
385 390 395 400

Ile Ile Leu Thr Gly Lys Arg Pro Gly Glu Val Ala Lys Lys Val Arg
405 410 415

Val Pro Tyr Leu Asn Ala His Ala Tyr His Asn Gly Pro Tyr Lys Gly
420 425 430

Phe Glu Gly Trp Val Arg Phe Ala Arg Asp Ile Tyr Asn Ala Ile Tyr
435 440 445

Ser Pro Ile His Gln Leu Ser Gly Ile Asp Ile Thr Lys Asp Asn Ala
450 455 460

Pro Glu Trp Gly Asn Gly Phe Arg Thr Arg Gln Met Leu Ser Asp Gly
465 470 475 480

Asn Leu Ser Asp Ala Val Arg Asn Ser Glu Thr Leu Arg Gln Tyr Thr
485 490 495

Gly Gly Tyr Asp Ser Val Ser Lys Leu Arg Glu Arg Glu Tyr Pro Ala
500 505 510

Phe Glu Arg Lys Val Gly
515

<210> SEQ ID NO 217
<211> LENGTH: 462
<212> TYPE: PRT
<213> ORGANISM: Azotobacter vinelandii

<400> SEQUENCE: 217

Met Thr Cys Glu Val Lys Glu Lys Gly Arg Val Gly Thr Ile Asn Pro
1 5 10 15

Ile Phe Thr Cys Gln Pro Ala Gly Ala Gln Phe Val Ser Ile Gly Ile
20 25 30

-continued

```
Lys Asp Cys Ile Gly Ile Val His Gly Gly Gln Gly Cys Val Met Phe
        35                  40                  45

Val Arg Leu Ile Phe Ser Gln His Tyr Lys Glu Ser Phe Glu Leu Ala
    50                  55                  60

Ser Ser Ser Leu His Glu Asp Gly Ala Val Phe Gly Ala Cys Gly Arg
65                  70                  75                  80

Val Glu Glu Ala Val Asp Val Leu Leu Ser Arg Tyr Pro Asp Val Lys
                85                  90                  95

Val Val Pro Ile Ile Thr Thr Cys Ser Thr Glu Ile Ile Gly Asp Asp
            100                 105                 110

Val Asp Gly Val Ile Lys Lys Leu Asn Glu Gly Leu Leu Lys Glu Lys
        115                 120                 125

Phe Pro Asp Arg Glu Val His Leu Ile Ala Met His Thr Pro Ser Phe
    130                 135                 140

Val Gly Ser Met Ile Ser Gly Tyr Asp Val Ala Val Arg Asp Val Val
145                 150                 155                 160

Arg His Phe Ala Lys Arg Glu Ala Pro Asn Asp Lys Ile Asn Leu Leu
                165                 170                 175

Thr Gly Trp Val Asn Pro Gly Asp Val Lys Glu Leu Lys His Leu Leu
            180                 185                 190

Gly Glu Met Asp Ile Glu Ala Asn Val Leu Phe Glu Ile Glu Ser Phe
        195                 200                 205

Asp Ser Pro Ile Leu Pro Asp Gly Ser Ala Val Ser His Gly Asn Thr
    210                 215                 220

Thr Ile Glu Asp Leu Ile Asp Thr Gly Asn Ala Arg Ala Thr Phe Ala
225                 230                 235                 240

Leu Asn Arg Tyr Glu Gly Thr Lys Ala Ala Glu Tyr Leu Gln Lys Lys
                245                 250                 255

Phe Glu Ile Pro Ala Ile Ile Gly Pro Thr Pro Ile Gly Ile Arg Asn
            260                 265                 270

Thr Asp Ile Phe Leu Gln Asn Leu Lys Lys Ala Thr Gly Lys Pro Ile
        275                 280                 285

Pro Gln Ser Leu Ala His Glu Arg Gly Val Ala Ile Asp Ala Leu Ala
    290                 295                 300

Asp Leu Thr His Met Phe Leu Ala Glu Lys Arg Val Ala Ile Tyr Gly
305                 310                 315                 320

Ala Pro Asp Leu Val Ile Gly Leu Ala Glu Phe Cys Leu Asp Leu Glu
                325                 330                 335

Met Lys Pro Val Leu Leu Leu Leu Gly Asp Asp Asn Ser Lys Tyr Val
            340                 345                 350

Asp Asp Pro Arg Ile Lys Ala Leu Gln Glu Asn Val Asp Tyr Gly Met
        355                 360                 365

Glu Ile Val Thr Asn Ala Asp Phe Trp Glu Leu Glu Asn Arg Ile Lys
    370                 375                 380

Asn Glu Gly Leu Glu Leu Asp Leu Ile Leu Gly His Ser Lys Gly Arg
385                 390                 395                 400

Phe Ile Ser Ile Asp Tyr Asn Ile Pro Met Leu Arg Val Gly Phe Pro
                405                 410                 415

Thr Tyr Asp Arg Ala Gly Leu Phe Arg Tyr Pro Thr Val Gly Tyr Gly
            420                 425                 430

Gly Ala Ile Trp Leu Ala Glu Gln Met Ala Asn Thr Leu Phe Ala Asp
        435                 440                 445
```

```
Met Glu His Lys Lys Asn Lys Glu Trp Val Leu Asn Val Trp
    450                 455                 460


<210> SEQ ID NO 218
<211> LENGTH: 275
<212> TYPE: PRT
<213> ORGANISM: Azotobacter vinelandii

<400> SEQUENCE: 218

Met Thr Arg Lys Val Ala Ile Tyr Gly Lys Gly Gly Ile Gly Lys Ser
1               5                   10                  15

Thr Thr Thr Gln Asn Thr Ala Ala Ala Leu Ala Tyr Phe His Asp Lys
            20                  25                  30

Lys Val Phe Ile His Gly Cys Asp Pro Lys Ala Asp Ser Thr Arg Leu
        35                  40                  45

Ile Leu Gly Gly Lys Pro Gln Glu Thr Leu Met Asp Met Leu Arg Asp
    50                  55                  60

Lys Gly Ala Glu Lys Ile Thr Asn Asp Asp Val Ile Lys Lys Gly Phe
65                  70                  75                  80

Leu Asp Ile Gln Cys Val Glu Ser Gly Gly Pro Glu Pro Gly Val Gly
                85                  90                  95

Cys Ala Gly Arg Gly Val Ile Thr Ala Ile Asp Leu Met Glu Glu Asn
            100                 105                 110

Gly Ala Tyr Thr Asp Asp Leu Asp Phe Val Phe Phe Asp Val Leu Gly
        115                 120                 125

Asp Val Val Cys Gly Gly Phe Ala Met Pro Ile Arg Asp Gly Lys Ala
    130                 135                 140

Gln Glu Val Tyr Ile Val Ala Ser Gly Glu Met Met Ala Ile Tyr Ala
145                 150                 155                 160

Ala Asn Asn Ile Cys Lys Gly Leu Val Lys Tyr Ala Lys Gln Ser Gly
                165                 170                 175

Val Arg Leu Gly Gly Ile Ile Cys Asn Ser Arg Lys Val Asp Gly Glu
            180                 185                 190

Arg Glu Phe Leu Glu Glu Phe Thr Ala Ala Ile Gly Thr Lys Met Ile
        195                 200                 205

His Phe Val Pro Arg Asp Asn Ile Val Gln Lys Ala Glu Phe Asn Lys
    210                 215                 220

Lys Thr Val Thr Glu Phe Ala Pro Glu Glu Asn Gln Ala Lys Glu Tyr
225                 230                 235                 240

Gly Glu Leu Ala Arg Lys Ile Ile Glu Asn Asp Glu Phe Val Ile Pro
                245                 250                 255

Lys Pro Leu Thr Met Asp Gln Leu Glu Asp Met Val Val Lys Tyr Gly
            260                 265                 270

Ile Ala Asp
        275


<210> SEQ ID NO 219
<211> LENGTH: 132
<212> TYPE: PRT
<213> ORGANISM: Azotobacter vinelandii

<400> SEQUENCE: 219

Met Ser Thr Ala Ser Ala Ala Ala Val Val Lys Gln Lys Val Glu Ala
1               5                   10                  15

Pro Val His Pro Met Asp Ala Arg Ile Asp Glu Leu Thr Asp Tyr Ile
            20                  25                  30
```

Met Lys Asn Cys Leu Trp Gln Phe His Ser Arg Ser Trp Asp Arg Glu
35 40 45

Arg Gln Asn Ala Glu Ile Leu Lys Lys Thr Lys Glu Leu Leu Cys Gly
50 55 60

Glu Pro Val Asp Leu Ser Thr Ser His Asp Arg Cys Tyr Trp Val Asp
65 70 75 80

Ala Val Cys Leu Ala Asp Asp Tyr Arg Glu His Tyr Pro Trp Ile Asn
85 90 95

Ser Met Ser Lys Glu Glu Ile Gly Ser Leu Met Gln Gly Leu Lys Asp
100 105 110

Arg Met Asp Tyr Leu Thr Ile Thr Gly Ser Leu Asn Glu Glu Leu Ser
115 120 125

Asp Lys His Tyr
130

<210> SEQ ID NO 220
<211> LENGTH: 4
<212> TYPE: PRT
<213> ORGANISM: Artificial Sequence
<220> FEATURE:
<223> OTHER INFORMATION: Peptide

<400> SEQUENCE: 220

Arg Arg Asn Phe
1

<210> SEQ ID NO 221
<211> LENGTH: 606
<212> TYPE: PRT
<213> ORGANISM: Nicotiana benthamiana

<400> SEQUENCE: 221

Met Ala Ser Ile Thr Thr Asn His Thr Phe Ser Arg Asn Leu Asn Phe
1 5 10 15

Ser Phe His Pro Gln Asn Pro Leu Ile Gln Thr Gln Ala Leu Phe Lys
20 25 30

Phe Lys Pro Ser Ile Pro Asn Cys Ser Pro Ile Ile Arg Cys Ala Ile
35 40 45

Arg Arg Arg Pro Glu Tyr Thr Pro Ser His Ile Pro Asp Pro Lys Tyr
50 55 60

Ile Arg Ile Phe Asp Thr Thr Leu Arg Asp Gly Glu Gln Ser Pro Gly
65 70 75 80

Ala Thr Met Thr Thr Lys Glu Lys Leu Asp Val Ala Arg Gln Leu Ala
85 90 95

Lys Leu Gly Val Asp Ile Ile Glu Ala Gly Phe Pro Ala Ser Ser Glu
100 105 110

Ala Asp Leu Glu Ala Val Lys Leu Ile Ala Lys Glu Val Gly Asn Gly
115 120 125

Val Tyr Glu Glu Gly His Val Pro Val Ile Cys Gly Leu Ala Arg Cys
130 135 140

Asn Lys Arg Asp Ile Asp Lys Ala Trp Glu Ala Val Lys Tyr Ala Lys
145 150 155 160

Lys Pro Arg Ile His Thr Phe Ile Ala Thr Ser Glu Ile His Met Lys
165 170 175

Phe Lys Leu Lys Met Ser Arg Asp Glu Val Val Glu Lys Ala Arg Ser
180 185 190

Met Val Ala Tyr Ala Arg Ser Ile Gly Cys Glu Asp Val Glu Phe Ser

```
        195                 200                 205

Pro Glu Asp Ala Gly Arg Ser Asp Pro Glu Phe Leu Tyr His Ile Leu
    210                 215                 220

Gly Glu Val Ile Lys Ala Gly Ala Thr Thr Leu Asn Ile Pro Asp Thr
225                 230                 235                 240

Val Gly Tyr Thr Val Pro Ser Glu Phe Gly Lys Leu Ile Ala Asp Ile
                245                 250                 255

Lys Ala Asn Thr Pro Gly Ile Gly Asp Val Ile Ile Ser Thr His Cys
            260                 265                 270

Gln Asn Asp Leu Gly Leu Ser Thr Ala Asn Thr Leu Ala Gly Ala Cys
        275                 280                 285

Ala Gly Ala Arg Gln Val Glu Val Thr Ile Asn Gly Ile Gly Glu Arg
    290                 295                 300

Ala Gly Asn Ala Ser Leu Glu Glu Val Val Met Ala Leu Lys Cys Arg
305                 310                 315                 320

Gly Glu Gln Val Leu Gly Gly Leu Tyr Thr Gly Ile Asn Thr Gln His
                325                 330                 335

Ile Leu Met Ser Ser Lys Met Val Glu Glu Tyr Thr Gly Leu His Val
            340                 345                 350

Gln Pro His Lys Ala Ile Val Gly Ala Asn Ala Phe Ala His Glu Ser
        355                 360                 365

Gly Ile His Gln Asp Gly Met Leu Lys His Lys Asp Thr Tyr Glu Ile
    370                 375                 380

Ile Ser Pro Glu Asp Ile Gly Leu Asn Arg Ala Asn Glu Ala Gly Ile
385                 390                 395                 400

Val Leu Gly Lys Leu Ser Gly Arg His Ala Leu Lys Ser Lys Met Leu
                405                 410                 415

Glu Leu Gly Tyr Asp Ile Glu Gly Lys Glu Leu Glu Asp Leu Phe Trp
            420                 425                 430

Arg Phe Lys Ser Val Ala Glu Lys Lys Lys Lys Val Thr Asp Asp Asp
        435                 440                 445

Ile Ile Ala Leu Met Ser Asp Glu Val Phe Gln Pro Gln Val Val Trp
    450                 455                 460

Gln Leu Ala Asp Val Gln Ile Thr Cys Gly Ser Leu Gly Leu Ser Thr
465                 470                 475                 480

Ala Thr Val Lys Leu Ile Asp Ser Asp Gly Gln Asp His Val Ala Cys
                485                 490                 495

Ser Val Gly Thr Gly Pro Val Asp Ala Ala Tyr Lys Ala Val Asp Leu
            500                 505                 510

Ile Val Lys Val Pro Ile Thr Leu Leu Glu Tyr Ser Met Asn Ala Val
        515                 520                 525

Thr Glu Gly Ile Asp Ser Ile Ala Ser Thr Arg Val Val Ile Arg Glu
    530                 535                 540

Glu Asp Asp His Ala Ile Thr Asn Gly Ser Ile Gly Leu Thr Leu His
545                 550                 555                 560

Arg Thr Phe Ser Gly Thr Gly Ala Asp Met Asp Val Val Ile Ser Ser
                565                 570                 575

Val Arg Ala Tyr Ile Gly Ala Leu Asn Lys Met Leu Ser Phe Gly Lys
            580                 585                 590

Leu Val Ser Arg Cys Asn Asn Pro Glu Gly Ser Val Val Val
        595                 600                 605
```

<210> SEQ ID NO 222

<211> LENGTH: 470
<212> TYPE: PRT
<213> ORGANISM: Nicotiana benthamiana

<400> SEQUENCE: 222

Met Ala Ser Ile Tyr Ala Asn Pro Thr Thr Ser Leu Asn Thr Ser Leu
1               5                   10                  15

Ser Ser Tyr Ser Lys Asn Ile Phe Leu Arg Ser Val Phe Lys Phe Met
            20                  25                  30

Pro Ser Ile Thr Lys Arg Cys His Cys Pro Tyr Thr Ser Thr Ala Val
        35                  40                  45

Arg Cys Thr Asn Val Arg Arg Pro Arg Pro Asn Tyr Arg Pro Gly Arg
    50                  55                  60

Phe Ser His Pro Asn Tyr Val Gly Ile Phe Asp Thr Thr Leu Arg Asp
65                  70                  75                  80

Gly Glu Gln Ala Pro Gly Ala Ala Met Thr Ile Thr Glu Lys Leu Asp
                85                  90                  95

Ile Ala Arg Gln Leu Ala Lys Leu Gly Val Asp Val Ile Glu Ala Gly
            100                 105                 110

Phe Pro Ala Ala Ser Asp Ala Asp Phe Glu Leu Val Lys Leu Val Ala
        115                 120                 125

Lys Glu Val Gly Asn Asn Val Asp Glu Glu Gly Tyr Val Pro Val Ile
    130                 135                 140

Cys Ala Ile Gly Arg Thr Thr Lys Lys Asp Ile Asp Arg Thr Trp Glu
145                 150                 155                 160

Ala Leu Lys Tyr Ala Lys Lys Pro Met Ile Ser Leu Phe Ile Ala Thr
                165                 170                 175

Ser Asp Ile His Met Lys Tyr Lys Leu Lys Met Ser Lys Glu Val Val
            180                 185                 190

Val Glu Lys Ala Arg Ser Met Val Ala Tyr Ala Lys Thr Leu Cys Glu
        195                 200                 205

Asp Val Arg Phe Cys Val Glu Asp Gly Ala Arg Ser Asp Arg Lys Phe
    210                 215                 220

Leu Tyr Tyr Ile Leu Gly Glu Gly Ile Lys Val Gly Ala Thr Ala Ile
225                 230                 235                 240

Cys Val Ala Asp Thr Val Gly Ser Ser Leu Pro Thr Glu Phe Gly Arg
                245                 250                 255

Leu Ile Ala Asp Ile Lys Ala Asn Thr Pro Gly Ile Glu Asp Val Ile
            260                 265                 270

Ile Ser Val His Cys His Asn Asp Leu Gly Leu Ala Thr Ala Asn Thr
        275                 280                 285

Leu Ala Gly Ala Cys Ala Gly Ala Arg Leu Val Asp Val Thr Val Asn
    290                 295                 300

Gly Ile Gly Glu Arg Ala Gly Asn Gly Ser Leu Glu Glu Ile Val Met
305                 310                 315                 320

Ala Leu Lys Tyr Arg Gly Glu Glu Val Leu Gly Gly Leu Tyr Ser Gly
                325                 330                 335

Ile Asn Thr Lys His Ile Ile Ala Thr Ser Lys Met Val Glu Glu Tyr
            340                 345                 350

Cys Gly Leu Lys Leu Gln Pro His Lys Pro Ile Val Gly Ala Asn Ala
        355                 360                 365

Phe Ser His Glu Ser Gly Ile His Gln Asp Gly Val Leu Lys Lys Arg
    370                 375                 380

Glu Thr Tyr Glu Phe Val Ser Pro Glu Asp Val Gly Phe Gln Arg Val 385 390 395 400

Thr Gly His Gly Ile Ile Leu Gly Lys Leu Ser Gly Arg His Ala Leu
405 410 415

Lys Ser Lys Met Phe Glu Leu Gly Tyr Glu Phe Glu Gly Lys Glu Leu
420 425 430

Asp Asp Ile Phe Arg Arg Phe Lys Ser Val Ala Glu Lys Lys Lys Lys
435 440 445

Ile Thr Glu Glu Asp Leu Arg Ala Leu Val Ser Asp Lys Val Cys Ser
450 455 460

Leu Lys Leu Leu Asp Ala
465 470

<210> SEQ ID NO 223
<211> LENGTH: 644
<212> TYPE: PRT
<213> ORGANISM: Mycobacterium tuberculosis

<400> SEQUENCE: 223

Met Ala Thr Ser Glu Ser Pro Asp Ala Tyr Thr Glu Ser Phe Gly Ala
1 5 10 15

His Thr Ile Val Lys Pro Ala Gly Pro Pro Arg Val Gly Gln Pro Ser
20 25 30

Trp Asn Pro Gln Arg Ala Ser Ser Met Pro Val Asn Arg Tyr Arg Pro
35 40 45

Phe Ala Glu Glu Val Glu Pro Ile Arg Leu Arg Asn Arg Thr Trp Pro
50 55 60

Asp Arg Val Ile Asp Arg Ala Pro Leu Trp Cys Ala Val Asp Leu Arg
65 70 75 80

Asp Gly Asn Gln Ala Leu Ile Asp Pro Met Ser Pro Ala Arg Lys Arg
85 90 95

Arg Met Phe Asp Leu Leu Val Arg Met Gly Tyr Lys Glu Ile Glu Val
100 105 110

Gly Phe Pro Ser Ala Ser Gln Thr Asp Phe Asp Phe Val Arg Glu Ile
115 120 125

Ile Glu Gln Gly Ala Ile Pro Asp Asp Val Thr Ile Gln Val Leu Thr
130 135 140

Gln Cys Arg Pro Glu Leu Ile Glu Arg Thr Phe Gln Ala Cys Ser Gly
145 150 155 160

Ala Pro Arg Ala Ile Val His Phe Tyr Asn Ser Thr Ser Ile Leu Gln
165 170 175

Arg Arg Val Val Phe Arg Ala Asn Arg Ala Glu Val Gln Ala Ile Ala
180 185 190

Thr Asp Gly Ala Arg Lys Cys Val Glu Gln Ala Ala Lys Tyr Pro Gly
195 200 205

Thr Gln Trp Arg Phe Glu Tyr Ser Pro Glu Ser Tyr Thr Gly Thr Glu
210 215 220

Leu Glu Tyr Ala Lys Gln Val Cys Asp Ala Val Gly Glu Val Ile Ala
225 230 235 240

Pro Thr Pro Glu Arg Pro Ile Ile Phe Asn Leu Pro Ala Thr Val Glu
245 250 255

Met Thr Thr Pro Asn Val Tyr Ala Asp Ser Ile Glu Trp Met Ser Arg
260 265 270

Asn Leu Ala Asn Arg Glu Ser Val Ile Leu Ser Leu His Pro His Asn
275 280 285

```
Asp Arg Gly Thr Ala Val Ala Ala Ala Glu Leu Gly Phe Ala Ala Gly
    290                 295                 300

Ala Asp Arg Ile Glu Gly Cys Leu Phe Gly Asn Gly Glu Arg Thr Gly
305                 310                 315                 320

Asn Val Cys Leu Val Thr Leu Gly Leu Asn Leu Phe Ser Arg Gly Val
                325                 330                 335

Asp Pro Gln Ile Asp Phe Ser Asn Ile Asp Glu Ile Arg Arg Thr Val
            340                 345                 350

Glu Tyr Cys Asn Gln Leu Pro Val His Glu Arg His Pro Tyr Gly Gly
        355                 360                 365

Asp Leu Val Tyr Thr Ala Phe Ser Gly Ser His Gln Asp Ala Ile Asn
    370                 375                 380

Lys Gly Leu Asp Ala Met Lys Leu Asp Ala Asp Ala Ala Asp Cys Asp
385                 390                 395                 400

Val Asp Asp Met Leu Trp Gln Val Pro Tyr Leu Pro Ile Asp Pro Arg
                405                 410                 415

Asp Val Gly Arg Thr Tyr Glu Ala Val Ile Arg Val Asn Ser Gln Ser
            420                 425                 430

Gly Lys Gly Gly Val Ala Tyr Ile Met Lys Thr Asp His Gly Leu Ser
        435                 440                 445

Leu Pro Arg Arg Leu Gln Ile Glu Phe Ser Gln Val Ile Gln Lys Ile
    450                 455                 460

Ala Glu Gly Thr Ala Gly Glu Gly Gly Glu Val Ser Pro Lys Glu Met
465                 470                 475                 480

Trp Asp Ala Phe Ala Glu Glu Tyr Leu Ala Pro Val Arg Pro Leu Glu
                485                 490                 495

Arg Ile Arg Gln His Val Asp Ala Ala Asp Asp Asp Gly Gly Thr Thr
            500                 505                 510

Ser Ile Thr Ala Thr Val Lys Ile Asn Gly Val Glu Thr Glu Ile Ser
        515                 520                 525

Gly Ser Gly Asn Gly Pro Leu Ala Ala Phe Val His Ala Leu Ala Asp
    530                 535                 540

Val Gly Phe Asp Val Ala Val Leu Asp Tyr Tyr Glu His Ala Met Ser
545                 550                 555                 560

Ala Gly Asp Asp Ala Gln Ala Ala Ala Tyr Val Glu Ala Ser Val Thr
                565                 570                 575

Ile Ala Ser Pro Ala Gln Pro Gly Glu Ala Gly Arg His Ala Ser Asp
            580                 585                 590

Pro Val Thr Ile Ala Ser Pro Ala Gln Pro Gly Glu Ala Gly Arg His
        595                 600                 605

Ala Ser Asp Pro Val Thr Ser Lys Thr Val Trp Gly Val Gly Ile Ala
    610                 615                 620

Pro Ser Ile Thr Thr Ala Ser Leu Arg Ala Val Val Ser Ala Val Asn
625                 630                 635                 640

Arg Ala Ala Arg


<210> SEQ ID NO 224
<211> LENGTH: 290
<212> TYPE: PRT
<213> ORGANISM: Azotobacter vinelandii

<400> SEQUENCE: 224

Met Ala Met Arg Gln Cys Ala Ile Tyr Gly Lys Gly Gly Ile Gly Lys
1               5                   10                  15
```

```
Ser Thr Thr Thr Gln Asn Leu Val Ala Ala Leu Ala Glu Met Gly Lys
            20                  25                  30

Lys Val Met Ile Val Gly Cys Asp Pro Lys Ala Asp Ser Thr Arg Leu
        35                  40                  45

Ile Leu His Ser Lys Ala Gln Asn Thr Ile Met Glu Met Ala Ala Glu
    50                  55                  60

Ala Gly Thr Val Glu Asp Leu Glu Leu Glu Asp Val Leu Lys Ala Gly
65                  70                  75                  80

Tyr Gly Gly Val Lys Cys Val Glu Ser Gly Gly Pro Glu Pro Gly Val
                85                  90                  95

Gly Cys Ala Gly Arg Gly Val Ile Thr Ala Ile Asn Phe Leu Glu Glu
            100                 105                 110

Glu Gly Ala Tyr Glu Asp Asp Leu Asp Phe Val Phe Tyr Asp Val Leu
        115                 120                 125

Gly Asp Val Val Cys Gly Gly Phe Ala Met Pro Ile Arg Glu Asn Lys
    130                 135                 140

Ala Gln Glu Ile Tyr Ile Val Cys Ser Gly Glu Met Met Ala Met Tyr
145                 150                 155                 160

Ala Ala Asn Asn Ile Ser Lys Gly Ile Val Lys Tyr Ala Asn Ser Gly
                165                 170                 175

Ser Val Arg Leu Gly Gly Leu Ile Cys Asn Ser Arg Asn Thr Asp Arg
            180                 185                 190

Glu Asp Glu Leu Ile Ile Ala Leu Ala Asn Lys Leu Gly Thr Gln Met
        195                 200                 205

Ile His Phe Val Pro Arg Asp Asn Val Val Gln Arg Ala Glu Ile Arg
    210                 215                 220

Arg Met Thr Val Ile Glu Tyr Asp Pro Lys Ala Lys Gln Ala Asp Glu
225                 230                 235                 240

Tyr Arg Ala Leu Ala Arg Lys Val Val Asp Asn Lys Leu Leu Val Ile
                245                 250                 255

Pro Asn Pro Ile Thr Met Asp Glu Leu Glu Glu Leu Leu Met Glu Phe
            260                 265                 270

Gly Ile Met Glu Val Glu Asp Glu Ser Ile Val Gly Lys Thr Ala Glu
        275                 280                 285

Glu Val
    290
```

<210> SEQ ID NO 225
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: X
<222> LOCATION: (12)..(12)
<223> OTHER INFORMATION: any amino acid

<400> SEQUENCE: 225

```
Tyr Gly Lys Gly Gly Ile Gly Lys Ser Thr Thr Xaa Gln Asn Thr
1               5                   10                  15
```

<210> SEQ ID NO 226
<211> LENGTH: 9
<212> TYPE: PRT
<213> ORGANISM: Artificial Sequence
<220> FEATURE:
<223> OTHER INFORMATION: Peptide

<400> SEQUENCE: 226

Ile His Gly Cys Asp Pro Lys Ala Asp
1 5

<210> SEQ ID NO 227
<211> LENGTH: 17
<212> TYPE: PRT
<213> ORGANISM: Artificial Sequence
<220> FEATURE:
<223> OTHER INFORMATION: Peptide

<400> SEQUENCE: 227

Cys Val Glu Ser Gly Gly Pro Glu Pro Gly Val Gly Cys Ala Gly Arg
1 5 10 15

Gly

<210> SEQ ID NO 228
<211> LENGTH: 14
<212> TYPE: PRT
<213> ORGANISM: Artificial Sequence
<220> FEATURE:
<223> OTHER INFORMATION: Peptide

<400> SEQUENCE: 228

Asp Val Leu Gly Asp Val Val Cys Gly Gly Phe Ala Met Pro
1 5 10

<210> SEQ ID NO 229
<211> LENGTH: 15
<212> TYPE: PRT
<213> ORGANISM: Artificial Sequence
<220> FEATURE:
<223> OTHER INFORMATION: Peptide
<220> FEATURE:
<221> NAME/KEY: X
<222> LOCATION: (9)..(9)
<223> OTHER INFORMATION: any amino acid

<400> SEQUENCE: 229

Val Ala Ser Gly Glu Met Met Ala Xaa Tyr Ala Ala Asn Asn Ile
1 5 10 15

<210> SEQ ID NO 230
<211> LENGTH: 5
<212> TYPE: PRT
<213> ORGANISM: Artificial Sequence
<220> FEATURE:
<223> OTHER INFORMATION: Peptide

<400> SEQUENCE: 230

Gln Ser Gly Val Arg
1 5

<210> SEQ ID NO 231
<211> LENGTH: 7
<212> TYPE: PRT
<213> ORGANISM: Artificial Sequence
<220> FEATURE:
<223> OTHER INFORMATION: Peptide
<220> FEATURE:
<221> NAME/KEY: X
<222> LOCATION: (5)..(5)
<223> OTHER INFORMATION: any amino acid

<400> SEQUENCE: 231

Cys Asn Ser Arg Xaa Val Asp
1 5

<210> SEQ ID NO 232
<211> LENGTH: 92
<212> TYPE: PRT
<213> ORGANISM: Azotobacter vinelandii

<400> SEQUENCE: 232

Met Ala Leu Lys Ile Val Glu Ser Cys Val Asn Cys Trp Ala Cys Val
1 5 10 15

Asp Val Cys Pro Ser Glu Ala Ile Ser Leu Ala Gly Pro His Phe Glu
20 25 30

Ile Ser Ala Ser Lys Cys Thr Glu Cys Asp Gly Asp Tyr Ala Glu Lys
35 40 45

Gln Cys Ala Ser Ile Cys Pro Val Glu Gly Ala Ile Leu Leu Ala Asp
50 55 60

Gly Thr Pro Ala Asn Pro Pro Gly Ser Leu Thr Gly Ile Pro Pro Glu
65 70 75 80

Arg Leu Ala Glu Ala Met Arg Glu Ile Gln Ala Arg
85 90

<210> SEQ ID NO 233
<211> LENGTH: 157
<212> TYPE: PRT
<213> ORGANISM: Artificial Sequence
<220> FEATURE:
<223> OTHER INFORMATION: Synthetic fusion polypeptide

<400> SEQUENCE: 233

Met Met Ala Met Ala Val Phe Arg Arg Glu Gly Arg Arg Leu Leu Pro
1 5 10 15

Ser Ile Ala Ala Arg Pro Ile Ala Ala Ile Arg Ser Pro Leu Ser Ser
20 25 30

Asp Gln Glu Glu Gly Leu Leu Gly Val Arg Ser Ile Ser Thr Gln Val
35 40 45

Val Arg Asn Arg Gly Gly Ala Leu Lys Ile Val Glu Ser Cys Val Asn
50 55 60

Cys Trp Ala Cys Val Asp Val Cys Pro Ser Glu Ala Ile Ser Leu Ala
65 70 75 80

Gly Pro His Phe Glu Ile Ser Ala Ser Lys Cys Thr Glu Cys Asp Gly
85 90 95

Asp Tyr Ala Glu Lys Gln Cys Ala Ser Ile Cys Pro Val Glu Gly Ala
100 105 110

Ile Leu Leu Ala Asp Gly Thr Pro Ala Asn Pro Pro Gly Ser Leu Thr
115 120 125

Gly Ile Pro Pro Glu Arg Leu Ala Glu Ala Met Arg Glu Ile Gln Ala
130 135 140

Arg Ala Gly Gly Tyr Pro Tyr Asp Val Pro Asp Tyr Ala
145 150 155

<210> SEQ ID NO 234
<211> LENGTH: 156
<212> TYPE: PRT
<213> ORGANISM: Artificial Sequence
<220> FEATURE:
<223> OTHER INFORMATION: Synthetic fusion polypeptide

<400> SEQUENCE: 234

Met Ala Met Ala Val Phe Arg Arg Glu Gly Arg Arg Leu Leu Pro Ser
1 5 10 15

```
Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Ala Leu Lys Ile Val Glu Ser Cys Val Asn Cys Trp Ala Cys Val Asp
65                  70                  75                  80

Val Cys Pro Ser Glu Ala Ile Ser Leu Ala Gly Pro His Phe Glu Ile
                85                  90                  95

Ser Ala Ser Lys Cys Thr Glu Cys Asp Gly Asp Tyr Ala Glu Lys Gln
            100                 105                 110

Cys Ala Ser Ile Cys Pro Val Glu Gly Ala Ile Leu Leu Ala Asp Gly
        115                 120                 125

Thr Pro Ala Asn Pro Pro Gly Ser Leu Thr Gly Ile Pro Pro Glu Arg
    130                 135                 140

Leu Ala Glu Ala Met Arg Glu Ile Gln Ala Arg Ala
145                 150                 155


<210> SEQ ID NO 235
<211> LENGTH: 156
<212> TYPE: PRT
<213> ORGANISM: Artificial Sequence
<220> FEATURE:
<223> OTHER INFORMATION: Synthetic fusion polypeptide

<400> SEQUENCE: 235

Met Ala Met Ala Val Phe Arg Arg Glu Ala Ala Ala Leu Leu Pro Ser
1               5                   10                  15

Ile Ala Ala Arg Pro Ile Ala Ala Ala Ala Ala Ala Ala Ser Ser Asp
            20                  25                  30

Gln Glu Glu Gly Leu Leu Ala Ala Ala Ala Ala Ala Ala Ala Val Val
        35                  40                  45

Arg Asn Arg Gly Gly Tyr Pro Tyr Asp Val Pro Asp Tyr Ala Gly Gly
    50                  55                  60

Ala Leu Lys Ile Val Glu Ser Cys Val Asn Cys Trp Ala Cys Val Asp
65                  70                  75                  80

Val Cys Pro Ser Glu Ala Ile Ser Leu Ala Gly Pro His Phe Glu Ile
                85                  90                  95

Ser Ala Ser Lys Cys Thr Glu Cys Asp Gly Asp Tyr Ala Glu Lys Gln
            100                 105                 110

Cys Ala Ser Ile Cys Pro Val Glu Gly Ala Ile Leu Leu Ala Asp Gly
        115                 120                 125

Thr Pro Ala Asn Pro Pro Gly Ser Leu Thr Gly Ile Pro Pro Glu Arg
    130                 135                 140

Leu Ala Glu Ala Met Arg Glu Ile Gln Ala Arg Ala
145                 150                 155


<210> SEQ ID NO 236
<211> LENGTH: 104
<212> TYPE: PRT
<213> ORGANISM: Artificial Sequence
<220> FEATURE:
<223> OTHER INFORMATION: Synthetic fusion polypeptide

<400> SEQUENCE: 236

Met Tyr Pro Tyr Asp Val Pro Asp Tyr Ala Gly Gly Ala Leu Lys Ile
```

```
1               5                   10                  15

Val Glu Ser Cys Val Asn Cys Trp Ala Cys Val Asp Val Cys Pro Ser
            20                  25                  30

Glu Ala Ile Ser Leu Ala Gly Pro His Phe Glu Ile Ser Ala Ser Lys
        35                  40                  45

Cys Thr Glu Cys Asp Gly Asp Tyr Ala Glu Lys Gln Cys Ala Ser Ile
    50                  55                  60

Cys Pro Val Glu Gly Ala Ile Leu Leu Ala Asp Gly Thr Pro Ala Asn
65                  70                  75                  80

Pro Pro Gly Ser Leu Thr Gly Ile Pro Pro Glu Arg Leu Ala Glu Ala
                85                  90                  95

Met Arg Glu Ile Gln Ala Arg Ala
            100
```

```
<210> SEQ ID NO 237
<211> LENGTH: 448
<212> TYPE: PRT
<213> ORGANISM: Artificial Sequence
<220> FEATURE:
<223> OTHER INFORMATION: Synthetic fusion polypeptide

<400> SEQUENCE: 237

Met Ala Met Ala Val Phe Arg Arg Glu Gly Arg Arg Leu Leu Pro Ser
1               5                   10                  15

Ile Ala Ala Arg Pro Ile Ala Ala Ile Arg Ser Pro Leu Ser Ser Asp
            20                  25                  30

Gln Glu Glu Gly Leu Leu Gly Val Arg Ser Ile Ser Thr Gln Val Val
        35                  40                  45

Arg Asn Arg Gly Gly Tyr Pro Tyr Asp Val Pro Asp Tyr Ala Gly Gly
    50                  55                  60

Met Ala Ser Val Ile Ile Asp Asp Thr Thr Leu Arg Asp Gly Glu Gln
65                  70                  75                  80

Ser Ala Gly Val Ala Phe Asn Ala Asp Glu Lys Ile Ala Ile Ala Arg
                85                  90                  95

Ala Leu Ala Glu Leu Gly Val Pro Glu Leu Glu Ile Gly Ile Pro Ser
            100                 105                 110

Met Gly Glu Glu Glu Arg Glu Val Met His Ala Ile Ala Gly Leu Gly
        115                 120                 125

Leu Ser Ser Arg Leu Leu Ala Trp Cys Arg Leu Cys Asp Val Asp Leu
    130                 135                 140

Ala Ala Ala Arg Ser Thr Gly Val Thr Met Val Asp Leu Ser Leu Pro
145                 150                 155                 160

Val Ser Asp Leu Met Leu His His Lys Leu Asn Arg Asp Arg Asp Trp
                165                 170                 175

Ala Leu Arg Glu Val Ala Arg Leu Val Gly Glu Ala Arg Met Ala Gly
            180                 185                 190

Leu Glu Val Cys Leu Gly Cys Glu Asp Ala Ser Arg Ala Asp Leu Glu
        195                 200                 205

Phe Val Val Gln Val Gly Glu Val Ala Gln Ala Ala Gly Ala Arg Arg
    210                 215                 220

Leu Arg Phe Ala Asp Thr Val Gly Val Met Glu Pro Phe Gly Met Leu
225                 230                 235                 240

Asp Arg Phe Arg Phe Leu Ser Arg Arg Leu Asp Met Glu Leu Glu Val
                245                 250                 255

His Ala His Asp Asp Phe Gly Leu Ala Thr Ala Asn Thr Leu Ala Ala
```

```
            260                 265                 270

Val Met Gly Gly Ala Thr His Ile Asn Thr Thr Val Asn Gly Leu Gly
        275                 280                 285

Glu Arg Ala Gly Asn Ala Ala Leu Glu Glu Cys Val Leu Ala Leu Lys
    290                 295                 300

Asn Leu His Gly Ile Asp Thr Gly Ile Asp Thr Arg Gly Ile Pro Ala
305                 310                 315                 320

Ile Ser Ala Leu Val Glu Arg Ala Ser Gly Arg Gln Val Ala Trp Gln
                325                 330                 335

Lys Ser Val Val Gly Ala Gly Val Phe Thr His Glu Ala Gly Ile His
            340                 345                 350

Val Asp Gly Leu Leu Lys His Arg Arg Asn Tyr Glu Gly Leu Asn Pro
        355                 360                 365

Asp Glu Leu Gly Arg Ser His Ser Leu Val Leu Gly Lys His Ser Gly
    370                 375                 380

Ala His Met Val Arg Asn Thr Tyr Arg Asp Leu Gly Ile Glu Leu Ala
385                 390                 395                 400

Asp Trp Gln Ser Gln Ala Leu Leu Gly Arg Ile Arg Ala Phe Ser Thr
                405                 410                 415

Arg Thr Lys Arg Ser Pro Gln Pro Ala Glu Leu Gln Asp Phe Tyr Arg
            420                 425                 430

Gln Leu Cys Glu Gln Gly Asn Pro Glu Leu Ala Ala Gly Gly Met Ala
        435                 440                 445


<210> SEQ ID NO 238
<211> LENGTH: 243
<212> TYPE: PRT
<213> ORGANISM: Azotobacter vinelandii

<400> SEQUENCE: 238

Met Val Thr Pro Val Asn Met Ser Arg Glu Thr Ala Leu Arg Ile Ala
1               5                   10                  15

Leu Ala Ala Arg Ala Leu Pro Gly Thr Thr Val Gly Gln Leu Leu Glu
            20                  25                  30

Ile Leu His Gln Arg Ile Glu Gly Pro Leu Thr Glu Glu Ser Leu Gln
        35                  40                  45

Gly Val Ser Val Thr Asp Leu Lys Ile Gly Leu Ala Gly Ser Glu Glu
    50                  55                  60

Asp Val Asp Met Leu Asp Thr Pro Met Ser Ala Leu Lys Asp Ala Val
65                  70                  75                  80

Arg Ile Leu Trp Gly Glu Ala Glu Val Asp Ser Leu Pro Gln Pro Val
                85                  90                  95

Lys Leu Glu Arg Val Pro Glu Gly Ser Ile Arg Val Ala Ile Ala Ser
            100                 105                 110

Asn Asn Gly Glu Gln Leu Asp Gly His Phe Gly Ser Cys Leu Arg Phe
        115                 120                 125

Leu Val Tyr Gln Val Ser Ala Lys Asp Ala Ser Leu Val Asp Ile Arg
    130                 135                 140

Ser Thr Leu Asp Val Ala Leu Ala Glu Asp Lys Asn Ala Trp Arg Val
145                 150                 155                 160

Glu Gln Ile Gln Asp Cys Gln Val Leu Tyr Val Val Ser Ile Gly Gly
                165                 170                 175

Pro Ala Ala Ala Lys Val Val Arg Ala Gly Ile His Pro Leu Lys Lys
            180                 185                 190
```

Pro Lys Gly Cys Ala Ala Gln Glu Ala Ile Ala Glu Leu Gln Thr Val
195 200 205

Met Ala Gly Ser Pro Pro Pro Trp Leu Ala Lys Leu Val Gly Val Ser
210 215 220

Ala Glu Glu Arg Val Arg Phe Ser Val Ser Asp Asp Glu Asp Glu Ala
225 230 235 240

Ala Arg Ala

<210> SEQ ID NO 239
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 239

Asp Leu Ile Arg
1

<210> SEQ ID NO 240
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 240

Asp Val Val Arg
1

<210> SEQ ID NO 241
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 241

Asp Ile Ile Arg
1

<210> SEQ ID NO 242
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 242

Asp Leu Thr Arg
1

<210> SEQ ID NO 243
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 243

Ile Asn Val Trp
1

<210> SEQ ID NO 244
<211> LENGTH: 4

```
<212> TYPE: PRT
<213> ORGANISM: Artificial Sequence
<220> FEATURE:
<223> OTHER INFORMATION: C-terminal amino acid sequence

<400> SEQUENCE: 244

Leu Asn Val Trp
1


<210> SEQ ID NO 245
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 245

Leu Asn Thr Trp
1


<210> SEQ ID NO 246
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 246

Leu Asn Met Trp
1


<210> SEQ ID NO 247
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 247

Leu Ala Met Trp
1


<210> SEQ ID NO 248
<211> LENGTH: 4
<212> TYPE: PRT
<213> ORGANISM: Artificial Sequence
<220> FEATURE:
<223> OTHER INFORMATION: C-terminal amino acid sequence

<400> SEQUENCE: 248

Leu Ser Val Trp
1
```

The invention claimed is:

1. A process for producing a plant cell comprising mitochondria and polynucleotides that encode at least 3 Nif polypeptides selected from the group consisting of NifF, NifW, NifY, NifZ, NifV and a NifD-linker-NifK fusion polypeptide, wherein the at least 3 Nif polypeptides comprise a NifV polypeptide, comprising steps of:

(i) introducing, into a plant cell, exogenous polynucleotides that encode at least 3 Nif polypeptides selected from the group consisting of NifF, NifW, NifY, NifZ, NifV and a NifD-linker-NifK fusion polypeptide, wherein the at least 3 Nif polypeptides comprise a NifV polypeptide, wherein the exogenous polynucleotides each comprise a promoter which is operably linked to a nucleotide sequence which encodes one of the Nif polypeptides and which expresses the nucleotide sequence in the plant cell, wherein the Nif polypeptides each independently comprise a mitochondrial targeting peptide (MTP), wherein each MTP is at the N-terminus of the Nif polypeptide, wherein the NifD-linker-NifK fusion polypeptide comprises (a) a mitochondrial targeting peptide (MTP) which has a C-terminus, (b) a NifD polypeptide (ND) which has a N-terminus and a C-terminus, (c) an oligopeptide linker, and (d) a NifK polypeptide (NK) which has a N-terminus, wherein the C-terminus of the MTP of (a) is translationally fused to the N-terminus of the ND such that the MTP and the ND are covalently joined by a peptide bond, and wherein the linker is translationally fused to the C-terminus of the ND and the N-terminus of the NK such that the linker is covalently joined to the C-terminus of the ND by a peptide bond and to the N-terminus of the NK by a peptide bond, (ii) culturing the plant cell for a sufficient time for the polynucleotides to be expressed;

(iii) assaying the solubility of the Nif polypeptides, or cleaved products thereof, in the cell or a progeny cell thereof, and (iv) selecting a plant cell wherein the at least 3 Nif polypeptides, or cleaved products thereof, are at least partially soluble in the mitochondria.

2. The process of claim 1, wherein the NifV polypeptide produces homocitrate in the cell.

3. The process of claim 1, wherein the plant cell further comprises an exogenous polynucleotide which encodes a NifH polypeptide, wherein the exogenous polynucleotide comprises a promoter which is operably linked to a nucleotide sequence which encodes the NifH polypeptide.

4. The process of claim 1, wherein each of the at least three Nif polypeptides is independently cleaved in its MTP in the plant cell with an efficiency of at least 50%.

5. A process for producing a transgenic plant, comprising steps of:

(i) carrying out the process of claim 1, and (ii) producing a transgenic plant from the selected plant cell, wherein the exogenous polynucleotides are integrated into the nuclear genome of the plant.

6. A transgenic plant produced by the process of claim 5, or a plant part, organ or tissue thereof, wherein the exogenous polynucleotides are integrated into the nuclear genome of the plant.

7. The process of claim 5, wherein the exogenous polynucleotides are integrated into the nuclear genome of the plant as a contiguous nucleic acid sequence.

8. The transgenic plant of claim 6, wherein the exogenous polynucleotides are integrated into the nuclear genome of the plant as a contiguous nucleic acid sequence.

* * * * *